United States Patent
Ammann et al.

(10) Patent No.: US 11,702,414 B2
(45) Date of Patent: *Jul. 18, 2023

(54) THIADIAZOLE IRAK4 INHIBITORS

(71) Applicant: Gilead Sciences, Inc., Foster City, CA (US)

(72) Inventors: Stephen Ammann, Redwood City, CA (US); Elizabeth M. Bacon, Burlingame, CA (US); Gediminas Brizgys, San Carlos, CA (US); Elbert Chin, San Mateo, CA (US); Chienhung Chou, Dublin, CA (US); Jeromy J. Cottell, Redwood City, CA (US); Marilyn Ndukwe, Lebanon, NH (US); Marina Shatskikh, San Francisco, CA (US); James G. Taylor, Burlingame, CA (US); Nathan E. Wright, Foster City, CA (US); Zheng-Yu Yang, Palo Alto, CA (US); Sheila M. Zipfel, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 141 days.

This patent is subject to a terminal disclaimer.

(21) Appl. No.: 17/204,463

(22) Filed: Mar. 17, 2021

(65) Prior Publication Data
US 2022/0402910 A1    Dec. 22, 2022

Related U.S. Application Data

(63) Continuation of application No. 16/539,834, filed on Aug. 13, 2019, now Pat. No. 11,046,686.

(60) Provisional application No. 62/718,262, filed on Aug. 13, 2018.

(51) Int. Cl.
*C07D 471/04* (2006.01)
*C07D 487/04* (2006.01)

(52) U.S. Cl.
CPC ........ *C07D 471/04* (2013.01); *C07D 487/04* (2013.01)

(58) Field of Classification Search
CPC ........................... C07D 471/04; C07D 487/04
USPC ........................................... 514/243
See application file for complete search history.

(56) References Cited

PUBLICATIONS

Ferra et al., Journal of Medicinal Chemistry (2011), 54(1), 211-221.*

* cited by examiner

*Primary Examiner* — Niloofar Rahmani

(57) ABSTRACT

A compound of Formula (I):

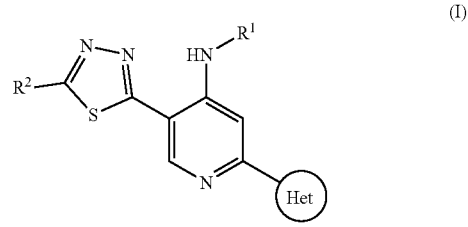

pharmaceutically acceptable salts thereof, deuterated analogs thereof, compositions thereof, and methods of treating disease using a compound thereof are disclosed.

4 Claims, No Drawings

THIADIAZOLE IRAK4 INHIBITORS

CROSS REFERENCE TO RELATED APPLICATION

This application is a Continuation of application Ser. No. 16/539,834 filed on Aug. 13, 2019 which claims the benefit of U.S. Provisional Patent Application 62/718,262 filed on Aug. 13, 2018. The entire contents of these applications are incorporated herein by reference in their entirety.

FIELD

The present disclosure relates to novel compounds that are inhibitors of the kinase IRAK4. The disclosure also relates to methods for preparing the compounds and to pharmaceutical compositions comprising such compounds.

BACKGROUND

Interleukin-1 receptor-associated kinase-4 (IRAK4) is a serine-threonine kinase which acts as a mediator in interleukin-1/Toll-like receptor (IL-1/TLR) signaling cascades. More particularly, IRAK4 is involved in activation of adaptor protein myeloid differentiation primary response gene 88 (MyD88) signaling cascades and is hypothesized to play a role in inflammatory and fibrotic disorders, such as rheumatoid arthritis (RA), inflammatory bowel disease (IBD), gout, Lyme disease, arthritis, psoriasis, pelvic inflammatory disease, systemic lupus erythematosus (SLE), Sjogren's syndrome, viral myocarditis, acute and chronic tissue injury, non-alcoholic steatohepatitis (NASH), alcoholic hepatitis and kidney disease, including chronic kidney disease and diabetic kidney disease. In addition, IRAK4 plays a role in certain cancers and is hypothesized to play a role in inflammation associated with gastrointestinal infections, including *C. difficile*. Signaling through IL-1R/TLR results in the activation of MyD88 which recruits IRAK4 and IRAK1 to form a signaling complex. This complex then interacts with a series of kinases, adaptor proteins, and ligases, ultimately resulting in the activation of nuclear factor kappa-light-chain-enhancer of activated B cells (NF-κB), activator protein-1 (AP1), cyclic AMP-responsive element-binding protein (CREB) and the interferon-regulatory factors (IRFs), including IRF5 and IRF7, inducing the generation of pro-inflammatory cytokines and type I interferons.

Therefore, inhibitors of IRAK4 may be useful in the treatment of inflammatory and fibrotic disorders, such as rheumatoid arthritis (RA), inflammatory bowel disease (IBD), gout, Lyme disease, arthritis, psoriasis, pelvic inflammatory disease, systemic lupus erythematosus (SLE), Sjogren's syndrome, inflammation associated with gastrointestinal infections, including *C. difficile*, viral myocarditis, acute and chronic tissue injury, non-alcoholic steatohepatitis (NASH), alcoholic hepatitis and kidney disease, including chronic kidney disease and diabetic kidney disease. (Joosten, L. A. B et al., TOLL-LIKE RECEPTORS AND CHRONIC INFLAMMATION IN RHEUMATIC DISEASES: NEW DEVELOPMENTS, Nat. Rev. Rheumatol., 346 I June 2016 12; 344-357 Published online 12 May 2016) (Valaperti, A. et al., INNATE IMMUNE INTERLEUKIN-1RECEPTOR-ASSOCIATED KINASE 4 EXACERBATES VIRAL MYOCARDITIS BY REDUCING CCR5+CD11b+ MONOCYTE MIGRATION AND IMPAIRING INTERFERON PRODUCTION, Circulation, 128 I September 2013 14; 1542-1554), as well as Type I interferonopathies, such as Aicardi-Goutieres syndrome, Familial chilblain lupus, and Retinal vasculopathy with cerebral leukodystrophy, (Lee-Kirsch et al., TYPE I INTERFERONOPATHIES—AN EXPANDING DISEASE SPECTRUM OF IMMUNODYSREGULATION, Semin. Immunopathol. (2015) 37:349-357), (Leaf, I. A. et al., PERICYTE MYD88 AND IRAK4 CONTROL INFLAMMATORY AND FIBROTIC RESPONSES TO TISSUE INJURY, The Journal of Clinical Investigation, 127 I January 2017 1; 321-334), (Seki, E. et al., TLR4 ENHANCES TGF-β SIGNALING AND HEPATIC FIBROSIS, Nature Medicine, 13 I Novenber 2007 11; 1324-1332), (Garcia-Martinez, I. et al., HEPATOCYTE MITOCHONDRIAL DNA DRIVES NON-ALCHOLIC STEATOHEPATITIS BY ACTIVATION OF TLR9, The Journal of Clinical Investigation, 126 I March 2016 3; 859-864).

In addition, certain cancers, including lymphomas, may contain one or more mutations in the MYD88 adaptor protein, leading to a constitutively active signaling cascade that may promote survival of tumor cells. (Kelly et al., IRAK4 inhibitors for autoimmunity and lymphoma, J. Exp. Med. 2015 Vol. 212 No. 13 2189-2201)

Therefore, an inhibitor of IRAK4 may be useful in the treatment of cancers, including lymphomas.

There are currently no approved IRAK4 inhibiting pharmaceuticals. Therefore, it would be useful to provide an IRAK4 inhibiting compound with properties suitable for administration as a pharmaceutical agent to a mammal, particularly a human. Considerations for selecting a pharmaceutical compound are multifactorial. Compound characteristics including on-target potency, pharmacokinetics, pKa, solubility, stability (e.g., metabolic stability) and off-target liabilities are frequently profiled.

WO2016210034, WO2016210036, WO2015150995, WO2016127024, and WO2016210037 recite compounds said to be useful as IRAK4 inhibitors.

IRAK1 functions as a cytokine initiated by the binding of ligands to IL-1R and TLRs. Activation of the IL-1 and TLR signaling pathways can be triggered by a variety of stimuli, including recognition of microbial pathogens or products, such as LPS, the presence of reactive oxygen species, recognition of DNA damage, abnormalities in the tissue matrix caused by chronic inflammation, and genetic factors, such as amplification of 1q21.3 and overproduction of S100A proteins.

The inflammatory cytokines sIL-17A, sIL-2, and sIL-6 are regulated by IRAK1, and inhibition of IRAK1 by the late-stage clinical compound pacritinib suppresses induced immunglobulin synthesis in normal human lymphocytes. In normal human monocytes, IRAK1 induces inflammatory cytokines upon LPS challenge. (See, for example, Singer, J. et al. INHIBITION OF INTERLEUKIN-1 RECEPTOR-ASSOCIATED KINASE 1 (IRAK1) AS A THERAPEUTIC STRATEGY, Oncotarget, Vol. 9, (No. 70), pp: 33416-33439 (2018)). Therefore, there is strong evidence to support the role of IRAK1 in a variety of inflammatory conditions.

SUMMARY OF THE INVENTION

Provided herein are compounds and pharmaceutical compositions useful as inhibitors of IRAK4 or IRAK1 or both IRAK4 and IRAK1. Some compounds of the disclosure may find use in pharmaceutical compositions, together with at least one pharmaceutically acceptable excipient, for treating a subject in need thereof. Compounds of the present disclosure also have been found to inhibit production of pro-inflammatory cytokines TNFα, IL-6, IL-1β, IL-8, IL-12, IL-23 and type I interferons IFNα and IFNβ, all of which are mediators of inflammation and the immune response. The disclosure also provides compositions, including pharmaceutical compositions, kits that include the compounds, and methods of using and making the compounds.

In one embodiment of the disclosure, there is provided a compound of Formula (I):

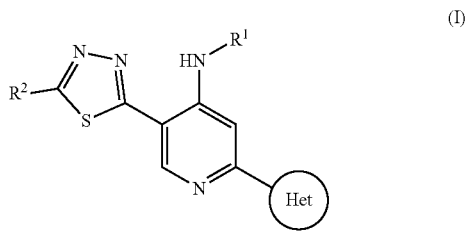

(I)

wherein "Het" is a bicyclic heteroaryl optionally substituted with X;

X is selected from —H, —F, —Cl, —Br, and —CN;
$R^1$ and $R^2$ are each independently selected from:
a) $C_{1-10}$ alkyl optionally substituted with $Z^1$;
b) $C_{3-10}$ cycloalkyl optionally substituted with $Z^1$;
c) 5-10 membered heteroaryl optionally substituted with $Z^1$;
d) $C_{6-10}$ aryl optionally substituted with $Z^1$;
e) 4-12 membered heterocyclyl optionally substituted with $Z^1$; and
f) —H, —O—$R^{12}$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$^{12}$S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$—S(O)$_2$N($R^{12}$)($R^{12}$) or sulfoximine;

$Z^1$ is independently oxo, imino, sulfoximino, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein any alkyl, alkenyl, alkynyl, cycloalkyl, haloalkyl, aryl, heteroaryl or heterocyclyl is optionally substituted with $Z^{1a}$;

each $Z^{1a}$ is independently oxo, imino, sulfoximino, halo, —NO$_2$, —CN, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein any alkyl, alkenyl, alkynyl, cycloalkyl, haloalkyl, aryl, heteroaryl or heterocyclyl is optionally substituted with $Z^{1b}$;

each $R^{12}$ is independently H, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with $Z^{1a}$;

each $Z^{1b}$ is independently oxo, imino, sulfoximino, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one or more halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)₂(aryl), —S(O)₂(heteroaryl), —S(O)₂(heterocyclyl), —S(O)₂NH(C₁₋₉ alkyl), —S(O)₂N(C₁₋₉ alkyl)₂, —O(C₃₋₁₅ cycloalkyl), —O(C₁₋₈ haloalkyl), —O(aryl), —O(heteroaryl), —O(heterocyclyl), or —O(C₁₋₉ alkyl);

or a pharmaceutically acceptable salt, stereoisomer, mixture of stereoisomers, or deuterated analog thereof.

In one embodiment, "Het" is selected from:

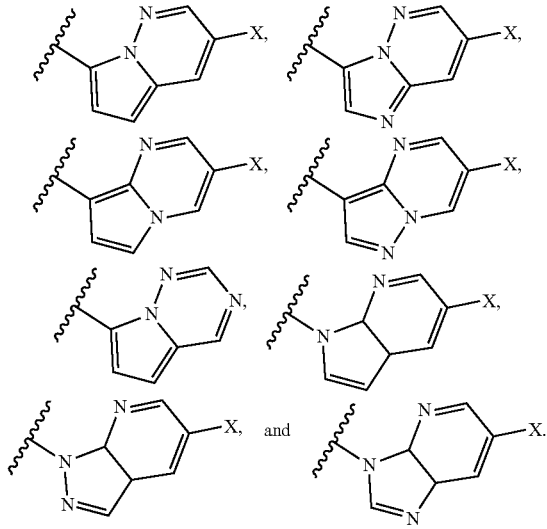

In one embodiment, $R^1$ is $C_{1-10}$ alkyl optionally substituted with $Z^1$.

In another embodiment, $R^1$ is $C_{1-5}$ alkyl optionally substituted with —F, —OH, or —CN.

In another embodiment, $R^1$ is 4-8 membered heterocycle optionally substituted with $Z^1$.

In another embodiment, $R^1$ is oxetane, tetrahydrofuran or tetrahydropyran optionally substituted with $Z^1$.

In another embodiment, $R^1$ is $C_{3-10}$ cycloalkyl optionally substituted with $Z^1$.

In still another embodiment, $R^1$ is $C_{3-10}$ cycloalkyl substituted with 5-10 membered heteroaryl wherein said 5-10 membered heteroaryl is optionally substituted with $Z^{1a}$.

In another embodiment, $R^1$ is $C_{3-10}$ cycloalkyl substituted with $C_{1-3}$ alkyl and said $C_{1-3}$ alkyl is further substituted with $Z^{1a}$.

In another embodiment, $R^1$ is 5-10 membered heteroaryl optionally substituted with $Z^1$.

In one embodiment, $R^2$ is $C_{1-10}$ alkyl optionally substituted with $Z^1$.

In another embodiment, $R^2$ is $C_{1-10}$ alkyl optionally substituted with one or more —F, —OH or combinations thereof.

In another embodiment, $R^2$ is $C_{3-10}$ cycloalkyl optionally substituted with $Z^1$.

In another embodiment, $R^2$ is $C_{3-8}$ cycloalkyl optionally substituted with —OH, —N(R¹²)C(O)(R¹²), —N(R¹²)C(O)O(R¹²), or —C(O)N(R¹²)(R¹²).

In another embodiment, $R^2$ is a 4-8 membered heterocyclyl optionally substituted with $Z^1$.

In another embodiment, $R^2$ is a 4-8 membered heterocyclyl substituted with —OH, —N(R¹²)C(O)(R¹²), —N(R¹²)C(O)O(R¹²), or —C(O)N(R¹²)(R¹²).

In another embodiment, $R^2$ is —C(O)—N(R¹²)(R¹²).

The disclosure also provides a compound of Formula (Ia):

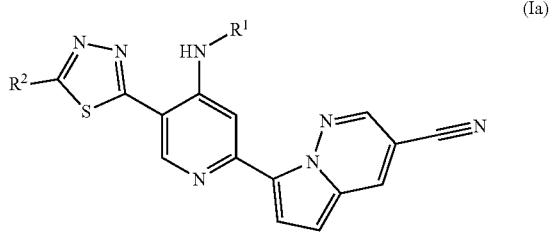

(Ia)

wherein $R^1$ and $R^2$ are each independently selected from:
a) $C_{1-10}$ alkyl optionally substituted with $Z^1$;
b) $C_{3-10}$ cycloalkyl optionally substituted with $Z^1$;
c) 5-10 membered heteroaryl optionally substituted with $Z^1$;
d) $C_{6-10}$ aryl optionally substituted with $Z^1$;
e) 4-12 membered heterocyclyl optionally substituted with $Z^1$; and
f) —H, —O—R¹², —C(O)—R¹², —C(O)O—R¹², —C(O)—N(R¹²)(R¹²), —N(R¹²)(R¹²), —N(R¹²)₂(R¹²)⁺, —N(R¹²)C(O)—R¹², —N(R¹²)C(O)O—R¹², —N(R¹²)C(O)N(R¹²)(R¹²), —N(R¹²)S(O)₂(R¹²), —NR¹²S(O)₂N(R¹²)(R¹²), —N¹²S(O)₂O(R¹²), —OC(O)R¹², —OC(O)OR¹², —OC(O)—N(R¹²)(R¹²), —Si(R¹²)₃, —S—R¹², —S(O)R¹², —S(O)(NH)R¹², —S(O)₂R¹²—S(O)₂N(R¹²)(R¹²) or sulfoximine;

and wherein $Z^1$ is independently imino, sulfoximino oxo, halo, —NO₂, —N₃, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—R¹², —C(O)—R¹², —C(O)O—R¹², —C(O)—N(R¹²)(R¹²), —N(R¹²)(R¹²), —N(R¹²)₂(R¹²)⁺, —N(R¹²)C(O)—R¹², —N(R¹²)C(O)O—R¹², —N(R¹²)C(O)N(R¹²)(R¹²), —N(R¹²)S(O)₂(R¹²), —NR¹²S(O)₂N(R¹²)(R¹²), —NR¹²S(O)₂O(R¹²), —OC(O)R¹², —OC(O)OR¹², —OC(O)—N(R¹²)(R¹²), —Si(R¹²)₃, —S—R¹², —S(O)R¹², —(O)(NH)R¹², —S(O)₂R¹² or —S(O)₂N(R¹²)(R¹²);

wherein any alkyl, alkenyl, alkynyl, cycloalkyl, haloalkyl, aryl, heteroaryl or heterocyclyl is optionally substituted with $Z^{1a}$;

each $Z^{1a}$ is independently oxo, imino, sulfoximino, halo, —NO₂, —CN, —N₃, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—R¹², —C(O)R¹², —C(O)O—R¹², —C(O)N(R¹²)(R¹²), —N(R¹²)(R¹²), —N(R¹²)₂(R¹²)⁺, —N(R¹²)—C(O)R¹², —N(R¹²)C(O)O(R¹²), —N(R¹²)C(O)N(R¹²)(R¹²), —N(R¹²)S(O)₂(R¹²), —N(R¹²)S(O)₂—N(R¹²)(R¹²), —N(R¹²)S(O)₂O(R¹²), —OC(O)R¹², —OC(O)OR¹², —OC(O)—N(R¹²)(R¹²), —Si(R¹²)₃, —S—R¹², —S(O)R¹², —S(O)(NH)R¹², —S(O)₂R¹² or —S(O)₂N(R¹²)(R¹²);

wherein any alkyl, alkenyl, alkynyl, cycloalkyl, haloalkyl, aryl, heteroaryl or heterocyclyl is optionally substituted with $Z^{1b}$;

each $R^{12}$ is independently H, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with $Z^{1a}$;

each $Z^{1b}$ is independently oxo, imino, sulfoximino, hydroxy, halo, —NO₂, —N₃, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —NH₂, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one or more halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

or a pharmaceutically acceptable salt, stereoisomer, mixture of stereoisomers, or deuterated analog thereof.

In another embodiment the disclosure provides a pharmaceutical composition comprising a compound of Formula (I) or (Ia) or a pharmaceutically acceptable salt, stereoisomer, mixture of stereoisomers or deuterated analog thereof, together with a pharmaceutically acceptable carrier.

In still other embodiments the disclosure provides a method of treating an inflammatory condition in a patient in need thereof, comprising administering to said patient a compound of Formula (I) or (Ia) or the composition comprising a compound of Formula (I) or (Ia).

In some embodiments the inflammatory condition is selected from IBD, SLE, Psoriasis and Rheumatoid Arthritis.

DETAILED DESCRIPTION OF THE INVENTION

Definitions

The following description sets forth exemplary methods, parameters and the like. It should be recognized, however, that such description is not intended as a limitation on the scope of the present disclosure but is instead provided as a description of exemplary embodiments.

A dash ("—") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Alkenyl" refers to an alkyl group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Amino" refers to the group —NR$^y$R$^y$ wherein each R$^y$ is independently selected from the group consisting of hydrogen, alkyl, alkenyl, alkynyl, aryl, heterocyclyl, cycloalkyl or heteroaryl, each of which is optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cyano" refers to the group —CN.

"Keto" or "oxo" refers to a group =O.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl" refers to —C(O)OH.

"Ester" refers to both —OC(O)R and —C(O)OR, wherein R is a substituent; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bicyclic heterocyclyl groups, bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring atoms (i.e., 4-20 membered heterocyclyl), 2 to ring atoms (i.e., 4-12 membered heterocyclyl), 4 to 10 ring atoms (i.e., 4-10 membered heterocyclyl), 4 to 8 ring atoms (i.e., 4-8 membered heterocyclyl), or 4 to 6 ring carbon atoms (i.e., 4-6 membered heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include pyrrolidinyl, piperidinyl, piperazinyl, oxetanyl, dioxolanyl, azetidinyl, azetidinyl, morpholinyl, thiomorpholinyl, 4-7 membered sultam, 4-7 membered cyclic carbamate, 4-7 membered cyclic carbonate, 4-7 membered cyclic sulfide and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, and isoindolinyl, where the heterocyclyl can be bound via either ring of the fused system. As used herein, a bicyclic heterocyclyl group is a heterocyclyl group attached at two points to another cyclic group, wherein the other cyclic group may itself be a heterocyclic group, or a carbocyclic group.

As used herein, the term "nitrogen or sulfur containing heterocyclyl" means a heterocyclyl moiety that contains at least one nitrogen atom or at least one sulfur atom, or both a nitrogen atom and a sulfur atom within the ring structure. It is to be understood that other heteroatoms, including oxygen, may be present in addition to the nitrogen, sulfur, or combinations thereof. Examples of nitrogen or sulfur containing heterocyclyls include morpholinyl, thiomorpholinyl, thiazolyl, isothiazolyl, oxazolidinone 1,2 dithiolyl, piperidinyl, piperazinyl, and the like.

"Hydroxy" or "hydroxyl" refers to the group —OH. "Hydroxyalkyl" refers to an unbranched or branched alkyl group as defined above, wherein one or more hydrogen atoms are replaced by a hydroxyl.

"Nitro" refers to the group —NO$_2$.

"Imino" refers to a group =N—R$^y$, or =N—C(O)R$^y$, wherein R$^y$ is selected from the group consisting of hydrogen, alkyl, aryl, cyano, haloalkyl, or heteroaryl; each of which may be optionally substituted.

"Sulfoximine" or "sulfoximino" refers to a substituted or unsubstituted moiety of the general formula

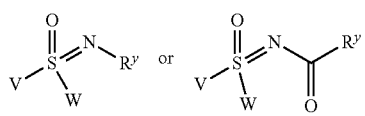

wherein R$^y$ is selected from the group consisting of hydrogen, alkyl, amino, aryl, cyano, haloalkyl, heterocyclyl, or heteroaryl; V and W are each independently selected from a bond, alkyl, amino, aryl, haloalkyl, heterocyclyl or heteroaryl; each of which may be optionally substituted and wherein R$^y$ and V, R$^y$ and W, and V and W together with the atoms to which they are attached may be joined together to form a ring.

"Sulfonyl" refers to the group —S(O)$_2$R, where R is a substituent, or a defined group.

"Alkylsulfonyl" refers to the group —S(O)$_2$R, where R is a substituent, or a defined group.

"Alkylsulfinyl" refers to the group —S(O)R, where R is a substituent, or a defined group.

"Thiocyanate" —SCN.

"Thiol" refers to the group —SR, where R is a substituent, or a defined group.

"Thioxo" or "thione" refer to the group (=S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. "Optionally substituted" may be zero to the maximum number of possible substitutions, and each occurance is independent. When the term "substituted" is used, then that substitution is required to be made at a substitutable hydrogen atom of the indicated substituent. An optional substitution may be the same or different from a (required) substitution.

When a moiety is "optionally substituted," and reference is made to a general term, such as any "alkyl," "alkenyl," "alkynyl," "haloalkyl," "cycloalkyl," "aryl"or "heteroaryl," then the general term can refer to any antecedent specifically recited term, such as (C$_{1-3}$ alkyl), (C$_{4-6}$ alkyl), —O(C$_{1-4}$ alkyl), (C$_{3-10}$ cycloalkyl), O-(C$_{3-10}$ cycloalkyl) and the like. For example, "any aryl" includes both "aryl" and "—O(aryl) as well as examples of aryl, such as phenyl or naphthyl and the like. Also, the term "any heterocyclyl" includes both the terms "heterocyclyl" and O—(heterocyclyl)," as well as examples of heterocyclyls, such as oxetanyl, tetrahydropyranyl, morpholino, piperidinyl and the like. In the same manner, the term "any heteroaryl" includes the terms "heteroaryl" and "O—(heteroryl)," as well as specific heteroaryls, such as pyridine and the like.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^{2}H$ (deuterium, D), $^{3}H$ (tritium), 11C, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^{3}H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogues" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Combinations

Patients being treated by administration of the IRAK4 inhibitors of the disclosure often exhibit diseases or conditions that benefit from treatment with other therapeutic agents. These diseases or conditions can be of an inflammatory nature or can be related to cancer, metabolic disorders, gastrointestinal disorders and the like. Thus, one aspect of the disclosure is a method of treating an inflammation related disease or condition, or a metabolic disorder, gastrointestinal disorder, or cancer and the like comprising administering a compound of the in combination with one or more compounds useful for the treatment of such diseases to a subject, particularly a human subject, in need thereof.

In some embodiments, a compound of the present disclosure is co-formulated with the additional one or more active ingredients. In some embodiments, the other active ingredient is administered at approximately the same time, in a separate dosage form. In some embodiments, the other active ingredient is administered sequentially, and may be administered at different times in relation to a compound of the present disclosure.

Combinations for Inflammatory Diseases and Conditions

For example, a compound of the present disclosure may be combined with one or more 5-Lipoxygenase inhibitors, Acetylcholinesterase inhibitors, Acetyl-CoA carboxylase (ACC) inhibitors, ACTH receptor agonists, Activin receptor antagonists, Acyltransferase inhibitors, Adrenocorticotrophic hormone ligands, AKT1 gene inhibitors, Alkaline phosphatase modulators, Alkaline phosphatase stimulators, Androgen receptor agonists, Apolipoprotein C3 antagonists, ASK1 kinase inhibitors, Bactericidal permeability protein stimulators, Beta adrenoceptor antagonists, Beta-glucuronidase inhibitors, B-lymphocyte antigen CD20 inhibitors, Bradykinin receptor modulators, BTK kinase inhibitors, Calcineurin inhibitors, Calcium channel inhibitors, Cannabinoid CB1 receptor modulators, Cannabinoid CB2 receptor modulators, Cannabinoid receptor antagonists, Cannabinoid receptor modulators, Caspase inhibitors, Cathepsin S inhibitors, CCN protein stimulators, CCR3 chemokine antagonists, CCR5 chemokine antagonists, CCR9 chemokine antagonists, CD3 modulators, CD40 ligand inhibitors, CD40 ligand receptor antagonists, CD49b antagonists, CD49d antagonists, CD89 agonists, Cell adhesion molecule inhibitors, Chemokine CXC ligand inhibitors, CHST15 gene inhibitors, Collagen modulators, CSF-1 agonists, CSF-1 antagonists, CXC10 chemokine ligand inhibitors, CXCR2 chemokine antagonists, Cyclic GMP phosphodiesterase inhibitors, Cyclooxygenase 2 inhibitors, Cyclooxygenase inhibitors, Cyclooxygenase stimulators, Cytochrome P450 3A4 inhibitors, Cytotoxic T-lymphocyte protein-4 stimulators, Dihydroceramide delta 4 desaturase inhibitors, Dihydroorotate dehydrogenase inhibitors, DNA polymerase inhibitors, DPP-4 inhibitors, EGFR family tyrosine kinase receptor modulators, Eosinophil peroxidase inhibitors, Eotaxin ligand inhibitors, EP4 prostanoid receptor agonists, Epidermal growth factor agonists, Epidermal growth factor ligands, Estrogen receptor beta agonists, Factor XIII agonists, FGF-10 ligands, FGF2 receptor agonists, Fractalkine ligand inhibitors, Free fatty acid receptor 2 antagonists, FXR agonists, GATA 3 transcription factor inhibitors, Glucagon-like peptide 1 agonists , Glucagon-like peptide 2 agonists, Glucocorticoid agonists, GM-CSF receptor agonists, G-protein coupled receptor 84 antagonists, Guanylate cyclase receptor agonists, Histamine H2 receptor antagonists, Histone acetyltransferase inhibitors, Histone deacetylase inhibitors, HLA class II antigen modulators, Hydrolase inhibitors, HSD17β13 inhibitors, ICAM1 gene inhibitors, ICAM-1 inhibitors, IL1 gene inhibitors, IL-10 agonists, IL10 gene stimulators, IL-11 agonists, IL-12 antagonists, IL12 gene inhibitors, IL-13 antagonists, IL-17 antagonists, IL-2 antagonists, IL-2 receptor alpha subunit inhibitors, IL-21 antagonists, IL-23 antagonists, IL-6 antagonists, IL6 gene inhibitors, IL-6 receptor modulators, IL-7 antagonists, IL-8 antagonists, Immunoglobulin G1 agonists, Immunoglobulin G2 modulators, Inosine monophosphate dehydrogenase inhibitors, Insulin sensitizers, Integrin alpha-4/beta-1 antagonists, Integrin alpha-4/beta-7 antagonists, Integrin alpha-E antagonists, Integrin antagonists, Integrin beta-7 antagonists, Interferon beta ligands, Interleukin 17E ligand inhibitors, Interleukin ligand inhibitors, Interleukin receptor 17A antagonists, Interleukin receptor 17B antagonists, Interleukin-1 beta ligands, Interleukin-1 beta ligand modulators, Interleukin-6 ligand inhibitors, JAK tyrosine kinase inhibitors, Jak1 tyrosine kinase inhibitors, JAK2 gene inhibitors, Jak3 tyrosine kinase inhibitors, Jun N terminal kinase inhibitors, LanC like protein 2 modulators, Leukotriene BLT receptor antagonists, Lipoxygenase modulators, L-Selectin antagonists, MAdCAM inhibitors, Matrix metalloprotease inhibitors, Matrix metalloprotease modulators, Melanocortin agonists, Membrane copper amine oxidase inhibitors, Metalloprotease-2 inhibitors, Metalloprotease-9 inhibitors, MIP 3 alpha ligand inhibitors, Mitochondrial 10 kDa heat shock protein stimulators, Monocyte differentiation antigen CD14 inhibitors, mTOR inhibitors, Mucin stimulators, NAD-dependent deacetylase sirtuin-1 stimulators, Natriuretic peptide receptor C agonists, Neuregulin-4 ligands, Nicotinic acetylcholine receptor agonists, Nicotinic ACh receptor alpha 4 subunit modulators, Nicotinic ACh receptor alpha 7 subunit stimulators, Nicotinic ACh receptor beta 2 subunit modulators, NK1 receptor antagonists, NKG2 D activating NK receptor antagonists, Nuclear factor kappa B inhibitors, Opioid growth factor receptor agonists, Opioid receptor antagonists, Opioid receptor delta antagonists, Oxidoreductase inhibitors, P2X7 purinoceptor agonists, p38 MAP kinase inhibitors, PARP inhibitors, PDE 4 inhibitors, PDGF receptor agonists, Phagocytosis stimulating peptide modulators, Phospho MurNAc pentapeptide transferase inhibitors, Phospholipase A2 inhibitors, Platelet activating factor receptor antagonists, Potassium channel inhibitors, PPAR alpha agonists, PPAR delta agonists, PPAR gamma agonists, Protein CYR61 stimulators, Protein fimH inhibitors, Protein kinase C alpha inhibitors, Protein kinase C beta inhibitors, Protein kinase C delta inhibitors, Protein kinase C epsilon inhibitors, Protein kinase C eta inhibitors, Protein kinase C theta inhibitors, Protein kinase G inhibitors, Protein kinase inhibitors, P-selectin glycoprotein ligand-1 inhibitors, PurH purine biosynthesis protein inhibitors, Retinoic acid receptor alpha agonists, Retinoic acid receptor beta agonists, Retinoid receptor agonists, RNA polymerase inhibitors, SMAD-7 inhibitors, Sodium channel inhibitors, Somatostatin receptor agonists, Sphingosine 1 phosphate phosphatase 1 stimulators, Sphingosine 1 phosphate phosphatase modulators, Sphingosine kinase 1 inhibitors, Sphingosine kinase 2 inhibitors, Sphingosine-1-phosphate receptor-1 agonists, Sphingosine-1-phosphate receptor-1 antagonists, Sphingosine-1-phosphate receptor-1 modulators, Sphingosine-1-phosphate receptor-5 modulators, STAT3 gene inhibitors, STAT-3 inhibitors, STAT-4 inhibitors, Stem cell antigen-1 inhibitors, Superoxide dismutase modulators, Superoxide dismutase stimulators, SYK kinase inhibitors, T cell surface glycoprotein CD28 inhibitors, TGF beta 1 ligand inhibitors, Thymulin agonists, THR-β agonists, TLR-2 antagonists, TLR-4 antagonists, TLR-9 agonists, TNF alpha ligand inhibitors, TNF alpha ligand modulators, TNF antagonists, TPL2 kinase inhibitors, Trefoil factor modulators, Tryptase inhibitors, Tryptophan 5-hydroxylase inhibitors, Tumor necrosis factor 14 ligand modulators, TYK2 kinase inhibitors, Type I TNF receptor antagonists, Type II TNF receptor modulators, Unspecified growth factor receptor modulators, Vanilloid VR1 agonists, Vitamin D3 receptor agonists, Zonulin inhibitors, abatacept; acemannan; adalimumab; DCCT-10; apremilast; AST-120; balsalazide; balsalazide sodium; basiliximab; beclomethasone dipropionate; budesonide; D-9421; budesonide MMX; catridecacog; certolizumab pegol; Clostridium butyricum; etanercept; fingolimod; glatiramer acetate; golimumab; infliximab; infliximab biosimilar; infliximab follow-on biologic; interferon beta-1a,; lenalidomide; mesalazine; GED-0001; AJG-501; metenkefalin acetate with tridecactide acetat, mycophenolate mofetil; naltrexone; natalizumab; nitazoxanide; olsalazine; oprelvekin; propionyl-L-carnitine; recombinant interferon beta-1a; remestemcel-L; rifaximin; rituximab; ropivacaine; rosiglitazone; sargramostim; secukinumab; SPD-480; tacrolimus; tamibarotene; teduglutide; thalidomide; tocilizumab; RO-4877533; tofacitinib ; CP-690550; Trichuris suis ova; ASP-1002; ustekinumab; valganciclovir; vedolizumab; zileuton; anti-CD3 imaging agent (antibody fragment, cancer/autoimmune disease), ImaginAb; AVX-470; ciclosporin; CXCR1/2 ligands mAb (immunology), Eli Lilly; FFP-102; GSK-3050002; INN-108; IR-777; SGM-1019; peg-ilodecakin; PF-06480605; PF-06651600; SER-287; Syn-1002; Thetanix; tolerogenic dendritic cell therapy TOP-1288; VBY-036; VBY-129; 946414-98-8; BMS-936557; 99mTc-annexin V-128; ABC-294640; abrilumab; Alequel; AMG-139; amiselimod; APD-334; ASP-3291; beclomethasone dipropionate; bertilimumab; ciclosporin; clazakizumab; DLX-105; dolcanatide; E-6011; ETX-201; FFP-104; filgotinib; foralumab; GED-0507-34-Levo; givinostat; GLPG-0974; GLPG-1205; iberogast N (ulcerative colitis), Bayer; BAY98-7410; INV-103; JNJ-40346527; K(D)PT; KAG-308; KHK-4083; KRP-203; larazotide acetate; CB-01-05-MMX; LY-3074828; mesalamine with N-acetylcysteine; midismase; molgramostim follow on biologic with fosfomycin with carbapenem, Reponex; multipotent adult progenitor cell therapy (ischemia/cerebral palsy), Athersys/Healios; NN-8828; olokizumab; OvaSave; P-28-GST; PDA-002; PF-4236921; PF-547659; prednisolone; PUR-0110; QBECO; RBX-2660; repurposed naltrexone; JKB-122; SB-012; sotrastaurin; STNM-01; TAK-114; tetomilast; Debio-0512; TRK-170; TRX-318; vatelizumab; VB-201; ZP-1848; zucapsaicin ; ABT-494; alicaforsen; Ampion; BI-655066; briakinumab; cannabidiol; carotegast methyl; cobitolimod; dexamethasone sodium phosphate; elafibranor; etrolizumab; GS-5745; HMPL-004; LP-02; mesalazine; metronidazole mongersen; ocrelizumab; ozanimod; peficitinib; RHB-104; rifaximin; tildrakizumab; tralokinumab; brodalumab; laquinimod; plecanatide; telotristat etiprate; infliximab biosimilar, Samsung Bioepis; AZD-058; and rifabutin with clarithromycin and further with clofazimine.

Also, the following non-exhaustive list of classes of compounds and compounds may be combined with a compound of the present disclosure: 5-Lipoxygenase inhibitors, such as zileuton, etalocibm FPL-64170, E-3040, and BU-4601A; Acetylcholinesterase inhibitors, such as BL-7040; ACTH receptor agonists, such as metenkefalin acetate with tridecactide acetate, and FAR-404; Activin receptor antagonists such as follistatin; Acyltransferase inhibitors such as AZD-0585; Adrenocorticotrophic hormone ligands, such as metenkefalin acetate with tridecactide acetate, and FAR-404; AKT1 gene inhibitors, such as vidofludimus; Alkaline phosphatase modulators such as recombinant human alkaline phosphatase (oral, ulcerative colitis), AM-Pharma; Alkaline phosphatase stimulators such as bovine alkaline phosphatase; Androgen receptor agonists, such as PB-005; Apolipoprotein C3 antagonists, such as AZD-0585; Bactericidal permeability protein stimulators, such as opebacan; Beta adrenoceptor antagonists, such as NM-001; Beta-glucuronidase inhibitors, such as KD-018; B-lymphocyte antigen CD20 inhibitors, such as ocrelizumab, rituximab; Bradykinin receptor modulators, such as givinostat; Calcineurin inhibitors, such as tacrolimus, ciclosporin; Calcium channel inhibitors, such as clotrimazole; Cannabinoid CB1 receptor modulators, such as GWP42003-P, cannabidiol; Cannabinoid CB2 receptor modulators, such as GWP42003-P, cannabidiol; Cannabinoid receptor antagonists, such as fingolimod; Cannabinoid receptor modulators, such as GWP42003-P, cannabidiol; Cathepsin S inhibitors, such as VBY-129, VBY-036; CCN protein stimulators, such as CSA-13; CCR3 chemokine antagonists, such as bertilimumab; CCR5 chemokine antagonists, such as HGS-1025; CCR9 chemokine antagonists, such as MLN-3126, vercirnon, CCX-025; CD3 modulators, such as visilizumab; CD40 ligand inhibitors, such as FFP-104; CD40 ligand receptor antagonists, such as FFP-104, FFP-102, toralizumab; CD49b antagonists, such as vatelizumab; CD49d antagonists, such as ELND-004; CD89 agonists, such as HF-1020; Cell adhesion molecule inhibitors, such as natalizumab, alicaforsen (intravenous), ASP-2002, ISIS-2302; Chemokine CXC ligand inhibitors, such as CXCR1/2 ligands mAb (immunology), Eli Lilly; CHST15 gene inhibitors, such as STNM-01; Collagen modulators, such as adipose-derived stem cell therapy (Celution System), Cytori, DCCT-10; CSF-1 agonists, such as sargramostim, molgramostim follow on biologic with fosfomycin with carbapenem (intraintestinal, Crohn's disease), Reponex; CSF-1 antagonists, such as JNJ-40346527; CXC10 chemokine ligand inhibitors, such as 946414-98-8, BMS-936557; CXCR2 chemokine antagonists, such as elubrixin; Cyclic GMP phosphodiesterase inhibitors, such as CEL-031; Cyclooxygenase 2 inhibitors, such as P-54; Cyclooxygenase inhibitors, such as mesalazine, 4-aminosalicylate sodium, AJG-501, AGI-022; Cyclooxygenase stimulators, such as nicotine polacrilex; Cytochrome P450 3A4 inhibitors, such as KD-018; Cytotoxic T-lymphocyte protein-4 stimulators, such as abatacept; Dihydroceramide delta 4 desaturase inhibitors, such as ABC-294640; Dihydroorotate dehydrogenase inhibitors, such as vidofludimus; DNA polymerase inhibitors, such as valganciclovir; EGFR family tyrosine kinase receptor modulators, such as neuregulin 4 (Crohn's disease/ulcerative colitis/necrotizing enterocolitis), Avexegen Therapeutics/Children's Hospital of Los Angeles; Eosinophil peroxidase inhibitors, such as AWEPOPD-01, AWEPO-003; Eotaxin ligand inhibitors, such as bertilimumab; EP4 prostanoid receptor agonists, such as KAG-308; Epidermal growth factor agonists, such as heparin-EGF-like factor, Scios Nova; Epidermal growth factor ligands, such as Hebervis; Estrogen receptor beta agonists, such as prinaberel; Factor XIII agonists, such as catridecacog; FGF-10 ligands, such as repifermin; FGF2 receptor agonists, such as F2A; Fractalkine ligand inhibitors, such as E-6011; Free fatty acid receptor 2 antagonists, such as GLPG-0974; GATA 3 transcription factor inhibitors, such as SB-012; Glucagon-like peptide 2 agonists, such as teduglutide, ZP-1848, NB-1002; Glucocorticoid agonists, such as budesonide, beclomethasone dipropionate, dexamethasone sodium phosphate, AJG-511, DOR-201, D-9421-C; GM-CSF receptor agonists, such as sargramostim, molgramostim follow on biologic with fosfomycin with carbapenem (intraintestinal, Crohn's disease), Reponex; G-protein coupled receptor 84 antagonists, such as GLPG-1205; Guanylate cyclase receptor agonists, such as dolcanatide, SP-333; Histamine H2 receptor antagonists, such as bismuth, Medeva; Histone acetyltransferase inhibitors, such as TIP60 inhibitors (ulcerative colitis/inflammatory bowel disease/autoimmune diseases), University of Pennsylvania; Histone deacetylase inhibitors, such as givinostat; HLA class II antigen modulators, such as HLA class II protein modulators (Crohns disease), Nextera AS; Hydrolase inhibitors, such as SC-56938; ICAM1 gene inhibitors, such as alicaforsen; ICAM-1 inhibitors, such as alicaforsen (intravenous), ISIS-2302; IL1 gene inhibitors, such as PLR-14; IL-10 agonists, such as peg-ilodecakin, AM-0010; IL10 gene stimulators, such as gene therapy (IL-10), Imperial College; IL-11 agonists, such as oprelvekin, YM-294; IL-12 antagonists, such as ustekinumab, briakinumab, apilimod; IL12 gene inhibitors, such as RDP-58; IL-13 antagonists, such as tralokinumab, anrukinzumab; IL-17 antagonists, such as secukinumab, vidofludimus; IL-2 antagonists, such as daclizumab; IL-2 receptor alpha subunit inhibitors, such as basiliximab, daclizumab, BSX-003, Ro-34-7375; IL-21 antagonists, such as NN-8828, ATR-107; IL-23 antagonists, such as tildrakizumab, ustekinumab, BI-655066, AMG-139, briakinumab, LY-3074828, apilimod; IL-6 antagonists, such as tocilizumab, clazakizumab, olokizumab, HMPL-004, AMG-220, FM-101; IL6 gene inhibitors, such as YSIL6-T-PS; IL-6 receptor modulators, such as tocilizumab; IL-7 antagonists, such as interleukin-7 receptor modulators (ulcerative colitis/T-cell acute lymphoblastic leukaemia), Effimune; IL-8 antagonists, such as elubrixin, clotrimazole; Immunoglobulin G1 agonists, such as HF-1020; Immunoglobulin G2 modulators, such as PF-547659; Inosine monophosphate dehydrogenase inhibitors, such as mycophenolate mofetil; Insulin sensitizers, such as elafibranor, rosiglitazone, HE-3286, EGS-21; Integrin alpha-4/beta-1 antagonists, such as natalizumab, TRK-170, firategrast; Integrin alpha-4/beta-7 antagonists, such as etrolizumab, vedolizumab, abrilumab, carotegast methyl, TRK-170, firategrast; Integrin alpha-E antagonists, such as etrolizumab; Integrin antagonists, such as vatelizumab, ASP-2002; Integrin beta-7 antagonists, such as etrolizumab; Interferon beta ligands, such as interferon beta-1a, recombinant interferon beta-1a, Serono; Interleukin 17E ligand inhibitors, such as anti-IL-17BR humanized antibody (lung fibrosis/asthma/ulcerative colitis), Medical Research Council Technology; Interleukin ligand inhibitors, such as HE-3286; Interleukin receptor 17A antagonists, such as brodalumab; Interleukin receptor 17B antagonists, such as anti-IL-17BR humanized antibody (lung fibrosis/asthma/ulcerative colitis), Medical Research Council Technology; Interleukin-1 beta ligands, such as K(D)PT, PUR-0110, HMPL-004; Interleukin-1 beta ligand modulators, such as PUR-0110, HMPL-004; Interleukin-6 ligand inhibitors, such as PF-4236921; JAK tyrosine kinase inhibitors, such as tofacitinib, peficitinib; Jak1 tyrosine kinase inhibitors, such as ABT-494, tofacitinib, filgotinib, peficitinib, GLPG-0555, solcitinib; JAK2 gene inhibitors, such as vidofludimus; Jak3 tyrosine kinase inhibitors, such as tofacitinib, peficitinib; Jun N terminal kinase inhibitors, such as semapimod; LanC like protein 2 modulators, such as BT-11; Leukotriene BLT receptor antagonists, such as ONO-4057, etalocib, SC-53228, SC-52798; Lipoxygenase modulators, such as mesalazine; L-Selectin antagonists, such as BNP-001; MAdCAM inhibitors, such as vedolizumab, PF-547659; Matrix metalloprotease inhibitors, such as D-5410; Matrix metalloprotease modulators, such as D-5410; Melanocortin agonists, such as ASP-3291; Membrane copper amine oxidase inhibitors, such as vepalimomab; Metalloprotease-2 inhibitors, such as KD-018, RWJ-68354; Metalloprotease-9 inhibitors, such as GS-5745; MIP 3 alpha ligand inhibitors, such as GSK-3050002; Mitochondrial 10 kDa heat shock protein stimulators, such as INV-103; Monocyte differentiation antigen CD14 inhibitors, such as CD14 anti-inflammatory, Cornell; mTOR inhibitors, such as P-2281; Mucin stimulators, such as rebamipide; NAD-dependent deacetylase sirtuin-1 stimulators, such as SRT-2104; Natriuretic peptide receptor C agonists, such as plecanatide; Neuregulin-4 ligands, such as neuregulin 4 (Crohn's disease/ulcerative colitis/necrotizing enterocolitis), Avexegen Therapeutics/Children's Hospital of Los Angeles; Nicotinic acetylcholine receptor agonists, such as TC-2403, nicotine polacrilex, nicotine; Nicotinic ACh receptor alpha 4 subunit modulators, such as TC-2403; Nicotinic ACh receptor alpha 7 subunit stimulators, such as GTS-21; Nicotinic ACh receptor beta 2 subunit modulators, such as TC-2403; NK1 receptor antagonists, such as KD-018, nolpitantium besilate; NKG2 D activating NK receptor antagonists, such as NNC-0142-002; Nuclear factor kappa B inhibitors, such as KD-018, cobitolimod, CSA-13, HE-3286, HMPL-004, Avrina, mesalamine with N-acetylcysteine, P-54; Opioid growth factor receptor agonists, such as metenkefalin acetate with tridecactide acetate, FAR-404; Opioid receptor antagonists, such as naltrexone, IRT-103; Opioid receptor delta antagonists, such as KD-018; Oxidoreductase inhibitors, such as olsalazine; P2X7 purinoceptor agonists, such as givinostat; p38 MAP kinase inhibitors, such as RDP-58, doramapimod, semapimod, RWJ-68354; PARP inhibitors, such as EB-47, INO-1003; PDE 4 inhibitors, such as apremilast, tetomilast, CC-1088; PDGF receptor agonists, such as oprelvekin, YM-294; Phagocytosis stimulating peptide modulators, such as 99mTc-RP-128; Phospho MurNAc pentapeptide transferase inhibitors, such as SQ-641; Phospholipase A2 inhibitors, such as varespladib methyl; Platelet activating factor receptor antagonists, such as dersalazine sodium; Potassium channel inhibitors, such as clotrimazole; PPAR alpha agonists, such as elafibranor (GFT-1007); PPAR delta agonists, such as elafibranor (GFT-1007); PPAR gamma agonists, such as rosiglitazone, GED-0507-34-Levo, etalocib; Protein CYR61 stimulators, such as CSA-13; Protein fimH inhibitors, such as EB-8018; Protein kinase C alpha inhibitors, such as sotrastaurin (AEB-071); Protein kinase C beta inhibitors, such as sotrastaurin (AEB-071); Protein kinase C delta inhibitors, such as sotrastaurin (AEB-071); Protein kinase C epsilon inhibitors, such as sotrastaurin (AEB-071); Protein kinase C eta inhibitors, such as sotrastaurin (AEB-071); Protein kinase C theta inhibitors, such as sotrastaurin (AEB-071); Protein kinase G inhibitors, such as CEL-031; Protein kinase inhibitors, such as TOP-1288; P-selectin glycoprotein ligand-1 inhibitors, such as SEL-K2; PurH purine biosynthesis protein inhibitors, such as mycophenolate mofetil; Retinoic acid receptor alpha agonists, such as tamibarotene; Retinoic acid receptor beta agonists, such as tamibarotene; Retinoid receptor agonists, such as tamibarotene; RNA polymerase inhibitors, such as rifaximin; SMAD-7 inhibitors, such as mongersen (GED-0301); Sodium channel inhibitors, such as ropivacaine; Somatostatin receptor agonists, such as vapreotide; Sphingosine 1 phosphate phosphatase 1 stimulators, such as APD-334; Sphingosine 1 phosphate phosphatase modulators, such as S1P modulators (oral, multiple sclerosis/ulcerative colitis/rheumatoid arthritis), Akaal Pharma; Sphingosine kinase 1 inhibitors, such as ABC-294640; Sphingosine kinase 2 inhibitors, such as ABC-294640; Sphingosine-1-phosphate receptor-1 agonists, such as ozanimod (RPC-1063), KRP-203; Sphingosine-1-phosphate receptor-1 antagonists, such as amiselimod (MT-1303); Sphingosine-1-phosphate receptor-1 modulators, such as fingolimod (FTY-720), ozanimod (RPC-1063), amiselimod (MT-1303); Sphingosine-1-phosphate receptor-5 modulators, such as ozanimod; STAT3 gene inhibitors, such as vidofludimus; STAT-3 inhibitors, such as TAK-114; STAT-4 inhibitors, such as STAT-4 antisense oligonucleotide (Crohns disease/colitis), NIAID; Stem cell antigen-1 inhibitors, such as Ampion, DMI-9523; Superoxide dismutase modulators, such as midismase, LT-0011; Superoxide dismutase stimulators, such as superoxide dismutase; T cell surface glycoprotein CD28 inhibitors, such as abatacept; TGF beta 1 ligand inhibitors, such as mongersen, GED-0301; Thymulin agonists, such as Syn-1002; TLR-2 antagonists, such as VB-201; TLR-4 antagonists, such as JKB-122, VB-201; TLR-9 agonists, such as BL-7040, cobitolimod; TNF alpha ligand inhibitors, such as adalimumab, certolizumab pegol, infliximab biosimilar, infliximab, golimumab, ISIS-104838, CSA-13, DLX-105, adalimumab biosimilar, dersalazine sodium, Debio-0512, HMPL-004, DLX-105, infliximab follow-on biologic, AZD-9773, CYT-020-TNFQb, DOM-0200; TNF alpha ligand modulators, such as PUR-0110, CDP-571; TNF antagonists, such as etanercept, certolizumab pegol, AVX-470, onercept; Trefoil factor modulators, such as AG-012; Tryptase inhibitors, such as APC-2059; Tryptophan 5-hydroxylase inhibitors, such as telotristat etiprate; Tumor necrosis factor 14 ligand modulators, such as SAR-252067; Type I TNF receptor antagonists, such as DOM-0100; Type II TNF receptor modulators, such as etanercept; Unspecified growth factor receptor modulators, such as AP-005; Vanilloid VR1 agonists, such as zucapsaicin; Vitamin D3 receptor agonists, such as calcitriol; and Zonulin inhibitors, such as larazotide acetate, AT-1001.

Also, the following non-exhaustive list of classes of compounds and compounds may be combined with a compound of the present disclosure: 14-3-3 protein eta inhibitors, 5-Lipoxygenase inhibitors, Abl tyrosine kinase inhibitors, ACTH receptor agonists, Adenosine A3 receptor agonists, Adenosine deaminase inhibitors, ADP ribosyl cyclase-1 modulators, ADP ribosylation factor 6 inhibitors, Adrenocorticotrophic hormone ligands, Aggrecanase-2 inhibitors, Albumin modulators, AP1 transcription factor inhibitors, Basigin inhibitors, Bcr protein inhibitors, B-lymphocyte antigen CD19 inhibitors, B-lymphocyte antigen CD20 inhibitors, B-lymphocyte antigen CD20 modulators, B-lymphocyte stimulator ligand inhibitors, Bradykinin receptor modulators, BRAF gene inhibitors, Branched amino acid aminotransferase 1 inhibitors, Bromodomain containing protein inhibitors, Btk tyrosine kinase inhibitors, Cadherin-11 antagonists, Calcineurin inhibitors, Calcium channel inhibitors, Carbonic anhydrase inhibitors, Cathepsin K inhibitors, Cathepsin S inhibitors, CCR1 chemokine antagonists, CCR2 chemokine antagonists, CCR3 gene modulators, CCR5 chemokine antagonists, CD126 antagonists, CD29 modulators, CD3 modulators, CD39 agonists, CD4 agonists, CD4 antagonists, CD40 ligand inhibitors, CD40 ligand receptor antagonists, CD40 ligand receptor modulators, CD52 antagonists, CD73 agonists, CD79b modulators, CD80 antagonists, CD86 antagonists, CD95 antagonists, Cell adhesion molecule inhibitors, Choline kinase inhibitors, Clusterin stimulators, Complement C5 factor inhibitors, Complement Factor stimulators, C-reactive protein inhibitors, CSF-1 antagonists, CXC10 chemokine ligand inhibitors, CXCR4 chemokine antagonists, Cyclin-dependent kinase inhibitor 1 inhibitors, Cyclin-dependent kinase-2 inhibitors, Cyclin-dependent kinase-4 inhibitors, Cyclin-dependent kinase-5 inhibitors, Cyclin-dependent kinase-6 inhibitors, Cyclin-dependent kinase-7 inhibitors, Cyclin-dependent kinase-9 inhibitors, Cyclooxygenase 2 inhibitors, Cyclooxygenase 2 modulators, Cyclooxygenase inhibitors, Cytosolic phospholipase A2 inhibitors, Cytotoxic T-lymphocyte protein-4 modulators, Cytotoxic T-lymphocyte protein-4 stimulators, DHFR inhibitors, Diamine acetyltransferase inhibitors, Dihydroorotate dehydrogenase inhibitors, Elongation factor 2 inhibitors, Eotaxin 2 ligand inhibitors, EP4 prostanoid receptor antagonists, Erythropoietin receptor agonists, Fas ligands, FGF-2 ligand inhibitors, FK506 binding protein-12 modulators, Folate antagonists, Folate receptor agonists, Folate receptor beta antagonists, Folate receptor modulators, Fractalkine ligand inhibitors, Fyn tyrosine kinase inhibitors, G protein coupled receptor 15 antagonists, GABA A receptor modulators, Glucocorticoid agonists, Glucocorticoid antagonists, Glucocorticoid induced leucine zipper stimulators, GM-CSF ligand inhibitors, GM-CSF receptor antagonists, GM-CSF receptor modulators, Growth regulated protein alpha ligand inhibitors, Hwith Kwith ATPase inhibitors, Histamine H4 receptor antagonists, Histone deacetylase inhibitors, Histone deacetylase-6 inhibitors, HIV-1 gp120 protein inhibitors, HLA class II antigen DQ-2 alpha modulators, HLA class II antigen inhibitors, HLA class II antigen modulators, Hsp 70 family inhibitors, Hypoxia inducible factor-1 inhibitors, IFNB gene stimulators, I-kappa B kinase beta inhibitors, I-kappa B kinase inhibitors, IL-1 antagonists, IL-10 agonists, IL-11 agonists, IL-12 antagonists, IL-15 antagonists, IL-17 antagonists, IL-17 receptor modulators, IL-2 agonists, IL-2 antagonists, IL-21 antagonists, IL-23 antagonists, IL-3 antagonists, IL-4 agonists, IL-6 antagonists, IL-6 receptor modulators, Immunoglobulin antagonists, Immunoglobulin G1 agonists, Immunoglobulin G1 antagonists, Immunoglobulin G1 modulators, Immunoglobulin G2 antagonists, Immunoglobulin G2 modulators, Immunoglobulin gamma Fc receptor II modulators, Immunoglobulin gamma Fc receptor IIB antagonists, Immunoglobulin kappa modulators, Immunoglobulin M antagonists, Inducible nitric oxide synthase inhibitors, Inosine monophosphate dehydrogenase inhibitors, Insulin sensitizers, Integrin alpha-1/beta-1 antagonists, Integrin alpha-4/beta-1 antagonists, Integrin antagonists, Interferon beta ligands, Interferon gamma ligands, Interleukin 17A ligand inhibitors, Interleukin 17F ligand inhibitors, Interleukin 23A inhibitors, Interleukin ligands, Interleukin receptor 17A antagonists, Interleukin-1 beta ligand inhibitors, Interleukin-10 ligands, Interleukin-2 ligands, Interleukin-4 ligands, Interleukin-6 ligand inhibitors, Itk tyrosine kinase inhibitors, JAK tyrosine kinase inhibitors, Jak1 tyrosine kinase inhibitors, Jak2 tyrosine kinase inhibitors, JAK3 gene inhibitors, Jak3 tyrosine kinase inhibitors, Jun N terminal kinase inhibitors, KCNA voltage-gated potassium channel-4 modulators, Kelch like ECH associated protein 1 modulators, Kit tyrosine kinase inhibitors, LanC like protein 2 modulators, LITAF gene inhibitors, Lymphocyte function antigen-3 receptor antagonists, Lyn tyrosine kinase inhibitors, Macrophage mannose receptor 1 modulators, MAdCAM inhibitors, MAP kinase modulators, MAP3K2 gene inhibitors, MAPKAPK5 inhibitors, Matrix metalloprotease inhibitors, MCL1 gene inhibitors, MEK protein kinase inhibitors, MEK-1 protein kinase inhibitors, MEK-2 protein kinase inhibitors, Membrane copper amine oxidase inhibitors, Metalloprotease-2 inhibitors, Metalloprotease-9 inhibitors, Midkine ligand inhibitors, Mitochondrial 10 kDa heat shock protein stimulators, mTOR complex 1 inhibitors, mTOR inhibitors, NAD ADP ribosyltransferase stimulators, NAMPT gene inhibitors, NF kappa B inhibitor stimulators, NFAT gene inhibitors, NFE2L2 gene stimulators, Nicotinic acetylcholine receptor antagonists, NK cell receptor modulators, NKG2 A B activating NK receptor antagonists, NKG2 D activating NK receptor antagonists, Nuclear erythroid 2-related factor 2 stimulators, Nuclear factor kappa B inhibitors, Nuclear factor kappa B modulators, Nuclear factor kappa B p105 inhibitors, Opioid growth factor receptor agonists, Opioid receptor delta antagonists, Osteoclast differentiation factor antagonists, Osteoclast differentiation factor ligand inhibitors, Oxidoreductase inhibitors, P2X7 purinoceptor agonists, p38 MAP kinase alpha inhibitors, p38 MAP kinase inhibitors, PDE 4 inhibitors, PDE 5 inhibitors, PDGF receptor agonists, PDGF receptor antagonists, PDGF-B ligand inhibitors, PERK gene inhibitors, Phosphoinositide-3 kinase delta inhibitors, Phosphoinositide-3 kinase gamma inhibitors, Phospholipase A2 inhibitors, Platelet activating factor receptor antagonists, PPAR gamma agonists, Programmed cell death protein 1 modulators, Prostaglandin D synthase stimulators, Protein arginine deiminase inhibitors, Protein tyrosine kinase inhibitors, PurH purine biosynthesis protein inhibitors, Rho associated protein kinase 2 inhibitors, Seprase inhibitors, Signal transducer CD24 modulators, Signal transduction inhibitors, Sodium glucose transporter-2 inhibitors, Sphingosine 1 phosphate phosphatase modulators, STAT3 gene inhibitors, Superoxide dismutase stimulators, SYK family tyrosine kinase inhibitors, Syk tyrosine kinase inhibitors, Syndecan-1 inhibitors, T cell receptor antagonists, T cell receptor modulators, T cell surface glycoprotein CD28 inhibitors, T cell surface glycoprotein CD28 stimulators, TAK1 binding protein modulators, Talin modulators, T-cell differentiation antigen CD6 inhibitors, T-cell surface glycoprotein CD8 inhibitors, Tenascin modulators, TGF beta agonists, Thymulin agonists, TLR-2 antagonists, TLR-4 antagonists, TLR-9 antagonists, TNF alpha ligand inhibitors, TNF alpha ligand modulators, TNF antagonists, TNF gene inhibitors, TNF receptor modulators, TNFSF11 gene inhibitors, Transcription factor p65 inhibitors, Transcription factor RelB inhibitors, Transferrin modulators, Tumor necrosis factor 13C receptor antagonists, Tumor necrosis factor 15 ligand inhibitors, Tumor necrosis factor ligand 13 inhibitors, Tumor necrosis factor ligand inhibitors, Type I IL-1 receptor antagonists, Type I TNF receptor antagonists, Type II TNF receptor modulators, Unspecified GPCR agonists, VEGF receptor antagonists, VEGF-2 receptor antagonists, VEGF-2 receptor modulators, VEGF-B ligand inhibitors, X-linked inhibitor of apoptosis protein inhibitors, Zap70 tyrosine kinase inhibitors, 99mTc labelled annexin V-128, abatacept, abatacept biosimilar, ABBV-257, ABT-122, ABT-494, acalabrutinib, aceclofenac, actarit, MS-392, adalimumab, adalimumab biosimilar, adalimumab follow-on biologic, AK-106, ALX-0061, aminopterin, anakinra, anakinra biosimilar, anakinra follow-on biologic, ARG-301, ASLAN-003, ASP-5094, AT-132, AZD-9567, baricitinib, BI-655064, bimekizumab, BiP (rheumatoid arthritis), Kings College London, BLHP-006, blisibimod, BMS-986104, BMS-986142, ABBV-105, BTT-1023, canakinumab, Cartistem, CCX-354, CD24-IgFc, celecoxib, cerdulatinib, certolizumab pegol, CF-101, CFZ-533, CHR-5154, cibinetide, ciclosporin, clazakizumab, CNTO-6785, corticotropin, Mallinckrodt, CR-6086, CreaVax-RA, CWG-92, CWG-940, Cx-611, DE-098, deflazacort, Rheumavax, denosumab, diacerein, diclofenac, E-6011, eicosapentaenoic acid monoglycerides, etanercept, etanercept biosimilar, etanercept follow-on biologic, etodolac, etoricoxib, filgotinib, fosdagrocorat, gerilimzumab, ginsenoside C-K, givinostat, goat polyclonal antibodies, golimumab, GS-5745, GS-9876, GSK-3196165, HM-71224, HMPL-523, hyaluronate sodium, IB-RA (injectable, rheumatoid arthritis), Innobioscience, IB-RA (oral, rheumatoid arthritis), Innobioscience, iguratimod, IMD-2560, imidazole salicylate, infliximab, infliximab biobetter, infliximab biosimilar, INSIX RA, interferon gamma follow-on biologic, interleukin-2 (injectable), interleukin-2 follow-on biologic, INV-103, IR-501, itolizumab, JNJ-40346527, Ka Shu Ning, KD-025, ketoprofen with omeprazole, leflunomide, lenzilumab, LLDT-8, lumiracoxib, LY-3090106, masitinib, mavrilimumab, MBS-2320, MEDI-5117, meloxicam, methotrexate, MGD-010, misoprostol with diclofenac, MM-A01-01, monalizumab, MORAb-022, MPC-300-IV, MRC-375, nabumetone, namilumab, naproxen with esomeprazole, naproxen with esomeprazole strontium, ocaratuzumab, ofatumumab, OHR-118, olokizumab, OM-89, once-daily naproxen (oral controlled release, pain), Alvogen, ONO-4059, Oralgam, ozoralizumab, peficitinib, pelubiprofen, PF-06687234, piperidone hydrochloridum, piroxicam, prednisolone, prednisone, Prosorba, PRT-2607, PRTX-100, PRX-167700, QBSAU, rabeximod, RCT-18, recombinant human CD22 monoclonal antibody (iv infusion), Lonn Ryonn Pharma/SinoMab Bioscience (Shenzhen), recombinant human interleukin-1 receptor antagonist (rheumatoid arthritis), Shanghai Fudan-Zhangjiang Bio-Pharmaceutical, recombinant human interleukin-2 recombinant TNF receptor 2-Fc fusion protein mutant, RG-6125, RhuDex, rifabutin with clarithromycin with clofazimine, rituximab, rituximab biosimilar, rituximab follow-on biologic, RPI-78, SAN-300, sarilumab, SBI-087, seliciclib, SHR-0302, sirukumab, spebrutinib, SSS-07, KDDF-201110-06, Syn-1002, T-5224, TAB-08, tacrolimus, TAK-020, TAK-079, tarenflurbil (transdermal spraygel, skin disease/rheumatoid arthritis), MIKA Pharma/GALENpharma, technetium Tc 99m tilmanocept, technetium[99Tc] methylenediphosphonate, tenoxicam, Debio-0512, tocilizumab, tofacitinib, Trichuris suis ova, umbilical cord-derived mesenchymal stem cells (iv, RA/liver disease), Alliancells/Zhongyuan Union, ustekinumab, VAY-736, VB-201, WF-10, XmAb-5871, YHB-1411-2; 14-3-3 protein eta inhibitors, such as anti-AGX-020 mAbs (rheumatoid arthritis), Augurex; 5-Lipoxygenase inhibitors, such as tenoxicam, darbufelone, tebufelone, licofelone, ZD-2138, etalocib, tenidap, tepoxalin, flobufen, SKF-86002, PGV-20229, L-708780, WY-28342, T-0757, T-0799, ZM-216800, L-699333, BU-4601A, SKF-104351, CI-986; Abl tyrosine kinase inhibitors, such as imatinib; ACTH receptor agonists, such as FAR-404, metenkefalin acetate with tridecactide acetate; Adenosine A3 receptor agonists, such as CF-101; Adenosine deaminase inhibitors, such as cladribine, pentostatin, FR-221647; ADP ribosyl cyclase-1 modulators, such as indatuximab ravtansine; ADP ribosylation factor 6 inhibitors, such as NAV-2729; Adrenocorticotrophic hormone ligands, such as corticotropin, Mallinckrodt, FAR-404, metenkefalin acetate with tridecactide acetate; Aggrecanase-2 inhibitors, such as GIBH-R-001-2; Albumin modulators, such as ALX-0061, ONS-1210; AP1 transcription factor inhibitors, such as T-5224, tarenflurbil, SP-10030; Basigin inhibitors, such as ERG-240; Bcr protein inhibitors, such as imatinib; B-lymphocyte antigen CD19 inhibitors, such as XmAb-5871, MDX-1342; B-lymphocyte antigen CD20 inhibitors, such as ocrelizumab, ofatumumab, rituximab, rituximab biosimilar, veltuzumab, rituximab follow-on biologic, ocaratuzumab, BLX-301, IDEC-102, ABP-798, GP-2013, MK-8808, HLX-01, CT-P10, TL-011, PF-05280586, IBPM-001RX, IBI-301, AME-133v, BCD-020, BT-D004, SAIT-101; B-lymphocyte antigen CD20 modulators, such as rituximab biosimilar, SBI-087, TRU-015, DXL-625; B-lymphocyte stimulator ligand inhibitors, such as belimumab, RCT-18, blisibimod, tahalumab, atacicept, briobacept; Bradykinin receptor modulators, such as givinostat; BRAF gene inhibitors, such as binimetinib; Branched amino acid aminotransferase 1 inhibitors, such as ERG-240; Bromodomain containing protein inhibitors, such as RVX-297, ZEN-003694; Btk tyrosine kinase inhibitors, such as acalabrutinib, HM-71224, spebrutinib, BTK inhibitor (rheumatoid arthritis), Humanwell Healthcare/Wuxi AppTech, BMS-986142, TAK-020, ONO-4059, TAS-5315, ABBV-105, AC-0025, RN-486, CG-026806, GDC-0834; Cadherin-11 antagonists, such as RG-6125; Calcineurin inhibitors, such as HS-378, ciclosporin; Calcium channel inhibitors, such as RP-3128; Carbonic anhydrase inhibitors, such as polmacoxib; Cathepsin K inhibitors, such as CRA-013783, T-5224, AM-3876, VEL-0230, NPI-2019; Cathepsin S inhibitors, such as MIV-247, AM-3876, RWJ-445380, NPI-2019; CCR1 chemokine antagonists, such as BX-471, BMS-817399, BI-638683, CCX-354, MLN-3701, MLN-3897, CP-481715, PS-375179; CCR2 chemokine antagonists, such as MK-0812, AZD-6942; CCR3 gene modulators, such as CM-102; CCR5 chemokine antagonists, such as maraviroc, OHR-118, NIBR-6465, AZD-5672, AZD-8566; CD126 antagonists, such as sarilumab; CD29 modulators, such as PF-06687234; CD3 modulators, such as otelixizumab; CD39 agonists, such as AAV5-CD39/CD73 (rheumatoid arthritis), Arthrogen; CD4 agonists, such as maraviroc; CD4 antagonists, such as tregalizumab, zanolimumab, MTRX-1011A, BW-4162W94, EP-1645, clenoliximab; CD40 ligand inhibitors, such as dapirolizumab pegol; CD40 ligand receptor antagonists, such as BI-655064, anti-CD40-XTEN, teneliximab; CD40 ligand receptor modulators, such as CFZ-533; CD52 antagonists, such as alemtuzumab; CD73 agonists, such as AAV5-CD39/CD73 (rheumatoid arthritis), Arthrogen; CD79b modulators, such as MGD-010; CD80 antagonists, such as RhuDex, XENP-9523, ASP-2408, abatacept biobetter; CD86 antagonists, such as ES-210, abatacept biosuperior, ASP-2408, XENP-9523; CD95 antagonists, such as DE-098, CS-9507; Cell adhesion molecule inhibitors, such as natalizumab, alicaforsen, NPC-17923, TK-280, PD-144795; Choline kinase inhibitors, such as choline kinase inhibitors (rheumatoid arthritis), UC San Diego; Clusterin stimulators, such as alemtuzumab; Complement C5 factor inhibitors, such as eculizumab, antisense oligonucleotides (rheumatoid arthritis), Leiden University Medical Center; Complement Factor stimulators, such as CM-101; C-reactive protein inhibitors, such as IB-RA (oral, rheumatoid arthritis), Innobioscience, ISIS-353512; CSF-1 antagonists, such as masitinib, FPA-008, JNJ-27301937, JNJ-40346527, PLX-5622, CT-1578, PD-360324, JNJ-28312141; CXC10 chemokine ligand inhibitors, such as 946414-98-8, BMS-936557; CXCR4 chemokine antagonists, such as plerixafor; Cyclin-dependent kinase inhibitor 1 inhibitors, such as CDK-1/2/5/7/9 inhibitors (cancer/tumorogenesis/rheumatoid arthritis), BioPatterns; Cyclin-dependent kinase-2 inhibitors, such as seliciclib, BP-14; Cyclin-dependent kinase-4 inhibitors, such as CDK-4/6 inhibitor (rheumatoid arthritis), Teijin; Cyclin-dependent kinase-5 inhibitors, such as BP-14; Cyclin-dependent kinase-6 inhibitors, such as CDK-4/6 inhibitor (rheumatoid arthritis), Teijin; Cyclin-dependent kinase-7 inhibitors, such as BP-14, seliciclib; Cyclin-dependent kinase-9 inhibitors, such as BP-14, seliciclib; Cyclooxygenase 2 inhibitors, such as celecoxib, etoricoxib, polmacoxib, laflunimus, etodolac, meloxicam, IB-RA (injectable, rheumatoid arthritis), Innobioscience, IB-RA (oral, rheumatoid arthritis), Innobioscience, SKLB-023, meloxicam, lumiracoxib; Cyclooxygenase 2 modulators, such as DRGT-46; Cyclooxygenase inhibitors, such as aceclofenac, diclofenac, imidazole salicylate, naproxcinod, naproxen etemesil, misoprostol with diclofenac, nabumetone, naproxen with esomeprazole, naproxen with esomeprazole strontium, once-daily naproxen (oral controlled release, pain), Alvogen, pelubiprofen, LY-210073, tenoxicam, licofelone, NS-398, bromfenac, L-746483, LY-255283, tenidap, tepoxalin, flobufen, ibuprofen, flurbiprofen, SKF-86002, SC-57666, WY-28342, CI-986, bermoprofen; Cytosolic phospholipase A2 inhibitors, such as AVX-002; Cytotoxic T-lymphocyte protein-4 modulators, such as belatacept, ES-210; Cytotoxic T-lymphocyte protein-4 stimulators, such as abatacept, abatacept biosimilar, BMS-188667; DHFR inhibitors, such as methotrexate, MPI-2505, MBP-Y003; Diamine acetyltransferase inhibitors, such as diminazene aceturate; Dihydroorotate dehydrogenase inhibitors, such as DHODH inhibitors (rheumatoid arthritis/autoimmune diseases), East China University of Science and Technology, ASLAN-003, laflunimus, leflunomide, HWA-486, ABR-224050; Elongation factor 2 inhibitors, such as denileukin diftitox; Eotaxin 2 ligand inhibitors, such as CM-102; EP4 prostanoid receptor antagonists, such as CR-6086; Erythropoietin receptor agonists, such as cibinetide; Fas ligands, such as AP-300; FGF-2 ligand inhibitors, such as RBM-007; FK506 binding protein-12 modulators, such as temsirolimus; Folate antagonists, such as methotrexate, MBP-Y003; Folate receptor agonists, such as folate receptor modulators (chimeric protein, cancer/rheumatoid arthritis), Proda Biotech; Folate receptor modulators, such as technetium (99mTc) etarfolatide; Fractalkine ligand inhibitors, such as E-6011; Fyn tyrosine kinase inhibitors, such as masitinib, laflunimus; G protein coupled receptor 15 antagonists, such as GPR15 antagonists (rheumatoid arthritis/HIV-mediated enteropathy), Omeros; GABA A receptor modulators, such as laflunimus; Glucocorticoid agonists, such as prednisolone, fosdagrocorat; Glucocorticoid antagonists, such as REC-200; Glucocorticoid induced leucine zipper stimulators, such as ART-G01; GM-CSF ligand inhibitors, such as namilumab, MORAb-022, lenzilumab; GM-CSF receptor antagonists, such as mavrilimumab; GM-CSF receptor modulators, such as GSK-3196165; Growth regulated protein alpha ligand inhibitors, such as T-5224; Hwith Kwith ATPase inhibitors, such as naproxen with esomeprazole, naproxen with esomeprazole strontium, ketoprofen with omeprazole, KEO-25001, HC-1004, PN-40020; Histamine H4 receptor antagonists, such as toreforant, GD-48; Histone deacetylase inhibitors, such as givinostat, CHR-5154; Histone deacetylase-6 inhibitors, such as CKD-506; HIV-1 gp120 protein inhibitors, such as maraviroc; HLA class II antigen DQ-2 alpha modulators, such as NexVax2; HLA class II antigen inhibitors, such as HLA-DR1/DR4 inhibitors (rheumatoid arthritis), Provid; HLA class II antigen modulators, such as ARG-301, recombinant T-cell receptor ligand (rheumatoid arthritis), Artielle; Hsp 70 family inhibitors, such as gusperimus trihydrochloride; Hypoxia inducible factor-1 inhibitors, such as 2-methoxyestradiol; IFNB gene stimulators, such as ART-102; I-kappa B kinase beta inhibitors, such as IMD-2560, IMD-0560; I-kappa B kinase inhibitors, such as bardoxolone methyl; IL-1 antagonists, such as rilonacept, IBPB-007-IL, antisense oligonucleotides (rheumatoid arthritis), Leiden University Medical Center, recombinant human interleukin-1 receptor antagonist (rheumatoid arthritis), Shanghai Fudan-Zhangjiang Bio-Pharmaceutical; IL-10 agonists, such as peg-ilodecakin; IL-11 agonists, such as oprelvekin; IL-12 antagonists, such as ustekinumab, briakinumab, ddRNAi therapy (rheumatoid arthritis), Medistem/Benitec; IL-15 antagonists, such as AMG-714, BNZ-132-2; IL-17 antagonists, such as ixekizumab, secukinumab, KD-025; IL-17 receptor modulators, such as CNTO-6785; IL-2 agonists, such as interleukin-2 follow-on biologic; IL-2 antagonists, such as IB-RA (injectable, rheumatoid arthritis), Innobioscience, IB-RA (oral, rheumatoid arthritis), Innobioscience, BNZ-132-2; IL-21 antagonists, such as NN-8828, BNZ-132-2; IL-23 antagonists, such as ustekinumab, briakinumab; IL-3 antagonists, such as anti-IL-3 mAbs (rheumatoid arthritis), University of Regensburg; IL-4 agonists, such as SER-130-AMI; IL-6 antagonists, such as olokizumab, clazakizumab, sirukumab, SA-237, tocilizumab, ALX-0061, FB-704A, OP-R003, peptide IL-6 antagonist, MEDI-5117, T-5224, humanized anti-IL-6 mAb, tocilizumab biosimilar, IL-6 neutralizing human antibodies, anti-IL6 antibody, RN-486, BLX-1002, AMG-220, FM-101, K-832, BLX-1025, esonarimod, TA-383; IL-6 receptor modulators, such as tocilizumab, tocilizumab biosimilar, RO-4877533; Immunoglobulin antagonists, such as iguratimod; Immunoglobulin G1 agonists, such as canakinumab, infliximab biobetter, infliximab biosimilar, BX-2922, STI-002, HF-1020; Immunoglobulin G1 antagonists, such as YHB-1411-2; Immunoglobulin G1 modulators, such as CFZ-533, lenzilumab; Immunoglobulin G2 antagonists, such as denosumab; Immunoglobulin G2 modulators, such as PF-547659; Immunoglobulin gamma Fc receptor II modulators, such as MGD-010; Immunoglobulin gamma Fc receptor IIB antagonists, such as XmAb-5871; Immunoglobulin kappa modulators, such as lenzilumab; Immunoglobulin M antagonists, such as IB-RA (injectable, rheumatoid arthritis), Innobioscience, IB-RA (oral, rheumatoid arthritis), Innobioscience; Inducible nitric oxide synthase inhibitors, such as SKLB-023; Inosine monophosphate dehydrogenase inhibitors, such as mycophenolate mofetil; Insulin sensitizers, such as rosiglitazone, THR-0921, HE-3286, BLX-1002; Integrin alpha-1/beta-1 antagonists, such as SAN-300; Integrin alpha-4/beta-1 antagonists, such as natalizumab; Integrin antagonists, such as PEG-HM-3, CY-9652; Interferon beta ligands, such as recombinant interferon beta-1a, TA-383; Interferon gamma ligands, such as interferon gamma follow-on biologic; Interleukin 17A ligand inhibitors, such as ABT-122, bimekizumab, ABBV-257; Interleukin 17F ligand inhibitors, such as bimekizumab; Interleukin 23A inhibitors, such as guselkumab; Interleukin ligands, such as IBPB-007-IL; Interleukin receptor 17A antagonists, such as brodalumab; Interleukin-1 beta ligand inhibitors, such as canakinumab, rilonacept, T-5224, gevokizumab, BLX-1002, LY-2189102, PMI-001, K-832, CDP-484; Interleukin-10 ligands, such as PF-06687234; Interleukin-2 ligands, such as denileukin diftitox, recombinant interleukin-2, interleukin-2 follow-on biologic, recombinant human interleukin-2, interleukin-2 (injectable); Interleukin-4 ligands, such as Tetravil; Interleukin-6 ligand inhibitors, such as gerilimzumab, PF-4236921; Itk tyrosine kinase inhibitors, such as ARN-4079; JAK tyrosine kinase inhibitors, such as tofacitinib, SHR-0302, cerdulatinib, peficitinib, deuterated tofacitinib analog, SD-900, CVXL-0074; Jak1 tyrosine kinase inhibitors, such as ABT-494, baricitinib, ruxolitinib, filgotinib, tofacitinib, itacitinib, peficitinib, NIP-585, CS-944X, YJC-50018, GLPG-0555, MRK-12; Jak2 tyrosine kinase inhibitors, such as baricitinib, ruxolitinib, CT-1578; JAK3 gene inhibitors, such as GBL-5b; Jak3 tyrosine kinase inhibitors, such as decernotinib, tofacitinib, peficitinib, AC-0025, CS-944X, DNX-04042, MTF-003, ARN-4079, PS-020613; Jun N terminal kinase inhibitors, such as IQ-1S; KCNA voltage-gated potassium channel-3 modulators, such as MRAD-P1; Kelch like ECH associated protein 1 modulators, such as dimethyl fumarate; Kit tyrosine kinase inhibitors, such as imatinib, masitinib; LanC like protein 2 modulators, such as BT-11; LITAF gene inhibitors, such as GBL-5b; Lymphocyte function antigen-3 receptor antagonists, such as alefacept; Lyn tyrosine kinase inhibitors, such as masitinib; Macrophage mannose receptor 1 modulators, such as technetium Tc 99m tilmanocept; MAdCAM inhibitors, such as PF-547659; MAP kinase modulators, such as SKLB-023; MAP3K2 gene inhibitors, such as GBL-5b; MAPKAPKS inhibitors, such as GLPG-0259; Matrix metalloprotease inhibitors, such as GLPG-0259; MCL1 gene inhibitors, such as seliciclib; MEK protein kinase inhibitors, such as binimetinib, AD-GL0001; MEK-1 protein kinase inhibitors, such as binimetinib; MEK-2 protein kinase inhibitors, such as binimetinib; Membrane copper amine oxidase inhibitors, such as BTT-1023, PRX-167700, vepalimomab; Metalloprotease-2 inhibitors, such as ERG-240; Metalloprotease-9 inhibitors, such as GS-5745, ERG-240; Midkine ligand inhibitors, such as CAB-102; Mitochondrial 10 kDa heat shock protein stimulators, such as INV-103; mTOR complex 1 inhibitors, such as everolimus; mTOR inhibitors, such as everolimus, temsirolimus; NAD ADP ribosyltransferase stimulators, such as denileukin diftitox; NAMPT gene inhibitors, such as ART-D01; NF kappa B inhibitor stimulators, such as denosumab; NFAT gene inhibitors, such as T-5224; NFE2L2 gene stimulators, such as bardoxolone methyl; Nicotinic acetylcholine receptor antagonists, such as RPI-78, RPI-MN; NK cell receptor modulators, such as masitinib; NKG2 A B activating NK receptor antagonists, such as monalizumab; NKG2 D activating NK receptor antagonists, such as NNC-0142-002; Nuclear erythroid 2-related factor 2 stimulators, such as dimethyl fumarate; Nuclear factor kappa B inhibitors, such as bardoxolone methyl, IB-RA (injectable, rheumatoid arthritis), Innobioscience, dehydroxymethylepoxyquinomicin, HE-3286, IMD-0560, MP-42, tarenflurbil, VGX-1027, SKLB-023, SP-650003, MG-132, SIM-916, VGX-350, VGX-300, GIT-027, SP-100030, MLN-1145, NVP-IKK-005; Nuclear factor kappa B modulators, such as REM-1086; Nuclear factor kappa B p105 inhibitors, such as REM-1086; Opioid growth factor receptor agonists, such as metenkefalin acetate with tridecactide acetate, FAR-404; Opioid receptor delta antagonists, such as HS-378; Osteoclast differentiation factor antagonists, such as denosumab, cyclic peptidomimetics (rheumatoid arthritis/osteoporosis), University of Michigan; Osteoclast differentiation factor ligand inhibitors, such as denosumab; Oxidoreductase inhibitors, such as etodolac, imidazole salicylate; P2X7 purinoceptor agonists, such as givinostat; p38 MAP kinase alpha inhibitors, such as VX-745, BMS-582949 prodrugs, BMS-751324; p38 MAP kinase inhibitors, such as BCT-197, losmapimod, ARRY-797; PDE 4 inhibitors, such as apremilast; PDE 5 inhibitors, such as PDE5 inhibitors (rheumatoid arthritis), University of Rochester; PDGF receptor agonists, such as oprelvekin; PDGF receptor antagonists, such as imatinib, masitinib; PDGF-B ligand inhibitors, such as SL-1026; PERK gene inhibitors, such as binimetinib; Phosphoinositide-3 kinase delta inhibitors, such as duvelisib, RP-6503, CT-732, INK-007, GNE-293; Phosphoinositide-3 kinase gamma inhibitors, such as duvelisib, RP-6503; Phospholipase A2 inhibitors, such as AVX-002, human secreted phospholipase A2 type IIA-integrin binding inhibiting peptides (rheumatoid arthritis/asthma/Alzheimer's disease/cancer), University of California, Davis, AK-106, varespladib methyl, Ro-31-4493, BM-162353, Ro-23-9358, YM-26734; Platelet activating factor receptor antagonists, such as piperidone hydrochloridum; PPAR gamma agonists, such as rosiglitazone, THR-0921, rosiglitazone XR, etalocib; Programmed cell death protein 1 modulators, such as INSIX RA; Prostaglandin D synthase stimulators, such as HF-0220; Protein arginine deiminase inhibitors, such as PAD inhibitors (rheumatoid arthritis), Leiden University Medical Center/LURIS; Protein tyrosine kinase inhibitors, such as leflunomide; PurH purine biosynthesis protein inhibitors, such as mycophenolate mofetil; Rho associated protein kinase 2 inhibitors, such as KD-025; Seprase inhibitors, such as anti-fibroblast-activation protein (FAP) antibody radiotracers (rheumatoid arthritis), Hoffmann-La Roche/Radboud University; Signal transducer CD24 modulators, such as CD24-IgFc; Signal transduction inhibitors, such as imatinib; Sodium glucose transporter-2 inhibitors, such as THR-0921; Sphingosine 1 phosphate phosphatase modulators, such as S1P modulators (oral, multiple sclerosis/ulcerative colitis/rheumatoid arthritis), Akaal Pharma; STAT3 gene inhibitors, such as bardoxolone methyl, vidofludimus; Superoxide dismutase stimulators, such as imisopasem manganese; SYK family tyrosine kinase inhibitors, such as MK-8457; Syk tyrosine kinase inhibitors, such as fostamatinib, entospletinib, KDDF-201110-06, HMPL-523, cerdulatinib, AB-8779, GS-9876, PRT-2607, CVXL-0074, CG-103065and CG-026806; Syndecan-1 inhibitors, such as indatuximab ravtansine; T cell receptor antagonists, such as TCR inhibiting SCHOOL peptides (systemic/topical, rheumatoid arthritis/dermatitis/scleroderma), SignaBlok, CII modified peptide (rheumatoid arthritis), Peking University; T cell receptor modulators, such as ARG-301; T cell surface glycoprotein CD28 inhibitors, such as abatacept, belatacept, abatacept biosimilar, RhuDex, BMS-188667; T cell surface glycoprotein CD28 stimulators, such as TAB-08; TAK1 binding protein modulators, such as epigallocatechin 3-gallate; Talin modulators, such as short-form talin regulators (rheumatoid arthritis), KayteeBio; T-cell differentiation antigen CD6 inhibitors, such as itolizumab; T-cell surface glycoprotein CD8 inhibitors, such as tregalizumab; Tenascin modulators, such as Tetravil; TGF beta agonists, such as tregalizumab; Thymulin agonists, such as Syn-1002; TLR-2 antagonists, such as VB-201, P-13; TLR-4 antagonists, such as VB-201, P-13; TLR-9 antagonists, such as P-13; TNF alpha ligand inhibitors, such as adalimumab biosimilar YHB-1411-2, adalimumab, infliximab, infliximab biosimilar, recombinant humanized anti-TNF-alpha monoclonal antibody, certolizumab pegol, golimumab, ozoralizumab, AT-132, etanercept biosimilar, ISIS-104838, ISU-202, CT-P17, MB-612, Debio-0512, anti-TNF alpha human monoclonal antibody, infliximab biobetter, UB-721, KN-002, DA-3113, BX-2922, R-TPR-015, BOW-050, PF-06410293, CKD-760, CHS-1420, GS-071, ABP-710, STI-002, BOW-015, FKB-327, BAX-2200, HLX-03, BI-695501, CNTO-148, MYL-1401AABP-501, HOT-3010, BAX-2923, SCH-215596, ABT-D2E7, BAT-1406, XPro-1595, Atsttrin, SSS-07, golimumab biosimilar, TA-101, adalimumab follow-on biologic, BLX-1002, ABX-0401, TAQ-588, golimumab biosimilar, TeHL-1, placulumab, PMI-001, tgAAV-TNFR:Fc, K-832, CYT-007-TNFQb, SSR-150106, PassTNF, Verigen, DOM-0200, DOM-0215, AME-527, anti-TNF-alpha mAb, GENZ-38167, BLX-1028, CYT-020-TNFQb, CC-1080, CC-1069; TNF alpha ligand modulators, such as MM-A01-01, CDP-571, camobucol; TNF antagonists, such as etanercept, certolizumab pegol, etanercept follow-on biologic, etanercept biosimilar, DNX-114, TNF antagonist with IL-12 antagonist (rheumatoid arthritis), University of Oxford, BN-006, SCB-131, pegsunercept, GBL-5b, ACE-772, onercept, DE-096, PN-0615, lenercept, ITF-1779, MDL-201112, BAX-2200, SCB-808, DA-3853, HD-203; TNF gene inhibitors, such as GIBH-R-001-2; TNF receptor modulators, such as recombinant TNF receptor 2-Fc fusion protein mutant, T-0001, tgAAV-TNFR:Fc; TNFSF11 gene inhibitors, such as denosumab; Transcription factor p65 inhibitors, such as REM-1086; Transcription factor RelB inhibitors, such as REM-1086; Transferrin modulators, such as methotrexate, MBP-Y003; Tumor necrosis factor 13C receptor antagonists, such as VAY-736; Tumor necrosis factor 15 ligand inhibitors, such as anti-TL1A antibodies (rheumatoid arthritis/inflammatory bowel disease), NIAMS; Tumor necrosis factor ligand 13 inhibitors, such as atacicept; Tumor necrosis factor ligand inhibitors, such as ABBV-257, etanercept biosimilar, ABT-122; Type I IL-1 receptor antagonists, such as anakinra, anakinra biosimilar, anakinra follow-on biologic, AXXO; Type I TNF receptor antagonists, such as NM-9405; Type II TNF receptor modulators, such as etanercept, SCB-131, etanercept biosimilar, etanercept follow-on biologic, BAX-2200, SCB-808, LBEC-0101, DMB-3853, DWP-422, BT-D001, DA-3853; Unspecified GPCR agonists, such as NCP-70X; VEGF receptor antagonists, such as 2-methoxyestradiol and NSC-650853, SL-1026; VEGF-2 receptor antagonists, such as CG-026806; VEGF-2 receptor modulators, such as VEGFR2 neutralizing antibody (rheumatoid arthritis), University of Rochester; VEGF-B ligand inhibitors, such as CSL-346; X-linked inhibitor of apoptosis protein inhibitors, such as IAP inhibitors (oral), Pharmascience; and. Zap70 tyrosine kinase inhibitors, such as MK-8457, CT-5332.

Combinations for Metabolic Diseases or Conditions

Examples of metabolic disorders include, without limitation, diabetes, including type I and type II diabetes, metabolic syndrome, dyslipidemia, obesity, glucose intolerance, hypertension, elevated serum cholesterol, and elevated triglycerides. Examples of therapeutic agents used to treat metabolic disorders include antihypertensive agents and lipid lowering agents. Additional therapeutic agents used to treat metabolic disorders include insulin, sulfonylureas peroxisome proliferator activated receptor gamma (PPAR-γ) agonists, such as thiazolidinediones such as pioglitazones, biguanides, alpha-glucosidase inhibitors, Vitamin E and incretin mimetics. Thus, one aspect of the disclosure is a method of treating a metabolic disease comprising administering a compound of the disclosure in combination with one or more compounds useful for the treatment of metabolic diseases to a subject, particularly a human subject, in need thereof.

Pharmaceutical Compositions

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipient, etc.) which constitutes one or more accessory ingredients. In general the formulations are prepared by uniformly and intimately bringing into association the active ingredient with liquid carriers or finely divided solid carriers or both, and then, if necessary, shaping the product.

In certain embodiments, formulations suitable for oral administration are presented as discrete units such as capsules, cachets or tablets each containing a predetermined amount of the active ingredient.

In certain embodiments, the pharmaceutical formulations include one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight). In some embodiments, the pharmaceutical compositions described herein contain about 1 to 800 mg, 1 to 600 mg, 1 to 400 mg, 1 to 200 mg, 1 to 100 mg or 1 to 50 mg of the compound of Formula I, or a pharmaceutically acceptable salt thereof. In some embodiments, the pharmaceutical compositions described herein contain not more than about 400 mg of the compound of Formula I. In some embodiments, the pharmaceutical compositions described herein contain about 100 mg of the compound of Formula I, or a pharmaceutically acceptable salt thereof.

It should be understood that in addition to the ingredients particularly mentioned above the formulations disclosed herein may include other agents conventional in the art having regard to the type of formulation in question, for example those suitable for oral administration may include flavoring agents.

Veterinary compositions comprising at least one active ingredient as above defined together with a veterinary carrier are further provided.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of Formula I (herein referred to as the active ingredients), or a pharmaceutically acceptable salt thereof, are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally. Accordingly, in one embodiment, the pharmaceutical compositions described herein are oral dosage forms. In certain embodiments, the pharmaceutical compositions described herein are oral solid dosage forms.

| Formulation Example 1 Hard gelatin capsules containing the following ingredients are prepared: | |
|---|---|
| Ingredient | Quantity (mg/capsule) |
| Active Ingredient | 30.0 |
| Starch | 305.0 |
| Magnesium stearate | 5.0 |

The above ingredients are mixed and filled into hard gelatin capsules.

| Formulation Example 2 A tablet Formula is prepared using the ingredients below: | |
|---|---|
| Ingredient | Quantity (mg/tablet) |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

| Formulation Example 3 A dry powder inhaler formulation is prepared containing the following components: | |
|---|---|
| Ingredient | Weight % |
| Active Ingredient | 5 |
| Lactose | 95 |

The active ingredient is mixed with the lactose and the mixture is added to a dry powder inhaling appliance.

| Formulation Example 4 Tablets, each containing 30 mg of active ingredient, are prepared as follows: | |
|---|---|
| Ingredient | Quantity (mg/tablet) |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 120 mg.

| Formulation Example 5 Suppositories, each containing 25 mg of active ingredient are made as follows: | |
|---|---|
| Ingredient | Amount |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Formulation Example 6 Suspensions, each containing 50 mg of active ingredient per 5.0 mL dose are made as follows: | |
|---|---|
| Ingredient | Amount |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Formulation Example 7

A subcutaneous formulation may be prepared as follows:

| Ingredient | Quantity |
| --- | --- |
| Active Ingredient | 5.0 mg |
| Corn Oil | 1.0 mL |

Formulation Example 8

An injectable preparation is prepared having the following composition:

| Ingredients | Amount |
| --- | --- |
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Formulation Example 9

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients and water then added q.s. 100 g.

Formulation Example 10

Sustained Release Composition

| Ingredient | Weight Range % |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

Sustained release formulations of this disclosure may be prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate) and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma) and the like. These film-forming agents may optionally contain colorants, plasticizers and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg and 900-1100 mg.

In order to influence the dissolution rate, the time during which the compound containing powder is wet mixed is controlled. Preferably the total powder mix time, i.e., the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Formulation Example 11

A tablet Formula Is prepared using the ingredients below:

| Ingredient | Quantity (mg/tablet) |
| --- | --- |
| Active Ingredient | 300.0 |
| Cellulose, microcrystalline | 100.0 |
| Colloidal silicon dioxide | 10.0 |
| Stearic acid | 5.0 |

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

List of Abbreviations and Acronyms

| Abbreviation | Meaning |
| --- | --- |
| ° C. | Degree Celsius |
| Ac | Acetyl |
| aq. | Aqueous |
| ATP | Adenosine triphosphate |

-continued

| Abbreviation | Meaning |
|---|---|
| $B_2Pin_2$ | Bis(pinacolato)diboron |
| BOC | tert-Butoxycarbonyl |
| Br | Broad |
| BSA | Bovine serum albumin |
| D | Doublet |
| DCM | Dichloromethane |
| Dd | Doublet of doublets |
| Ddd | Doublet of doublet of doublets |
| DIPEA | N,N-Diisopropylethylamine (Hüig's Base) |
| DMA | Dimethylacetamide |
| DME | 1,2-Dimethoxyethane |
| DMF | Dimethylformamide |
| DMSO | Dimethylsulfoxide |
| Dt | Doublet-triplet |
| DTT | Dithiothreitol (Cleland's reagent) |
| $EC_{50}$ | The half maximal effective concentration |
| EDC | l-(3-dimethylaminopropyl)-3-ethylcarbodiimide |
| EDTA | Ethylenediaminetetraacetic acid |
| EGFR | Epidermal growth factor receptor |
| Eq | Equivalents |
| ES/MS | Electrospray mass spectrometry |
| Et | Ethyl |
| EtOAc | Ethyl acetate |
| EtOH | Ethanol (Ethyl alcohol) |
| FBS | Fetal bovine serum |
| G | Grams |
| HATU | 1-[Bis(dimethylamino)methylene]-1H-1,2,3-triazolo[4,5-b]pyridinium 3-oxidhexafluorophosphate |
| HEPES | 2-[4-(2-hydroxyethyl)piperazin-1-yl]ethanesulfonic acid |
| HCl | Hydrochloric acid |
| HPLC | High pressure liquid chromatography |
| Hrs | Hours |
| HTRF® | Homogeneous time resolved fluorescence, a registered trademark of Cisbio Bioassays, parc marcel boiteux 30200 codolet, France |
| Hz | Hertz |
| IBD | Inflammatory bowel disease |
| $IC_{50}$ | Half-maximal inhibitory concentration |
| i-pr | Isopropyl |
| J | Coupling constant (MHz) |
| $K_3PO_4$ | Tripotasium phosphate |
| KOtBu | Potassium tert-butoxide |
| KOAc | Potassium Acetate |
| Lawesson's Reagent | 2,4-Bis-(4-methoxyphenyl)-1,3-dithia-2,4-diphosphetane 2,4-disulfide |
| LCMS | Liquid chromatography-mass spectrometry |
| Li HMDS | Lithium bis(trimethylsilyl)amide |
| LiOH | Lithium hydroxide |
| LiI | Lithium iodide |
| LPS | Lipopolysaccharide |
| M | Molar |
| M | Multiplet |
| M+ | Mass peak |
| M + H+ | Mass peak plus hydrogen |
| Me | Methyl |
| MeCN | Acetonitrile |
| MeOH | Methanol (Methyl alcohol) |
| MeLi | Methyllithium |
| MeMgX | Methylmagnesium halide (Grignard reagent), where X is Fluoro, Chloro, Bromo or Iodo |
| $Me_6Sn_2$ | Hexamethyldistannane (hexamethylditin) |
| Mg | Milligram |
| $MgSO_4$ | Magnesium sulfate |
| MHz | Megahertz |
| Min | Minute |
| ml/mL | Milliliter |
| mM | Millimolar |
| Mmol | Millimole |
| MS | Mass spectroscopy |
| MsCl | Mesyl chloride |
| NBS | N-Bromosuccinimide |
| n- | Normal |
| nBu/Bu | n-Butyl (normal Butyl) |
| n-BuLi | n-Butyl Lithium |
| NaH | Sodium hydride |
| $NaHCO_3$ | Sodium bicarbonate |
| $NaN_3$ | Sodium azide |

-continued

| Abbreviation | Meaning |
|---|---|
| $Na_3PO_4$ | Trisodium phosphate |
| $Na_2SO_4$ | Sodium sulfate |
| nL | Nanoliter |
| Nm | Nanometer |
| NMP | 1-methylpyrrolidin-2-one |
| NMR | Nuclear magnetic resonance |
| NP-40 | Nonyl phenoxypolyethoxylethanol |
| Pd-PEPPSI™-IPent | [1,3-bis(2,6-di-3-pentylphenyl)imidazol-2-ylidene] (3-chloropyridyl)palladium(II) dichloride |
| Pen-Strep | Penicillin-Streptomycin (5,000 units of penicillin G sodium salt, and 5,000 μg streptomycin sulfate in 0.85% saline) |
| Ph | Phenyl |
| Q | Quartet |
| q.s. | Quantity sufficient to achieve a stated function |
| RP | Reverse phase |
| RPMI | Roswell Park Memorial Institute medium |
| Rt | Room temperature |
| s | Singlet |
| sat. | Saturated |
| Selectfluor® | 1-Chloromethyl-4-fluoro-1,4-diazoniabicyclo[2.2.2]octane bis (a trademark of Air Products and Chemicals) |
| SFC | Supercritical fluid chromatography |
| SiliaMetS® Thiol | Silica-based Palladium scavenger, registered trademark of Silicycle |
| T | Triplet |
| THF | Tetrahydrofuran |
| TFA | Trifluoroacetic acid |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate |

EXPERIMENTAL PROCEDURES

General Schemes

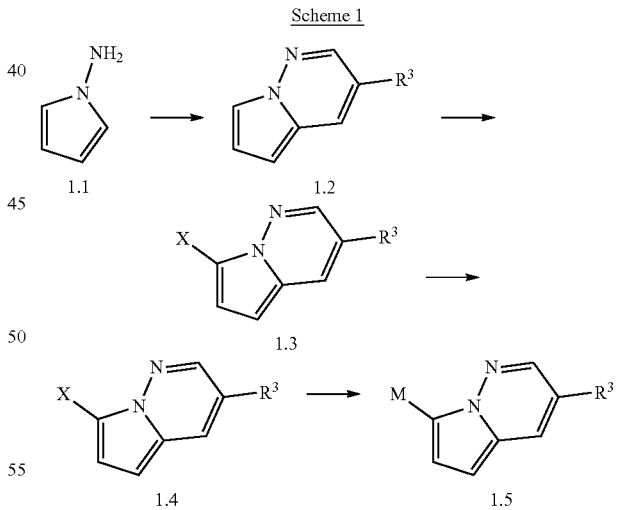

Scheme 1

The compounds of formula 1.5 may be accessed according to the method outlined in Scheme 1. 1-aminopyrrole 1.1 may be condensed with a suitable coupling partner to produce substituted pyrrolo[1,2-b]pyridazine 1.2 using a suitable catalyst (e.g., HCl, etc.) and suitable solvent (e.g., EtOH, etc.). Halogenation at the position shown using a known halogenating reagent (e.g., NBS, etc.) can form the intermediate 1.3, which can be further substituted either via C—H activation or electrophilic aromatic substitution with a suitable reagent (e.g., selectfluor, etc.) to produce intermediate 1.4. Halogen metal exchange of —X to —M can then be achieved using a suitable reagent (e.g., n-BuLi, etc.) or transition metal coupling using a palladium catalyst and metal source (e.g., $B_2Pin_2$, $Me_6Sn_2$, etc.) to give intermediate 1.5.

Scheme 2

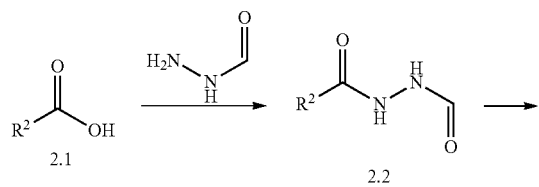

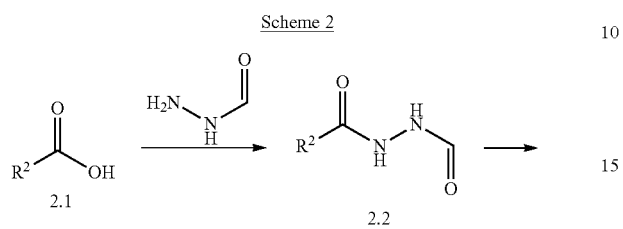

The compounds of the formula 2.3 may be accessed according to the method outlined in Scheme 2. The acid 2.1 can be converted to the corresponding acyl hydrazine using a coupling reagent (e.g., HATU, etc.) in the presence of a base (e.g., DIPEA, etc.). Cyclization of compound 2.2 can be accomplished by heating in the presence of a thionating reagent (e.g., Lawesson's reagent, etc.) to provide compound 2.3.

Scheme 3

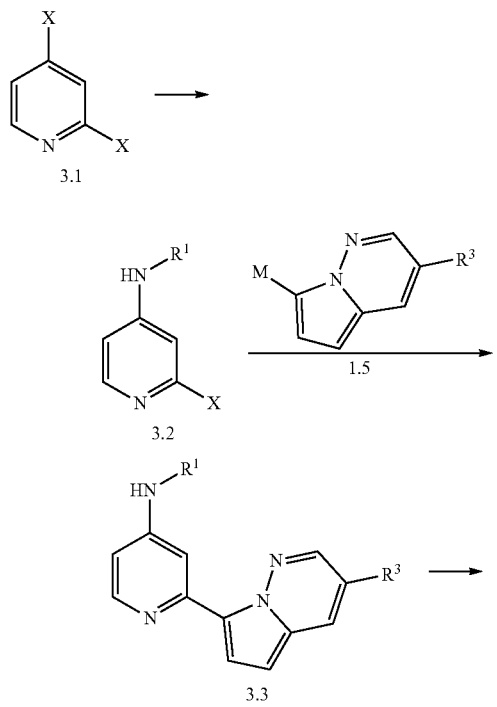

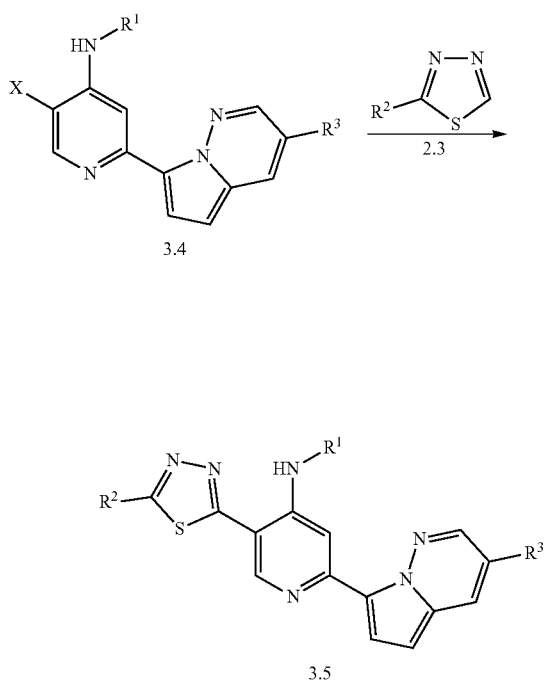

The compounds of formula 3.6 may be accessed according to the method outlined in Scheme 3. Dihalopyridine 3.1 may be converted to compound 3.2 via displacement of one of the halogen groups (e.g., nucleophilic aromatic substitution, etc.). Further functionalization of compound 3.2 using a metal-containing heterocyclic species (e.g., compound 1.5) with a suitable catalyst, such as a palladium catalyst, can afford compound 3.3. Halogenation at the position shown using a known halogenating reagent (e.g., NBS, etc.) can form the intermediate 3.4 which can be further substituted through a cross-coupling reaction using a suitable catalyst, such as a palladium catalyst, to provide compound 3.5.

Scheme 4

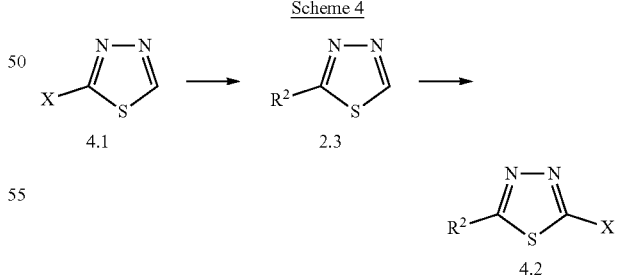

Compounds of formula 4.2 may be assembled following Scheme 4. Displacement of the halogen group (e.g., nucleophilic aromatic substitution, etc.) of a halothiadiazole 4.1 with a nucleophile (e.g., an amine, etc.) can provide compound 2.3. Halogenation at the position shown using a known halogenating reagent (e.g., NBS, etc.) can form the intermediate 4.2.

Scheme 5

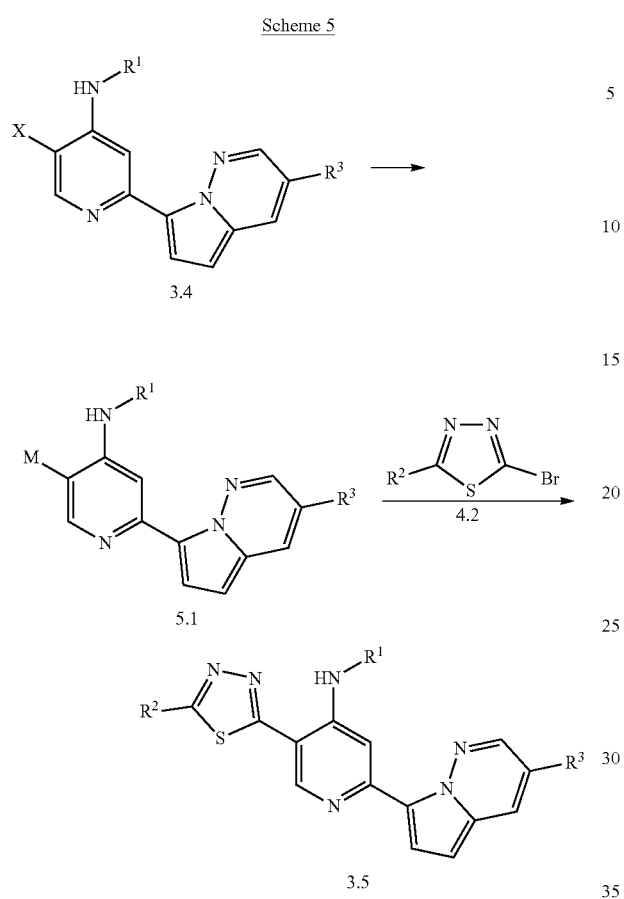

Compounds of formula 3.5 may also be assembled following Scheme 5. Halogen metal exchange of —X to —M can then be achieved using a suitable reagent (e.g., n-BuLi, etc.) or transition metal coupling using a palladium catalyst and metal source (e.g., $B_2Pin_2$, $Me_6Sn_2$, etc.) to give intermediate 5.1. Functionalization of compound 5.1 can be done utilizing a cross-coupling reaction with compound 4.2 using a suitable catalyst, such as a palladium catalyst, to provide compound 3.5.

Scheme 6

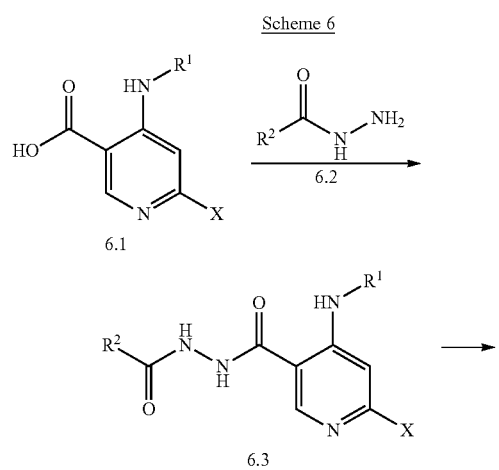

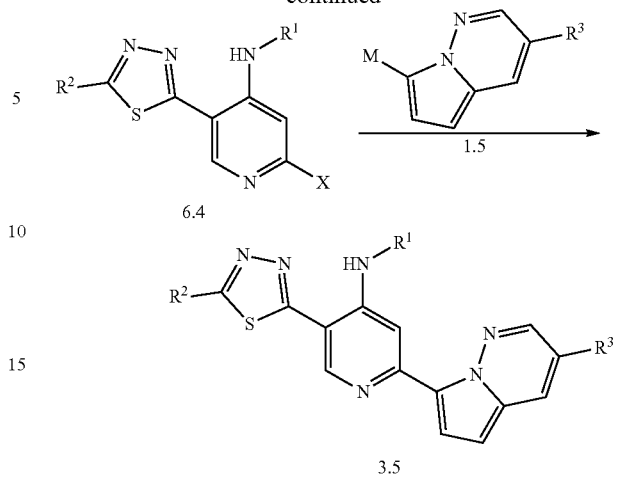

An alternative method of access compound 3.5 is shown in Scheme 6. Starting from the nicotinic acid 6.1, the corresponding acyl hydrazine can be prepared using a coupling reagent (e.g., HATU, etc.) in the presence of a base (e.g., DIPEA, etc.). Cyclization of compound 6.3 can be accomplished by heating in the presence of a thionating reagent (e.g., Lawesson's reagent, etc.) to provide compound 6.4. Further functionalization of compound 6.4 using a metal-containing heterocyclic species (e.g., compound 1.5) with a suitable catalyst, such as a palladium catalyst, can afford compound 3.5.

Scheme 7

It is also noted that synthetic manipulations of the incorporated R groups are possible following their incorporation. A specific illustrative example of an alteration to the $R^2$ group is shown in Scheme 7 wherein the secondary carbamate 7.1 is converted the primary amine 7.2. Other functional groups may also be present in the $R^2$ and can be manipulated. These groups and manipulations can include, but are not limited to, oxidation, elimination or displacement using suitable reagents known to those skilled in the art. The order of synthetic manipulations may be carried out in a fashion that is consistent with the methods outlined in Schemes 1-6 and should not be limited to the final step of compound preparation.

Synthesis of Intermediates

Preparation of Intermediate I-1

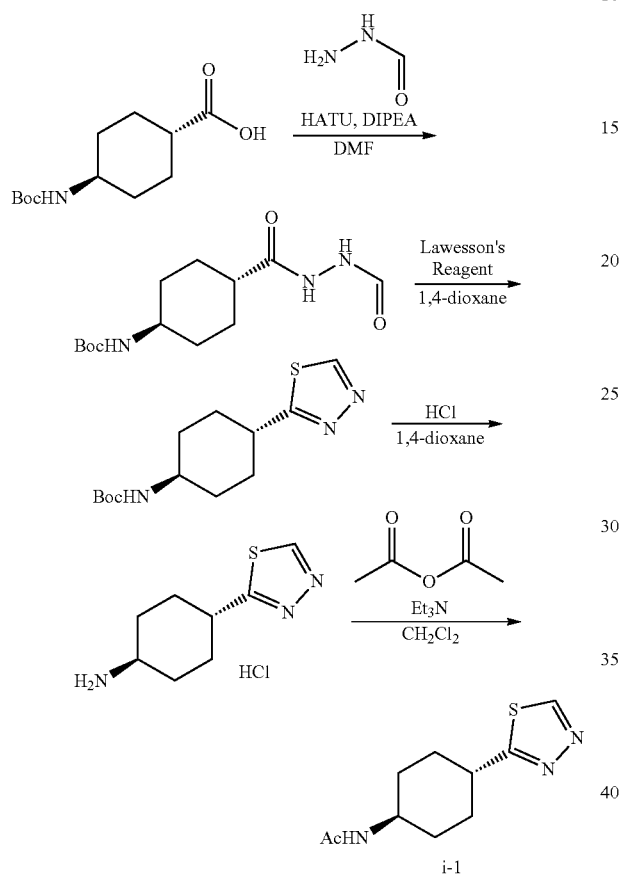

tert-butyl ((1r,4r)-4-(2-formylhydrazine-1-carbonyl)cyclohexyl)carbamate: To a solution of (1r,4r)-4-((tert-butoxycarbonyl)amino)cyclohexane-1-carboxylic acid (250 mg, 1.0 mmol) in DMF (2 mL) was added formic acid hydrazide (80 mg, 1.3 mmol), HATU (469 mg, 1.2 mmol), and finally DIPEA (0.45 mL, 2.6 mmol) and the resulting mixture stirred at room temperature for 15 minutes. Upon completion, the reaction mixture was poured into water (5 mL) and extracted with EtOAc (2×15 mL). The combined organic layers were dried over MgSO$_4$, filtered and concentrated. The resulting crude residue was purified by silica gel chromatography (eluent: EtOAc/hexanes) to give the desired product.
ES/MS: 285.9 [M+H]$^+$ tert-butyl ((1r,4r)-4-(1,3,4-thiadiazol-2-yl)cyclohexyl)carbamate: To a solution of tert-butyl ((1r,4r)-4-(2-formylhydrazine-1-carbonyl)cyclohexyl)carbamate (193 mg, 0.68 mmol) in dioxane (5 mL) was added Lawesson's Reagent (301 mg, 0.74 mmol) and the resulting reaction mixture heated to 100° C. for 3 hours. Upon completion, the reaction mixture was poured into water (5 mL) and extracted with EtOAc (2×15 mL). The combined organic layers were dried over MgSO$_4$, filtered and concentrated. The resulting crude residue was purified by silica gel chromatography (eluent: EtOAc/hexanes) to give the desired product.
ES/MS: 284.0 [M+H]$^+$ (1r,4r)-4-(1,3,4-thiadiazol-2-yl)cyclohexan-1-amine hydrochloride: tert-butyl ((1r,4r)-4-(1,3,4-thiadiazol-2-yl)cyclohexyl)carbamate (59 mg, 0.21 mmol) was then dissolved in HCl (4.0M in dioxane, 4 mL, 16 mmol) and stirred at room temperature for 7 hours after which the reaction mixture was concentrated to dryness directly to give the desired product as an HCl salt which was used without further purification.
ES/MS: 184.1 [M+H]$^+$ N-((1r,4r)-4-(1,3,4-thiadiazol-2-yl)cyclohexyl)acetamide (I-1): (1r,4r)-4-(1,3,4-thiadiazol-2-yl)cyclohexan-1-amine hydrochloride (175 mg, 0.8 mmol) was dissolved in CH$_2$Cl$_2$ (4 mL) and the reaction mixture was cooled to 0° C. Triethylamine (0.33 mL, 2.39 mmol) was added, followed by acetic anhydride (0.094 mL, 1 mmol). The reaction was stirred at 0° C. for 30 minutes after which the mixture was diluted with CH$_2$Cl$_2$ and washed with water. The organic layer was dried over MgSO$_4$, filtered, and concentrated. The crude material was purified by silica gel chromatography (eluent EtOAc/hexanes followed by methanol/EtOAc) to give I-1.
ES/MS: 226.1 [M+H]$^+$ The following intermediates were synthesized as described for I-1 using the appropriate starting carboxylic acid, and appropriate anhydride, carbonyl-chloride, or alkyl triflate:

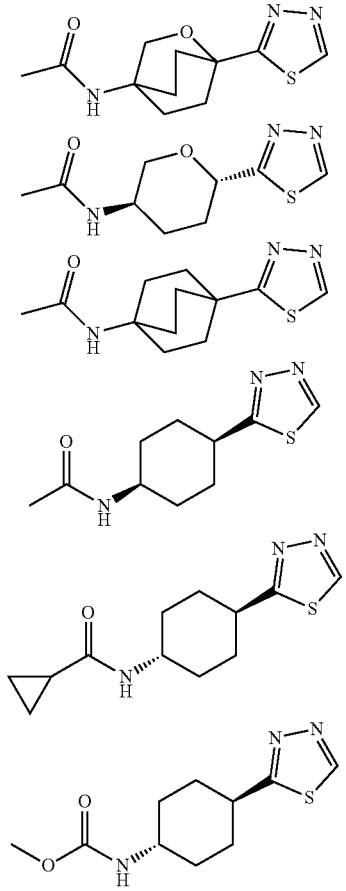

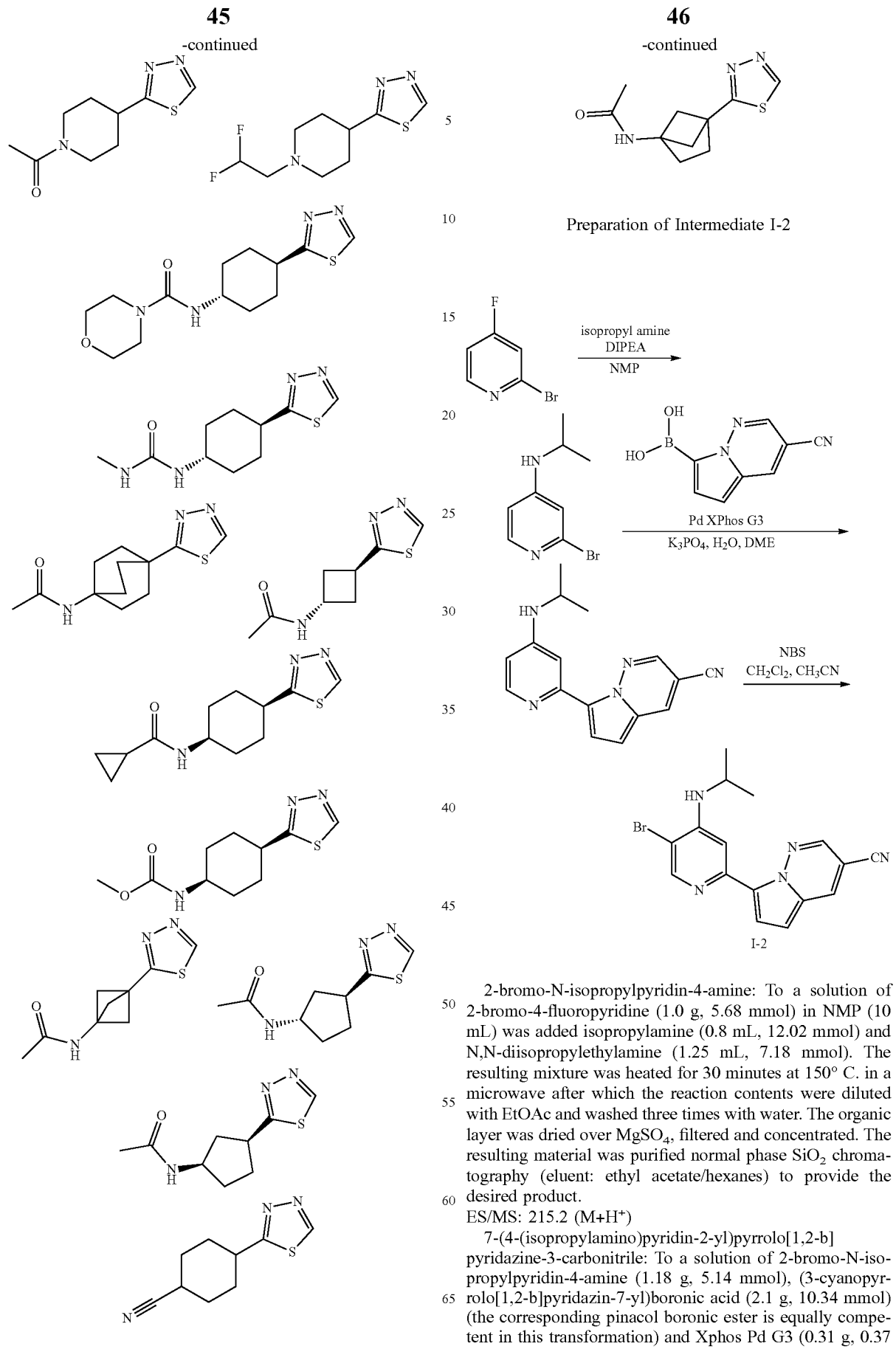

Preparation of Intermediate I-2

2-bromo-N-isopropylpyridin-4-amine: To a solution of 2-bromo-4-fluoropyridine (1.0 g, 5.68 mmol) in NMP (10 mL) was added isopropylamine (0.8 mL, 12.02 mmol) and N,N-diisopropylethylamine (1.25 mL, 7.18 mmol). The resulting mixture was heated for 30 minutes at 150° C. in a microwave after which the reaction contents were diluted with EtOAc and washed three times with water. The organic layer was dried over MgSO$_4$, filtered and concentrated. The resulting material was purified normal phase SiO$_2$ chromatography (eluent: ethyl acetate/hexanes) to provide the desired product.

ES/MS: 215.2 (M+H$^+$)

7-(4-(isopropylamino)pyridin-2-yl)pyrrolo[1,2-b]pyridazine-3-carbonitrile: To a solution of 2-bromo-N-isopropylpyridin-4-amine (1.18 g, 5.14 mmol), (3-cyanopyrrolo[1,2-b]pyridazin-7-yl)boronic acid (2.1 g, 10.34 mmol) (the corresponding pinacol boronic ester is equally competent in this transformation) and Xphos Pd G3 (0.31 g, 0.37 mmol) in DME (12.3 mL) was added aqueous potasium phosphate (2M, 4.9 mL, 9.9 mmol). The resulting solution was degassed with argon for 2 min and heated under microwave conditions for 40 min at 120° C. after which silica gel was added, and the resulting slurry was filtered through celite, rinsing with EtOAc. The material was concentrated, and the resulting crude material was purified by normal phase SiO$_2$ chromatography (eluent: ethyl acetate/hexanes) to provide the desired product.
ES/MS: 278.2 (M+H$^+$)

7-(5-bromo-4-(isopropylamino)pyridin-2-yl)pyrrolo[1,2-b]pyridazine-3-carbonitrile (I-2): To a solution of 7-[4-(isopropylamino)-2-pyridyl]pyrrolo[1,2-b]pyridazine-3-carbonitrile (0.75 g, 2.4 mmol) in DCM:MeCN (1:1, 60 mL) at 0° C. was added a solution of N-bromosuccinimide (0.433 g, 2.4 mmol) in 9 mL of 1:1 DCM:MeCN, and the resulting mixture stirred at zero degrees. After 30 minutes, significant precipitate was observed, and the reaction mixture was concentrated under vacuum. The crude material was purified by silica gel chromatography (EtOAc/hexanes) to give I-2.
ES/MS: 356.2 (M+H$^+$)

The following intermediates were prepared as described for I-2, using the appropriate amine for step 1 or boronate ester/boronic acid for step 2:

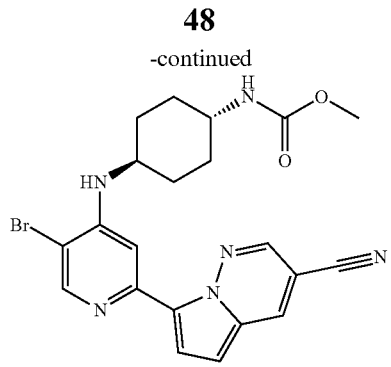

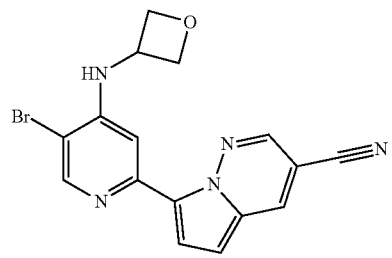

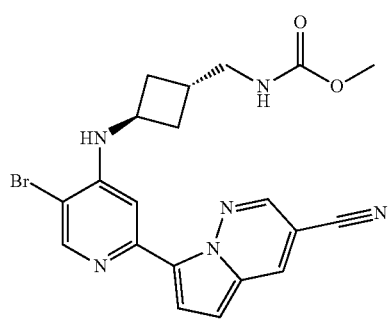

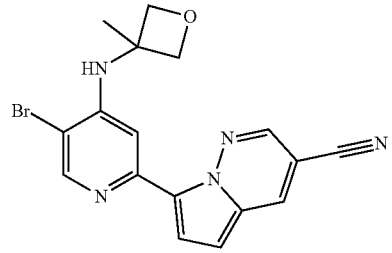

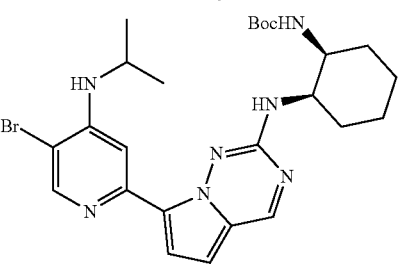

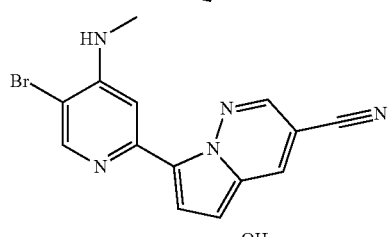

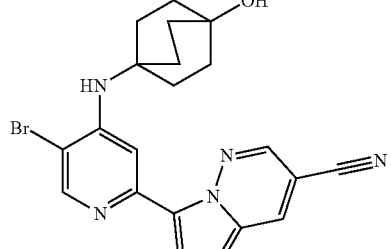

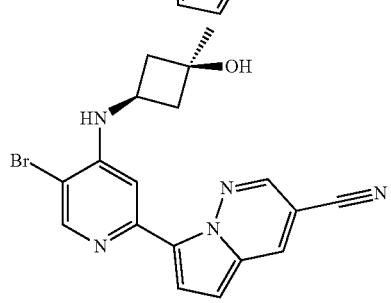

49
-continued

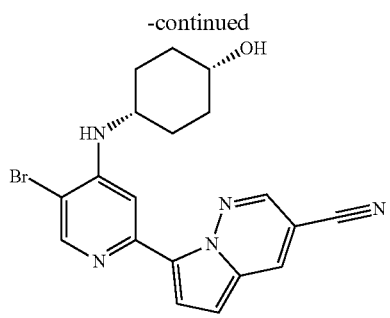

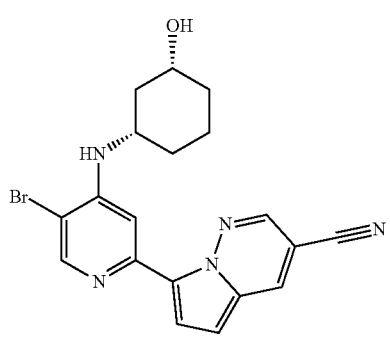

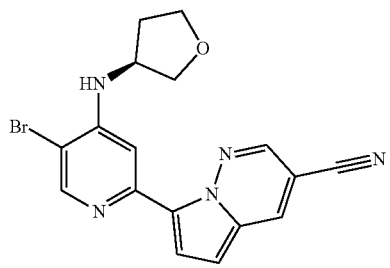

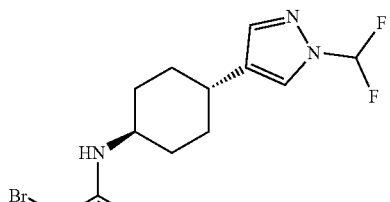

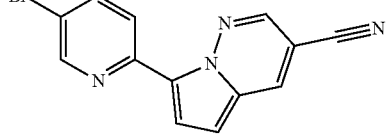

Preparation of Intermediate I-3

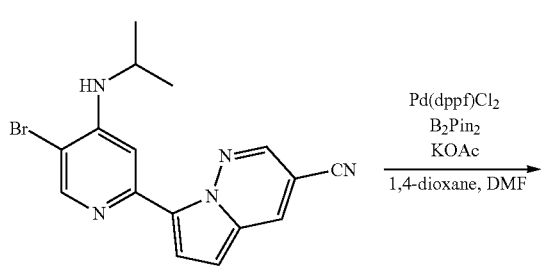

50
-continued

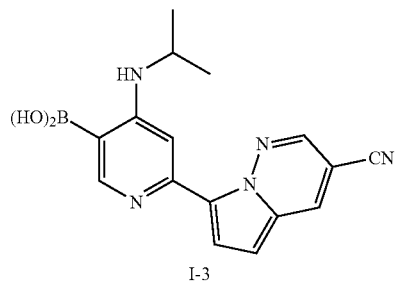

I-3

(6-(3-cyanopyrrolo[1,2-b]pyridazin-7-yl)-4-(isopropylamino)pyridin-3-yl)boronic acid (I-3): To a microwave vial containing 7-(5-bromo-4-(isopropylamino)pyridin-2-yl)pyrrolo[1,2-b]pyridazine-3-carbonitrile (I-2) (120 mg, 0.34 mmol), bis(pinacolato)diboron (171 mg, 0.674 mmol), [1,1'-Bis(diphenylphosphino)ferrocene]dichloropalladium(II) (37 mg, 0.05 mmol), and potassium acetate (99 mg, 1 mmol) was added 1,4-dioxane (1 mL) and DMF (0.5 mL). The mixture was degassed with argon for 1 min, sealed, and heated under microwave conditions for 20 min at 120° C., after which the resulting crude material was filtered and purified by RP-HPLC (eluent: water/MeCN*0.1% TFA) to yield the product (I-3) as a trifluoroacetate salt.

ES/MS: 322.2 (M+H$^+$)

The following intermediates were prepared as described for I-3 from the appropriate 3-bromo-pyridines:

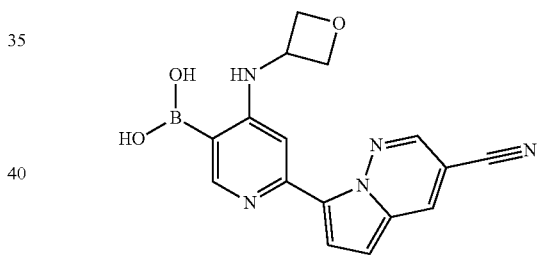

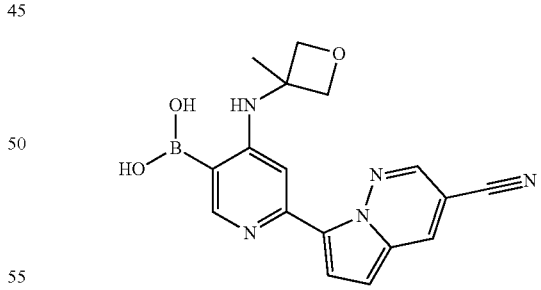

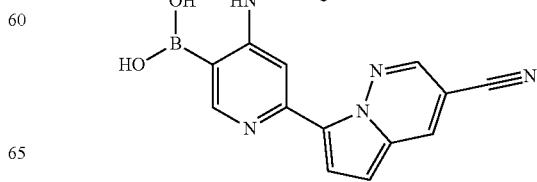

51

-continued

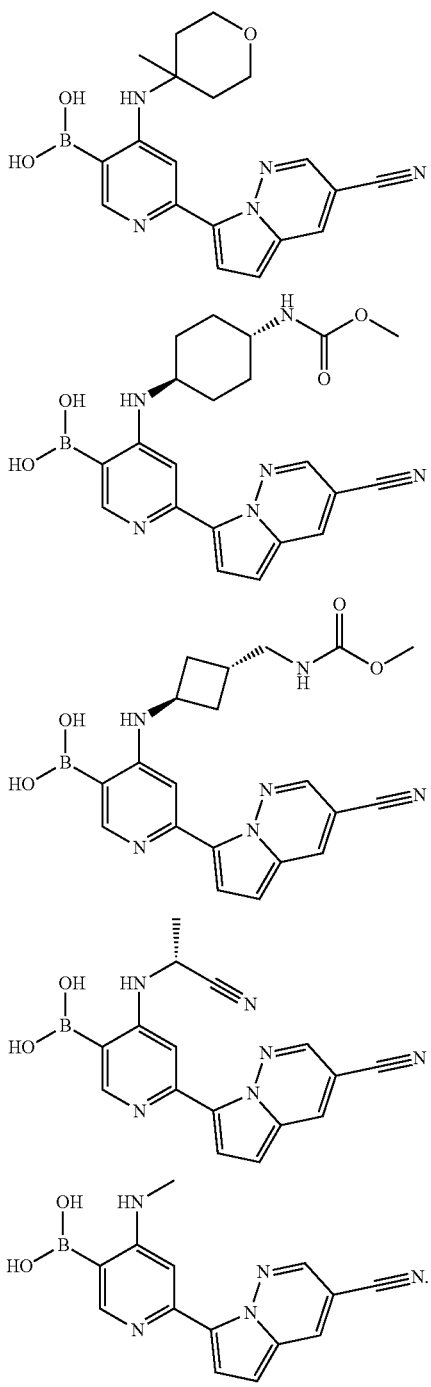

Preparation of Intermediate I-4

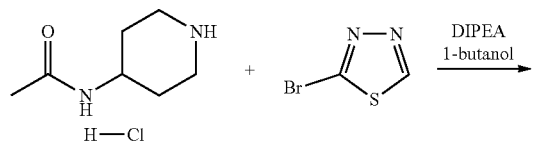

52

-continued

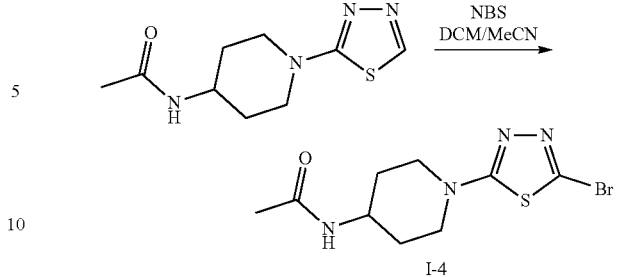

N-(1-(1,3,4-thiadiazol-2-yl)piperidin-4-yl)acetamide: To a solution of 2-bromo-1,3,4-thiadiazole (100.0 mg, 0.61 mmol) and N-(piperidin-4-yl)acetamide hydrochloride (270.7 mg, 1.5 mmol) in n-butanol (1.2 mL) was added N,N-diisopropylethylamine (0.42 mL, 2.4 mmol). The reaction mixture was heated thermally at 120° C. for 1 hour. The reaction mixture was cooled, concentrated in vacuo to provide the crude product that was used without purification. ES/MS: 227.12 [M+H$^+$].

N-(1-(5-bromo-1,3,4-thiadiazol-2-yl)piperidin-4-yl)acetamide (I-4): To a solution of crude N-(1-(1,3,4-thiadiazol-2-yl)piperidin-4-yl)acetamide (50.0 mg, 0.22 mmol) in DCM (0.5 mL) and MeCN (0.5 mL) was added N-bromosuccinimide (118.0 mg, 0.66 mmol) in one portion. After stirring at room temperature for 5 minutes, the reaction mixture was concentrated in vacuo and purified by silica gel column chromatography (eluent: MeOH/DCM) to provide I-4.
ES/MS: 305.1, 307.0 [M+H$^+$].

Preparation of Intermediate I-5

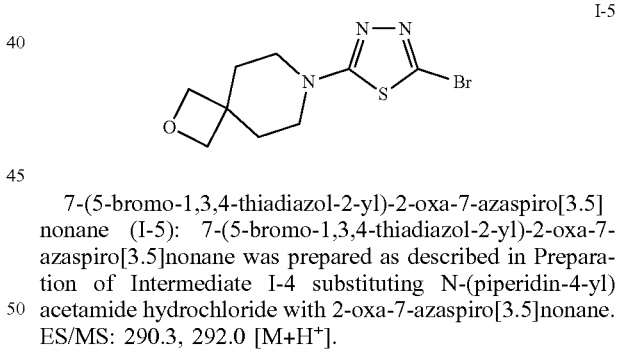

7-(5-bromo-1,3,4-thiadiazol-2-yl)-2-oxa-7-azaspiro[3.5]nonane (I-5): 7-(5-bromo-1,3,4-thiadiazol-2-yl)-2-oxa-7-azaspiro[3.5]nonane was prepared as described in Preparation of Intermediate I-4 substituting N-(piperidin-4-yl)acetamide hydrochloride with 2-oxa-7-azaspiro[3.5]nonane.
ES/MS: 290.3, 292.0 [M+H$^+$].

Preparation of Intermediate I-6

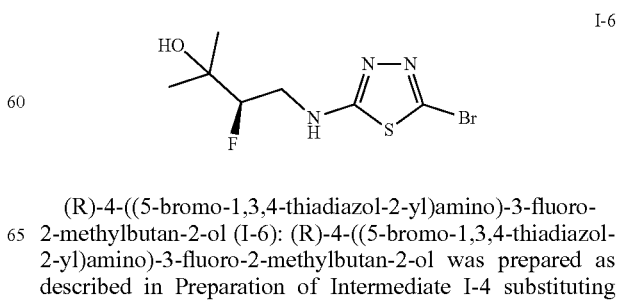

(R)-4-((5-bromo-1,3,4-thiadiazol-2-yl)amino)-3-fluoro-2-methylbutan-2-ol (I-6): (R)-4-((5-bromo-1,3,4-thiadiazol-2-yl)amino)-3-fluoro-2-methylbutan-2-ol was prepared as described in Preparation of Intermediate I-4 substituting N-(piperidin-4-yl)acetamide hydrochloride with (R)-4-amino-3-fluoro-2-methylbutan-2-ol hydrochloride.

ES/MS: 284.0, 285.9 [M+H⁺].

Preparation of Intermediate I-7

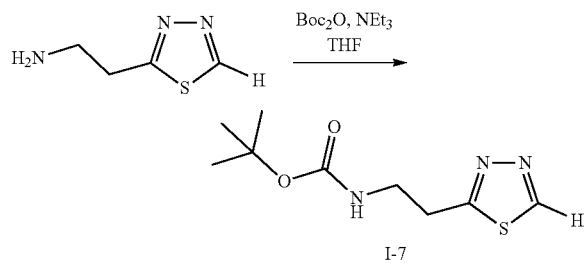

tert-butyl (2-(1,3,4-thiadiazol-2-yl)ethyl)carbamate (I-7): To a solution of 2-(1,3,4-thiadiazol-2-yl)ethan-1-amine (100.0 mg, 0.77 mmol) and di-tert-butyl dicarbonate (186 mg, 0.85 mmol) in THF at 0° C. was added triethylamine (0.13 mL, 0.93 mmol). The reaction mixture was warmed to room temperature and stirred for 90 minutes. The reaction mixture was concentrated in vacuo and purified by silica gel column chromatography (eluent: MeOH/DCM) to provide I-7.

ES/MS: 229.9 [M+H⁺].

Preparation of Intermediate I-8

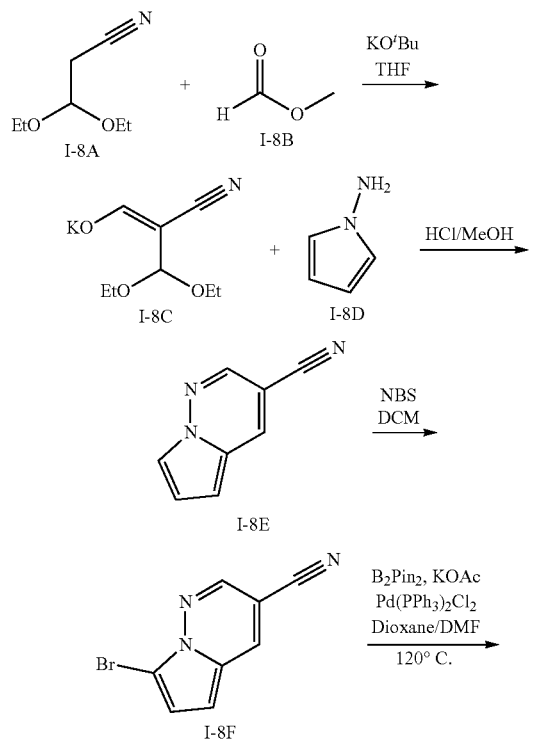

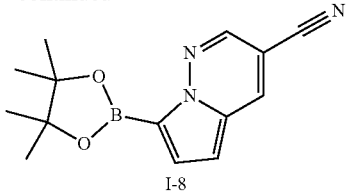

3,3-Diethoxy-2-formylpropionitrile Potassium Salt (I-8C): To a stirred solution of 3,3-diethoxypropane-nitrile (I-8A, 283.80 g, 1.98 moles) and methyl formate (I-8B, 148.80 g, 2.48 moles) in anhydrous THF (1.1 L) at 10° C. was added 1.0 M potassium tert-butoxide in THF (2.2 L, 2.2 moles). The temperature was maintained in the range of 10° C. to 15° C. throughout the 45 minute addition. Following the addition, the resulting slurry was stirred for 2 hours at ambient temperature. Hexane (400 mL) was then added and stirring was continued for another 20 min. The slurry was filtered and the cake washed with 1/1 hexanes/THF and dried overnight at 60° C. in a vacuum oven to provide I-8C. ¹H-NMR (CD₃OD) was consistent with the desired structure.

Pyrrolo[1,2-b]pyridazine-3-carbonitrile (I-8E): A stirred suspension of 3,3-diethoxy-2-formylpropionitrile potassium salt (I-8C, 5.10 g, 24.36 mmol) was cooled to 0° C., and concentrated HCl (7.11 mL, 85.26 mmol) was added dropwise at such a rate that the internal temperature of the reaction did not go above 20° C. After addition was complete, the reaction was stirred at room temperature for 20 minutes. To this reaction mixture was added a solution of 1-aminopyrrole (I-8D, 1.00 g, 12.18 mmol) in methanol (4.0 mL). After addition, the reaction mixture was refluxed at 90° C. for 2 hours. When heating was complete, the reaction was cooled to room temperature and concentrated to about half of the original volume. Saturated aqueous sodium bicarbonate was added carefully to the resulting residue until bubbling stopped. The solution was extracted with two portions of ethyl acetate. The combined organic layers were dried over sodium sulfate, filtered, concentrated in vacuo, and the resulting residue was purified by silica gel chromatography (eluent: EtOAc/hexanes) to provide I-8E.

1H NMR (400 MHz, Chloroform-d) δ 8.16-8.03 (m, 2H), 7.93 (ddd, J=2.6, 1.4, 0.6 Hz, 1H), 7.04 (dd, J=4.5, 2.7 Hz, 1H), 6.84 (dd, J=4.6, 1.4 Hz, 1H).

7-bromopyrrolo[1,2-b]pyridazine-3-carbonitrile (I-8F): To a solution of pyrrolo[1,2-b]pyridazine-3-carbonitrile (I-8E, 840.0 mg, 5.9 mmol) in MeCN (30 mL) at room temperature was added N-bromosuccinimide in one portion. The reaction was stirred at room temperature for 30 minutes then poured into saturated aqueous sodium bicarbonate. The solution was concentrated in vacuo to remove the acetonitrile. The resulting aqueous layer was extracted with three portions of EtOAc. The combined organic layers were dried over sodium sulfate, filtered, concentrated in vacuo, and purified by silica gel chromatography (eluent: EtOAc/hexanes) to provide I-8F.

1H NMR (400 MHz, Chloroform-d) δ 8.28 (d, J=2.1 Hz, 1H), 8.10 (d, J=2.1 Hz, 1H), 7.12 (d, J=4.8 Hz, 1H), 6.93 (d, J=4.8 Hz, 1H).

7-(4,4,5,5-tetramethyl-1,3,2-dioxaborolan-2-yl)pyrrolo[1,2-b]pyridazine-3-carbonitrile (I-8): A microwave vial was charged with 7-bromopyrrolo[1,2-b]pyridazine-3-carbonitrile (I-8F, 416.5 mg, 1.9 mmol), bis(pinacolato)diboron (762.1 mg, 3.0 mmol), potassium acetate (552.3 mg, 5.6 mmol), and bis(triphenylphosphine)palladium(II) dichloride (65.8 mg, 0.094 mmol). Dioxane (8.0 mL) and DMF (4.0 mL) were added, and the reaction mixture was degassed with bubbling argon for 2 minutes. The vial was sealed and the reaction was heated at 120° C. in a microwave reactor for 60 minutes. After cooling, the reaction mixture was filtered and concentrated in vacuo. The resulting residue was partitioned between EtOAc and water. The aqueous layer was extracted with a second portion of EtOAc, and the combined organic layers were dried over sodium sulfate, filtered through a plug of Celite, and concentrated in vacuo. The resulting residue was purified by silica gel chromatography (eluent: EtOAc/hexanes) to provide I-8.

1H NMR (400 MHz, Chloroform-d) δ 8.31 (d, J=2.3 Hz, 1H), 8.14 (d, J=2.2 Hz, 1H), 7.52 (d, J=4.6 Hz, 1H), 6.84 (d, J=4.6 Hz, 1H), 1.41 (s, 12H).

Preparation of Intermediate I-9

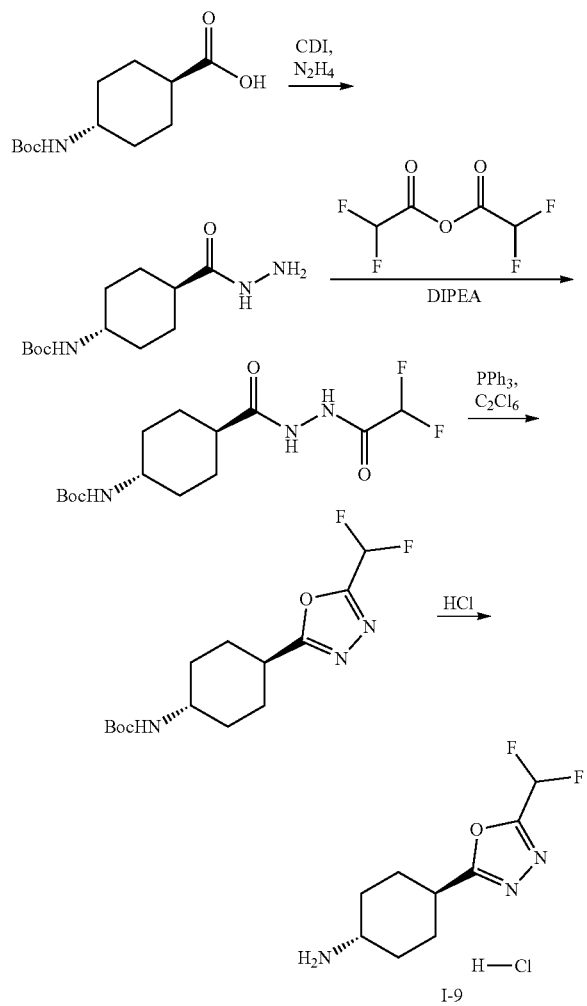

tert-butyl ((1r,4r)-4-(hydrazinecarbonyl)cyclohexyl)carbamate: To a solution of (1r,4r)-4-((tert-butoxycarbonyl)amino)cyclohexane-1-carboxylic acid (10.0 g, 41.1 mmol) in THF (360 mL) was added 1,1'-carbonyldiimidazole (10.7 g, 65.8 mmol) as a single portion and the resulting mixture stirred for 16 h at room temperature. Hydrazine hydrate (10.0 mL, 206 mmol) was then added as a single portion. After 15 minutes approximately 200 mL THF was removed by rotary evaporation and the resulting slurry filtered rinsing with THF. The solid was dried under vacuum to give tert-butyl ((1r,4r)-4-(hydrazinecarbonyl)cyclohexyl)carbamate which was used without further purification.

ES/MS: 202.2 (M+H$^+$).

tert-butyl ((1r,4r)-4-(2-(2,2-difluoroacetyl)hydrazine-1-carbonyl)cyclohexyl)carbamate: To a solution of tert-butyl ((1r,4r)-4-(hydrazinecarbonyl)cyclohexyl)carbamate (1.50 g, 5.83 mmol) and diisopropylethylamine (2.6 mL, 14.9 mmol) in THF (20 mL) was added difluoroacetic anhydride (0.93 mL, 7.43 mmol) and the reaction mixture allowed to stir at room temperature. After 30 minutes additional difluoroacetic anhydride (0.40 mL, 3.20 mmol) was added and the reaction mixture allowed to stir for 30 minutes. The reaction mixture was then poured into water (20 mL), extracted with EtOAc (2×40 mL), washed with brine (1×15 mL), dried over MgSO$_4$, filtered and concentrated to give crude tert-butyl ((1r,4r)-4-(2-(2,2-difluoroacetyl)hydrazine-1-carbonyl)cyclohexyl)carbamate which was used without further purification.

ES/MS: 280.0 (M+H$^+$).

tert-butyl ((1r,4r)-4-(5-(difluoromethyl)-1,3,4-oxadiazol-2-yl)cyclohexyl)carbamate: To a solution of tert-butyl ((1r,4r)-4-(2-(2,2-difluoroacetyl)hydrazine-1-carbonyl)cyclohexyl)carbamate (1.66 g, 4.96 mmol) in dry acetonitrile (40 mL) was added sequentially triphenylphosphine (3.90 g, 14.9 mmol), hexachloroethane (1.76 g, 7.34 mmol) and diisopropylethylamine (5.2 mL, 29.7 mmol) and the resulting solution allowed to stir for 15 minutes at room temperature. Upon completion the reaction mixture was poured into saturated aqueous NH$_4$Cl (30 mL, and extracted with EtOAc (2×60 mL). The combined organics were washed with brine (1×15 mL), dried over MgSO$_4$, filtered and concentrated to give a crude residue which was further purified using silica gel chromatography (eluent: EtOAc/hexanes) to give the product tert-butyl ((1r,4r)-4-(5-(difluoromethyl)-1,3,4-oxadiazol-2-yl)cyclohexyl)carbamate.

(1r,4r)-4-(5-(difluoromethyl)-1,3,4-oxadiazol-2-yl)cyclohexan-1-amine hydrochloride (I-9): Tert-butyl ((1r,4r)-4-(5-(difluoromethyl)-1,3,4-oxadiazol-2-yl)cyclohexyl)carbamate (1.26 g, 3.96 mmol) was dissolved in HCl solution (4.0M in dioxane, 12 mL, 48 mmol) and the resulting mixture was stirred in a preheated 50° C. heating block for 30 minutes. Upon completion the suspension was filtered directly washing with dioxane (1×4 mL) and the solid dried under vacuum to give (1r,4r)-4-(5-(difluoromethyl)-1,3,4-oxadiazol-2-yl)cyclohexan-1-amine hydrochloride (I-9) which was used without further purification.

ES/MS: 218.0 (M+H$^+$).

Preparation of Intermediate I-10

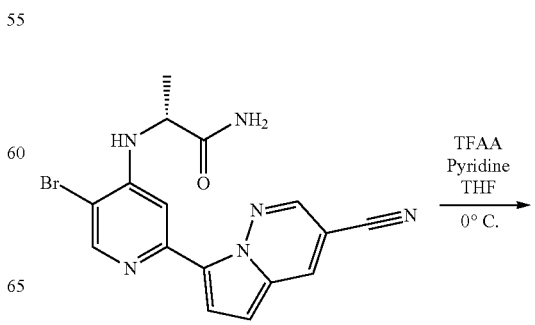

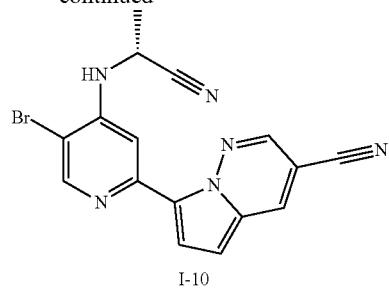

I-10

(R)-7-(5-bromo-4-((1-cyanoethyl)amino)pyridin-2-yl)pyrrolo[1,2-b]pyridazine-3-carbonitrile (I-10): A solution of (R)-2-((5-bromo-2-(3-cyanopyrrolo[1,2-b]pyridazin-7-yl)pyridin-4-yl)amino)propanamide (prepared as described for I-2 using the appropriate amine in step 1) (500 mg, 1.30 mmol) in THF (6.5 mL) was cooled to 0° C. To the cooled solution was added pyridine (0.52 mL, 6.49 mmol) followed by trifluoroacetic anhydride (0.27 mL, 1.95 mmol). The reaction mixture was allowed to warm to RT. After 2 hours, trifluoroacetic lanhydride (36 µL, 0.26 mmol) was added. The reaction mixture was stirred at RT for an additional 30 minutes, then concentrated in vacuo and purified by silica gel column chromatography (eluent: MeOH/DCM) to provide I-10.

ES/MS: 367.43, 369.09 [M+H⁺].

Preparation of Intermediate I-11

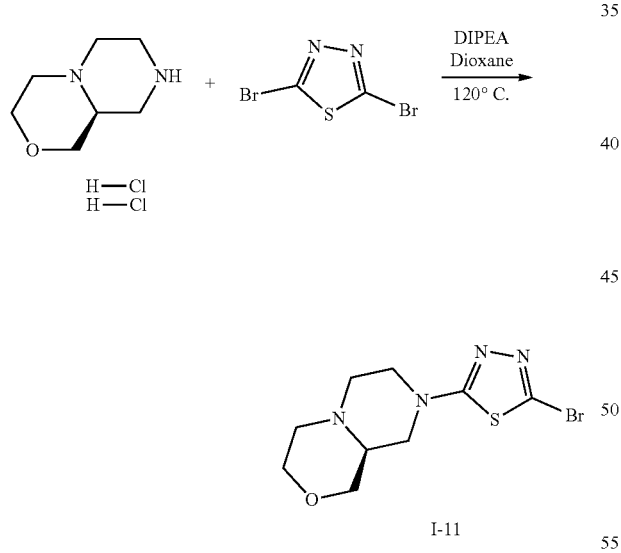

I-11

(S)-8-(5-bromo-1,3,4-thiadiazol-2-yl)octahydropyrazino[2,1-c][1,4]oxazine (I-11): To a solution of 2,5-dibromo-1,3,4-thiadiazole (100 mg, 0.41 mmol) and (S)-octahydropyrazino[2,1-c][1,4]oxazine dihydrochloride (106 mg, 0.49 mmol) in 1,4-dioxane (1.0 mL) was added N,N-diisopropylethylamine (0.29 mL, 1.64 mmol). The reaction mixture was heated in a sealed vial for one hour, then concentrated in vacuo and purified by silica gel column chromatography (eluent: MeOH/DCM) to provide I-11.

ES/MS: 305.31, 307.03 [M+H⁺].

The following intermediates were synthesized as described for I-11 using the appropriate starting amine:

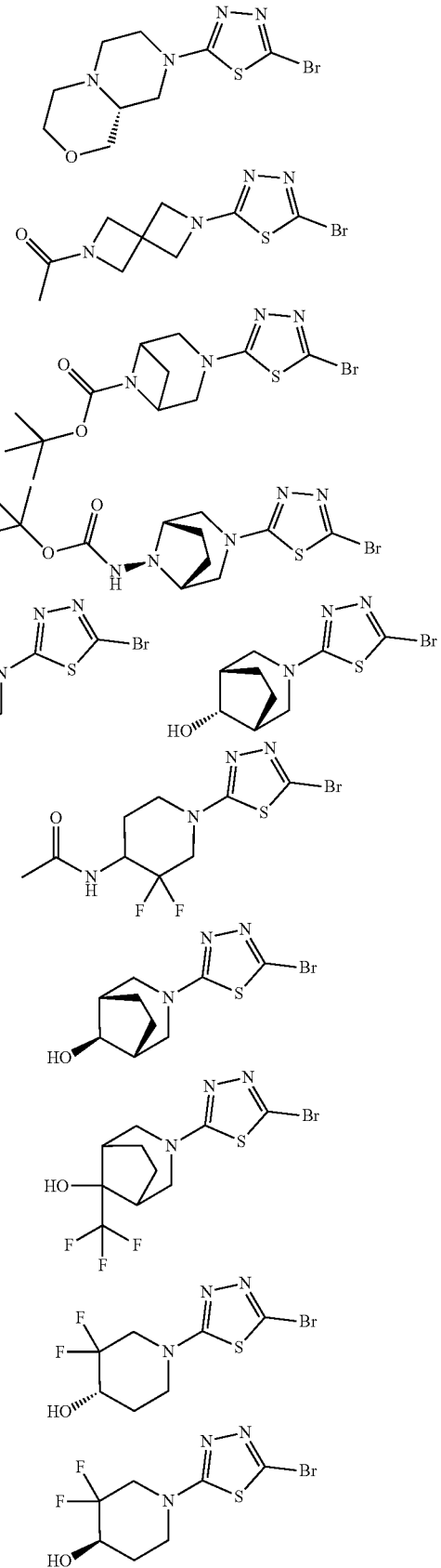

-continued
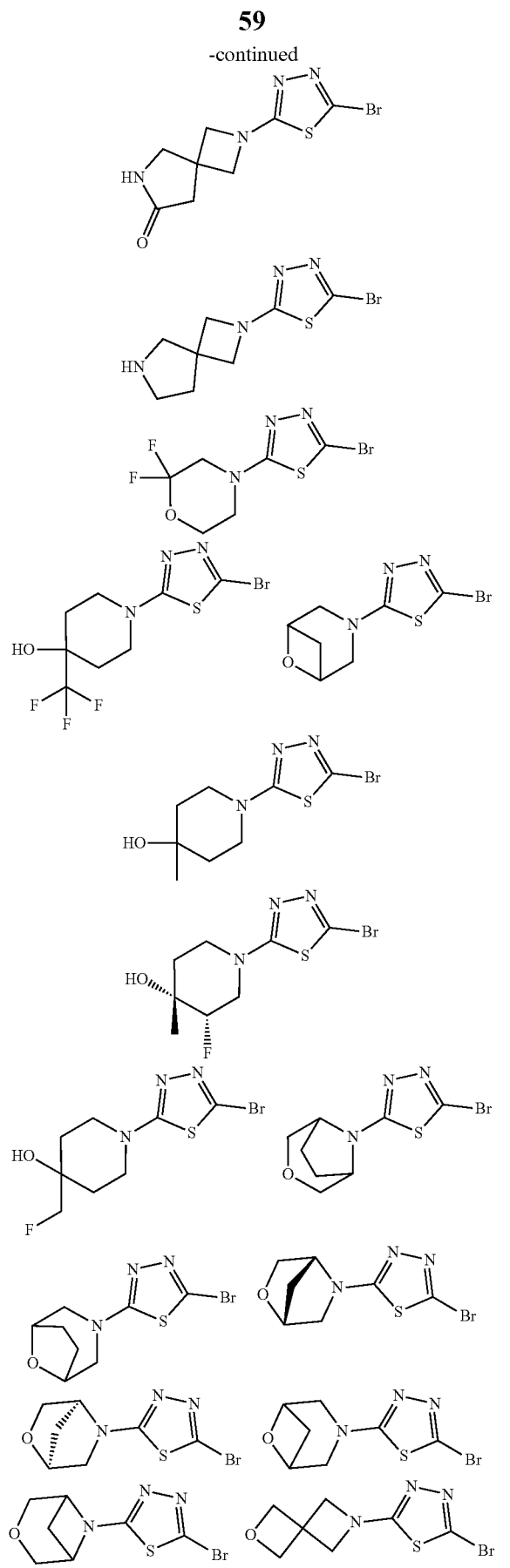
-continued
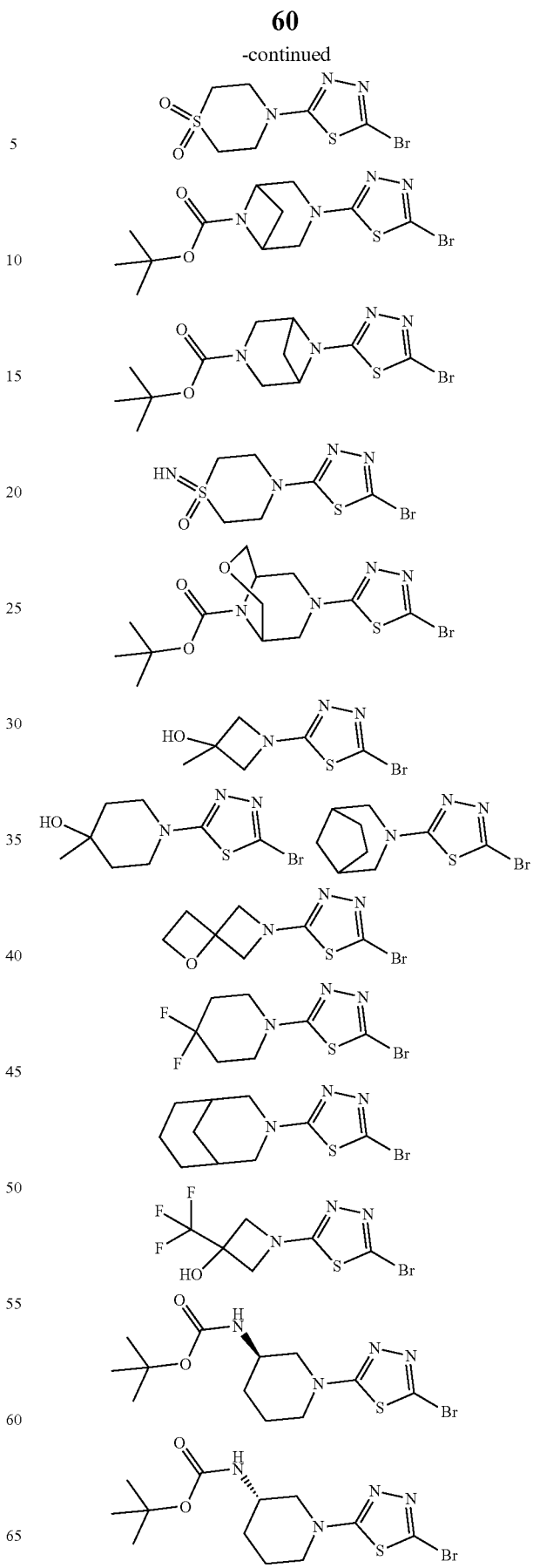

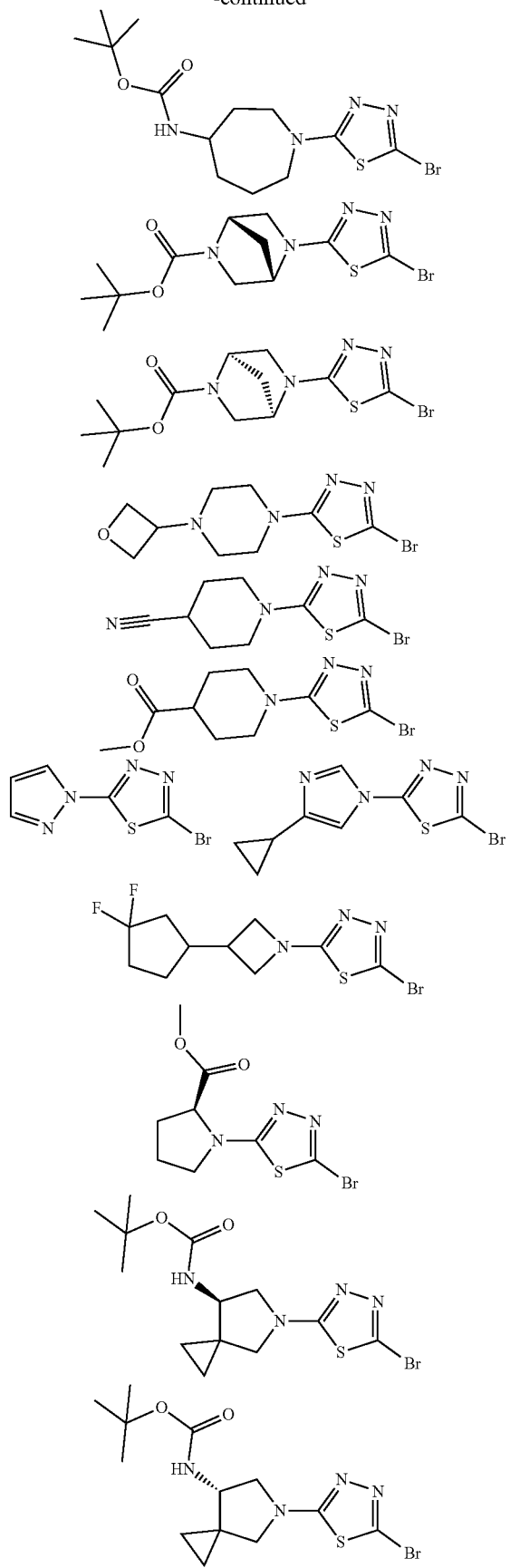
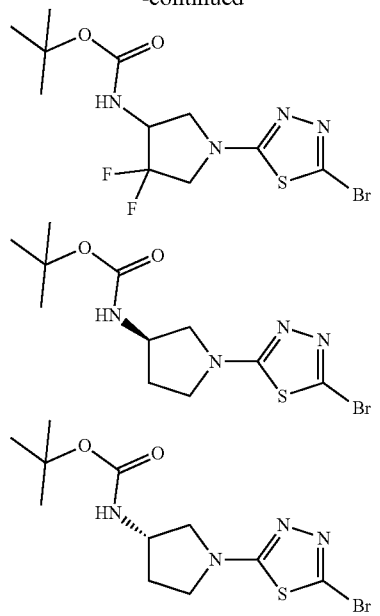

Preparation of Intermediate I-12

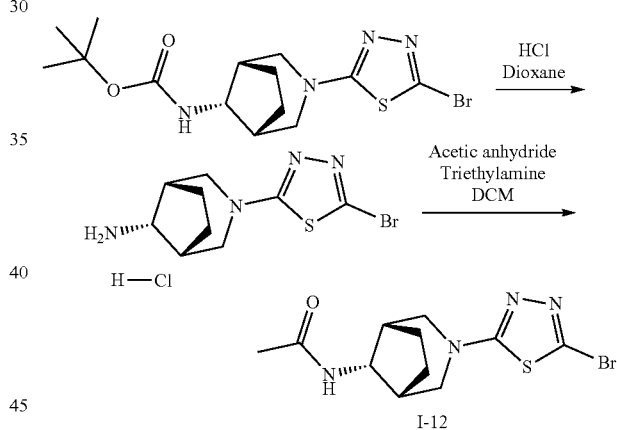

(1R,5S,8r)-3-(5-bromo-1,3,4-thiadiazol-2-yl)-3-azabicyclo[3.2.1]octan-8-amine hydrochloride: To a solution of tert-butyl ((1R,5S,8r)-3-(5-bromo-1,3,4-thiadiazol-2-yl)-3-azabicyclo[3.2.1]octan-8-yl)carbamate (synthesized as described for I-11) (40.0 mg, 0.10 mmol) in 1,4-dioxane (0.5 mL) was added hydrochloric acid (4M in dioxane, 0.13 mL, 0.51 mmol). The reaction mixture was stirred at 40° C. for 90 minutes, then concentrated in vacuo and used without additional purification.
ES/MS: 289.17, 291.07 [M+H$^+$].

N-((1R,5S,8r)-3-(5-bromo-1,3,4-thiadiazol-2-yl)-3-azabicyclo[3.2.1]octan-8-yl)acetamide (I-12): To a suspension of (1R,5S,8r)-3-(5-bromo-1,3,4-thiadiazol-2-yl)-3-azabicyclo[3.2.1]octan-8-amine hydrochloride (29.7 mg, 0.10 mmol) in DCM (1.0 mL) was added triethylamine (57 µL, 0.41 mmol) followed by acetic anhydride (11.7 µL, 0.12 mmol). The reaction mixture was stirred at RT for 10 minutes, then concentrated in vacuo and purified by silica gel column chromatography (eluent: MeOH/DCM) to provide I-12.
ES/MS: 331.37, 333.03 [M+H$^+$].

The following intermediates were synthesized as described for I-12 using the appropriate amine in step 1, and the appropriate anhydride, acid chloride, chloroformate, or sulfonyl chloride in step 2:
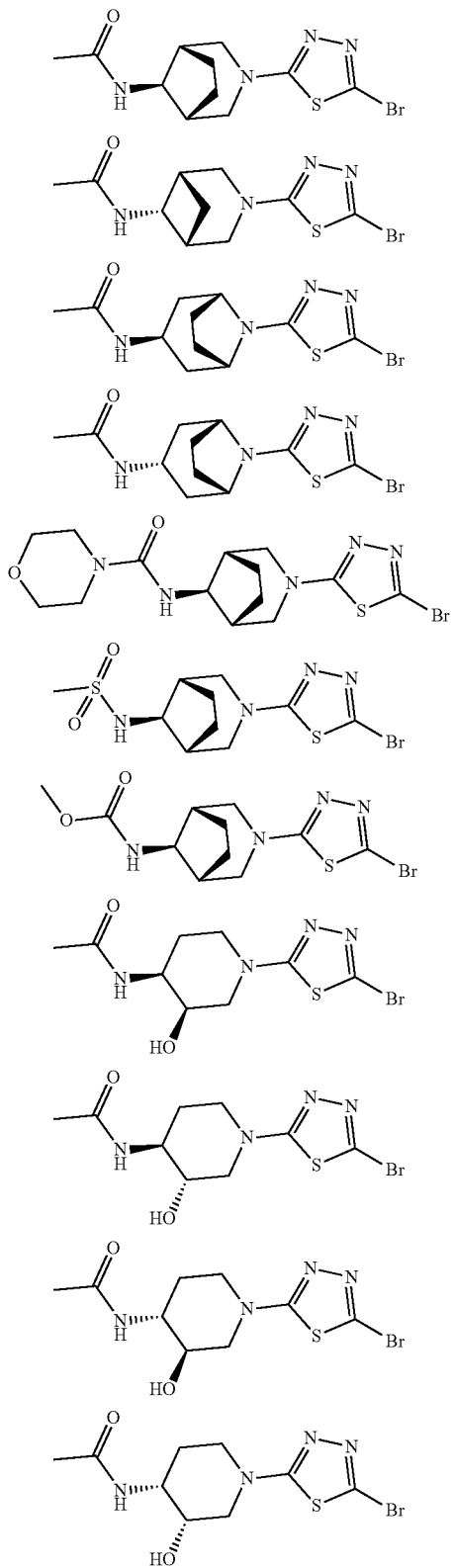
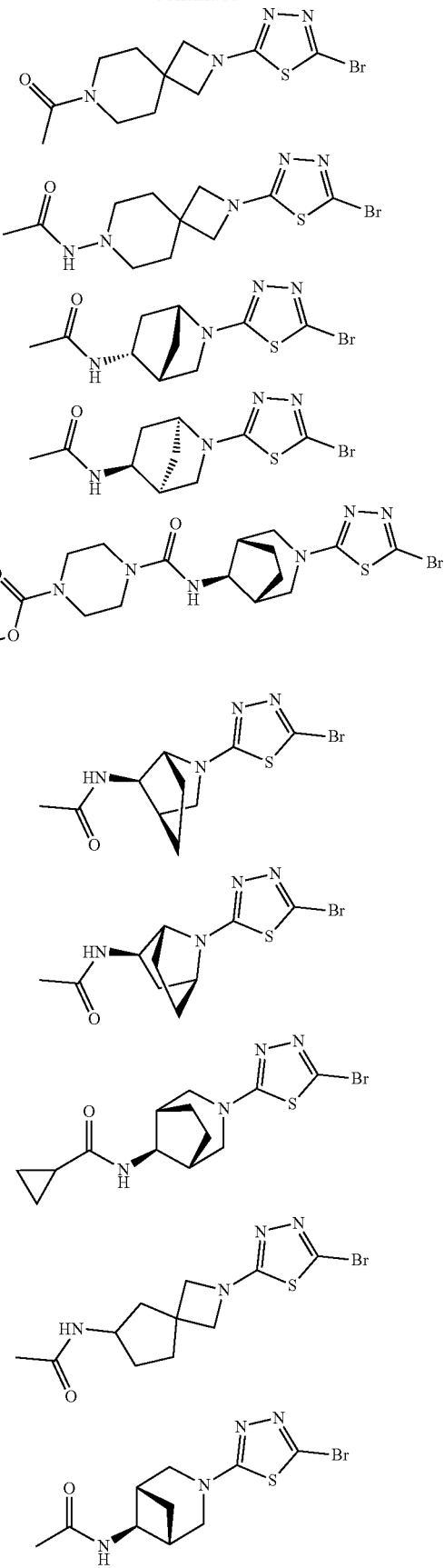

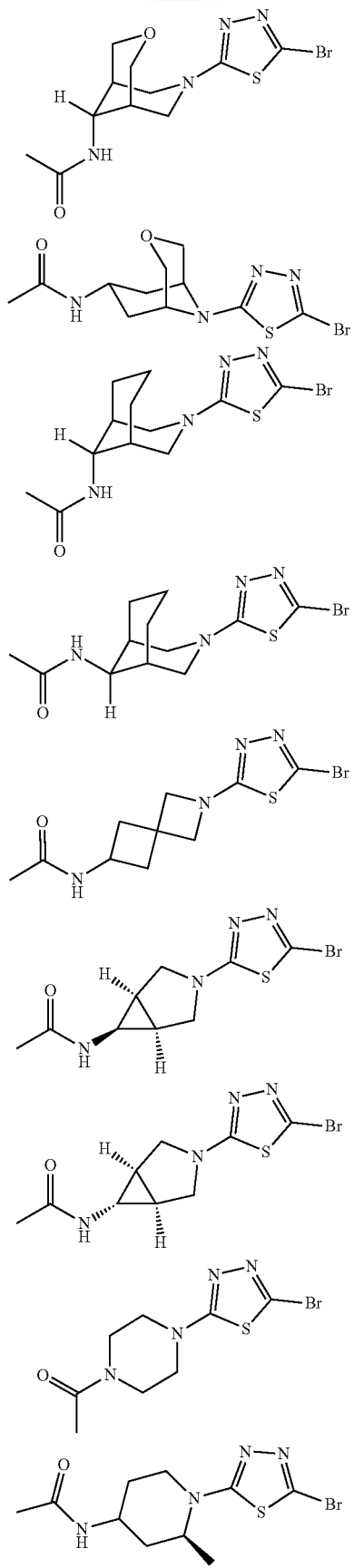
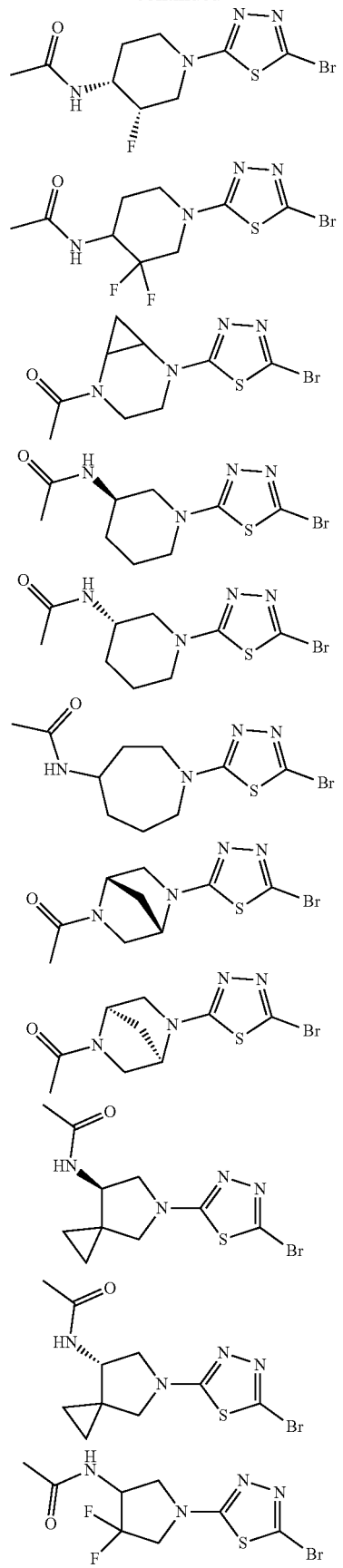

-continued

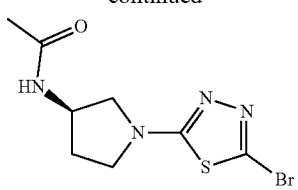

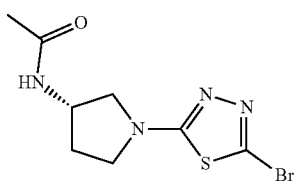

Preparation of Intermediate I-13

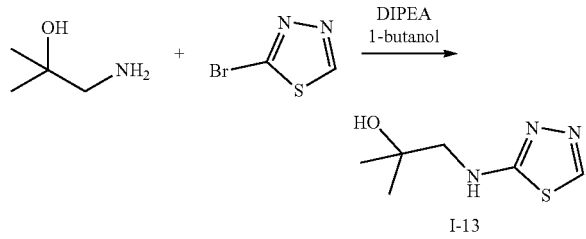

1-((1,3,4-thiadiazol-2-yl)amino)-2-methylpropan-2-ol (I-13): To a solution of 2-bromo-1,3,4-thiadiazole (100 mg, 0.61 mmol) and 1-amino-2-methyl-propan-2-ol (56 µL, 0.91 mmol) in 1-butanol (1.2 mL) was added N,N-diisopropylethylamine (264 µL, 1.52 mmol). The reaction mixture was stirred in a sealed vial at 120° C. for 1 hour, then concentrated and purified by silica gel column chromatography (eluent: MeOH/DCM) to provide I-13.

Preparation of Intermediate: I-14

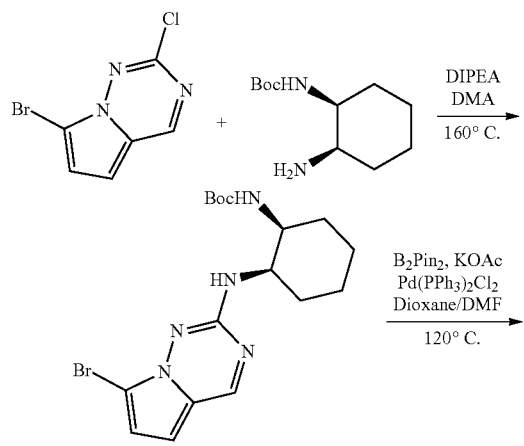

-continued

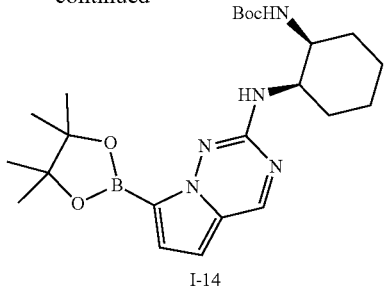

I-14 tert-butyl ((1S,2R)-2-((7-bromopyrrolo[2,1-f][1,2,4]triazin-2-yl)amino)cyclohexyl)carbamate: To a solution of 7-bromo-2-chloropyrrolo[2,1-f][1,2,4]triazine (150 mg, 0.65 mmol) and tert-butyl ((1S,2R)-2-aminocyclohexyl)carbamate (152 mg, 0.71 mmol) in DMA (2.0 mL) was added N,N-diisopropylethylamine. The reaction mixture was heated to 160° C. in a microwave reactor for one hour. The cooled reaction mixture was diluted with water and extracted 3× with EtOAc. The combined organic layers were washed with saturated aqueous ammonium chloride and brine, then dried over sodium sulfate, isolated by vacuum filtration, and concentrated in vacuo. The resulting oil was purified by silica gel column chromatography (eluent: EtOAc/hexanes) to provide the desired material.
ES/MS: 410.90, 412.04 [M+H⁺].

tert-butyl ((1S,2R)-2-((7-(4,4,5,5-tetramethyl-1,3,2-dioxaborolan-2-yl)pyrrolo[2,1-f][1,2,4]triazin-2-yl)amino)cyclohexyl)carbamate (I-14): A microwave vial was charged with tert-butyl ((1S,2R)-2-((7-bromopyrrolo[2,1-f][1,2,4]triazin-2-yl)amino)cyclohexyl)carbamate (150 mg, 0.37 mmol), bis(pinacolato)diboron (149 mg, 0.59 mmol), trans-dichlorobis(triphenylphosphine)palladium (II) (12.9 mg, 0.018 mmol), and potassium acetate (109 mg, 1.11 mmol). Dioxane (0.82 mL) and DMF (0.4 mL) were added, and the reaction mixture was degassed by bubbling argon through the mixture for 60 seconds. The vial was sealed, and the reaction mixture was heated at 150° C. in a microwave reactor for 20 minutes. The reaction mixture was filtered, and the filtrate was concentrated and purified by silica gel column chromatography (eluent: EtOAc/hexanes) to provide I-14. Mass fragmentation provided the mass of the boronic acid.
ES/MS: 376.21 [M+H⁺].

Preparation of Intermediates I-15

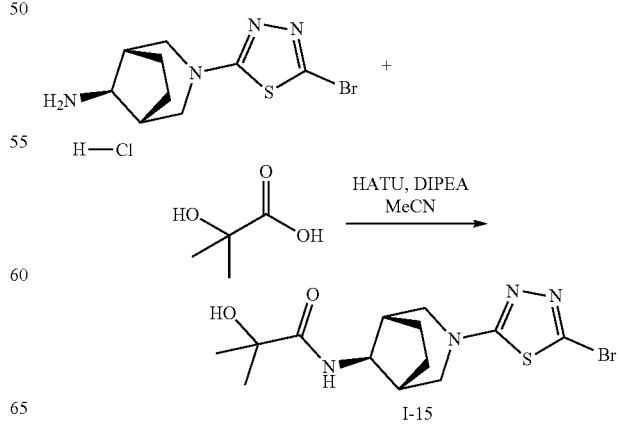

N-((1R,5S,8s)-3-(5-bromo-1,3,4-thiadiazol-2-yl)-3-azabicyclo[3.2.1]octan-8-yl)-2-hydroxy-2-methylpropanamide (I-15): To a solution of 2-hydroxyisobutyric acid (35.2 mg, 0.34 mmol) and HATU (128 mg, 0.34 mmol) in MeCN (0.5 mL) was added N,N-diisopropylethylamine (0.12 mL, 0.65 mmol). The mixture was stirred for 5 minutes, then a solution of (1R,5S,8s)-3-(5-bromo-1,3,4-thiadiazol-2-yl)-3-azabicyclo[3.2.1]octan-8-amine hydrochloride (100 mg, 0.31 mmol) and N,N-diisopropylethylamine (0.16 mL, 0.92 mmol) in MeCN (0.5 mL) was added. Upon completion, the reaction mixture was concentrated and purified by silica gel column chromatography (eluent: MeOH/DCM) to provide I-15.
ES/MS: 375.44, 377.07 [M+H$^+$].

Preparation of Intermediate I-16

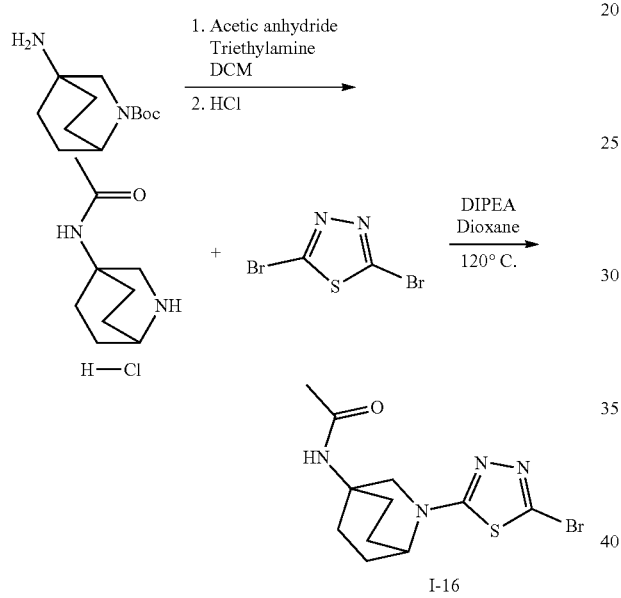

I-16

N-(2-azabicyclo[2.2.2]octan-4-yl)acetamide hydrochloride: To a solution of tert-butyl 4-amino-2-azabicyclo[2.2.2]octane-2-carboxylate (200 mg, 0.88 mmol) in DCM (2.0 mL) was added triethylamine (0.25 mL, 1.77 mmol) followed by acetic anhydride (92 µL, 0.97 mmol). The reaction mixture was stirred for 30 minutes, then concentrated in vacuo. To the resulting oil was added HCl (4M in 1,4-dioxane, 2.2 mL, 8.8 mmol). The suspension was stirred at 40° C. for 2 hours, then concentrated and used without additional purification.

N-(2-(5-bromo-1,3,4-thiadiazol-2-yl)-2-azabicyclo[2.2.2]octan-4-yl)acetamide (I-16): To a crude suspension of N-(2-azabicyclo[2.2.2]octan-4-yl)acetamide hydrochloride (132 mg, 0.65 mmol) in dioxane (2 mL) was added 2,5-dibromo-1,3,4-thiadiazole (75.0 mg, 0.31 mmol) followed by N,N-diisopropylethylamine (0.27 mL, 1.5 mmol). The reaction mixture was heated at 120° C. for 1 hour. The cooled reaction mixture was concentrated in vacuo and purified by silica gel column chromatography (eluent: MeOH/DCM) to provide I-16.
ES/MS: 331.19, 333.10 [M+H$^+$].

The following intermediates were synthesized as described for I-16 using the appropriate starting amine:

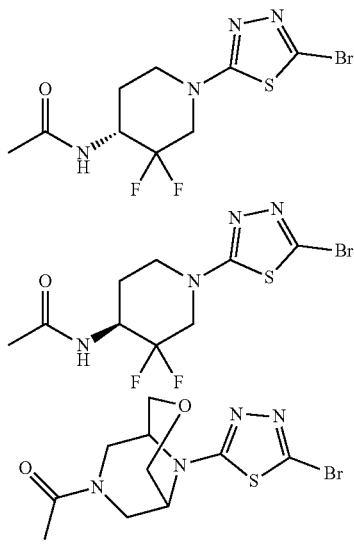

Preparation of Intermediate I-17

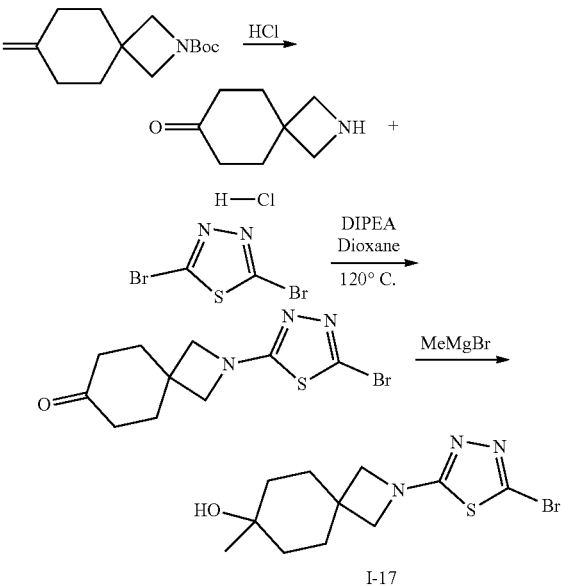

I-17

2-azaspiro[3.5]nonan-7-one hydrochloride: Tert-butyl 7-oxo-2-azaspiro[3.5]nonane-2-carboxylate (150 mg, 0.63 mmol) was taken in HCl (4M in 1,4-dioxane, 1.6 mL, 6.27 mmol) and heated at 40° C. for 30 minutes. The reaction mixture was concentrated and used without purification.

2-(5-bromo-1,3,4-thiadiazol-2-yl)-2-azaspiro[3.5]nonan-7-one: To a suspension of crude 2-azaspiro[3.5]nonan-7-one hydrochloride (110 mg, 0.63 mmol) in dioxane (2.0 mL) was added 2,5-dibromo-1,3,4-thiadiazole (125 mg, 0.51 mmol) and N,N-diisopropylethylamine (0.45 mL, 2.56 mmol). The reaction mixture was heated at 120° C. for one hour, then concentrated in vacuo and used without purification.

2-(5-bromo-1,3,4-thiadiazol-2-yl)-7-methyl-2-azaspiro[3.5]nonan-7-ol (I-17): To a solution of crude 2-(5-bromo-1,3,4-thiadiazol-2-yl)-2-azaspiro[3.5]nonan-7-one (155 mg, 0.51 mmol) in THF (1.0 mL) at 0° C. was added methylmagnesium bromide (3M in diethyl ether, 0.26 mL, 0.77 mmol). The reaction mixture was warmed to RT and stirred for one hour. The reaction mixture was quenched with saturated aqueous sodium bicarbonate and extracted with three portions of EtOAc. The combined organic layers were dried over sodium sulfate, isolated by filtration, concentrated in vacuo and purified by silica gel column chromatography (eluent: MeOH/DCM) to provide I-17.

ES/MS: 318.09, 320.06 [M+H⁺].

Preparation of Intermediate I-18

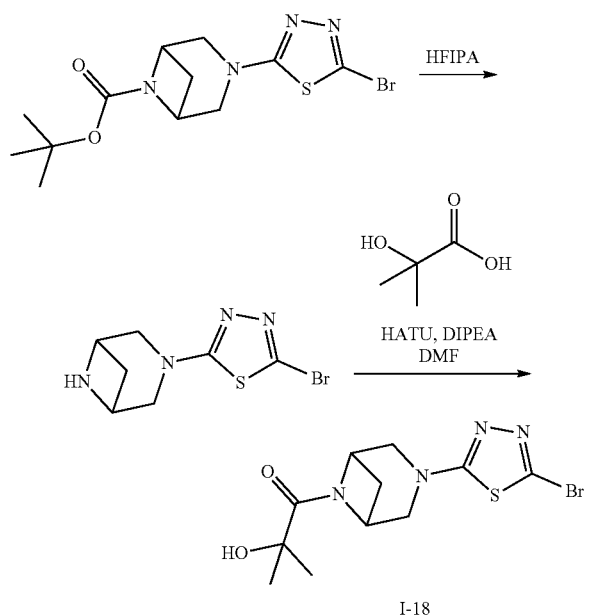

I-18

2-(3,6-diazabicyclo[3.1.1]heptan-3-yl)-5-bromo-1,3,4-thiadiazole: A solution of tert-butyl 3-(5-bromo-1,3,4-thiadiazol-2-yl)-3,6-diazabicyclo[3.1.1]heptane-6-carboxylate (synthesized following the protocol for I-11 using the appropriate amine) (150 mg, 0.42 mmol) in 1,1,1,3,3,3-hexafluoro-2-propanol (2.2 mL, 20.8 mmol) was heated in a microwave reactor 30 minutes at 150° C. The cooled reaction was concentrated in vacuo to provide the desired product which was used without purification.

ES/MS: 261.05, 263.02 [M+H⁺].

1-(3-(5-bromo-1,3,4-thiadiazol-2-yl)-3,6-diazabicyclo[3.1.1]heptan-6-yl)-2-hydroxy-2-methylpropan-1-one (I-18): To a solution of crude 2-(3,6-diazabicyclo[3.1.1]heptan-3-yl)-5-bromo-1,3,4-thiadiazole (108 mg, 0.42 mmol) and 2-hydroxy-2-methylpropanoic acid (56.2 mg, 0.54 mmol) in DMF (0.5 mL) was added N,N-diisopropylethylamine (0.30 mL, 1.66 mmol) followed by a solution of HATU (237 mg, 0.62 mmol) in DMF (0.5 mL). The reaction mixture was stirred at RT for 15 minutes, then concentrated in vacuo and partitioned between water and EtOAc. The aqueous later was extracted two additional times with EtOAc, and the combined organic layers were dried over sodium sulfate, isolated by filtration, concentrated in vacuo, and purified by silica gel column chromatography (eluent: MeOH/DCM) to provide I-18.

ES/MS: 347.04, 349.03 [M+H⁺].

Preparation of Intermediate I-19

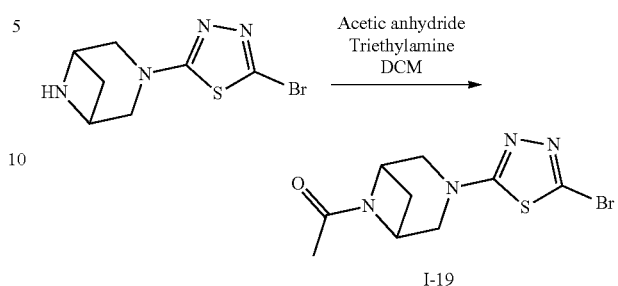

I-19

1-(3-(5-bromo-1,3,4-thiadiazol-2-yl)-3,6-diazabicyclo[3.1.1]heptan-6-yl)ethan-1-one (I-19): To a solution of crude 2-(3,6-diazabicyclo[3.1.1]heptan-3-yl)-5-bromo-1,3,4-thiadiazole (41.9 mg, 0.16 mmol) in DCM (3.2 mL) was added triethylamine (92 µL, 0.66 mmol) followed by acetic anhydride (16.7 µL, 0.18 mmol). The reaction mixture was stirred at RT for 30 minutes then concentrated in vacuo and purified by silica gel column chromatography (eluent: MeOH/DCM) to provide I-19.

ES/MS: 303.15, 305.08 [M+H⁺].

The following intermediates were synthesized as described for I-19 using the appropriate amine and the appropriate anhydride, acid chloride, chloroformate, or sulfonyl chloride:

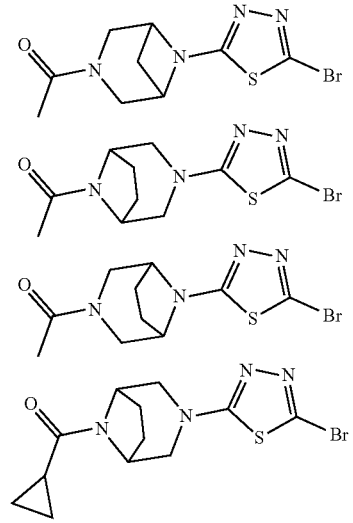

Preparation of Intermediate I-20

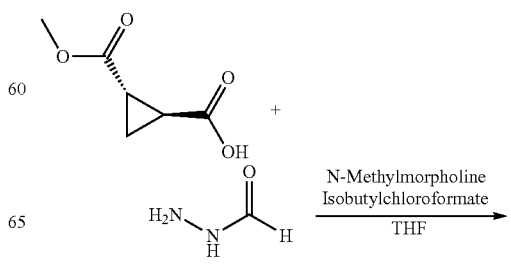

-continued

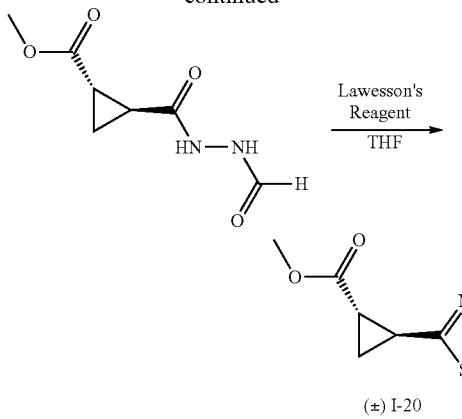

(±) I-20

(±) methyl trans-2-(2-formylhydrazine-1-carbonyl)cyclopropane-1-carboxylate: To a suspension of racemic trans-2-methoxycarbonylcyclopropanecarboxylic acid (2 g, 13.9 mmol) and N-methylmorpholine (1.68 mL, 15.3 mmol) in THF (50 mL) at 0° C. was added isobutyl chloroformate (1.98 mL, 15.3 mmol) dropwise. The suspension was stirred for 15 minutes at 0° C., and then formohydrazide (917 mg, 15.3 mmol) was added in one portion. The suspension was stirred for 10 minutes at 0° C., and was then stirred for 30 minutes at room temperature. Methanol (10 mL) was added to the reaction mixture, and slurry was filtered, rinsing with methanol. The filtrate was concentrated and used without further purification.

ES/MS: 187.009 (M+H⁺)

(±) methyl trans-2-(1,3,4-thiadiazol-2-yl)cyclopropane-1-carboxylate (±I-20): To a solution of methyl (1S,2S)-2-(2-formylhydrazine-1-carbonyl)cyclopropane-1-carboxylate (2 g, 10.7 mmol) in THF (50 mL) at 65° C. was added Lawesson's Reagent (6.52 g, 16.1 mmol) in one portion. The reaction was stirred at 65° C. for 20 minutes, until conversion of the starting material to desired product was observed by LCMS. The flask was cooled, and diluted with EtOAc (100 mL). The organic layer was washed with water (50 mL). The aqueous layer was back-extracted with EtOAc (2×50 mL), and the combined organic layers were dried over MgSO₄, filtered, and concentrated under reduced pressure. The crude material was purified twice by silica gel chromatography (eluent EtOAc/hexanes followed by methanol/EtOAc) to give ±I-20 as a clear viscous oil.

ES/MS: 185.023 [M+H]⁺

1H NMR (400 MHz, Methanol-d4) δ 9.32 (s, 1H), 3.76 (s, 3H), 3.13-2.98 (m, 1H), 2.41 (ddd, J=8.8, 5.7, 4.0 Hz, 1H), 1.76 (dddd, J=19.3, 8.8, 6.0, 4.5 Hz, 2H).

Preparation of Intermediates I-21

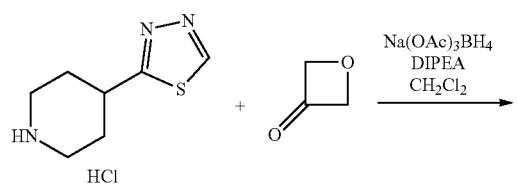

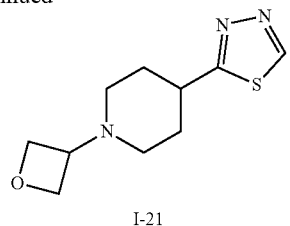

I-21

2-(1-(oxetan-3-yl)piperidin-4-yl)-1,3,4-thiadiazole (I-21): To a solution of 2-(piperidin-4-yl)-1,3,4-thiadiazole hydrochloride (synthesized as described for I-1 using the appropriate carboxylic acid) (200 mg, 0.97 mmol) in CH₂Cl₂ (5 mL) was added N,N-Diisopropylethylamine (0.17 mL, 0.97 mmol). The mixture was cooled to 0° C., and then oxetan-3-one (0.14 g, 1.94 mmol) was added, followed by sodium triacetoxyborohydride (618 mg, 2.92 mmol). The mixture was stirred under nitrogen for 90 minutes, upon which time conversion of the starting material to desired product was observed by LCMS. The reaction was quenched with 5 drops of sat. aq. NaHCO₃, and the crude reaction was dry-loaded onto silica. The crude material was purified by silica gel chromatography (eluent EtOAc/hexanes followed by methanol/EtOAc) to give I-21.

ES/MS: 226.178 [M+H]⁺

Preparation of Intermediate I-22

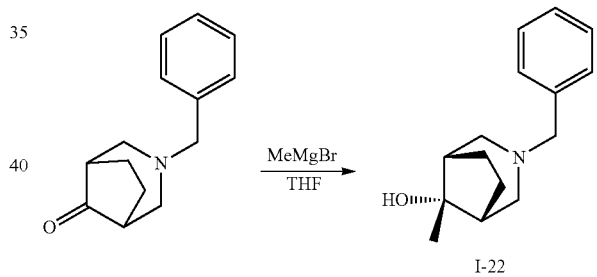

(1R,5S,8r)-3-benzyl-8-methyl-3-azabicyclo[3.2.1]octan-8-ol (I-22): To an oven-dried 250 mL round bottom flask was added 3-benzyl-3-azabicyclo[3.2.1]octan-8-one (3 g, 13.9 mmol), and the flask was placed under an N₂ atmosphere. THF (100 mL) was added, and the solution was cooled to −78° C. MeMgBr (3M in ether, 13.9 mL, 41.8 mmol) was added dropwise, and the reaction was stirred 30 min at −78° C. LCMS aliquot showed conversion to desired product. 10 mL sat. aq. ammonium chloride was added dropwise, and the mixture was allowed to warm to RT. The mixture was diluted with 200 mL EtOAc and 50 mL water, and the layers separated. The aq. layer was extracted twice with 50 mL EtOAc, and the combined organic layers were dried over MgSO₄, filtered, and concentrated. The crude material was purified by silica gel chromatography (eluent EtOAc/hexanes) to give I-22.

ES/MS: 232.390 [M+H]⁺

1H NMR (400 MHz, Chloroform-d) δ 7.40-7.22 (m, 5H), 3.57 (s, 2H), 2.69 (d, J=10.6 Hz, 2H), 2.53-2.44 (m, 2H), 1.82 (dt, J=8.0, 2.2 Hz, 2H), 1.69 (d, J=4.1 Hz, 4H), 1.29 (s, 3H).

Preparation of Intermediate I-23

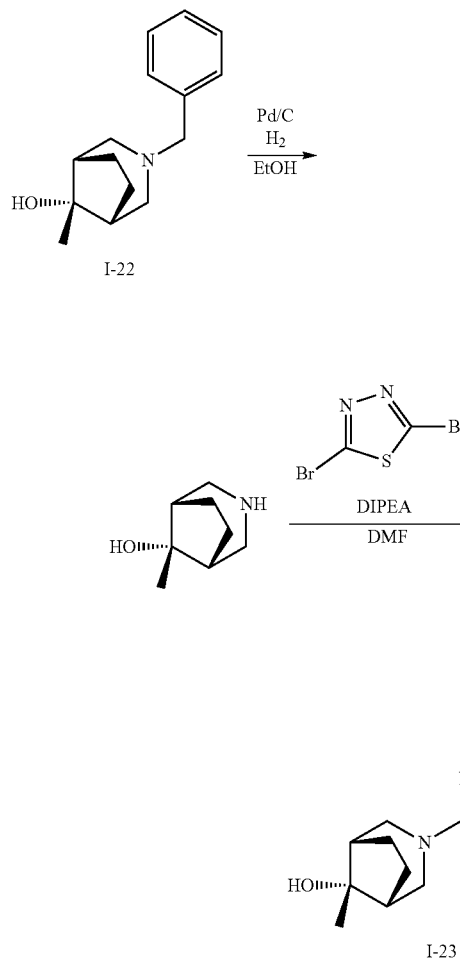

Preparation of Intermediate I-24

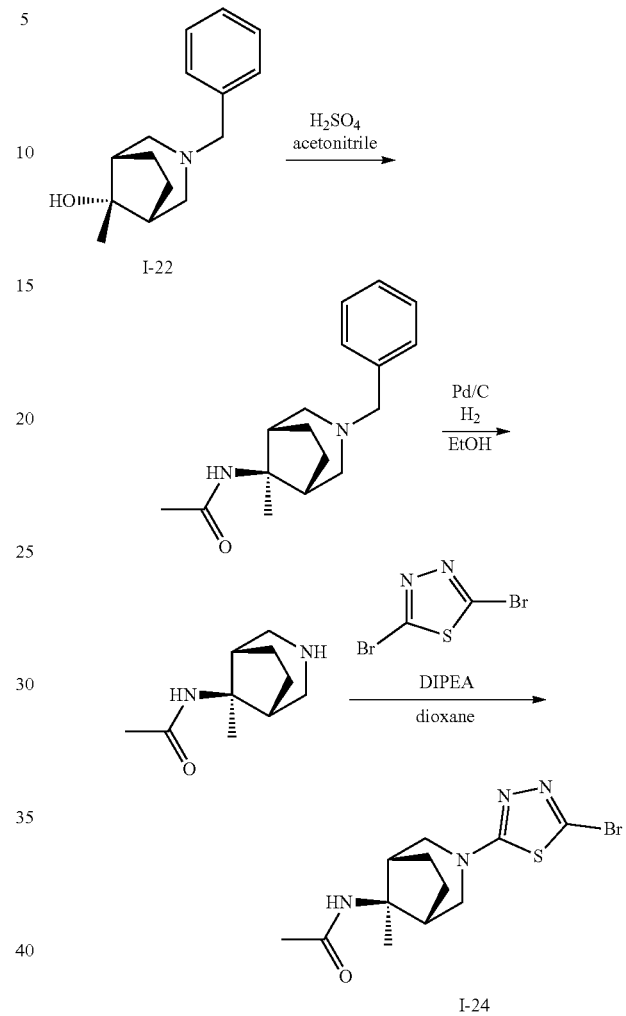

(1R,5S,8r)-8-methyl-3-azabicyclo[3.2.1]octan-8-ol: To a 25 mL round bottom flask was added I-22 (0.75 g, 3.24 mmol) and ethanol (10 mL). Pd on carbon (10% wt, 0.1 g) was added in one portion, and the mixture was degassed with $H_2$ before stirring overnight under an $H_2$ atmosphere. LCMS showed complete conversion to the desired product, and the mixture was degassed with argon. The mixture was filtered over celite to remove the solids, rinsing with EtOH. The filtrate was concentrated, and used directly for next step. ES/MS: 142.189 [M+H]$^+$ (1R,5S,8r)-3-(5-bromo-1,3,4-thiadiazol-2-yl)-8-methyl-3-azabicyclo[3.2.1]octan-8-ol (I-23): To a solution of 2,5-dibromo-1,3,4-thiadiazole (777 mg, 3.19 mmol) and (1R,5S,8r)-8-methyl-3-azabicyclo[3.2.1]octan-8-ol (450 mg, 3.19 mmol) in DMF (2.0 mL) was added N,N-diisopropylethylamine (1.11 mL, 6.37 mmol). The reaction mixture was stirred at 120° C. in a sealed vial for one hour. The cooled reaction mixture was diluted with EtOAc (50 mL), and washed twice with water (15 mL). The organic layer was dried over MgSO$_4$, filtered, concentrated under reduced pressure, and purified by silica gel column chromatography (eluent: EtOAc/hexanes) to provide I-23.
ES/MS: 304.309 [M+H$^+$].

N-((1R,5S,8s)-3-benzyl-8-methyl-3-azabicyclo[3.2.1]octan-8-yl)acetamide: To a 250 mL round bottomed flask was added 3-benzyl-8-methyl-3-azabicyclo[3.2.1]octan-8-ol (I-22) (2 g, 8.65 mmol) and acetonitrile (15 mL), and the solution was then cooled to 0° C. Concentrated Sulfuric acid (12 mL) was added dropwise, and the reaction was warmed to RT and stirred overnight. The reaction mixture was poured into ice, and the resulting solution was adjusted (carefully) to pH 10 with sat. aq. KOH. Significant precipitates appeared. Mixture extracted with EtOAc (3×200 mL), and organic layers were dried over MgSO$_4$, filtered, and concentrated. The crude material purified by silica gel column chromatography (eluent: EtOAc/hexanes, then MeOH/EtOAc) to provide the product.
ES/MS: 273.250 [M+H]$^+$
1H NMR (400 MHz, Chloroform-d) δ 7.38-7.19 (m, 5H), 5.11 (s, 1H), 3.56 (s, 2H), 2.61-2.49 (m, 4H), 2.29 (s, 2H), 1.94 (s, 3H), 1.89-1.74 (m, 4H), 1.53 (s, 3H).

N-((1R,5S,8s)-8-methyl-3-azabicyclo[3.2.1]octan-8-yl)acetamide: To a 25 mL round bottom flask was added N-((1R,5S,8s)-3-benzyl-8-methyl-3-azabicyclo[3.2.1]octan-8-yl)acetamide (0.14 g, 0.514 mmol) and ethanol (6 mL). Pd on carbon (10% wt, 55 mg) was added in one portion, and the mixture was degassed with $H_2$ before stirring overnight under an $H_2$ atmosphere. LCMS showed complete conversion to the desired product, and the mixture was degassed with argon. The mixture was filtered over celite to remove the solids, rinsing with EtOH. The filtrate was concentrated, and used directly for next step.
ES/MS: 183.203 [M+H]$^+$ N-((1R,5S,8s)-3-(5-bromo-1,3,4-thiadiazol-2-yl)-8-methyl-3-azabicyclo[3.2.1]octan-8-yl)acetamide (I-24): To a solution of 2,5-dibromo-1,3,4-thiadiazole (132 mg, 0.543 mmol) and N-((1R,5S,8s)-8-methyl-3-azabicyclo[3.2.1]octan-8-yl)acetamide (90 mg, 0.494 mmol) in 1,4-dioxane (0.5 mL) was added N,N-diisopropylethylamine (0.22 mL, 1.23 mmol). The reaction mixture was stirred at 120° C. in a sealed vial for one hour. The cooled reaction mixture was concentrated under reduced pressure, and purified by silica gel column chromatography (eluent: EtOAc/hexanes, then MeOH/EtOAc) to provide I-24.
ES/MS: 345.151 [M+H$^+$].
1H NMR (400 MHz, Chloroform-d) δ 5.20 (s, 1H), 3.61-3.43 (m, 4H), 2.66-2.55 (m, 2H), 2.04-1.90 (m, 5H), 1.73-1.65 (m, 2H), 1.62 (s, 3H).

Preparation of Intermediates I-25 and I-26

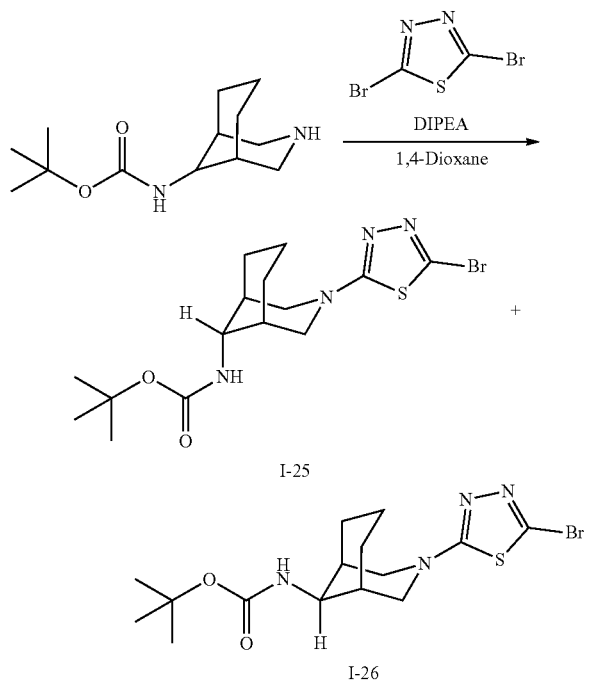

Exo-N-((1R,5S,9r)-3-(5-bromo-1,3,4-thiadiazol-2-yl)-3-azabicyclo[3.3.1]nonan-9-yl)acetamide (I-SEA6) and Endo-N-((1R,5S,9s)-3-(5-bromo-1,3,4-thiadiazol-2-yl)-3-azabicyclo[3.3.1]nonan-9-yl)acetamide (I-26): To a solution of 2,5-dibromo-1,3,4-thiadiazole (250 mg, 1.02 mmol) and tert-butyl N-(3-azabicyclo[3.3.1]nonan-9-yl)carbamate (246 mg, 1.02 mmol) in 1,4-dioxane (1 mL) was added N,N-Diisopropylethylamine (0.36 mL, 2.05 mmol). The reaction mixture was stirred at 120° C. in a sealed vial for one hour. The cooled reaction mixture was concentrated under reduced pressure, and purified by silica gel column chromatography (eluent: EtOAc/hexanes) to separate both isomers endo- (I-25) and exo- (I-26). The endo- and exo-isomers were distinguished by 2D NOESY spectroscopy.

I25: ES/MS: 403.851 [M+H$^+$].
1H NMR (400 MHz, Chloroform-d) δ 4.75 (s, 1H), 3.82-3.71 (m, 1H), 3.68-3.60 (m, 2H), 3.60-3.45 (m, 2H), 2.19 (s, 2H), 1.99-1.63 (m, 6H), 1.47 (s, 9H).

I-26: ES/MS: 403.204 [M+H$^+$].
1H NMR (400 MHz, Chloroform-d) δ 4.93 (d, J=7.4 Hz, 1H), 3.95-3.80 (m, 3H), 3.56 (dd, J=12.7, 3.5 Hz, 2H), 2.10 (s, 2H), 1.88-1.59 (m, 6H), 1.49 (s, 9H).

Preparation of Intermediate I-27

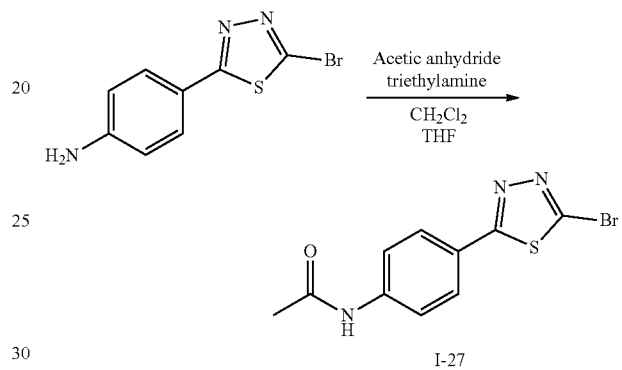

N-(4-(5-bromo-1,3,4-thiadiazol-2-yl)phenyl)acetamide (I-27): To a suspension of 4-(5-bromo-1,3,4-thiadiazol-2-yl) aniline (200 mg, 1.13 mmol) in $CH_2Cl_2$ (5 mL) and THF (5 mL) at 0° C. was added triethylamine (0.315 mL, 2.26 mmol) followed by acetic anhydride (0.11 mL, 1.13 mmol). The reaction mixture was stirred at RT for 1 hour, followed by 30 minutes at 40° C. The reaction was diluted with 20 mL EtOAc, and washed with 10 mL water. The aqueous layer was extracted with 3×10 mL EtOac, and the combined organic layers were dried over $MgSO_4$ and concentrated under reduced pressure. The residue was purified by silica gel column chromatography (eluent: EtOAc/hexanes, then MeOH/EtOAc) to provide I-27.
ES/MS: 220.113 [M+H$^+$].

Preparation of Intermediates I-28 and I-29

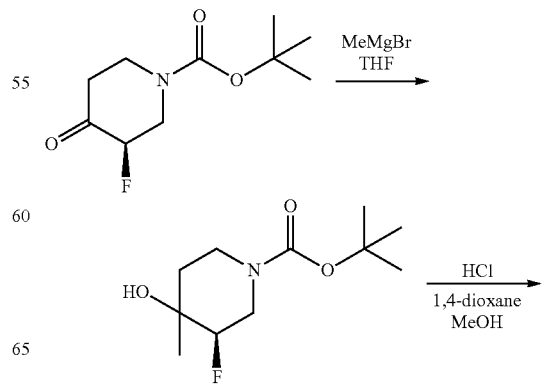

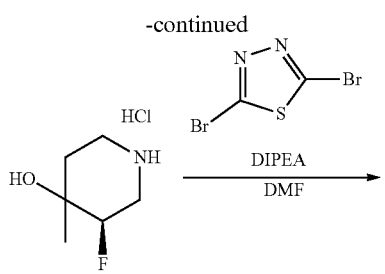

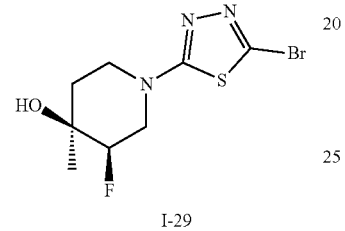

tert-butyl (3R)-3-fluoro-4-hydroxy-4-methylpiperidine-1-carboxylate: To an oven-dried 100 mL round bottom flask was added tert-butyl (3S)-3-fluoro-4-oxo-piperidine-1-carboxylate (1 g, 4.6 mmol), and the flask was placed under an $N_2$ atmosphere. THF (40 mL) was added, and the solution was cooled to −78° C. MeMgBr (3M in ether, 3.84 mL, 11.5 mmol) was added dropwise, and the reaction was stirred 5 minutes at −78° C. LCMS aliquot showed conversion to desired product. 5 mL Sat. aq. ammonium chloride was added dropwise, and the mixture was allowed to warm to RT. The mixture was diluted with 100 mL EtOAc and 50 mL water, and the layers separated. The aq. layer was extracted twice with 50 mL EtOAc, and the combined organic layers were dried over $MgSO_4$, filtered, and concentrated. The crude material was purified by silica gel chromatography (eluent EtOAc/hexanes) to give the product as a diastereomeric mixture.
ES/MS: 233.69 [M+H]$^+$ (3R)-3-fluoro-4-methylpiperidin-4-ol hydrochloride: To a solution of tert-butyl (3R)-3-fluoro-4-hydroxy-4-methylpiperidine-1-carboxylate (mixture of diastereomers) (1.03 g, 4.42 mmol) in 1,4-dioxane (8 mL) and methanol (3 mL) was added hydrochloric acid (4M in dioxane, 4.7 mL, 18.7 mmol). The reaction mixture was stirred at RT for 4 hours, then concentrated under reduced pressure and used without additional purification.
ES/MS: 134.129 [M+H$^+$].

(3R,4R)-1-(5-bromo-1,3,4-thiadiazol-2-yl)-3-fluoro-4-methylpiperidin-4-ol (I-28) and (3R,4S)-1-(5-bromo-1,3,4-thiadiazol-2-yl)-3-fluoro-4-methylpiperidin-4-ol (I-29): To a solution of 2,5-dibromo-1,3,4-thiadiazole (800 mg, 3.28 mmol) and (3R)-3-fluoro-4-methylpiperidin-4-ol hydrochloride (700 mg, 4.13 mmol) in DMF (4.0 mL) was added N,N-diisopropylethylamine (1.71 mL, 9.84 mmol). The reaction mixture was stirred at 120° C. in a sealed vial for one hour. The cooled reaction mixture was diluted with EtOAc (50 mL), and washed with sat. aq. NH$_4$Cl (20 mL). The aqueous was back-extracted three times with EtOAc (20 mL). The combined organic layers were dried over MgSO$_4$, filtered, concentrated under reduced pressure, and purified by silica gel column chromatography (eluent: EtOAc/hexanes) to provide a mixture of diastereomers, which were further separated by SFC.
I-28: ES/MS: 296.039 [M+H$^+$].
I-29: ES/MS: 296.034 [M+H$^+$].

The following intermediates were synthesized as described for I-28 using tert-butyl (3S)-3-fluoro-4-hydroxy-4-methylpiperidine-1-carboxylate in step 1:

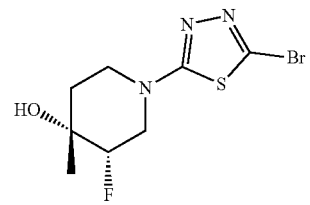

Preparation of Intermediate I-30

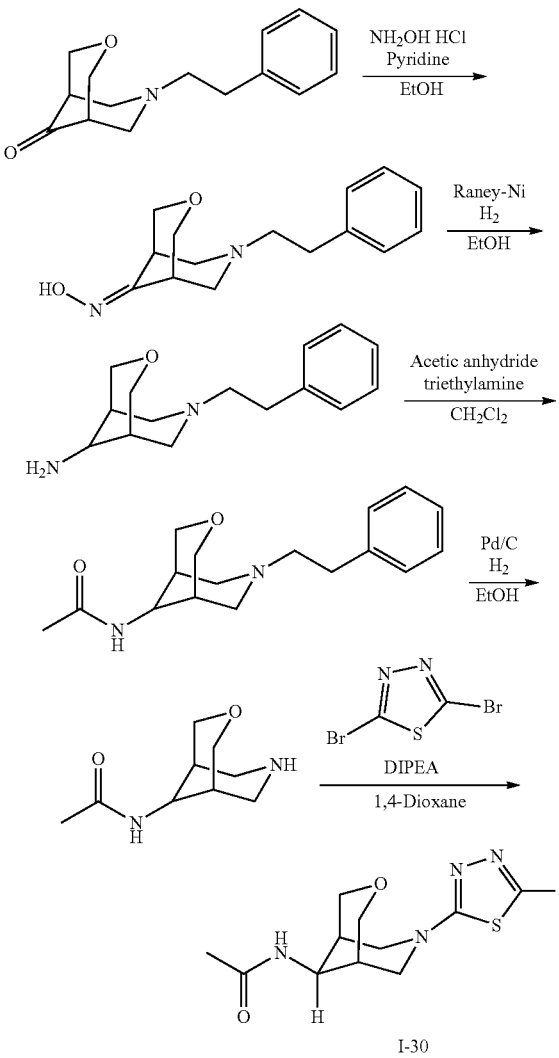

Endo-7-benzyl-3-oxa-7-azabicyclo[3.3.1]nonan-9-one oxime: 7-benzyl-3-oxa-7-azabicyclo[3.3.1]nonan-9-one (2 g, 8.65 mmol), hydroxylamine hydrochloride (900 mg, 13 mmol) and pyridine (1.2 mL, 14.9 mmol) in ethanol (20 mL) was heated to 100° C. for 2 hours. The reaction mixture was concentrated under reduced pressure. 2.5 N Aqueous sodium hydroxide solution (10 mL) was added to the residue. The resulting solution was extracted 2× with ethyl acetate (50 mL), washed with water, dried over magnesium sulfate, filtered and concentrated under reduced pressure. The crude product was purified by column chromatography on silica gel (eluent: EtOAc/hexane mixture) to afford the product.

7-benzyl-3-oxa-7-azabicyclo[3.3.1]nonan-9-amine: To a de-oxygentated solution of 7-benzyl-3-oxa-7-azabicyclo [3.3.1]nonan-9-one oxime (1.77 g, 7.19 mmol) in ethanol (50 mL) was added Raney nickel (0.6 g, suspension in water) under an argon atmosphere. The reaction was hydrogenated using a hydrogen balloon overnight. The reaction was filtered through a bed of celite and the filtrate was concentrated to dryness. Care was taken to avoid drying out the filtered nickel catalyst. The crude residue was purified by flash column chromatography on silica gel (eluent: MeOH/ $CH_2Cl_2$). A mixture of exo-and endo-isomers was obtained. ES/MS: 233.198 [M+H$^+$].

N-(7-benzyl-3-oxa-7-azabicyclo[3.3.1]nonan-9-yl)acetamide: To a suspension of 7-benzyl-3-oxa-7-azabicyclo [3.3.1]nonan-9-amine (1.43 g, 6.16 mmol) in $CH_2Cl_2$ (20 mL) at 0° C., was added triethylamine (1.72 mL, 12.3 mmol) and then acetic anhydride (0.64 mL, 6.77 mmol). The reaction mixture was stirred at 0° C. for 15 minutes, then diluted with EtOAc (50 mL) and sat. aq. $NH_4Cl$. The layers were separated, and the aqueous layer was extracted with EtOAc (5×20 mL). the combined organic layers were concentrated under reduced pressure and purified by silica gel column chromatography (eluent: EtOAc/hexanes, then MeOH/EtOAc) to provide the product.
ES/MS: 275.267 [M+H$^+$].

N-(3-oxa-7-azabicyclo[3.3.1]nonan-9-yl)acetamide: To a 100 mL round bottom flask was added N-(7-benzyl-3-oxa-7-azabicyclo[3.3.1]nonan-9-yl)acetamide (1.35 g, 4.92 mmol) and ethanol (20 mL). Pd on carbon (10% wt, 524 mg) was added in one portion, and the mixture was degassed with $H_2$ before stirring overnight under an $H_2$ atmosphere. LCMS showed complete conversion to the desired product, and the mixture was degassed with argon. The mixture was filtered over celite to remove the solids, rinsing with EtOH. The filtrate was concentrated, and used directly for next step.
ES/MS: 185.213 [M+H$^+$].

Endo-N-(7-(5-bromo-1,3,4-thiadiazol-2-yl)-3-oxa-7-azabicyclo[3.3.1]nonan-9-yl)acetamide (I-30): To a solution of 2,5-dibromo-1,3,4-thiadiazole (1.13 g, 4.64 mmol) and N-(3-oxa-7-azabicyclo[3.3.1]nonan-9-yl)acetamide (900 mg, 4.89 mmol) in 1,4-dioxane (6 mL) was added N,N-Diisopropylethylamine (1.7 mL, 9.77 mmol). The reaction mixture was stirred at 120° C. in a sealed vial for one hour. The cooled reaction mixture was concentrated under reduced pressure, and purified by silica gel column chromatography (eluent: EtOAc/hexanes) to yield a mixture of endo- and exo- isomers (approximately 1:4 endo:exo). The mixture was further purified by SFC to isolate the endo-isomer I-30.
ES/MS: 347.079 [M+H$^+$].
1H NMR (400 MHz, Methanol-d4) δ 4.15 (d, J=3.0 Hz, 1H), 4.10-4.00 (m, 4H), 3.89-3.77 (m, 2H), 3.77-3.67 (m, 2H), 2.06 (s, 3H), 1.97 (q, J=2.2 Hz, 2H).

Preparation of Intermediate I-31

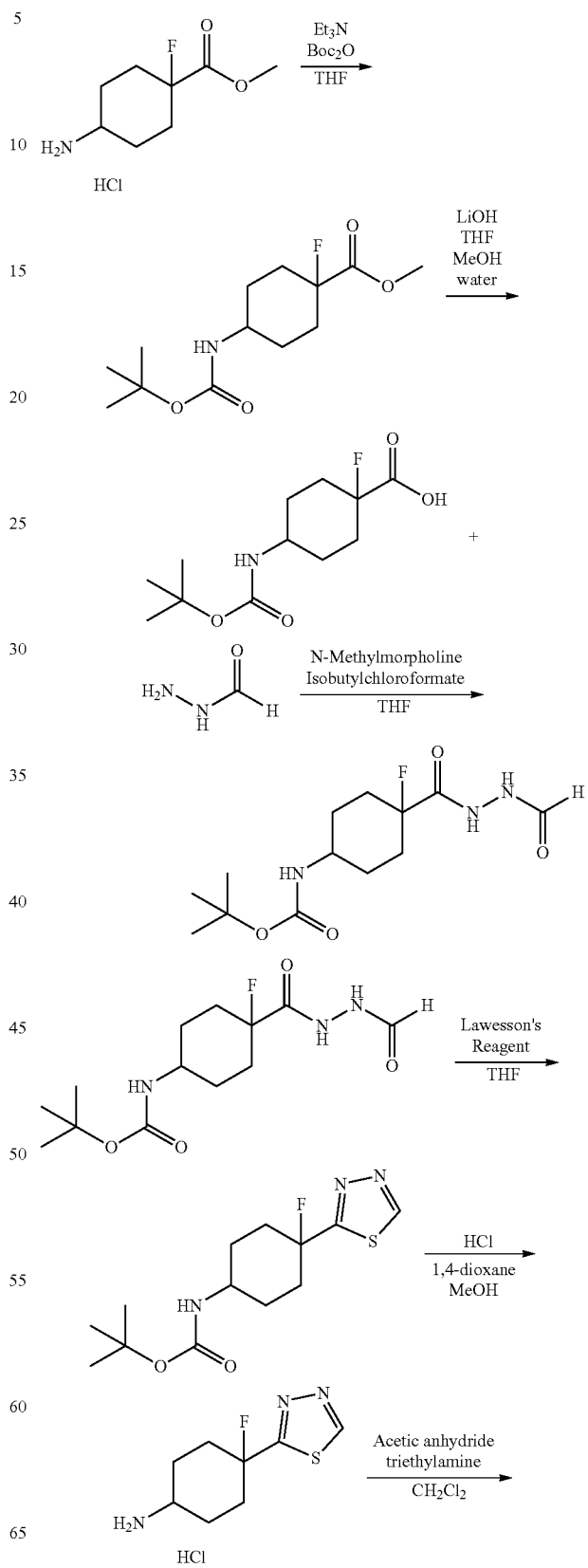

83

-continued

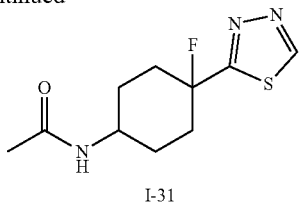

I-31 methyl 4-((tert-butoxycarbonyl)amino)-1-fluorocyclohexane-1-carboxylate: To a solution of trans-4-aminocyclohexane-1-fluoro-1-carboxylic acid methyl ester hydrochloride (3 g, 14.2 mmol) in THF (50 mL) was added triethylamine (4.35 mL, 31.2 mmol) and di-tert-butyl dicarbonate (3.4 g, 15.6 mmol) at room temperature. The mixture was stirred at room temperature overnight, then poured into saturated aqueous ammonium chloride (50mL) and extracted with ethyl acetate (3×100 mL). The combined organic phases were washed with water and brine, dried over anhydrous $MgSO_4$ and concentrated under reduced pressure to obtain the product. Material was used without further purification.
ES/MS: 233.924 $[M+H-^tBu]^+$.

4-((tert-butoxycarbonyl)amino)-1-fluorocyclohexane-1-carboxylic acid: To a 250 mL round bottom flask with methyl 4-((tert-butoxycarbonyl)amino)-1-fluorocyclohexane carboxylate (3.9 g, 14.2 mmol) was added THF (50 mL), MeOH (10 mL) and water (5 mL). LiOH (1M aq., 42.5 mL, 42.5 mmol) was added, and the mixture was stirred overnight at rt. The mixture was concentrated on the rotovap, and dissolved in EtOAc (100 mL). The mixture was acidified with 50% citric acid, and the layers separated. The aqueous layer was back extracted with 2×50 mL EtOAc. The combined organic layers were dried over $MgSO_4$, filtered, and concentrated under reduced pressure. Material was used without further purification.
ES/MS: 206.003 $[M+H-^tBu]^+$.

tert-butyl (4-fluoro-4-(2-formylhydrazine-1-carbonyl)cyclohexyl)carbamate: To a suspension of 4-((tert-butoxycarbonyl)amino)-1-fluorocyclohexane-1-carboxylic acid (3.6 g, 13.8 mmol) and N-methylmorpholine (1.67 mL, 15.2 mmol) in THF (50 mL) at 0° C. was added isobutyl chloroformate (1.97 mL, 15.2 mmol) dropwise. The suspension was stirred for 20 minutes at 0° C., and then formohydrazide (1.24 mg, 20.7 mmol) was added in one portion. The suspension was stirred for 1 hour at room temperature. Methanol (10 mL) was added to the reaction mixture, and slurry was filtered, rinsing with methanol. The filtrate was concentrated used without further purification.
ES/MS: 247.979 $(M+H-^tBu)^+$ tert-butyl (4-fluoro-4-(1,3,4-thiadiazol-2-yl)cyclohexyl)carbamate: To a solution of tert-butyl (4-fluoro-4-(2-formylhydrazine-1-carbonyl)cyclohexyl)carbamate (3.79 g, 12.5 mmol) in THF (100 mL) at 65° C. was added Lawesson's Reagent (7.58 g, 18.7 mmol) in one portion. The reaction was stirred at 65° C. for 60 minutes, until conversion of the starting material to desired product was observed by LCMS. The flask was cooled, and diluted with EtOAc (100 mL). The organic layer was washed with water (50 mL). The aqueous layer was back-extracted with EtOAc (2×50 mL), and the combined organic layers were dried over $MgSO_4$, filtered, and concentrated under reduced pressure. The crude material was purified by silica gel chromatography (eluent EtOAc/hexanes followed by methanol/EtOAc) to give the product.

84

ES/MS: 301.919 $(M+H^+)$ 4-fluoro-4-(1,3,4-thiadiazol-2-yl)cyclohexan-1-amine hydrochloride: To a solution of tert-butyl (4-fluoro-4-(1,3,4-thiadiazol-2-yl)cyclohexyl)carbamate (2.5 g, 8.3 mmol) in 1,4-dioxane (20 mL) and methanol (4 mL) was added hydrochloric acid (4M in dioxane, 10 mL, 40 mmol). The reaction mixture was stirred at RT for 1 hour, then overnight at 55° C. The mixture was concentrated under reduced pressure and used without additional purification.
ES/MS: 202.246 $[M+H^+]$.

N-(4-fluoro-4-(1,3,4-thiadiazol-2-yl)cyclohexyl)acetamide (I-31): To a suspension of 4-fluoro-4-(1,3,4-thiadiazol-2-yl)cyclohexan-1-amine hydrochloride (2.1 g, 8.83 mmol) in $CH_2Cl_2$ (50 mL) at 0° C., was added triethylamine (3.70 mL, 26.5 mmol) and then acetic anhydride (0.835 mL, 8.83 mmol). The reaction mixture was stirred at 0° C. for 15 minutes, then diluted with EtOAc (100 mL) and sat. aq. $NH_4Cl$ (30 mL). The layers were separated, and the aqueous layer was extracted with EtOAc (5×40 mL). The combined organic layers were concentrated under reduced pressure and purified by silica gel column chromatography (eluent: EtOAc/hexanes, then MeOH/EtOAc), then by silica gel column chromatography (eluent: MeOH/EtOAc) to provide the product I-31 as a mixture of diastereomers.
ES/MS: 244.045 $[M+H^+]$.

Preparation of Intermediate I-32

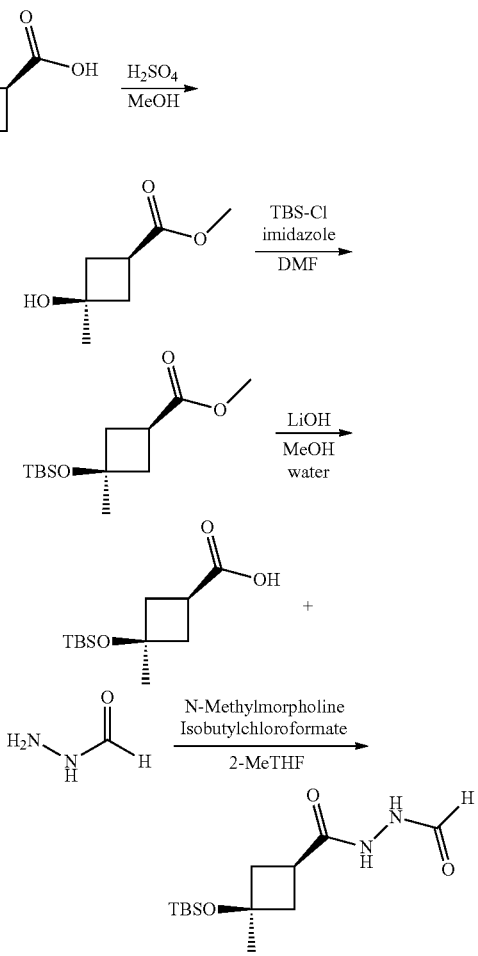

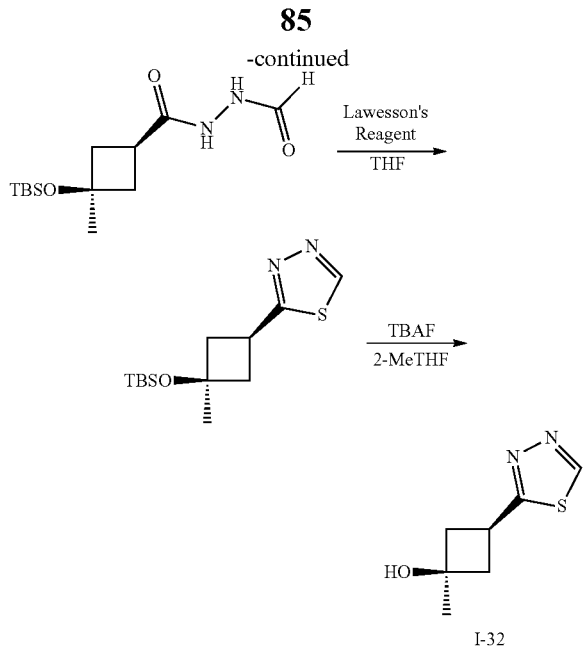

I-32 methyl trans-3-hydroxy-3-methylcyclobutane-1-carboxylate: To a solution trans-3-hydroxy-3-methylcyclobutane-1-carboxylic acid (850 mg, 6.53 mmol) in methanol (15 mL) was added concentrated sulfuric acid (0.142 mL). The mixture was refluxed overnight and then concentrated. The residue was dissolved in water (10 mL) and the mixture was extracted with ethyl acetate (20 mL×2). The combined organic phases were washed with sat. aq. NaHCO$_3$ (100 mL), and dried over MgSO$_4$. Concentration gave the methyl ester, which was carried forward.

methyl trans-3-((tert-butyldimethylsilyl)oxy)-3-methylcyclobutane-1-carboxylate: To methyl trans-3-hydroxy-3-methylcyclobutane-1-carboxylate (900 mg, 6.24 mmol) in anhydrous DMF (15 mL), was added imidazole (1.27 g, 18.7 mmol) and tert-Butyldimethylsilyl chloride (2.82 g, 18.7 mmol). The resulting mixture was heated at 80° C. overnight. After cooling to room temperature, water (20 mL) was added and the aqueous layer was extracted with ethyl acetate (40 mL×3). The combined organic layers were washed with brine and dried over anhydrous MgSO$_4$. The solid was filtered off and the filtrate was concentrated in vacuo. The residue was purified by silica gel chromatography, (eluent: EtOAc/hexanes)
ES/MS: 258.948 [M+H$^+$].

trans-3-((tert-butyldimethylsilyl)oxy)-3-methylcyclobutane-1-carboxylic acid: To a 50 mL round bottom flask was added methyl trans-3-((tert-butyldimethylsilyl)oxy)-3-methylcyclobutane-1-carboxylate (1.36 g, 5.26 mmol) and dissolved in MeOH (15 mL) and water (1 mL). Solid LiOH (378 mg, 15.8 mmol) was added, and the mixture was stirred overnight at 50° C. Most of the methanol was evaporated under reduced pressure, and the residue was dissolved in EtOAc (100 mL). The mixture was acidified with 50% aq. citric acid, and the layers were separated. The aq layer was extracted 2×50 mL EtOAc. The combined organic layers were dried over MgSO$_4$, filtered, and concentrated under reduced pressure. The material was carried forward without further purification.
ES/MS: 245.133 [M+H$^+$].

N-[[3-[tert-butyl(dimethyl)silyl]oxy-3-methyl-cyclobutanecarbonyl]amino]formamide: To a suspension of trans-3-((tert-butyldimethylsilyl)oxy)-3-methylcyclobutane-1-carboxylic acid (1.17 g, 4.79 mmol) and N-methylmorpholine (0.579 mL, 5.27 mmol) in 2-MeTHF (15 mL) at 0° C. was added isobutyl chloroformate (0.683 mL, 5.27 mmol) dropwise. The suspension was stirred for 20 minutes at 0° C., and then formohydrazide (575 mg, 9.57 mmol) was added in one portion. The suspension was stirred for 1 hour at room temperature. The resulting slurry was filtered. The filtrate was concentrated used without further purification.
ES/MS: 287.211 (M+H$^+$)

2-(trans-3-((tert-butyldimethylsilyl)oxy)-3-methylcyclobutyl)-1,3,4-thiadiazole: To a solution of N-[[3-[tert-butyl(dimethyl)silyl]oxy-3-methyl-cyclobutanecarbonyl]amino]formamide (1.3 g, 4.54 mmol) in THF (20 mL) at 65° C. was added Lawesson's Reagent (2.75 g, 6.81 mmol) in one portion. The reaction was stirred at 65° C. for 10 minutes, until conversion of the starting material to desired product was observed by LCMS. The flask was cooled, and dry loaded onto silica. The crude material was purified by silica gel chromatography (eluent EtOAc/hexanes followed by methanol/EtOAc) to give the product.
ES/MS: 285.226 (M+H$^+$)
1H NMR (400 MHz, Methanol-d4) δ 9.37 (s, 1H), 3.65 (tt, J=9.7, 8.0 Hz, 1H), 2.77-2.59 (m, 2H), 2.59-2.37 (m, 2H), 1.52 (d, J=0.9 Hz, 3H), 0.92 (s, 9H), 0.14 (s, 6H).

trans-1-methyl-3-(1,3,4-thiadiazol-2-yl)cyclobutan-1-ol (I-32): To a solution of 2-(trans-3-((tert-butyldimethylsilyl)oxy)-3-methylcyclobutyl)-1,3,4-thiadiazole (660 mg, 2.32 mmol) in 2-MeTHF (5 mL) was added TBAF (1M THF, 2.3 mL, 2.32 mmol). The reaction was stirred at room temperature overnight. Water (5 mL) was added to the reaction mixture and the resulting mixture was extracted with ethyl acetate (3×10 mL). The combined organic extracts were washed with brine, dried over MgSO$_4$, filtered and concentrated under reduced pressure. The crude material was purified by silica gel chromatography (eluent EtOAc/hexanes followed by methanol/EtOAc) to give the product I-32.
ES/MS: 171.049 (M+H$^+$)
1H NMR (400 MHz, Chloroform-d) δ 9.06 (s, 1H), 3.63 (p, J=8.5 Hz, 1H), 2.81-2.68 (m, 2H), 2.52 (td, J=9.4, 2.9 Hz, 2H), 1.53 (s, 3H).

Preparation of Intermediate I-33

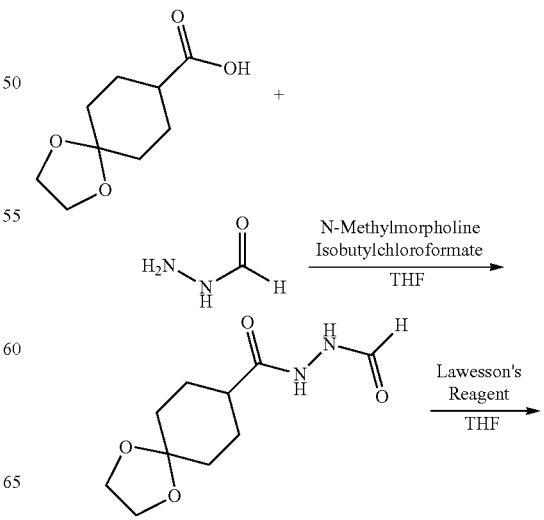

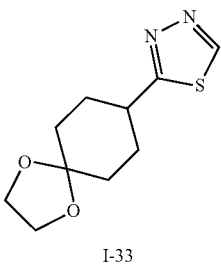

I-33

N'-formyl-1,4-dioxaspiro[4.5]decane-8-carbohydrazide: To a suspension of 1,4-dioxaspiro[4.5]decane-8-carboxylic acid (0.8 g, 4.3 mmol) and N-methylmorpholine (0.496 mL, 4.51 mmol) in THF (15 mL) at 0° C. was added isobutyl chloroformate (0.585 mL, 4.51 mmol) dropwise. The suspension was stirred for 30 minutes at 0° C., and then formohydrazide (387 mg, 6.44 mmol) was added in one portion. The suspension was stirred for 30 minutes at room temperature. The resulting slurry was filtered. The filtrate was concentrated used without further purification.

ES/MS: 229.032 (M+H$^+$)

2-(1,4-dioxaspiro[4.5]decan-8-yl)-1,3,4-thiadiazole (I-33): To a solution of N'-formyl-1,4-dioxaspiro[4.5]decane-8-carbohydrazide (0.9 g, 3.94 mmol) in THF (20 mL) at 65° C. was added Lawesson's Reagent (1.91 g, 4.73 mmol) in one portion. The reaction was stirred at 65° C. for 20 minutes, until conversion of the starting material to desired product was observed by LCMS. The flask was cooled, and dry loaded onto silica. The crude material was purified twice by silica gel chromatography (eluent EtOAc/hexanes followed by methanol/EtOAc) to give the product I-33.

ES/MS: 227.118 (M+H$^+$)

Preparation of Intermediate I-34

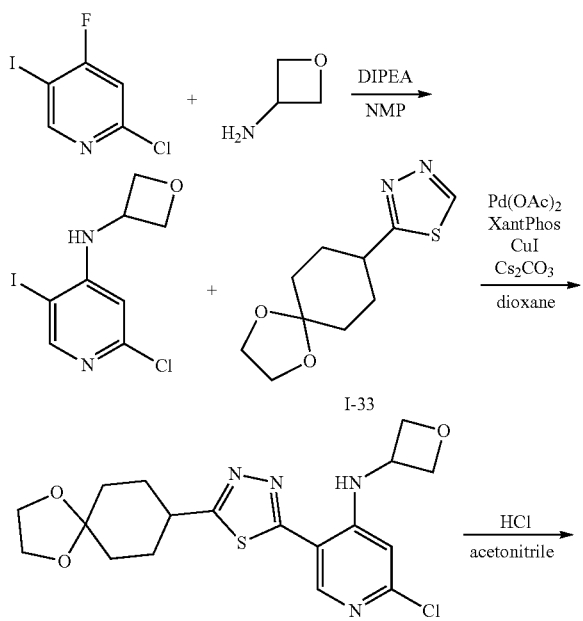

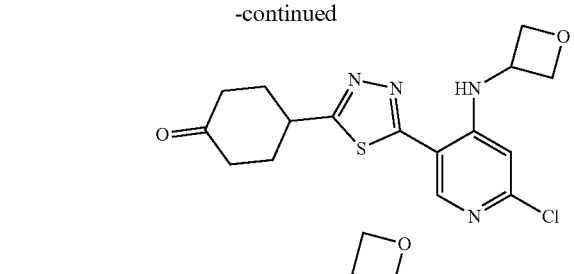

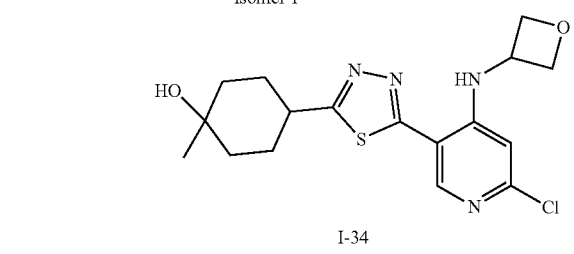

I-34 Isomer 1

I-34 Isomer 2

2-chloro-5-iodo-N-(oxetan-3-yl)pyridin-4-amine: To a solution of 2-chloro-4-fluoro-5-iodo-pyridine (750 mg, 2.91 mmol) and oxetan-3-amine (4.23 g, 68.0 mmol) in NMP (4.0 mL) was added N,N-diisopropylethylamine (319 mg, 4.37 mmol). The reaction mixture was heated in a microwave at 150° C. for 60 minutes, then cooled and diluted with EtOAc (50 mL) and water (10 mL). The resulting mixture was extracted with ethyl acetate (4×20 mL). The combined organic extracts were washed with brine, dried over MgSO$_4$, filtered and concentrated under reduced pressure. The crude material was purified by silica gel chromatography (eluent EtOAc/hexanes) to give the product

ES/MS: 311.183 (M+H$^+$)

5-(5-(1,4-dioxaspiro[4.5]decan-8-yl)-1,3,4-thiadiazol-2-yl)-2-chloro-N-(oxetan-3-yl)pyridin-4-amine: To a vial was added 2-chloro-5-iodo-N-(oxetan-3-yl)pyridin-4-amine (250 mg, 0.805 mmol), 2-(1,4-dioxaspiro[4.5]decan-8-yl)-1,3,4-thiadiazole (I-33) (219 mg, 0.0.966 mmol), Pd(OAc)$_2$ (45 mg, 0.2 mmol), Xantphos (234 mg, 0.4 mmol), copper(I) iodide (92 mg, 0.48 mmol), and cesium carbonate (787 mg, 2.4 mmol). 1,4-Dioxane (3 mL), was added, and the mixture was degassed with argon for 1 minute. The vial was sealed and stirred 1 hour at 105° C. Afterward, the vial was cooled, and purified by silica gel chromatography (eluent: EtOAc/hexanes, then MeOH/EtOAc) to yield the product.

ES/MS: 409.199 (M+H$^+$)

4-(5-(6-chloro-4-(oxetan-3-ylamino)pyridin-3-yl)-1,3,4-thiadiazol-2-yl)cyclohexan-1-one: To a vial with 5-(5-(1,4- dioxaspiro[4.5]decan-8-yl)-1,3,4-thiadiazol-2-yl)-2-chloro-N-(oxetan-3-yl)pyridin-4-amine (159 mg, 0.389 mmol) was added acetonitrile (5 mL) and HCl (1N aq, 2 mL, 2 mmol). The reaction was stirred for 4 hours at RT, then diluted with EtOAc (40 mL), and neutralized with sat. aq. NaHCO₃. The layers were separated, and the aqueous layer was extracted twice with 20 mL EtOAc. The combined organic layers were dried over MgSO₄, filtered, and concentrated under reduced pressure. The crude material was purified by silica gel chromatography (eluent: EtOAc/hexanes, then MeOH/EtOAc) to provide the product.
ES/MS: 365.131 (M+H⁺)

4-(5-(6-chloro-4-(oxetan-3-ylamino)pyridin-3-yl)-1,3,4-thiadiazol-2-yl)-1-methylcyclohexan-1-ol (I-34): To an oven-dried vial was added 4-(5-(6-chloro-4-(oxetan-3-ylamino)pyridin-3-yl)-1,3,4-thiadiazol-2-yl)cyclohexan-1-one (110 mg, 0.3 mmol), and the flask was placed under an N₂ atmosphere. THF (5 mL) was added, and the solution was cooled to −78° C. MeMgBr (3M in ether, 0.4 mL, 1.2 mmol) was added dropwise, and the reaction was stirred 15 minutes at −78° C. LCMS aliquot showed conversion to desired product. 5 mL Sat. aq.
ammonium chloride was added dropwise, and the mixture was allowed to warm to RT. The mixture was diluted with 30 mL EtOAc and 5 mL water, and the layers separated. The aq. layer was extracted twice with 10 mL EtOAc, and the combined organic layers were dried over MgSO₄, filtered, and concentrated. The crude material was purified by silica gel chromatography (eluent EtOAc/hexanes, then MeOH/EtOAc) to afford both separable isomers of the product I-34.
Isomer 1: ES/MS: 381.167 [M+H]⁺
Isomer 2: ES/MS: 381.207 [M+H]⁺

Preparation of Intermediate I-35

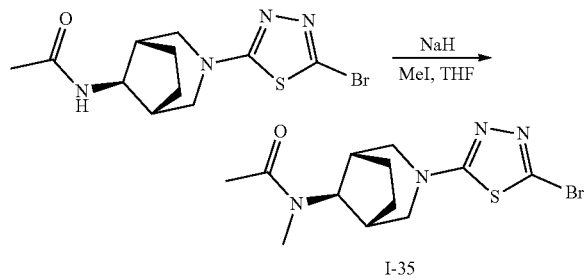

N-((1R,5S,8s)-3-(5-bromo-1,3,4-thiadiazol-2-yl)-3-azabicyclo[3.2.1]octan-8-yl)-N-methylacetamide (I-35): To a solution of N-((1R,5S,8s)-3-(5-bromo-1,3,4-thiadiazol-2-yl)-3-azabicyclo[3.2.1]octan-8-yl)acetamide (50 mg, 0.15 mmol) in THF (1.5 mL) was added sodium hydride (5 mg, 0.22 mmol). Gas evolution was observed and the resulting mixture stirred at room temperature for 5 minutes before iodomethane (0.011 mL, 0.18 mmol) was added. The reaction was stirred at room temperature for 3 days before additional sodium hydride (5 mg, 0.22 mmol) and iodomethane (0.011 mL, 0.18 mmol) was added. Upon completion, the reaction mixture was poured into water/NH₄Cl and extracted with EtOAc. The combined organic layers were dried over MgSO₄, filtered and concentrated. The resulting crude residue was purified by silica gel chromatography (eluent: MeOH/CH₂Cl₂) to give I-35.
ES/MS: 345.160 [M+H]⁺

Preparation of Intermediate I-36

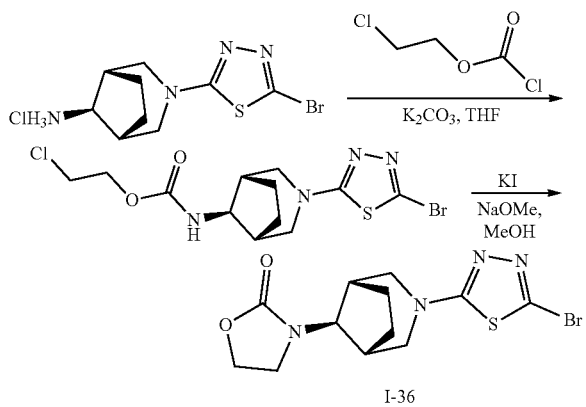

2-Chloroethyl ((1R,5S,8s)-3-(5-bromo-1,3,4-thiadiazol-2-yl)-3-azabicyclo[3.2.1]octan-8-yl)carbamate: To a solution of (1R,5S,8s)-3-(5-bromo-1,3,4-thiadiazol-2-yl)-3-azabicyclo[3.2.1]octan-8-amine hydrochloride (150 mg, 0.46 mmol) in THF (4.5 mL) was added potassium carbonate (190 mg, 1.37 mmol) and 2-chloroethyl chloroformate (98 mg, 0.68 mmol). The resulting slurry was stirred at room temperature for 2 days. Additional 2-chloroethyl chloroformate (98 mg, 0.68 mmol) was added and stirred for 4.5 hours. The reaction was filtered through celite, washed with EtOAc, and concentrated to dryness. The resulting crude residue was purified by silica gel chromatography (eluent: EtOAc/Hexanes) to give the desired product.
ES/MS: 395.900 [M+H]⁺

3-((1R,5S,8s)-3-(5-bromo-1,3,4-thiadiazol-2-yl)-3-azabicyclo[3.2.1]octan-8-yl)oxazolidin-2-one (I-36): To a solution of 2-Chloroethyl ((1R,5S,8s)-3-(5-bromo-1,3,4-thiadiazol-2-yl)-3-azabicyclo[3.2.1]octan-8-yl)carbamate (24.5 mg, 0.062 mmol) in MeOH (0.75 mL) was added sodium methoxide (0.023 mL, 0.10 mmol). After stirring at room temperature for 3 days, the reaction was concentrated and dissolved in EtOAc. The organic layer was washed with NH₄Cl/H₂O, dried over MgSO₄, and concentrated. The resulting crude residue was purified by silica gel chromatography (eluent: MeOH/CH₂Cl₂) to give I-36.
ES/MS: 359.160 [M+H]⁺

Preparation of Intermediate I-37

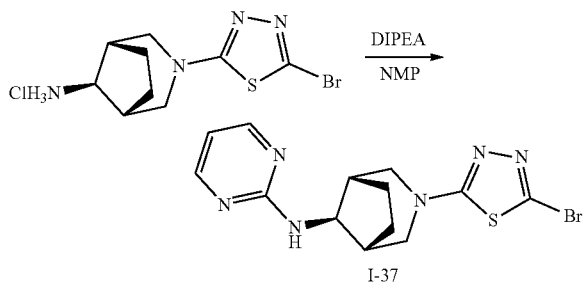

(1R,5S,8s)-3-(5-bromo-1,3,4-thiadiazol-2-yl)-N-(pyrimidin-2-yl)-3-azabicyclo[3.2.1]octan-8-amine (I-37): To a solution of (1R,5S,8s)-3-(5-bromo-1,3,4-thiadiazol-2-yl)-3-azabicyclo[3.2.1]octan-8-amine hydrochloride (25 mg, 0.077 mmol) in NMP (0.4 mL) was added 2-chloropyridine (19 mg, 0.17 mmol) and N,N-diisopropylethylamine (0.07 mL, 0.40 mmol). The reaction was sealed and heated in a microwave to 150° C. for 30 min. The reaction mixture was purified by RP-HPLC (eluent: water/MeCN*0.1% TFA). The resulting product fractions were combined and concentrated to dryness. The residue was dissolved in CH₂Cl₂ and washed with aqueous bicarbonate. The aqueous layer was back-extracted with CH₂Cl₂ and the combined organic layers were dried over MgSO₄ and concentrated to give I-37.

ES/MS: 367.210 [M+H]⁺

Preparation of Intermediate I-38

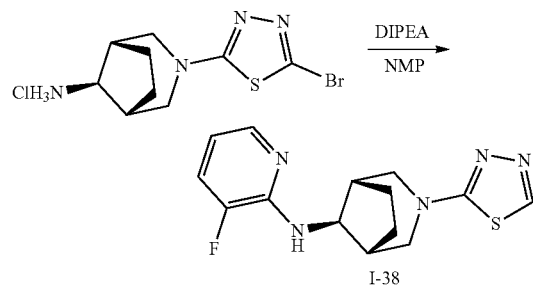

I-38

(1R,5S,8s)-3-(5-bromo-1,3,4-thiadiazol-2-yl)-N-(pyrimidin-2-yl)-3-azabicyclo[3.2.1]octan-8-amine (I-38): To a solution of (1R,5S,8s)-3-(5-bromo-1,3,4-thiadiazol-2-yl)-3-azabicyclo[3.2.1]octan-8-amine hydrochloride (75 mg, 0.23 mmol) in NMP (1.2 mL) was added 2,3-difluoropyridine (82 mg, 0.71 mmol) and N,N-diisopropylethylamine (0.2 mL, 1.15 mmol). The reaction was sealed and heated 120° C. for 4 days. The reaction mixture was purified by RP-HPLC (eluent: water/MeCN*0.1% TFA). The resulting product fractions were combined and concentrated to dryness. The residue was dissolved in CH₂Cl₂ and washed with aqueous bicarbonate. The aqueous layer was back-extracted with CH₂Cl₂ and the combined organic layers were dried over MgSO₄ and concentrated to give I-38.

ES/MS: 384.349 [M+H]⁺

Preparation of Intermediate I-39

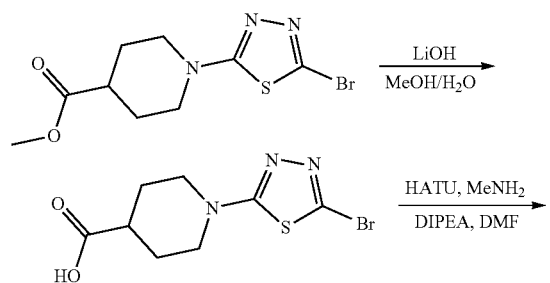

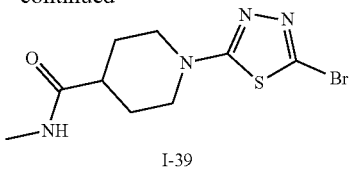

I-39

1-(5-bromo-1,3,4-thiadiazol-2-yl)piperidine-4-carboxylic acid: To a solution of methyl 1-(5-bromo-1,3,4-thiadiazol-2-yl)piperidine-4-carboxylate (22 mg, 0.073 mmol) in MeOH (0.15 mL) and THF (0.3 mL) was added aqueous lithium hydroxide (1M, 0.15 mL, 0.15 mmol). The resulting solution was stirred at room temperature for 3 days. The mixture was concentrated to dryness and used crude in the next step.

ES/MS: 292.095 [M+H]⁺

1-(5-bromo-1,3,4-thiadiazol-2-yl)-N-methylpiperidine-4-carboxamide (I-39): To a solution of 1-(5-bromo-1,3,4-thiadiazol-2-yl)piperidine-4-carboxylic acid (21 mg, 0.72 mmol) in DMF (0.3 mL) was added a THF solution of methylamine (2M, 0.35 mL, 0.7 mmol), HATU (33 mg, 0.087 mmol), and N,N-diisopropylethylamine (0.1 mL, 0.57 mmol). The reaction was stirred at room temperature for 1.5 h and concentrated to dryness. The resulting crude residue was purified by silica gel chromatography (eluent: MeOH/CH₂Cl₂) to give I-39.

ES/MS: 305.137 [M+H]⁺

Preparation of Intermediate I-40

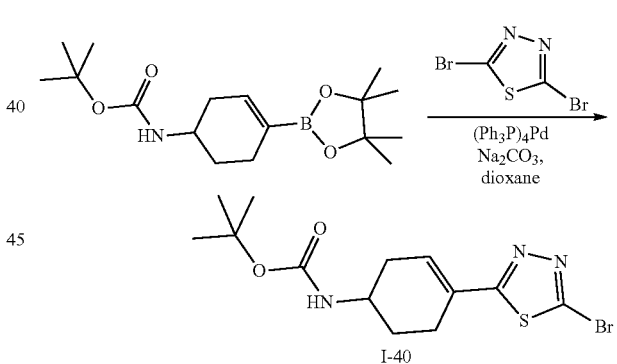

I-40

Tert-butyl (4-(5-bromo-1,3,4-thiadiazol-2-yl)cyclohex-3-en-1-yl)carbamate (I-40): To a solution of tert-butyl (4-(4,4,5,5-tetramethyl-1,3,2-dioxaborolan-2-yl)cyclohex-3-en-1-yl)carbamate (100 mg, 0.31 mmol) in dioxane (1.5 mL) was added 2,5-dibromo-1,3,4-thiadiazole (150 mg, 0.62 mmol), Tetrakis(triphenylphosphine)palladium (36 mg, 0.031 mmol), and aqueous sodium carbonate (2M, 0.3 mL, 0.6 mmol). The resulting slurry was degassed with argon for 2 min, sealed, and heated in a microwave at 150° C. for 2.5 hours. The resulting mixture was filtered through celite and washed with ethyl acetate. The combine filtrates were concentrated to dryness. The crude residue was dissolved in DMF and purified by RP-HPLC (eluent: water/MeCN*0.1% TFA) to yield I-40 as a trifluoroacetate salt.

ES/MS: 360.003 [M+H]⁺

Preparation of Intermediate I-41

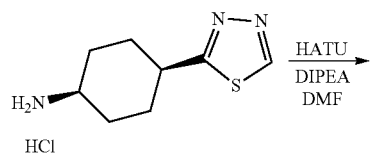

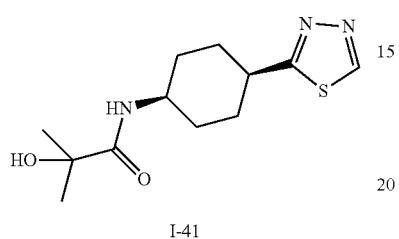

I-41

N-((1s,4s)-4-(1,3,4-thiadiazol-2-yl)cyclohexyl)-2-hydroxy-2-methylpropanamide (I-41): To a slurry of (1s,4s)-4-(1,3,4-thiadiazol-2-yl)cyclohexan-1-amine hydrochloride (100 mg, 0.46 mmol) in DMF (1 mL) was added 2-Hydroxyisobutyric acid (60.0 mg, 0.576 mmol), HATU (190 mg, 0.5 mmol), and N,N-diisopropylethylamine (0.4 mL, 2.3 mmol). The reaction was stirred at room temperature for 16 h and concentrated to dryness. The resulting crude residue was purified by silica gel chromatography (eluent: MeOH/CH$_2$Cl$_2$) to give I-41.

ES/MS: 270.302 [M+H]$^+$

Preparation of Intermediate I-42

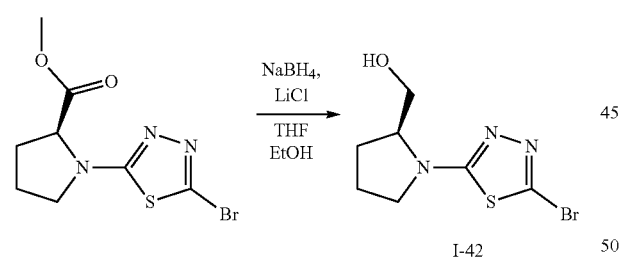

I-42

(S)-(1-(5-bromo-1,3,4-thiadiazol-2-yl)pyrrolidin-2-yl)methanol (I-42): To a solution of methyl (2S)-1-(5-bromo-1,3,4-thiodiazol-2-yl)pyrrolidine-2-carboxylate (64.74 mg, 0.221 mmol) in tetrahydrofuran (0.55mL), lithium chloride (28.2 mg, 0.664 mmol) and sodium borohydride (25.1 mg, 0.664 mmol) were added at rt followed by addition of ethanol (1 mL), and the mixture was stirred at the same temperature as above for 24 hours. Water (0.5 mL) was carefully added thereto, and the mixture was concentrated under reduced pressure. Purified on silica using 30%-100% Hexanes/EtOAc, then flushed with 100% MeOH. Compound containing fractions were concentrated to yield I-42.

ES/MS: 264.32, 266.03 [M+H$^+$].

Preparation of Intermediate I-43

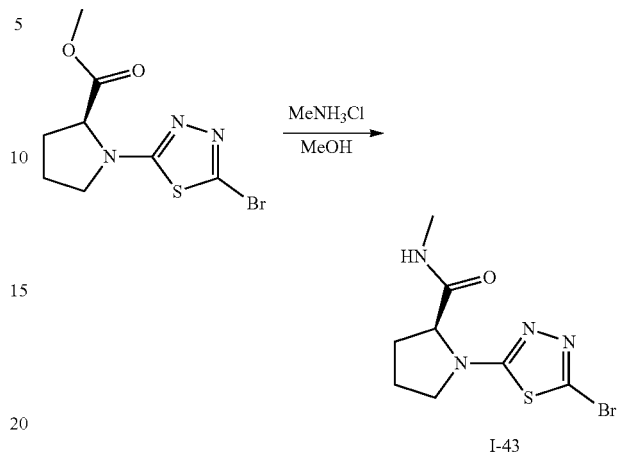

I-43

(S)-1-(5-bromo-1,3,4-thiadiazol-2-yl)-N-methylpyrrolidine-2-carboxamide (I-43): To a solution of methyl (2S)-1-(5-bromo-1,3,4-thiodiazol-2-yl)pyrrolidine-2-carboxylate (38.0 mg, 0.130 mmol) in methanol (0.650 mL), methylamine hydrochloride (13.2 mg, 0.195 mmol) was added at rt. The mixture was stirred at the same temperature as above for 24 hours. Saturated sodium bicarbonate solution (5 mL) was carefully added and the mixture was extracted twice with 10 mL of EtOAc, washed with 5 mL Brine, and dried over MgSO$_4$. The mixture was filtered and concentrated under reduced pressure to provide I-43 which was used without additional purification.

ES/MS: 294.08 [M+H+].

Preparation of Intermediate I-44

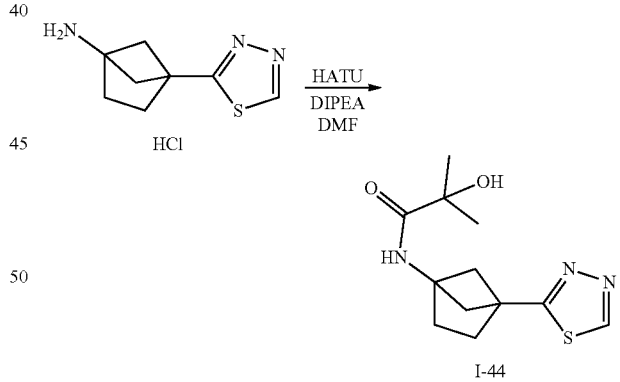

I-44

2-hydroxy-2-methyl-N-[4-(1,3,4-thiadiazol-2-yl)-1-bicyclo[2.1.1]hexanyl]propenamide (I-44): To a solution of crude 4-(1,3,4-thiadiazol-2-yl)bicyclo[2.1.1]hexan-1-amine;hydrochloride (45.0 mg, 0.207 mmol) and 2-hydroxy-2-methyl-propanoic acid (23.7 mg, 0.227 mmol) in DMF (0.5 mL) was added N,N-diisopropylethylamine (0.118 mL, 0.661 mmol) followed by the addition of a solution of HATU (82.5 mg, 0.217 mmol) in DMF (0.5 mL). The reaction mixture was stirred at RT overnight then directly purified by RP-HPLC (eluent: water/MeCN*0.1% TFA) to yield I-44 as a trifluoroacetate salt.

ES/MS: 268.2 [M+H]$^+$

Preparation of Intermediate I-45

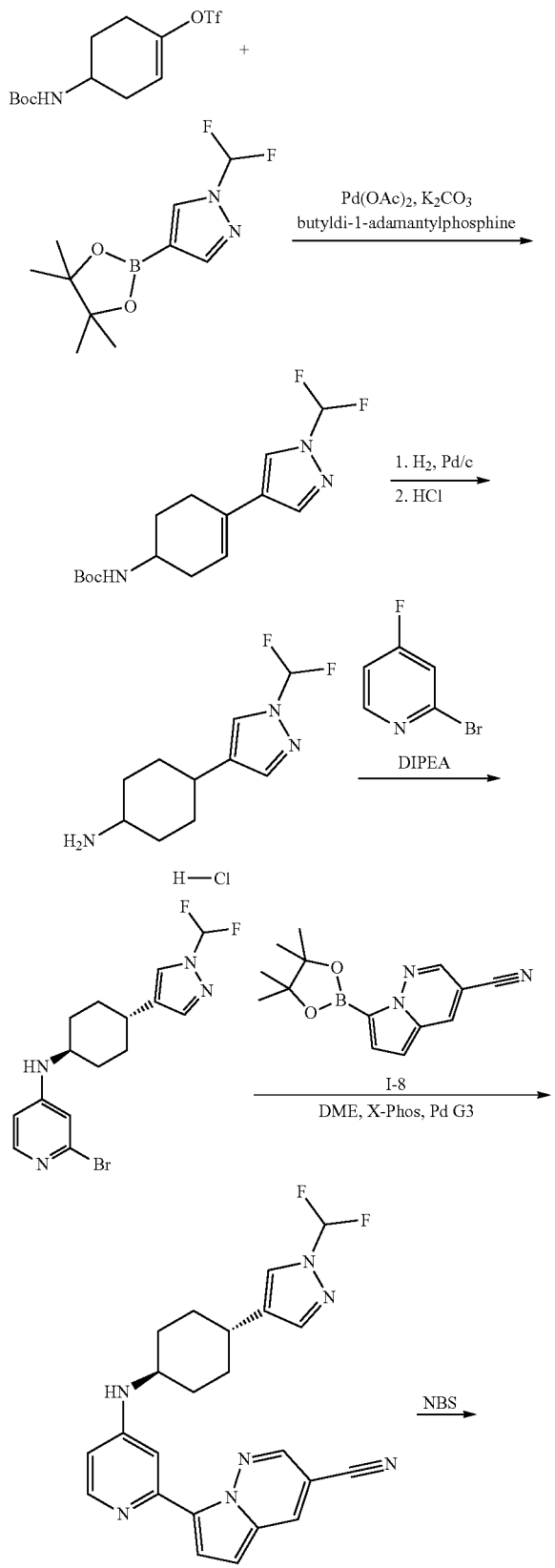

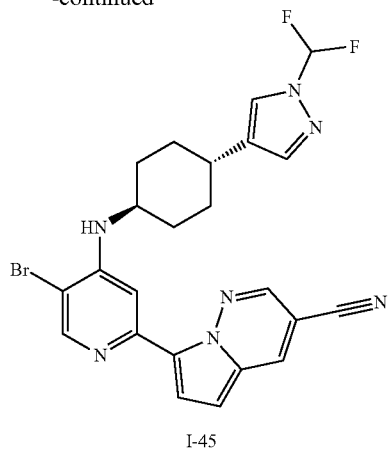

I-45 tert-butyl (4-(1-(difluoromethyl)-1H-pyrazol-4-yl)cyclohex-3-en-1-yl)carbamate: 4-((tert-butoxycarbonyl)amino)cyclohex-1-en-1-yl trifluoromethanesulfonate (3.52 g, 10.2 mmol), 1-(difluoromethyl)-4-(4,4,5,5-tetramethyl-1,3,2-dioxaborolan-2-yl)-1H-pyrazole (3.11 g, 12.7 mmol), Pd(OAc)$_2$ (0.11 g, 0.51 mmol), butyldi-1-adamantylphosphine (0.37 g, 1.02 mmol), and K$_2$CO$_3$ (2.82 g, 10.4 mmol) were combined in a sealed tube along with DME (20 mL) and water (10 mL) and the resulting slurry was degassed with argon then heated at 80° C. for 16 h. The reaction contents were diluted with EtOAc (70 mL), washed with brine (1×15 mL), and dried over MgSO$_4$. The crude residue was then purified via silica gel chromatography (eluent: EtOAc/hexanes) to give the product tert-butyl (4-(1-(difluoromethyl)-1H-pyrazol-4-yl)cyclohex-3-en-1-yl)carbamate. ES/MS: 258.0 (M+H$^+$).

4-(1-(difluoromethyl)-1H-pyrazol-4-yl)cyclohexan-1-amine hydrochloride: A suspension of tert-butyl (4-(1-(difluoromethyl)-1H-pyrazol-4-yl)cyclohex-3-en-1-yl)carbamate (0.23 g, 0.75 mmol) in EtOH (15 mL) was degassed with argon and vacuum. Pd/C (10%, 91 mg, 0.086 mmol) was added and the mixture was stirred with a balloon of H$_2$ overnight. The reaction was filtered over a Celite plug, rinsed with EtOAc and the filtrate was concentrated to give tert-butyl (4-(1-(difluoromethyl)-1H-pyrazol-4-yl)cyclohexyl)carbamate which was carried forward without further purification assuming quantitative yield. To a solution of tert-butyl (4-(1-(difluoromethyl)-1H-pyrazol-4-yl)cyclohexyl)carbamate (0.24 g, 0.75 mmol) in DCM (6 mL) was added HCl (4.0M in dioxane, 3 mL, 12 mmol) and the resulting solution stirred at room temperature for 16 h. Upon completion the reaction mixture was concentrated to dryness to give 4-(1-(difluoromethyl)-1H-pyrazol-4-yl)cyclohexan-1-amine hydrochloride (I-9) which was used without further purification.
ES/MS: 216.1 (M+H$^+$).

2-bromo-N-((1r,4r)-4-(1-(difluoromethyl)-1H-pyrazol-4-yl)cyclohexyl)pyridin-4-amine: To a solution of 2-bromo-4-fluoropyridine (0.23 g, 1.29 mmol) in NMP (7 mL) was added 4-(1-(difluoromethyl)-1H-pyrazol-4-yl)cyclohexan-1-amine hydrochloride (0.38 g, 1.51 mmol) and N,N-diisopropylethylamine (0.70 mL, 4.02 mmol). The resulting mixture was heated for 1 h at 160° C. in a microwave after which the reaction contents diluted with EtOAc, washed 3 times with 5% aqueous LiCl, dried and concentrated to give a crude residue which was purified by normal phase SiO$_2$ chromatography (eluent: ethyl acetate/hexanes) to give both the cis and trans products. The trans product 2-bromo-N-((1r,4r)-4-(1-(difluoromethyl)-1H-pyrazol-4-yl)cyclohexyl)pyridin-4-amine was isolated and carried forward.
ES/MS: 371.3, 373.0 (M+H⁺).
1H NMR (400 MHz, Chloroform-d) δ 7.91 (d, J=5.8 Hz, 1H), 7.62 (s, 1H), 7.56 (s, 1H), 7.17 (t, J=60.7 Hz, 1H), 6.61 (d, J=2.2 Hz, 1H), 6.38 (dd, J=5.8, 2.2 Hz, 1H), 4.29 (d, J=7.8 Hz, 1H), 3.33 (dtd, J=11.3, 7.6, 3.9 Hz, 1H), 2.58 (tt, J=12.0, 3.6 Hz, 1H), 2.28-2.09 (m, 4H), 1.64-1.44 (m, 2H), 1.44-1.16 (m, 2H).

7-(5-bromo-4-(((1r,4r)-4-(1-(difluoromethyl)-1H-pyrazol-4-yL)cyclohexyl)amino)pyridin-2-yl)pyrrolo[1,2-b]pyridazine-3-carbonitrile (I-45): 2-bromo-N-((1r,4r)-4-(1-(difluoromethyl)-1H-pyrazol-4-yl)cyclohexyl)pyridin-4-amine was elaborated to the final intermediate 7-(5-bromo-4-(((1r,4r)-4-(1-(difluoromethyl)-1H-pyrazol-4-yl)cyclohexyl)amino)pyridin-2-yl)pyrrolo[1,2-b]pyridazine-3-carbonitrile (I-45) in the same manner as described in steps 2-3 of Preparation of Intermediate 1-2.
ES/MS: 512.14 (M+H⁺).

EXAMPLE PROCEDURES AND COMPOUND EXAMPLES

The following compounds were made with the procedures herein, using the appropriate starting materials and protecting group chemistry as needed:

| Structure | # | ES/MS m/z | Name | Procedure |
|---|---|---|---|---|
| 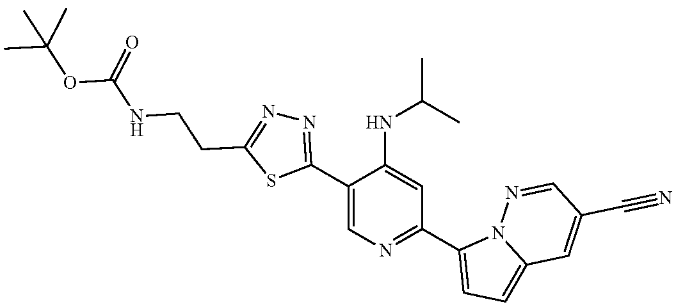 [SMILES: CC(C)Nc1cc(-c2ccc3cc(C#N)cnn23)ncc1-c1nnc(CCNC(=O)OC(C)(C)C)s1] | 1 | 505.193 | tert-butyl (2-(5-(6-(3-cyanopyrrolo[1,2-b]pyridazin-7-yl)-4-(isopropylamino)pyridin-3-yl)-1,3,4-thiadiazol-2-yl)ethyl)carbamate | 1 |
| 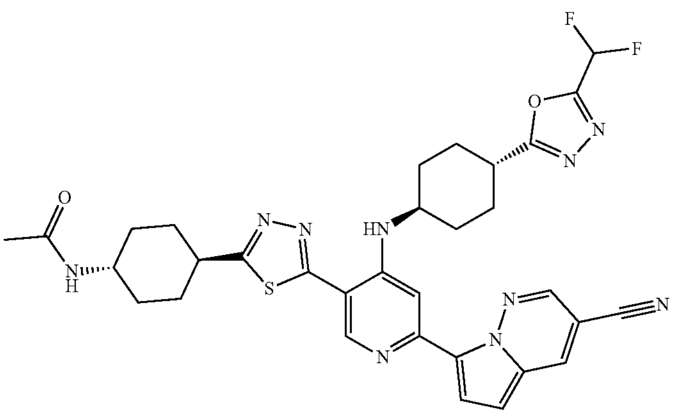 [SMILES: CC(=O)N[C@H]1CC[C@H](c2nnc(-c3cnc(-c4ccc5cc(C#N)cnn45)cc3N[C@H]3CC[C@H](c4nnc(C(F)F)o4)CC3)s2)CC1] | 2 | 659.3 | N-((1R,4r)-4-(5-(6-(3-cyanopyrrolo[1,2-b]pyridazin-7-yl)-4-((1r,4R)-4-(5-(difluoromethyl)-1,3,4-oxadiazol-2-yl)cyclohexyl)amino)pyridin-3-yl)-1,3,4-thiadiazol-2-yl)cyclohexyl)acetamide | 1 |
| 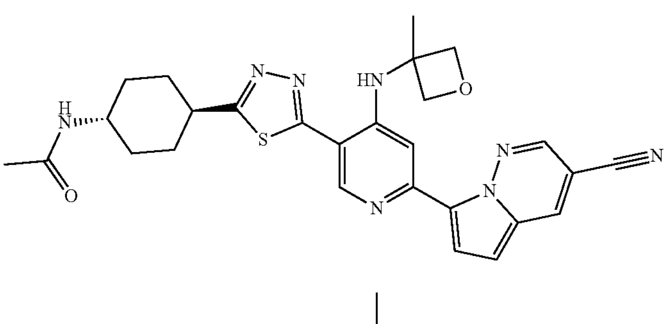 | 3 | 529.315 | N-((1r,4r)-4-(5-(6-(3-cyanopyrrolo[1,2-b]pyridazin-7-yl)-4-((3-methyloxetan-3-yl)amino)pyridin-3-yl)-1,3,4-thiadiazol-2-yl)cyclohexyl)acetamide | 1 |
| 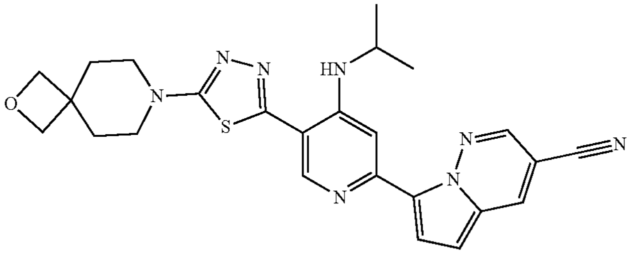 [SMILES: CC(C)Nc1cc(-c2ccc3cc(C#N)cnn23)ncc1-c1nnc(N2CCC3(CC2)COC3)s1] | 4 | 487.26 | 7-(5-(5-(2-oxa-7-azaspiro[3.5]nonan-7-yl)-1,3,4-thiadiazol-2-yl)-4-(isopropylamino)pyridin-2-yl)pyrrolo[1,2-b]pyridazine-3-carbonitrile | 2 |

Procedure 7: Example 5

7-(5-(5-(hydroxymethyl)-1,3,4-thiadiazol-2-yl)-4-(isopropylamino)pyridin-2-yl)pyrrolo[1,2-b]pyridazine-3-carbonitrile (Example 5)

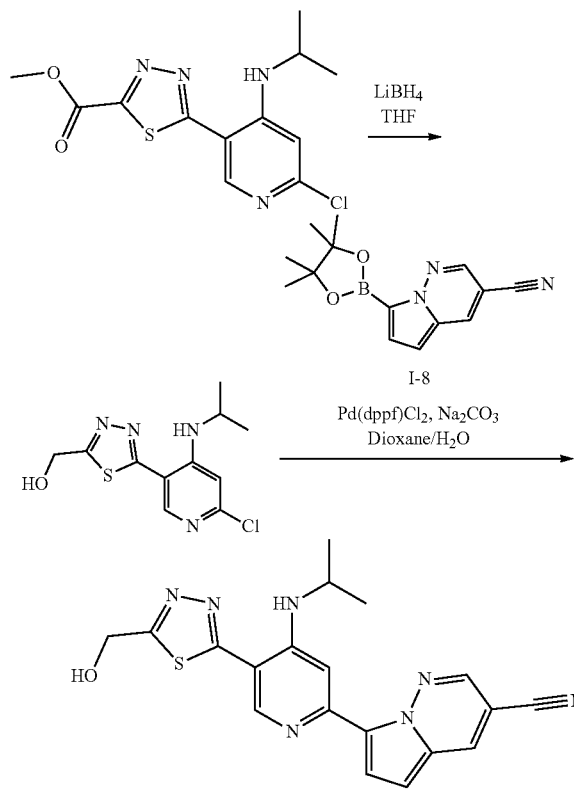

Example 5

(5-(6-chloro-4-(isopropylamino)pyridin-3-yl)-1,3,4-thiadiazol-2-yl)methanol: To a solution of methyl 5-(6-chloro-4-(isopropylamino)pyridin-3-yl)-1,3,4-thiadiazole-2-carboxylate (50.0 mg, 0.16 mmol) in THF (0.5 mL) was added lithium borohydride (2M in THF, 80 μL, 0.16 mmol). The reaction mixture was stirred at room temperature for 15 minutes, then quenched with a few drops of saturated aqueous ammonium chloride. The reaction mixture was concentrated in vacuo and purified by silica gel column chromatography (eluent:MeOH/DCM) to provide (5-(6-chloro-4-(isopropylamino)pyridin-3-yl)-1,3,4-thiadiazol-2-yl)methanol.

ES/MS: 285.1 [M+H$^+$].

7-(5-(5-(hydroxymethyl)-1,3,4-thiadiazol-2-yl)-4-(isopropylamino)pyridin-2-yl)pyrrolo[1,2-b]pyridazine-3-carbonitrile (Example 5): A solution of (5-(6-chloro-4-(isopropylamino)pyridin-3-yl)-1,3,4-thiadiazol-2-yl)methanol (15.3 mg, 0.054 mmol), 7-(4,4,5,5-tetramethyl-1,3,2-dioxaborolan-2-yl)pyrrolo[1,2-b]pyridazine-3-carbonitrile (I-8) (20.2 mg, 0.075 mmol), [1,1'-Bis(diphenylphosphino)ferrocene]dichloropalladium(II) (11.0 mg, 0.013 mmol), and sodium carbonate (2N in water, 54 μL, 0.11 mmol) in 1,4-dioxane (0.4 mL) was sparged with argon for 60 seconds, then heated in a microwave reactor at 125° C. for 20 minutes. Upon cooling, the reaction mixture was filtered and purified by reverse phase high pressure liquid chromatography (eluent:water/MeCN*0.1% TFA) to provide the final compound Example 5.

ES/MS: 392.2 [M+H$^+$].

1H NMR (400 MHz, Methanol-d4) δ 8.75 (d, J=2.2 Hz, 1H), 8.74 (s, 1H), 8.68 (d, J=2.2 Hz, 1H), 8.06 (d, J=5.0 Hz, 1H), 7.99 (s, 1H), 7.23 (d, J=5.0 Hz, 1H), 5.05 (s, 2H), 4.30 (hept, J=6.4 Hz, 1H), 1.49 (d, J=6.4 Hz, 6H).

Procedure 4: Example 6

N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)acetamide (Example 6)

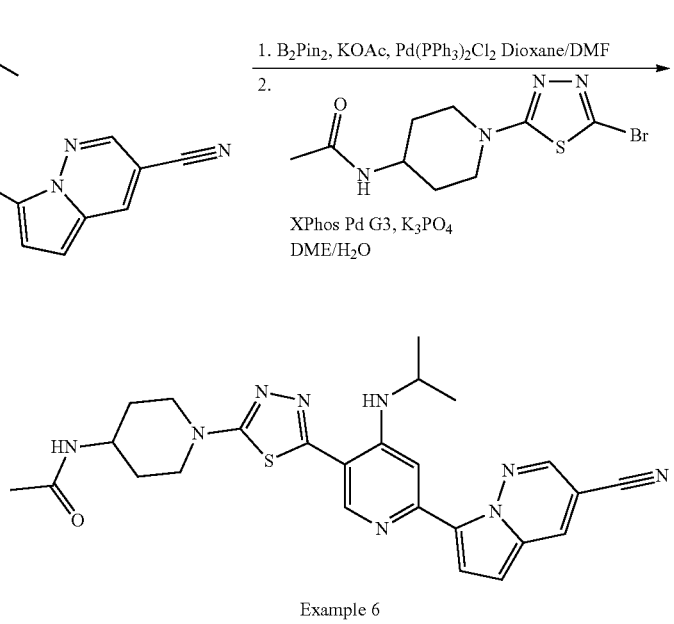

Example 6

N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)acetamide (Example 6): A solution of 7-(5-bromo-4-(isopropylamino)pyridin-2-yl)pyrrolo[1,2-b]pyridazine-3-carbonitrile (I-2) (42.0 mg, 0.12 mmol), bis(pinacolato) diboron (60.5 mg, 0.24 mmol), bis(triphenylphosphine) palladium(II) dichloride (8.4 mg, 0.012 mmol), and potassium acetate (36.0 mg, 0.37 mmol) in 1,4-dioxane (1.2 mL) and DMF (0.4 mL) was sparged with argon for 60 seconds, then heated in a microwave reactor at 120° C. for 20 minutes. The reaction mixture was cooled, and to the crude mixture was added N-(1-(5-bromo-1,3,4-thiadiazol-2-yl)piperidin-4-yl)acetamide (I-4, 28.7 mg, 0.094 mmol), XPhos Pd G3 (8.4 mg, 0.0099 mmol), potassium phosphate tribasic (75.1 mg, 0.35 mmol), DME (1.3 mL) and water (0.18 mL). The reaction mixture was sparged with argon for 60 seconds, then heated in a microwave reactor at 120° C. for 30 minutes. Upon cooling, the reaction mixture was filtered and purified by reverse phase high pressure liquid chromatography (eluent:water/MeCN*0.1% TFA) to provide the final compound Example 6.

ES/MS: 502.3 [M+H$^+$].

1H NMR (400 MHz, Methanol-d4) δ 8.76 (d, J=2.1 Hz, 1H), 8.68 (d, J=2.2 Hz, 1H), 8.47 (s, 1H), 8.12 (d, J=7.6 Hz, 1H), 8.06 (d, J=5.1 Hz, 1H), 7.87 (s, 1H), 7.23 (d, J=5.0 Hz, 1H), 4.29 (p, J=6.4 Hz, 1H), 4.09-3.90 (m, 3H), 3.52-3.39 (m, 2H), 2.05 (dd, J=12.8, 3.9 Hz, 2H), 1.96 (s, 3H), 1.75-1.54 (m, 2H), 1.47 (d, J=6.4 Hz, 6H).

The following compounds were made according to the procedures herein, using the appropriate starting materials and protecting group chemistry as needed:

| Structure | # | ES/MS m/z | Name | Procedure |
|---|---|---|---|---|
| 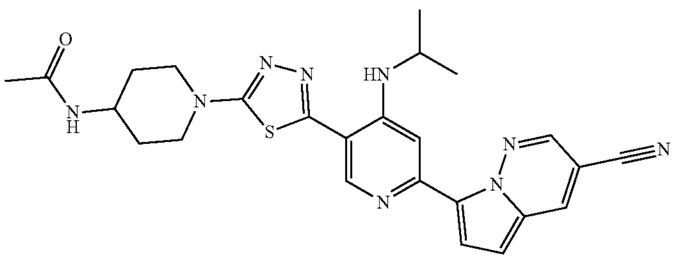 [SMILES: CC(=O)NC1CCN(c2nnc(-c3cnc(-c4ccc5cc(C#N)cnn45)cc3NC(C)C)s2)CC1] | 6 | 502.31 | N-(1-(5-(6-(3-cyanopyrrolo[1,2-b]pyridazin-7-yl)-4-(isopropylamino)pyridin-3-yl)-1,3,4-thiadiazol-2-yl)piperidin-4-yl)acetamide | 4 |
| 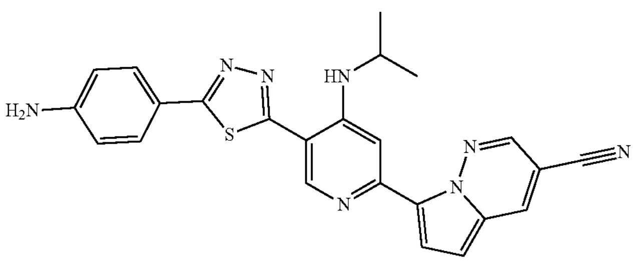 [SMILES: CC(C)Nc1cc(-c2ccc3cc(C#N)cnn23)ncc1-c1nnc(-c2ccc(N)cc2)s1] | 7 | 453.177 | 7-(5-(5-(4-aminophenyl)-1,3,4-thiadiazol-2-yl)-4-(isopropylamino)pyridin-2-yl)pyrrolo[1,2-b]pyridazine-3-carbonitrile | 1 |
| 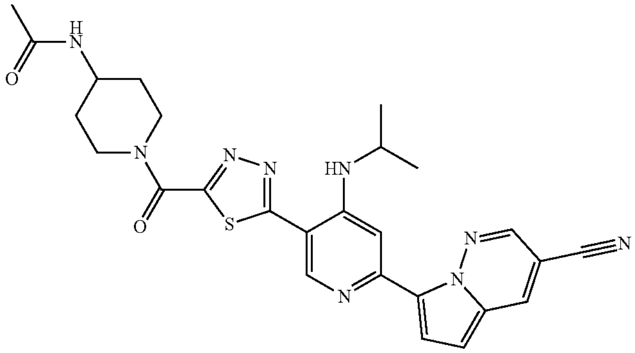 [SMILES: CC(=O)NC1CCN(C(=O)c2nnc(-c3cnc(-c4ccc5cc(C#N)cnn45)cc3NC(C)C)s2)CC1] | 8 | 530.268 | N-(1-(5-(6-(3-cyanopyrrolo[1,2-b]pyridazin-7-yl)-4-(isopropylamino)pyridin-3-yl)-1,3,4-thiadiazole-2-carbonyl)piperidin-4-yl)acetamide | 5 |
| 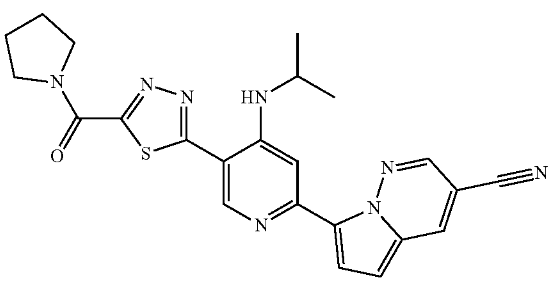 [SMILES: CC(C)Nc1cc(-c2ccc3cc(C#N)cnn23)ncc1-c1nnc(C(=O)N2CCCC2)s1] | 9 | 459.280 | 7-(4-(isopropylamino)-5-(5-(pyrrolidine-1-carbonyl)-1,3,4-thiadiazol-2-yl)pyridin-2-yl)pyrrolo[1,2-b]pyridazine-3-carbonitrile | 5 |

-continued

| Structure | # | ES/MS m/z | Name | Procedure |
|---|---|---|---|---|
| 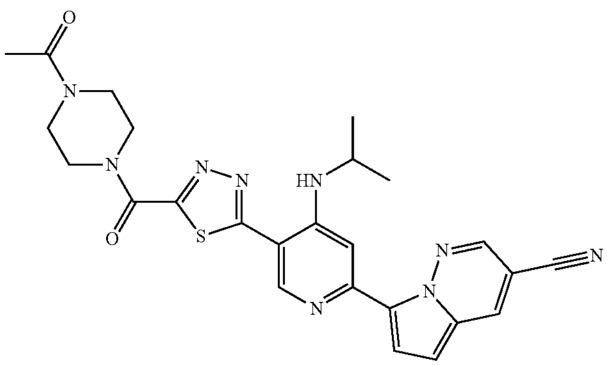 [SMILES: CC(=O)N1CCN(C(=O)c2nnc(-c3cnc(-c4ccc5cc(C#N)cnn45)cc3NC(C)C)s2)CC1] | 10 | 516.221 | 7-(5-(5-(4-acetylpiperazine-1-carbonyl)-1,3,4-thiadiazol-2-yl)-4-(isopropylamino)pyridin-2-yl)pyrrolo[1,2-b]pyridazine-3-carbonitrile | 5 |
| 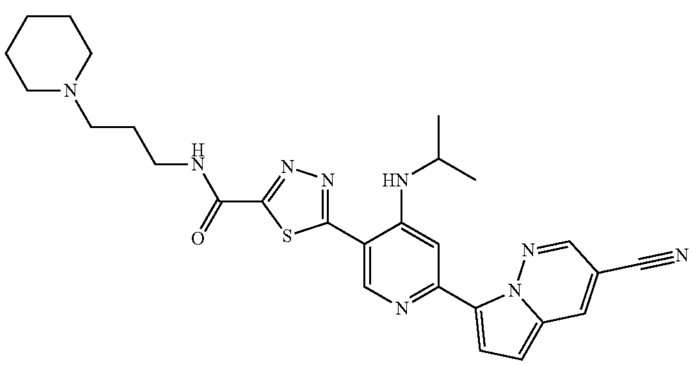 [SMILES: CC(C)Nc1cc(-c2ccc3cc(C#N)cnn23)ncc1-c1nnc(C(=O)NCCCN2CCCCC2)s1] | 11 | 530.257 | 5-(6-(3-cyanopyrrolo[1,2-b]pyridazin-7-yl)-4-(isopropylamino)pyridin-3-yl)-N-(3-(piperidin-1-yl)propyl)-1,3,4-thiadiazole-2-carboxamide | 5 |
| 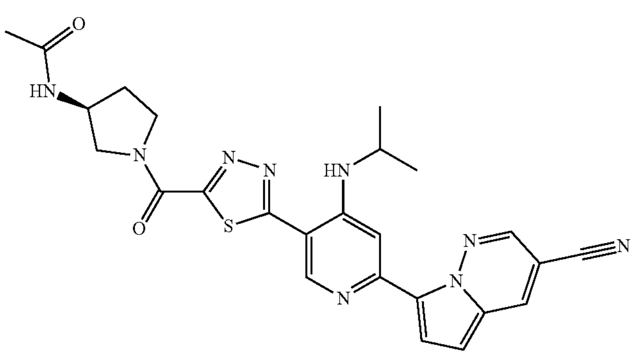 [SMILES: CC(=O)N[C@H]1CCN(C(=O)c2nnc(-c3cnc(-c4ccc5cc(C#N)cnn45)cc3NC(C)C)s2)C1] | 12 | 516.257 | (S)-N-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)acetamide | 5 |
| 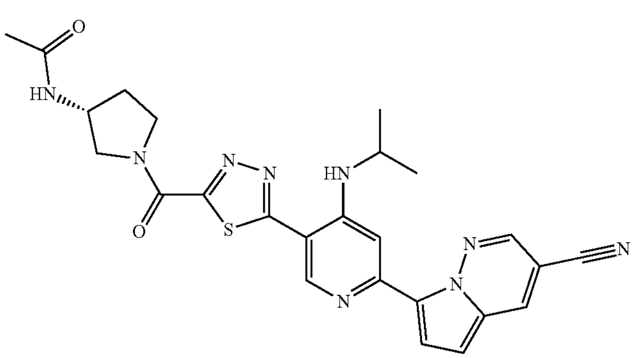 [SMILES: CC(=O)N[C@@H]1CCN(C(=O)c2nnc(-c3cnc(-c4ccc5cc(C#N)cnn45)cc3NC(C)C)s2)C1] | 13 | 516.266 | (R)-N-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)acetamide | 5 |

-continued

| Structure | # | ES/MS m/z | Name | Procedure |
|---|---|---|---|---|
| 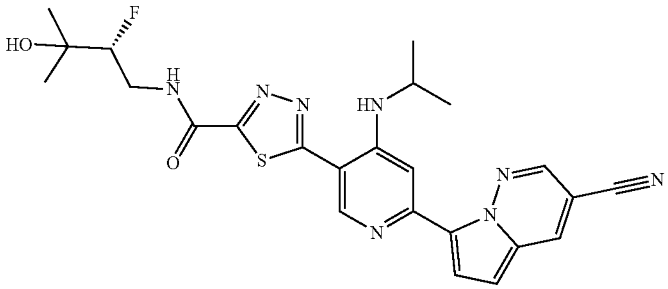 [SMILES: CC(C)Nc1cc(-c2ccc3cc(C#N)cnn23)ncc1-c1nnc(C(=O)NC[C@@H](F)C(C)(C)O)s1] | 14 | 509.240 | (R)-5-(6-(3-cyanopyrrolo[1,2-b]pyridazin-7-yl)-4-(isopropylamino)pyridin-3-yl)-N-(2-fluoro-3-hydroxy-3-methylbutyl)-1,3,4-thiadiazole-2-carboxamide | 5 |
| 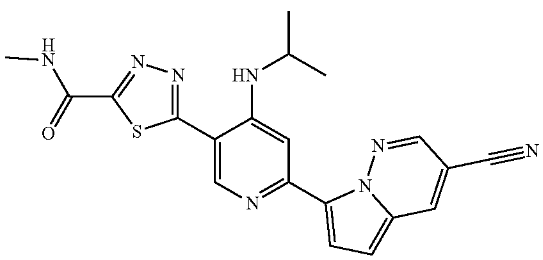 [SMILES: CNC(=O)c1nnc(-c2cnc(-c3ccc4cc(C#N)cnn34)cc2NC(C)C)s1] | 15 | 419.202 | 5-(6-(3-cyanopyrrolo[1,2-b]pyridazin-7-yl)-4-(isopropylamino)pyridin-3-yl)-N-methyl-1,3,4-thiadiazole-2-carboxamide | 5 |

Procedure 5: Example 16

(S)-7-(5-(5-(3-hydroxypyrrolidine-1-carbonyl)-1,3,4-thiadiazol-2-yl)-4-(isopropylamino)pyridin-2-yl)pyrrolo[1,2-b]pyridazine-3-carbonitrile (Example 16)

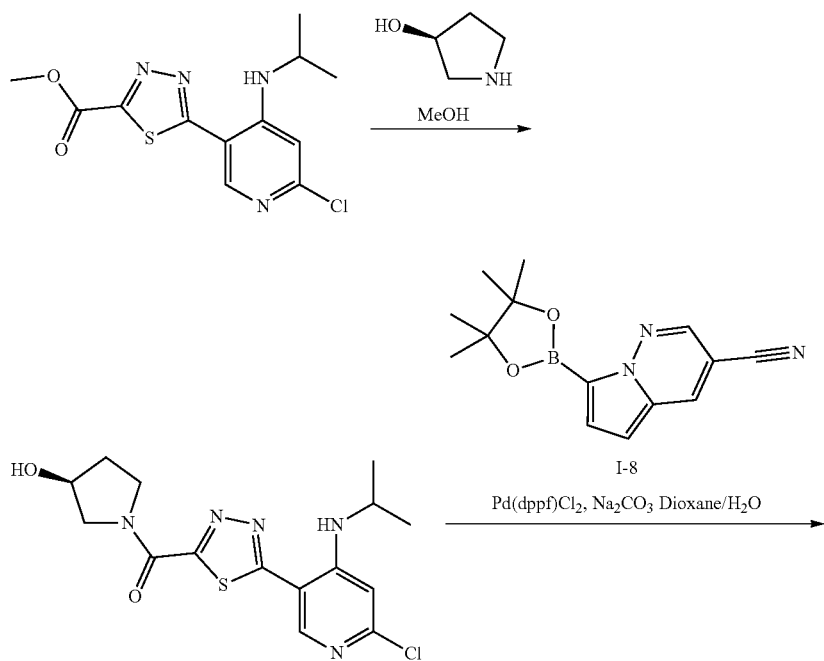

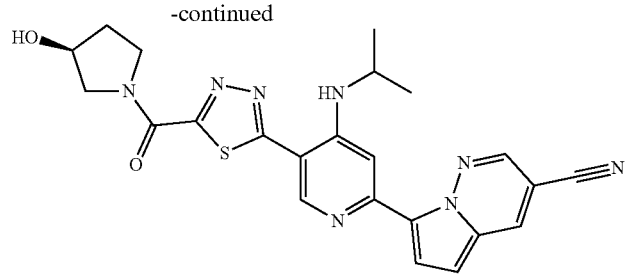

Example 16

(S)-(5-(6-chloro-4-(isopropylamino)pyridin-3-yl)-1,3,4-thiadiazol-2-yl)(3-hydroxypyrrolidin-1-yl)methanonea: To a solution of methyl 5-(6-chloro-4-(isopropylamino)pyridin-3-yl)-1,3,4-thiadiazole-2-carboxylate (50.0 mg, 0.16 mmol) in MeOH (0.5 mL) was added (S)-3-hydroxypyrrolidine (13 μL, 0.16 mmol). The reaction mixture was heated at 80° C. for 1 hour, then concentrated in vacuo and purified by silica gel column chromatography (eluent: MeOH/DCM) to provide (S)-(5-(6-chloro-4-(isopropylamino)pyridin-3-yl)-1,3,4-thiadiazol-2-yl)(3-hydroxypyrrolidin-1-yl)methanonea. ES/MS: 368.1 [M+H⁺].

(S)-7-(5-(5-(3-hydroxypyrrolidine-1-carbonyl)-1,3,4-thiadiazol-2-yl)-4-(isopropylamino)pyridin-2-yl)pyrrolo[1,2-b]pyridazine-3-carbonitrile (Example 16): A solution of (S)-(5-(6-chloro-4-(isopropylamino)pyridin-3-yl)-1,3,4-thiadiazol-2-yl)(3-hydroxypyrrolidin-1-yl)methanonea (25.0 mg, 0.068 mmol), 7-(4,4,5,5-tetramethyl-1,3,2-dioxaborolan-2-yl)pyrrolo[1,2-b]pyridazine-3-carbonitrile (22.0 mg, 0.082 mmol), [1,1'-Bis(diphenylphosphino)ferrocene]dichloropalladium(II) (14.0 mg, 0.017 mmol), and sodium carbonate (2N in water, 68 μL, 0.14 mmol) in 1,4-dioxane (0.57 mL) was sparged with argon for 60 seconds, then heated in a microwave reactor at 125° C. for 20 minutes. Upon cooling, the reaction mixture was filtered and purified by reverse phase high pressure liquid chromatography (eluent: water/MeCN*0.1% TFA) to provide the final compound Example 16.
ES/MS: 475.3 [M+H⁺].
1H NMR (400 MHz, Methanol-d4) δ 8.85 (s, 1H), 8.79 (d, J=2.1 Hz, 1H), 8.72 (d, J=2.2 Hz, 1H), 8.10 (d, J=5.1 Hz, 1H), 8.02 (s, 1H), 7.26 (d, J=5.1 Hz, 1H), 4.61 (q, J=3.0, 2.1 Hz, 0H), 4.54 (t, J=3.4 Hz, 1H), 4.46-4.11 (m, 3H), 3.86 (dt, J=10.2, 5.1 Hz, 1H), 3.77 (d, J=2.9 Hz, 1H), 2.27-2.00 (m, 2H), 1.53 (d, J=6.4 Hz, 6H).

The following compounds were made according to the procedures herein, using the appropriate starting materials and protecting group chemistry as needed:

| Structure | # | ES/MS m/z | Name | Procedure |
|---|---|---|---|---|
| 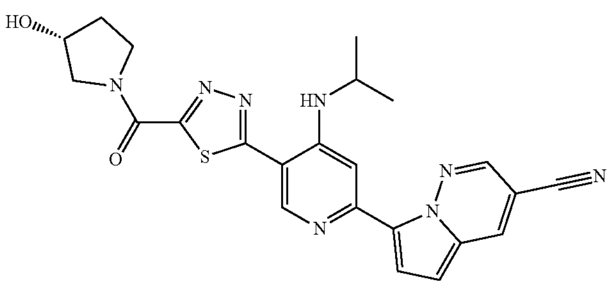 [SMILES: CC(C)Nc1cc(-c2ccc3cc(C#N)cnn23)ncc1-c1nnc(C(=O)N2CC[C@@H](O)C2)s1] | 17 | 475.249 | (R)-7-(5-(5-(3-hydroxypyrrolidine-1-carbonyl)-1,3,4-thiadiazol-2-yl)-4-(isopropylamino)pyridin-2-yl)pyrrolo[1,2-b]pyridazine-3-carbonitrile | 5 |
| 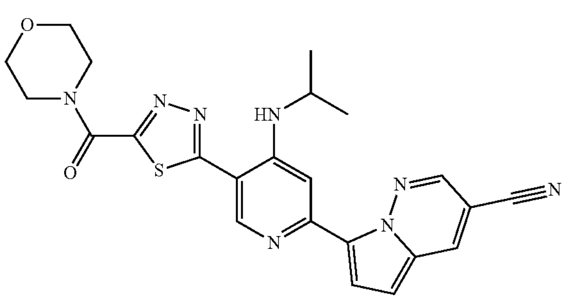 [SMILES: CC(C)Nc1cc(-c2ccc3cc(C#N)cnn23)ncc1-c1nnc(C(=O)N2CCOCC2)s1] | 18 | 475.236 | 7-(4-(isopropylamino)-5-(5-(morpholine-4-carbonyl)-1,3,4-thiadiazol-2-yl)pyridin-2-yl)pyrrolo[1,2-b]pyridazine-3-carbonitrile | 5 |

-continued

| Structure | # | ES/MS m/z | Name | Procedure |
|---|---|---|---|---|
| 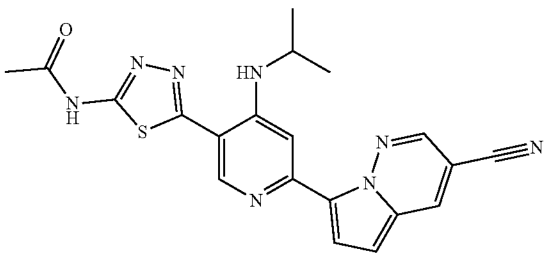 [SMILES: CC(=O)Nc1nnc(-c2cnc(-c3ccc4cc(C#N)cnn34)cc2NC(C)C)s1] | 19 | 419.165 | N-(5-(6-(3-cyanopyrrolo[1,2-b]pyridazin-7-yl)-4-(isopropylamino)pyridin-3-yl)-1,3,4-thiadiazol-2-yl)acetamide | 4 |
| 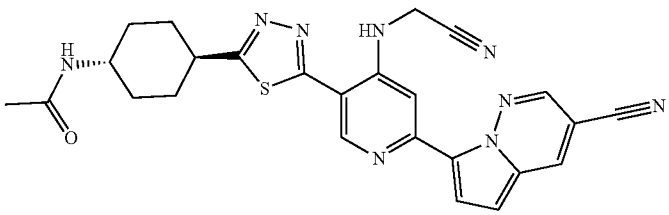 [SMILES: CC(=O)N[C@H]1CC[C@H](c2nnc(-c3cnc(-c4ccc5cc(C#N)cnn45)cc3NCC#N)s2)CC1] | 20 | 498.251 | N-((1r,4r)-4-(5-(4-((cyanomethyl)amino)-6-(3-cyanopyrrolo[1,2-b]pyridazin-7-yl)pyridin-3-yl)-1,3,4-thiadiazol-2-yl)cyclohexyl)acetamide | 1 |
| 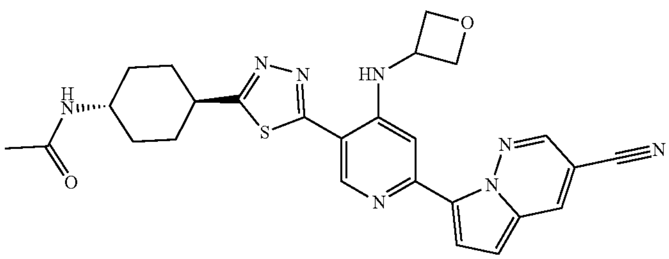 [SMILES: CC(=O)N[C@H]1CC[C@H](c2nnc(-c3cnc(-c4ccc5cc(C#N)cnn45)cc3NC3COC3)s2)CC1] | 21 | 515.235 | N-((1r,4r)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)acetamide | 1 |
| 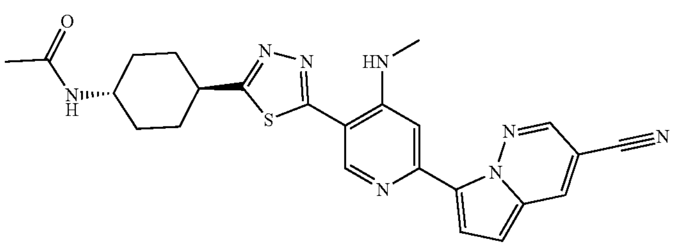 [SMILES: CNc1cc(-c2ccc3cc(C#N)cnn23)ncc1-c1nnc([C@H]2CC[C@H](NC(C)=O)CC2)s1] | 22 | 473.271 | N-((1r,4r)-4-(5-(6-(3-cyanopyrrolo[1,2-b]pyridazin-7-yl)-4-(methylamino)pyridin-3-yl)-1,3,4-thiadiazol-2-yl)cyclohexyl)acetamide | 1 |
| 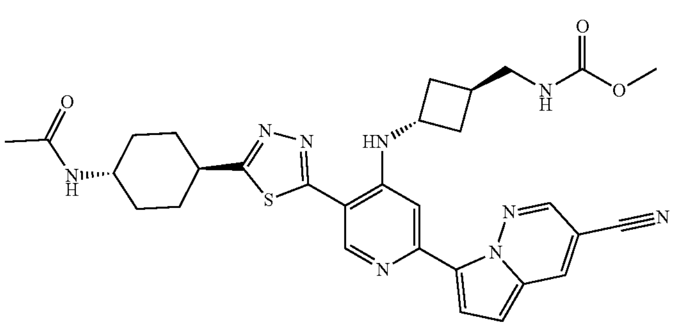 [SMILES: COC(=O)NC[C@H]1C[C@H](Nc2cc(-c3ccc4cc(C#N)cnn34)ncc2-c2nnc([C@H]3CC[C@H](NC(C)=O)CC3)s2)C1] | 23 | 600.266 | methyl (((1R,3r)-3-((5-(5-((1r,4R)-4-acetamidocyclohexyl)-1,3,4-thiadiazol-2-yl)-2-(3-cyanopyrrolo[1,2-b]pyridazin-7-yl)pyridin-4-yl)amino)cyclobutyl)methyl)carbamate | 1 |

Procedure 1: Example 24

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)acetamide (Example 24)

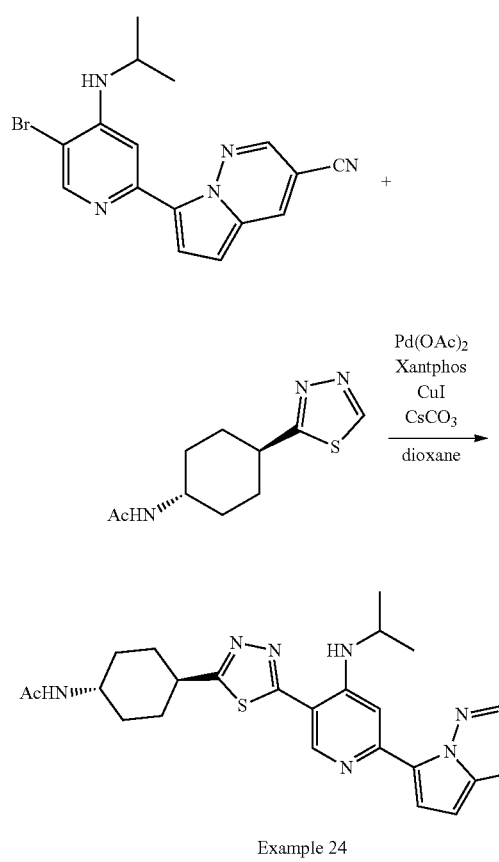

Example 24

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)acetamide (Example 24): To a vial was added 7-(5-bromo-4-(isopropylamino)pyridin-2-yl)pyrrolo[1,2-b]pyridazine-3-carbonitrile (I-2) (35 mg, 0.098 mmol), N-((1r,4r)-4-(1,3,4-thiadiazol-2-yl)cyclohexyl)acetamide (I-1) (32 mg, 0.14 mmol), Pd(OAc)$_2$ (5.5 mg, 0.024 mmol), Xantphos (28.5 mg, 0.049 mmol), copper(I) iodide (9.4 mg, 0.049 mmol), and cesium carbonate (64 mg, 0.197 mmol). 1,4-Dioxane (0.5 mL), was added, and the mixture was degassed with argon for 1 minute. The vial was sealed and stirred 2 hours at 105° C. Afterward, the vial was cooled and the crude material was diluted with DMF (0.5 mL). This mixture was filtered, and purified by RP-HPLC (eluent: water/MeCN*0.1% TFA) to yield the product Example 24 as a trifluoroacetate salt.

ES/MS: 501.3 (M+H$^+$)

1H NMR (400 MHz, Methanol-d4) δ 8.79 (d, J=2.2 Hz, 1H), 8.74 (s, 1H), 8.71 (d, J=2.2 Hz, 1H), 8.10 (d, J=5.1 Hz, 1H), 7.97 (s, 1H), 7.26 (d, J=5.0 Hz, 1H), 4.39-4.29 (m, 1H), 3.83-3.67 (m, 1H), 3.32-3.25 (m, 1H), 2.33 (d, J=13.1 Hz, 2H), 2.12 (d, J=12.7 Hz, 2H), 1.97 (s, 3H), 1.82 (qd, J=13.0, 3.3 Hz, 2H), 1.57-1.42 (m, 8H).

Procedure 9: Example 25

7-(4-(isopropylamino)-5-(5-methyl-1,3,4-thiadiazol-2-yl)pyridin-2-yl)pyrrolo[1,2-b]pyridazine-3-carbonitrile (Example 25)

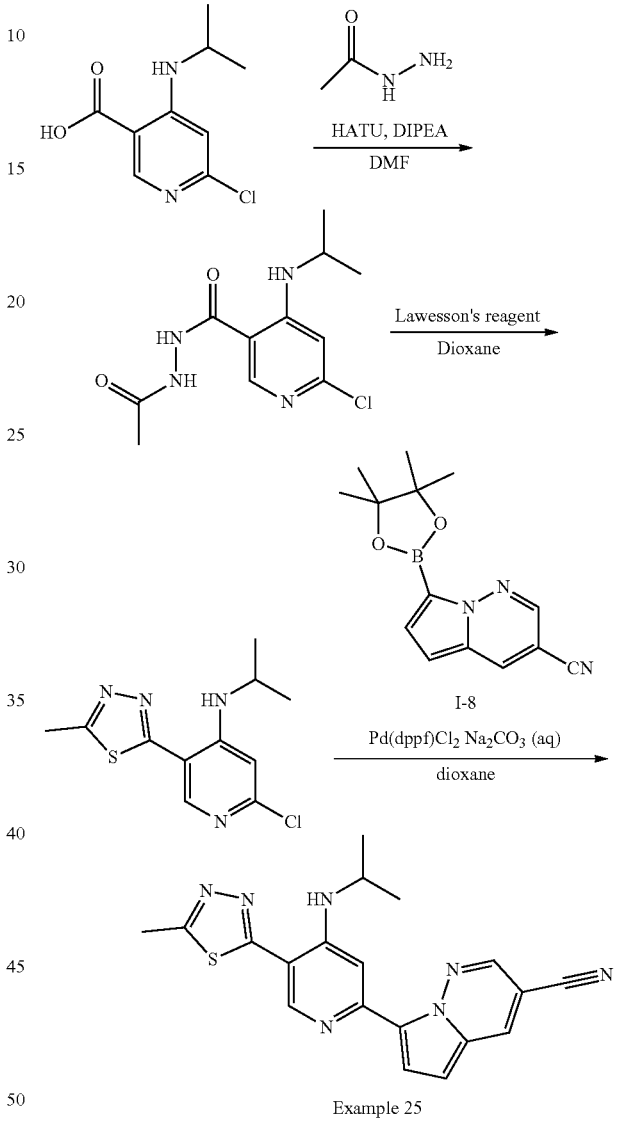

Example 25

N'-acetyl-6-chloro-4-(isopropylamino)nicotinohydrazide: A solution of 6-chloro-4-(isopropylamino)nicotinic acid (0.2 g, 0.93 mmol), acetohydrazide (138.05 mg, 1.86 mmol), HATU (425.1 mg, 1.12 mmol), and N,N-Diisopropylethylamine (0.41 ml, 2.33 mmol) in DMF (1.8 mL) was stirred at room temperature for 18 hours. The reaction solution was diluted in ethyl acetate and washed three times with aqueous saturated ammonium chloride solution. The organic extract was dried over sodium sulfate, filtered, and concentrated to give N'-acetyl-6-chloro-4-(isopropylamino)nicotinohydrazide

ES/MS: 271.279 [M+H$^+$].

2-chloro-N-isopropyl-5-(5-methyl-1,3,4-thiadiazol-2-yl)pyridin-4-amine: A suspension of N'-acetyl-6-chloro-4-(isopropylamino)pyridine-3-carbohydrazide (0.13 g, 0.46 mmol) and Lawesson's reagent (0.21 g, 0.51 mmol) in 1,4-dioxane (2.3 mL) was heated at 80° C. for 18 hours in an aluminum heating block. The crude reaction mixture was purified by normal phase silica gel chromatography (eluent: EtOAc/hexanes) to give 2-chloro-N-isopropyl-5-(5-methyl-1,3,4-thiadiazol-2-yl)pyridin-4-amine.
ES/MS: 269.145 [M+H$^+$].

7-(4-(isopropylamino)-5-(5-methyl-1,3,4-thiadiazol-2-yl)pyridin-2-yl)pyrrolo[1,2-b]pyridazine-3-carbonitrile (Example 25): A mixture of 2-chloro-N-isopropyl-5-(5-methyl-1,3,4-thiadiazol-2-yl)pyridin-4-amine (0.03 g, 0.13 mmol), 7-(4,4,5,5-tetramethyl-1,3,2-dioxaborolan-2-yl)pyrrolo[1,2-b]pyridazine-3-carbonitrile (I-8) (0.05 g, 0.18 mmol), Dichloro 1,1'-bis(diphenylphosphino)ferrocene palladium (II) (0.02 g, 0.02 mmol), and Sodium Carbonate solution (aq, 2M, 0.13 ml) in 1,4-dioxane (0.6 mL) was degassed with N$_2$ for 2 mins, then heated at 80 deg for 20 minutes in a microwave reactor. The crude reaction was purified by RP-HPLC (eluent: water/MeCN*0.1% TFA) and further purified by normal phase silica gel chromatography (eluent: EtOAc/dichloromethane) to give 7-(4-(isopropylamino)-5-(5-methyl-1,3,4-thiadiazol-2-yl)pyridin-2-yl)pyrrolo[1,2-b]pyridazine-3-carbonitrile (Example 25).
ES/MS: 376.265 [M+H$^+$].
1H NMR (400 MHz, Methanol-d4) δ 8.63-8.55 (m, 1H), 8.52 (s, 1H), 8.32 (d, J=2.9 Hz, 1H), 7.84 (t, J=4.5 Hz, 1H), 7.10 (t, J=5.0 Hz, 1H), 5.48 (s, 0H), 5.34 (s, 1H), 4.04 (s, 0H), 2.82 (d, J=3.7 Hz, 1H), 2.18 (s, 1H), 2.08-1.97 (m, 2H), 1.60 (s, 1H), 1.46-1.40 (m, 3H), 1.29 (s, 1H), 0.95-0.82 (m, 2H).

Procedure 8: Example 26

7-(5-(5-(2-aminoethyl)-1,3,4-thiadiazol-2-yl)-4-(isopropylamino)pyridin-2-yl)pyrrolo[1,2-b]pyridazine-3-carbonitrile (Example 26)

Example 31

Example 26

7-(5-(5-(2-aminoethyl)-1,3,4-thiadiazol-2-yl)-4-(isopropylamino)pyridin-2-yl)pyrrolo[1,2-b]pyridazine-3-carbonitrile (Example 26): To a solution of tert-butyl (2-(5-(6-(3-cyanopyrrolo[1,2-b]pyridazin-7-yl)-4-(isopropylamino)pyridin-3-yl)-1,3,4-thiadiazol-2-yl)ethyl)carbamate (Example 31) (obtained as described in Procedure 1) (4.6 mg, 0.0091 mmol) in 1,4-dioxane (0.25 mL) was added HCl (4M in 1,4-dioxane, 11.0 μL, 0.046 mmol). The reaction mixture was heated to 30° C. for 30 minutes, then concentrated in vacuo and purified by reverse phase high pressure liquid chromatography (eluent: water/MeCN*0.1% TFA) to provide the final compound Example 26.

ES/MS: 405.2 [M+H$^+$].

1H NMR (400 MHz, Methanol-d4) δ 8.82-8.63 (m, 3H), 8.07 (d, J=5.3 Hz, 2H), 7.24 (d, J=5.0 Hz, 1H), 4.31 (p, J=6.4 Hz, 1H), 3.66-3.55 (m, 4H), 1.50 (d, J=6.4 Hz, 6H).

The following compounds were made according to the procedures herein, using the appropriate starting materials and protecting group chemistry as needed:

| Structure | # | ES/MS m/z | Name | Procedure |
|---|---|---|---|---|
| 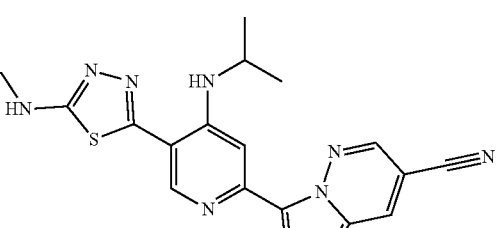 | 27 | 481.3 | (R)-7-(5-(5-((2-fluoro-3-hydroxy-3-methylbutyl)amino)-1,3,4-thiadiazol-2-yl)-4-(isopropylamino)pyridin-2-yl)pyrrolo[1,2-b]pyridazine-3-carbonitrile | 2 |
| 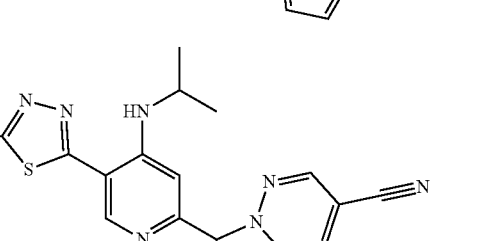 | 28 | 427.3 | 7-(5-(5-(1H-pyrrol-1-yl)-1,3,4-thiadiazol-2-yl)-4-(isopropylamino)pyridin-2-yl)pyrrolo[1,2-b]pyridazine-3-carbonitrile | 1 |

Procedure 2: Example 29

7-(4-(isopropylamino)-5-(5-(pyrrolidin-1-yl)-1,3,4-thiadiazol-2-yl)pyridin-2-yl)pyrrolo[1,2-b]pyridazine-3-carbonitrile (Example 29)

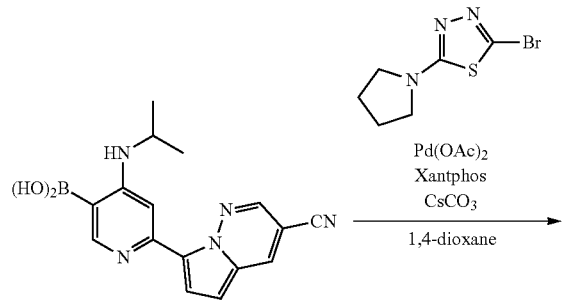

-continued

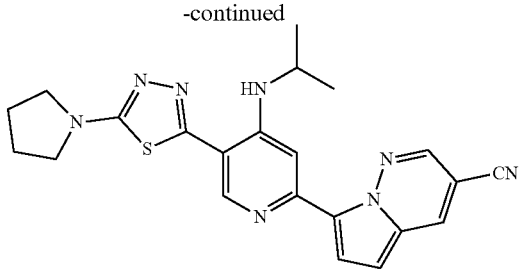

Example 29

7-(4-(isopropylamino)-5-(5-(pyrrolidin-1-yl)-1,3,4-thiadiazol-2-yl)pyridin-2-yl)pyrrolo[1,2-b]pyridazine-3-carbonitrile (Example 29): To a microwave vial containing (6-(3-cyanopyrrolo[1,2-b]pyridazin-7-yl)-4-(isopropylamino)pyridin-3-yl)boronic acid (I-3) as a trifluoroacetate salt (10 mg, 0.023 mmol), 2-bromo-5-pyrrolidin-1-yl-1,3,4-thiadiazole (6 mg, 0.025 mmol), Pd(OAc)$_2$ (1 mg, 0.0046 mmol), Xantphos (5.3 mg, 0.0092 mmol), and cesium carbonate (22.5 mg, 0.069 mmol) was added 1,4-dioxane (0.5 mL). The mixture was degassed with argon for 1 min, sealed, and heated under microwave conditions for 20 min at 150° C. Afterward, the vial was cooled and the crude material was diluted with DMF (0.5 mL). This mixture was filtered, and purified by RP-HPLC (eluent: water/MeCN*0.1% TFA) to yield the product Example 29 as a trifluoroacetate salt.
ES/MS: 341.3 (M+H⁺)
1H NMR (400 MHz, Methanol-d4) δ 8.78 (d, J=2.2 Hz, 1H), 8.69 (d, J=2.2 Hz, 1H), 8.49 (s, 1H), 8.08 (d, J=5.1 Hz, 1H), 7.89 (s, 1H), 7.25 (d, J=5.1 Hz, 1H), 4.37-4.24 (m, 1H), 3.67-3.60 (m, 4H), 2.22-2.15 (m, 4H), 1.53-1.43 (m, 6H).

Procedure 6: Example 30

7-(4-(isopropylamino)-5-(1,3,4-thiadiazol-2-yl)pyridin-2-yl)pyrrolo[1,2-b]pyridazine-3-carbonitrile (Example 30)

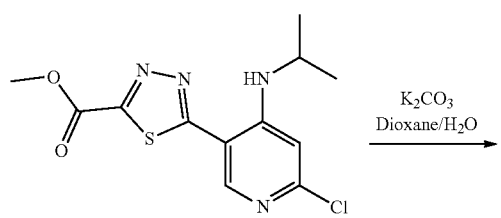

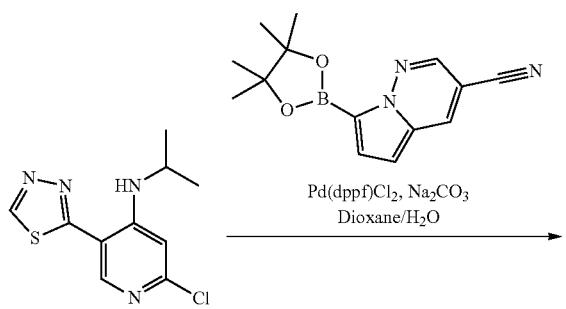

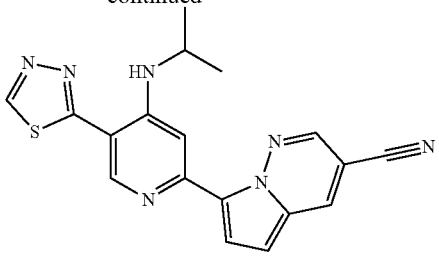

Example 30

2-chloro-N-isopropyl-5-(1,3,4-thiadiazol-2-yl)pyridin-4-amine: To a solution of methyl 5-(6-chloro-4-(isopropylamino)pyridin-3-yl)-1,3,4-thiadiazole-2-carboxylate (50.0 mg, 0.16 mmol) in 1,4-dioxane (2.0 mL) was added potassium carbonate (2.4M in water, 0.20 mL, 0.48 mmol). The reaction mixture was heated at 110° C. for 2 hours. The reaction was concentrated and partitioned between water and EtOAc. The organic layer was isolated, and the aqueous layer was extracted with two additional portions of EtOAc. The organic layers were combined, dried over sodium sulfate, filtered, and concentrated to provide 2-chloro-N-isopropyl-5-(1,3,4-thiadiazol-2-yl)pyridin-4-amine which was used without additional purification.
ES/MS: 255.1 [M+H⁺].

7-(4-(isopropylamino)-5-(1,3,4-thiadiazol-2-yl)pyridin-2-yl)pyrrolo[1,2-b]pyridazine-3-carbonitrile (Example 30): A solution of 2-chloro-N-isopropyl-5-(1,3,4-thiadiazol-2-yl) pyridin-4-amine (32.0 mg, 0.13 mmol), 7-(4,4,5,5-tetramethyl-1,3,2-dioxaborolan-2-yl)pyrrolo[1,2-b]pyridazine-3-carbonitrile (I-8) (40.3 mg, 0.15 mmol), [1,1'-Bis(diphenylphosphino)ferrocene]dichloropalladium(II) (25.0 mg, 0.031 mmol), and sodium carbonate (2N in water, 125 μL, 0.14 mmol) in 1,4-dioxane (1.0 mL) was sparged with argon for 60 seconds, then heated in a microwave reactor at 125° C. for 20 minutes. Upon cooling, the reaction mixture was filtered and purified by reverse phase high pressure liquid chromatography (eluent: water/MeCN*0.1% TFA) to provide the final compound Example 30.
ES/MS: 362.2 [M+H⁺].
1H NMR (400 MHz, Methanol-d4) δ 9.62 (s, 1H), 8.83 (s, 1H), 8.78 (d, J=2.2 Hz, 1H), 8.71 (d, J=2.2 Hz, 1H), 8.10 (d, J=5.0 Hz, 1H), 8.02 (s, 1H), 7.26 (d, J=5.1 Hz, 1H), 4.35 (hept, J=6.3 Hz, 1H), 1.53 (d, J=6.4 Hz, 6H).

Procedure 3: Example 31

7-(5-(5-(3-hydroxy-3-methylbutyl)-1,3,4-thiadiazol-2-yl)-4-(isopropylamino)pyridin-2-yl)pyrrolo[1,2-b]pyridazine-3-carbonitrile (Example 31)

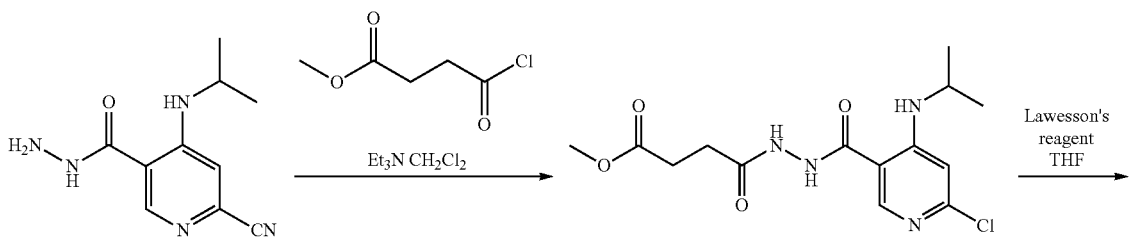

-continued

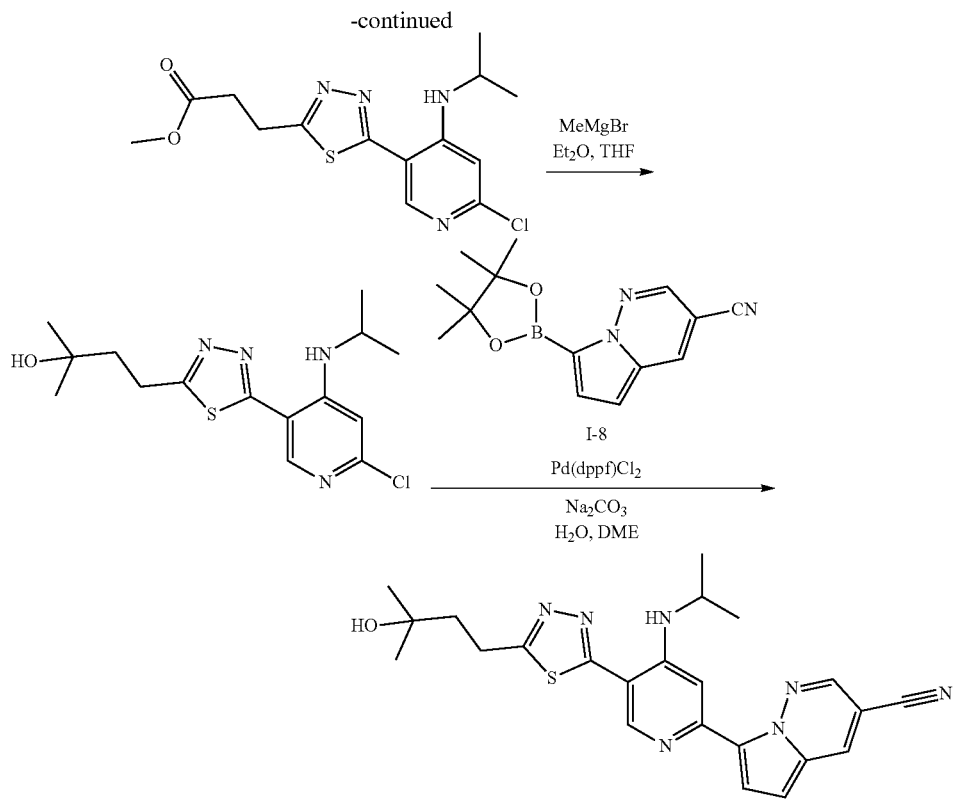

Example 31

Methyl 4-(2-(6-chloro-4-(isopropylamino)nicotinoyl)hydrazinyl)-4-oxobutanoate: To a solution of known compound 6-chloro-4-(isopropylamino)nicotinohydrazide (2 g, 8.75 mmol) in dichoromethane (100 mL) was added triethylamine (3.66 mL, 26.2 mmol), and the reaction was cooled to 0° C. To the reaction was added methyl 4-chloro-4-oxobutanoate (1.72 mL, 14 mmol) dropwise, and the resulting mixture stirred at room temperature for 5 hours. Afterward, saturated aqueous NaHCO$_3$ was added, and layers were separated. The organic layer was extracted with dichloromethane. The combined organic layers were dried over MgSO$_4$, filtered and concentrated. The resulting crude residue was purified by silica gel chromatography (eluent: EtOAc/hexanes, then MeOH/EtOAc) to give the desired product.

ES/MS: 343.4 [M+H]$^+$

Methyl 3-(5-(6-chloro-4-(isopropylamino)pyridin-3-yl)-1,3,4-thiadiazol-2-yl)propanoate: To a solution of methyl 4-(2-(6-chloro-4-(isopropylamino)nicotinoyl)hydrazinyl)-4-oxobutanoate (710 mg, 2.07 mmol) in THF (50 mL) was added Lawesson's reagent (1.68 g, 4.14 mmol) in one portion, and the reaction was stirred at reflux for 90 minutes. Afterward, the reaction was cooled, and the mixture was diluted with EtOAc, and the organics were washed twice with 50% (by volume) aqueous NaHCO$_3$. The organic layer was dried over MgSO$_4$, filtered and concentrated. The resulting crude residue was purified by silica gel chromatography (eluent: EtOAc/hexanes) to give the desired product.

ES/MS: 341.3 [M+H]$^+$ 4-(5-(6-chloro-4-(isopropylamino)pyridin-3-yl)-1,3,4-thiadiazol-2-yl)-2-methylbutan-2-ol: To a flask with methyl 3-(5-(6-chloro-4-(isopropylamino)pyridin-3-yl)-1,3,4-thiadiazol-2-yl)propanoate (216 mg, 0.63 mmol) under N$_2$ was added THF (7 mL), and the reaction was cooled to 0° C. To the reaction was added methylmagnesium bromide (3M solution in Et$_2$O, 1.48 mL, 4.44 mmol) dropwise, and the reaction was stirred for 30 min at 0° C. Afterward, the reaction was quenched by dropwise addition of saturated aqueous NH$_4$Cl, and the mixture was diluted with EtOAc and water. The layers were separated, and the aqueous layer was washed once with EtOAc. The combined organic layers were dried over MgSO$_4$, filtered and concentrated. The resulting crude residue was purified by silica gel chromatography (eluent: EtOAc/hexanes) to give the desired product.

ES/MS: 341.2 [M+H]$^+$ 7-(5-(5-(3-hydroxy-3-methylbutyl)-1,3,4-thiadiazol-2-yl)-4-(isopropylamino)pyridin-2-yl)pyrrolo[1,2-b]pyridazine-3-carbonitrile (Example 31): To a microwave vial was added 4-(5-(6-chloro-4-(isopropylamino)pyridin-3-yl)-1,3,4-thiadiazol-2-yl)-2-methylbutan-2-ol (50 mg, 0.15 mmol), 7-(4,4,5,5-tetramethyl-1,3,2-dioxaborolan-2-yl)pyrrolo[1,2-b]pyridazine-3-carbonitrile (I-8) (55 mg, 0.21 mmol), [1,1'-Bis(diphenylphosphino)ferrocene]dichloropalladium(II) (21.8 mg, 0.029 mmol). To the vial was added DME (1.0 mL) and sodium carbonate (2M solution in water, 0.15 mL, 0.29 mmol). The mixture was degassed with argon for 1 min, sealed, and heated under microwave conditions for 20 min at 120° C. Afterward, the vial was cooled and the mixture was concentrated under vacuum. The crude material was diluted with DMF (1 mL). This mixture was filtered, and purified by RP-HPLC (eluent: water/MeCN*0.1% TFA) to yield the product Example 31 as a trifluoroacetate salt.

ES/MS: 448.5 [M+H]$^+$

1H NMR (400 MHz, Methanol-d4) δ 8.80 (d, J=2.2 Hz, 1H), 8.74-8.71 (m, 2H), 8.11 (d, J=5.1 Hz, 1H), 7.97 (s, 1H), 7.26 (d, J=5.1 Hz, 1H), 4.35 (hept, J=6.4 Hz, 1H), 3.41-3.35 (m, 2H), 2.12-1.99 (m, 2H), 1.52 (d, J=6.4 Hz, 6H), 1.33 (s, 6H).

The following compounds were made according to the procedures set forth previously, using the appropriate starting materials and protecting group chemistry as needed:

| # | ES/MS m/z | Procedure | Name |
|---|---|---|---|
| 32 | 446.3 | 2 | 7-(4-(isopropylamino)-5-(5-(tetrahydro-2H-pyran-4-yl)-1,3,4-thiadiazol-2-yl)pyridin-2-yl)pyrrolo[1,2-b]pyridazine-3-carbonitrile |
| 33 | 474.45 | 2 | N-(1-(5-(6-(3-cyanopyrrolo[1,2-b]pyridazin-7-yl)-4-(isopropylamino)pyridin-3-yl)-1,3,4-thiadiazol-2-yl)azetidin-3-yl)acetamide |
| 34 | 614.32 | 1 | methyl ((1R,4r)-4-((5-(5-((1r,4R)-4-acetamidocyclohexyl)-1,3,4-thiadiazol-2-yl)-2-(3-cyanopyrrolo[1,2-b]pyridazin-7-yl)pyridin-4-yl)amino)cyclohexyl)carbamate |
| 35 | 502.57 | 2 | (S)-7-(5-(5-(hexahydropyrazino[2,1-c][1,4]oxazin-8(1H)-yl)-1,3,4-thiadiazol-2-yl)-4-(isopropylamino)pyridin-2-yl)pyrrolo[1,2-b]pyridazine-3-carbonitrile |
| 36 | 502.45 | 2 | (R)-7-(5-(5-(hexahydropyrazino[2,1-c][1,4]oxazin-8(1H)-yl)-1,3,4-thiadiazol-2-yl)-4-(isopropylamino)pyridin-2-yl)pyrrolo[1,2-b]pyridazine-3-carbonitrile |
| 37 | 449.48 | 1 | 7-(5-(5-((2-hydroxy-2-methylpropyl)amino)-1,3,4-thiadiazol-2-yl)-4-(isopropylamino)pyridin-2-yl)pyrrolo[1,2-b]pyridazine-3-carbonitrile |
| 38 | 528.40 | 2 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)acetamide |
| 39 | 528.42 | 2 | N-((1R,5S,8r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)acetamide |
| 40 | 515.36 | 5 | (R)-N-(1-(2-(6-(3-cyanopyrrolo[1,2-b]pyridazin-7-yl)-4-(isopropylamino)pyridin-3-yl)thiazole-5-carbonyl)pyrrolidin-3-yl)acetamide |
| 41 | 530.47 | 5 | (S)-N-((1-(5-(6-(3-cyanopyrrolo[1,2-b]pyridazin-7-yl)-4-(isopropylamino)pyridin-3-yl)-1,3,4-thiadiazole-2-carbonyl)pyrrolidin-2-yl)methyl)acetamide |
| 42 | 530.56 | 5 | (R)-N-((1-(5-(6-(3-cyanopyrrolo[1,2-b]pyridazin-7-yl)-4-(isopropylamino)pyridin-3-yl)-1,3,4-thiadiazole-2-carbonyl)pyrrolidin-2-yl)methyl)acetamide |
| 43 | 532.45 | 5 | methyl (S)-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)carbamate |
| 44 | 532.42 | 5 | methyl (R)-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)carbamate |
| 45 | 514.45 | 2 | N-((1R,5S,6r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.1]heptan-6-yl)acetamide |
| 46 | 542.52 | 5 | (S)-N-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)cyclopropanecarboxamide |
| 47 | 542.59 | 5 | (R)-N-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)cyclopropanecarboxamide |
| 48 | 530.53 | 5 | (S)-N-(1-(5-(6-(3-cyanopyrrolo[1,2-b]pyridazin-7-yl)-4-(isopropylamino)pyridin-3-yl)-1,3,4-thiadiazole-2-carbonyl)piperidin-3-yl)acetamide |
| 49 | 530.60 | 5 | (R)-N-(1-(5-(6-(3-cyanopyrrolo[1,2-b]pyridazin-7-yl)-4-(isopropylamino)pyridin-3-yl)-1,3,4-thiadiazole-2-carbonyl)piperidin-3-yl)acetamide |

Procedure 10: Example 50

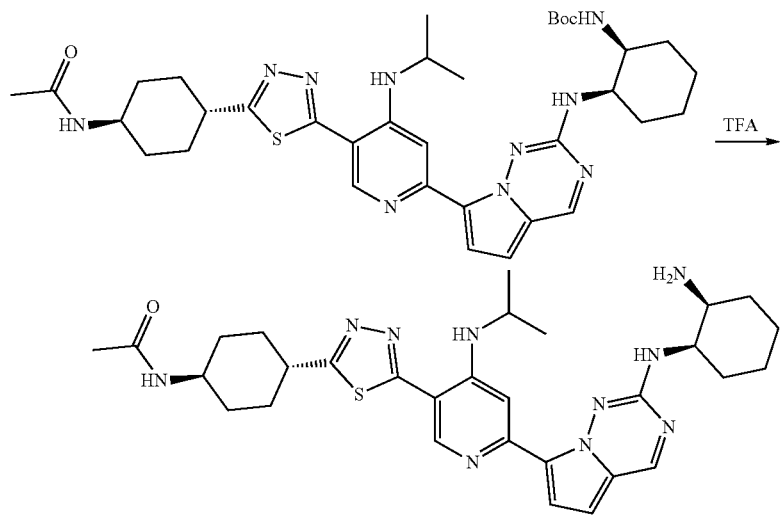

Example 50

N-((1r,4r)-4-(5-(6-(2-(((1R,2S)-2-aminocyclohexyl)amino)pyrrolo[2,1-f][1,2,4]triazin-7-yl)-4-(isopropylamino)pyridin-3-yl)-1,3,4-thiadiazol-2-yl)cyclohexypacetamide (Example 50): Tert-butyl ((1S,2R)-2-((7-(5-(5-((1r,4r)-4-acetamidocyclohexyl)-1,3,4-thiadiazol-2-yl)-4-(isopropylamino)pyridin-2-yl)pyrrolo[2,1-f][1,2,4]triazin-2-yl)amino)cyclohexyl)carbamate (prepared as described in Procedure 1 from the appropriate 3-bromo-pyridine and thiadiazole) (39.1 mg, 0.057 mmol) was taken in trifluoroacetic acid (1.0 mL) and stirred at RT for 5 minutes. The reaction was concentrated and purified by RP-HPLC (eluent: water/MeCN*0.1% TFA) to yield the product Example 50 as a trifluoroacetate salt.
ES/MS: 589.82 (M+H$^+$)
1H NMR (400 MHz, Methanol-d4) δ 9.06 (s, 1H), 8.73 (s, 1H), 7.74 (d, J=5.2 Hz, 1H), 7.71 (s, 1H), 7.08 (d, J=5.1 Hz, 1H), 4.65-4.57 (m, 1H), 4.33 (p, J=6.4 Hz, 1H), 3.84-3.68 (m, 1H), 3.63-3.52 (m, 1H), 2.31 (d, J=13.0 Hz, 2H), 2.10 (d, J=12.8 Hz, 2H), 2.06-1.65 (m, 13H), 1.67-1.36 (m, 9H).

The following compounds were made according to the previous procedures, using the appropriate starting materials and protecting group chemistry as needed:

| # | EMS/MS m/z | Procedure | Name |
|---|---|---|---|
| 51 | 601.46 | 2 | methyl (((1R,3r)-3-((2-(3-cyanopyrrolo[1,2-b]pyridazin-7-yl)-5-(5-((R)-hexahydropyrazino[2,1-c][1,4]oxazin-8(1H)-yl)-1,3,4-thiadiazol-2-yl)pyridin-4-yl)amino)cyclobutyl)methyl)carbamate |
| 52 | 627.50 | 2 | methyl (((1R,3r)-3-((5-(5-((1R,5S,8S)-8-acetamido-3-azabicyclo[3.2.1]octan-3-yl)-1,3,4-thiadiazol-2-yl)-2-(3-cyanopyrrolo[1,2-b]pyridazin-7-yl)pyridin-4-yl)amino)cyclobutyl)methyl)carbamate |

Procedure 11: Example 53

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)acetamide (Example 53)

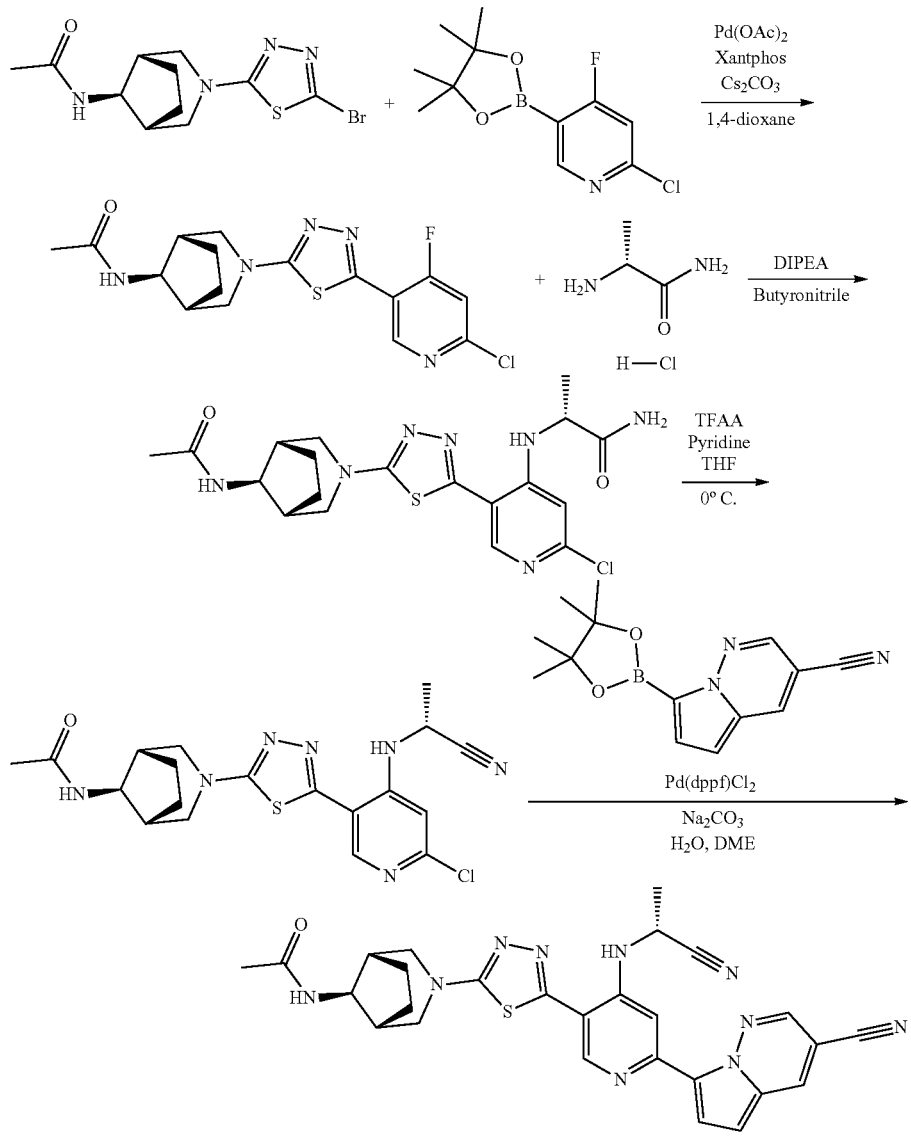

Example 53

N-((1R,5S,8s)-3-(5-(6-chloro-4-fluoropyridin-3-yl)-1,3,4-thiadiazol-2-yl)-3-azabicyclo[3.2.1]octan-8-yl)acetamide: A microwave vial was charged with N-((1R,5S,8s)-3-(5-bromo-1,3,4-thiadiazol-2-yl)-3-azabicyclo[3.2.1]octan-8-yl)acetamide (200 mg, 0.60 mmol), 2-chloro-4-fluoro-5-(4,4,5,5-tetramethyl-1,3,2-dioxaborolan-2-yl)pyridine (171 mg, 0.66 mmol), palladium(II) acetate (20.3 mg, 0.091 mmol), Xantphos (105 mg, 0.18 mmol), and cesium carbonate (590 mg, 0.18 mmol). Dioxane (3.0 mL) was added, and the reaction mixture was degassed by bubbling argon for 60 seconds. The vial was sealed and heated with stirring at 120° C. for 20 minutes in a microwave reactor. The cooled reaction mixture was filtered through a pad of Celite with EtOAc, concentrated in vacuo, and used without additional purification.

(R)-2-((5-(5-(((1R,5S,8S)-8-acetamido-3-azabicyclo [3.2.1]octan-3-yl)-1,3,4-thiadiazol-2-yl)-2-chloropyridin-4-yl)amino)propenamide: To a solution of crude N-((1R,5S,8s)-3-(5-(6-chloro-4-fluoropyridin-3-yl)-1,3,4-thiadiazol-2-yl)-3-azabicyclo[3.2.1]octan-8-yl)acetamide (231 mg, 0.60 mmol) in butyronitrile (3.0 mL) was added D-alaninamide hydrochloride (90.3 mg, 0.73 mmol) and N,N-diisopropylethylamine (0.47 mL, 2.7 mmol). The reaction was heated at 130° C. for 45 minutes. The cooled reaction was concentrated in vacuo and used without additional purification.

N-((1R,5S,8S)-3-(5-(6-chloro-4-(((R)-1-cyanoethyl)amino)pyridin-3-yl)-1,3,4-thiadiazol-2-yl)-3-azabicyclo[3.2.1]octan-8-yl)acetamide: A solution of crude (R)-2-((5-(5-(((1R,5S,8S)-8-acetamido-3-azabicyclo[3.2.1]octan-3-yl)-1,3,4-thiadiazol-2-yl)-2-chloropyridin-4-yl)amino)propanamide (272 mg, 0.60 mmol) in THF (3.0 mL) was cooled to 0° C. To the solution was added pyridine (0.24 mL, 3.0 mmol) and trifluoroacetic anhydride (0.13 mL, 0.91 mmol). The reaction was allowed to warm to room temperature while stirred for 25 minutes. The reaction mixture was concentrated in vacuo and purified by silica gel column chromatography (eluent: MeOH/DCM) to provide the desired product.
ES/MS: 432.61 (M+H$^+$)

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)acetamide (Example 53): A microwave vial was charged with N-((1R,5S,8S)-3-(5-(6-chloro-4-(((R)-1-cyanoethyl)amino)pyridin-3-yl)-1,3,4-thiadiazol-2-yl)-3-azabicyclo[3.2.1]octan-8-yl)acetamide (84.0 mg, 0.19 mmol), 7-(4,4,5,5-tetramethyl-1,3,2-dioxaborolan-2-yl)pyrrolo[1,2-b]pyridazine-3-carbonitrile (Intermediate I-8, 78.5 mg, 0.29 mmol), and [1,1'-Bis(diphenylphosphino)ferrocene]dichloropalladium(II) (28.9 mg, 0.039 mmol). To the flask was added DME (4.0 mL) and a 2M aqueous solution of sodium carbonate (0.39 mL, 0.78 mmol). The reaction mixture was degassed by bubbling argon for 60 seconds. The vial was sealed and heated with stirring at 120° C. for 15 minutes in a microwave reactor. The cooled reaction mixture was concentrated and purified by RP-HPLC (eluent: water/MeCN*0.1% TFA) to yield the product Example 53 as a trifluoroacetate salt.
ES/MS: 539.38 (M+H$^+$)
1H NMR (400 MHz, Methanol-d4) δ 8.80 (d, J=2.2 Hz, 1H), 8.72 (d, J=2.1 Hz, 1H), 8.64 (s, 1H), 8.14 (d, J=5.1 Hz, 1H), 8.08 (s, 1H), 8.03 (d, J=5.8 Hz, 1H), 7.27 (d, J=5.0 Hz, 1H), 5.26 (q, J=6.9 Hz, 1H), 4.01 (d, J=4.9 Hz, 1H), 3.84 (d, J=12.0 Hz, 2H), 3.57 (d, J=11.9 Hz, 2H), 2.46 (s, 2H), 2.08-1.98 (m, 5H), 1.92 (d, J=7.0 Hz, 3H), 1.75-1.64 (m, 2H).

The following compounds were made according to the previous procedures, using the appropriate starting materials and protecting group chemistry as needed:

| # | ES/MS m/z | Procedure | Name |
|---|---|---|---|
| 54 | 641.55 | 2 | methyl ((1R,4r)-4-((5-(5-(((1R,5S,8S)-8-acetamido-3-azabicyclo[3.2.1]octan-3-yl)-1,3,4-thiadiazol-2-yl)-2-(3-cyanopyrrolo[1,2-b]pyridazin-7-yl)pyridin-4-yl)amino)cyclohexyl)carbamate |
| 55 | 528.61 | 2 | N-((1R,3r,5S)-8-(5-(6-(3-cyanopyrrolo[1,2-b]pyridazin-7-yl)-4-(isopropylamino)pyridin-3-yl)-1,3,4-thiadiazol-2-yl)-8-azabicyclo[3.2.1]octan-3-yl)acetamide |
| 56 | 528.62 | 2 | N-((1R,3s,5S)-8-(5-(6-(3-cyanopyrrolo[1,2-b]pyridazin-7-yl)-4-(isopropylamino)pyridin-3-yl)-1,3,4-thiadiazol-2-yl)-8-azabicyclo[3.2.1]octan-3-yl)acetamide |
| 57 | 599.56 | 2 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)morpholine-4-carboxamide |
| 58 | 564.46 | 2 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)methanesulfonamide |
| 59 | 544.56 | 2 | methyl ((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamate |
| 60 | 486.48 | 2 | 7-(5-(5-((1R,5S,8s)-8-amino-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile |

Procedure 12: Example 61

N-((1R,5S,8S)-3-(5-(6-(2-(((1R,2S)-2-aminocyclohexyl)amino)pyrrolo[2,1-f][1,2,4]triazin-7-yl)-4-(((R)-1-cyanoethyl)amino)pyridin-3-yl)-1,3,4-thiadiazol-2-yl)-3-azabicyclo[3.2.1]octan-8-yl)acetamide (Example 61)

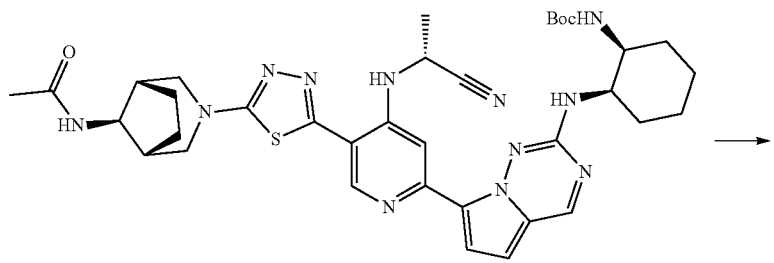

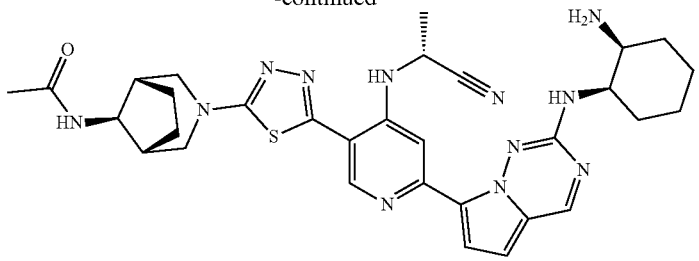

Example 61

N-((1R,5S,8S)-3-(5-(6-(2-(((1R,2S)-2-aminocyclohexyl)amino)pyrrolo[2,1-f][1,2,4]triazin-7-yl)-4-(((R)-1-cyanoethyl)amino)pyridin-3-yl)-1,3,4-thiadiazol-2-yl)-3-azabicyclo[3.2.1]octan-8-yl)acetamide (Example 61): To a solution of tert-butyl ((1S,2R)-2-((7-(5-(5-((1R,5S,8S)-8-acetamido-3-azabicyclo[3.2.1]octan-3-yl)-1,3,4-thiadiazol-2-yl)-4-(((R)-1-cyanoethyl)amino)pyridin-2-yl)pyrrolo[2,1-f][1,2,4]triazin-2-yl)amino)cyclohexyl)carbamate (synthesized as described in Example P-GJB2 using the appropriate boronate ester in place of I-8) (25.2 mg, 0.035 mmol) in DCM (1.0 mL) was added trifluoroacetic acid (0.5 mL, 7.0 mmol). The reaction mixture was stirred at RT for 20 minutes, then concentrated in vacuo and purified by RP-HPLC (eluent: water/MeCN*0.1% TFA) to yield the product Example 61 as a trifluoroacetate salt.
ES/MS: 627.53 (M+H$^+$)
1H NMR (400 MHz, Methanol-d4) δ 9.07 (s, 1H), 8.65 (s, 1H), 8.02 (d, J=5.8 Hz, 1H), 7.97 (s, 1H), 7.70 (d, J=5.1 Hz, 1H), 7.09 (d, J=5.1 Hz, 1H), 5.22 (q, J=6.9 Hz, 1H), 4.64 (d, J=4.1 Hz, 1H), 4.07-3.95 (m, 1H), 3.81 (d, J=11.9 Hz, 2H), 3.55 (d, J=11.6 Hz, 3H), 2.44 (s, 2H), 2.06-1.93 (m, 6H), 1.93-1.72 (m, 8H), 1.75-1.63 (m, 4H), 1.62-1.49 (m, 1H).

The following compounds were made according to the previous procedures, using the appropriate starting materials and protecting group chemistry as needed:

| # | ES/MS m/z | Procedure | Name |
|---|---|---|---|
| 62 | 518.44 | 2 | N-((3R,4S)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide |
| 63 | 518.43 | 2 | N-((3S,4R)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide |
| 64 | 518.59 | 2 | N-((3S,4S)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide |
| 65 | 518.41 | 2 | N-((3R,4R)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide |
| 66 | 528.57 | 2 | N-(2-(5-(6-(3-cyanopyrrolo[1,2-b]pyridazin-7-yl)-4-(isopropylamino)pyridin-3-yl)-1,3,4-thiadiazol-2-yl)-2-azabicyclo[2.2.2]octan-4-yl)acetamide |
| 67 | 528.50 | 2 | 7-(5-(5-(7-acetyl-2,7-diazaspiro[3.5]nonan-2-yl)-1,3,4-thiadiazol-2-yl)-4-(isopropylamino)pyridin-2-yl)pyrrolo[1,2-b]pyridazine-3-carbonitrile |
| 68 | 500.42 | 2 | 7-(5-(5-(6-acetyl-2,6-diazaspiro[3.3]heptan-2-yl)-1,3,4-thiadiazol-2-yl)-4-(isopropylamino)pyridin-2-yl)pyrrolo[1,2-b]pyridazine-3-carbonitrile |
| 69 | 542.49 | 2 | N-(2-(5-(6-(3-cyanopyrrolo[1,2-b]pyridazin-7-yl)-4-(isopropylamino)pyridin-3-yl)-1,3,4-thiadiazol-2-yl)-2-azaspiro[3.5]nonan-7-yl)acetamide |
| 70 | 541.30 | 1 | N-(4-(5-(6-(3-cyanopyrrolo[1,2-b]pyridazin-7-yl)-4-(oxetan-3-ylamino)pyridin-3-yl)-1,3,4-thiadiazol-2-yl)bicyclo[2.2.2]octan-1-yl)acetamide |
| 71 | 569.43 | 1 | N-(4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)acetamide |

Procedure 13: Example 72

(R)-N-(4-(5-(4-((1-cyanoethyl)amino)-6-(3-cyanopyrrolo[1,2-b]pyridazin-7-yl)pyridin-3-yl)-1,3,4-thiadiazol-2-yl)bicyclo[2.2.2]octan-1-yl)acetamide (Example 72)

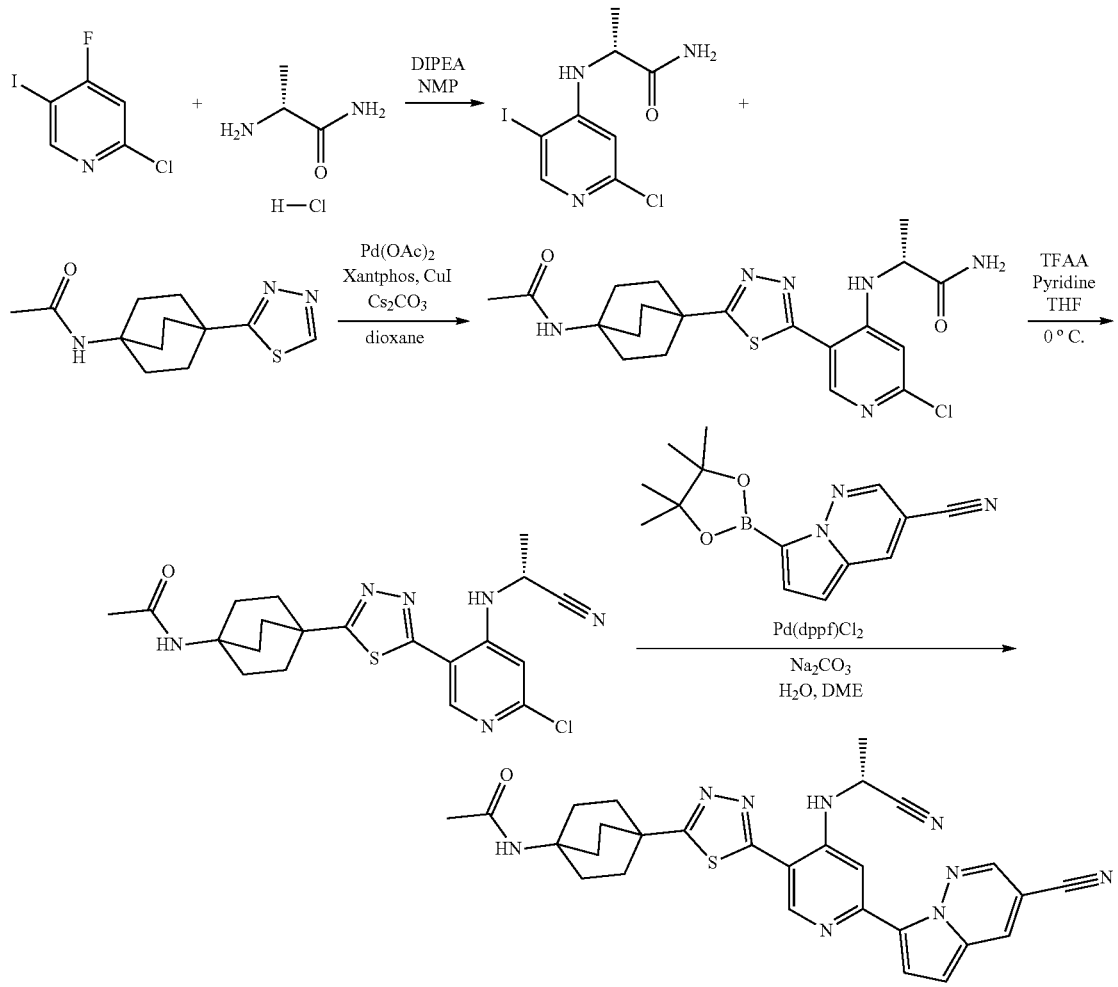

Example 72

(R)-2-((2-chloro-5-iodopyridin-4-yl)amino)propenamide: To a solution of 2-chloro-4-fluoro-5-iodo-pyridine (3.50 g, 13.6 mmol) and D-alaninamide hydrochloride (4.23 g, 68.0 mmol) in NMP (30.0 mL) was added N,N-diisopropylethylamine (11.8 mL, 68.0 mmol). The reaction mixture was heated to 150° C. overnight, then cooled and diluted with water (125 mL). The solution was stirred at RT for 2 hours, then the resulting solid was isolated by vacuum filtration, washed with water, and dried by high vacuum. The crude solids were used without additional purification.

sES/MS: 326.24 (M+H$^+$)

(R)-2-((5-(5-(4-acetamidobicyclo[2.2.2]octan-1-yl)-1,3,4-thiadiazol-2-yl)-2-chloropyridin-4-yl)amino)propenamide: (R)-2-((5-(5-(4-acetamidobicyclo[2.2.2]octan-1-yl)-1,3,4-thiadiazol-2-yl)-2-chloropyridin-4-yl)amino)propenamide was prepared following the protocol in Procedure 1, using the appropriate coupling partners.
ES/MS: 449.28 (M+H$^+$)

(R)-N-(4-(5-(6-chloro-4-((1-cyanoethyl)amino)pyridin-3-yl)-1,3,4-thiadiazol-2-yl)bicyclo[2.2.2]octan-1-yl)acetamide: (R)-N-(4-(5-(6-chloro-4-((1-cyanoethyl)amino)pyridin-3-yl)-1,3,4-thiadiazol-2-yl)bicyclo[2.2.2]octan-1-yl)acetamide was prepared following the protocol in step 3 of Procedure 11.
ES/MS: 431.33 (M+H$^+$)

(R)-N-(4-(5-(4-((1-cyanoethyl)amino)-6-(3-cyanopyrrolo[1,2-b]pyridazin-7-yl)pyridin-3-yl)-1,3,4-thiadiazol-2-yl)bicyclo[2.2.2]octan-1-yL)acetamide (Example 72): Example 72 was prepared following the protocol in step 4 of Procedure 11 using the appropriate coupling partners to provide Example 72 as a trifluoroacetate salt.
ES/MS: 538.39 (M+H$^+$).
1H NMR (400 MHz, Methanol-d4) δ 8.84 (s, 1H), 8.78 (d, J=2.1 Hz, 1H), 8.71 (d, J=2.1 Hz, 1H), 8.16 (s, 1H), 8.13 (d, J=5.1 Hz, 1H), 7.25 (d, J=5.1 Hz, 1H), 5.25 (q, J=6.9 Hz, 1H), 2.27-2.16 (m, 6H), 2.17-2.08 (m, 6H), 1.92 (d, J=7.0 Hz, 3H), 1.90 (s, 3H).

The following compounds were made according to the previous procedures, using the appropriate starting materials and protecting group chemistry as needed:

| # | ES/MS m/z | Procedure | Name |
|---|-----------|-----------|------|
| 73 | 514.35 | 2 | N-((1R,4R,5R)-2-(5-(6-(3-cyanopyrrolo[1,2-b]pyridazin-7-yl)-4-(isopropylamino)pyridin-3-yl)-1,3,4-thiadiazol-2-yl)-2-azabicyclo[2.2.1]heptan-5-yl)acetamide |
| 74 | 514.32 | 2 | N-((1S,4S,5S)-2-(5-(6-(3-cyanopyrrolo[1,2-b]pyridazin-7-yl)-4-(isopropylamino)pyridin-3-yl)-1,3,4-thiadiazol-2-yl)-2-azabicyclo[2.2.1]heptan-5-yl)acetamide |
| 75 | 542.35 | 2 | 7-(5-(5-(7-acetyl-2,7-diazaspiro[3.5]nonan-2-yl)-1,3,4-thiadiazol-2-yl)-4-(oxetan-3-ylamino)pyridin-2-yl)pyrrolo[1,2-b]pyridazine-3-carbonitrile |
| 76 | 570.51 | 2 | 7-(5-(5-(7-acetyl-2,7-diazaspiro[3.5]nonan-2-yl)-1,3,4-thiadiazol-2-yl)-4-((tetrahydro-2H-pyran-4-yl)amino)pyridin-2-yl)pyrrolo[1,2-b]pyridazine-3-carbonitrile |
| 77 | 553.33 | 2 | (R)-N-(2-(5-(4-((1-cyanoethyl)amino)-6-(3-cyanopyrrolo[1,2-b]pyridazin-7-yl)pyridin-3-yl)-1,3,4-thiadiazol-2-yl)-2-azaspiro[3.5]nonan-7-yl)acetamide |
| 78 | 556.36 | 2 | N-(2-(5-(6-(3-cyanopyrrolo[1,2-b]pyridazin-7-yl)-4-(oxetan-3-ylamino)pyridin-3-yl)-1,3,4-thiadiazol-2-yl)-2-azaspiro[3.5]nonan-7-yl)acetamide |
| 79 | 584.36 | 2 | N-(2-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-2-azaspiro[3.5]nonan-7-yl)acetamide |
| 80 | 420.26 | 1 | 7-(5-(5-(2-hydroxypropan-2-yl)-1,3,4-thiadiazol-2-yl)-4-(isopropylamino)pyridin-2-yl)pyrrolo[1,2-b]pyridazine-3-carbonitrile |
| 81 | 503.38 | 1 | N-((3R,6S)-6-(5-(6-(3-cyanopyrrolo[1,2-b]pyridazin-7-yl)-4-(isopropylamino)pyridin-3-yl)-1,3,4-thiadiazol-2-yl)tetrahydro-2H-pyran-3-yl)acetamide |
| 82 | 515.45 | 2 | 7-(5-(5-(7-hydroxy-7-methyl-2-azaspiro[3.5]nonan-2-yl)-1,3,4-thiadiazol-2-yl)-4-(isopropylamino)pyridin-2-yl)pyrrolo[1,2-b]pyridazine-3-carbonitrile |

Procedure 14: Example 83

N-(1-(5-(6-(3-cyanopyrrolo[1,2-b]pyridazin-7-yl)-4-(isopropylamino)pyridin-3-yl)-1,3,4-thiadiazol-2-yl)-2-oxabicyclo[2.2.2]octan-4-yl)acetamide (Example 83)

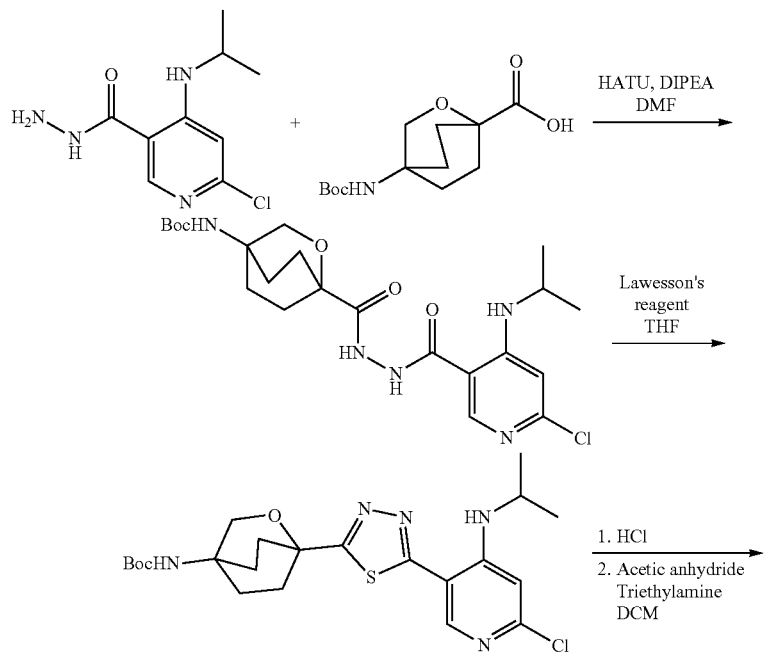

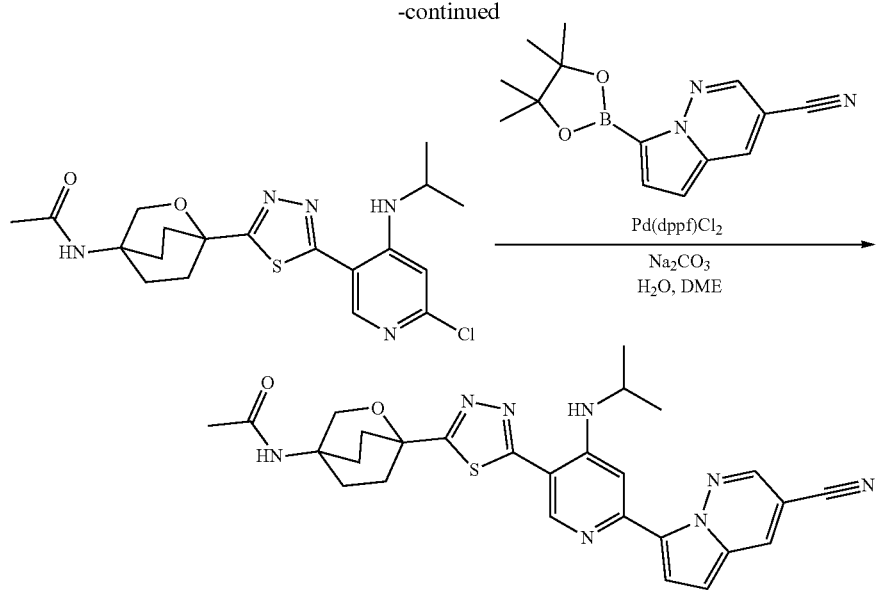

Example 83 tert-butyl (1-(2-(6-chloro-4-(isopropylamino)nicotinoyl)hydrazine-1-carbonyl)-2-oxabicyclo[2.2.2]octan-4-yl)carbamate: To a solution of 6-chloro-4-(isopropylamino)nicotinohydrazide (123 mg, 0.54 mmol), 4-((tert-butoxycarbonyl)amino)-2-oxabicyclo[2.2.2]octane-1-carboxylic acid (175 mg, 0.65 mmol), and HATU (215 mg, 0.57 mmol) in DMF (0.5 mL) was added N,N-diisopropylethylamine (0.31 mL, 1.72 mmol). The reaction mixture was stirred at RT for 15 minutes, then diluted with water (10 mL) and extracted with EtOAc (2×10 mL). The combined organic layers were dried over sodium sulfate, isolated by vacuum filtration, concentrated in vacuo, and purified by silica gel column chromatography (eluent: MeOH/DCM) to provide the desired product.
ES/MS: 482.67 (M+H$^+$).

tert-butyl (1-(5-(6-chloro-4-(isopropylamino)pyridin-3-yl)-1,3,4-thiadiazol-2-yl)-2-oxabicyclo[2.2.2]octan-4-yl)carbamate: To a solution of tert-butyl (1-(2-(6-chloro-4-(isopropylamino)nicotinoyl)hydrazine-1-carbonyl)-2-oxabicyclo[2.2.2]octan-4-yl)carbamate (240 mg, 0.50 mmol) in THF (6.0 mL) at 65° C. was added Lawesson's Reagent (302 mg, 0.75 mmol). The RM was stirred at 65° C. for 15 minutes, then concentrated in vacuo and purified by silica gel column chromatography (eluent: MeOH/DCM) to provide the desired product.
ES/MS: 480.80 (M+H$^+$).

N-(1-(5-(6-chloro-4-(isopropylamino)pyridin-3-yl)-1,3,4-thiadiazol-2-yl)-2-oxabicyclo[2.2.2]octan-4-yl)acetamide: Tert-butyl (1-(5-(6-chloro-4-(isopropylamino)pyridin-3-yl)-1,3,4-thiadiazol-2-yl)-2-oxabicyclo[2.2.2]octan-4-yl)carbamate (152 mg, 0.32 mmol) was suspended in HCl (4M in dioxane, 0.8 mL, 3.17 mmol) and heated with stirring at 40° C. for 2 hours. The reaction mixture was cooled and concentrated in vacuo. The resulting residue was suspended in DCM (2.0 mL). To the suspension was added triethylamine (60 μL, 0.43 mmol) and acetic anhydride (11.2 μL, 0.12 mmol). The reaction mixture was stirred at RT for 15 minutes, then concentrated in vacuo and purified by silica gel column chromatography (eluent: MeOH/DCM) to provide the desired product.
ES/MS: 422.32 (M+H$^+$).

N-(1-(5-(6-(3-cyanopyrrolo[1,2-b]pyridazin-7-yl)-4-(isopropylamino)pyridin-3-yl)-1,3,4-thiadiazol-2-yl)-2-oxabicyclo[2.2.2]octan-4-yl)acetamide (Example 83): Example 83 was prepared following the protocol in step 4 of Procedure 11 using the appropriate coupling partners to provide Example 83 as a trifluoroacetate salt.
ES/MS: 529.36 (M+H$^+$).
1H NMR (400 MHz, Methanol-d4) δ 8.77 (d, J=2.2 Hz, 1H), 8.74 (s, 1H), 8.69 (d, J=2.1 Hz, 1H), 8.08 (d, J=5.1 Hz, 1H), 7.95 (s, 1H), 7.23 (d, J=5.0 Hz, 1H), 4.40-4.20 (m, 3H), 2.59-2.24 (m, 6H), 2.15-2.05 (m, 2H), 1.91 (s, 3H), 1.48 (d, J=6.4 Hz, 6H).

The following compounds were made according to the previous procedures, using the appropriate starting materials and protecting group chemistry as needed:

| # | ES/MS m/z | Procedure | Name |
|---|---|---|---|
| 83 | 529.36 | 14 | N-(1-(5-(6-(3-cyanopyrrolo[1,2-b]pyridazin-7-yl)-4-(isopropylamino)pyridin-3-yl)-1,3,4-thiadiazol-2-yl)-2-oxabicyclo[2.2.2]octan-4-yl)acetamide |
| 84 | 503.32 | 14 | N-((3S,6S)-6-(5-(6-(3-cyanopyrrolo[1,2-b]pyridazin-7-yl)-4-(isopropylamino)pyridin-3-yl)-1,3,4-thiadiazol-2-yl)tetrahydro-2H-pyran-3-yl)acetamide |
| 85 | 572.49 | 2 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-2-hydroxy-2-methylpropanamide |

| # | ES/MS m/z | Procedure | Name |
|---|---|---|---|
| 86 | 583.37 | 2 | N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)-2-hydroxy-2-methylpropanamide |
| 87 | 586.36 | 2 | N-((1R,5S,8s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.2.1]octan-8-yl)-2-hydroxy-2-methylpropanamide |

Procedure 15: Example 88

N-(1-(5-(6-(3-cyanopyrrolo[1,2-b]pyridazin-7-yl)-4-(isopropylamino)pyridin-3-yl)-1,3,4-thiadiazol-2-yl)-2-oxabicyclo[2.2.2]octan-4-yl)acetamide (Example 88)

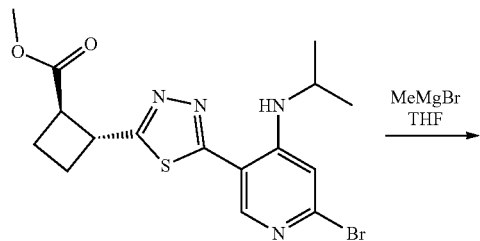

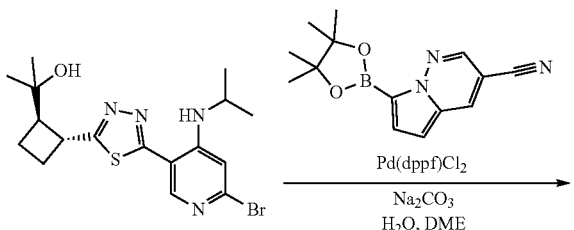

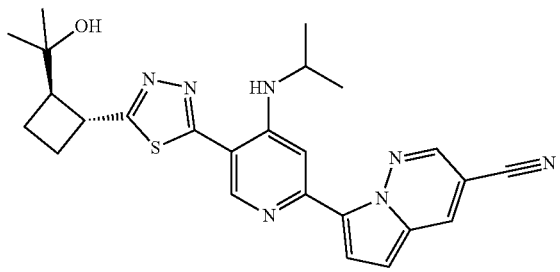

Example 88

2-((1,2-trans)-2-(5-(6-chloro-4-(isopropylamino)pyridin-3-yl)-1,3,4-thiadiazol-2-yl)cyclobutyl)propan-2-ol: To a solution of methyl (1,2-trans)-2-(5-(6-chloro-4-(isopropylamino)pyridin-3-yl)-1,3,4-thiadiazol-2-yl)cyclobutane-1-carboxylate (prepared following the protocol in steps 1 and 2 of Procedure 14 using the appropriate carboxylic acid) (100 mg, 0.24 mmol) in THF (0.5 mL) at 0° C. was added methylmagnesium bromide (3M in diethyl ether, 0.12 mL, 0.37 mmol). The reaction mixture was allowed to warm to RT with stirring over 30 minutes, then quenched with saturated aqueous ammonium chloride. The reaction was partitioned between water and EtOAc, and the aqueous layer was extracted two additional times with EtOAc. The combined organic layers were dried over sodium sulfate, isolated by vacuum filtration, concentrated in vacuo, and purified by silica gel column chromatography (eluent: MeOH/DCM) to provide the desired product.

ES/MS: 411.45, 413.19 (M+H$^+$).

7-(5-(5-((1,2-trans)-2-(2-hydroxypropan-2-yl)cyclobutyl)-1,3,4-thiadiazol-2-yl)-4-(isopropylamino)pyridin-2-yl)pyrrolo[1,2-b]pyridazine-3-carbonitrile (Example 88): Example 88 was prepared following the protocol in step 4 of Procedure 11 using the appropriate coupling partners to provide Example 88 as a trifluoroacetate salt and a mixture of trans-stereoisomers.

ES/MS: 474.36 (M+H$^+$).

1H NMR (400 MHz, Methanol-d4) δ 8.71 (d, J=2.2 Hz, 1H), 8.67 (s, 1H), 8.64 (d, J=2.2 Hz, 1H), 8.05 (s, 1H), 8.01 (d, J=5.0 Hz, 1H), 7.19 (d, J=5.0 Hz, 1H), 4.24 (hept, J=6.1 Hz, 1H), 4.04 (q, J=9.0 Hz, 1H), 2.82 (q, J=9.1 Hz, 1H), 2.51-2.32 (m, 1H), 2.30-2.18 (m, 1H), 2.17-2.06 (m, 1H), 2.05-1.90 (m, 1H), 1.48 (d, J=6.4 Hz, 6H), 1.17 (s, 3H), 1.13 (s, 3H).

The following compound was made according to Proedure 9, using the appropriate starting materials and protecting group chemistry as needed:

| # | ES/MS m/z | Procedure | Name |
|---|---|---|---|
| 89 | 486.33 | 9 | 7-(5-(5-(4-hydroxybicyclo[2.2.2]octan-1-yl)-1,3,4-thiadiazol-2-yl)-4-(isopropylamino)pyridin-2-yl)pyrrolo[1,2-b]pyridazine-3-carbonitrile |

Procedure 16: Example 90
(R)-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-2-hydroxypropanamide (Example 90)
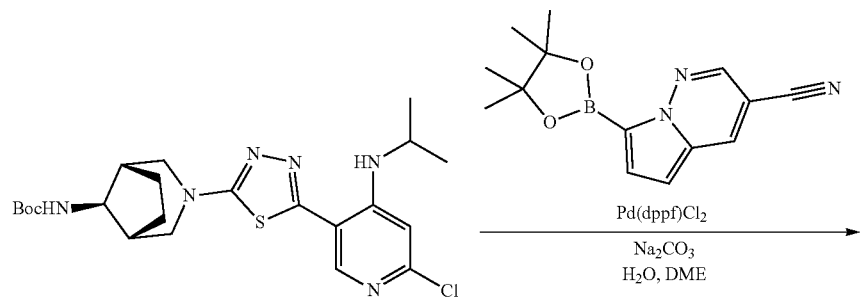
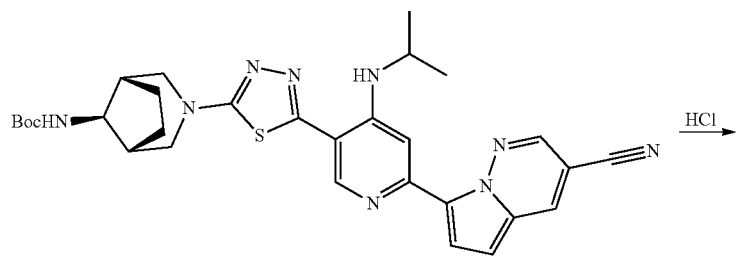
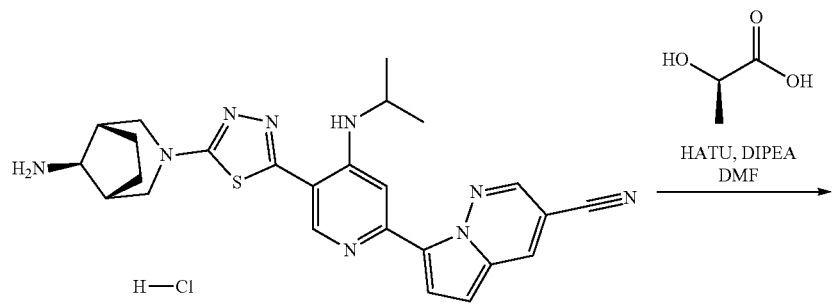
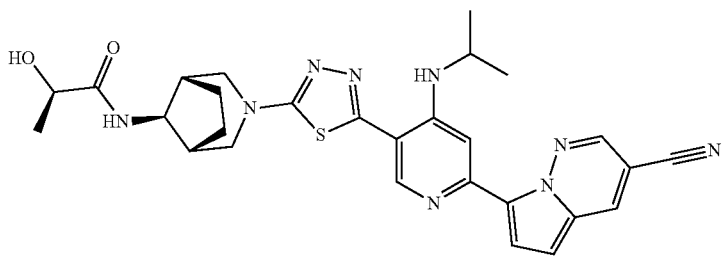
Example 90 tert-butyl ((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamate: Tert-butyl ((4R,5S,8S)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamate was prepared from tert-butyl ((1R,5S,8s)-3-(5-(6-chloro-4-(isopropylamino)pyridin-3-yl)-1,3,4-thiadiazol-2-yl)-3-azabicyclo[3.2.1]octan-8-yl)carbamate (prepared following the protocol in steps 1 and 2 of Procedure 11 using the appropriate 2-bromo-thiadiazole in step 1 and the appropriate amine in step 2) following the protocol in step 4 of Procedure 11. ES/MS: 586.59 (M+H$^+$).

7-(5-(5-((1R,5S,8s)-8-amino-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile hydrochloride: To a solution of tert-butyl ((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamate (180 mg, 0.31 mmol) in 1,4-dioxane (1.0 mL) was added HCl (4M in 1,4-dioxane, 0.77 mL, 3.1 mmol). The reaction mixture was stirred at 40° C. for 1 hour, then concentrated and used without purification. ES/MS: 486.60 (M+H$^+$).

(R)-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-2-hydroxypropanamide (Example 90): To a solution of 7-(5-(5-((1R,5S,8s)-8-amino-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile hydrochloride (12.0 mg, 0.023 mmol) and (R)-2-hydroxypropanoic acid (2.7 mg, 0.03 mmol) in DMF (0.5 mL) was added N,N-diisopropylethylamine (20.5 µL, 0.12 mmol). To the solution was added HATU (13.1 mg, 0.035 mmol) in DMF (0.5 mL). The reaction mixture was stirred at RT for 15 minutes then purified by RP-HPLC (eluent: water/MeCN*0.1% TFA) to yield the product Example 90 as a trifluoroacetate salt. ES/MS: 558.42 (M+H$^+$)

1H NMR (400 MHz, Methanol-d4) δ 8.76 (d, J=2.1 Hz, 1H), 8.68 (d, J=2.2 Hz, 1H), 8.48 (s, 1H), 8.06 (d, J=5.1 Hz, 1H), 7.87 (s, 1H), 7.50 (d, J=6.1 Hz, 1H), 7.23 (d, J=5.1 Hz, 1H), 4.29 (p, J=6.4 Hz, 1H), 4.14 (q, J=6.8 Hz, 1H), 4.01 (d, J=6.0 Hz, 1H), 3.82 (dd, J=12.1, 3.1 Hz, 2H), 3.56 (d, J=11.9 Hz, 2H), 2.49 (s, 2H), 2.02-1.96 (m, 2H), 1.81-1.65 (m, 2H), 1.47 (d, J=6.4 Hz, 6H), 1.36 (d, J=6.8 Hz, 3H).

The following compounds were made according to Procedure 16, using the appropriate starting materials and protecting group chemistry as needed:

| # | ES/MS m/z | Procedure | Name |
|---|-----------|-----------|------|
| 91 | 558.40 | 16 | (S)-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-2-hydroxypropanamide |
| 92 | 598.48 | 16 | (1r,3R)-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-3-hydroxy-3-methylcyclobutane-1-carboxamide |
| 93 | 598.49 | 16 | (1s,3S)-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-3-hydroxy-3-methylcyclobutane-1-carboxamide |
| 94 | 584.56 | 16 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-3-methyloxetane-3-carboxamide |
| 95 | 612.43 | 16 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-methyltetrahydro-2H-pyran-4-carboxamide |

Procedure 17: Example 96

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-methylpiperazine-1-carboxamide (Example 96)

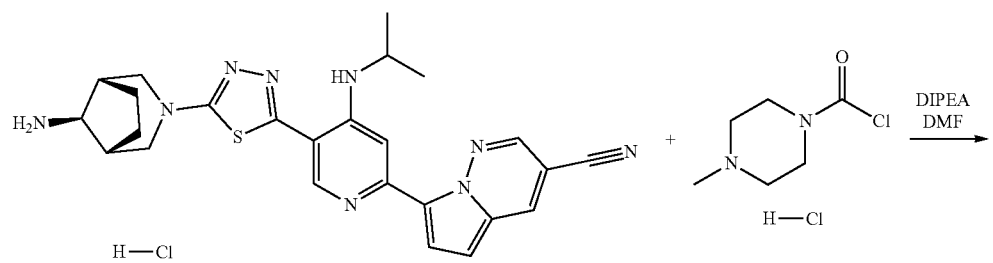

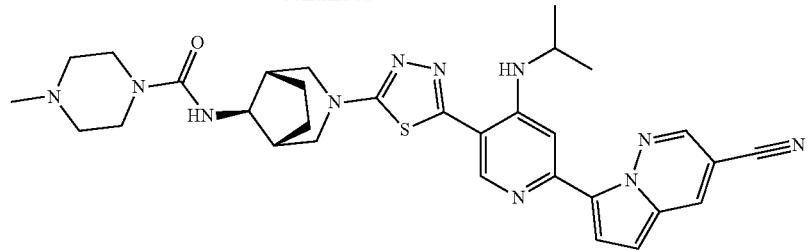

Example 96

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-methylpiperazine-1-carboxamide (Example 96): To a suspension of 7-(5-(5-((1R,5S,8s)-8-amino-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile hydrochloride (synthesized following the protocol in Procedure 16) (12.0 mg, 0.023 mmol) in DMF (0.5 mL) was added N,N-diisopropylethylamine (20.5 µL, 0.12 mmol). To the resulting solution was added a solution of 4-methylpiperazine-1-carbonyl chloride hydrochloride (6.0 mg, 0.030 mmol) and N,N-diisopropylethylamine (8.2 82 L, 0.046 mmol) in DMF (0.5 mL). The reaction mixture was stirred at RT for 3 hours then directly purified by RP-HPLC (eluent: water/MeCN*0.1% TFA) to yield the product Example 96 as a trifluoroacetate salt. ES/MS: 612.35 (M+H$^+$)

1H NMR (400 MHz, Methanol-d4) δ 8.76 (d, J=2.2 Hz, 1H), 8.68 (d, J=2.1 Hz, 1H), 8.49 (s, 1H), 8.07 (d, J=5.1 Hz, 1H), 7.87 (s, 1H), 7.23 (d, J=5.1 Hz, 1H), 4.38-4.10 (m, 3H), 3.88 (s, 1H), 3.80 (dd, J=12.2, 3.1 Hz, 2H), 3.62-3.44 (m, 4H), 3.25-3.02 (m, 4H), 2.94 (s, 3H), 2.50 (s, 2H), 2.11-1.96 (m, 2H), 1.73-1.61 (m, 2H), 1.47 (d, J=6.4 Hz, 6H). Additional peak obscured by solvent.

The following compounds were made according to the previous procedures, using the appropriate starting materials and protecting group chemistry as needed:

| # | ES/MS m/z | Procedure | Name |
|---|---|---|---|
| 97 | 600.34 | 16 | 3-(((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)amino)-2,2-dimethyl-3-oxopropanoic acid |
| 98 | 619.38 | 16 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-2-((dimethyl(oxo)-16-sulfanylidene)amino)acetamide |
| 99 | 570.36 | 2 | N-(2-(5-(6-(3-cyanopyrrolo[1,2-b]pyridazin-7-yl)-4-((3-methyloxetan-3-yl)amino)pyridin-3-yl)-1,3,4-thiadiazol-2-yl)-2-azaspiro[3.5]nonan-7-yl)acetamide |
| 100 | 611.41 | 16 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-1-methylpiperidine-4-carboxamide |
| 101 | 614.40 | 2 | N-((1R,5S,8s)-3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-3-azabicyclo[3.2.1]octan-8-yl)-2-hydroxy-2-methylpropanamide |
| 102 | 584.4 | 16 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-1-methylazetidine-3-carboxamide |
| 103 | 633.39 | 16 | N1-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-N2-(dimethyl(oxo)-16-sulfanylidene)oxalamide |

Procedure 18: Example 104

4-acetyl-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperazine-1-carboxamide (Example 104)

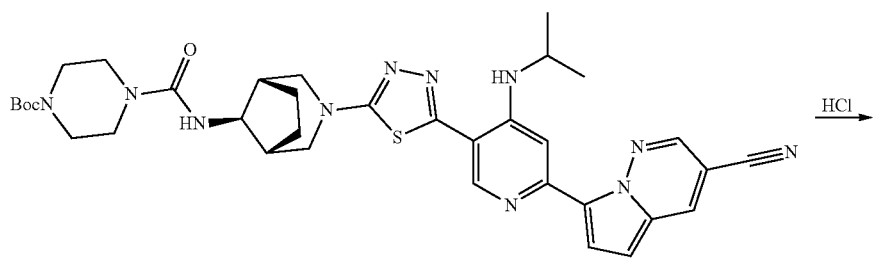

-continued

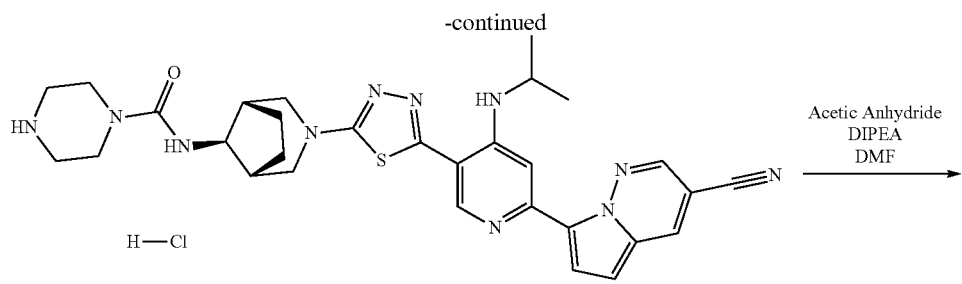

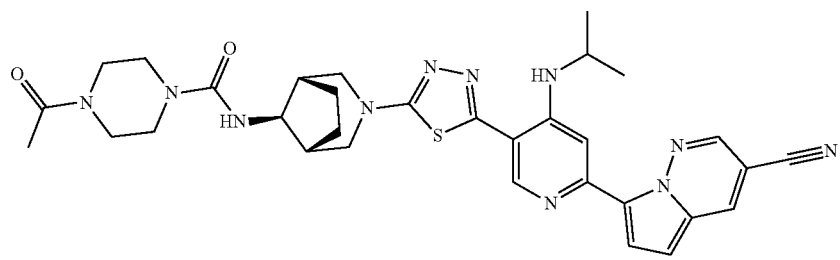

Example 104

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperazine-1-carboxamide hydrochloride: Tert-butyl 4-(((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamoyl)piperazine-1-carboxylate (synthesized following the protocol in Procedure 2 using the appropriate coupling partners) (130 mg, 0.19 mmol) was stirred in a solution of HCl (4M in 1,4-dioxane, 0.93 mL, 3.73 mmol) at 40° C. for 1 hour. The reaction mixture was concentrated and the resulting solid used without purification.
ES/MS: 598.42 (M+H$^+$)

4-acetyl-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperazine-1-carboxamide (Example 104): To a suspension of crude N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperazine-1-carboxamide hydrochloride (10.0 mg, 0.016 mmol) in DMF was added triethylamine (8.8 μL, 0.063 mmol) followed by acetic anhydride (1.8 μL, 0.019 mmol). The reaction mixture was stirred at RT for 15 minutes, then directly purified by RP-HPLC (eluent: water/MeCN*0.1% TFA) to yield the product Example 104 as a trifluoroacetate salt.
ES/MS: 640.41 (M+H$^+$)
1H NMR (400 MHz, Methanol-d4) δ 8.76 (d, J=2.2 Hz, 1H), 8.68 (d, J=2.2 Hz, 1H), 8.48 (s, 1H), 8.06 (d, J=5.0 Hz, 1H), 7.87 (s, 1H), 7.23 (d, J=5.0 Hz, 1H), 4.29 (p, J=6.4 Hz, 1H), 3.88 (s, 1H), 3.80 (dd, J=12.3, 3.1 Hz, 2H), 3.66-3.52 (m, 6H), 3.51-3.47 (m, 2H), 3.45-3.39 (m, 2H), 2.50 (s, 2H), 2.13 (s, 3H), 2.08-2.00 (m, 2H), 1.72-1.59 (m, 2H), 1.47 (d, J=6.4 Hz, 6H).

The following compounds were made according to Procedure 18, using the appropriate starting materials and protecting group chemistry as needed:

| # | ES/MS m/z | Procedure | Name |
|---|---|---|---|
| 105 | 656.45 | 18 | methyl 4-(((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamoyl)piperazine-1-carboxylate |
| 106 | 676.36 | 18 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-(methylsulfonyl)piperazine-1-carboxamide |

Procedure 19: Example 107

7-(5-(5-(6-(2-(((dimethyl(oxo)-l6-sulfanylidene)amino)acetyl)-3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile (Example 107)

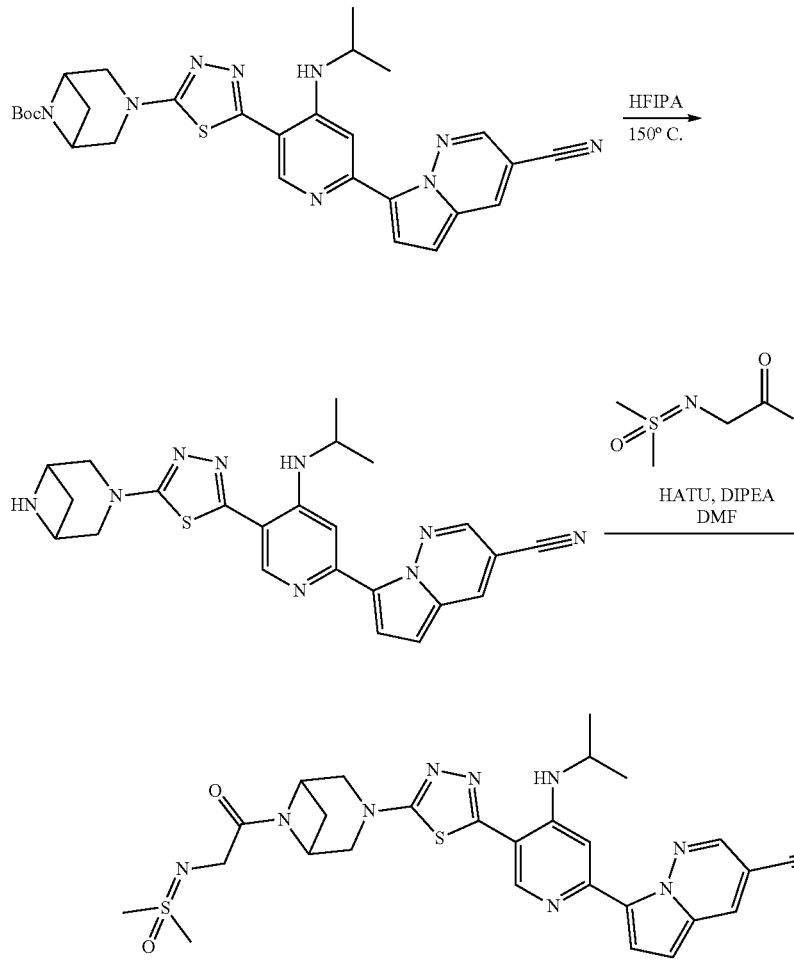

Example 107

7-(5-(5-(3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile: A solution of tert-butyl 3-(5-(6-(3-cyanopyrrolo[1,2-b]pyridazin-7-yl)-4-(isopropylamino)pyridin-3-yl)-1,3,4-thiadiazol-2-yl)-3,6-diazabicyclo[3.1.1]heptane-6-carboxylate (synthesized following the protocol in Procedure 2 using the appropriate coupling partners) (153 mg, 0.28 mmol) in 1,1,1,3,3,3-hexafluoro-2-propanol (1.9 mL, 17.9 mmol) was heated in a microwave reactor 30 minutes at 150° C. The cooled reaction was concentrated in vacuo to provide the desired product which was used without purification.
ES/MS: 458.45 (M+H⁺)

7-(5-(5-(6-(2-(((dimethyl(oxo)-λ⁶-sulfanylidene)amino)acetyl)-3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile (Example 107): To a solution of crude 7-(5-(5-(3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile (15.0 mg, 0.033 mmol) and 2-(((dimethyl(oxo)-λ⁶-sulfanylidene)amino)acetic acid (6.4 mg, 0.043 mmol) in DMF (0.5 mL) was added N,N-diisopropylethylamine (23 µL, 0.13 mmol) followed by the addition of a solution of HATU (18.7 mg, 0.049 mmol) in DMF (0.5 mL). The reaction mixture was stirred at RT for 15 minutes then directly purified by RP-HPLC (eluent: water/MeCN*0.1% TFA) to yield the product Example 107 as a trifluoroacetate salt.
ES/MS: 591.31 (M+H⁺)
1H NMR (400 MHz, Methanol-d4) δ 8.77 (d, J=2.2 Hz, 1H), 8.68 (d, J=2.2 Hz, 1H), 8.53 (s, 1H), 8.07 (d, J=5.0 Hz, 1H), 7.88 (s, 1H), 7.23 (d, J=5.0 Hz, 1H), 4.65 (s, 1H), 4.30 (p, J=6.2 Hz, 1H), 4.17 (dd, J=32.3, 11.3 Hz, 2H), 3.96-3.76 (m, 4H), 3.30 (s, 6H), 3.02 (s, 1H), 2.98-2.91 (m, 1H), 1.85 (d, J=9.3 Hz, 1H), 1.48 (d, J=6.4 Hz, 6H).

Procedure 20: Example 108

7-(4-(isopropylamino)-5-(5-(6-(4-methylpiperazine-1-carbonyl)-3,6-diazabicyclo[3.1.1]heptan-3-yl)-1,3,4-thiadiazol-2-yl)pyridin-2-yl)pyrrolo[1,2-b]pyridazine-3-carbonitrile (Example 108)

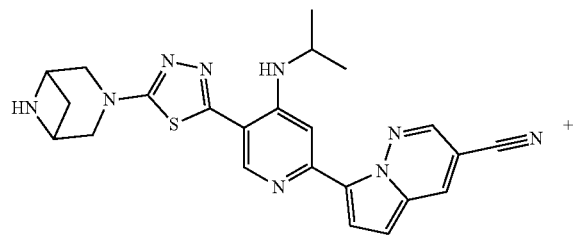

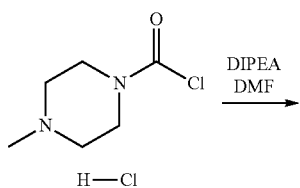 DIPEA DMF →

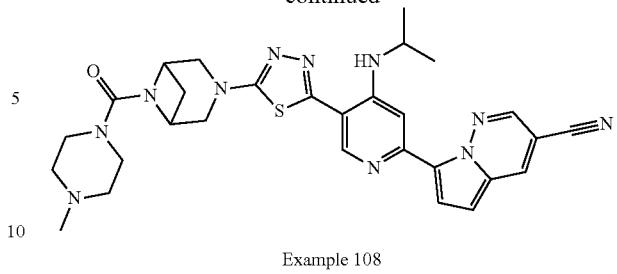

Example 108

7-(4-(isopropylamino)-5-(5-(6-(4-methylpiperazine-1-carbonyl)-3,6-diazabicyclo[3.1.1]heptan-3-yl)-1,3,4-thiadiazol-2-yl)pyridin-2-yl)pyrrolo[1,2-b]pyridazine-3-carbonitrile (Example 108): To a solution of crude 7-(5-(5-(3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile (synthesized as described in Procedure 19) (15 mg, 0.033 mmol) in DMF (0.5 mL) was added N,N-diisopropylethylamine (11.7 µL, 0.066 mmol) a solution of 4-methylpiperazine-1-carbonyl chloride hydrochloride (8.5 mg, 0.43 mmol) and N,N-diisopropylethylamine (11.7 µL, 0.066 mmol) in DMF (0.5 mL). The reaction mixture was stirred at RT for 3 hours then directly purified by RP-HPLC (eluent: water/MeCN*0.1% TFA) to yield the product Example 108 as a trifluoroacetate salt.
ES/MS: 584.46 (M+H$^+$)
1H NMR (400 MHz, Methanol-d4) δ 8.76 (d, J=2.1 Hz, 1H), 8.68 (d, J=2.2 Hz, 1H), 8.54 (s, 1H), 8.07 (d, J=5.1 Hz, 1H), 7.89 (s, 1H), 7.23 (d, J=5.0 Hz, 1H), 4.49 (d, J=6.4 Hz, 2H), 4.35-4.19 (m, 3H), 4.20-3.0 (br m, 8H), 3.73 (d, J=11.3 Hz, 2H), 2.97-2.81 (m, 4H), 1.75 (d, J=9.2 Hz, 1H), 1.47 (d, J=6.4 Hz, 6H).

The following compounds were made according to the previous procedures, using the appropriate starting materials and protecting group chemistry as needed:

| # | ES/MS m/z | Procedure | Name |
|---|---|---|---|
| 109 | 647.35 | 19 | N-((1R,5S,8s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.2.1]octan-8-yl)-2-((dimethyl(oxo)-16-sulfanylidene)amino)acetamide |
| 110 | 640.36 | 20 | N-((1R,5S,8s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.2.1]octan-8-yl)-4-methylpiperazine-1-carboxamide |
| 111 | 528.32 | 20 | 7-(5-(5-(6-acetyl-3,6-diazabicyclo[3.1.1]heptan-3-yl)-1,3,4-thiadiazol-2-yl)-4-((3-methyloxetan-3-yl)amino)pyridin-2-yl)pyrrolo[1,2-b]pyridazine-3-carbonitrile |
| 112 | 572.39 | 19 | 7-(5-(5-(6-(2-hydroxy-2-methylpropanoyl)-3,6-diazabicyclo[3.1.1]heptan-3-yl)-1,3,4-thiadiazol-2-yl)-4-((3-methyloxetan-3-yl)amino)pyridin-2-yl)pyrrolo[1,2-b]pyridazine-3-carbonitrile |
| 113 | 619.30 | 19 | 7-(5-(5-(6-(2-((dimethyl(oxo)-16-sulfanylidene)amino)acetyl)-3,6-diazabicyclo[3.1.1]heptan-3-yl)-1,3,4-thiadiazol-2-yl)-4-((3-methyloxetan-3-yl)amino)pyridin-2-yl)pyrrolo[1,2-b]pyridazine-3-carbonitrile |
| 114 | 612.34 | 20 | 7-(4-((3-methyloxetan-3-yl)amino)-5-(5-(6-(4-methylpiperazine-1-carbonyl)-3,6-diazabicyclo[3.1.1]heptan-3-yl)-1,3,4-thiadiazol-2-yl)pyridin-2-yl)pyrrolo[1,2-b]pyridazine-3-carbonitrile |
| 115 | 555.30 | 2 | 7-(4-(((R)-l-cyanoethyl)amino)-5-(5-(6-(2-hydroxy-2-methylpropanoyl)-3,6-diazabicyclo[3.1.1]heptan-3-yl)-1,3,4-thiadiazol-2-yl)pyridin-2-yl)pyrrolo[1,2-b]pyridazine-3-carbonitrile |

Procedure 21: Example 116

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-(oxetan-3-yl)piperazine-1-carboxamide (Example 116)

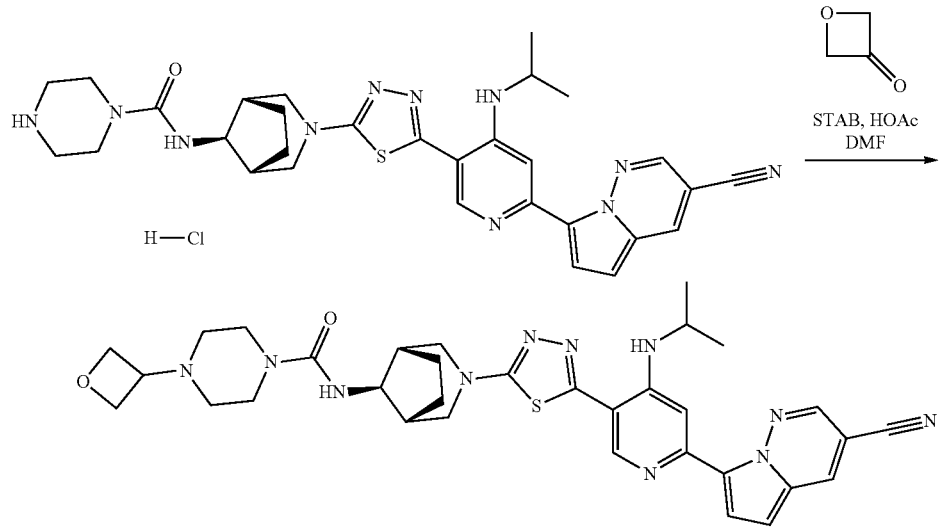

Example 116

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-(oxetan-3-yl)piperazine-1-carboxamide (Example 116): To a suspension of crude N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperazine-1-carboxamide hydrochloride (20.0 mg, 0.032 mmol) in DMF (1.0 mL) was added 3-oxetanone (9.1 mg, 0.13 mmol), sodium triacetoxyborohydride (33.4 mg, 0.16 mmol), and acetic acid (9.0 μL, 0.16 mmol). The reaction mixture was stirred at RT for 90 minutes then directly purified by RP-HPLC (eluent: water/MeCN*0.1% TFA) to yield the product Example 116 as a trifluoroacetate salt.
ES/MS: 654.43 (M+H⁺)
1H NMR (400 MHz, Methanol-d4) δ 8.76 (d, J=2.1 Hz, 1H), 8.68 (d, J=2.2 Hz, 1H), 8.49 (s, 1H), 8.07 (d, J=5.0 Hz, 1H), 7.87 (s, 1H), 7.23 (d, J=5.0 Hz, 1H), 4.92-4.83 (m, 2H), 4.82-4.76 (m, 2H), 4.38-4.25 (m, 2H), 3.88 (s, 1H), 3.80 (dd, J=12.3, 3.1 Hz, 2H), 3.71 (s, 4H), 3.60-3.51 (m, 2H), 3.18-3.08 (m, 4H), 2.49 (s, 2H), 2.08-1.95 (m, 2H), 1.72-1.62 (m, 2H), 1.47 (d, J=6.4 Hz, 6H).

The following compounds were made according to Procedure 19, using the appropriate starting materials and protecting group chemistry as needed:

| # | ES/MS m/z | Procedure | Name |
|---|-----------|-----------|------|
| 117 | 583.42 | 19 | 7-(4-(isopropylamino)-5-(5-(6-(1-methylpiperidine-4-carbonyl)-3,6-diazabicyclo[3.1.1]heptan-3-yl)-1,3,4-thiadiazol-2-yl)pyridin-2-yl)pyrrolo[1,2-b]pyridazine-3-carbonitrile |
| 118 | 611.35 | 19 | 7-(4-((3-methyloxetan-3-yl)amino)-5-(5-(6-(1-methylpiperidine-4-carbonyl)-3,6-diazabicyclo[3.1.1]heptan-3-yl)-1,3,4-thiadiazol-2-yl)pyridin-2-yl)pyrrolo[1,2-b]pyridazine-3-carbonitrile |
| 119 | 639.37 | 19 | N-((1R,5S,8s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.2.1]octan-8-yl)-1-methylpiperidine-4-carboxamide |

Procedure 22: Example 120

N-(4-(5-(6-(3-cyanopyrrolo[1,2-b]pyridazin-7-yl)-4-(isopropylamino)pyridin-3-yl)-1,3,4-thiadiazol-2-yl)bicyclo[2.2.2]octan-1-yl)-2-hydroxy-2-methylpropanamide (Example 120)

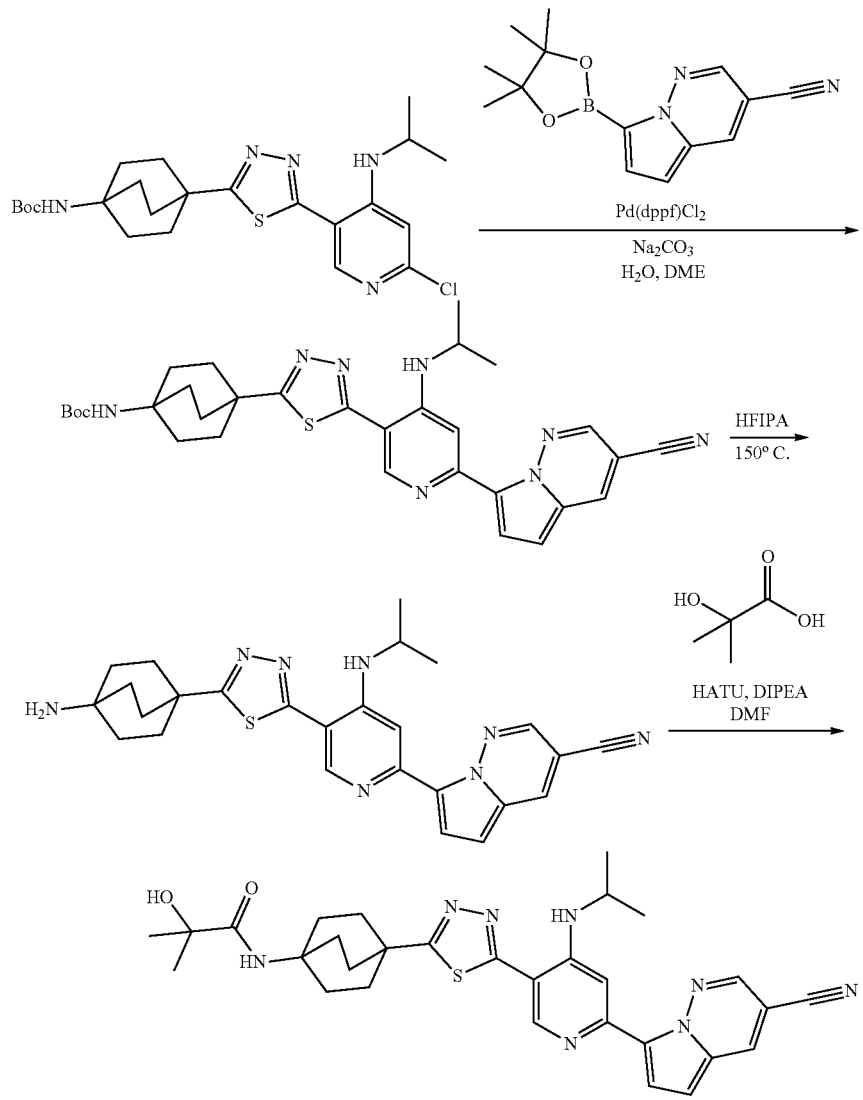

Example 120 tert-butyl (4-(5-(6-(3-cyanopyrrolo[1,2-b]pyridazin-7-yl)-4-(isopropylamino)pyridin-3-yl)-1,3,4-thiadiazol-2-yl)bicyclo[2.2.2]octan-1-yl)carbamate: Tert-butyl (4-(5-(6-(3-cyanopyrrolo[1,2-b]pyridazin-7-yl)-4-(isopropylamino)pyridin-3-yl)-1,3,4-thiadiazol-2-yl)bicyclo[2.2.2]octan-1-yl)carbamate was synthesized from tert-butyl (4-(5-(6-chloro-4-(isopropylamino)pyridin-3-yl)-1,3,4-thiadiazol-2-yl)bicyclo[2.2.2]octan-1-yl)carbamate (synthesized following the protocol in steps 1 and 2 of Procedure 14 using the appropriate carboxylic acid) following the protocol in step 4 of Procedure 14.
ES/MS: 585.62 (M+H$^+$)

7-(5-(5-(4-aminobicyclo[2.2.2]octan-1-yl)-1,3,4-thiadiazol-2-yl)-4-(isopropylamino)pyridin-2-yl)pyrrolo[1,2-b]pyridazine-3-carbonitrile: A solution of tert-butyl (4-(5-(6-(3-cyanopyrrolo[1,2-b]pyridazin-7-yl)-4-(isopropylamino)pyridin-3-yl)-1,3,4-thiadiazol-2-yl)bicyclo[2.2.2]octan-1-yl)carbamate in 1,1,1,3,3,3-hexafluoro-2-propanol was heated at 150° C. in a microwave reactor for 90 minutes. The cooled reaction mixture was concentrated to provide the desired product which was used without purification.
ES/MS: 485.47 (M+H$^+$)

N-(4-(5-(6-(3-cyanopyrrolo[1,2-b]pyridazin-7-yl)-4-(isopropylamino)pyridin-3-yl)-1,3,4-thiadiazol-2-yl)bicyclo[2.2.2]octan-1-yl)-2-hydroxy-2-methylpropanamide (Example 120): To a solution of crude 7-(5-(5-(4-aminobicyclo[2.2.2]octan-1-yl)-1,3,4-thiadiazol-2-yl)-4-(isopropylamino)pyridin-2-yl)pyrrolo[1,2-b]pyridazine-3- carbonitrile (10.0 mg, 0.021 mmol) and 2-hydroxy-2-methylpropanoic acid (2.8 mg, 0.027 mmol) in DMF (0.5 mL) was added N,N-diisopropylethylamine (14.7 µL, 0.083 mmol) followed by a solution of HATU (11.8 mg, 0.031 mmol) in DMF (0.5 mL). The reaction mixture was stirred at RT for 15 minutes then directly purified by RP-HPLC (eluent: water/MeCN*0.1% TFA) to yield the product Example 120 as a trifluoroacetate salt.
ES/MS: 571.49 (M+H$^+$)
1H NMR (400 MHz, Methanol-d4) δ 8.77 (d, J=2.2 Hz, 1H), 8.71 (s, 1H), 8.69 (d, J=2.1 Hz, 1H), 8.07 (d, J=5.1 Hz, 1H), 7.95 (s, 1H), 7.24 (d, J=5.1 Hz, 1H), 4.31 (p, J=6.3 Hz, 1H), 2.27-2.09 (m, 12H), 1.49 (d, J=6.4 Hz, 6H), 1.34 (s, 6H).

The following compounds were made according to Procedure 22, using the appropriate starting materials and protecting group chemistry as needed:

| # | ES/MS m/z | Procedure | Name |
|---|---|---|---|
| 121 | 618.34 | 22 | N-(4-(5-(6-(3-cyanopyrrolo[1,2-b]pyridazin-7-yl)-4-(isopropylamino)pyridin-3-yl)-1,3,4-thiadiazol-2-yl)bicyclo[2.2.2]octan-1-yl)-2-((dimethyl(oxo)-16-sulfanylidene)amino)acetamide |
| 122 | 610.43 | 22 | N-(4-(5-(6-(3-cyanopyrrolo[1,2-b]pyridazin-7-yl)-4-(isopropylamino)pyridin-3-yl)-1,3,4-thiadiazol-2-yl)bicyclo[2.2.2]octan-1-yl)-1-methylpiperidine-4-carboxamide |

Procedure 23: Example 123

1-acetyl-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperidine-4-carboxamide (Example 123)

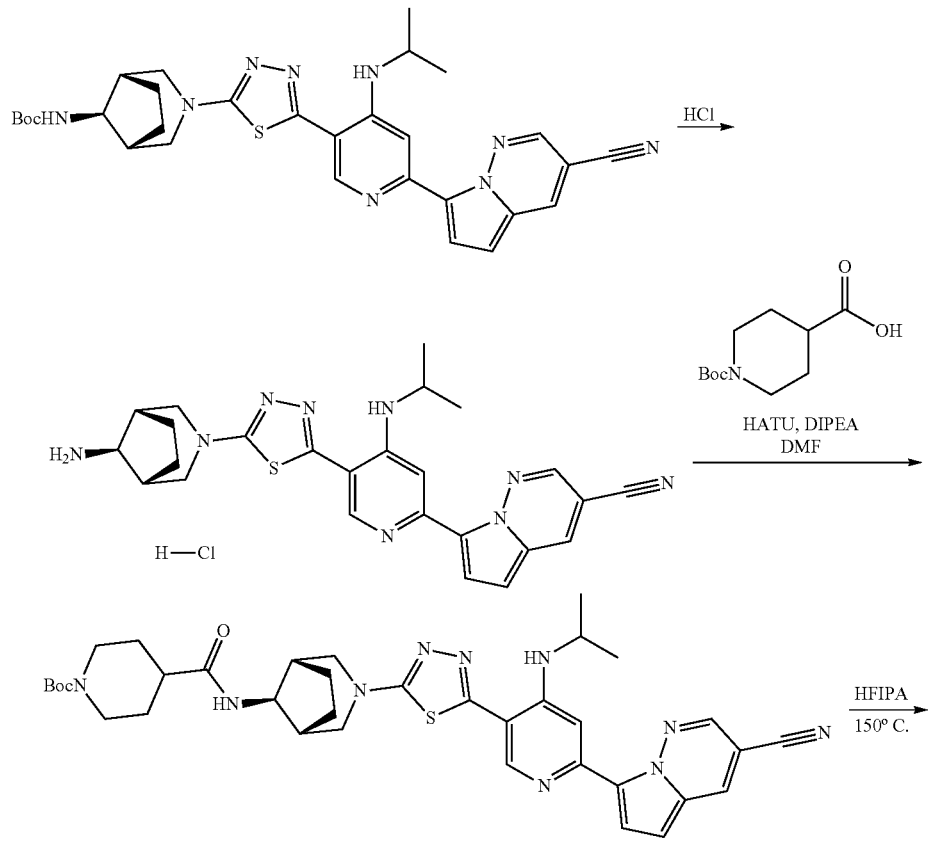

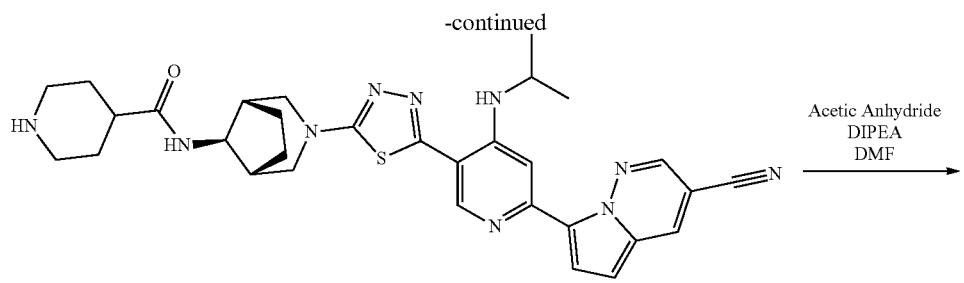

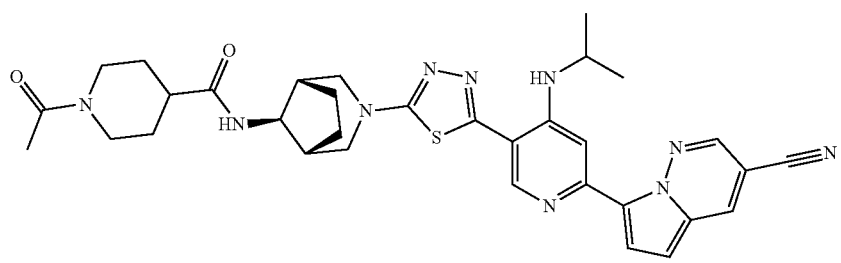

Example 123

7-(5-(5-(((1R,5S,8s)-8-amino-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile hydrochloride: Tert-butyl (((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamate (synthesized following the protocol in Procedure 2 using the appropriate coupling partners) (451 mg, 0.77 mmol) was stirred with HCl (4M in 1,4-dioxane, 3.9 mL, 15.4 mmol) at 40° C. for 1 hour. The cooled reaction was concentrated in vacuo to provide the desired product which was used without purification.
ES/MS: 486.38 (M+H+)

tert-butyl 4-(((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamoyl)piperidine-1-carboxylate: To a solution of crude 7-(5-(5-(((1R,5S,8s)-8-amino-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile hydrochloride (50.0 mg, 0.096 mmol) and 1-(tert-butoxycarbonyl)piperidine-4-carboxylic acid (65.9 mg, 0.29 mmol) in DMF (0.5 mL) was added N,N-diisopropylamine (0.21 mL) followed by a solution of HATU (142 mg, 0.37 mmol) in DMF (0.5 mL). The reaction mixture was stirred at RT for 15 minutes then partitioned between water and EtOAc. The aqueous layer was extracted with two additional portions of EtOAc. The combined organic layers were dried over sodium sulfate, isolated by vacuum filtration, and purified by silica gel column chromatography (eluent: EtOAc/hexanes) to provide the desired product.
ES/MS: 697.54 (M+H+).

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperidine-4-carboxamide: A solution of tert-butyl 4-(((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamoyl)piperidine-1-carboxylate (135 mg, 0.19 mmol) in 1,1,1,3,3,3-hexafluoro-2-propanol (2.0 mL, 19.4 mmol) was heated in a microwave reactor for 75 minutes at 140° C. The cooled reaction was concentrated to provide the desire product which was used without purification.
ES/MS: 697.39 (M+H+).

1-acetyl-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperidine-4-carboxamide (Example 123): To a solution of crude N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperidine-4-carboxamide (10.0 mg, 0.017 mmol) in DMF (1.0 mL) was added triethylamine (7.0 µL, 0.050 mmol) followed by acetic anhydride (2.0 µL, 0.022 mmol). The reaction mixture was stirred at RT for 15 minutes then directly purified by RP-HPLC (eluent: water/MeCN*0.1% TFA) to yield the product Example 123 as a trifluoroacetate salt.
ES/MS: 639.46 (M+H+)
1H NMR (400 MHz, Methanol-d4) δ 8.76 (d, J=2.1 Hz, 1H), 8.68 (d, J=2.2 Hz, 1H), 8.48 (s, 1H), 8.07 (d, J=5.0 Hz, 1H), 7.90 (d, J=5.6 Hz, 1H), 7.87 (s, 1H), 7.23 (d, J=5.1 Hz, 1H), 4.54 (d, J=13.3 Hz, 1H), 4.29 (p, J=6.4 Hz, 1H), 4.09-3.92 (m, 2H), 3.86-3.75 (m, 2H), 3.54 (d, J=12.0 Hz, 2H), 3.23-3.10 (m, 1H), 2.68 (td, J=12.9, 2.9 Hz, 1H), 2.53 (tt, J=11.4, 3.9 Hz, 1H), 2.44 (s, 2H), 2.11 (s, 3H), 2.06-1.97 (m, 2H), 1.88-1.74 (m, 2H), 1.74-1.63 (m, 3H), 1.58 (qd, J=12.6, 4.4 Hz, 1H), 1.47 (d, J=6.4 Hz, 6H).

Procedure 24: Example 124

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-1-(oxetan-3-yl)piperidine-4-carboxamide (Example 124)

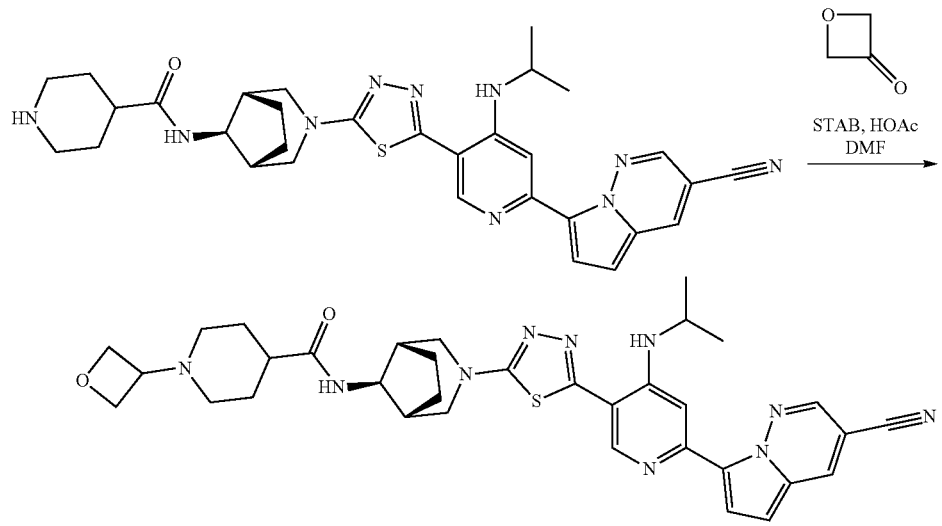

Example 124

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-1-(oxetan-3-yl)piperidine-4-carboxamide (Example 124): To a solution of crude N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperidine-4-carboxamide (10.0 mg, 0.017 mmol) and 3-oxetanone (4.8 mg, 0.067 mmol) in DMF (1.0 mL) was added acetic acid (4.8 μL, 0.084 mmol) and sodium triacetoxyborohydride (17.8 mg, 0.084 mmol). The reaction mixture was stirred at 40° C. for 30 minutes, then directly purified by RP-HPLC (eluent: water/MeCN*0.1% TFA) to yield the product Example 124 as a trifluoroacetate salt.

ES/MS: 653.42 (M+H$^+$)

1H NMR (400 MHz, Methanol-d4) δ 8.76 (d, J=2.1 Hz, 1H), 8.68 (d, J=2.2 Hz, 1H), 8.49 (s, 1H), 8.07 (d, J=5.1 Hz, 1H), 8.03 (d, J=5.5 Hz, 1H), 7.87 (s, 1H), 7.23 (d, J=5.0 Hz, 1H), 4.79 (dd, J=8.3, 5.7 Hz, 2H), 4.39 (s, 1H), 4.29 (p, J=6.5 Hz, 1H), 3.99 (d, J=5.4 Hz, 1H), 3.81 (dd, J=12.4, 3.1 Hz, 2H), 3.62-3.51 (m, 3H), 2.95-2.81 (m, 2H), 2.68-2.53 (m, 1H), 2.45 (s, 2H), 2.19-1.91 (m, 7H), 1.77-1.64 (m, 2H), 1.47 (d, J=6.4 Hz, 6H). Additional peak obscured by solvent.

The following compounds were made according to Procedure 1, using the appropriate starting materials and protecting group chemistry as needed:

| # | ES/MS m/z | Procedure | Name |
|---|---|---|---|
| 125 | 527.457 | 1 | N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)cyclopropanecarboxamide |
| 126 | 517.607 | 1 | methyl ((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)carbamate |
| 127 | 501.585 | 1 | N-((1s,4s)-4-(5-(6-(3-cyanopyrrolo[1,2-b]pyridazin-7-yl)-4-(isopropylamino)pyridin-3-yl)-1,3,4-thiadiazol-2-yl)cyclohexyl)acetamide |
| 128 | 487.538 | 1 | 7-(5-(5-(1-acetylpiperidin-4-yl)-1,3,4-thiadiazol-2-yl)-4-(isopropylamino)pyridin-2-yl)pyrrolo[1,2-b]pyridazine-3-carbonitrile |

Procedure 25: Example 129

7-(4-(isopropylamino)-5-(5-(piperidin-4-yl)-1,3,4-thiadiazol-2-yl)pyridin-2-yl)pyrrolo[1,2-b]pyridazine-3-carbonitrile (Example 129)

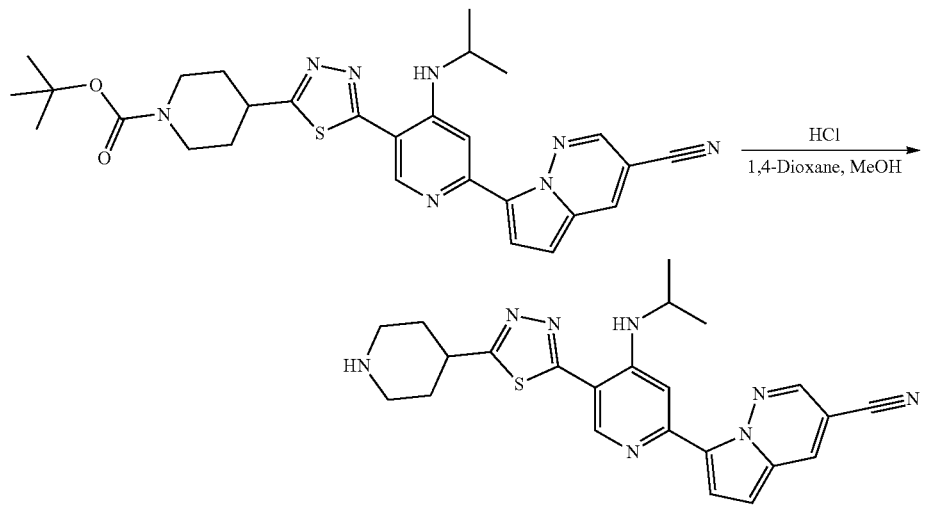

Example 129

7-(4-(isopropylamino)-5-(5-(piperidin-4-yl)-1,3,4-thiadiazol-2-yl)pyridin-2-yl)pyrrolo[1,2-b]pyridazine-3-carbonitrile (Example 129): To an RBF with tert-butyl 4-(5-(6-(3-cyanopyrrolo[1,2-b]pyridazin-7-yl)-4-(isopropylamino)pyridin-3-yl)-1,3,4-thiadiazol-2-yl)piperidine-1-carboxylate (prepared via Procedure 1) (40 mg, 0.061 mmol) was added 1,4-dioxane (7 mL) and methanol (1.5 mL). HCl (4.0M in dioxane, 1 mL) was added, and the reaction was stirred at 50° C. for 2 hours. The reaction was then concentrated under reduced pressure, and the crude material was dissolved in DMF, then purified by RP-HPLC (eluent: water/MeCN*0.1% TFA) to yield the product Example 129 as a trifluoroacetate salt.

ES/MS: 445.530 (M+H+)

1H NMR (400 MHz, Methanol-d4) δ 8.80 (d, J=2.2 Hz, 1H), 8.77 (s, 1H), 8.71 (d, J=2.2 Hz, 1H), 8.11 (d, J=5.0 Hz, 1H), 8.01 (s, 1H), 7.26 (d, J=5.0 Hz, 1H), 4.41-4.25 (m, 1H), 3.84-3.65 (m, 1H), 3.65-3.50 (m, 2H), 3.26 (d, J=12.6 Hz, 2H), 2.50 (d, J=14.2 Hz, 2H), 2.29-2.12 (m, 2H), 1.51 (d, J=6.4 Hz, 6H).

The following compounds were made according to Procedure 2, using the appropriate starting materials and protecting group chemistry as needed:

| # | ES/MS m/z | Procedure | Name |
|---|---|---|---|
| 130 | 446.531 | 2 | 7-(4-(isopropylamino)-5-(5-(piperazin-1-yl)-1,3,4-thiadiazol-2-yl)pyridin-2-yl)pyrrolo[1,2-b]pyridazine-3-carbonitrile |
| 131 | 447.380 | 2 | 7-(4-(isopropylamino)-5-(5-morpholino-1,3,4-thiadiazol-2-yl)pyridin-2-yl)pyrrolo[1,2-b]pyridazine-3-carbonitrile |

Procedure 26: Example 132

±7-(5-(5-(trans-2-(2-hydroxypropan-2-yl)cyclopropyl)-1,3,4-thiadiazol-2-yl)-4-(isopropylamino)pyridin-2-yl)pyrrolo[1,2-b]pyridazine-3-carbonitrile (Example 132)

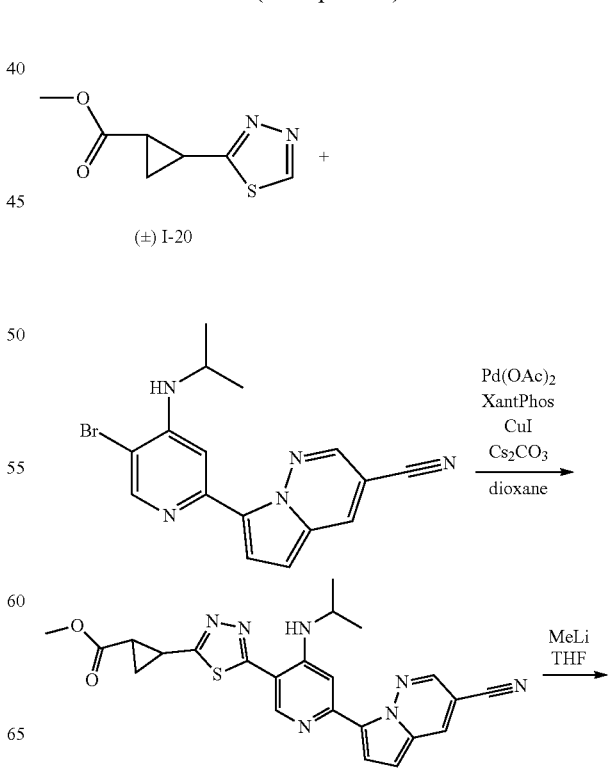

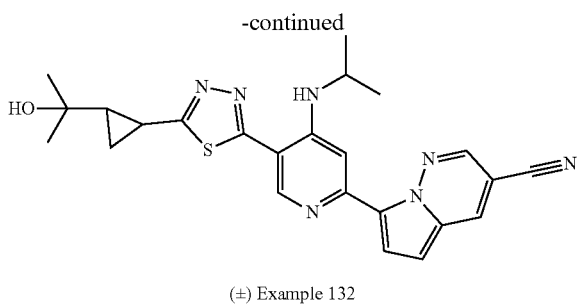

(±) Example 132

±methyl trans-2-(5-(6-(3-cyanopyrrolo[1,2-b]pyridazin-7-yl)-4-(isopropylamino)pyridin-3-yl)-1,3,4-thiadiazol-2-yl)cyclopropane-1-carboxylate: To a vial was added 7-(5-bromo-4-(isopropylamino)pyridin-2-yl)pyrrolo[1,2-b]pyridazine-3-carbonitrile (I-2) (60 mg, 0.168 mmol), (±) methyl trans-2-(1,3,4-thiadiazol-2-yl)cyclopropane-1-carboxylate (I-20) (47 mg, 0.253 mmol), Pd(OAc)$_2$ (9.5 mg, 0.042 mmol), Xantphos (49 mg, 0.084 mmol), copper(I) iodide (16 mg, 0.084 mmol), and cesium carbonate (165 mg, 0.5 mmol). 1,4-Dioxane (1 mL), was added, and the mixture was degassed with argon for 1 minute. The vial was sealed and stirred 2 hours at 105° C. Afterward, the vial was cooled and the crude material was diluted with DMF (0.5 mL). This mixture was filtered, and purified by RP-HPLC (eluent: water/MeCN*0.1% TFA) to yield the product as a trifluoroacetate salt. The purified material was dissolved in EtOAc and neutralized with sat. aq. NaHCO$_3$. The layers were separated, and the organic layer was dried over MgSO$_4$, filtered, and concentrated under reduced pressure.
ES/MS: 460.550 (M+H$^+$)

±7-(5-(5-(trans-2-(2-hydroxypropan-2-yl)cyclopropyl)-1,3,4-thiadiazol-2-yl)-4-(isopropylamino)pyridin-2-yl)pyrrolo[1,2-b]pyridazine-3-carbonitrile (Example 132): To a solution of ±methyl trans-2-(5-(6-(3-cyanopyrrolo[1,2-b]pyridazin-7-yl)-4-(isopropylamino)pyridin-3-yl)-1,3,4-thiadiazol-2-yl)cyclopropane-1-carboxylate (40 mg, 0.087 mmol) in THF (2 mL) at −78° C. was added methyllithium (1.6M in ether, 0.16 mL, 0.26 mmol) dropwise. The reaction was quenched at −78° C. with dropwise addition of saturated aqueous ammonium chloride, then slowly allowed to warm to room temperature. The reaction was partitioned between water and EtOAc, and the aqueous layer was extracted two additional times with EtOAc. The combined organic layers were dried over magnesium sulfate, filtered, concentrated under reduced pressure, and then purified by RP-HPLC (eluent: water/MeCN*0.1% TFA) to yield the product Example 132 as a trifluoroacetate salt.
ES/MS: 460.413 (M+H$^+$).
1H NMR (400 MHz, Methanol-d4) δ 8.79 (d, J=2.2 Hz, 1H), 8.71 (d, J=2.2 Hz, 1H), 8.68 (s, 1H), 8.09 (d, J=5.1 Hz, 1H), 7.96 (s, 1H), 7.26 (d, J=5.1 Hz, 1H), 4.40-4.23 (m, 1H), 2.63 (dt, J=9.1, 4.8 Hz, 1H), 1.81 (ddd, J=9.3, 6.7, 4.6 Hz, 1H), 1.56-1.43 (m, 7H), 1.43-1.28 (m, 7H).

The following compounds were made according to the previous procedures, using the appropriate starting materials and protecting group chemistry as needed:

| # | ES/MS m/z | Procedure | Name |
| --- | --- | --- | --- |
| 132 Isomer 1 | 460.487 | 26 | 7-(5-(5-((1R,2R)-2-(2-hydroxypropan-2-yl)cyclopropyl)-1,3,4-thiadiazol-2-yl)-4-(isopropylamino)pyridin-2-yl)pyrrolo[1,2-b]pyridazine-3-carbonitrile |
| 132 Isomer 2 | 460.586 | 26 | 7-(5-(5-((1S,2S)-2-(2-hydroxypropan-2-yl)cyclopropyl)-1,3,4-thiadiazol-2-yl)-4-(isopropylamino)pyridin-2-yl)pyrrolo[1,2-b]pyridazine-3-carbonitrile |
| 133 | 509.466 | 1 | 7-(5-(5-(1-(2,2-difluoroethyl)piperidin-4-yl)-1,3,4-thiadiazol-2-yl)-4-(isopropylamino)pyridin-2-yl)pyrrolo[1,2-b]pyridazine-3-carbonitrile |
| 134 | 626.725 | 1 | methyl (((1R,3r)-3-((2-(3-cyanopyrrolo[1,2-b]pyridazin-7-yl)-5-(5-((1r,4R)-4-(cyclopropanecarboxamido)cyclohexyl)-1,3,4-thiadiazol-2-yl)pyridin-4-yl)amino)cyclobutyl)methyl)carbamate |
| 135 | 541.582 | 1 | N-((1r,4r)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)cyclopropanecarboxamide |

Procedure 30: Example 136

7-(5-(5-(trans-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile (±Example 136)

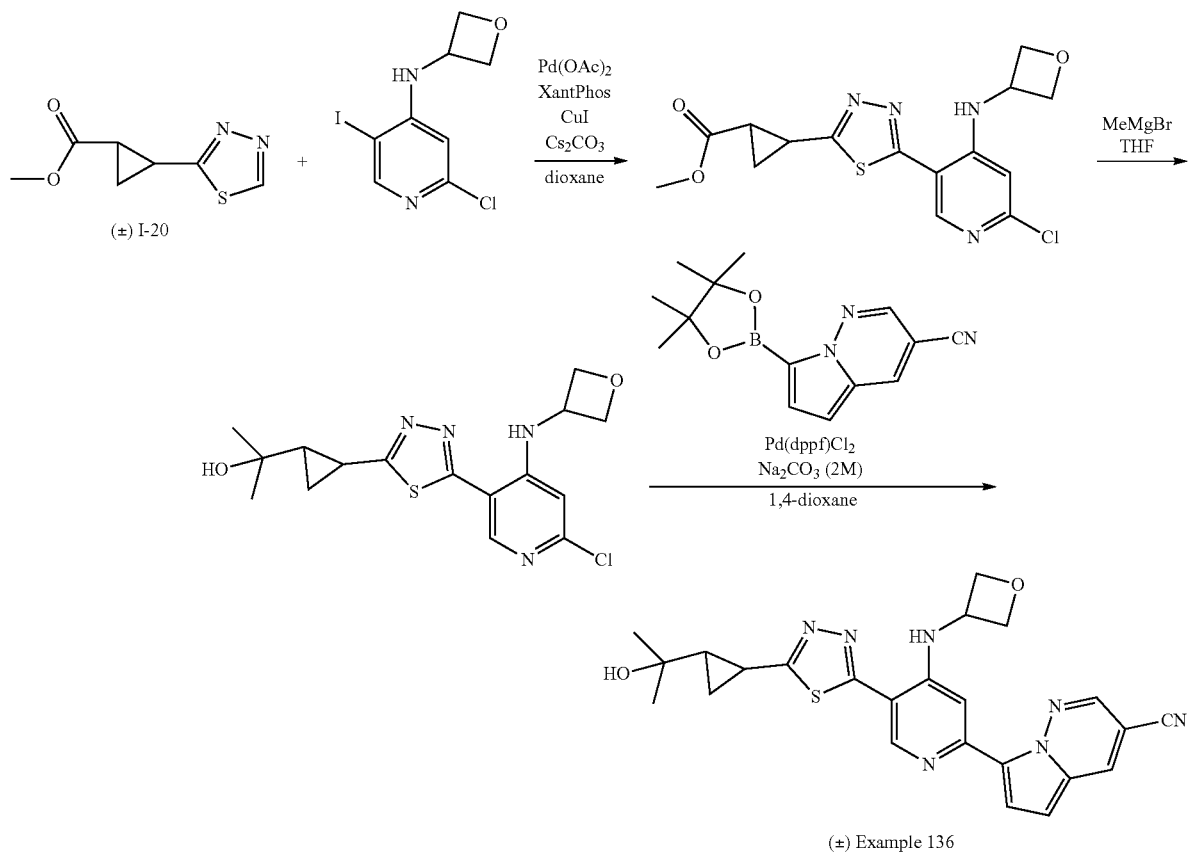

(±) Example 136 methyl trans-2-(5-(6-chloro-4-(oxetan-3-ylamino)pyridin-3-yl)-1,3,4-thiadiazol-2-yl)cyclopropane-1-carboxylate: To a vial was added 2-chloro-5-iodo-N-(oxetan-3-yl)pyridin-4-amine (synthesized in step 1 of I-34) (60 mg, 0.0.19 mmol), (±) methyl trans-2-(1,3,4-thiadiazol-2-yl)cyclopropane-1-carboxylate (I-20) (40 mg, 0.213 mmol), Pd(OAc)$_2$ (8.7 mg, 0.039 mmol), Xantphos (45 mg, 0.077 mmol), copper(I) iodide (15 mg, 0.077 mmol), and cesium carbonate (189 mg, 0.58 mmol). 1,4-Dioxane (1 mL), was added, and the mixture was degassed with argon for 1 minute. The vial was sealed and stirred 90 minutes at 105° C. Afterward, the vial was cooled and the crude material was diluted with DMF (0.5 mL). This mixture was filtered, and purified by RP-HPLC (eluent: water/MeCN*0.1% TFA) to yield the product as a trifluoroacetate salt. The purified material was dissolved in EtOAc and neutralized with sat. aq. NaHCO$_3$. The layers were separated, and the organic layer was dried over MgSO$_4$, filtered, and concentrated under reduced pressure. ES/MS: 367.290 (M+H$^+$)

2-(trans-2-(5-(6-chloro-4-(oxetan-3-ylamino)pyridin-3-yl)-1,3,4-thiadiazol-2-yl)cyclopropyl)propan-2-ol: To a solution of methyl trans-2-(5-(6-chloro-4-(oxetan-3-ylamino)pyridin-3-yl)-1,3,4-thiadiazol-2-yl)cyclopropane-1-carboxylate (80 mg, 0.218 mmol) in THF (10 mL) at −78° C. was added methyllithium (1.6M in ether, 0.2 mL, 0.33 mmol) dropwise, and the reaction was stirred 5 minutes at −78° C. The reaction was quenched at −78° C. with dropwise addition of 1 mL saturated aqueous ammonium chloride, then slowly allowed to warm to room temperature. The reaction was partitioned between water and EtOAc, and the aqueous layer was extracted two additional times with EtOAc. The combined organic layers were dried over magnesium sulfate, filtered, concentrated under reduced pressure, and then purified by silica gel chromatography (eluent: EtOAc/hexanes, then MeOH/EtOAc) to yield the product. ES/MS: 367.195 (M+H$^+$)

7-(5-(5-(trans-2-(2-hydroxypropan-2-yl)cyclopropyl)-1, 3,4-thiadiazol-2-yl)-4-(oxetan-3-ylamino)pyridin-2-yl)pyrrolo[1,2-b]pyridazine-3-carbonitrile (±P-SEA6): A microwave vial was charged with 2-(trans-2-(5-(6-chloro-4-(oxetan-3-ylamino)pyridin-3-yl)-1,3,4-thiadiazol-2-yl)cyclopropyl)propan-2-ol (50 mg, 0.136 mmol), 7-(4,4,5,5-tetramethyl-1,3,2-dioxaborolan-2-yl)pyrrolo[1,2-b]pyridazine-3-carbonitrile (I-8, 51.3 mg, 0.191 mmol), and [1,1'-Bis(diphenylphosphino)ferrocene]dichloropalladium (II) (20 mg, 0.027 mmol). To the flask was added 1,4-dioxane (1.0 mL) and a 2M aqueous solution of sodium carbonate (0.136 mL, 0.27 mmol). The reaction mixture was degassed by bubbling argon for 30 seconds. The vial was sealed and heated with stirring at 120° C. for 20 minutes in a microwave reactor. The cooled reaction mixture was concentrated and purified by RP-HPLC (eluent: water/MeCN*0.1% TFA) to yield the product ±Example 136 as a trifluoroacetate salt.
ES/MS: 474.503 (M+H$^+$)
1H NMR (400 MHz, Methanol-d4) δ 8.79 (d, J=2.2 Hz, 1H), 8.77-8.72 (m, 2H), 8.08 (d, J=5.1 Hz, 1H), 7.73 (s, 1H), 7.25 (d, J=5.1 Hz, 1H), 5.37-5.13 (m, 3H), 4.82 (dd, J=6.7, 5.3 Hz, 2H), 2.65 (dt, J=8.7, 4.9 Hz, 1H), 1.82 (ddd, J=9.3, 6.7, 4.6 Hz, 1H), 1.54 (ddd, J=8.8, 6.8, 4.7 Hz, 1H), 1.46-1.24 (m, 7H).

Single isomers were isolated by chiral supercritical fluid chromatography separation.

The following compounds were made according to the previous pocedures, using the appropriate starting materials and protecting group chemistry as needed:

| # | ES/MS m/z | Procedure | Name |
|---|---|---|---|
| 136 Isomer 1 | 474.358 | | 7-(5-(5-((1S,2S)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile |
| 136 Isomer 2 | 474.324 | | 7-(5-(5-((1R,2R)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile |
| 136 Isomer 3 | 474.366 | | 7-(5-(5-((1S,2R)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile |
| 136 Isomer 4 | 474.366 | | 7-(5-(5-((1R,2S)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile |
| 137 | 514.642 | 2 | N-((1R,4R,7R)-2-(5-(6-(3-cyanopyrrolo[1,2-b]pyridazin-7-yl)-4-(isopropylamino)pyridin-3-yl)-1,3,4-thiadiazol-2-yl)-2-azabicyclo[2.2.1]heptan-7-yl)acetamide |
| 138 | 501.588 | 1 | 7-(4-(isopropylamino)-5-(5-(1-(oxetan-3-yl)piperidin-4-yl)-1,3,4-thiadiazol-2-yl)pyridin-2-yl)pyrrolo[1,2-b]pyridazine-3-carbonitrile |
| 139 | 572.739 | 1 | N-((1r,4r)-4-(5-(6-(3-cyanopyrrolo[1,2-b]pyridazin-7-yl)-4-(isopropylamino)pyridin-3-yl)-l,3,4-thiadiazol-2-yl)cyclohexyl)morpholine-4-carboxamide |
| 140 | 516.411 | 1 | 1-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-methylurea |
| 141 | 514.422 | 2 | N-((1R,2R,4S)-7-(5-(6-(3-cyanopyrrolo[1,2-b]pyridazin-7-yl)-4-(isopropylamino)pyridin-3-yl)-1,3,4-thiadiazol-2-yl)-7-azabicyclo[2.2.1]heptan-2-yl)acetamide |
| 142 | 586.500 | 1 | N-((1r,4r)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)morpholine-4-carboxamide |
| 143 | 671.672 | 1 | methyl (((1R,3r)-3-((2-(3-cyanopyrrolo[1,2-b]pyridazin-7-yl)-5-(5-((1r,4R)-4-(morpholine-4-carboxamido)cyclohexyl)-1,3,4-thiadiazol-2-yl)pyridin-4-yl)amino)cyclobutyl)methyl)carbamate |
| 144 | 556.350 | 2 | N-((1R,5S,8s)-3-(5-(6-(3-cyanopyrrolo[l,2-b]pyridazin-7-yl)-4-((3-methyloxetan-3-yl)amino)pyridin-3-yl)-l,3,4-thiadiazol-2-yl)-3-azabicyclo[3.2.1]octan-8-yl)acetamide |
| 145 | 501.322 | 2 | 7-(5-(5-((1R,5S)-8-oxa-3-azabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile |
| 146 | 487.353 | 2 | 7-(5-(5-((1R,5S,8r)-8-hydroxy-3-azabicyclo[3.2.1]octan-3-yl)-1,3,4-thiadiazol-2-yl)-4-(isopropylamino)pyridin-2-yl)pyirolo[1,2-b]pyridazine-3-carbonitrile |
| 147 | 566.469 | 2 | N-(1-(5-(6-(3-cyanopyrrolo[1,2-b]pyridazin-7-yl)-4-((3-methyloxetan-3-yl)amino)pyridin-3-yl)-1,3,4-thiadiazol-2-yl)-3,3-difluoropiperidin-4-yl)acetamide |
| 147 Isomer 1 | 566.499 | | (R)-N-(1-(5-(6-(3-cyanopyrrolo[1,2-b]pyridazin-7-yl)-4-((3-methyloxetan-3-yl)amino)pyridin-3-yl)-1,3,4-thiadiazol-2-yl)-3,3-difluoropiperidin-4-yl)acetamide |
| 147 Isomer 2 | 566.321 | | (S)-N-(1-(5-(6-(3-cyanopyrrolo[1,2-b]pyridazin-7-yl)-4-((3-methyloxetan-3-yl)amino)pyridin-3-yl)-1,3,4-thiadiazol-2-yl)-3,3-difluoropiperidin-4-yl)acetamide |

Procedure 27: Example 148

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)cyclopropanecarboxamide (Example 148)

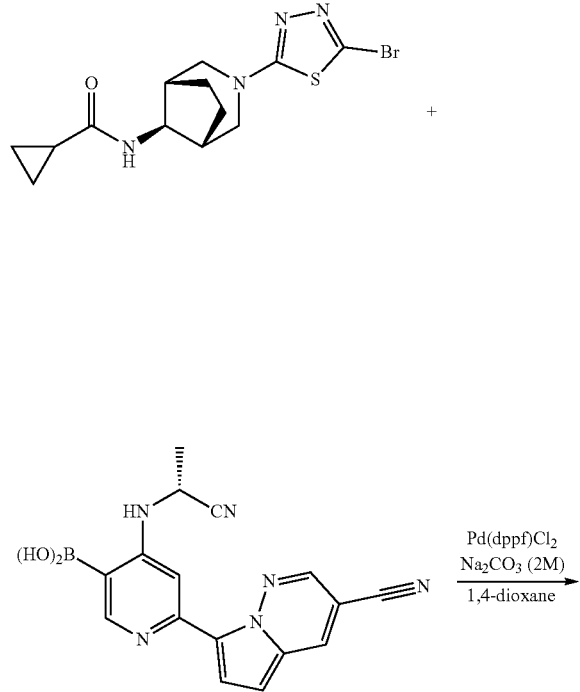

+

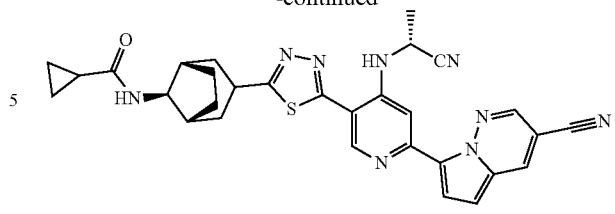

Example 148

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)cyclopropanecarboxamide (Example 148): To a vial containing (R)-(4-((1-cyanoethyl)amino)-6-(3-cyanopyrrolo[1,2-b]pyridazin-7-yl)pyridin-3-yl)boronic acid as a trifluoroacetate salt (25 mg, 0.056 mmol), N-((1R,5S,8s)-3-(5-bromo-1,3,4-thiadiazol-2-yl)-3-azabicyclo[3.2.1]octan-8-yl)cyclopropanecarboxamide (20 mg, 0.056 mmol), Pd(dppf)Cl$_2$ (1.8 mg, 0.014 mmol), was added 1,4-dioxane (1 mL) and sodium carbonate (2M Aqueous, 0.085 mL, 0.17 mmol). The mixture was degassed with argon for 30 seconds, sealed, and heated for 1 hour at 120° C. Afterward, the vial was cooled and the crude material was diluted with DMF (0.5 mL). This mixture was filtered, and purified by RP-HPLC (eluent: water/MeCN*0.1% TFA) to yield the product Example 148 as a trifluoroacetate salt.
ES/MS: 565.573 (M+H$^+$)
1H NMR (400 MHz, Methanol-d4) δ 8.79 (d, J=2.2 Hz, 1H), 8.71 (d, J=2.2 Hz, 1H), 8.64 (s, 1H), 8.16-8.08 (m, 2H), 7.27 (d, J=5.1 Hz, 1H), 5.24 (q, J=7.0 Hz, 1H), 4.02 (s, 1H), 3.84 (d, J=12.1 Hz, 2H), 3.57 (d, J=11.9 Hz, 2H), 2.47 (s, 2H), 2.13-2.03 (m, 2H), 1.92 (d, J=6.9 Hz, 3H), 1.77-1.60 (m, 3H), 0.88 (dt, J=6.1, 3.1 Hz, 2H), 0.79 (dt, J=8.1, 3.2 Hz, 2H).

The following compounds were made according to the previous procedures, using the appropriate starting materials and protecting group chemistry as needed:

| #   | ES/MS m/z | Procedure | Name |
|-----|-----------|-----------|------|
| 149 | 515.332   | 2         | 7-(5-(5-((1R,5S,8r)-8-hydroxy-3-azabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile |
| 150 | 554.440   | 2         | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)cyclopropanecarboxamide |
| 151 | 549.286   | 27        | N-((R)-1-(5-(4-(((R)-1-cyanoethyl)amino)-6-(3-cyanopyrrolo[1,2-b]pyridazin-7-yl)pyridin-3-yl)-1,3,4-thiadiazol-2-yl)-3,3-difluoropiperidin-4-yl)acetamide |
| 152 | 549.292   | 27        | N-((S)-1-(5-(4-(((R)-1-cyanoethyl)amino)-6-(3-cyanopyrrolo[1,2-b]pyridazin-7-yl)pyridin-3-yl)-1,3,4-thiadiazol-2-yl)-3,3-difluoropiperidin-4-yl)acetamide |
| 153 | 501.420   | 2         | 7-(5-(5-((1R,5S,8r)-8-hydroxy-8-methyl-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile |
| 154 | 487.381   | 2         | 7-(5-(5-((1R,5S,8s)-8-hydroxy-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile |
| 155 | 542.465   | 2         | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-8-methyl-3-azabicyclo[3.2.1]octan-8-yl)acetamide |
| 156 | 569.655   | 1         | N-((1r,4r)-4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)cyclohexyl)cyclopropanecarboxamide |
| 157 | 553.480   | 27        | N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-8-methyl-3-azabicyclo[3.2.1]octan-8-yl)acetamide |
| 158 | 555.630   | 1         | N-((1r,4r)-4-(5-(6-(3-cyanopyrrolo[1,2-b]pyridazin-7-yl)-4-((3-methyloxetan-3-yl)amino)pyridin-3-yl)-1,3,4-thiadiazol-2-yl)cyclohexyl)cyclopropanecarboxamide |

-continued

| # | ES/MS m/z | Procedure | Name |
|---|---|---|---|
| 159 | 555.574 | 2 | 7-(5-(5-(8-hydroxy-8-(trifluoromethyl)-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile |
| 160 | 538.404 | 13 | N-((1R,4r)-4-(5-(4-(((R)-1-cyanoethyl)amino)-6-(3-cyanopyrrolo[1,2-b]pyridazin-7-yl)pyridin-3-yl)-1,3,4-thiadiazol-2-yl)cyclohexyl)cyclopropanecarboxamide |
| 161 | 497.337 | 2 | (S)-7-(5-(5-(3,3-difluoro-4-hydroxypiperidin-1-yl)-1,3,4-thiadiazol-2-yl)-4-(isopropylamino)pyridin-2-yl)pyrrolo[1,2-b]pyridazine-3-carbonitrile |
| 162 | 497.475 | 2 | (R)-7-(5-(5-(3,3-difluoro-4-hydroxypiperidin-1-yl)-1,3,4-thiadiazol-2-yl)-4-(isopropylamino)pyridin-2-yl)pyrrolo[1,2-b]pyridazine-3-carbonitrile |
| 163 | 486.281 | 2 | 7-(4-(isopropylamino)-5-(5-(7-oxo-2,6-diazaspiro[3.4]octan-2-yl)-1,3,4-thiadiazol-2-yl)pyridin-2-yl)pyrrolo[1,2-b]pyridazine-3-carbonitrile |
| 164 | 486.309 | 2 | 7-(4-(isopropylamino)-5-(5-(5-oxo-2,6-diazaspiro[3.4]octan-2-yl)-1,3,4-thiadiazol-2-yl)pyridin-2-yl)pyrrolo[1,2-b]pyridazine-3-carbonitrile |
| 165 | 542.516 | 2 | N-((1R,5S,9r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.3.1]nonan-9-yl)acetamide |
| 166 | 542.472 | 2 | N-((1R,5S,9s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.3.1]nonan-9-yl)acetamide |
| 167 | 483.323 | 2 | 7-(5-(5-(2,2-difluoromorpholino)-1,3,4-thiadiazol-2-yl)-4-(isopropylamino)pyridin-2-yl)pyrrolo[1,2-b]pyridazine-3-carbonitrile |
| 168 | 538.327 | 2 | (R)-N-(1-(5-(6-(3-cyanopyrrolo[1,2-b]pyridazin-7-yl)-4-(isopropylamino)pyridin-3-yl)-1,3,4-thiadiazol-2-yl)-3,3-difluoropiperidin-4-yl)acetamide |
| 169 | 538.324 | 2 | (S)-N-(1-(5-(6-(3-cyanopyrrolo[1,2-b]pyridazin-7-yl)-4-(isopropylamino)pyridin-3-yl)-1,3,4-thiadiazol-2-yl)-3,3-difluoropiperidin-4-yl)acetamide |
| 170 | 528.436 | 2 | N-(2-(5-(6-(3-cyanopyrrolo[1,2-b]pyridazin-7-yl)-4-(isopropylamino)pyridin-3-yl)-1,3,4-thiadiazol-2-yl)-2-azaspiro[3.4]octan-6-yl)acetamide |
| 171 | 570.466 | 2 | N-((1R,5S,8s)-3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-3-azabicyclo[3.2.1]octan-8-yl)acetamide |
| 172 | 529.475 | 2 | 7-(5-(5-(4-hydroxy-4-(trifluoromethyl)piperidin-1-yl)-1,3,4-thiadiazol-2-yl)-4-(isopropylamino)pyridin-2-yl)pyrrolo[1,2-b]pyridazine-3-carbonitrile |
| 173 | 514.334 | 2 | N-((1R,5S,6s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.1]heptan-6-yl)acetamide |
| 174 | 525.277 | 27 | N-((1R,5S,6S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.1.1]heptan-6-yl)acetamide |
| 175 | 542.297 | 2 | N-((1R,5S,6s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.1.1]heptan-6-yl)acetamide |
| 176 | 486.270 | 2 | N-((1R,5S,6s)-3-(5-(6-(3-cyanopyrrolo[1,2-b]pyridazin-7-yl)-4-(methylamino)pyridin-3-yl)-1,3,4-thiadiazol-2-yl)-3-azabicyclo[3.1.1]heptan-6-yl)acetamide |
| 177 | 501.284 | 2 | 7-(5-(5-(6-oxa-3-azabicyclo[3.1.1]heptan-3-yl)-1,3,4-thiadiazol-2-yl)-4-((tetrahydro-2H-pyran-4-yl)amino)pyridin-2-yl)pyrrolo[1,2-b]pyridazine-3-carbonitrile |
| 178 | 470.211 | 27 | 7-(5-(5-(6-oxa-3-azabicyclo[3.1.1]heptan-3-yl)-1,3,4-thiadiazol-2-yl)-4-(((R)-1-cyanoethyl)amino)pyridin-2-yl)pyrrolo[1,2-b]pyridazine-3-carbonitrile |
| 179 | 528.342 | 2 | N-((1R,5S,6s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.1.1]heptan-6-yl)acetamide |
| 180 | 486.255 | 27 | (R)-7-(4-((1-cyanoethyl)amino)-5-(5-(4-hydroxy-4-methylpiperidin-1-yl)-1,3,4-thiadiazol-2-yl)pyridin-2-yl)pyrrolo[1,2-b]pyridazine-3-carbonitrile |
| 181 | 503.309 | 2 | 7-(5-(5-(4-hydroxy-4-methylpiperidin-1-yl)-1,3,4-thiadiazol-2-yl)-4-((3-methyloxetan-3-yl)amino)pyridin-2-yl)pyrrolo[1,2-b]pyridazine-3-carbonitrile |
| 182 | 544.553 | 2 | N-((1R,5S,9r)-7-(5-(6-(3-cyanopyrrolo[1,2-b]pyridazin-7-yl)-4-(isopropylamino)pyridin-3-yl)-1,3,4-thiadiazol-2-yl)-3-oxa-7-azabicyclo[3.3.1]nonan-9-yl)acetamide |
| 183 | 552.285 | 2 | (R)-N-(1-(5-(6-(3-cyanopyrrolo[1,2-b]pyridazin-7-yl)-4-(oxetan-3-ylamino)pyridin-3-yl)-1,3,4-thiadiazol-2-yl)-3,3-difluoropiperidin-4-yl)acetamide |

-continued

| # | ES/MS m/z | Procedure | Name |
|---|---|---|---|
| 184 | 542.307 | 2 | N-((1R,5S,8s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.2.1]octan-8-yl)acetamide |
| 185 | 495.220 | 1 | N-(4-(5-(6-(3-cyanopyrrolo[1,2-b]pyridazin-7-yl)-4-(isopropylamino)pyridin-3-yl)-1,3,4-thiadiazol-2-yl)phenyl)acetamide |
| 186 | 493.590 | 2 | 7-(5-(5-((3S,4R)-3-fluoro-4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile |
| 187 | 489.289 | 2 | 7-(5-(5-(4-hydroxy-4-methylpiperidin-1-yl)-1,3,4-thiadiazol-2-yl)-4-(oxetan-3-ylamino)pyridin-2-yl)pyirolo[1,2-b]pyridazine-3-carbonitrile |
| 188 | 517.625 | 2 | 7-(5-(5-(4-hydroxy-4-methylpiperidin-l-yl)-1,3,4-thiadiazol-2-yl)-4-((tetrahydro-2H-pyran-4-yl)amino)pyridin-2-yl)pyrrolo[1,2-b]pyridazine-3-carbonitrile |
| 189 | 493.358 | 2 | 7-(5-(5-(4-(fluoromethyl)-4-hydroxypiperidin-1-yl)-1,3,4-thiadiazol-2-yl)-4-(isopropylamino)pyridin-2-yl)pyrrolo[1,2-b]pyridazine-3-carbonitrile |
| 190 | 493.432 | 2 | 7-(5-(5-((3S,4S)-3-fluoro-4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile |
| 191 | 493.288 | 2 | 7-(5-(5-((3R,$R)-3-fluoro-4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile |
| 192 | 493.345 | 2 | 7-(5-(5-((3R,4S)-3-fluoro-4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile |
| 193 | 544.573 | 2 | N-((1R,5S)-7-(5-(6-(3-cyanopyrrolo[1,2-b]pyridazin-7-yl)-4-(isopropylamino)pyridin-3-yl)-1,3,4-thiadiazol-2-yl)-3-oxa-7-azabicyclo[3.3.1]nonan-9-yl)acetamide |
| 194 | 519.561 | 1 | N-(4-(5-(6-(3-cyanopyrrolo[1,2-b]pyridazin-7-yl)-4-(isopropylamino)pyridin-3-yl)-1,3,4-thiadiazol-2-yl)-4-fluorocyclohexyl)acetamide |

Procedure 28: Examples 195 and 196

N-(4-(5-(6-(3-cyanopyrrolo[1,2-b]pyridazin-7-yl)-4-(oxetan-3-ylamino)pyridin-3-yl)-1,3,4-thiadiazol-2-yl)-4-fluorocyclohexyl)acetamide (Example 195 and 196)

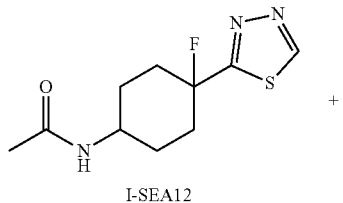

I-SEA12

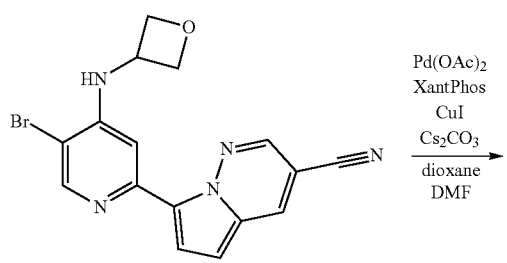

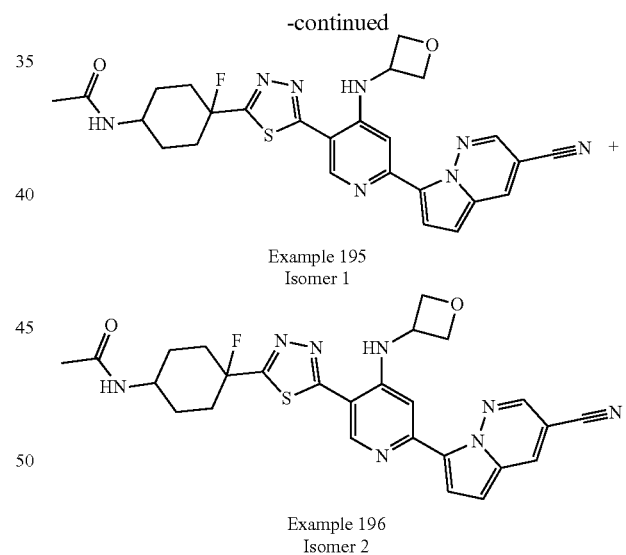

Example 195
Isomer 1

Example 196
Isomer 2

N-(4-(5-(6-(3-cyanopyrrolo[1,2-b]pyridazin-7-yl)-4-(oxetan-3-ylamino)pyridin-3-yl)-1,3,4-thiadiazol-2-yl)-4-fluorocyclohexyl)acetamide (Examples 195 and 196): To a vial was added 7-(5-bromo-4-(oxetan-3-ylamino)pyridin-2-yl)pyrrolo[1,2-b]pyridazine-3-carbonitrile (30 mg, 0.081 mmol), N-(4-fluoro-4-(1,3,4-thiadiazol-2-yl)cyclohexyl)acetamide (I-31) (40 mg, 0.162 mmol), Pd(OAc)$_2$ (4.5 mg, 0.02 mmol), Xantphos (23.5 mg, 0.04 mmol), copper(I) iodide (7.7 mg, 0.04 mmol), and cesium carbonate (80 mg, 0.24 mmol). 1,4-Dioxane (0.75 mL) and DMF (0.25 mL) was added, and the mixture was degassed with argon for 1 minute. The vial was sealed and stirred 1 hour at 105° C.

Afterward, the vial was cooled and the crude material was diluted with DMF (0.5 mL). This mixture was filtered, and purified by RP-HPLC (eluent: water/MeCN*0.1% TFA) to yield the products Example 195 Isomer 1 and Example 196 Isomer 2 as separable isomers. Isomers isolated as a trifluoroacetate salt.

Isomer 1 (Example 195): ES/MS: 533.319 (M+H$^+$)
1H NMR (400 MHz, Methanol-d4) δ 8.87 (s, 1H), 8.81 (d, J=2.2 Hz, 1H), 8.75 (d, J=2.2 Hz, 1H), 8.10 (d, J=5.1 Hz, 1H), 7.75 (s, 1H), 7.27 (d, J=5.1 Hz, 1H), 5.38-5.26 (m, 1H), 5.22 (q, J=6.8, 6.1 Hz, 2H), 4.83 (dd, J=6.9, 5.6 Hz, 2H), 3.98-3.85 (m, 1H), 2.50-2.22 (m, 2H), 2.04 (d, J=14.2 Hz, 4H), 1.98 (s, 3H), 1.86-1.70 (m, 2H).

Isomer 2 (Example 196): ES/MS: 533.297 (M+H$^+$)
1H NMR (400 MHz, Methanol-d4) δ 8.88 (s, 1H), 8.80 (d, J=2.2 Hz, 1H), 8.75 (d, J=2.1 Hz, 1H), 8.10 (d, J=5.1 Hz, 1H), 7.77 (s, 1H), 7.26 (d, J=5.1 Hz, 1H), 5.38-5.26 (m, 1H), 5.26-5.19 (m, 2H), 4.82 (dd, J=6.9, 5.5 Hz, 2H), 4.09-3.99 (m, 1H), 2.53 (dddd, J=23.8, 13.7, 9.2, 4.2 Hz, 2H), 2.35-2.19 (m, 2H), 2.09 (ddd, J=14.3, 9.3, 4.6 Hz, 2H), 2.00 (s, 3H), 1.98-1.81 (m, 2H).

The following compounds were made according to the previous procedures, using the appropriate starting materials and protecting group chemistry as needed:

| # | ES/MS m/z | Procedure | Name |
|---|---|---|---|
| 197 | 521.207 | 14 | N-(4-(5-(6-(3-cyanopyrrolo[1,2-b]pyridazin-7-yl)-4-(isopropylamino)pyridin-3-yl)-1,3,4-thiadiazol-2-yl)cuban-1-yl)acetamide |
| 198 | 543.299 | 1 | N-(1-(5-(6-(3-cyanopyrrolo[1,2-b]pyridazin-7-yl)-4-(oxetan-3-ylamino)pyridin-3-yl)-1,3,4-thiadiazol-2-yl)-2-oxabicyclo[2.2.2]octan-4-yl)acetamide |
| 199 | 446.248 | 1 | 7-(5-(5-((1s,3s)-3-hydroxy-3-methylcyclobutyl)-1,3,4-thiadiazol-2-yl)-4-(isopropylamino)pyridin-2-yl)pyrrolo[1,2-b]pyridazine-3-carbonitrile |
| 200 | 460.223 | 1 | 7-(5-(5-((1s,3s)-3-hydroxy-3-methylcyclobutyl)-1,3,4-thiadiazol-2-yl)-4-(oxetan-3-ylamino)pyridin-2-yl)pyrrolo[1,2-b]pyridazine-3-carbonitrile |
| 201 | 515.303 | 1 | N-((1r,3r)-3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)cyclobutyl)acetamide |
| 202 | 487.235 | 1 | N-((1r,3r)-3-(5-(6-(3-cyanopyrrolo[1,2-b]pyridazin-7-yl)-4-(oxetan-3-ylamino)pyridin-3-yl)-1,3,4-thiadiazol-2-yl)cyclobutyl)acetamide |
| 203 | 541.317 | 1 | N-((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)cyclopropanecarboxamide |
| 204 | 535.300 | 2 | 7-(5-(5-((3S,4S)-3-fluoro-4-hydroxy-4-methylpiperidin-l-yl)-1,3,4-thiadiazol-2-yl)-4-((tetrahydro-2H-pyran-4-yl)amino)pyridin-2-yl)pyrrolo[1,2-b]pyridazine-3-carbonitrile |
| 205 | 531.455 | 1 | methyl ((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)carbamate |

Procedure 29: Example 206

7-(5-(5-(4-hydroxy-4-methylcyclohexyl)-1,3,4-thiadiazol-2-yl)-4-(oxetan-3-ylamino)pyridin-2-yl)pyrrolo[1,2-b]pyridazine-3-carbonitrile (Example 206)

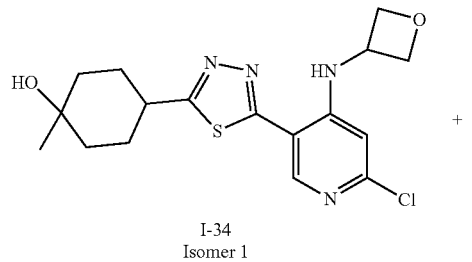

I-34
Isomer 1

+

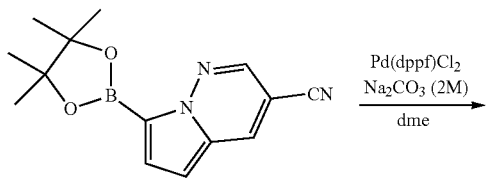

Pd(dppf)Cl₂
Na₂CO₃ (2M)
dme

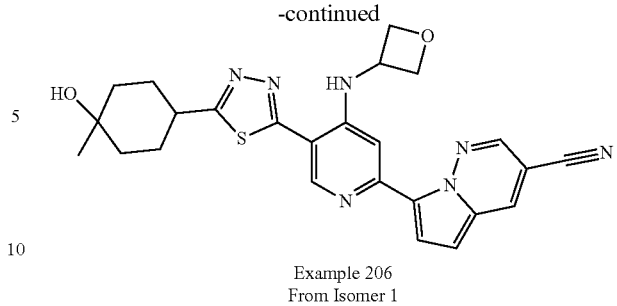

Example 206
From Isomer 1

7-(5-(5-(4-hydroxy-4-methylcyclohexyl)-1,3,4-thiadiazol-2-yl)-4-(oxetan-3-ylamino)pyridin-2-yl)pyrrolo[1,2-b]pyridazine-3-carbonitrile (Example 206 from Isomer 1): A microwave vial was charged with 4-(5-(6-chloro-4-(oxetan-3-ylamino)pyridin-3-yl)-1,3,4-thiadiazol-2-yl)-1-methylcyclohexan-1-ol (I-34 Isomer 1) (21.1 mg, 0.055 mmol), 7-(4,4,5,5-tetramethyl-1,3,2-dioxaborolan-2-yl)pyrrolo[1,2-b]pyridazine-3-carbonitrile (I-8, 20.9 mg, 0.078 mmol), and [1,1'-Bis(diphenylphosphino)ferrocene]dichloropalladium (II) (8.2 mg, 0.011 mmol). To the flask was added DME (1.0 mL) and a 2M aqueous solution of sodium carbonate (0.06 mL, 0.11 mmol). The reaction mixture was degassed by bubbling argon for 30 seconds. The vial was sealed and heated with stirring at 120° C. for 20 minutes in a microwave reactor. The cooled reaction mixture was concentrated and purified by RP-HPLC (eluent: water/MeCN*0.1% TFA) to yield the product Example 206 from Isomer 1 as a trifluoroacetate salt.

ES/MS: 488.296 (M+H⁺)

1H NMR (400 MHz, Methanol-d4) δ 8.80-8.76 (m, 2H), 8.72 (d, J=2.2 Hz, 1H), 8.07 (d, J=5.0 Hz, 1H), 7.78 (s, 1H), 7.24 (d, J=5.1 Hz, 1H), 5.30-5.19 (m, 3H), 4.86-4.78 (m, 2H), 3.45-3.36 (m, 1H), 2.35-2.20 (m, 2H), 1.99-1.78 (m, 4H), 1.78-1.64 (m, 2H), 1.31 (s, 3H).

The following compounds were made according to the previous procedures, using the appropriate starting materials and protecting group chemistry as needed:

| # | ES/MS m/z | Procedure | Name |
|---|---|---|---|
| 207 | 507.278 | 2 | 7-(5-(5-((3S,4S)-3-fluoro-4-hydroxy-4-methylpiperidin-1-yl)-1,3,4-thiadiazol-2-yl)-4-(oxetan-3-ylamino)pyridin-2-yl)pyrrolo[1,2-b]pyridazine-3-carbonitrile |
| 208 | 488.296 | 29 | 7-(5-(5-((1s,4s)-4-hydroxy-4-methylcyclohexyl)-1,3,4-thiadiazol-2-yl)-4-(oxetan-3-ylamino)pyridin-2-yl)pyrrolo[1,2-b]pyridazine-3-carbonitrile |
| 209 | 544.340 | 2 | N-((1R,5S,7r)-9-(5-(6-(3-cyanopyrrolo[1,2-b]pyridazin-7-yl)-4-(isopropylamino)pyridin-3-yl)-1,3,4-thiadiazol-2-yl)-3-oxa-9-azabicyclo[3.3.1]nonan-7-yl)acetamide |
| 210 | 600.357 | 2 | N-((1R,5S,8s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.2.1]octan-8-yl)-2-hydroxy-2-methylpropanamide |
| 211 | 362.172 | 6 | 7-(4-(isopropylamino)-5-(1,3,4-thiadiazol-2-yl)pyridin-2-yl)pyrrolo[1,2-b]pyridazine-3-carbonitrile |
| 212 | 405.209 | 8 | 7-(5-(5-(2-aminoethyl)-1,3,4-thiadiazol-2-yl)-4-(isopropylamino)pyridin-2-yl)pyrrolo[1,2-b]pyridazine-3-carbonitrile |
| 213 | 475.211 | 5 | 5-(6-(3-cyanopyrrolo[1,2-b]pyridazin-7-yl)-4-(isopropylamino)pyridin-3-yl)-N-((1r,3r)-3-hydroxycyclobutyl)-1,3,4-thiadiazole-2-carboxamide |
| 214 | 489.324 | 5 | (R)-7-(5-(5-(2-(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile |
| 215 | 475.210 | 5 | 5-(6-(3-cyanopyrrolo[1,2-b]pyridazin-7-yl)-4-(isopropylamino)pyridin-3-yl)-N-((1s,3s)-3-hydroxycyclobutyl)-1,3,4-thiadiazole-2-carboxamide |

| # | ES/MS m/z | Procedure | Name |
|---|---|---|---|
| 216 | 489.272 | 5 | (R)-7-(5-(5-(3-(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile |
| 217 | 489.322 | 5 | (S)-7-(5-(5-(2-(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile |
| 218 | 489.313 | 5 | 5-(6-(3-cyanopyrrolo[1,2-b]pyridazin-7-yl)-4-(isopropylamino)pyridin-3-yl)-N-((1s,3s)-3-hydroxy-3-methylcyclobutyl)-1,3,4-thiadiazole-2-carboxamide |
| 219 | 489.376 | 5 | 5-(6-(3-cyanopyrrolo[1,2-b]pyridazin-7-yl)-4-(isopropylamino)pyridin-3-yl)-N-((1r,3r)-3-hydroxy-3-methylcyclobutyl)-1,3,4-thiadiazole-2-carboxamide |
| 220 | 503.284 | 5 | 5-(6-(3-cyanopyrrolo[1,2-b]pyridazin-7-yl)-4-(isopropylamino)pyridin-3-yl)-N-((1r,4r)-4-hydroxycyclohexyl)-1,3,4-thiadiazole-2-carboxamide |
| 221 | 489.261 | 5 | (S)-7-(5-(5-(3-(hydroxymethyl)pyrrolidine-l-carbonyl)-1,3,4-thiadiazol-2-yl)-4-(isopropylamino)pyridin-2-yl)pyrrolo[1,2-b]pyridazine-3-carbonitrile |
| 222 | 574.235 | 5 | tert-butyl (R)-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)carbamate |
| 223 | 574.237 | 5 | tert-butyl (S)-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)carbamate |
| 224 | 503.254 | 5 | 5-(6-(3-cyanopyrrolo[1,2-b]pyridazin-7-yl)-4-(isopropylamino)pyridin-3-yl)-N-((1s,4s)-4-hydroxycyclohexyl)-1,3,4-thiadiazole-2-carboxamide |
| 225 | 588.337 | 5 | tert-butyl (S)-(1-(5-(6-(3-cyanopyrrolo[1,2-b]pyridazin-7-yl)-4-(isopropylamino)pyridin-3-yl)-1,3,4-thiadiazole-2-carbonyl)piperidin-3-yl)carbamate |
| 226 | 588.345 | 5 | tert-butyl (S)-((1-(5-(6-(3-cyanopyrrolo[1,2-b]pyridazin-7-yl)-4-(isopropylamino)pyridin-3-yl)-1,3,4-thiadiazole-2-carbonyl)pyrrolidin-2-yl)methyl)carbamate |
| 227 | 657.3 | 1 | N-((1R,4r)-4-(5-(6-(3-cyanopyrrolo[1,2-b]pyridazin-7-yl)-4-(((1r,4R)-4-(1-(difluoromethyl)-1H-pyrazol-4-yl)cyclohexyl)amino)pyridin-3-yl)-1,3,4-thiadiazol-2-yl)cyclohexyl)acetamide |
| 228 | 588.254 | 5 | tert-butyl (R)-((1-(5-(6-(3-cyanopyrrolo[1,2-b]pyridazin-7-yl)-4-(isopropylamino)pyridin-3-yl)-1,3,4-thiadiazole-2-carbonyl)pyrrolidin-2-yl)methyl)carbamate |

Procedure 31: Example 229

(S)-7-(5-(5-(2-(aminomethyl)pyrrolidine-1-carbonyl)-1,3,4-thiadiazol-2-yl)-4-(isopropylamino)pyridin-2-yl)pyrrolo[1,2-b]pyridazine-3-carbonitrile (Example 229)

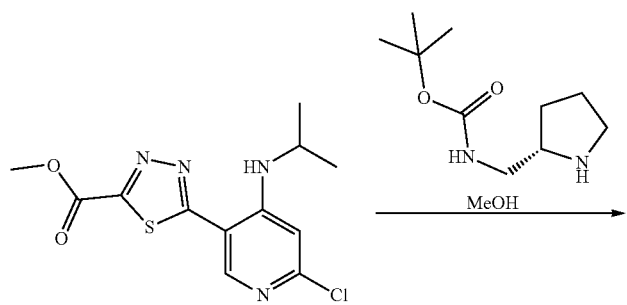

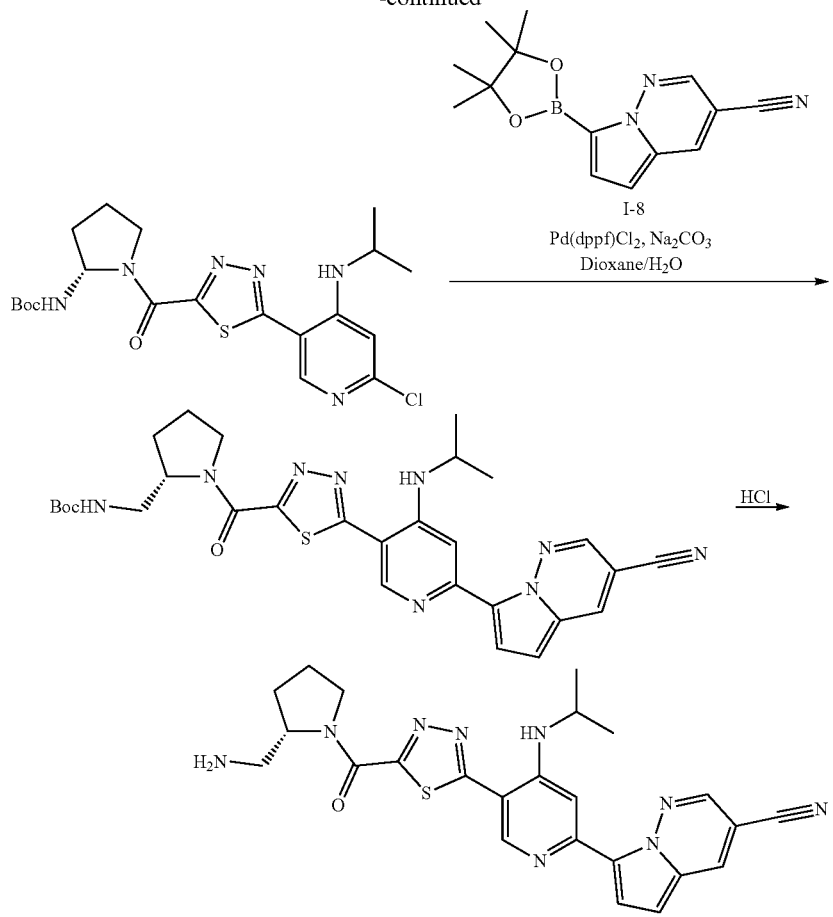

Example 229 tert-butyl (S)-((1-(5-(6-chloro-4-(isopropylamino)pyridin-3-yl)-1,3,4-thiadiazole-2-carbonyl)pyrrolidin-2-yl)methyl)carbamate: To a solution of methyl 5-(6-chloro-4-(isopropylamino)pyridin-3-yl)-1,3,4-thiadiazole-2-carboxylate (50.0 mg, 0.16 mmol) in MeOH (0.5 mL) was added tert-butyl (S)-(pyrrolidin-2-ylmethyl)carbamate (38.4 mg, 0.19 mmol). The reaction mixture was heated at 80° C. for 1 hour, then concentrated in vacuo and purified by silica gel column chromatography (eluent: MeOH/DCM) to provide tert-butyl (S)-((1-(5-(6-chloro-4-(isopropylamino)pyridin-3-yl)-1,3,4-thiadiazole-2-carbonyl)pyrrolidin-2-yl)methyl)carbamate.

ES/MS: 481.6 [M+H$^+$].

tert-butyl (S)-((1-(5-(6-(3-cyanopyrrolo[1,2-b]pyridazin-7-yl)-4-(isopropylamino)pyridin-3-yl)-1,3,4-thiadiazole-2-carbonyl)pyrrolidin-2-yl)methyl)carbamate: A solution of tert-butyl (S)-((1-(5-(6-chloro-4-(isopropylamino)pyridin-3-yl)-1,3,4-thiadiazole-2-carbonyl)pyrrolidin-2-yl)methyl)carbamate (40.7 mg, 0.084 mmol), 7-(4,4,5,5-tetramethyl-1,3,2-dioxaborolan-2-yl)pyrrolo[1,2-b]pyridazine-3-carbonitrile (27.3 mg, 0.10 mmol), [1,1'-Bis(diphenylphosphino)ferrocene]dichloropalladium(II) (17.3 mg, 0.021 mmol), and sodium carbonate (2N in water, 85 µL, 0.17 mmol) in 1,4-dioxane (0.71 mL) was sparged with argon for 60 seconds, then heated in a microwave reactor at 125° C. for 20 minutes. Upon cooling, the reaction mixture was filtered and purified by reverse phase high pressure liquid chromatography (eluent: water/MeCN*0.1% TFA) to provide tert-butyl (S)-((1-(5-(6-(3-cyanopyrrolo[1,2-b]pyridazin-7-yl)-4-(isopropylamino)pyridin-3-yl)-1,3,4-thiadiazole-2-carbonyl)pyrrolidin-2-yl)methyl)carbamate.

ES/MS: 588.2 [M+H$^+$].

(S)-7-(5-(5-(2-(aminomethyl)pyrrolidine-1-carbonyl)-1,3,4-thiadiazol-2-yl)-4-(isopropylamino)pyridin-2-yl)pyrrolo[1,2-b]pyridazine-3-carbonitrile (Example 229): To a solution of tert-butyl (S)-((1-(5-(6-(3-cyanopyrrolo[1,2-b]pyridazin-7-yl)-4-(isopropylamino)pyridin-3-yl)-1,3,4-thiadiazole-2-carbonyl)pyrrolidin-2-yl)methyl)carbamate (19 mg, 0.032mmol) in dioxane (0.25 mL) was added hydrochloric acid (4N in dioxane, 121.2 µL, 0.48 mmol) and stirred for 3 hours. The reaction mixture was concentrated, filtered and purified by reverse phase high pressure liquid chromatography (eluent: water/MeCN*0.1% TFA) to provide the final compound Example 229.

ES/MS: 488.2 [M+H$^+$].

1H NMR (400 MHz, Methanol-d4) δ 8.84 (d, J=5.6 Hz, 1H), 8.76 (d, J=2.2 Hz, 1H), 8.69 (d, J=2.2 Hz, 1H), 8.13 (s, 1H), 8.06 (d, J=5.0 Hz, 1H), 7.24 (d, J=5.0 Hz, 1H), 4.61 (dd, J=8.4, 4.2 Hz, 1H), 4.42-4.18 (m, 3H), 3.29-3.20 (m, 1H), 2.35-2.08 (m, 4H), 1.94 (dq, J=11.1, 5.2, 4.7 Hz, 1H), 1.52 (d, J=6.4 Hz, 6H).

The following compounds were made according to the previous procedures, using the appropriate starting materials and protecting group chemistry as needed:

| # | ES/MS m/z | Procedure | Name |
|---|---|---|---|
| 230 | 488.268 | 31 | (R)-7-(5-(5-(2-(aminomethyl)pyrrolidine-1-carbonyl)-1,3,4-thiadiazol-2-yl)-4-(isopropylamino)pyridin-2-yl)pyrrolo[1,2-b]pyridazine-3-carbonitrile |
| 231 | 514.4 | 2 | N-(2-(5-(6-(3-cyanopyrrolo[1,2-b]pyridazin-7-yl)-4-(isopropylamino)pyridin-3-yl)-1,3,4-thiadiazol-2-yl)-2-azaspiro[3.3]heptan-6-yl)acetamide |
| 232 | (M + H) 488.3 | 2 | 7-(5-(5-(4-acetylpiperazin-1-yl)-1,3,4-thiadiazol-2-yl)-4-(isopropylamino)pyridin-2-yl)pyrrolo[1,2-b]pyridazine-3-carbonitrile |
| 233 | (M + H) 459.4 | 2 | 7-(5-(5-(6-oxa-3-azabicyclo[3.1.1]heptan-3-yl)-1,3,4-thiadiazol-2-yl)-4-(isopropylamino)pyridin-2-yl)pyrrolo[1,2-b]pyridazine-3-carbonitrile |
| 234 | (M + H) 459.4 | 2 | 7-(5-(5-(3-oxa-6-azabicyclo[3.1.1]heptan-6-yl)-1,3,4-thiadiazol-2-yl)-4-(isopropylamino)pyridin-2-yl)pyrrolo[1,2-b]pyridazine-3-carbonitrile |
| 235 | (M + H) 473.6 | 2 | 7-(5-(5-(8-oxa-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile |
| 236 | (M + H) 473.4 | 2 | 7-(5-(5-(3-oxa-8-azabicyclo[3.2.1]octan-8-yl)-1,3,4-thiadiazol-2-yl)-4-(isopropylamino)pyridin-2-yl)pyrrolo[1,2-b]pyridazine-3-carbonitrile |
| 237 | (M + H) 459.4 | 2 | 7-(5-(5-((1R,4R)-2-oxa-5-azabicyclo[2.2.1]heptan-5-yl)-1,3,4-thiadiazol-2-yl)-4-(isopropylamino)pyridin-2-yl)pyrrolo[1,2-b]pyridazine-3-carbonitrile |
| 238 | (M + H) 459.3 | 2 | 7-(5-(5-((1S,4S)-2-oxa-5-azabicyclo[2.2.1]heptan-5-yl)-1,3,4-thiadiazol-2-yl)-4-(isopropylamino)pyridin-2-yl)pyrrolo[1,2-b]pyridazine-3-carbonitrile |
| 239 | (M + H) 500.3 | 2 | N-((1R,5S,6r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.0]hexan-6-yl)acetamide |
| 240 | (M + H) 500.3 | 2 | N-((1R,5S,6s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.0]hexan-6-yl)acetamide |
| 241 | 583.614 | 1 | N-((1r,4r)-4-(5-(6-(3-cyanopyrrolo[1,2-b]pyridazin-7-yl)-4-((4-hydroxybicyclo[2.2.2]octan-1-yl)amino)pyridin-3-yl)-1,3,4-thiadiazol-2-yl)cyclohexyl)acetamide |
| 242 | 502.509 | 5 | (S)-7-(5-(5-(2-(aminomethyl)pyrrolidine-1-carbonyl)-1,3,4-thiadiazol-2-yl)-4-(isopropylamino)pyridin-2-yl)pyrrolo[1,2-b]pyridazine-3-carbonitrile |
| 243 | 543.597 | 1 | N-((1R,4r)-4-(5-(6-(3-cyanopyrrolo[1,2-b]pyridazin-7-yl)-4-(((1s,3S)-3-hydroxy-3-methylcyclobutyl)amino)pyridin-3-yl)-1,3,4-thiadiazol-2-yl)cyclohexyl)acetamide |
| 244 | 555.286 | 1 | N-((1R,4r)-4-(5-(6-(3-cyanopyrrolo[1,2-b]pyridazin-7-yl)-4-(((1s,4S)-4-hydroxycyclohexyl)amino)pyridin-3-yl)-1,3,4-thiadiazol-2-yl)cyclohexyl)acetamide |
| 245 | 557.575 | 1 | N-((1S,4r)-4-(5-(6-(3-cyanopyrrolo[1,2-b]pyridazin-7-yl)-4-(((1S,3R)-3-hydroxycyclohexyl)amino)pyridin-3-yl)-1,3,4-thiadiazol-2-yl)cyclohexyl)acetamide |
| 246 | 485.515 | 1 | N-(3-(5-(6-(3-cyanopyrrolo[1,2-b]pyridazin-7-yl)-4-(isopropylamino)pyridin-3-yl)-1,3,4-thiadiazol-2-yl)bicyclo[1.1.1]pentan-1-yl)acetamide |
| 247 | 487.644 | 1 | N-((1S,3S)-3-(5-(6-(3-cyanopyrrolo[1,2-b]pyridazin-7-yl)-4-(isopropylamino)pyridin-3-yl)-1,3,4-thiadiazol-2-yl)cyclopentyl)acetamide |
| 248 | 487.635 | 1 | N-((1R,3S)-3-(5-(6-(3-cyanopyrrolo[1,2-b]pyridazin-7-yl)-4-(isopropylamino)pyridin-3-yl)-1,3,4-thiadiazol-2-yl)cyclopentyl)acetamide |
| 249 | 516.638 | 2 | N-((2S)-1-(5-(6-(3-cyanopyrrolo[1,2-b]pyridazin-7-yl)-4-(isopropylamino)pyridin-3-yl)-1,3,4-thiadiazol-2-yl)-2-methylpiperidin-4-yl)acetamide |
| 250 | 520.576 | 2 | N-((3S,4R)-1-(5-(6-(3-cyanopyrrolo[1,2-b]pyridazin-7-yl)-4-(isopropylamino)pyridin-3-yl)-1,3,4-thiadiazol-2-yl)-3-fluoropiperidin-4-yl)acetamide |
| 251 | 538.530 | 2 | N-(1-(5-(6-(3-cyanopyrrolo[1,2-b]pyridazin-7-yl)-4-(isopropylamino)pyridin-3-yl)-1,3,4-thiadiazol-2-yl)-3,3-difluoropiperidin-4-yl)acetamide |
| 252 | 459.349 | 2 | 7-(5-(5-(2-oxa-6-azaspiro[3.3]heptan-6-yl)-1,3,4-thiadiazol-2-yl)-4-(isopropylamino)pyridin-2-yl)pyrrolo[1,2-b]pyridazine-3-carbonitrile |
| 253 | 599.408 | 1 | methyl ((1r,4r)-4-(5-(6-(3-cyanopyrrolo[1,2-b]pyridazin-7-yl)-4-((4-hydroxybicyclo[2.2.2]octan-1-yl)amino)pyridin-3-yl)-1,3,4-thiadiazol-2-yl)cyclohexyl)carbamate |
| 254 | 637.421 | 2 | methyl (((1r,3r)-3-((5-(5-(4-acetamido-3,3-difluoropiperidin-1-yl)-1,3,4-thiadiazol-2-yl)-2-(3-cyanopyrrolo[1,2-b]pyridazin-7-yl)pyridin-4-yl)amino)cyclobutyl)methyl)carbamate |

-continued

| # | ES/MS m/z | Procedure | Name |
|---|---|---|---|
| 255 | 543.38 | 1 | N-((1r,4r)-4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)cyclohexyl)acetamide |
| 256 | 515.41 | 2 | 7-(5-(5-(8-oxa-3-azabicyclo[3.2.1]octan-3-yl)-1,3,4-thiadiazol-2-yl)-4-((tetrahydro-2H-pyran-4-yl)amino)pyridin-2-yl)pyrrolo[1,2-b]pyridazine-3-carbonitrile |
| 257 | 495.24 | 2 | 7-(5-(5-(1,1-dioxidothiomorpholino)-1,3,4-thiadiazol-2-yl)-4-(isopropylamino)pyridin-2-yl)pyrrolo[1,2-b]pyridazine-3-carbonitrile |
| 258 | 500.31 | 20 | 7-(5-(5-(6-acetyl-3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile |
| 259 | 514.36 | 2 | 7-(5-(5-(8-acetyl-3,8-diazabicyclo[3.2.1]octan-3-yl)-1,3,4-thiadiazol-2-yl)-4-(isopropylamino)pyridin-2-yl)pyrrolo[1,2-b]pyridazine-3-carbonitrile |
| 260 | 514.33 | 2 | 7-(5-(5-(3-acetyl-3,8-diazabicyclo[3.2.1]octan-8-yl)-1,3,4-thiadiazol-2-yl)-4-(isopropylamino)pyridin-2-yl)pyrrolo[1,2-b]pyridazine-3-carbonitrile |
| 261 | 500.30 | 20 | 7-(5-(5-(3-acetyl-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile |
| 262 | 494.22 | 2 | 7-(5-(5-(1-imino-1-oxido-1l6-thiomorpholino)-1,3,4-thiadiazol-2-yl)-4-(isopropylamino)pyridin-2-yl)pyrrolo[1,2-b]pyridazine-3-carbonitrile |
| 263 | 540.41 | 16 | 7-(5-(5-(8-(cyclopropanecarbonyl)-3,8-diazabicyclo[3.2.1]octan-3-yl)-1,3,4-thiadiazol-2-yl)-4-(isopropylamino)pyridin-2-yl)pyrrolo[1,2-b]pyridazine-3-carbonitrile |
| 264 | 542.34 | 2 | 7-(5-(5-(8-acetyl-3,8-diazabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile |
| 265 | 530.28 | 18 | 7-(5-(5-((1R,5S)-9-acetyl-3-oxa-7,9-diazabicyclo[3.3.1]nonan-7-yl)-1,3,4-thiadiazol-2-yl)-4-(isopropylamino)pyridin-2-yl)pyrrolo[1,2-b]pyridazine-3-carbonitrile |
| 266 | 530.42 | 2 | 7-(5-(5-((1R,5S)-7-acetyl-3-oxa-7,9-diazabicyclo[3.3.1]nonan-9-yl)-1,3,4-thiadiazol-2-yl)-4-(isopropylamino)pyridin-2-yl)pyrrolo[1,2-b]pyridazine-3-carbonitrile |
| 267 | 500.27 | 2 | 7-(5-(5-(5-acetyl-2,5-diazabicyclo[4.1.0]heptan-2-yl)-1,3,4-thiadiazol-2-yl)-4-(isopropylamino)pyridin-2-yl)pyrrolo[1,2-b]pyridazine-3-carbonitrile |
| 268 | 557.30 | 1 | N-((1r,4r)-4-(5-(6-(3-cyanopyrrolo[1,2-b]pyridazin-7-yl)-4-((4-methyltetrahydro-2H-pyran-4-yl)amino)pyridin-3-yl)-1,3,4-thiadiazol-2-yl)cyclohexyl)acetamide |
| 269 | 572.30 | 18 | 7-(5-(5-((1R,5S)-9-acetyl-3-oxa-7,9-diazabicyclo[3.3.1]nonan-7-yl)-1,3,4-thiadiazol-2-yl)-4-((tetrahydro-2H-pyran-4-yl)amino)pyridin-2-yl)pyrrolo[1,2-b]pyridazine-3-carbonitrile |
| 270 | 527.31 | 1 | N-(3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[1.1.1]pentan-1-yl)acetamide |
| 271 |  |  | tert-butyl 3-(5-(6-(3-cyanopyrrolo[1,2-b]pyridazin-7-yl)-4-(isopropylamino)pyridin-3-yl)-1,3,4-thiadiazol-2-yl)-3,6-diazabicyclo[3.1.1]heptane-6-carboxylate |
| 272 | 584.56 | 2 | N-((1R,5S,8s)-3-(5-(6-(3-cyanopyrrolo[1,2-b]pyridazin-7-yl)-4-((4-methyltetrahydro-2H-pyran-4-yl)amino)pyridin-3-yl)-1,3,4-thiadiazol-2-yl)-3-azabicyclo[3.2.1]octan-8-yl)acetamide |
| 273 | 544.37 | 19 | 7-(5-(5-(6-(2-hydroxy-2-methylpropanoyl)-3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile |
| 274 | 458.49 | 19 | 7-(5-(5-(3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile |
| 275 | 544.58 | 19 | 7-(5-(5-(3-(2-hydroxy-2-methylpropanoyl)-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile |

-continued

| # | ES/MS m/z | Procedure | Name |
|---|---|---|---|
| 276 | 591.31 | 19 | 7-(5-(5-(3-(2-(((dimethyl(oxo)-l6-sulfanylidene)amino)acetyl)-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile |
| 277 | 584.35 | 20 | 7-(4-(isopropylamino)-5-(5-(3-(4-methylpiperazine-1-carbonyl)-3,6-diazabicyclo[3.1.1]heptan-6-yl)-1,3,4-thiadiazol-2-yl)pyridin-2-yl)pyrrolo[1,2-b]pyridazine-3-carbonitrile |
| 278 | 473.39 | 14 | N-((1r,3r)-3-(5-(6-(3-cyanopyrrolo[1,2-b]pyridazin-7-yl)-4-(isopropylamino)pyridin-3-yl)-1,3,4-thiadiazol-2-yl)cyclobutyl)acetamide |
| 279 | 473.4 | 14 | N-((1s,3s)-3-(5-(6-(3-cyanopyrrolo[1,2-b]pyridazin-7-yl)-4-(isopropylamino)pyridin-3-yl)-1,3,4-thiadiazol-2-yl)cyclobutyl)acetamide |
| 280 | 527.66 | 14 | N-(4-(5-(6-(3-cyanopyrrolo[1,2-b]pyridazin-7-yl)-4-(isopropylamino)pyridin-3-yl)-1,3,4-thiadiazol-2-yl)bicyclo[2.2.2]octan-1-yl)acetamide |

Procedure 32: Example 281

N-((1s,3s)-3-(5-(6-(3-cyanopyrrolo[1,2-b]pyridazin-7-yl)-4-(isopropylamino)pyridin-3-yl)-1,3,4-thiadiazol-2-yl)cyclobutyl)cyclopropanecarboxamide (Example 281)

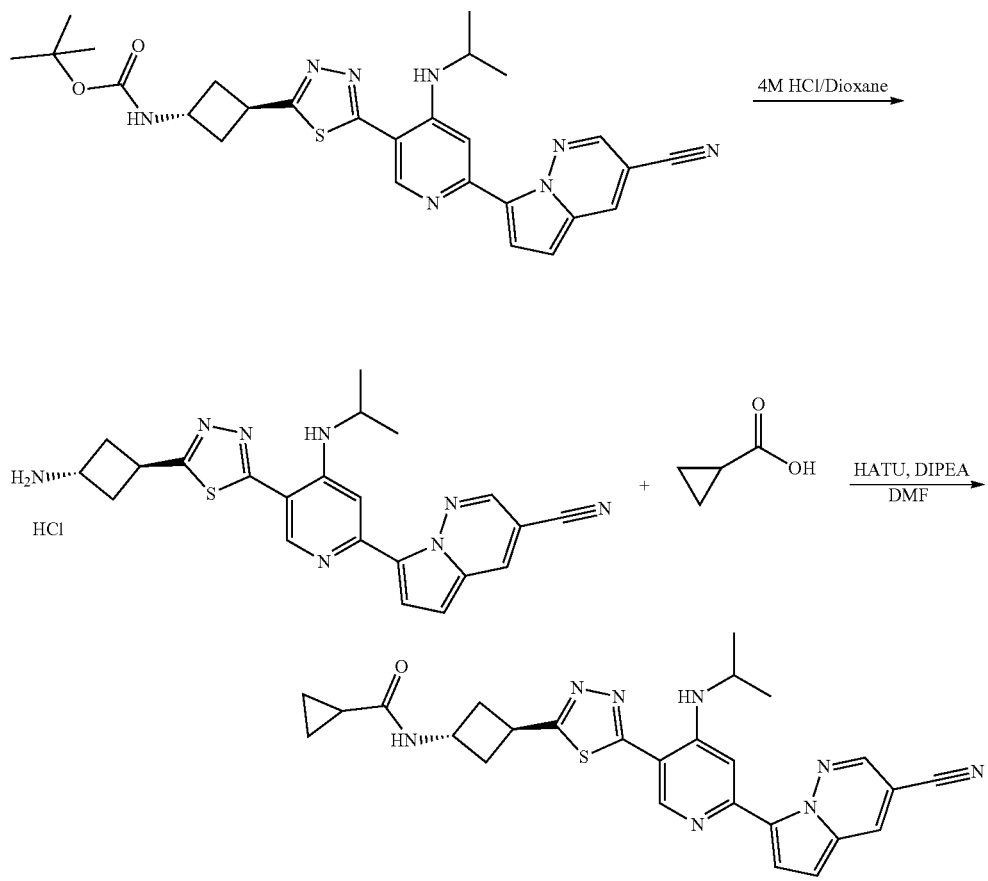

Example 281

7-(5-(5-((1r,3r)-3-aminocyclobutyl)-1,3,4-thiadiazol-2-yl)-4-(isopropylamino)pyridin-2-yl)pyrrolo[1,2-b]pyridazine-3-carbonitrile hydrochloride: tert-butyl ((1r,3r)-3-(5-(6-(3-cyanopyrrolo[1,2-b]pyridazin-7-yl)-4-(isopropylamino)pyridin-3-yl)-1,3,4-thiadiazol-2-yl)cyclobutyl)carbamate (150 mg, 0.28 mmol) was then dissolved in HCl (4.0M in dioxane, 2 mL, 8 mmol) and stirred at room temperature for 1 hour after which the reaction mixture was concentrated to dryness directly to give the desired product as an HCl salt which was used without further purification.

ES/MS: 431.3 [M+H]+

N-((1s,3s)-3-(5-(6-(3-cyanopyrrolo[1,2-b]pyridazin-7-yl)-4-(isopropylamino)pyridin-3-yl)-1,3,4-thiadiazol-2-yl)cyclobutyl)cyclopropanecarboxamide (Example 281): A flask of Cyclopropane carboxylic acid (12 mg, 0.14 mmol), DIPEA (39 mg, 0.3 mmol) and HATU (61.5 mg, 0.16 mmol) was dissolved in DMF (1 mL), 7-(5-(5-((1r,3r)-3-aminocyclobutyl)-1,3,4-thiadiazol-2-yl)-4-(isopropylamino)pyridin-2-yl)pyrrolo[1,2-b]pyridazine-3-carbonitrile hydrochloride (50 mg, 0.11 mmol) was added to the solution. It was stirred for 20 minutes. This mixture was filtered, and purified by RP-HPLC (eluent: water/MeCN*0.1% TFA) to yield the product Example 281 as a trifluoroacetate salt.

ES/MS: 499.4 [M+H+].

1H NMR (400 MHz, Methanol-d4) δ 8.68 (s, 1H), 8.57 (t, J=1.9 Hz, 2H), 8.05-7.91 (m, 2H), 7.17 (d, J=5.1 Hz, 1H), 4.64 (p, J=8.0 Hz, 1H), 4.18 (p, J=6.5 Hz, 1H), 4.02 (dt, J=9.5, 4.8 Hz, 1H), 2.78 (ddd, J=12.6, 7.6, 4.0 Hz, 2H), 2.67 (td, J=12.8, 11.2, 8.3 Hz, 2H), 1.49 (d, J=6.4 Hz, 7H), 0.87 (p, J=4.2 Hz, 2H), 0.74 (dq, J=7.4, 4.3, 3.9 Hz, 2H).

Example 282 was made according to Procedure 14, using the appropriate starting materials and protecting group chemistry as needed:

| # | ES/MS m/z | Procedure | Name |
|---|---|---|---|
| 282 | 445.29 | 14 | N-((1r,3r)-3-(5-(6-(3-cyanopyrrolo[1,2-b]pyridazin-7-yl)-4-(methylamino)pyridin-3-yl)-1,3,4-thiadiazol-2-yl)cyclobutyl)acetamide |

Procedure 33: Example 283

7-(4-(isopropylamino)-5-(5-((1r,3r)-3-(oxetan-3-ylamino)cyclobutyl)-1,3,4-thiadiazol-2-yl)pyridin-2-yl)pyrrolo[1,2-b]pyridazine-3-carbonitrile (Example 283)

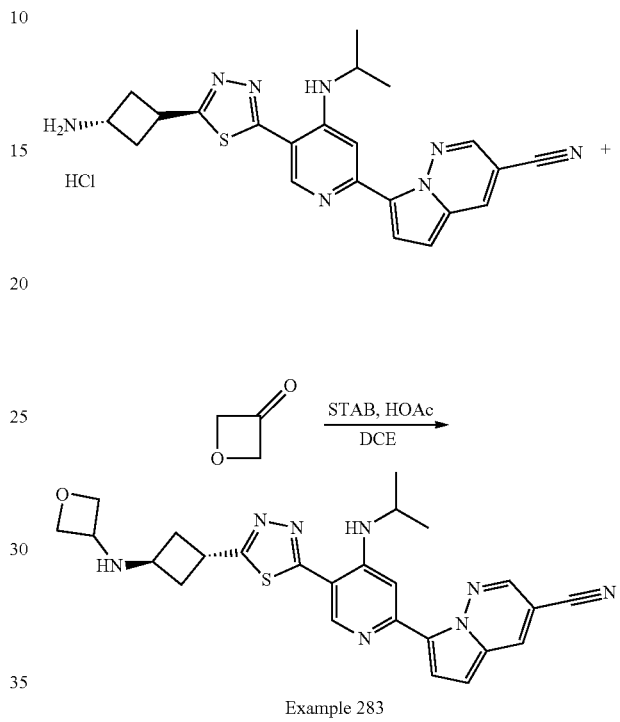

Example 283

7-[4-(isopropylamino)-5-[5-[rac-(2R)-2-(aminomethyl)pyrrolidine-1-carbonyl]-1,3,4-thiadiazol-2-yl]-2-pyridyl]pyrrolo[1,2-b]pyridazine-3-carbonitrile (Example 283): To a solution of 7-(5-(5-((1r,3r)-3-aminocyclobutyl)-1,3,4-thiadiazol-2-yl)-4-(isopropylamino)pyridin-2-yl)pyrrolo[1,2-b]pyridazine-3-carbonitrile hydrochloride (30 mg, 0.064 mmol), oxetan-3-one (32.4 mg, 0.45 mmol) in 1 mL of DCE and 1 mL of acetic acid, sodium triacetoxy borohydride (95.3 mg, 0.45 mmol) was added to the suspension. It was stirred for overnight. Oxetan-3-one (32.4 mg, 0.45 mmol) and sodium triacetoxy borohydride (95.3 mg, 0.45 mmol) was added to the mixture. After 5 hours, diluted with EtOAc (20 mL) and washed with 10 mL of saturated NaHCO3. The organic layer was dried and concentrated. This mixture was filtered, and purified by RP-HPLC (eluent: water/MeCN*0.1% TFA) to yield the product Example 283 as a trifluoroacetate salt. ES/MS: 487.6 [M+H+].

1H NMR (400 MHz, Methanol-d4) δ 8.76 (d, J=2.2 Hz, 1H), 8.72 (s, 1H), 8.67 (d, J=2.2 Hz, 1H), 8.07 (d, J=5.1 Hz, 1H), 7.99 (s, 1H), 7.23 (d, J=5.1 Hz, 1H), 4.93 (t, J=7.5 Hz, 2H), 4.68 (dd, J=8.0, 5.2 Hz, 2H), 4.44 (h, J=6.1, 5.6 Hz, 1H), 4.31 (p, J=6.6 Hz, 1H), 4.23 (q, J=6.9 Hz, 1H), 4.20-4.09 (m, 1H), 2.89 (t, J=7.5 Hz, 4H), 1.48 (d, J=6.4 Hz, 6H).

The following compounds were made according to the previous procedures, using the appropriate starting materials and protecting group chemistry as needed:

| # | ES/MS m/z | Procedure | Name |
|---|---|---|---|
| 284 | 513.48 | 14 | N-(4-(5-(6-(3-cyanopyrrolo[1,2-b]pyridazin-7-yl)-4-(isopropylamino)pyridin-3-yl)-1,3,4-thiadiazol-2-yl)bicyclo[2.2.1]heptan-1-yl)acetamide |
| 285 | 513.5 | 14 | N-(5-(5-(6-(3-cyanopyrrolo[1,2-b]pyridazin-7-yl)-4-(isopropylamino)pyridin-3-yl)-1,3,4-thiadiazol-2-yl)bicyclo[2.2.1]heptan-2-yl)acetamide |
| 286 | 447.36 | 2 | 7-(5-(5-(3-hydroxy-3-methylazetidin-1-yl)-1,3,4-thiadiazol-2-yl)-4-(isopropylamino)pyridin-2-yl)pyrrolo[1,2-b]pyridazine-3-carbonitrile |
| 287 | 475.4 | 2 | 7-(5-(5-(4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile |
| 288 | 499.34 | 14 | N-(4-(5-(6-(3-cyanopyrrolo[1,2-b]pyridazin-7-yl)-4-(isopropylamino)pyridin-3-yl)-1,3,4-thiadiazol-2-yl)bicyclo[2.1.1]hexan-1-yl)acetamide |
| 289 | 487.55 | 14 | N-(((1s,3s)-3-(5-(6-(3-cyanopyrrolo[1,2-b]pyridazin-7-yl)-4-(isopropylamino)pyridin-3-yl)-1,3,4-thiadiazol-2-yl)cyclobutyl)methyl)acetamide |
| 290 | 487.54 | 14 | N-(((1r,3r)-3-(5-(6-(3-cyanopyrrolo[1,2-b]pyridazin-7-yl)-4-(isopropylamino)pyridin-3-yl)-1,3,4-thiadiazol-2-yl)cyclobutyl)methyl)acetamide |
| 291 | 471.584 | 2 | 7-(5-(5-(3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile |
| 292 | 500.370 | 2 | N-((1R,5S,8s)-3-(5-(6-(3-cyanopyrrolo[1,2-b]pyridazin-7-yl)-4-(methylamino)pyridin-3-yl)-1,3,4-thiadiazol-2-yl)-3-azabicyclo[3.2.1]octan-8-yl)acetamide |
| 293 | 459.370 | 2 | 7-(5-(5-(1-oxa-6-azaspiro[3.3]heptan-6-yl)-1,3,4-thiadiazol-2-yl)-4-(isopropylamino)pyridin-2-yl)pyrrolo[1,2-b]pyridazine-3-carbonitrile |
| 294 | 481.571 | 2 | 7-(5-(5-(4,4-difluoropiperidin-1-yl)-1,3,4-thiadiazol-2-yl)-4-(isopropylamino)pyridin-2-yl)pyrrolo[1,2-b]pyridazine-3-carbonitrile |
| 295 | 485.636 | 2 | 7-(5-(5-(3-azabicyclo[3.3.1]nonan-3-yl)-1,3,4-thiadiazol-2-yl)-4-(isopropylamino)pyridin-2-yl)pyrrolo[1,2-b]pyridazine-3-carbonitrile |
| 296 | 502.399 | 2 | (R)-N-(1-(5-(6-(3-cyanopyrrolo[1,2-b]pyridazin-7-yl)-4-(isopropylamino)pyridin-3-yl)-1,3,4-thiadiazol-2-yl)piperidin-3-yl)acetamide |
| 297 | 501.294 | 2 | 7-(5-(5-(3-hydroxy-3-(trifluoromethyl)azetidin-1-yl)-1,3,4-thiadiazol-2-yl)-4-(isopropylamino)pyridin-2-yl)pyrrolo[1,2-b]pyridazine-3-carbonitrile |
| 298 | 516.461 | 2 | N-(1-(5-(6-(3-cyanopyrrolo[1,2-b]pyridazin-7-yl)-4-(isopropylamino)pyridin-3-yl)-1,3,4-thiadiazol-2-yl)azepan-4-yl)acetamide |
| 299 | 502.535 | 2 | (S)-N-(1-(5-(6-(3-cyanopyrrolo[1,2-b]pyridazin-7-yl)-4-(isopropylamino)pyridin-3-yl)-1,3,4-thiadiazol-2-yl)piperidin-3-yl)acetamide |
| 300 | 542.388 | 2 | N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-N-methylacetamide |
| 301 | 556.449 | 2 | 7-(4-(isopropylamino)-5-(5-((1R,5S,8s)-8-(2-oxooxazolidin-3-yl)-3-azabicyclo[3.2.1]octan-3-yl)-1,3,4-thiadiazol-2-yl)pyridin-2-yl)pyrrolo[1,2-b]pyridazine-3-carbonitrile |
| 302 | 500.352 | 2 | 7-(5-(5-((1S,4S)-5-acetyl-2,5-diazabicyclo[2.2.1]heptan-2-yl)-1,3,4-thiadiazol-2-yl)-4-(isopropylamino)pyridin-2-yl)pyrrolo[1,2-b]pyridazine-3-carbonitrile |
| 303 | 500.367 | 2 | 7-(5-(5-((1R,4R)-5-acetyl-2,5-diazabicyclo[2.2.1]heptan-2-yl)-1,3,4-thiadiazol-2-yl)-4-(isopropylamino)pyridin-2-yl)pyrrolo[1,2-b]pyridazine-3-carbonitrile |
| 304 | 502.364 | 2 | 7-(4-(isopropylamino)-5-(5-(4-(oxetan-3-yl)piperazin-1-yl)-1,3,4-thiadiazol-2-yl)pyridin-2-yl)pyrrolo[1,2-b]pyridazine-3-carbonitrile |
| 305 | 502.319 | 2 | 1-(5-(6-(3-cyanopyrrolo[1,2-b]pyridazin-7-yl)-4-(isopropylamino)pyridin-3-yl)-1,3,4-thiadiazol-2-yl)-N-methylpiperidine-4-carboxamide |
| 306 | 510.262 | 2 | (R)-N-(1-(5-(6-(3-cyanopyrrolo[1,2-b]pyridazin-7-yl)-4-(methylamino)pyridin-3-yl)-1,3,4-thiadiazol-2-yl)-3,3-difluoropiperidin-4-yl)acetamide |
| 307 | 510.267 | 2 | (S)-N-(1-(5-(6-(3-cyanopyrrolo[1,2-b]pyridazin-7-yl)-4-(methylamino)pyridin-3-yl)-1,3,4-thiadiazol-2-yl)-3,3-difluoropiperidin-4-yl)acetamide |
| 308 | 564.424 | 2 | 7-(4-(isopropylamino)-5-(5-((1R,5S,8s)-8-(pyrimidin-2-ylamino)-3-azabicyclo[3.2.1]octan-3-yl)-1,3,4-thiadiazol-2-yl)pyridin-2-yl)pyrrolo[1,2-b]pyridazine-3-carbonitrile |
| 309 | 581.515 | 2 | 7-(5-(5-((1R,5S,8s)-8-((3-fluoropyridin-2-yl)amino)-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile |

-continued

| # | ES/MS m/z | Procedure | Name |
|---|---|---|---|
| 310 | 470.377 | 2 | 7-(5-(5-(4-cyanopiperidin-1-yl)-1,3,4-thiadiazol-2-yl)-4-(isopropylamino)pyridin-2-yl)pyrrolo[1,2-b]pyridazine-3-carbonitrile |
| 311 | 559.450 | 1 | N-((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)-2-hydroxy-2-methylpropanamide |
| 312 | 545.697 | 1 | N-((1s,4s)-4-(5-(6-(3-cyanopyrrolo[1,2-b]pyridazin-7-yl)-4-(isopropylamino)pyridin-3-yl)-1,3,4-thiadiazol-2-yl)cyclohexyl)-2-hydroxy-2-methylpropanamide |
| 313 | 499.585 | 18 | N-(4-(5-(6-(3-cyanopyrrolo[1,2-b]pyridazin-7-yl)-4-(isopropylamino)pyridin-3-yl)-1,3,4-thiadiazol-2-yl)cyclohex-3-en-1-yl)acetamide |

Procedure 34: Example 314

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-methyloxetane-3-carboxamide (Example 314)

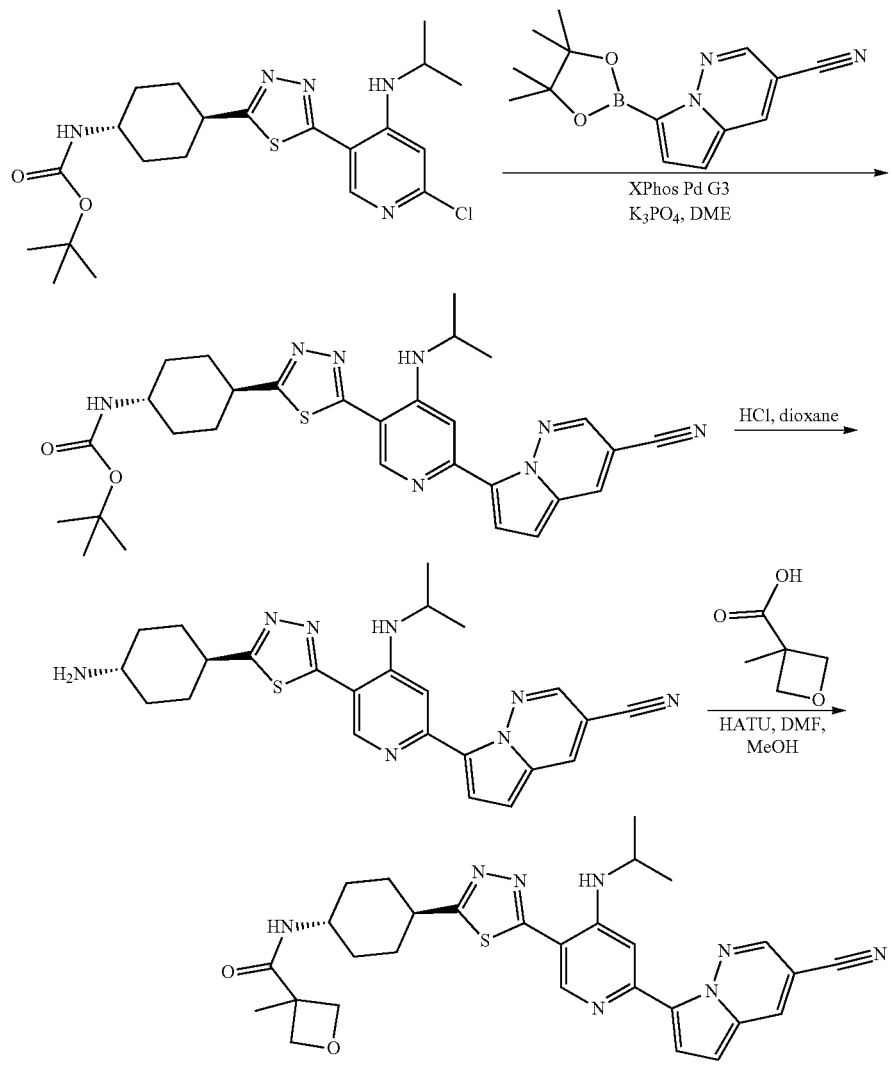

Example 314

Tert-butyl ((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)carbamate: To a slurry of tert-butyl ((1r,4r)-4-(5-(6-chloro-4-(isopropylamino)pyridin-3-yl)-1,3,4-thiadiazol-2-yl)cyclohexyl)carbamate (prepared following the protocol in steps 1 and 2 of Procedure 14 using the appropriate carboxylic acid) (89 mg, 0.20 mmol) in DME (3 mL) was added 7-(4,4,5,5-tetramethyl-1,3,2-dioxaborolan-2-yl)pyrrolo[1,2-b]pyridazine-3-carbonitrile (85 mg, 0.32 mmol), XPhos Pd G3 (12 mg, 0.15 mmol) and aqueous potassium phosphate, tribasic (2M, 0.2 mL, 0.4 mmol). The resulting mixture was degassed with argon for 2 min, sealed, and heated in a microwave at 120° C. for 20 min. The resulting slurry was diluted with Et$_2$O, filtered, and washed with Et$_2$O. The resulting solid was purified by silica gel chromatography (eluent: MeOH/CH$_2$Cl$_2$) to give the desired product.
ES/MS: 559.605 [M+H]$^+$ 7-(5-(5-(((1R,4R)-4-aminocyclohexyl)-1,3,4-thiadiazol-2-yl)-4-(isopropylamino)pyridin-2-yl)pyrrolo[1,2-b]pyridazine-3-carbonitrile: To a solution of tert-butyl ((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)carbamate (75 mg, 0.13 mmol) in CH$_2$Cl$_2$ (2.5 mL) was added solution of hydrochloric acid in dioxane (4M, 0.5 mL, 2 mmol). The resulting slurry was stirred at 50° C. for 1 hour. Additional hydrochloric acid in dioxane (4M, 0.5 mL, 2 mmol) and methanol (0.5 mL) was added and the solution was stirred at 50° C. for 2 hours, followed by stirring at room temperature for 18 hours. The reaction mixture was concentrated and the crude product was used directly in the next step.
ES/MS: 459.622 [M+H]$^+$ N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-methyloxetane-3-carboxamide (Example 314): To a slurry of 7-(5-(5-(((1R,4R)-4-aminocyclohexyl)-1,3,4-thiadiazol-2-yl)-4-(isopropylamino)pyridin-2-yl)pyrrolo[1,2-b]pyridazine-3-carbonitrile in DMF (0.8 mL) and MeOH (0.5 mL) was added N,N-diisopropylethylamine (0.06 mL, 0.34 mmol), 3-[2-[2-[2-(tert-butoxycarbonylamino)ethoxy]ethoxy]ethoxy]propanoic acid (18 mg, 0.056 mmol), and HATU (20 mg, 0.053 mmol). The solution was stirred at room temperature for 16 hours and concentrated. The crude material was dissolved in DMF and purified by RP-HPLC (eluent: water/MeCN*0.1% TFA) to yield the product Example 314 as a trifluoroacetate salt.
ES/MS: 557.537 [M+H]$^+$
1H NMR (400 MHz, Methanol-d4) δ 8.79 (d, J=2.2 Hz, 1H), 8.74 (s, 1H), 8.71 (d, J=2.1 Hz, 1H), 8.10 (d, J=5.1 Hz, 1H), 7.97 (s, 1H), 7.88 (d, J=7.8 Hz, 1H), 7.26 (d, J=5.1 Hz, 1H), 4.42 (d, J=6.1 Hz, 2H), 4.34 (p, J=6.4 Hz, 1H), 3.93-3.77 (m, 1H), 2.35 (d, J=13.0 Hz, 2H), 2.12 (d, J=12.6 Hz, 2H), 1.84 (qd, J=13.1, 3.4 Hz, 3H), 1.62 (s, 3H), 1.51 (d, J=6.4 Hz, 8H). Additional peak obscured by solvent.

Example 315 was made according to Procedure 34, using the appropriate starting materials and protecting group chemistry as needed:

| # | ES/MS m/z | Procedure | Name |
|---|---|---|---|
| 315 | 545.530 | 34 | N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-2-hydroxy-2-methylpropanamide |

Procedure 35: Example 316

N-((1R,4r)-4-(5-(4-(((R)-1-cyanoethyl)amino)-6-(3-cyanopyrrolo[1,2-b]pyridazin-7-yl)pyridin-3-yl)-1,3,4-thiadiazol-2-yl)cyclohexyl)acetamide (Example 316)

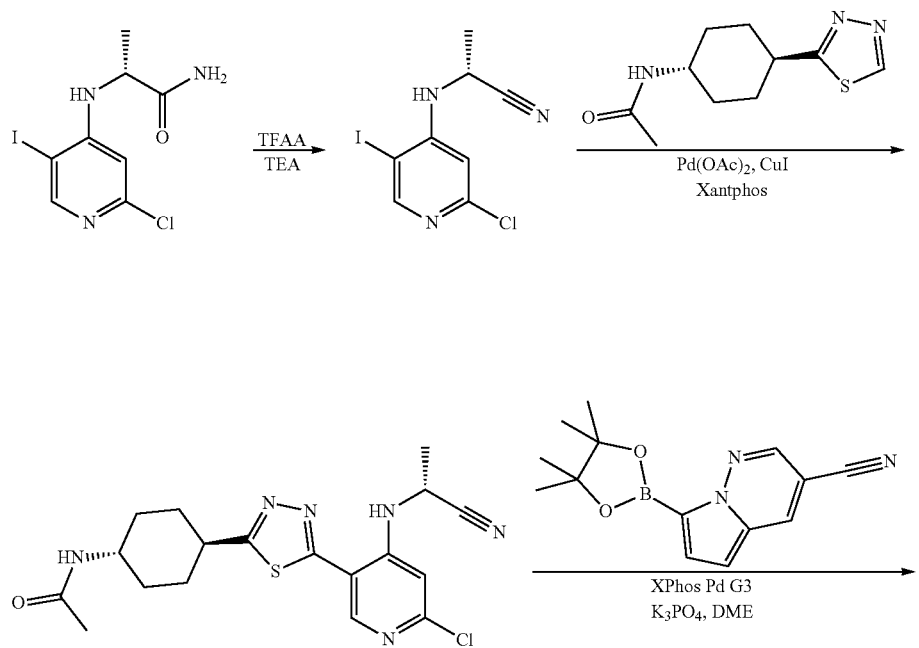

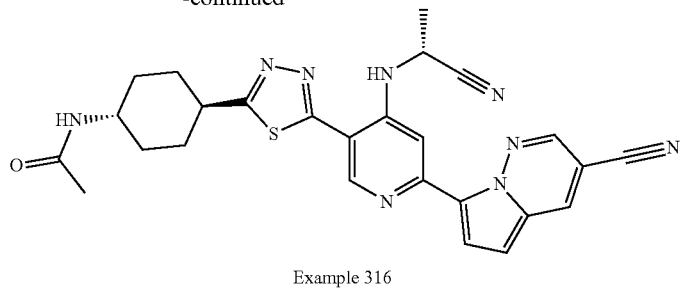

Example 316

(R)-2-((2-chloro-5-iodopyridin-4-yl)amino)propanenitrile: To a solution of (R)-2-((2-chloro-5-iodopyridin-4-yl)amino)propanamide (10.1 g, 30 mmol) in methyl-THF (165 mL) was added trimethylamine (21 mL, 154 mmol). To the slurry was slowly added trifluoroacetic anhydride (1.15 mL, 8.27 mmol) in methyl-THF (10 mL) over 15 min. The resulting solution is stirred at room temperature for 45 min before dilution with H$_2$O and washing with aqueous NH$_4$Cl. The aqueous layers are back-extracted with ethyl acetate and the combine organic layers are dried over MgSO$_4$ and concentrated to dryness. The crude material was dissolved in hot ethyl acetate, to which hexanes was added until precipitation initiated. The solution was allowed to cool to room temperature for 18 hours and the resulting precipitate was filtered and washed with hexanes to provide the desired product.
ES/MS: 308.052 [M+H]$^+$ N-((1R,4r)-4-(5-(6-chloro-4-(((R)-1-cyanoethyl)amino)pyridin-3-yl)-1,3,4-thiadiazol-2-yl)cyclohexyl)acetamide: To a solution of (R)-2-((2-chloro-5-iodopyridin-4-yl)amino)propanenitrile (80 mg, 0.26 mmol) in dioxane (3.3 mL) was added N-((1r,4r)-4-(1,3,4-thiadiazol-2-yl)cyclohexyl)acetamide (62 mg, 0.27 mmol), Palladium acetate (9 mg, 0.04 mmol), 9,9-Dimethyl-4,5-bis(diphenylphosphino)xanthene (50 mg, 0.08 mmol), Copper(i) iodide (20 mg, 0.08 mmol), and cesium carbonate (108 mg, 0.33 mmol). The reaction mixture was degassed with argon for 3 min, sealed, and heated to 100° C. for 1.5 hours. The reaction mixture was purified by RP-HPLC (eluent: water/MeCN*0.1% TFA) to yield the desired product as a trifluoroacetate salt.
ES/MS: 405.213 [M+H]$^+$ N-((1R,4r)-4-(5-(4-(((R)-1-cyanoethyl)amino)-6-(3-cyanopyrrolo[1,2-b]pyridazin-7-yl)pyridin-3-yl)-1,3,4-thiadiazol-2-yl)cyclohexyl)acetamide (Example 316): To a solution of N-((1R,4r)-4-(5-(6-chloro-4-(((R)-1-cyanoethyl)amino)pyridin-3-yl)-1,3,4-thiadiazol-2-yl)cyclohexyl)acetamide (6 mg, 0.012 mmol) in DME (0.5 mL) was added 7-(4,4,5,5-tetramethyl-1,3,2-dioxaborolan-2-yl)pyrrolo[1,2-b]pyridazine-3-carbonitrile (6 mg, 0.023 mmol), XPhos Pd G3 (3 mg, 0.0035 mmol) and aqueous potassium phosphate, tribasic (2M, 0.023 mL, 0.01 mmol). The resulting mixture was degassed with argon for 2 min, sealed, and heated in a microwave at 120° C. for 15 min. The reaction mixture was diluted with DMF and purified by RP-HPLC (eluent: water/MeCN*0.1% TFA) to yield the product Example 316 as a trifluoroacetate salt.
ES/MS: 512.397 [M+H]$^+$
1H NMR (400 MHz, Methanol-d4) δ 8.83 (s, 1H), 8.73 (d, J=2.1 Hz, 1H), 8.67 (d, J=2.1 Hz, 1H), 8.23 (s, 1H), 8.08 (d, J=5.0 Hz, 1H), 7.22 (d, J=5.1 Hz, 1H), 5.20 (q, J=6.9 Hz, 1H), 3.75 (ddq, J=12.1, 7.8, 4.2 Hz, 1H), 2.31 (d, J=13.2 Hz, 1H), 2.09 (d, J=12.3 Hz, 2H), 1.94 (s, 3H), 1.91 (d, J=6.9 Hz, 3H), 1.80 (qd, J=12.7, 2.4 Hz, 3H), 1.47 (qd, J=12.9, 12.4, 2.9 Hz, 3H).

Procedure 36: Example 317

7-(5-(5-(3-hydroxy-3-(methyl-d3)butyl-4,4,4-d3)-1,3,4-thiadiazol-2-yl)-4-(isopropylamino)pyridin-2-yl)pyrrolo[1,2-b]pyridazine-3-carbonitrile (Example 317)

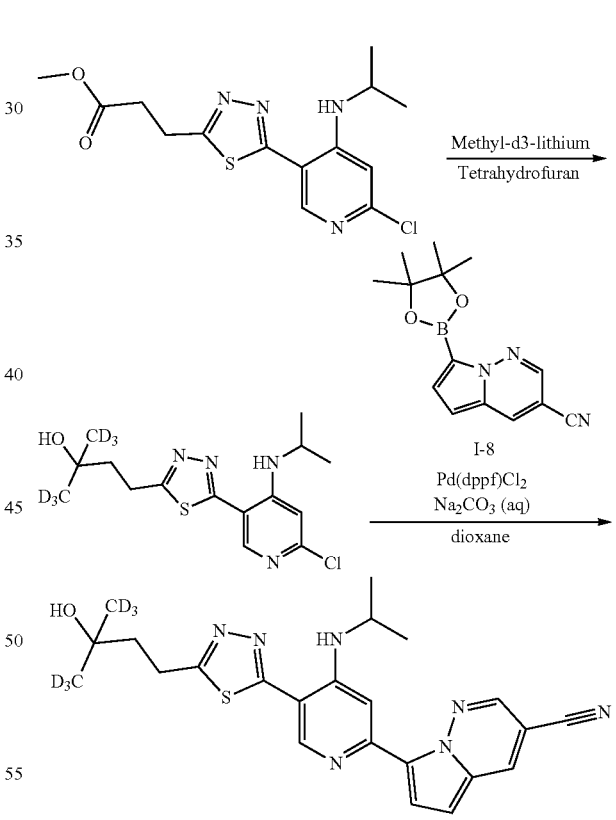

Example 317

4-(5-(6-chloro-4-(isopropylamino)pyridin-3-yl)-1,3,4-thiadiazol-2-yl)-2-(methyl-d3)butan-1,1,1-d3-2-ol: To a flask with methyl 3-(5-(6-chloro-4-(isopropylamino)pyridin-3-yl)-1,3,4-thiadiazol-2-yl)propanoate (100 mg, 0.29 mmol) under N$_2$ was added THF (2 mL), and the reaction was cooled to 0° C. To the reaction was added Methyl-d3-lithium, as complex with lithium iodide solution (117 mg, 0.73 mmol) dropwise, and the reaction was stirred for 30 min at 0° C. Afterward, the reaction was quenched by dropwise addition of saturated aqueous NH$_4$Cl, and the mixture was diluted with EtOAc and water. The layers were separated, and the aqueous layer was washed once with EtOAc. The combined organic layers were dried over MgSO$_4$, filtered and concentrated. The resulting crude residue was purified by silica gel chromatography (eluent: EtOAc/hexanes) to give the desired product.
ES/MS: 347.27[M+H]$^+$ 7-(5-(5-(3-hydroxy-3-(methyl-d3)butyl-4,4,4-d3)-1,3,4-thiadiazol-2-yl)-4-(isopropylamino)pyridin-2-yl)pyrrolo[1,2-b]pyridazine-3-carbonitrile (Example 317): Coupling performed as in Procedure 9 to yield the product Example 317 as a trifluoroacetate salt.
ES/MS: 454.59 (M+H$^+$)
1H NMR (400 MHz, Methanol-d4) δ 8.81-8.62 (m, 3H), 8.07 (d, J=5.1 Hz, 1H), 7.95 (s, 1H), 7.23 (d, J=5.1 Hz, 1H), 4.31 (hept, J=6.3 Hz, 1H), 3.33 (d, J=6.0 Hz, 2H), 2.12-1.97 (m, 2H), 1.49 (d, J=6.4 Hz, 6H).

Example 318 was made according to Procedure 9, using the appropriate starting materials and protecting group chemistry as needed:

| # | ES/MS m/z | Procedure | Name |
|---|---|---|---|
| 318 | 448.53 | 9 | ethyl 2-(5-(6-(3-cyanopyrrolo[1,2-b]pyridazin-7-yl)-4-(isopropylamino)pyridin-3-yl)-1,3,4-thiadiazol-2-yl)acetate |

Procedure 37: Example 319

2-(5-(6-(3-cyanopyrrolo[1,2-b]pyridazin-7-yl)-4-(isopropylamino)pyridin-3-yl)-1,3,4-thiadiazol-2-yl) acetic acid (Example 319)

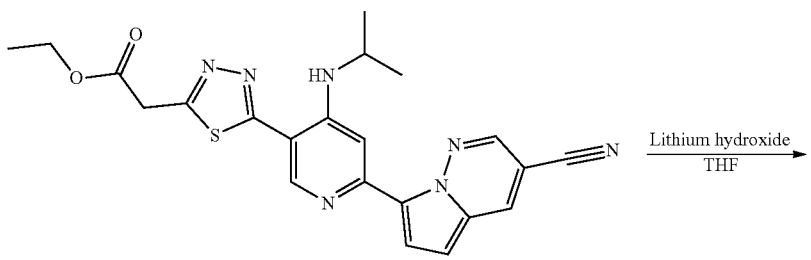

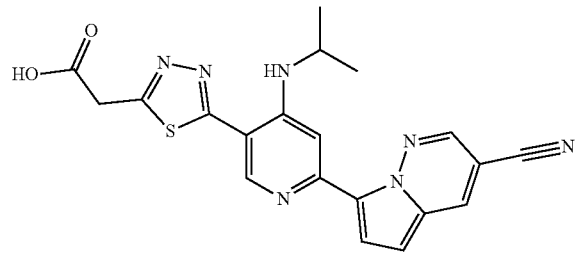

Example 319

2-(5-(6-(3-cyanopyrrolo[1,2-b]pyridazin-7-yl)-4-(isopropylamino)pyridin-3-yl)-1,3,4-thiadiazol-2-yl)acetic acid (Example 319): To ethyl 2-(5-(6-(3-cyanopyrrolo[1,2-b]pyridazin-7-yl)-4-(isopropylamino)pyridin-3-yl)-1,3,4-thiadiazol-2-yl)acetate (10 mg, 0.022 mmol) in THF (0.5 mL) was added lithium hydroxide (3 mg, 0.125 mmol). The reaction mixture was stirred at RT for 6 hours then directly purified by RP-HPLC (eluent: water/MeCN*0.1% TFA) to yield the product Example 319 as a trifluoroacetate salt.
ES/MS: 420.19 (M+H$^+$)
1H NMR (400 MHz, Methanol-d4) δ 9.58 (s, 1H), 8.87-8.74 (m, 2H), 8.68 (d, J=2.1 Hz, 1H), 8.13-7.92 (m, 2H), 7.22 (d, J=5.1 Hz, 1H), 4.42-4.25 (m, 1H), 2.99 (s, 1H), 2.86 (d, J=0.8 Hz, 1F1), 1.49 (dd, J=6.4, 4.8 Hz, 6H).

Procedure 38: Example 320

7-(5-(5-(2-hydroxy-2-methylpropyl)-1,3,4-thiadiazol-2-yl)-4-(isopropylamino)pyridin-2-yl)pyrrolo[1,2-b]pyridazine-3-carbonitrile (Example 320)

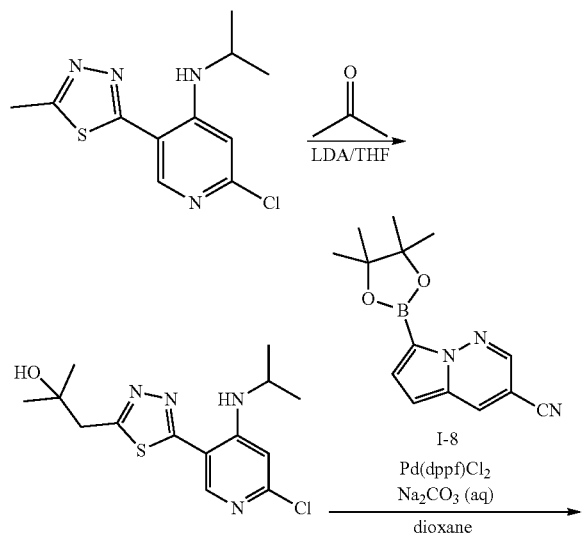

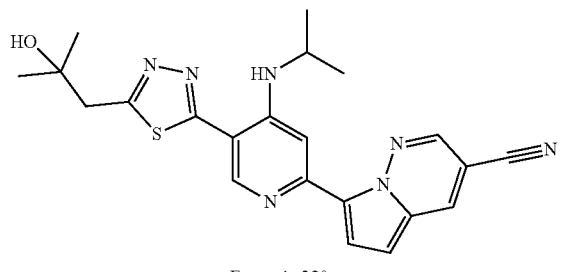

Example 320

1-(5-(6-chloro-4-(isopropylamino)pyridin-3-yl)-1,3,4-thiadiazol-2-yl)-2-methylpropan-2-ol Ethyl (60 mg, 0.22 mmol) in THF (1 mL) was added lithium diisopropylamide (2.0M THF, 0.56 mmol). The temperature was maintained in the range of −70° C. to −78° C. throughout the 15 minute addition. Following the addition, the resulting slurry was stirred for 2 hours at ambient temperature then directly purified by RP-HPLC (eluent: water/MeCN*0.1% TFA) to yield the product 7-(5-(5-(2-hydroxy-2-methylpropyl)-1,3,4-thiadiazol-2-yl)-4-(isopropylamino)pyridin-2-yl)pyrrolo[1,2-b]pyridazine-3-carbonitrile (Example 320): Coupling performed as in Procedure 9 to yield the product Example 320 as a trifluoroacetate salt.

ES/MS: 434.36 (M+H$^+$)
1H NMR (400 MHz, Methanol-d4) δ 8.82-8.74 (m, 2H), 8.68 (d, J=2.2 Hz, 1H), 8.08 (d, J=5.1 Hz, 1H), 7.95 (d, J=1.9 Hz, 1H), 7.23 (d, J=5.0 Hz, 1H), 4.38-4.25 (m, 1H), 3.34 (s, 2H), 1.73 (s, 1H), 1.49 (dd, J=6.5, 2.4 Hz, 6H), 1.31 (s, 5H).

The following compounds were made according to the previous procedures, using the appropriate starting materials and protecting group chemistry as needed:

| #   | ES/MS m/z | Procedure | Name |
|-----|-----------|-----------|------|
| 321 | 401.33    | 9 | 7-(5-(5-(cyanomethyl)-1,3,4-thiadiazol-2-yl)-4-(isopropylamino)pyridin-2-yl)pyrrolo[1,2-b]pyridazine-3-carbonitrile |
| 322 | 432.35    | 9 | 7-(4-(isopropylamino)-5-(5-(tetrahydrofuran-3-yl)-1,3,4-thiadiazol-2-yl)pyridin-2-yl)pyrrolo[1,2-b]pyridazine-3-carbonitrile |
| 323 | 514.32    | 2 | (R)-N-(5-(5-(6-(3-cyanopyrrolo[1,2-b]pyridazin-7-yl)-4-(isopropylamino)pyridin-3-yl)-1,3,4-thiadiazol-2-yl)-5-azaspiro[2.4]heptan-7-yl)acetamide |
| 324 | 514.32    | 2 | (S)-N-(5-(5-(6-(3-cyanopyrrolo[1,2-b]pyridazin-7-yl)-4-(isopropylamino)pyridin-3-yl)-1,3,4-thiadiazol-2-yl)-5-azaspiro[2.4]heptan-7-yl)acetamide |
| 325 | 428.2     | 2 | 7-(5-(5-(1H-pyrazol-1-yl)-1,3,4-thiadiazol-2-yl)-4-(isopropylamino)pyridin-2-yl)pyrrolo[1,2-b]pyridazine-3-carbonitrile |
| 326 | 468.26    | 2 | 7-(5-(5-(4-cyclopropyl-1H-imidazol-1-yl)-1,3,4-thiadiazol-2-yl)-4-(isopropylamino)pyridin-2-yl)pyrrolo[1,2-b]pyridazine-3-carbonitrile |
| 327 | 524.3     | 2 | N-(1-(5-(6-(3-cyanopyrrolo[1,2-b]pyridazin-7-yl)-4-(isopropylamino)pyridin-3-yl)-1,3,4-thiadiazol-2-yl)-4,4-difluoropyrrolidin-3-yl)acetamide |
| 328 | 522.26    | 2 | 7-(5-(5-(3-(3,3-difluoropyrrolidin-1-yl)azetidin-1-yl)-1,3,4-thiadiazol-2-yl)-4-(isopropylamino)pyridin-2-yl)pyrrolo[1,2-b]pyridazine-3-carbonitrile |

-continued

| # | ES/MS m/z | Procedure | Name |
|---|---|---|---|
| 329 | 461.27 | 2 | (S)-7-(5-(5-(2-(hydroxymethyl)pyrrolidin-1-yl)-1,3,4-thiadiazol-2-yl)-4-(isopropylamino)pyridin-2-yl)pyrrolo[1,2-b]pyridazine-3-carbonitrile |
| 330 | 488.28 | 2 | (R)-N-(1-(5-(6-(3-cyanopyrrolo[1,2-b]pyridazin-7-yl)-4-(isopropylamino)pyridin-3-yl)-1,3,4-thiadiazol-2-yl)pyrrolidin-3-yl)acetamide |
| 331 | 488.28 | 2 | (S)-N-(1-(5-(6-(3-cyanopyrrolo[1,2-b]pyridazin-7-yl)-4-(isopropylamino)pyridin-3-yl)-1,3,4-thiadiazol-2-yl)pyrrolidin-3-yl)acetamide |
| 332 | 503.22 | 2 | (S)-1-(5-(6-(3-cyanopyrrolo[1,2-b]pyridazin-7-yl)-4-(oxetan-3-ylamino)pyridin-3-yl)-1,3,4-thiadiazol-2-yl)-N-methylpyrrolidine-2-carboxamide |
| 333 | 468.28 | 1 | 7-(5-(5-(4-cyanocyclohexyl)-1,3,4-thiadiazol-2-yl)-4-(isopropylamino)pyridin-2-yl)pyrrolo[1,2-b]pyridazine-3-carbonitrile |
| 334 | 513.23 | 1 | N-(4-(5-(6-(3-cyanopyrrolo[1,2-b]pyridazin-7-yl)-4-(oxetan-3-ylamino)pyridin-3-yl)-1,3,4-thiadiazol-2-yl)bicyclo[2.1.1]hexan-1-yl)acetamide |
| 335 | 557.39 | 1 | N-(4-(5-(6-(3-cyanopyrrolo[1,2-b]pyridazin-7-yl)-4-(oxetan-3-ylamino)pyridin-3-yl)-1,3,4-thiadiazol-2-yl)bicyclo[2.1.1]hexan-1-yl)-2-hydroxy-2-methylpropanamide |

Procedure 39: Example 336

7-(5-(5-(4-aminobicyclo[2.2.2]octan-1-yl)-1,3,4-thiadiazol-2-yl)-4-((tetrahydro-2H-pyran-4-yl)amino)pyridin-2-yl)pyrrolo[1,2-b]pyridazine-3-carbonitrile (Example 336)

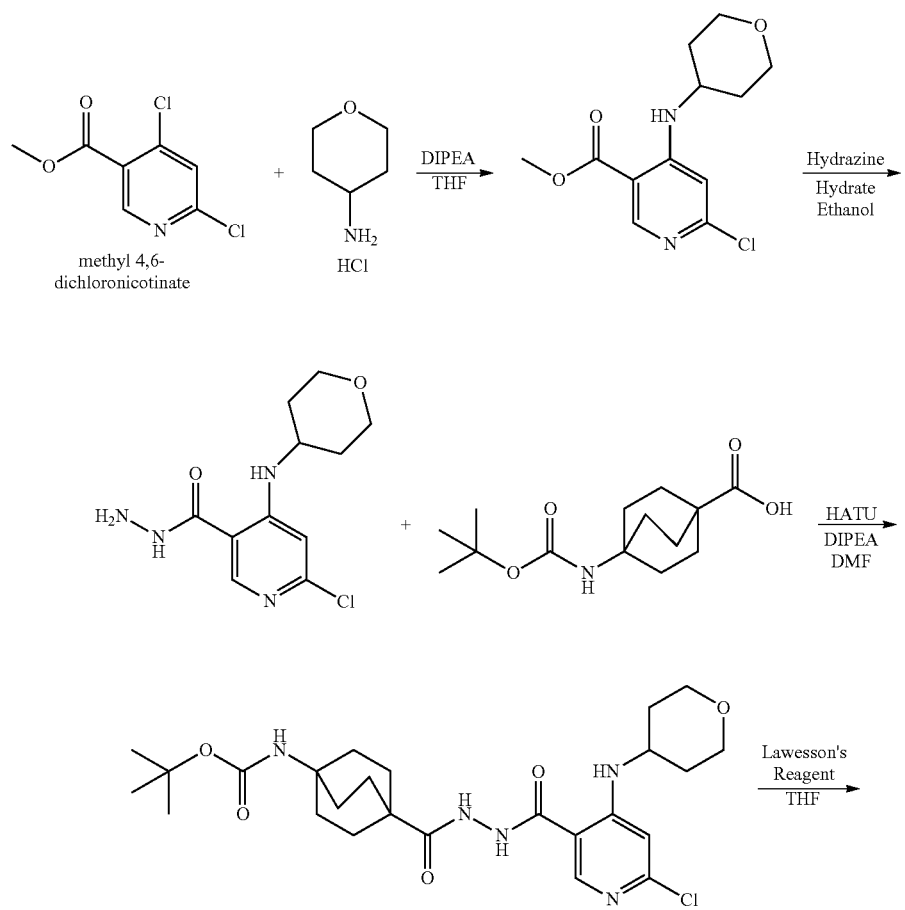

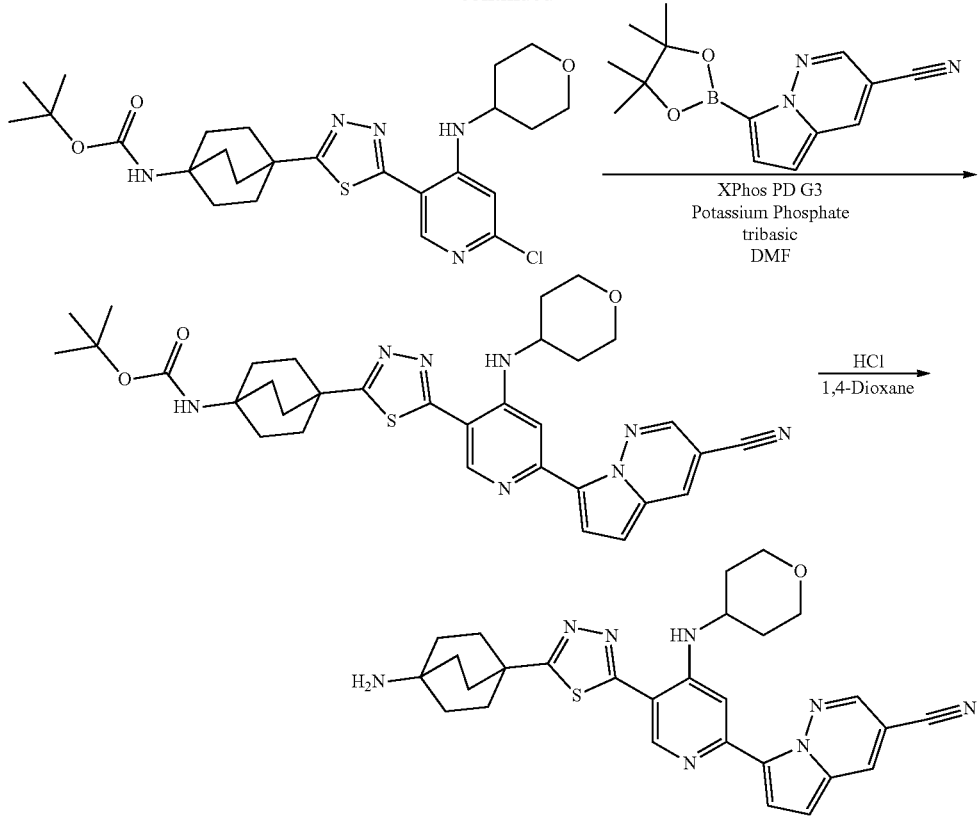

Example 336 methyl 6-chloro-4-((tetrahydro-2H-pyran-4-yl)amino) nicotinate: To a solution of methyl 4,6-dichloropyridine-3-carboxylate (4.00 g, 19.4 mmol) and tetrahydropyran-4-amine hydrochloride (4.01 g, 29.1 mmol) in THF (20 mL) was added N,N-diisopropylethylamine (10.1 mL, 58.2 mmol). The reaction mixture was heated to 120° C. overnight. The reaction was cooled to rt then partitioned between water and EtOAc, and the aqueous layer was extracted two additional times with EtOAc. The combined organic layers were washed with brine and dried over magnesium sulfate, isolated by vacuum filtration, concentrated in vacuo, and purified by silica gel column chromatography (eluent: EtOAc/Hexanes) to provide the desired product.
ES/MS: 271.24 (M+H$^+$)

6-chloro-4-((tetrahydro-2H-pyran-4-yl)amino)nicotinohydrazide: To a solution of methyl 6-chloro-4-((tetrahydro-2H-pyran-4-yl)amino)nicotinate (3.03 g, 11.2 mmol) in EtOH (18 mL) was added hydrazine hydrate (4.42 mL, 90.9 mmol). The solution was refluxed at 80° C. for 3 hours. The solution was cooled, concentrated and carried forward without further purification.
ES/MS: 271.20 (M+H$^+$)

tert-butyl (4-(2-(6-chloro-4-((tetrahydro-2H-pyran-4-yl)amino)nicotinoyl)hydrazine-1-carbonyl)bicyclo[2.2.2]octan-1-yl)carbamate: To a solution of crude 6-chloro-4-((tetrahydro-2H-pyran-4-yl)amino)nicotinohydrazide (2.7 g, 9.97 mmol) and 4-(tert-butoxycarbonylamino)bicyclo [2.2.2]octane-1-carboxylic acid (2.8 g, 10.5 mmol) in DMF (50 mL) was added N,N-diisopropylethylamine (5.70 mL, 31.9 mmol) followed by a solution of HATU (4.55 g, 12.0 mmol). The reaction mixture was stirred at RT for 15 minutes, then concentrated in vacuo, and purified by silica gel column chromatography (eluent: MeOH/DCM).
ES/MS: 522.89 [M+H$^+$].

tert-butyl (4-(5-(6-chloro-4-((tetrahydro-2H-pyran-4-yl)amino)pyridin-3-yl)-1,3,4-thiadiazol-2-yl)bicyclo[2.2.2]octan-1-yl)carbamate: To a solution of tert-butyl (4-(2-(6-chloro-4-((tetrahydro-2H-pyran-4-yl)amino)nicotinoyl) hydrazine-1-carbonyl)bicyclo[2.2.2]octan-1-yl)carbamate (5.00 g, 9.58 mmol) in 2-methyltetrahydrofuran (47.9 mL), Lawesson's Reagent (4.26 g, 10.5 mmol) was added, and the resulting reaction mixture heated to 50° C. overnight. Upon completion, the reaction mixture concentrated and purified by silica gel chromatography (eluent: EtOAc/hexanes). Product containing fractions were combined and stirred with 5 g of 10% Palladium on carbon and filtered. The solution was concentrated and purified by silica gel chromatography (eluent: MeOH/DCM).
ES/MS: 520.2 [M+H]$^+$ tert-butyl (4-(5-(6-(3-cyanopyrrolo[1,2-b]pyridazin-7-yl)-4-((tetrahydro-2H-pyran-4-yl)amino)pyridin-3-yl)-1,3, 4-thiadiazol-2-yl)bicyclo[2.2.2]octan-1-yl)carbamate: A microwave vial was charged with tert-butyl (4-(5-(6-chloro-4-((tetrahydro-2H-pyran-4-yl)amino)pyridin-3-yl)-1,3,4-thiadiazol-2-yl)bicyclo[2.2.2]octan-1-yl)carbamate (86.0 mg, 0.136 mmol), 2 7-(4,4,5,5-tetramethyl-1,3,2-dioxaborolan-2-yl)pyrrolo[1,2-b]pyridazine-3-carbonitrile (I-8, 58.7 mg, 0.218 mmol), XPhos Pd G3 (8.63 mg, 0.010 mmol), 2M aqueous potassium phosphate tribasic (0.138 mL, 0.276 mmol). DMF (2.0 mL) was added, and the reaction mixture was degassed by bubbling argon for 60 seconds. The vial was sealed and heated with stirring at 120° C. for 30 minutes in a microwave reactor. The cooled reaction mixture was diluted with THF and filtered through a syringe filer, concentrated in vacuo, and purified by RP-HPLC (eluent: water/MeCN*0.1% TFA) to yield the product as a trifluoroacetate salt.
ES/MS: 539.38 (M+H$^+$)

7-(5-(5-(4-aminobicyclo[2.2.2]octan-1-yl)-1,3,4-thiadiazol-2-yl)-4-((tetrahydro-2H-pyran-4-yl)amino)pyridin-2-yl)pyrrolo[1,2-b]pyridazine-3-carbonitrile (Example 336): To a solution of tert-butyl (4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl) carbamate (24.8 mg, 0.039 mmol) in 0.04 mL 1,2-dichloroethane was added 4M HCl in dioxane (0.0964 mL, 0.039 mmol). The solution was stirred for 1 h at rt during which time a precipitate formed. The reaction mixture was concentrated in vacuo, and purified by RP-HPLC (eluent: water/MeCN*0.1% TFA) to yield the product Example 336 as a trifluoroacetate salt.
ES/MS: 527.33 (M+H$^+$)
1H NMR (400 MHz, Acetonitrile-d3) δ 9.90 (s, 1H), 8.69 (d, J=2.1 Hz, 1H), 8.65 (d, J=2.1 Hz, 1H), 8.57 (d, J=2.7 Hz, 1H), 8.54 (d, J=5.1 Hz, 1H), 7.94 (d, J=1.7 Hz, 1H), 7.55 (s, 1H), 7.23 (d, J=5.1 Hz, 1H), 6.71 (dd, J=2.8, 1.7 Hz, 1H), 5.48 (s, 2H), 5.38 (t, J=4.9 Hz, 1H), 4.32 (dq, J=13.1, 6.5 Hz, 1H), 2.30-2.25 (m, 1H), 2.23-2.16 (m, 1H), 2.11 (s, 1H), 2.05 (q, J=6.7 Hz, 3H), 1.47 (d, J=6.4 Hz, 7H).

Procedure 40: Example 337

N-(4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)-2-hydroxy-2-methylpropanamide (Example 337)

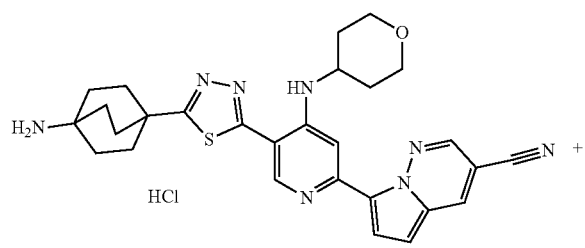

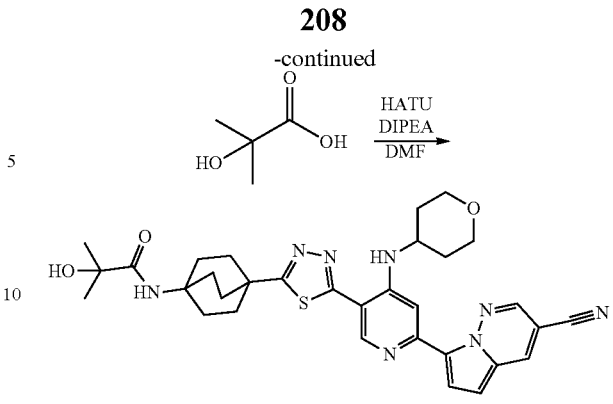

Example 337

N-(4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)-2-hydroxy-2-methylpropanamide (Example 337): To a solution of crude 7-(5-(5-(4-aminobicyclo[2.2.2]octan-1-yl)-1,3,4-thiadiazol-2-yl)-4-((tetrahydro-2H-pyran-4-yl)amino)pyridin-2-yl)pyrrolo[1,2-b]pyridazine-3-carbonitrile hydrochloride (12.0 mg, 0.018 mmol) and 2-hydroxy-2-methyl-propanoic acid (23.7 mg, 0.227 mmol) in DMF (0.5 mL) was added N,N-diisopropylethylamine (0.011 mL, 0.059 mmol) followed by the addition of a solution of HATU (7.48 mg, 0.019 mmol) in DMF (0.1 mL). The reaction mixture was stirred at RT overnight then directly purified by RP-HPLC (eluent: water/MeCN*0.1% TFA) to yield the product Example 337 as a trifluoroacetate salt.
ES/MS: 613.40 [M+H]$^+$
1H NMR (400 MHz, Acetonitrile-d3) δ 10.14 (d, J=7.7 Hz, 1H), 8.69 (s, 1H), 8.65-8.60 (m, 2H), 8.11 (d, J=5.1 Hz, 1H), 7.80 (s, 1H), 7.21 (d, J=5.1 Hz, 1H), 6.71 (s, 1H), 4.24-4.14 (m, 1H), 4.01 (dt, J=12.0, 3.8 Hz, 3H), 3.67 (ddd, J=12.0, 10.6, 2.4 Hz, 3H), 2.19 (dd, J=10.8, 4.4 Hz, 6H), 2.10 (dd, J=10.6, 4.6 Hz, 6H), 1.32 (s, 6H).

Single isomers were isolated by chiral supercritical fluid chromatography separation.

The following compounds were made according to the previous procedures, using the appropriate starting materials and protecting group chemistry as needed:

| # | ES/MS m/z | Name | Procedure |
|---|-----------|------|-----------|
| 338 | 660.85 | N-(4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)-2-((dimethyl(oxo)-l6-sulfanylidene)amino)acetamide | 40 |
| 339 | 592.33 | N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-2-((dimethyl(oxo)-l6-sulfanylidene)amino)acetamide | 34 |
| 340 | 584.38 | N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-1-methylpiperidine-4-carboxamide | 34 |
| 341 | 573.21 | 3-(((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)amino)-2,2-dimethyl-3-oxopropanoic acid | 34 |
| 342 | 529.32 | N-((1S,4r)-4-(5-(6-(3-cyanopyrrolo[1,2-b]pyridazin-7-yl)-4-(((S)-tetrahydrofuran-3-yl)amino)pyridin-3-yl)-1,3,4-thiadiazol-2-yl)cyclohexyl)acetamide | 34 |
| 343 | 652.4 | N-(4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)-1-methylpiperidine-4-carboxamide | 40 |

1HNMR

Proton NMR data for each compound exemplified is shown in Table 1.

TABLE 1

| Compound | 1H-NMR |
|---|---|
| 1 | 1H NMR (400 MHz, Methanol-d4) δ 8.79 (d, J = 2.2 Hz, 1H), 8.73 (s, 1H), 8.71 (d, J = 2.2 Hz, 1H), 8.10 (d, J = 5.1 Hz, 1H), 7.98 (s, 1H), 7.25 (d, J = 5.0 Hz, 1H), 4.34 (p, J = 6.4 Hz, 1H), 3.56 (t, J = 6.4 Hz, 2H), 3.40 (t, J = 6.4 Hz, 2H), 1.51 (d, J = 6.4 Hz, 6H), 1.44 (s, 9H). |
| 2 | 1H NMR (400 MHz, Methanol-d4) δ 8.75 (d, J = 2.1 Hz, 1H), 8.73 (s, 1H), 8.69 (d, J = 2.2 Hz, 1H), 8.10 (d, J = 5.1 Hz, 1H), 8.02 (s, 1H), 7.38-6.97 (m, 2H), 4.21-4.05 (m, 1H), 3.85-3.68 (m, 0H), 3.29-3.17 (m, 2H), 2.49-2.35 (m, 4H), 2.34-2.26 (m, 2H), 2.14-2.06 (m, 2H), 2.06-1.96 (m, 2H), 1.94 (s, 3H), 1.90-1.68 (m, 4H), 1.55-1.40 (m, 2H). |
| 3 | 1H NMR (400 MHz, Methanol-d4) δ 8.82-8.70 (m, 3H), 7.98 (d, J = 5.0 Hz, 1H), 7.76 (s, 1H), 7.26 (d, J = 5.1 Hz, 1H), 5.05 (d, J = 6.6 Hz, 2H), 3.83-3.70 (m, 1H), 2.42-2.08 (m, 4H), 2.00-1.93 (m, 6H), 1.83 (dd, J = 12.5, 3.3 Hz, 2H), 1.51 (dd, J = 11.9,3.4 Hz, 2H). |
| 4 | 1H NMR (400 MHz, Methanol-d4) δ 8.76 (d, J = 2.2 Hz, 1H), 8.68 (d, J = 2.2 Hz, 1H), 8.47 (s, 1H), 8.06 (d, J = 5.1 Hz, 1H), 7.86 (s, 1H), 7.23 (d, J = 5.1 Hz, 1H), 4.53 (s, 4H), 4.28 (p, J = 6.4 Hz, 1H), 3.68-3.61 (m, 4H), 2.11-2.04 (m, 4H), 1.46 (d, J = 6.4 Hz, 6H). |
| 5 | 1H NMR (400 MHz, Methanol-d4) δ 8.75 (d, J = 2.2 Hz, 1H), 8.74 (s, 1H), 8.68 (d, J = 2.2 Hz, 1H), 8.06 (d, J = 5.0 Hz, 1H), 7.99 (s, 1H), 7.23 (d, J = 5.0 Hz, 1H), 5.05 (s, 2H), 4.30 (hept, J = 6.4 Hz, 1H), 1.49 (d, J = 6.4 Hz, 6H). |
| 6 | 1H NMR (400 MHz, Methanol-d4) δ 8.76 (d, J = 2.1 Hz, 1H), 8.68 (d, J = 2.2 Hz, 1H), 8.47 (s, 1H), 8.12 (d, J = 7.6 Hz, 1H), 8.06 (d, J = 5.1 Hz, 1H), 7.87 (s, 1H), 7.23 (d, J = 5.0 Hz, 1H), 4.29 (p, J = 6.4 Hz, 1H), 4.09-3.90 (m, 3H), 3.52-3.39 (m, 2H), 2.05 (dd, J = 12.8, 3.9 Hz, 2H), 1.96 (s, 3H), 1.75-1.54 (m, 2H), 1.47 (d, J = 6.4 Hz, 6H). |
| 7 | 1H NMR (400 MHz, Methanol-d4) δ 8.75 (d, J = 2.1 Hz, 1H), 8.69 (dd, J = 5.5, 2.0 Hz, 2H), 8.07 (d, J = 5.1 Hz, 1H), 7.98 (s, 1H), 7.75 (d, J = 8.3 Hz, 2H), 7.24 (d, J = 4.9 Hz, 1H), 6.73 (d, J = 7.8 Hz, 2H), 4.31 (dq, J = 12.7, 6.8, 6.3 Hz, 1H), 1.53 (d, J = 6.4 Hz, 6H). |
| 8 | 1H NMR (400 MHz, Methanol-d4) δ 8.84 (s, 1H), 8.80 (d, J = 2.2 Hz, 1H), 8.72 (d, J = 2.2 Hz, 1H), 8.11 (d, J = 5.1 Hz, 1H), 8.02 (s, 1H), 7.27 (d, J = 5.0 Hz, 1H), 5.00 (d, J = 14.2 Hz, 1H), 4.57 (d, J = 13.7 Hz, 1H), 4.36 (p, J = 6.4 Hz, 1H), 4.05 (dq, J = 10.2, 5.2, 4.1 Hz, 1H), 3.55 (t, J = 12.8 Hz, 1H), 3.26-3.17 (m, 1H), 2.13-2.02 (m, 2H), 1.98 (s, 3H), 1.53 (d, J = 6.4 Hz, 8H). |
| 9 | 1H NMR (400 MHz, Methanol-d4) δ 8.84 (s, 1H), 8.79 (d, J = 2.2 Hz, 1H), 8.72 (d, J = 2.2 Hz, 1H), 8.10 (d, J = 5.1 Hz, 1H), 8.02 (s, 1H), 7.26 (d, J = 5.1 Hz, 1H), 4.35 (p, J = 6.5 Hz, 1H), 4.19 (t, J = 6.8 Hz, 2H), 3.73 (t, J = 6.9 Hz, 2H), 2.12 (q, J = 6.6 Hz, 2H), 2.04 (p, J = 6.5 Hz, 2H), 1.52 (d, J = 6.4 Hz, 6H). |
| 10 | 1H NMR (400 MHz, Methanol-d4) δ 8.85 (d, J = 1.1 Hz, 1H), 8.79 (d, J = 2.2 Hz, 1H), 8.72 (d, J = 2.1 Hz, 1H), 8.11 (d, J = 5.1 Hz, 1H), 8.02 (s, 1H), 7.26 (d, J = 5.0 Hz, 1H), 4.37 (ddt, J = 18.8, 12.0, 5.5 Hz, 3H), 3.92 (dd, J = 6.5, 4.0 Hz, 1H), 3.86 (t, J = 5.5 Hz, 1H), 3.82-3.73 (m, 4H), 2.20 (d, J = 4.3 Hz, 3H), 1.52 (d,J = 6.4 Hz, 6H). |
| 11 | 1H NMR (400 MHz, Methanol-d4) δ 8.88 (s, 1H), 8.79 (d, J = 2.2 Hz, 1H), 8.71 (d, J = 2.2 Hz, 1H), 8.11 (d, J = 5.0 Hz, 1H), 8.04 (s, 1H), 7.26 (d, J = 5.1 Hz, 1H), 4.35 (hept, J = 6.4 Hz, 1H), 3.58 (t, J = 6.6 Hz, 4H), 3.27-3.19 (m, 2H), 2.97 (td, J = 12.6, 3.1 Hz, 2H), 2.19-2.08 (m, 2H), 1.99 (d, J = 14.2 Hz, 2H), 1.81 (ddt, J = 18.6, 15.7, 10.0 Hz, 3H), 1.62-1.46 (m, 7H). |
| 12 | 1H NMR (400 MHz, Methanol-d4) δ 8.84 (d, J = 1.9 Hz, 1H), 8.79 (d, J = 2.1 Hz, 1H), 8.71 (d, J = 2.2 Hz, 1H), 8.43 (d, J = 6.2 Hz, 0H), 8.09 (d, J = 5.1 Hz, 1H), 8.03 (d, J = 2.2 Hz, 1H), 7.26 (d, J = 5.0 Hz, 1H), 4.49 (dt, J = 12.3, 5.4 Hz, 1H), 4.36 (ddd, J = 29.8, 13.4, 6.7 Hz, 3H), 4.13 (dd, J = 12.4, 4.5 Hz, 1H), 3.96 (dd, J = 13.0, 6.3 Hz, 1H), 3.91-3.78 (m, 1H), 3.65 (dd, J = 13.1, 4.3 Hz, 1H), 2.32 (ddd, J = 30.8, 13.3, 6.2 Hz, 1H), 2.16-2.00 (m, 1H), 1.99 (d, J = 3.6 Hz, 3H), 1.52 (dd, J = 6.4, 1.3 Hz, 6H). |
| 13 | 1H NMR (400 MHz, Methanol-d4) δ 8.85 (d, J = 2.0 Hz, 1H), 8.79 (d, J = 2.2 Hz, 1H), 8.72 (d, J = 2.2 Hz, 1H), 8.10 (d, J = 5.1 Hz, 1H), 8.02 (d, J = 2.0 Hz, 1H), 7.26 (d, J = 5.1 Hz, 1H), 4.55-4.44 (m, 1H), 4.43-4.28 (m, 3H), 4.13 (dd, J = 12.4, 4.5 Hz, 1H), 3.96 (dd, J = 13.1, 6.3 Hz, 1H), 3.90-3.77 (m, 1H), 3.65 (dd, J = 13.0, 4.3 Hz, 0H), 2.41-2.23 (m, 1H), 2.18-2.00 (m, 1H), 1.99 (d, J = 3.6 Hz, 3H), 1.52 (dd, J = 6.4, 1.4 Hz, 6H). |
| 14 | 1H NMR (400 MHz, Methanol-d4) δ 9.35 (t, J = 5.9 Hz, 1H), 8.84 (s, 1H), 8.78 (d, J = 2.2 Hz, 1H), 8.71 (d, J = 2.1 Hz, 1H), 8.09 (d, J = 5.1 Hz, 1H), 8.04 (s, 1H), 7.25 (d, J = 5.1 Hz, 1H), 4.48 (ddd, J = 48.7, 9.0, 2.4 Hz, 1H), 4.33 (h, J = 6.3 Hz, 1H), 4.01-3.84 (m, 1H), 3.77-3.62 (m, 1H), 1.52 (d, J = 6.4 Hz, 6H), 1.32 (d, J = 1.5 Hz, 6H). |
| 15 | 1H NMR (400 MHz, Methanol-d4) δ 8.84 (s, 1H), 8.79 (d, J = 2.2 Hz, 1H), 8.72 (d, J = 2.2 Hz, 1H), 8.10 (d, J = 5.0 Hz, 1H), 8.02 (s, 1H), 7.26 (d, J = 5.0 Hz, 1H), 4.35 (dt, J = 12.9, 6.0 Hz, 1H), 3.05-3.01 (m, 3H), 1.52 (d, J = 6.4 Hz, 6H). |

TABLE 1-continued

| Compound | 1H-NMR |
|---|---|
| 16 | 1H NMR (400 MHz, Methanol-d4) δ 8.85 (s, 1H), 8.79 (d, J = 2.1 Hz, 1H), 8.72 (d, J = 2.2 Hz, 1H), 8.10 (d, J = 5.1 Hz, 1H), 8.02 (s, 1H), 7.26 (d, J = 5.1 Hz, 1H), 4.61 (q, J = 3.0, 2.1 Hz, 0H), 4.54 (t, J = 3.4 Hz, 1H), 4.46-4.11 (m, 3H), 3.86 (dt, J = 10.2, 5.1 Hz, 1H), 3.77 (d, J = 2.9 Hz, 1H), 2.27-2.00 (m, 2H), 1.53 (d, J = 6.4 Hz, 6H). |
| 17 | 1H NMR (400 MHz, Methanol-d4) δ 8.85 (s, 1H), 8.79 (d, J = 2.2 Hz, 1H), 8.72 (d, J = 2.2 Hz, 1H), 8.10 (d, J = 5.0 Hz, 1H), 8.02 (s, 1H), 7.26 (d, J = 5.0 Hz, 1H), 4.63-4.58 (m, 0H), 4.54 (t, J = 3.3 Hz, 1H), 4.45-4.12 (m, 3H), 3.86 (dt, J = 10.1, 5.1 Hz, 1H), 3.77 (d, J = 2.8 Hz, 1H), 2.26-2.00 (m, 2H), 1.53 (d, J = 6.4 Hz, 6H). |
| 18 | 1H NMR (400 MHz, DMSO-d6) δ 9.48 (s, 1H), 8.99 (d, J = 2.2 Hz, 1H), 8.91 (s, 1H), 8.86 (d, J = 2.2 Hz, 1H), 8.12 (s, 1H), 8.08 (d, J = 5.0 Hz, 1H), 7.24 (d, J = 5.0 Hz, 1H), 4.33-4.13 (m, 6H), 1.40 (d, J = 6.3 Hz, 6H). |
| 19 | 1H NMR (400 MHz, Methanol-d4) δ 8.78 (d, J = 2.2 Hz, 1H), 8.72 (s, 1H), 8.71 (d, J = 2.2 Hz, 1H), 8.09 (d, J = 5.1 Hz, 1H), 7.95 (s, 1H), 7.25 (d, J = 5.1 Hz, 1H), 4.39-4.27 (m, 1H), 2.34 (s, 3H), 1.52-1.47 (m, 6H). |
| 20 | 1H NMR (400 MHz, Methanol-d4) δ 8.84 (s, 1H), 8.77 (d, J = 2.2 Hz, 1H), 8.70 (s, 1H), 8.24 (s, 1H), 8.13 (d, J = 5.0 Hz, 1H), 7.25 (d, J = 5.0 Hz, 1H), 3.84-3.70 (m, 2H), 2.34 (d, J = 13.3 Hz, 2H), 2.12 (d, J = 13.0 Hz, 2H), 1.97 (s, 3H), 1.91-1.69 (m, 2H), 1.50 (d, J = 12.4 Hz, 2H). |
| 21 | 1H NMR (400 MHz, Methanol-d4) δ 8.82-8.77 (m, 2H), 8.73 (d, J = 2.1 Hz, 1H), 8.08 (d, J = 5.1 Hz, 1H), 7.76 (s, 1H), 7.25 (d, J = 5.1 Hz, 1H), 5.33-5.17 (m, 3H), 4.82 (dd, J = 6.7, 5.4 Hz, 2H), 3.87-3.73 (m, 1H), 2.35 (d, J = 13.1 Hz, 2H), 2.12 (d, J = 12.8 Hz, 2H), 1.97 (s, 3H), 1.91-1.76 (m, 2H), 1.60-1.42 (m, 2H). |
| 22 | 1H NMR (400 MHz, Methanol-d4) δ 8.76 (s, 1H), 8.68 (s, 2H), 8.08 (d, J = 5.0 Hz, 1H), 7.89 (s, 1H), 7.23 (s, 1H), 3.81-3.68 (m, 1H), 2.19 (dd, J = 84.7, 13.0 Hz, 4H), 2.03 (d, J = 1.8 Hz, 1H), 1.94 (d, J = 1.9 Hz, 3H), 1.79 (q, J = 12.9 Hz, 2H), 1.47 (q, J = 12.6 Hz, 2H), 1.33 (d, J = 37.6 Hz, 1H), 0.94-0.80 (m, 1H). |
| 23 | 1H NMR (400 MHz, Methanol-d4) δ 8.76 (d, J = 7.3 Hz, 2H), 8.70 (s, 1H), 8.03 (d, J = 5.3 Hz, 1H), 7.91 (s, 1H), 7.23 (d, J = 5.0 Hz, 1H), 4.60-4.54 (m, 1H), 3.74 (s, 2H), 3.68 (s, 3H), 3.37 (d, J = 7.3 Hz, 2H), 2.54 (s, 4H), 2.31 (d, J = 13.8 Hz, 5H), 2.09 (d, J = 12.8 Hz, 3H), 1.94 (s, 3H), 1.85-1.70 (m, 2H), 1.58-1.40 (m, 1H), 1.28 (s, 2H), 0.89 (s, 1H). |
| 24 | 1H NMR (400 MHz, Methanol-d4) δ 8.79 (d, J = 2.2 Hz, 1H), 8.74 (s, 1H), 8.71 (d, J = 2.2 Hz, 1H), 8.10 (d, J = 5.1 Hz, 1H), 7.97 (s, 1H), 7.26 (d, J = 5.1 Hz, 1H), 4.42-4.28 (m, 1H), 3.89-3.67 (m, 2H), 2.34 (d, J = 13.5 Hz, 2H), 2.12 (d, J = 12.7 Hz, 2H), 1.97 (s, 3H), 1.82 (q, J = 13.3, 12.7 Hz, 2H), 1.61-1.42 (m, 8H). |
| 25 | 1H NMR (400 MHz, Methanol-d4) δ 8.63-8.55 (m, 1H), 8.52 (s, 1H), 8.32 (d, J = 2.9 Hz, 1H), 7.84 (t, J = 4.5 Hz, 1H), 7.10 (t, J = 5.0 Hz, 1H), 5.48 (s, 0H), 5.34 (s, 1H), 4.04 (s, 0H), 2.82 (d, J = 3.7 Hz, 1H), 2.18 (s, 1H), 2.08-1.97 (m, 2H), 1.60 (s, 1H), 1.46-1.40 (m, 3H), 1.31 (d, J = 15.4 Hz, 13H), 0.95-0.82 (m, 2H). |
| 26 | 1H NMR (400 MHz, Methanol-d4) δ 8.82-8.63 (m, 3H), 8.07 (d, J = 5.3 Hz, 2H), 7.24 (d, J = 5.0 Hz, 1H), 4.31 (p, J = 6.4 Hz, 1H), 3.66-3.55 (m, 4H), 1.50 (d, J = 6.4 Hz, 6H). |
| 27 | 1H NMR (400 MHz, Methanol-d4) δ 8.76 (d, J = 2.2 Hz, 1H), 8.67 (d, J = 2.2 Hz, 1H), 8.43 (s, 1H), 8.06 (d, J = 5.1 Hz, 1H), 7.87 (s, 1H), 7.23 (d, J = 5.1 Hz, 1H), 4.68-4.40 (m, 1H), 4.28 (p, J = 6.5 Hz, 1H), 4.07-3.85 (m, 1H), 3.63 (td, J = 15.0, 9.6 Hz, 1H), 1.47 (d, J = 6.4 Hz, 6H), 1.29 (d, J = 1.5 Hz, 6H). |
| 28 | 1H NMR (400 MHz, Methanol-d4) δ 8.78 (d, J = 2.2 Hz, 1H), 8.70 (d, J = 1.9 Hz, 2H), 8.09 (d, J = 5.0 Hz, 1H), 7.96 (s, 1H), 7.56-7.45 (m, 2H), 7.25 (d, J = 5.0 Hz, 1H), 6.48 (t, J = 2.2 Hz, 2H), 4.34 (p, J = 6.4 Hz, 1H), 1.50 (d, J = 6.4 Hz, 6H). |
| 29 | 1H NMR (400 MHz, Methanol-d4) δ 8.78 (d, J = 2.2 Hz, 1H), 8.69 (d, J = 2.2 Hz, 1H), 8.49 (s, 1H), 8.08 (d, J = 5.1 Hz, 1H), 7.89 (s, 1H), 7.25 (d, J = 5.1 Hz, 1H), 4.37-4.24 (m, 1H), 3.67-3.60 (m, 4H), 2.22-2.15 (m, 4H), 1.53-1.43 (m, 6H). |
| 30 | 1H NMR (400 MHz, Methanol-d4) δ 9.62 (s, 1H), 8.83 (s, 1H), 8.78 (d, J = 2.2 Hz, 1H), 8.71 (d, J = 2.2 Hz, 1H), 8.10 (d, J = 5.0 Hz, 1H), 8.02 (s, 1H), 7.26 (d, J = 5.1 Hz, 1H), 4.35 (hept, J = 6.3 Hz, 1H), 1.53 (d, J = 6.4 Hz, 6H). |
| 31 | 1H NMR (400 MHz, Methanol-d4) δ 8.80 (d, J = 2.2 Hz, 1H), 8.74-8.71 (m, 2H), 8.11 (d, J = 5.1 Hz, 1H), 7.97 (s, 1H), 7.26 (d, J = 5.1 Hz, 1H), 4.35 (hept, J = 6.4 Hz, 1H), 3.41-3.35 (m, 2H), 2.12-1.99 (m, 2H), 1.52 (d, J = 6.4 Hz, 6H), 1.33 (s, 6H). |
| 32 | 1H NMR (400 MHz, Methanol-d4) d 8.77 (d, J = 2.1 Hz, 1H), 8.73 (s, 1H), 8.69 (d, J = 2.1 Hz, 1H), 8.08 (d, J = 5.1 Hz, 1H), 7.96 (s, 1H), 7.24 (d, J = 5.0 Hz, 1H), 4.32 (p, J = 6.4 Hz, 1H), 4.13-4.03 (m, 2H), 3.68-3.54 (m, 3H), 2.19-2.11 (m, 2H), 2.07-1.92 (m, 2H), 1.49 (d, J = 6.4 Hz, 6H). |
| 33 | 1H NMR (400 MHz, Methanol-d4) δ 8.76 (d, J = 2.2 Hz, 1H), 8.68 (d, J = 2.2 Hz, 1H), 8.48 (s, 1H), 8.06 (d, J = 5.1 Hz, 1H), 7.88 (s, 1H), 7.23 (d, J = 5.0 Hz, 1H), 4.54 (t, J = 8.3 Hz, 2H), 4.29 (p, J = 6.5 Hz, 1H), 4.17 (dd, J = 8.8, 5.4 Hz, 2H), 2.00 (s, 3H), 1.46 (d, J = 6.4 Hz, 6H), 1.39-1.28 (m, 1H). |

TABLE 1-continued

| Compound | 1H-NMR |
|---|---|
| 34 | 1H NMR (400 MHz, Methanol-d4) δ 8.77 (d, J = 2.2 Hz, 1H), 8.72 (s, 1H), 8.68 (d, J = 2.1 Hz, 1H), 8.09 (d, J = 5.1 Hz, 1H), 7.98 (s, 1H), 7.24 (d, J = 5.0 Hz, 1H), 4.08-3.94 (m, 1H), 3.84-3.70 (m, 1H), 3.65 (s, 3H), 3.58-3.44 (m, 1H), 3.31-3.23 (m, 1H), 2.39-2.22 (m, 4H), 2.19-2.04 (m, 4H), 1.95 (s, 3H), 1.90-1.73 (m, 2H), 1.73-1.40 (m, 6H). |
| 35 | 1H NMR (400 MHz, Methanol-d4) δ 8.77 (d, J = 2.2 Hz, 1H), 8.68 (d, J = 2.1 Hz, 1H), 8.52 (s, 1H), 8.07 (d, J = 5.0 Hz, 1H), 7.89 (s, 1H), 7.23 (d, J = 5.1 Hz, 1H), 4.30 (hept, J = 6.2 Hz, 1H), 4.23-3.99 (m, 4H), 3.91-3.79 (m, 1H), 3.74-3.61 (m, 1H), 3.61-3.51 (m, 1H), 3.46-3.37 (m, 1H), 3.20-3.07 (m, 1H), 3.07-2.93 (m, 1H), 1.47 (d, J = 6.4 Hz, 6H). - 3 protons hidden below pentet of deuterated methanol at 3.31 ppm |
| 36 | 1H NMR (400 MHz, Methanol-d4) δ 8.77 (d, J = 2.1 Hz, 1H), 8.68 (d, J = 2.1 Hz, 1H), 8.52 (s, 1H), 8.07 (d, J = 5.0 Hz, 1H), 7.89 (s, 1H), 7.23 (d, J = 5.1 Hz, 1H), 4.40-4.23 (m, 1H), 4.22-4.14 (m, 1H), 4.14-4.08 (m, 1H), 4.07-3.98 (m, 2H), 3.90-3.78 (m, 1H), 3.72-3.60 (m, 1H), 3.59-3.49 (m, 1H), 3.43-3.36 (m, 1H), 3.31-3.17 (m, 3H), 3.13-3.03 (m, 1H), 3.03-2.94 (m, 1H), 1.47 (d, J = 6.4 Hz, 6H). |
| 37 | 1H NMR (400 MHz, Methanol-d4) δ 8.75 (d, J = 2.2 Hz, 1H), 8.68-8.64 (m, 2H), 8.58 (s, 1H), 8.04 (d, J = 5.0 Hz, 1H), 7.78 (s, 1H), 7.21 (d, J = 5.1 Hz, 1H), 4.27-4.13 (m, 3H), 1.35 (d, J = 6.4 Hz, 6H), 1.28 (s, 6H). |
| 38 | 1H NMR (400 MHz, Methanol-d4) δ 8.76 (d, J = 2.2 Hz, 1H), 8.68 (d, J = 2.2 Hz, 1H), 8.48 (s, 1H), 8.06 (d, J = 5.0 Hz, 1H), 8.00 (d, J = 5.7 Hz, 1H), 7.87 (s, 1H), 7.23 (d, J = 5.0 Hz, 1H), 4.29 (p, J = 6.4 Hz, 1H), 4.01-3.94 (m, 1H), 3.80 (dd, J = 12.4, 3.1 Hz, 2H), 3.54 (d, J = 11.9 Hz, 2H), 2.43 (s, 2H), 2.08-1.99 (m, 2H), 1.98 (s, 3H), 1.73-1.62 (m, 2H), 1.47 (d, J = 6.4 Hz, 6H). |
| 39 | 1H NMR (400 MHz, Methanol-d4) δ 8.76 (d, J = 2.2 Hz, 1H), 8.68 (d, J = 2.2 Hz, 1H), 8.49 (s, 1H), 8.07 (d, J = 5.0 Hz, 1H), 7.87 (s, 1H), 7.23 (d, J = 5.0 Hz, 1H), 4.29 (p, J = 6.4 Hz, 1H), 3.98 (t, J = 4.8 Hz, 1H), 3.71-3.56 (m, 4H), 2.46 (s, 2H), 2.04 (s, 3H), 2.02-1.93 (m, 2H), 1.77-1.63 (m, 2H), 1.47 (d, J = 6.4 Hz, 6H). |
| 40 | 1H NMR (400 MHz, Methanol-d4) δ 8.82 (d, J = 5.6 Hz, 1H), 8.79 (d, J = 2.2 Hz, 1H), 8.71 (d, J = 2.2 Hz, 1H), 8.38 (s, 1H), 8.10 (d, J = 5.1 Hz, 1H), 7.96 (d, J = 2.7 Hz, 1H), 7.26 (d, J = 5.0 Hz, 1H), 4.46 (d, J = 6.0 Hz, 1H), 4.40-4.28 (m, 1H), 4.24 (dd, J = 11.2, 6.0 Hz, 1H), 4.09-4.01 (m, 1H), 3.99-3.93 (m, 0H), 3.91-3.76 (m, 2H), 3.62 (dd, J = 12.8, 4.7 Hz, 0H), 2.29 (dq, J = 13.6, 6.8 Hz, 1H), 2.13-1.99 (m, 1H), 1.98 (d, J = 19.5 Hz, 3H), 1.53-1.47 (m, 6H). |
| 41 | 1H NMR (400 MHz, Methanol-d4) δ 8.83 (d, J = 1.1 Hz, 1H), 8.78 (d, J = 2.2 Hz, 1H), 8.70 (d, J = 2.2 Hz, 1H), 8.09 (d, J = 5.1 Hz, 1H), 8.01 (d, J = 1.5 Hz, 1H), 7.24 (d, J = 5.1 Hz, 1H), 4.46 (s, 1H), 4.39-4.29 (m, 1H), 4.27-4.10 (m, 1H), 3.86-3.57 (m, 2H), 3.47 (dd, J = 13.6, 4.6 Hz, 1H), 2.27-2.01 (m, 4H), 1.99-1.85 (m, 3H), 1.56-1.43 (m, 6H). |
| 42 | 1H NMR (400 MHz, Methanol-d4) δ 8.83 (d, J = 1.1 Hz, 1H), 8.78 (d, J = 2.2 Hz, 1H), 8.70 (d, J = 2.2 Hz, 1H), 8.09 (d, J = 5.0 Hz, 1H), 8.00 (d, J = 1.5 Hz, 1H), 7.24 (d, J = 5.0 Hz, 1H), 4.55-4.40 (m, 1H), 4.40-4.29 (m, 1H), 4.28-4.10 (m, 1H), 3.85-3.66 (m, 1H), 3.66-3.57 (m, 1H), 3.52-3.43 (m, 1H), 2.23-2.00 (m, 4H), 1.98-1.83 (m, 3H), 1.51 (dd, J = 6.5, 1.8Hz, 6H). |
| 43 | 1H NMR (400 MHz, Methanol-d4) δ 8.83 (d, J = 1.3 Hz, 1H), 8.78 (d, J = 2.2 Hz, 1H), 8.70 (d, J = 2.2 Hz, 1H), 8.09 (d, J = 5.1 Hz, 1H), 8.00 (s, 1H), 7.24 (d, J = 5.1 Hz, 1H), 4.42-4.22 (m, 4H), 4.14-3.88 (m, 1H), 3.87-3.74 (m, 1H), 3.69-3.60 (m, 3H), 2.40-2.19 (m, 1H), 2.16-1.96 (m, 1H), 1.51 (d, J = 6.4 Hz, 6H). |
| 44 | 1H NMR (400 MHz, Methanol-d4) δ 8.83 (d, J = 1.3 Hz, 1H), 8.77 (d, J = 2.2 Hz, 1H), 8.70 (d, J = 2.1 Hz, 1H), 8.09 (d, J = 5.1 Hz, 1H), 8.00 (s, 1H), 7.24 (d, J = 5.0 Hz, 1H), 4.43-4.23 (m, 4H), 4.18-3.88 (m, 1H), 3.86-3.74 (m, 1H), 3.72-3.58 (m, 3H), 2.43-2.18 (m, 1H), 2.17-1.95 (m, 1H), 1.51 (d, J = 6.4 Hz, 6H). |
| 45 | 1H NMR (400 MHz, Methanol-d4) δ 8.77 (d, J = 2.1 Hz, 1H), 8.68 (d, J = 2.2 Hz, 1H), 8.54 (s, 1H), 8.07 (d, J = 5.1 Hz, 1H), 7.88 (s, 1H), 7.23 (d, J = 5.0 Hz, 1H), 4.37-4.23 (m, 2H), 3.88-3.66 (m, 4H), 2.87-2.78 (m, 2H), 2.15 (dt, J = 10.9, 5.9 Hz, 1H), 1.96 (s, 3H), 1.61 (d, J = 10.2 Hz, 1H), 1.48 (d, J = 6.4 Hz, 6H). |
| 46 | 1H NMR (400 MHz, Methanol-d4) δ 8.83 (d, J = 2.7 Hz, 1H), 8.78 (d, J = 2.2 Hz, 1H), 8.70 (d, J = 2.1 Hz, 1H), 8.09 (d, J = 5.1 Hz, 1H), 8.00 (d, J = 2.5 Hz, 1H), 7.24 (d, J = 5.1 Hz, 1H), 4.49 (dt, J = 11.8, 5.8 Hz, 1H), 4.43-4.24 (m, 3H), 4.03 (ddd, J = 67.1, 12.7, 5.4 Hz, 1H), 3.83 (qd, J = 13.0, 6.2 Hz, 1H), 3.64 (dd, J = 13.0, 4.3 Hz, 0.5H), 3.21 (q, J = 7.4 Hz, 0.5H), 2.30 (ddt, J = 27.5, 13.6, 6.5 Hz, 1H), 2.07 (ddt, J = 31.9, 12.7, 6.1 Hz, 1H), 1.60 (tq, J = 8.3, 4.6, 3.7 Hz, 1H), 1.51 (dd, J = 6.4, 1.7 Hz, 6H), 1.31 (t, J = 7.3 Hz, 0.5H), 1.07 (d, J = 6.7 Hz, 1H), 0.87 (td, J = 4.6, 2.6 Hz, 2H), 0.82-0.70 (m, 2H). |
| 47 | 1H NMR (400 MHz, Methanol-d4) δ 8.83 (d, J = 2.7 Hz, 1H), 8.77 (d, J = 2.2 Hz, 1H), 8.70 (d, J = 2.1 Hz, 1H), 8.09 (d, J = 5.1 Hz, 1H), 8.00 (d, J = 2.5 Hz, 1H), 7.24 (d, J = 5.1 Hz, 1H), 4.55-4.43 (m, 1H), 4.42-4.26 (m, 3H), 4.16-3.59 (m, 3H), 2.45-2.20 (m, 1H), 2.20-1.99 (m, 1H), 1.83-1.55 (m, 1H), 1.51 (dd, J = 6.4, 1.7 Hz, 6H), 1.10-1.04 (m, 1H), 0.93-0.83 (m, 2H), 0.82-0.73 (m, 2H). |
| 48 | 1H NMR (400 MHz, Methanol-d4) δ 8.82 (d, J = 2.3 Hz, 1H), 8.78 (d, J = 2.2 Hz, 1H), 8.70 (d, J = 2.2 Hz, 1H), 8.09 (d, J = 5.1 Hz, 1H), 8.00 (d, J = 2.0 Hz, 1H), 7.24 (d, J = 5.1 Hz, 1H), 4.70-4.46 (m, 1H), 4.43-3.86 (m, 3H), 3.82- |

TABLE 1-continued

| Compound | 1H-NMR |
|---|---|
| | 3.64 (m, 1H), 3.62-3.51 (m, 0.5H), 3.21 (dd, J = 12.7, 8.9 Hz, 0.5H), 2.17-1.89 (m, 5H), 1.85-1.60 (m, 2H), 1.51 (d, J = 6.4 Hz, 6H). |
| 49 | 1H NMR (400 MHz, Methanol-d4) δ 8.82 (d, J = 2.3 Hz, 1H), 8.78 (d, J = 2.2 Hz, 1H), 8.70 (d, J = 2.2 Hz, 1H), 8.09 (d, J = 5.0 Hz, 1H), 8.00 (d, J = 1.9 Hz, 1H), 7.24 (d, J = 5.1 Hz, 1H), 4.71-4.44 (m, 1H), 4.41-3.85 (m, 3H), 3.83-3.65 (m, 1H), 3.61-3.51 (m, 0H), 3.21 (dd, J = 12.6, 9.0 Hz, 0H), 2.12-1.90 (m, 5H), 1.83-1.61 (m, 2H), 1.51 (d, J = 6.4 Hz, 6H). |
| 50 | 1H NMR (400 MHz, Methanol-d4) δ 9.06 (s, 1H), 8.73 (s, 1H), 7.74 (d, J = 5.2 Hz, 1H),7.71 (s, 1H),7.08 (d, J = 5.1 Hz, 1H), 4.65-4.57 (m, 1H), 4.33 (p, J = 6.4 Hz, 1H), 3.84-3.68 (m, 1H), 3.63-3.52 (m, 1H), 2.31 (d, J = 13.0 Hz, 2H), 2.10 (d, J = 12.8 Hz, 2H), 2.06-1.65 (m, 13H), 1.67-1.36 (m, 9H). |
| 51 | 1H NMR (400 MHz, Methanol-d4) δ 8.76 (s, 2H), 8.51 (s, 1H), 8.05 (d, J = 5.1 Hz, 1H), 7.83 (s, 1H), 7.23 (d, J = 5.1 Hz, 1H), 4.56 (t, J = 7.4 Hz, 1H), 4.20-3.95 (m, 4H), 3.81 (t, J = 11.7 Hz, 1H), 3.69 (s, 3H), 3.69-3.57 (m, 1H), 3.55-3.45 (m, 1H), 3.37 (d, J = 7.4 Hz, 2H), 3.27-3.01 (m, 4H), 3.02-2.76 (m, 2H), 2.68-2.44 (m, 3H), 2.38-2.21 (m, 2H). |
| 52 | 1H NMR (400 MHz, Methanol-d4) δ 8.76 (s, 2H), 8.48 (s, 1H), 8.04 (d, J = 5.0 Hz, 1H), 8.01 (d, J = 5.7 Hz, 1H), 7.80 (s, 1H), 7.23 (d, J = 5.0 Hz, 1H), 4.68-4.49 (m, 1H), 4.03-3.95 (m, 1H), 3.87-3.76 (m, 2H), 3.69 (s, 3H), 3.54 (d, J = 11.9 Hz, 2H), 3.43-3.34 (m, 2H), 2.72-2.48 (m, 3H), 2.44 (s, 2H), 2.37-2.22 (m, 2H), 2.15-1.99 (m, 2H), 1.98 (s, 3H), 1.76-1.61 (m, 2H). |
| 53 | 1H NMR (400 MHz, Methanol-d4) δ 8.80 (d, J = 2.2 Hz, 1H), 8.72 (d, J = 2.1 Hz, 1H), 8.64 (s, 1H), 8.14 (d, J = 5.1 Hz, 1H), 8.08 (s, 1H), 8.03 (d, J = 5.8 Hz, 1H), 7.27 (d, J = 5.0 Hz, 1H), 5.26 (q, J = 6.9 Hz, 1H), 4.01 (d, J = 4.9 Hz, 1H), 3.84 (d, J = 12.0 Hz, 2H), 3.57 (d, J = 11.9 Hz, 2H), 2.46 (s, 2H), 2.08-1.98 (m, 5H), 1.92 (d, J = 7.0 Hz, 3H), 1.75-1.64 (m, 2H). |
| 54 | 1H NMR (400 MHz, Methanol-d4) δ 8.76 (d, J = 2.2 Hz, 1H), 8.67 (d, J = 2.2 Hz, 1H), 8.48 (s, 1H), 8.07 (d, J = 5.0 Hz, 1H), 8.00 (d, J = 5.8 Hz, 1H), 7.88 (s, 1H), 7.23 (d, J = 5.1 Hz, 1H), 4.05-3.91 (m, 2H), 3.80 (dd, J = 12.3, 3.1 Hz, 2H), 3.64 (s, 3H), 3.54 (d, J = 11.8 Hz, 3H), 2.43 (s, 2H), 2.33-2.22 (m, 2H), 2.13-1.97 (m, 4H), 1.98 (s, 3H), 1.76- 1.49 (m, 6H). |
| 55 | 1H NMR (400 MHz, Methanol-d4) δ 8.77 (d, J = 2.2 Hz, 1H), 8.68 (d, J = 2.1 Hz, 1H), 8.50 (s, 1H), 8.07 (d, J = 5.0 Hz, 1H), 7.88 (s, 1H), 7.23 (d, J = 5.0 Hz, 1H), 4.41 (s, 3H), 4.36-4.23 (m, 1H), 2.32-2.18 (m, 2H), 2.13-2.02 (m, 2H), 2.02-1.92 (m, 2H), 1.88 (s, 3H), 1.86-1.73 (m, 2H), 1.47 (d, J = 6.4 Hz, 6H). |
| 56 | 1H NMR (400 MHz, Methanol-d4) δ 8.76 (d, J = 2.2 Hz, 1H), 8.68 (d, J = 2.2 Hz, 1H), 8.48 (s, 1H), 8.07 (d, J = 5.1 Hz, 1H), 8.03 (d, J = 5.3 Hz, 1H), 7.87 (s, 1H), 7.23 (d, J = 5.1 Hz, 1H), 4.35 (s, 2H), 4.33-4.20 (m, 1H), 3.99-3.88 (m, 1H), 2.48-2.34 (m, 2H), 2.28-2.20 (m, 4H), 1.99 (s, 3H), 1.91 (d, J = 15.1 Hz, 2H), 1.47 (d, J = 6.4 Hz, 6H). |
| 57 | 1H NMR (400 MHz, Methanol-d4) δ 8.76 (d, J = 2.2 Hz, 1H), 8.68 (d, J = 2.2 Hz, 1H), 8.48 (s, 1H), 8.06 (d, J = 5.0 Hz, 1H), 7.87 (s, 1H), 7.23 (d, J = 5.1 Hz, 1H), 4.38-4.18 (m, 1H), 3.87 (s, 1H), 3.80 (dd, J = 12.3, 3.1 Hz, 2H), 3.66 (t, J = 4.8 Hz, 4H), 3.60-3.50 (m, 2H), 3.39 (t, J = 4.8 Hz, 4H), 2.49 (s, 2H), 2.09-1.97 (m, 2H), 1.72-1.59 (m, 2H), 1.47 (d, J = 6.4 Hz, 6H). |
| 58 | 1H NMR (400 MHz, Methanol-d4) δ 8.76 (d, J = 2.1 Hz, 1H), 8.68 (d, J = 2.2 Hz, 1H), 8.48 (s, 1H), 8.06 (d, J = 5.1 Hz, 1H), 7.87 (s, 1H), 7.23 (d, J = 5.0 Hz, 1H), 4.29 (p, J = 6.5 Hz, 1H), 3.81 (dd, J = 12.5, 3.2 Hz, 2H), 3.73 (s, 1H), 3.55 (s, 1H), 3.52 (s, 1H), 3.04 (s, 3H), 2.52 (s, 2H), 2.13-1.99 (m, 2H), 1.74-1.62 (m, 2H), 1.47 (d, J = 6.4 Hz, 6H). |
| 59 | 1H NMR (400 MHz, Methanol-d4) δ 8.76 (d, J = 2.2 Hz, 1H), 8.68 (d, J = 2.2 Hz, 1H), 8.48 (s, 1H), 8.06 (d, J = 5.0 Hz, 1H), 7.86 (s, 1H), 7.23 (d, J = 5.0 Hz, 1H), 4.37-4.22 (m, 1H), 3.83-3.63 (m, 6H), 3.56-3.42 (m, 2H), 2.48-2.35 (m, 2H), 2.10-1.89 (m, 2H), 1.71-1.57 (m, 2H), 1.47 (d, J = 6.4 Hz, 6H). |
| 60 | 1H NMR (400 MHz, Methanol-d4) δ 8.76 (d, J = 2.2 Hz, 1H), 8.67 (d, J = 2.2 Hz, 1H), 8.50 (s, 1H), 8.06 (d, J = 5.1 Hz, 1H), 7.89 (s, 1H), 7.23 (d, J = 5.0 Hz, 1H), 4.43-4.21 (m, 1H), 3.90 (dd, J = 12.6, 3.2 Hz, 2H), 3.65 (s, 1H), 3.55 (s, 1H), 3.52 (s, 1H), 2.59 (s, 2H), 2.12-1.99 (m, 2H), 1.93-1.79 (m, 2H), 1.46 (d, J = 6.4 Hz, 6H). |
| 61 | 1H NMR (400 MHz, Methanol-d4) δ 9.07 (s, 1H), 8.65 (s, 1H), 8.02 (d, J = 5.8 Hz, 1H), 7.97 (s, 1H), 7.70 (d, J = 5.1 Hz, 1H), 7.09 (d, J = 5.1 Hz, 1H), 5.22 (q, J = 6.9 Hz, 1H), 4.64 (d, J = 4.1 Hz, 1H), 4.07-3.95 (m, 1H), 3.81 (d, J = 11.9 Hz, 2H), 3.55 (d, J = 11.6 Hz, 3H), 2.44 (s, 2H), 2.06-1.93 (m, 6H), 1.93-1.72 (m, 8H), 1.75-1.63 (m, 4H), 1.62-1.49 (m, 1H). |
| 62 | 1H NMR (400 MHz, Methanol-d4) δ 8.76 (d, J = 2.2 Hz, 1H), 8.67 (d, J = 2.2 Hz, 1H), 8.45 (s, 1H), 8.06 (d, J = 5.1 Hz, 1H), 8.00 (d, J = 7.4 Hz, 1H), 7.87 (s, 1H), 7.23 (d, J = 5.1 Hz, 1H), 4.28 (p, J = 6.3 Hz, 1H), 4.14 (d, J = 13.2 Hz, 1H), 4.01 (d, J = 27.3 Hz, 3H), 3.59 (d, J = 12.4 Hz, 1H), 3.46-3.37 (m, 1H), 2.21-2.06 (m, 1H), 1.99 (s, 3H), 1.74 (d, J = 12.6 Hz, 1H), 1.47 (d, J = 6.4 Hz, 6H). |
| 63 | 1H NMR (400 MHz, Methanol-d4) δ 8.76 (d, J = 2.2 Hz, 1H), 8.67 (d, J = 2.2 Hz, 1H), 8.45 (s, 1H), 8.06 (d, J = 5.1 Hz, 1H), 8.00 (d, J = 7.5 Hz, 1H), 7.87 (s, 1H), 7.23 (d, J = 5.0 Hz, 1H), 4.28 (p, J = 6.4 Hz, 1H), 4.21-4.11 (m, 1H), 4.09-3.93 (m, 3H), 3.59 (d, J = 13.7 Hz, 1H), 3.41 (td, J = 12.8, 3.1 Hz, 1H), 2.17-2.05 (m, 1H), 1.99 (s, 3H), 1.79-1.67 (m, 1H), 1.47 (d, J = 6.4 Hz, 6H). |
| 64 | 1H NMR (400 MHz, Methanol-d4) δ 8.76 (d, J = 2.2 Hz, 1H), 8.68 (d, J = 2.2 Hz, 1H), 8.48 (s, 1H), 8.06 (d, J = 5.0 Hz, 1H), 7.88 (s, 1H), 7.23 (d, J = 5.1 Hz, |

TABLE 1-continued

| Compound | 1H-NMR |
|---|---|
| | 1H), 4.28 (p, J = 6.4 Hz, 1H), 4.14 (dd, J = 12.8, 4.6 Hz, 1H), 3.99-3.82 (m, 2H), 3.65 (td, J = 9.1, 4.6 Hz, 1H), 3.57-3.41 (m, 1H), 3.25 (dd, J = 13.0, 9.4 Hz, 1H), 2.21-2.06 (m, 1H), 2.00 (s, 3H), 1.72-1.57 (m, 1H), 1.47 (d, J = 6.4 Hz, 6H). |
| 65 | 1H NMR (400 MHz, Methanol-d4) δ 8.76 (d, J = 2.2 Hz, 1H), 8.68 (d, J = 2.2 Hz, 1H), 8.48 (s, 1H), 8.06 (d, J = 5.0 Hz, 1H), 7.87 (s, 1H), 7.23 (d, J = 5.1 Hz, 1H), 4.29 (p, J = 6.4 Hz, 1H), 4.14 (dd, J = 13.0, 4.6 Hz, 1H), 4.01-3.82 (m, 2H), 3.65 (td, J = 9.1, 4.6 Hz, 1H), 3.53-3.43 (m, 1H), 3.25 (dd, J = 13.0, 9.4 Hz, 1H), 2.20-2.06 (m, 1H), 2.00 (s, 3H), 1.72-1.57 (m, 1H), 1.47 (d, J = 6.4 Hz, 6H). |
| 66 | 1H NMR (400 MHz, Methanol-d4) δ 8.76 (d, J = 2.2 Hz, 1H), 8.68 (d, J = 2.1 Hz, 1H), 8.46 (s, 1H), 8.07 (d, J = 5.1 Hz, 1H), 7.90 (s, 1H), 7.86 (s, 1H), 7.23 (d, J = 5.0 Hz, 1H), 4.29 (hept, J = 6.4, 6.0 Hz, 1H), 4.07 (s, 1H), 3.90 (s, 2H), 2.32-2.20 (m, 2H), 2.19-2.09 (m, 2H), 1.94 (s, 7H), 1.47 (d, J = 6.4 Hz, 6H). |
| 67 | 1H NMR (400 MHz, Methanol-d4) δ 8.76 (d, J = 2.2 Hz, 1H), 8.68 (d, J = 2.2 Hz, 1H), 8.49 (s, 1H), 8.07 (d, J = 5.1 Hz, 1H), 7.87 (s, 1H), 7.23 (d, J = 5.0 Hz, 1H), 4.29 (hept, J = 6.1 Hz, 1H), 4.06 (s, 4H), 3.66-3.51 (m, 4H), 2.13 (s, 3H), 2.01-1.83 (m, 4H), 1.46 (d, J = 6.4 Hz, 6H). |
| 68 | 1H NMR (400 MHz, Methanol-d4) δ 8.76 (d, J = 2.1 Hz, 1H), 8.68 (d, J = 2.2 Hz, 1H), 8.48 (s, 1H), 8.06 (d, J = 5.0 Hz, 1H), 7.88 (s, 1H), 7.23 (d, J = 5.1 Hz, 1H), 4.46 (s, 2H), 4.43 (s, 4H), 4.28 (p, J = 6.5 Hz, 1H), 4.22 (s, 2H), 1.88 (s, 3H), 1.46 (d, J = 6.4 Hz, 6H). |
| 69 | 1H NMR (400 MHz, Methanol-d4) δ 8.76 (d, J = 2.2 Hz, 1H), 8.68 (d, J = 2.1 Hz, 1H), 8.48 (s, 1H), 8.07 (d, J = 5.1 Hz, 1H), 7.87 (s, 1H), 7.23 (d, J = 5.1 Hz, 1H), 4.28 (hept, J = 6.0, 5.6 Hz, 1H), 4.01 (s, 2H), 3.93 (s, 2H), 3.73-3.60 (m, 1H), 2.12-2.04 (m, 2H), 1.93 (s, 3H), 1.92-1.82 (m, 2H), 1.72 (td, J = 13.0, 3.6 Hz, 2H), 1.46 (d, J = 6.4 Hz, 6H), 1.40-1.25 (m, 2H). |
| 70 | 1H NMR (400 MHz, Methanol-d4) δ 8.77 (d, J = 1.9 Hz, 2H), 8.72 (d, J = 2.2 Hz, 1H), 8.07 (d, J = 5.1 Hz, 1H), 7.71 (s, 1H), 7.23 (d, J = 5.1 Hz, 1H), 5.32-5.22 (m, 1H), 5.23-5.15 (m, 2H), 4.80 (dd, J = 6.8, 5.4 Hz, 2H), 2.25-2.17 (m, 6H), 2.18-2.08 (m, 6H), 1.90 (s, 3H). |
| 71 | 1H NMR (400 MHz, Methanol-d4) δ 8.78 (d, J = 2.1 Hz, 1H), 8.75 (s, 1H), 8.70 (d, J = 2.2 Hz, 1H), 8.12 (d, J = 5.1 Hz, 1H), 7.99 (s, 1H), 7.24 (d, J = 5.0 Hz, 1H), 4.31 (dt, J = 9.8, 5.3 Hz, 1H), 4.10-3.98 (m, 2H), 3.79-3.66 (m, 2H), 2.28-2.16 (m, 6H), 2.16-2.05 (m, 8H), 1.90 (s, 3H), 1.87-1.74 (m, 2H). |
| 72 | 1H NMR (400 MHz, Methanol-d4) δ 8.84 (s, 1H), 8.78 (d, J = 2.1 Hz, 1H), 8.71 (d, J = 2.1 Hz, 1H), 8.16 (s, 1H), 8.13 (d, J = 5.1 Hz, 1H), 7.25 (d, J = 5.1 Hz, 1H), 5.25 (q, J = 6.9 Hz, 1H), 2.27-2.16 (m, 6H), 2.17-2.08 (m, 6H), 1.92 (d, J = 7.0 Hz, 3H), 1.90 (s, 3H). |
| 73 | 1H NMR (400 MHz, Methanol-d4) δ 8.77 (d, J = 2.2 Hz, 1H), 8.68 (d, J = 2.2 Hz, 1H), 8.48 (s, 1H), 8.07 (d, J = 5.0 Hz, 1H), 7.87 (s, 1H), 7.23 (d, J = 5.1 Hz, 1H), 4.41-4.24 (m, 3H), 3.63-3.52 (m, 2H), 3.03 (s, 1H), 2.30 (ddd, J = 13.7, 11.1, 2.8 Hz, 1H), 2.04 (d, J = 10.5 Hz, 1H), 1.95 (s, 3H), 1.90 (d, J = 10.5 Hz, 1H), 1.60 (dt, J = 13.5, 3.8 Hz, 1H), 1.47 (d, J = 6.4 Hz, 6H). |
| 74 | 1H NMR (400 MHz, Methanol-d4) δ 8.77 (d, J = 2.2 Hz, 1H), 8.68 (d, J = 2.1 Hz, 1H), 8.48 (s, 1H), 8.07 (d, J = 5.0 Hz, 1H), 7.87 (s, 1H), 7.23 (d, J = 5.0 Hz, 1H), 4.37-4.21 (m, 3H), 3.62-3.50 (m, 2H), 3.03 (s, 1H), 2.30 (ddd, J = 13.7, 11.1, 2.8 Hz, 1H), 2.04 (d, J =10.6 Hz, 1H), 1.95 (s, 3H), 1.90 (d, J = 10.4 Hz, 1H), 1.60 (dt, J = 13.6, 3.9 Hz, 1H), 1.47 (d, J = 6.4 Hz, 6H). |
| 75 | 1H NMR (400 MHz, Methanol-d4) δ 8.77 (d, J = 2.2 Hz, 1H), 8.70 (d, J = 2.1 Hz, 1H), 8.55 (s, 1H). 8.06 (d, J = 5.1 Hz, 1H), 7.63 (s, 1H), 7.23 (d, J = 5.1 Hz, 1H), 5.32-5.10 (m, 3H), 4.77 (dd, J = 6.6, 5.1 Hz, 2H), 4.08 (s, 4H), 3.58 (dt, J = 22.0, 5.7 Hz, 4H), 2.13 (s, 3H), 2.01-1.84 (m, 4H). |
| 76 | 1H NMR (400 MHz, Methanol-d4) δ 8.77 (d, J = 2.2 Hz, 1H), 8.68 (d, J = 2.1 Hz, 1H), 8.52 (s, 1H), 8.11 (d, J = 5.1 Hz, 1H), 7.92 (s, 1H), 7.23 (d, J = 5.1 Hz, 1H), 4.29 (dt, J = 9.7, 5.3 Hz, 1H), 4.07 (s, 4H), 4.06-3.98 (m, 2H), 3.78-3.67 (m, 2H), 3.57 (dt, J = 22.1, 5.7 Hz, 4H), 2.25-2.15 (m, 2H), 2.13 (s, 3H), 2.00-1.94 (m, 2H), 1.92-1.86 (m, 2H), 1.85-1.71 (m, 2H) |
| 77 | 1H NMR (400 MHz, Methanol-d4) δ 8.77 (d, J = 2.2 Hz, 1H), 8.68 (d, J = 2.2 Hz, 1H), 8.60 (s, 1H), 8.16-8.04 (m, 2H), 7.24 (d, J = 5.1 Hz, 1H), 5.21 (q, J = 7.0 Hz, 1H), 4.02 (s, 2H), 3.94 (s, 2H), 3.73-3.61 (m, 1H), 2.17-2.04 (m, 2H), 1.93 (s, 3H), 1.92-1.81 (m, 5H), 1.77-1.67 (m, 2H), 1.40-1.25 (m, 3H). |
| 78 | 1H NMR (400 MHz, Methanol-d4) δ 8.77 (d, J = 2.1 Hz, 1H), 8.70 (d, J = 2.2 Hz, 1H), 8.54 (s, 1H), 8.06 (d, J = 5.1 Hz, 1H), 7.63 (s, 1H), 7.23 (d, J = 5.1 Hz, 1H), 5.31-5.12 (m, 3H), 4.77 (dd, J = 6.6, 5.1 Hz, 2H), 4.03 (s, 2H), 3.95 (s, 2H), 3.74-3.60 (m, 1H), 2.09 (d, J = 13.5 Hz, 2H), 1.93 (s, 3H), 1.91-1.81 (m, 2H), 1.80-1.66 (m, 2H), 1.33 (q, J = 11.4, 10.9 Hz, 2H). |
| 79 | 1H NMR (400 MHz, Methanol-d4) δ 8.77 (d, J = 2.2 Hz, 1H), 8.68 (d, J = 2.1 Hz, 1H), 8.51 (s, 1H), 8.11 (d, J = 5.0 Hz, 1H), 7.91 (s, 1H), 7.23 (d, J = 5.0 Hz, 1H), 4.35-4.23 (m, 1H), 4.07-3.98 (m, 4H), 3.94 (s, 2H), 3.78-3.61 (m, 3H), 2.18 (d, J = 13.1 Hz, 2H), 2.08 (d, J = 13.4 Hz, 2H), 1.93 (s, 3H), 1.93-1.83 (m, 2H), 1.83-1.66 (m, 4H), 1.42-1.24 (m, 2H). |
| 80 | 1H NMR (400 MHz, Methanol-d4) δ 8.78 (d, J = 2.2 Hz, 1H), 8.74 (s, 1H), 8.70 (d, J = 2.2 Hz, 1H), 8.09 (d, J = 5.1 Hz, 1H), 7.95 (s, 1H), 7.24 (d, J = 5.1 Hz, 1H), 4.32 (hept, J = 6.3 Hz, 1H), 1.73 (s, 6H), 1.49 (d, J = 6.4 Hz, 6H). |
| 81 | 1H NMR (400 MHz, Methanol-d4) δ 8.77 (d, J = 2.2 Hz, 1H), 8.76 (s, 1H), 8.69 (d, J = 2.2 Hz, 1H), 8.08 (d, J = 5.1 Hz, 1H), 7.96 (s, 1H), 7.24 (d, J = 5.1 Hz, |

| Compound | 1H-NMR |
|---|---|
| | 1H), 4.95 (dd, J = 11.1, 2.6 Hz, 1H), 4.32 (hept, J = 6.5 Hz, 1H), 4.17 (ddd, J = 10.9, 4.8, 2.0 Hz, 1H), 4.03-3.87 (m, 1H), 3.38 (t, J = 10.7 Hz, 1H), 2.52-2.38 (m, 1H), 2.25-2.13 (m, 1H), 1.96 (s, 3H), 1.94-1.81 (m, 1H), 1.74 (qd, J = 12.4, 3.7 Hz, 1H), 1.49 (d, J = 6.4 Hz, 6H). |
| 82 | 1H NMR (400 MHz, Methanol-d4) δ 8.76 (d, J = 2.2 Hz, 1H), 8.68 (d, J = 2.2 Hz, 1H), 8.47 (s, 1H), 8.06 (d, J = 5.1 Hz, 1H), 7.87 (s, 1H), 7.23 (d, J = 5.1 Hz, 1H), 4.28 (p, J = 6.4 Hz, 1H), 3.96 (d, J = 14.7 Hz, 4H), 2.06-1.90 (m, 2H), 1.87-1.75 (m, 2H), 1.67-1.58 (m, 2H), 1.57-1.48 (m, 2H), 1.46 (d, J = 6.4 Hz, 6H), 1.22 (s, 3H). |
| 83 | 1H NMR (400 MHz, Methanol-d4) δ 8.77 (d, J = 2.2 Hz, 1H), 8.74 (s, 1H), 8.69 (d, J = 2.1 Hz, 1H), 8.08 (d, J = 5.1 Hz, 1H), 7.95 (s, 1H), 7.23 (d, J = 5.0 Hz, 1H), 4.40-4.20 (m, 3H), 2.59-2.24 (m, 6H), 2.15-2.05 (m, 2H), 1.91 (s, 3H), 1.48 (d, J = 6.4 Hz, 6H). |
| 84 | 1H NMR (400 MHz, Methanol-d4) δ 8.77 (d, J = 2.2 Hz, 1H), 8.75 (s, 1H), 8.69 (d, J = 2.2 Hz, 1H), 8.08 (d, J = 5.1 Hz, 1H), 7.97 (s, 1H), 7.24 (d, J = 5.1 Hz, 1H), 5.05 (dd, J = 9.7, 3.1 Hz, 1H), 4.32 (p, J = 6.4 Hz, 1H), 4.06-3.99 (m, 1H), 3.99-3.89 (m, 2H), 2.31-2.01 (m, 4H), 2.00 (s, 3H), 1.49 (d, J = 6.4 Hz, 6H). |
| 85 | 1H NMR (400 MHz, Methanol-d4) δ 8.76 (d, J = 2.2 Hz, 1H), 8.68 (d, J = 2.2 Hz, 1H), 8.48 (s, 1H), 8.07 (d, J = 5.1 Hz, 1H), 7.87 (s, 1H), 7.41 (d, J = 6.3 Hz, 1H), 7.23 (d, J = 5.1 Hz, 1H), 4.29 (p, J = 6.4 Hz, 1H), 3.98 (d, J = 6.1 Hz, 1H), 3.83 (dd, J = 12.4, 3.1 Hz, 2H), 3.56 (d, J = 11.9 Hz, 2H), 2.49 (s, 2H), 2.03-1.87 (m, 2H), 1.79-1.66 (m, 2H), 1.47 (d, J = 6.4 Hz, 6H), 1.38 (s, 6H). |
| 86 | 1H NMR (400 MHz, Methanol-d4) δ 8.78 (d, J = 2.2 Hz, 1H), 8.70 (d, J = 2.2 Hz, 1H), 8.63 (s, 1H), 8.12 (d, J = 5.1 Hz, 1H), 8.07 (s, 1H), 7.42 (d, J = 6.2 Hz, 1H), 7.25 (d, J = 5.1 Hz, 1H), 5.24 (q, J = 7.0 Hz, 1H), 3.99 (d, J = 6.1 Hz, 1H), 3.84 (d, J = 11.8 Hz, 2H), 3.57 (d, J = 12.0 Hz, 2H), 2.49 (s, 2H), 2.03-1.95 (m, 2H), 1.90 (d, J = 7.0 Hz, 3H), 1.81-1.66 (m, 2H), 1.38 (s, 6H). |
| 87 | 1H NMR (400 MHz, Methanol-d4) δ 8.78 (d, J = 2.2 Hz, 1H), 8.72 (d, J = 2.2 Hz, 1H), 8.57 (s, 1H), 8.07 (d, J = 5.1 Hz, 1H), 7.66 (s, 1H), 7.44 (d, J = 6.3 Hz, 1H), 7.25 (d, J = 5.1 Hz, 1H), 5.22 (dt, J = 13.1, 6.7 Hz, 3H), 4.80 (d, J = 6.6, 5.1 Hz, 2H), 4.01 (d, J = 6.0 Hz, 1H), 3.87 (dd, J = 12.4, 3.2 Hz, 2H), 3.59 (d, J = 11.8 Hz, 2H), 2.51 (s, 2H), 2.10-1.88 (m, 2H), 1.83-1.67 (m, 2H), 1.40 (s, 6H). |
| 88 | 1H NMR (400 MHz, Methanol-d4) δ 8.71 (d, J = 2.2 Hz, 1H), 8.67 (s, 1H), 8.64 (d, J = 2.2 Hz, 1H), 8.05 (s, 1H), 8.01 (d, J = 5.0 Hz, 1H), 7.19 (d, J = 5.0 Hz, 1H), 4.24 (hept, J = 6.1 Hz, 1H), 4.04 (q, J = 9.0 Hz, 1H), 2.82 (q, J = 9.1 Hz, 1H), 2.51-2.32 (m, 1H), 2.30-2.18 (m, 1H), 2.17-2.06 (m, 1H), 2.05- 1.90 (m, 1H), 1.48 (d, J = 6.4 Hz, 6H), 1.17 (s, 3H), 1.13 (s, 3H). |
| 89 | 1H NMR (400 MHz, Methanol-d4) δ 8.60 (s, 1H), 8.57 (d, J = 2.3 Hz, 1H), 8.52 (d, J = 2.3 Hz, 1H), 8.31 (s, 1H), 7.85 (d, J = 4.9 Hz, 1H), 7.10 (d, J = 4.9 Hz, 1H), 4.17-3.97 (m, 1H), 2.31-2.13 (m, 6H), 1.91-1.80 (m, 6H), 1.43 (d, J = 6.4 Hz, 6H). |
| 90 | 1H NMR (400 MHz, Methanol-d4) δ 8.76 (d, J = 2.1 Hz, 1H), 8.68 (d, J = 2.2 Hz, 1H), 8.48 (s, 1H), 8.06 (d, J = 5.1 Hz, 1H), 7.87 (s, 1H), 7.50 (d, J = 6.1 Hz, 1H), 7.23 (d, J = 5.1 Hz, 1H), 4.29 (p, J = 6.4 Hz, 1H), 4.14 (q, J = 6.8 Hz, 1H), 4.01 (d, J = 6.0 Hz, 1H), 3.82 (dd, J = 12.1, 3.1 Hz, 2H), 3.56 (d, J = 11.9 Hz, 2H), 2.49 (s, 2H), 2.02-1.96 (m, 2H), 1.81-1.65 (m, 2H), 1.47 (d, J = 6.4 Hz, 6H), 1.36 (d, J = 6.8 Hz, 3H). |
| 91 | 1H NMR (400 MHz, Methanol-d4) δ 8.76 (d, J = 2.2 Hz, 1H), 8.68 (d, J = 2.1 Hz, 1H), 8.48 (s, 1H), 8.06 (d, J = 5.1 Hz, 1H), 7.87 (s, 1H), 7.50 (d, J = 6.1 Hz, 1H), 7.23 (d, J = 5.1 Hz, 1H), 4.29 (p, J = 6.4 Hz, 1H), 4.14 (q, J = 6.7 Hz, 1H), 4.01 (d, J = 5.9 Hz, 1H), 3.82 (dd, J = 12.3, 3.1 Hz, 2H), 3.56 (d, J = 11.9 Hz, 2H), 2.49 (s, 2H), 2.03-1.96 (m, 2H), 1.79-1.65 (m, 2H), 1.47 (d, J = 6.4 Hz, 6H), 1.36 (d,J = 6.8 Hz, 3H). |
| 92 | 1H NMR (400 MHz, Methanol-d4) δ 8.76 (d, J = 2.1 Hz, 1H), 8.68 (d, J = 2.2 Hz, 1H), 8.48 (s, 1H), 8.06 (d, J = 5.1 Hz, 1H), 7.87 (s, 1H), 7.79 (d, J = 5.5 Hz, 1H), 7.23 (d, J = 5.0 Hz, 1H), 4.28 (h, J = 6.6 Hz, 1H), 4.01-3.93 (m, 1H), 3.80 (dd, J = 12.3, 3.1 Hz, 2H), 3.61-3.48 (m, 2H), 3.20-3.10 (m, 1H), 2.44 (s, 2H), 2.34-2.16 (m, 4H), 2.04-1.94 (m, 2H), 1.73-1.59 (m, 2H), 1.47 (d, J = 6.4 Hz, 6H), 1.34 (s, 3H). |
| 93 | 1H NMR (400 MHz, Methanol-d4) δ 8.76 (d, J = 2.2 Hz, 1H), 8.68 (d, J = 2.1 Hz, 1H), 8.48 (s, 1H), 8.06 (d, J = 5.0 Hz, 1H), 7.86 (s, 1H), 7.81 (d, J = 5.6 Hz, 1H), 7.23 (d, J = 5.0 Hz, 1H), 4.29 (p, J = 6.4 Hz, 1H), 4.01-3.92 (m, 1H), 3.80 (dd, J = 12.3, 3.1 Hz, 2H), 3.54 (d, J = 11.9 Hz, 2H), 2.67 (p, J = 8.5 Hz, 1H), 2.43 (s, 2H), 2.35-2.24 (m, 2H), 2.22-2.11 (m, 2H), 2.06-1.93 (m, 2H), 1.76-1.61 (m, 2H), 1.47 (d, J = 6.4 Hz, 6H), 1.36 (s, 3H). |
| 94 | 1H NMR (400 MHz, Methanol-d4) δ 8.76 (d, J = 2.2 Hz, 1H), 8.68 (d, J = 2.2 Hz, 1H), 8.49 (s, 1H), 8.07 (d, J = 5.1 Hz, 1H), 7.87 (s, 1H), 7.72 (d, J = 5.1 Hz, 1H), 7.23 (d, J = 5.0 Hz, 1H), 4.41 (d, J = 6.2 Hz, 2H), 4.29 (p, J = 6.4 Hz, 1H), 4.03-3.94 (m, 1H), 3.82 (dd, J = 12.3, 3.1 Hz, 2H), 3.56 (d, J = 11.7 Hz, 2H), 2.51 (s, 2H), 2.06-1.92 (m, 2H), 1.75-1.65 (m, 2H), 1.60 (s, 3H), 1.47 (d, J = 6.4 Hz, 6H). |
| 95 | 1H NMR (400 MHz, Methanol-d4) δ 8.76 (d, J = 2.2 Hz, 1H), 8.68 (d, J = 2.2 Hz, 1H), 8.49 (s, 1H), 8.07 (d, J = 5.1 Hz, 1H), 7.87 (s, 1H), 7.23 (d, J = 5.0 Hz, 1H), 7.17 (d, J = 4.5 Hz, 1H), 4.29 (hept, J = 6.5 Hz, 1H), 4.00-3.92 (m, 1H), |

| Compound | 1H-NMR |
|---|---|
| | 3.87-3.73 (m, 4H), 3.61-3.47 (m, 4H), 2.55 (s, 2H), 2.14-2.03 (m, 2H), 2.03-1.96 (m, 2H), 1.76-1.64 (m, 2H), 1.53 (ddd, J = 13.7, 9.6, 3.9 Hz, 2H), 1.47 (d, J = 6.4 Hz, 6H), 1.24 (s, 3H). |
| 96 | 1H NMR (400 MHz, Methanol-d4) δ 8.76 (d, J = 2.2 Hz, 1H), 8.68 (d, J = 2.1 Hz, 1H), 8.49 (s, 1H). 8.07 (d, J = 5.1 Hz, 1H), 7.87 (s, 1H), 7.23 (d, J = 5.1 Hz, 1H), 4.38-4.10 (m, 3H), 3.88 (s, 1H), 3.80 (dd, J = 12.2, 3.1 Hz, 2H), 3.62-3.44 (m, 4H), 3.25-3.02 (m, 4H), 2.94 (s, 3H), 2.50 (s, 2H), 2.11-1.96 (m, 2H), 1.73-1.61 (m, 2H), 1.47 (d, J = 6.4 Hz, 6H). Additional peak obscured by solvent. |
| 97 | 1H NMR (400 MHz, Methanol-d4) δ 8.76 (d, J = 2.1 Hz, 1H), 8.68 (d, J = 2.2 Hz, 1H), 8.48 (s, 1H), 8.06 (d, J = 5.0 Hz, 1H), 7.86 (s, 1H), 7.47 (d, J = 5.1 Hz, 1H), 7.23 (d, J = 5.1 Hz, 1H), 4.29 (p, J = 6.4 Hz, 1H), 3.96 (s, 1H), 3.81 (dd, J = 12.3, 3.1 Hz, 2H), 3.54 (d, J = 11.9 Hz, 2H), 2.53 (s, 2H), 2.08-1.95 (m, 2H), 1.77-1.63 (m, 2H), 1.47 (d, J = 6.4 Hz, 6H), 1.44 (s, 6H). |
| 98 | 1H NMR (400 MHz, Methanol-d4) δ 8.76 (d, J = 2.1 Hz, 1H), 8.68 (d, J = 2.2 Hz, 1H), 8.49 (s, 1H), 8.07 (d, J = 5.1 Hz, 1H), 7.87 (s, 1H), 7.23 (d, J = 5.0 Hz, 1H), 4.29 (p, J = 6.4 Hz, 1H), 4.05 (s, 1H), 3.89 (s, 2H), 3.82 (dd, J = 12.4, 3.1 Hz, 2H), 3.59-3.51 (m, 2H), 3.45 (s, 6H), 2.48 (s, 2H), 2.07-1.96 (m, 2H), 1.83-1.65 (m, 2H), 1.47 (d, J = 6.4 Hz, 6H). |
| 99 | 1H NMR (400 MHz, Methanol-d4) δ 8.76 (d, J = 2.2 Hz, 1H), 8.72 (d, J = 2.2 Hz, 1H), 8.52 (s, 1H), 7.94 (d, J = 5.1 Hz, 1H), 7.65 (s, 1H), 7.23 (d, J = 5.0 Hz, 1H), 4.99 (d, J = 6.6 Hz, 2H), 4.85 (d, J = 6.7 Hz, 2H), 4.02 (s, 2H), 3.94 (s, 2H), 3.75-3.60 (m, 1H), 2.17-2.04 (m, 2H), 1.94-1.92 (m, 6H), 1.93-1.81 (m, 2H), 1.73 (td, J = 12.9, 3.6 Hz, 2H), 1.41-1.23 (m, 2H). |
| 100 | 1H NMR (400 MHz, Methanol-d4) δ 8.76 (d, J = 2.1 Hz, 1H), 8.67 (d, J = 2.2 Hz, 1H), 8.49 (s, 1H), 8.07 (d, J = 5.1 Hz, 1H), 8.02 (d, J = 5.6 Hz, 1H), 7.87 (s, 1H), 7.23 (d, J = 5.0 Hz, 1H), 4.29 (hept, J = 6.7 Hz, 1H), 3.98 (d, J = 5.5 Hz, 1H), 3.90-3.76 (m, 2H), 3.66-3.51 (m, 4H), 3.09-2.94 (m, 2H), 2.88 (s, 3H), 2.64-2.49 (m, 1H), 2.45 (s, 2H), 2.13-1.87 (m, 6H), 1.77-1.61 (m, 2H), 1.47 (d, J = 6.4 Hz, 6H). |
| 101 | 1H NMR (400 MHz, Methanol-d4) δ 8.77 (d, J = 2.2 Hz, 1H), 8.68 (d, J = 2.2 Hz, 1H), 8.51 (s, 1H), 8.10 (d, J = 5.1 Hz, 1H), 7.91 (s, 1H), 7.42 (d, J = 6.2 Hz, 1H), 7.23 (d, J = 5.1 Hz, 1H), 4.36-4.21 (m, 1H), 4.03 (dt, J = 12.0, 4.0 Hz, 2H), 3.98 (d, J = 6.2 Hz, 1H), 3.84 (dd, J = 12.3, 3.1 Hz, 2H), 3.76-3.67 (m, 2H), 3.58 (s, 1H), 3.55 (s, 1H), 2.49 (s, 2H), 2.25-2.13 (m, 2H), 2.03-1.93 (m, 2H), 1.86-1.67 (m, 4H), 1.38 (s, 6H). |
| 102 | 1H NMR (400 MHz, Methanol-d4) δ 8.76 (d, J = 2.2 Hz, 1H), 8.67 (d, J = 2.2 Hz, 1H), 8.50 (s, 1H), 8.07 (d, J = 5.1 Hz, 1H), 7.88 (s, 1H), 7.23 (d, J = 5.1 Hz, 1H), 4.30 (h, J = 6.5 Hz, 1H), 3.97-3.78 (m, 3H), 3.65-3.53 (m, 2H), 3.06 (br s, 8H), 2.49 (s, 2H), 2.06-1.99 (m, 2H), 1.86-1.77 (m, 2H), 1.47 (d, J = 6.4 Hz, 6H). |
| 103 | 1H NMR (400 MHz, Methanol-d4) δ 8.76 (d, J = 2.2 Hz, 1H), 8.68 (d, J = 2.1 Hz, 1H), 8.48 (s, 1H), 8.12 (d, J = 5.9 Hz, 1H), 8.06 (d, J = 5.1 Hz, 1H), 7.87 (s, 1H), 7.23 (d, J = 5.1 Hz, 1H), 4.29 (p, J = 6.5 Hz, 1H), 4.04 (d, J = 5.5 Hz, 1H), 3.84 (dd, J = 12.4, 3.1 Hz, 2H), 3.57 (d, J = 12.0 Hz, 2H), 3.46 (s, 6H), 2.57 (s, 2H), 2.12-1.97 (m, 2H), 1.81-1.64 (m, 2H), 1.47 (d, J = 6.4 Hz, 6H). |
| 104 | 1H NMR (400 MHz, Methanol-d4) δ 8.76 (d, J = 2.2 Hz, 1H), 8.68 (d, J = 2.2 Hz, 1H), 8.48 (s, 1H), 8.06 (d, J = 5.0 Hz, 1H), 7.87 (s, 1H), 7.23 (d, J = 5.0 Hz, 1H), 4.29 (p, J = 6.4 Hz, 1H), 3.88 (s, 1H), 3.80 (dd, J = 12.3, 3.1 Hz, 2H), 3.66-3.52 (m, 6H), 3.51-3.47 (m, 2H), 3.45-3.39 (m, 2H), 2.50 (s, 2H), 2.13 (s, 3H), 2.08-2.00 (m, 2H), 1.72-1.59 (m, 2H), 1.47 (d, J = 6.4 Hz, 6H). |
| 105 | 1H NMR (400 MHz, Methanol-d4) δ 8.76 (d, J = 2.2 Hz, 1H), 8.68 (d, J = 2.2 Hz, 1H), 8.48 (s, 1H), 8.06 (d, J = 5.1 Hz, 1H), 7.87 (s, 1H), 7.23 (d, J = 5.1 Hz, 1H), 4.29 (p, J = 6.3 Hz, 1H), 3.87 (s, 1H), 3.80 (dd, J = 12.3, 3.1 Hz, 2H), 3.71 (s, 3H), 3.54 (d, J = 11.8 Hz, 2H), 3.50-3.39 (m, 8H), 2.49 (s, 2H), 2.11-1.96 (m, 2H), 1.73-1.58 (m, 2H), 1.47 (d, J = 6.4 Hz, 6H). |
| 106 | 1H NMR (400 MHz, Methanol-d4) δ 8.76 (d, J = 2.1 Hz, 1H), 8.68 (d, J = 2.2 Hz, 1H), 8.48 (s, 1H), 8.06 (d, J = 5.0 Hz, 1H), 7.87 (s, 1H), 7.23 (d, J = 5.0 Hz, 1H), 4.29 (p, J = 6.4 Hz, 1H), 3.87 (s, 1H), 3.80 (dd, J = 12.3, 3.1 Hz, 2H), 3.58-3.48 (m, 6H), 3.26-3.18 (m, 4H), 2.86 (s, 3H), 2.50 (s, 2H), 2.11-1.95 (m, 2H), 1.73-1.61 (m, 2H), 1.47 (d, J = 6.4 Hz, 6H). |
| 107 | 1H NMR (400 MHz, Methanol-d4) δ 8.77 (d, J = 2.2 Hz, 1H), 8.68 (d, J = 2.2 Hz, 1H), 8.53 (s, 1H), 8.07 (d, J = 5.0 Hz, 1H), 7.88 (s, 1H), 7.23 (d, J = 5.0 Hz, 1H), 4.65 (s, 1H), 4.30 (p, J = 6.2 Hz, 1H), 4.17 (dd, J = 32.3, 11.3 Hz, 2H), 3.96-3.76 (m, 4H), 3.30 (s, 6H), 3.02 (s, 1H), 2.98-2.91 (m, 1H), 1.85 (d, J = 9.3 Hz, 1H), 1.48 (d, J = 6.4 Hz, 6H). |
| 108 | 1H NMR (400 MHz, Methanol-d4) δ 8.76 (d, J = 2.1 Hz, 1H), 8.68 (d, J = 2.2 Hz, 1H), 8.54 (s, 1H), 8.07 (d, J = 5.1 Hz, 1H), 7.89 (s, 1H), 7.23 (d, J = 5.0 Hz, 1H), 4.49 (d, J = 6.4 Hz, 2H), 4.35-4.19 (m, 3H), 4.20-3.0 (br m, 8H), 3.73 (d, J = 11.3 Hz, 2H), 2.97-2.81 (m, 4H), 1.75 (d, J = 9.2 Hz, 1H), 1.47 (d, J = 6.4 Hz, 6H). |
| 109 | 1H NMR (400 MHz, Methanol-d4) δ 8.76 (d, J = 2.2 Hz, 1H), 8.72 (d, J = 2.2 Hz, 1H), 8.53 (s, 1H), 7.94 (d, J = 5.1 Hz, 1H), 7.65 (s, 1H), 7.23 (d, J = 5.1 Hz, 1H), 5.00 (d, J = 6.6 Hz, 2H), 4.85 (d, J = 6.6 Hz, 2H), 4.05 (s, 1H), 3.85 (s, 3H), 3.82 (d, J = 3.1 Hz, 1H), 3.56 (d, J = 11.9 Hz, 2H), 3.39 (s, 6H), 2.48 (s, 2H), 2.07-1.97 (m, 2H), 1.93 (s, 3H), 1.78-1.66 (m, 2H). |
| 110 | 1H NMR (400 MHz, Methanol-d4) δ 8.76 (d, J = 2.2 Hz, 1H), 8.72 (d, J = 2.2 Hz, 1H), 8.54 (s, 1H), 7.94 (d, J = 5.1 Hz, 1H), 7.66 (s, 1H), 7.23 (d, J = 5.0 Hz, |

TABLE 1-continued

| Compound | 1H-NMR |
|---|---|
| | 1H), 5.00 (d, J = 6.6 Hz, 2H), 4.85 (d, J = 6.6 Hz, 2H), 4.23 (s, 2H), 3.88 (s, 1H), 3.82 (dd, J = 12.3, 3.2 Hz, 2H), 3.54 (d, J = 11.8 Hz, 3H), 2.94 (s, 3H), 2.50 (s, 2H), 2.09- 1.98 (m, 2H), 1.92 (s, 3H), 1.76-1.61 (m, 2H). |
| 111 | 1H NMR (400 MHz, Methanol-d4) δ 8.76 (d, J = 2.2 Hz, 1H), 8.72 (d, J = 2.2 Hz, 1H), 8.57 (s, 1H), 7.94 (d, J = 5.1 Hz, 1H), 7.67 (s, 1H), 7.23 (d, J = 5.0 Hz, 1H), 5.01 (d, J = 6.6 Hz, 2H), 4.88-4.85 (m, 2H), 4.75 (s, 1H), 4.60 (s, 1H), 4.12 (d, J = 10.9 Hz, 1H), 4.07 (d, J = 12.9 Hz, 1H), 3.91 (d, J = 11.6 Hz, 1H), 3.79 (d, J = 10.8 Hz, 1H), 2.99-2.87 (m, 1H), 1.99 (s, 3H), 1.93 (s, 3H), 1.82 (d, J = 9.2 Hz, 1H). |
| 112 | 1H NMR (400 MHz, Methanol-d4) δ 8.76 (d, J = 2.2 Hz, 1H), 8.72 (d, J = 2.2 Hz, 1H), 8.58 (s, 1H), 7.94 (d, J = 5.1 Hz, 1H), 7.67 (s, 1H), 7.23 (d, J = 5.1 Hz, 1H), 5.11 (s, 1H),5.01 (d, J = 6.6 Hz, 2H), 4.87-4.86 (m, 2H), 4.59 (s, 1H), 4.24 (d, J = 11.1 Hz, 1H), 4.13 (d, J = 11.2 Hz, 1H), 3.89 (d, J = 11.0 Hz, 1H), 3.81 (d, J = 11.1 Hz, 1H), 2.96-2.87 (m, 1H), 1.93 (s, 3H), 1.80 (d, J = 9.3 Hz, 1H), 1.44 (s, 3H), 1.29 (s, 3H). |
| 113 | 1H NMR (400 MHz, Methanol-d4) δ 8.76 (d, J = 2.2 Hz, 1H), 8.72 (d, J = 2.2 Hz, 1H), 8.58 (s, 1H), 7.94 (d, J = 5.1 Hz, 1H), 7.67 (s, 1H), 7.23 (d, J = 5.1 Hz, 1H), 5.01 (d, J = 6.6 Hz, 2H), 4.92 (s, 1H), 4.87-4.85 (m, 2H), 4.65 (s, 1H), 4.21 (d, J = 11.6 Hz, 1H), 4.13 (d, J = 11.0 Hz, 1H), 3.94-3.78 (m, 4H), 3.29 (s, 6H), 2.99-2.90 (m, 1H), 1.93 (s, 3H), 1.85 (d, J = 9.2 Hz, 1H). |
| 114 | 1H NMR (400 MHz, Methanol-d4) δ 8.75 (d, J = 2.1 Hz, 1H), 8.71 (d, J = 2.2 Hz, 1H), 8.58 (s, 1H), 7.94 (d, J = 5.1 Hz, 1H), 7.70 (s, 1H), 7.22 (d, J = 5.1 Hz, 1H), 5.00 (d, J = 6.6 Hz, 2H), 4.89-4.86 (m, 3H), 4.50 (d, J = 6.4 Hz, 2H), 4.24 (d, J = 11.2 Hz, 2H), 3.74 (d, J = 11.3 Hz, 2H), 2.94 (s, 3H), 2.92-2.79 (m, 1H), 1.93 (s, 3H), 1.76 (d, J = 9.2 Hz, 1H). |
| 115 | 1H NMR (400 MHz, Methanol-d4) δ 8.78 (d, J = 2.2 Hz, 1H), 8.70 (d, J = 2.2 Hz, 1H), 8.67 (s, 1H), 8.13 (d, J = 5.1 Hz, 1H), 8.08 (s, 1H), 7.26 (d, J = 5.1 Hz, 1H), 5.25 (q, J = 6.9 Hz, 1H), 5.12 (s, 1H), 4.60 (s, 1H), 4.25 (d, J = 11.1 Hz, 1H), 4.14 (d, J = 10.8 Hz, 1H), 3.90 (d, J = 11.4 Hz, 1H), 3.82 (d, J = 10.9 Hz, 1H), 2.92 (q, J = 7.3 Hz, 1H), 1.91 (d, J = 7.0 Hz, 3H), 1.81 (d, J = 9.3 Hz, 1H), 1.44 (s, 3H), 1.30 (s, 3H). |
| 116 | 1H NMR (400 MHz, Methanol-d4) δ 8.76 (d, J = 2.1 Hz, 1H), 8.68 (d, J = 2.2 Hz, 1H), 8.49 (s, 1H), 8.07 (d, J = 5.0 Hz, 1H), 7.87 (s, 1H), 7.23 (d, J = 5.0 Hz, 1H), 4.92-4.83 (m, 2H), 4.82-4.76 (m, 2H), 4.38-4.25 (m, 2H), 3.88 (s, 1H), 3.80 (dd, J = 12.3,3.1 Hz, 2H), 3.71 (s, 4H), 3.60-3.51 (m, 2H), 3.18-3.08 (m, 4H), 2.49 (s, 2H), 2.08-1.95 (m, 2H), 1.72-1.62 (m, 2H), 1.47 (d, J = 6.4 Hz, 6H). |
| 117 | 1H NMR (400 MHz, Methanol-d4) δ 8.76 (d, J = 2.2 Hz, 1H), 8.67 (d, J = 2.2 Hz, 1H), 8.54 (s, 1H), 8.07 (d, J = 5.1 Hz, 1H), 7.90 (s, 1H), 7.23 (d, J = 5.0 Hz, 1H), 4.91-4.84 (m, 2H), 4.62 (s, 1H), 4.29 (p, J = 6.4 Hz, 1H), 4.16-4.02 (m, 2H), 3.97 (d, J = 12.2 Hz, 1H), 3.81 (d, J = 10.9 Hz, 1H), 3.57 (t, J = 14.1 Hz, 2H), 3.11-2.97 (m, 2H), 2.88 (s, 5H), 2.78-2.63 (m, 1H), 2.21-2.09 (m, 1H), 2.00- 1.82 (m, 3H), 1.47 (d, J = 6.3 Hz, 6H). |
| 118 | 1H NMR (400 MHz, Methanol-d4) δ 8.73 (d, J = 2.2 Hz, 1H), 8.69 (d, J = 2.2 Hz, 1H), 8.58 (s, 1H), 7.94 (d, J = 5.0 Hz, 1H), 7.72 (s, 1H), 7.21 (d, J = 5.1 Hz, 1H), 4.99 (d, J = 6.6 Hz, 2H), 4.90-4.83 (m, 3H), 4.62 (s, 1H), 4.09 (t, J = 12.0 Hz, 2H), 3.96 (d, J = 12.0 Hz, 1H), 3.82 (d, J = 11.0 Hz, 1H), 3.57 (t, J = 13.8 Hz, 2H), 3.11-2.97 (m, 2H), 2.88 (s, 4H), 2.79-2.64 (m, 1H), 2.22-2.09 (m, 1H), 1.99-1.83 (m, 7H). |
| 119 | 1H NMR (400 MHz, Methanol-d4) δ 8.74 (d, J = 2.2 Hz, 1H), 8.70 (d, J = 2.2 Hz, 1H), 8.53 (s, 1H), 8.00 (d, J = 5.7 Hz, 1H), 7.93 (d, J = 5.0 Hz, 1H), 7.68 (s, 1H), 7.21 (d, J = 5.1 Hz, 1H), 5.00 (d, J = 6.6 Hz, 2H), 4.83 (s, 1H), 3.99 (d, J = 5.4 Hz, 1H), 3.82 (dd, J = 12.2, 3.1 Hz, 2H), 3.65-3.50 (m, 4H), 3.45-3.36 (m, 1H), 3.08-2.96 (m, 2H), 2.93-2.85 (m, 3H), 2.63-2.50 (m, 1H), 2.45 (s, 2H), 2.10-1.94 (m, 5H), 1.96-1.86 (m, 4H), 1.75-1.65 (m, 2H). |
| 120 | 1H NMR (400 MHz, Methanol-d4) δ 8.77 (d, J = 2.2 Hz, 1H), 8.71 (s, 1H), 8.69 (d, J = 2.1 Hz, 1H), 8.07 (d, J = 5.1 Hz, 1H), 7.95 (s, 1H), 7.24 (d, J = 5.1 Hz, 1H), 4.31 (p, J = 6.3 Hz, 1H), 2.27-2.09 (m, 12H), 1.49 (d, J = 6.4 Hz, 6H), 1.34 (s, 6H). |
| 121 | 1H NMR (400 MHz, Methanol-d4) δ 8.77 (d, J = 2.2 Hz, 1H), 8.71 (s, 1H), 8.69 (d, J = 2.1 Hz, 1H), 8.08 (d, J = 5.1 Hz, 1H), 7.95 (s, 1H), 7.24 (d, J = 5.0 Hz, 1H), 4.31 (p, J = 6.4 Hz, 1H), 3.73 (s, 2H), 3.36 (s, 6H), 2.30-2.09 (m, 12H), 1.49 (d, J = 6.4 Hz, 6H). |
| 122 | 1H NMR (400 MHz, Methanol-d4) δ 8.76 (d, J = 2.2 Hz, 1H), 8.71 (s, 1H), 8.68 (d, J = 2.2 Hz, 1H), 8.07 (d, J = 5.1 Hz, 1H), 7.96 (s, 1H), 7.68 (s, 1H), 7.23 (d, J = 5.0 Hz, 1H), 4.30 (p, J = 6.3 Hz, 1H), 3.56 (d, J = 12.0 Hz, 2H), 3.08-2.94 (m, 2H), 2.87 (s, 3H), 2.55-2.37 (m, 1H), 2.28-2.07 (m, 12H), 2.06-1.96 (m, 2H), 1.96-1.80 (m, 2H), 1.48 (d, J = 6.4 Hz, 6H). |
| 123 | 1H NMR (400 MHz, Methanol-d4) δ 8.76 (d, J = 2.1 Hz, 1H), 8.68 (d, J = 2.2 Hz, 1H), 8.48 (s, 1H), 8.07 (d, J = 5.0 Hz, 1H), 7.90 (d, J = 5.6 Hz, 1H), 7.87 (s, 1H), 7.23 (d, J = 5.1 Hz, 1H), 4.54 (d, J = 13.3 Hz, 1H), 4.29 (p, J = 6.4 Hz, 1H), 4.09-3.92 (m, 2H), 3.86-3.75 (m, 2H), 3.54 (d, J = 12.0 Hz, 2H), 3.23-3.10 (m, 1H), 2.68 (td, J = 12.9, 2.9 Hz, 1H), 2.53 (tt, J = 11.4, 3.9 Hz, 1H), 2.44 (s, 2H), 2.11 (s, 3H), 2.06- 1.97 (m, 2H), 1.88-1.74 (m, 2H), 1.74-1.63 (m, 3H), 1.58 (qd, J = 12.6, 4.4 Hz, 1H), 1.47 (d, J = 6.4 Hz, 6H). |
| 124 | 1H NMR (400 MHz, Methanol-d4) δ 8.76 (d, J = 2.1 Hz, 1H), 8.68 (d, J = 2.2 Hz, 1H), 8.49 (s, 1H), 8.07 (d, J = 5.1 Hz, 1H), 8.03 (d, J = 5.5 Hz, 1H), 7.87 (s, 1H), 7.23 (d, J = 5.0 Hz, 1H), 4.79 (dd, J = 8.3, 5.7 Hz, 2H), 4.39 (s, 1H), 4.29 |

TABLE 1-continued

| Compound | 1H-NMR |
|---|---|
| | (p, J = 6.5 Hz, 1H), 3.99 (d, J = 5.4 Hz, 1H), 3.81 (dd, J = 12.4, 3.1 Hz, 2H), 3.62-3.51 (m, 3H), 2.95-2.81 (m, 2H), 2.68-2.53 (m, 1H), 2.45 (s, 2H), 2.19-1.91 (m, 7H), 1.77-1.64 (m, 2H), 1.47 (d, J = 6.4 Hz, 6H). Additional peak obscured by solvent. |
| 125 | 1H NMR (400 MHz, Methanol-d4) δ 8.77 (d, J = 2.2 Hz, 1H), 8.73 (s, 1H), 8.70 (d, J = 2.2 Hz, 1H), 8.08 (d, J = 5.2 Hz, 1H), 8.00 (s, 1H), 7.25 (d, J = 5.0 Hz, 1H), 4.31 (q, J = 6.3 Hz, 1H), 3.85-3.71 (m, 1H), 3.31-3.26 (m, 1H), 2.33 (d, J = 13.2 Hz, 2H), 2.12 (d, J = 12.8 Hz, 2H), 1.89-1.74 (m, 2H), 1.63-1.45 (m, 9H), 0.87 (dt, J = 4.7, 3.1 Hz, 2H), 0.83-0.70 (m, 2H). |
| 126 | 1H NMR (400 MHz, Methanol-d4) δ 8.79 (d, J = 2.2 Hz, 1H), 8.74 (s, 1H), 8.72 (s, 1H), 8.10 (d, J = 5.0 Hz, 1H), 7.97 (s, 1H), 7.26 (d, J = 5.1 Hz, 1H), 4.34 (p, J = 6.4 Hz, 1H), 3.66 (s, 3H), 3.57-3.46 (m, 1H), 3.32-3.25 (m, 1H), 2.33 (d, J = 13.1 Hz, 2H), 2.14 (d, J = 12.8 Hz, 2H), 1.88-1.71 (m, 2H), 1.60-1.44 (m, 8H). |
| 127 | 1H NMR (400 MHz, Methanol-d4) δ 8.80 (d, J = 2.2 Hz, 1H), 8.75 (s, 1H), 8.72 (d, J = 2.2 Hz, 1H), 8.11 (d, J = 5.0 Hz, 1H), 7.98 (s, 1H), 7.26 (d, J = 5.0 Hz, 1H), 4.35 (h, J = 6.4 Hz, 1H), 4.07-3.90 (m, 1H), 3.48 (dd, J = 8.6, 4.2 Hz, 1H), 2.22-2.08 (m, 4H), 1.98 (s, 3H), 1.90-1.74 (m, 4H), 1.52 (d, J = 6.4 Hz, 6H). |
| 128 | 1H NMR (400 MHz, Methanol-d4) δ 8.80 (d, J = 2.2 Hz, 1H), 8.75 (s, 1H), 8.72 (d, J = 2.2 Hz, 1H), 8.11 (d, J = 5.1 Hz, 1H), 7.98 (s, 1H), 7.26 (d, J = 5.1 Hz, 1H), 4.63 (d, J = 13.6 Hz, 1H), 4.35 (p, J = 6.4 Hz, 1H), 4.10 (d, J = 13.9 Hz, 1H), 3.64 (tt, J = 11.4,3.9 Hz, 1H), 3.45-3.35 (m, 1H), 3.04-2.90 (m, 1H), 2.39-2.22 (m, 2H), 2.18 (s, 3H), 1.89 (dqd, J = 48.9, 12.0, 4.3 Hz, 2H), 1.51 (d, J = 6.4 Hz, 6H). |
| 129 | 1H NMR (400 MHz, Methanol-d4) δ 8.80 (d, J = 2.2 Hz, 1H), 8.77 (s, 1H), 8.71 (d, J = 2.2 Hz, 1H), 8.11 (d, J = 5.0 Hz, 1H), 8.01 (s, 1H), 7.26 (d, J = 5.0 Hz, 1H), 4.41-4.25 (m, 1H), 3.84-3.65 (m, 1H), 3.65-3.50 (m, 2H), 3.26 (d, J = 12.6 Hz, 2H), 2.50 (d, J = 14.2 Hz, 2H), 2.29-2.12 (m, 2H), 1.51 (d, J = 6.4 Hz, 6H). |
| 130 | 1H NMR (400 MHz, Methanol-d4) δ 8.78 (d, J = 2.2 Hz, 1H), 8.69 (d, J = 2.2 Hz, 1H), 8.55 (d, J = 2.2 Hz, 1H), 8.08 (d, J = 5.0 Hz, 1H), 7.94 (s, 1H), 7.25 (d, J = 5.0 Hz, 1H), 4.36-4.24 (m, 1H), 3.95 (t, J = 5.3 Hz, 4H), 3.49 (q, J = 5.3, 4.2 Hz, 4H), 1.49 (d, J = 6.4 Hz, 6H). |
| 131 | 1H NMR (400 MHz, Methanol-d4) δ 8.79 (d, J = 2.2 Hz, 1H), 8.70 (d, J = 2.2 Hz, 1H), 8.51 (s, 1H), 8.09 (d, J = 5.1 Hz, 1H), 7.90 (s, 1H), 7.25 (d, J = 5.0 Hz, 1H), 4.38-4.23 (m, 1H), 3.92-3.84 (m, 4H), 3.71-3.60 (m, 4H), 1.49 (d, J = 6.4 Hz, 6H). |
| 132 | 1H NMR (400 MHz, Methanol-d4) δ 8.79 (d, J = 2.2 Hz, 1H), 8.71 (d, J = 2.2 Hz, 1H), 8.68 (s, 1H), 8.09 (d, J = 5.1 Hz, 1H), 7.96 (s, 1H), 7.26 (d, J = 5.1 Hz, 1H), 4.40-4.23 (m, 1H), 2.63 (dt, J = 9.1, 4.8 Hz, 1H), 1.81 (ddd, J = 9.3, 6.7, 4.6 Hz, 1H), 1.56-1.43 (m, 7H), 1.43-1.28 (m, 7H). |
| 132 Isomer 1 | 1H NMR (400 MHz, Methanol-d4) δ 8.79 (d, J = 2.1 Hz, 1H), 8.74-8.64 (m, 2H), 8.10 (d, J = 5.1 Hz, 1H), 7.97 (s, 1H), 7.25 (d, J = 5.1 Hz, 1H), 4.32 (hept, J = 6.4 Hz, 1H), 2.63 (dt, J = 8.7, 4.8 Hz, 1H), 1.81 (ddd, J = 9.3, 6.7, 4.7 Hz, 1H), 1.55-1.46 (m, 7H), 1.43-1.28 (m, 7H). |
| 132 Isomer 2 | 1H NMR (400 MHz, Methanol-d4) δ 8.79 (d, J = 2.2 Hz, 1H), 8.73-8.67 (m, 2H), 8.10 (d, J = 5.1 Hz, 1H), 7.97 (s, 1H),7.25 (d, J = 5.1 Hz, 1H), 4.42-4.22 (m, 1H), 2.63 (dt, J = 8.7, 4.9 Hz, 1H), 1.80 (ddd, J = 9.3, 6.7, 4.7 Hz, 1H), 1.54-1.46 (m, 7H), 1.40-1.27 (m, 7H). |
| 133 | 1H NMR (400 MHz, Methanol-d4) δ 8.78 (d, J = 2.2 Hz, 1H), 8.75 (s, 1H), 8.70 (d, J = 2.2 Hz, 1H), 8.09 (d, J = 5.0 Hz, 1H), 8.02 (s, 1H), 7.25 (d, J = 5.0 Hz, 1H), 6.30 (t, J = 54.4 Hz, 1H), 4.33 (hept, J = 6.4 Hz, 1H), 3.65-3.39 (m, 5H), 3.13-2.96 (m, 2H), 2.48-2.37 (m, 2H), 2.30-2.14 (m, 2H), 1.51 (d, J = 6.4 Hz, 6H). |
| 134 | 1H NMR (400 MHz, Methanol-d4) δ 8.86-8.78 (m, 2H), 8.74 (s, 1H), 8.08 (d, J = 5.1 Hz, 1H), 7.93 (s, 1H), 7.27 (d, J = 5.1 Hz, 1H), 4.62 (t, J = 7.4 Hz, 1H), 3.87-3.74 (m, 1H), 3.71 (s, 3H), 3.41 (d, J = 7.3 Hz, 2H), 2.72-2.47 (m, 3H), 2.36 (t, J = 10.8 Hz, 5H), 2.13 (d, J = 12.9 Hz, 2H), 1.90-1.70 (m, 2H), 1.66-1.43 (m, 3H), 0.94-0.72 (m, 4H). |
| 135 | 1H NMR (400 MHz, Methanol-d4) δ 8.86-8.76 (m, 2H), 8.74 (d, J = 2.2 Hz, 1H), 8.09 (d, J = 5.0 Hz, 1H), 7.75 (s, 1H), 7.25 (d, J = 5.0 Hz, 1H), 5.34-5.13 (m, 3H), 4.86-4.80 (m, 3H), 3.86-3.71 (m, 1H), 2.35 (d, J = 13.1 Hz, 2H), 2.13 (d, J = 12.8 Hz, 2H), 1.83 (d, J = 12.7 Hz, 1H), 1.64-1.46 (m, 3H), 0.92-0.82 (m, 2H), 0.78 (dt, J = 8.1, 3.2 Hz, 2H). |
| 136 | 1H NMR (400 MHz, Methanol-d4) δ 8.79 (d, J = 2.2 Hz, 1H), 8.77-8.72 (m, 2H), 8.08 (d, J = 5.1 Hz, 1H), 7.73 (s, 1H), 7.25 (d, J = 5.1 Hz, 1H), 5.37-5.13 (m, 3H), 4.82 (dd, J = 6.7, 5.3 Hz, 2H), 2.65 (dt, J = 8.7, 4.9 Hz, 1H), 1.82 (ddd, J = 9.3, 6.7, 4.6 Hz, 1H), 1.54 (ddd, J = 8.8, 6.8, 4.7 Hz, 1H), 1.46-1.24 (m, 7H). |
| 136 Isomer 1 | 1H NMR (400 MHz, Methanol-d4) δ 8.78 (d, J = 2.2 Hz, 1H), 8.76-8.68 (m, 2H), 8.08 (d, J = 5.0 Hz, 1H), 7.74 (s, 1H), 7.25 (d, J = 5.1 Hz, 1H), 5.33-5.14 (m, 3H), 4.82 (dd, J = 6.6, 5.1 Hz, 2H), 2.70-2.60 (m, 1H), 1.82 (ddd, J = 9.3, 6.7, 4.7 Hz, 1H), 1.59-1.48 (m, 1H), 1.45-1.26 (m, 7H). |
| 136 Isomer 2 | 1H NMR (400 MHz, Methanol-d4) δ 8.78 (d, J = 2.2 Hz, 1H), 8.75-8.68 (m, 2H), 8.07 (d, J = 5.1 Hz, 1H), 7.76 (s, 1H), 7.24 (d, J = 5.1 Hz, 1H), 5.34-5.16 (m, 3H), 4.84-4.79 (m, 2H), 2.65 (dt, J = 9.0, 4.8 Hz, 1H), 1.86-1.76 (m, 1H), 1.53 (t, J = 6.8 Hz, 1H), 1.44-1.28 (m, 7H). |

TABLE 1-continued

| Compound | 1H-NMR |
|---|---|
| 136 Isomer 3 | 1H NMR (400 MHz, Methanol-d4) δ 8.76-8.71 (m, 2H), 8.70 (d, J = 2.2 Hz, 1H), 8.04 (d, J = 5.0 Hz, 1H), 7.81 (s, 1H), 7.22 (d, J = 5.0 Hz, 1H), 5.25-5.17 (m, 3H), 4.84-4.78 (m, 2H), 2.63-2.51 (m, 1H), 1.74-1.64 (m, 1H), 1.59-1.50 (m, 1H), 1.50-1.41 (m, 1H), 1.39- 1.32 (m, 6H). |
| 136 Isomer 4 | 1H NMR (400 MHz, Methanol-d4) δ 8.75 (d, J = 2.2 Hz, 1H), 8.74-8.64 (m, 2H), 8.04 (d, J = 5.0 Hz, 1H), 7.80 (s, 1H), 7.22 (d, J = 5.0 Hz, 1H), 5.25-5.17 (m, 3H), 4.84-4.78 (m, 2H), 2.59 (td, J = 8.7, 6.3 Hz, 1H), 1.78-1.65 (m, 1H), 1.61-1.52 (m, 1H), 1.52-1.42 (m, 1H), 1.39-1.32 (m, 6H). |
| 137 | 1H NMR (400 MHz, Methanol-d4) δ 8.79 (d, J = 2.2 Hz, 1H), 8.70 (d, J = 2.2 Hz, 1H), 8.49 (s, 1H), 8.27 (d, J = 4.6 Hz, 1H), 8.09 (d, J = 5.1 Hz, 1H), 7.88 (s, 1H), 7.25 (d, J = 5.0 Hz, 1H), 4.41 (s, 1H), 4.38-4.25 (m, 1H), 4.07 (s, 1H), 3.79 (d, J = 9.2 Hz, 1H), 2.72 (s, 1H), 2.03 (s, 6H), 1.65 (s, 1H), 1.49 (d, J = 6.3 Hz, 7H). |
| 138 | 1H NMR (400 MHz, Methanol-d4) δ 8.83-8.75 (m, 2H), 8.71 (d, J = 2.2 Hz, 1H), 8.11 (d, J = 5.0 Hz, 1H), 8.01 (s, 1H), 7.26 (d, J = 5.1 Hz, 1H), 4.99-4.77 (m, 5H), 4.55-4.41 (m, 1H), 4.35 (hept, J = 6.5 Hz, 1H), 3.85-3.54 (m, 3H), 3.26-3.04 (m, 1H), 2.64-2.51 (m, 2H), 2.44-2.20 (m, 2H), 1.51 (d, J = 6.4 Hz, 6H). |
| 139 | 1H NMR (400 MHz, Methanol-d4) δ 8.80 (d, J = 2.1 Hz, 1H), 8.74 (s, 1H), 8.72 (d, J = 2.2 Hz, 1H), 8.10 (d, J = 5.0 Hz, 1H), 7.97 (s, 1H), 7.26 (d, J = 5.0 Hz, 1H), 4.34 (hept, J = 6.5 Hz, 1H), 3.75-3.63 (m, 5H), 3.44-3.36 (m, 5H), 2.33 (d, J = 13.1 Hz, 2H), 2.12 (d, J = 12.7 Hz, 2H), 1.91-1.75 (m, 2H), 1.64- 1.42 (m, 8H). |
| 140 | 1H NMR (400 MHz, Methanol-d4) δ 8.79 (d, J = 2.1 Hz, 1H), 8.74 (s, 1H), 8.71 (d, J = 2.2 Hz, 1H), 8.10 (d, J = 5.0 Hz, 1H), 7.97 (s, 1H), 7.26 (d, J = 5.1 Hz, 1H), 4.34 (p, J = 6.4 Hz, 1H), 3.66-3.52 (m, 1H), 3.31-3.25 (m, 1H), 2.73 (s, 3H), 2.32 (d, J = 13.2 Hz, 2H), 2.14 (d, J = 12.8 Hz, 2H), 1.88-1.69 (m, 2H), 1.57- 1.36 (m, 8H). |
| 141 | 1H NMR (400 MHz, Methanol-d4) δ 8.79 (d, J = 2.2 Hz, 1H), 8.71 (d, J = 2.1 Hz, 1H), 8.54 (s, 1H), 8.09 (d, J = 5.0 Hz, 1H), 7.91 (s, 1H), 7.25 (d, J = 5.1 Hz, 1H), 4.50 (dt, J = 20.9, 4.7 Hz, 2H), 4.38-4.23 (m, 2H), 2.45 (s, 1H), 2.09-1.92 (m, 6H), 1.92-1.81 (m, 1H), 1.81-1.67 (m, 1H), 1.49 (d, J = 6.4 Hz, 6H), 1.42 (dd, J = 12.8, 4.7 Hz, 1H). |
| 142 | 1H NMR (400 MHz, Methanol-d4) δ 8.85-8.79 (m, 2H), 8.74 (d, J = 2.2 Hz, 1H), 8.10 (dd, J = 5.1, 1.5 Hz, 1H), 7.75 (d, J = 5.0 Hz, 1H), 7.26 (d, J = 5.1 Hz, 1H), 5.37-5.07 (m, 3H), 4.86-4.73 (m, 2H), 3.76-3.57 (m, 5H), 3.43-3.37 (m, 5H), 2.40-2.29 (m, 2H), 2.19- 2.07 (m, 2H), 1.92-1.71 (m, 2H), 1.62-1.47 (m, 2H). |
| 143 | 1H NMR (400 MHz, Methanol-d4) δ 8.84-8.76 (m, 2H), 8.74 (s, 1H), 8.08 (d, J = 5.0 Hz, 1H), 7.93 (s, 1H), 7.26 (d, J = 5.1 Hz, 1H), 4.67-4.50 (m, 1H), 3.77-3.61 (m, 8H), 3.46-3.26 (m, 7H), 2.71-2.49 (m, 3H), 2.46-2.25 (m, 4H), 2.13 (d, J = 12.6 Hz, 2H), 1.90-1.75 (m, 2H), 1.63-1.47 (m, 2H). |
| 144 | 1H NMR (400 MHz, Methanol-d4) δ 8.78 (d, J = 2.2 Hz, 1H), 8.74 (d, J = 2.2 Hz, 1H), 8.54 (s, 1H), 7.96 (d, J = 5.1 Hz, 1H), 7.67 (s, 1H), 7.25 (d, J = 5.1 Hz, 1H), 5.02 (d, J = 6.6 Hz, 2H), 4.87 (d, J = 6.7 Hz, 2H), 4.04-3.99 (m, 1H), 3.83 (dd, J = 12.3, 3.1 Hz, 2H), 3.57 (d, J = 11.9 Hz, 2H), 2.50-2.41 (m, 2H), 2.09-2.01 (m, 2H), 2.00 (s, 3H), 1.95 (s, 3H), 1.70 (d, J = 8.3 Hz, 2H). |
| 145 | 1H NMR (400 MHz, Methanol-d4) δ 8.77 (d, J = 2.2 Hz, 1H), 8.73 (d, J = 2.2 Hz, 1H), 8.54 (s, 1H), 7.95 (d, J = 5.1 Hz, 1H), 7.70 (s, 1H), 7.24 (d, J = 5.1 Hz, 1H), 5.02 (d, J = 6.6 Hz, 2H), 4.86 (d, J = 6.6 Hz, 2H), 4.57-4.49 (m, 2H), 3.68 (d, J = 12.1 Hz, 2H), 3.62-3.53 (m, 2H), 2.12-2.03 (m, 2H), 1.98-1.91 (m, 5H). |
| 146 | 1H NMR (400 MHz, Methanol-d4) δ 8.78 (d, J = 2.2 Hz, 1H), 8.70 (d, J = 2.2 Hz, 1H), 8.50 (s, 1H), 8.08 (d, J = 5.1 Hz, 1H), 7.90 (s, 1H), 7.25 (d, J = 5.1 Hz, 1H), 4.36-4.23 (m, 1H), 4.15 (t, J = 5.2 Hz, 1H), 3.83 (d, J = 11.9 Hz, 2H), 3.59-3.50 (m, 2H), 2.29-2.19 (m, 2H), 1.97-1.83 (m, 2H), 1.75-1.63 (m, 2H), 1.49 (d, J = 6.4 Hz, 6H). |
| 147 | 1H NMR (400 MHz, Methanol-d4) δ 8.79 (d, J = 2.2 Hz, 1H), 8.75 (d, J = 2.2 Hz, 1H), 8.57 (s, 1H), 7.96 (d, J = 5.0 Hz, 1H), 7.67 (s, 1H), 7.25 (d, J = 5.1 Hz, 1H), 5.03 (d, J = 6.6 Hz, 2H), 4.87 (d, J = 6.6 Hz, 2H), 4.67-4.50 (m, 1H), 4.50-4.36 (m, 1H), 4.13 (d, J = 13.8 Hz, 1H), 3.80 (dd, J = 29.4, 14.1 Hz, 1H), 3.67-3.55 (m, 1H), 2.13-1.98 (m, 5H), 1.95 (s, 3H). |
| 147 Isomer 1 | 1H NMR (400 MHz, Methanol-d4) δ 8.78 (d, J = 2.2 Hz, 1H), 8.75 (d, J = 2.2 Hz, 1H), 8.57 (s, 1H), 8.54-8.49 (m, 1H), 7.96 (d, J = 5.1 Hz, 1H), 7.69 (s, 1H), 7.25 (d, J = 5.1 Hz, 1H), 5.02 (d, J = 6.6 Hz, 2H), 4.87 (d, J = 6.7 Hz, 2H), 4.67-4.50 (m, 1H), 4.42 (d, J = 9.6 Hz, 1H), 4.13 (d, J = 13.7 Hz, 1H), 3.80 (dd, J = 29.4, 14.1 Hz, 1H), 3.62 (t, J = 12.2 Hz, 1H), 2.00 (d, J = 38.6 Hz, 8H). |
| 147 Isomer 2 | 1H NMR (400 MHz, Methanol-d4) δ 8.77 (d, J = 2.2 Hz, 1H), 8.74 (d, J = 2.2 Hz, 1H), 8.56 (s, 1H), 8.54-8.47 (m, 1H), 7.95 (d, J = 5.0 Hz, 1H), 7.70 (s, 1H), 7.24 (d, J = 5.1 Hz, 1H), 5.02 (d, J = 6.6 Hz, 2H), 4.86 (d, J = 6.6 Hz, 2H), 4.69-4.35 (m, 2H), 4.13 (d, J = 13.4 Hz, 1H), 3.80 (dd, J = 29.5, 14.0 Hz, 1H), 3.61 (t, J = 12.5 Hz, 1H), 2.16-1.86 (m, 8H). |
| 148 | 1H NMR (400 MHz, Methanol-d4) δ 8.79 (d, J = 2.2 Hz, 1H), 8.71 (d, J = 2.2 Hz, 1H), 8.64 (s, 1H), 8.16-8.08 (m, 2H), 7.27 (d, J = 5.1 Hz, 1H), 5.24 (q, J = 7.0 Hz, 1H), 4.02 (s, 1H), 3.84 (d, J = 12.1 Hz, 2H), 3.57 (d, J = 11.9 Hz, 2H), 2.47 (s, 2H), 2.13-2.03 (m, 2H), 1.92 (d, J = 6.9 Hz, 3H), 1.77-1.60 (m, 3H), 0.88 (dt, J = 6.1, 3.1 Hz, 2H), 0.79 (dt, J = 8.1, 3.2 Hz, 2H). |

TABLE 1-continued

| Compound | 1H-NMR |
|---|---|
| 149 | 1H NMR (400 MHz, Methanol-d4) δ 8.77 (d, J = 2.3 Hz, 1H), 8.74 (d, J = 2.1 Hz, 1H), 8.54 (s, 1H), 7.95 (d, J = 5.0 Hz, 1H), 7.69 (s, 1H), 7.24 (d, J = 5.0 Hz, 1H), 5.02 (d, J = 6.5 Hz, 2H), 4.87 (d, J = 6.6 Hz, 2H), 4.15 (t, J = 5.2 Hz, 1H), 3.88-3.78 (m, 3H), 3.56 (d, J = 11.5 Hz, 2H), 2.29-2.20 (m, 2H), 1.97-1.88 (m, 4H), 1.75-1.66 (m, 2H). |
| 150 | 1H NMR (400 MHz, Methanol-d4) δ 8.79 (d, J = 2.2 Hz, 1H), 8.70 (d, J = 2.2 Hz, 1H), 8.50 (s, 1H), 8.09 (d, J = 5.0 Hz, 1H), 7.89 (s, 1H), 7.25 (d, J = 5.0 Hz, 1H), 4.31 (hept, J = 6.4 Hz, 1H), 4.00 (d, J = 11.5 Hz, 1H), 3.89-3.77 (m, 2H), 3.56 (d, J = 11.9 Hz, 2H), 2.51-2.45 (m, 2H), 2.14-2.03 (m, 2H), 1.76-1.63 (m, 2H), 1.49 (d, J = 6.4 Hz, 6H), 0.93-0.86 (m, 2H), 0.84-0.69 (m, 2H). |
| 151 | 1H NMR (400 MHz, Methanol-d4) δ 8.79 (d, J = 2.1 Hz, 1H), 8.71 (d, J = 2.2 Hz, 1H), 8.66 (s, 1H), 8.16 (s, 1H), 8.12 (d, J = 5.0 Hz, 1H), 7.26 (d, J = 5.1 Hz, 1H), 5.30-5.17 (m, 1H), 4.66-4.29 (m, 2H), 4.14 (d, J = 14.1 Hz, 1H), 3.80 (dd, J = 29.4, 13.9 Hz, 1H), 3.62 (t, J = 11.7 Hz, 1H), 2.12-1.95 (m, 5H), 1.92 (d, J = 6.9 Hz, 3H). |
| 152 | 1H NMR (400 MHz, Methanol-d4) δ 8.73 (s, 1H), 8.70-8.60 (m, 2H), 8.28 (s, 1H), 8.05 (d, J = 4.9 Hz, 1H), 7.22 (d, J = 4.9 Hz, 1H), 5.18-5.09 (m, 1H), 4.67-4.02 (m, 3H), 3.78 (dd, J = 29.2, 14.0 Hz, 1H), 3.65-3.53 (m, 1H), 2.13-1.94 (m, 5H), 1.91 (d, J = 7.0 Hz, 3H). |
| 153 | 1H NMR (400 MHz, Methanol-d4) δ 8.78 (d, J = 2.2 Hz, 1H), 8.70 (d, J = 2.2 Hz, 1H), 8.50 (s, 1H), 8.08 (d, J = 5.0 Hz, 1H), 7.90 (s, 1H), 7.25 (d, J = 5.1 Hz, 1H), 4.31 (hept, J = 12.4, 6.1 Hz, 1H), 3.89 (d, J = 11.2 Hz, 2H), 3.56 (d, J = 11.3 Hz, 2H), 2.06-1.84 (m, 4H), 1.74-1.60 (m, 2H), 1.49 (d, J = 6.4 Hz, 6H), 1.38 (s, 3H). |
| 154 | 1H NMR (400 MHz, Methanol-d4) δ 8.78 (d, J = 2.1 Hz, 1H), 8.70 (d, J = 2.2 Hz, 1H), 8.49 (s, 1H), 8.08 (d, J = 5.1 Hz, 1H), 7.89 (s, 1H), 7.25 (d, J = 5.0 Hz, 1H), 4.36-4.24 (m, 1H), 4.10 (s, 1H), 3.84-3.74 (m, 2H), 3.53-3.48 (m, 2H), 2.37-2.31 (m, 2H), 2.12-2.02 (m, 2H), 1.62 (d, J = 8.0 Hz, 2H), 1.49 (d, J = 6.4 Hz, 6H). |
| 155 | 1H NMR (400 MHz, Methanol-d4) δ 8.79 (d, J = 2.2 Hz, 1H), 8.70 (d, J = 2.2 Hz, 1H), 8.51 (s, 1H), 8.08 (d, J = 5.1 Hz, 1H), 7.89 (s, 1H), 7.83-7.78 (m, 1H), 7.25 (d, J = 5.0 Hz, 1H), 4.37-4.24 (m, 1H), 3.78-3.61 (m, 4H), 2.78-2.66 (m, 2H), 2.18-2.02 (m, 2H), 1.95 (s, 3H), 1.75-1.66 (m, 2H), 1.64 (s, 3H), 1.49 (d, J = 6.4 Hz, 6H). |
| 156 | 1H NMR (400 MHz, Methanol-d4) δ 8.80 (d, J = 2.2 Hz, 1H), 8.77 (s, 1H), 8.72 (d, J = 2.2 Hz, 1H), 8.14 (d, J = 5.0 Hz, 1H), 8.01 (s, 1H), 7.26 (d, J = 5.1 Hz, 1H), 4.34 (dt, J = 9.6, 5.2 Hz, 1H), 4.07 (dt, J = 12.0, 4.0 Hz, 2H), 3.85-3.68 (m, 3H), 2.34 (d, J = 13.1 Hz, 2H), 2.22 (d, J = 13.0 Hz, 2H), 2.13 (d, J = 12.7 Hz, 2H), 1.91-1.74 (m, 4H), 1.66-1.45 (m, 3H), 0.91-0.84 (m, 2H), 0.83-0.73 (m, 2H). |
| 157 | 1H NMR (400 MHz, Methanol-d4) δ 8.81 (d, J = 2.1 Hz, 1H), 8.72 (d, J = 2.1 Hz, 1H), 8.66 (s, 1H), 8.15 (d, J = 5.0 Hz, 1H), 8.09 (s, 1H), 7.82-7.79 (m, 1H), 7.28 (d, J = 5.1 Hz, 1H), 5.27 (q, J = 6.9 Hz, 1H), 3.77-3.66 (m, 4H), 2.76-2.70 (m, 2H), 2.15-2.04 (m, 2H), 1.95 (s, 3H), 1.92 (d, J = 6.9 Hz, 3H), 1.73-1.66 (m, 2H), 1.64 (s, 3H). |
| 158 | 1H NMR (400 MHz, Methanol-d4) δ 8.83-8.70 (m, 3H), 7.98 (d, J = 5.1 Hz, 1H), 7.75 (s, 1H), 7.26 (d, J = 5.1 Hz, 1H), 5.05 (d, J = 6.6 Hz, 2H), 4.88 (d, J = 6.6 Hz, 2H), 3.85-3.71 (m, 1H), 2.34 (d, J = 13.1 Hz, 2H), 2.13 (d, J = 12.8 Hz, 2H), 1.96 (s, 3H). 1.92-1.69 (m, 3H), 1.66-1.42 (m, 4H), 0.96-0.82 (m, 2H), 0.78 (dt, J = 8.2, 3.2 Hz, 2H). |
| 159 | 1H NMR (400 MHz, Methanol-d4) δ 8.79 (d, J = 2.1 Hz, 1H), 8.70 (d, J = 2.1 Hz, 1H), 8.52 (s, 1H), 8.09 (d, J = 5.0 Hz, 1H), 7.89 (s, 1H), 7.25 (d, J = 5.0 Hz, 1H), 4.32 (p, J = 6.4 Hz, 1H), 3.95-3.87 (m, 2H), 3.69 (d, J = 11.4 Hz, 2H), 2.52-2.47 (m, 2H), 2.14-2.02 (m, 2H), 1.82 (d, J = 8.8 Hz, 2H), 1.49 (d, J = 6.4 Hz, 6H). |
| 160 | 1H NMR (400 MHz, Methanol-d4) δ 8.87 (s, 1H), 8.80 (d, J = 2.1 Hz, 1H), 8.72 (d, J = 2.2 Hz, 1H), 8.23 (s, 1H), 8.14 (d, J = 5.0 Hz, 1H), 7.27 (d, J = 5.1 Hz, 1H), 5.26 (q, J = 6.9 Hz, 1H), 3.88-3.71 (m, 1H), 2.35 (d, J = 13.1 Hz, 2H), 2.13 (d, J = 12.9 Hz, 2H), 1.94 (d, J = 6.9 Hz, 3H), 1.83 (q, J = 10.8 Hz, 2H), 1.69-1.42 (m, 3H), 0.94-0.85 (m, 2H), 0.85-0.68 (m, 2H). |
| 161 | 1H NMR (400 MHz, Methanol-d4) δ 8.79 (d, J = 2.2 Hz, 1H), 8.70 (d, J = 2.2 Hz, 1H), 8.51 (s, 1H), 8.09 (d, J = 5.1 Hz, 1H), 7.90 (s, 1H), 7.25 (d, J = 5.0 Hz, 1H), 4.31 (hept, J = 6.4 Hz, 1H), 4.20-3.95 (m, 3H), 3.95-3.82 (m, 1H), 3.82-3.67 (m, 1H), 2.15 (td, J = 11.1, 9.0, 4.1 Hz, 1H), 2.07-1.91 (m, 1H), 1.49 (d, J = 6.4 Hz, 6H). |
| 162 | 1H NMR (400 MHz, Methanol-d4) δ 8.79 (d, J = 2.2 Hz, 1H), 8.70 (d, J = 2.1 Hz, 1H), 8.52 (s, 1H), 8.09 (d, J = 5.1 Hz, 1H), 7.90 (s, 1H), 7.25 (d, J = 5.0 Hz, 1H), 4.31 (hept, J = 6.4 Hz, 1H), 4.17-3.95 (m, 3H), 3.95-3.82 (m, 1H), 3.82-3.66 (m, 1H), 2.21-2.08 (m, 1H), 2.06-1.91 (m, 1H), 1.49 (d, J = 6.4 Hz, 6H). |
| 163 | 1H NMR (400 MHz, Methanol-d4) δ 8.79 (d, J = 2.2 Hz, 1H), 8.70 (d, J = 2.2 Hz, 1H), 8.51 (s, 1H), 8.09 (d, J = 5.1 Hz, 1H), 7.89 (s, 1H), 7.25 (d, J = 5.0 Hz, 1H), 4.36-4.26 (m, 5H), 3.75 (s, 2H), 2.77 (s, 2H), 1.48 (d, J = 6.3 Hz, 6H). |
| 164 | 1H NMR (400 MHz, Methanol-d4) δ 8.79 (d, J = 2.1 Hz, 1H), 8.70 (d, J = 2.2 Hz, 1H), 8.51 (s, 1H), 8.09 (d, J = 5.1 Hz, 1H), 7.90 (s, 1H), 7.25 (d, J = 5.1 Hz, 1H), 4.46-4.37 (m, 2H), 4.36-4.21 (m, 3H), 3.40 (t, J = 6.8 Hz, 2H), 2.61 (t, J = 6.8 Hz, 2H), 1.49 (d, J = 6.4 Hz, 6H). |

TABLE 1-continued

| Compound | 1H-NMR |
|---|---|
| 165 | 1H NMR (400 MHz, Methanol-d4) δ 8.79 (d, J = 2.2 Hz, 1H), 8.70 (d, J = 2.2 Hz, 1H), 8.51 (s, 1H), 8.09 (d, J = 5.1 Hz, 1H), 7.89 (s, 1H), 7.25 (d, J = 5.0 Hz, 1H), 4.37-4.24 (m, 1H), 4.05-3.99 (m, 1H), 3.84-3.78 (m, 4H), 2.23-2.13 (m, 2H), 2.04 (s, 3H), 2.02-1.71 (m, 5H), 1.61-1.53 (m, 1H), 1.49 (d, J = 6.4 Hz, 6H). |
| 166 | 1H NMR (400 MHz, Methanol-d4) δ 8.79 (d, J = 2.2 Hz, 1H), 8.70 (d, J = 2.2 Hz, 1H), 8.51 (s, 1H), 8.09 (d, J = 5.1 Hz, 1H), 7.89 (s, 1H), 7.25 (d, J = 5.1 Hz, 1H), 4.31 (hept, J = 6.4 Hz, 1H), 4.22-4.13 (m, 1H), 4.06 (d, J = 12.6 Hz, 2H), 3.76 (d, J = 12.7 Hz, 2H), 2.19-2.11 (m, 2H), 2.11-1.99 (m, 4H), 1.90-1.71 (m, 3H), 1.61-1.52 (m, 1H), 1.49 (d, J = 6.4 Hz, 6H). |
| 167 | 1H NMR (400 MHz, Methanol-d4) δ 8.79 (d, J = 2.2 Hz, 1H), 8.70 (d, J = 2.2 Hz, 1H), 8.54 (s, 1H), 8.09 (d, J = 5.1 Hz, 1H), 7.91 (s, 1H), 7.25 (d, J = 5.1 Hz, 1H), 4.36-4.23 (m, 3H), 4.09 (t, J = 7.9 Hz, 2H), 3.85 (t, J = 5.0 Hz, 2H), 1.49 (d, J = 6.4 Hz, 6H). |
| 168 | 1H NMR (400 MHz, Methanol-d4) δ 8.78 (d, J = 2.1 Hz, 1H), 8.70 (d, J = 2.1 Hz, 1H), 8.52 (s, 1H), 8.08 (d, J = 5.0 Hz, 1H), 7.91 (s, 1H), 7.25 (d, J = 5.1 Hz, 1H), 4.57 (ddd, J = 22.4, 11.3, 5.6 Hz, 1H), 4.47-4.37 (m, 1H), 4.31 (p, J = 6.4 Hz, 1H), 4.13 (d, J = 13.7 Hz, 1H), 3.79 (dd, J = 29.4, 14.1 Hz, 1H), 3.67-3.55 (m, 1H), 2.17-1.87 (m, 5H), 1.49 (d, J = 6.4 Hz, 6H). |
| 169 | 1H NMR (400 MHz, Methanol-d4) δ 8.77 (d, J = 2.2 Hz, 1H), 8.68 (d, J = 2.2 Hz, 1H), 8.51 (s, 1H), 8.06 (d, J = 5.0 Hz, 1H), 7.94 (s, 1H), 7.24 (d, J = 5.0 Hz, 1H), 4.58 (dd, J = 22.9, 11.7 Hz, 1H), 4.41 (t, J = 12.0 Hz, 1H), 4.36-4.23 (m, 1H), 4.12 (d, J = 13.5 Hz, 1H), 3.79 (dd, J = 29.4, 14.1 Hz, 1H), 3.68-3.55 (m, 1H), 2.12-1.90 (m, 5H), 1.49 (d, J = 6.4 Hz, 6H). |
| 170 | 1H NMR (400 MHz, Methanol-d4) δ 8.78 (d, J = 2.2 Hz, 1H), 8.70 (d, J = 2.2 Hz, 1H), 8.49 (s, 1H), 8.08 (d, J = 5.0 Hz, 1H), 7.89 (s, 1H), 7.25 (d, J = 5.1 Hz, 1H), 4.37-4.25 (m, 1H), 4.25-4.03 (m, 5H), 2.41 (dd, J = 13.5, 7.7 Hz, 1H), 2.21-1.99 (m, 3H), 1.95 (s, 3H), 1.87 (dd, J = 13.5, 7.1 Hz, 1H), 1.61 (dd, J = 12.3, 6.2 Hz, 1H), 1.48 (d, J = 6.4 Hz, 6H). |
| 171 | 1H NMR (400 MHz, Methanol-d4) δ 8.79 (d, J = 2.2 Hz, 1H), 8.70 (d, J = 2.2 Hz, 1H), 8.53 (s, 1H), 8.12 (d, J = 5.1 Hz, 1H), 7.93 (s, 1H), 7.25 (d, J = 5.0 Hz, 1H), 4.30 (dq, J = 9.4, 4.7, 4.2 Hz, 1H), 4.04 (ddd, J = 17.0, 8.5, 4.5 Hz, 3H), 3.83 (dd, J = 12.2, 3.1 Hz, 2H), 3.78-3.68 (m, 2H), 3.63-3.51 (m, 2H), 2.46 (s, 2H), 2.20 (d, J = 13.1 Hz, 2H), 2.00 (s, 5H), 1.81 (ddt, J = 13.8, 9.6, 5.0 Hz, 2H), 1.70 (d, J = 8.4 Hz, 2H). |
| 172 | 1H NMR (400 MHz, Methanol-d4) δ 8.78 (d, J = 2.2 Hz, 1H), 8.70 (d, J = 2.2 Hz, 1H), 8.50 (s, 1H), 8.09 (d, J = 5.1 Hz, 1H), 7.89 (s, 1H), 7.25 (d, J = 5.0 Hz, 1H), 4.31 (hept, J = 6.4 Hz, 1H), 4.10-3.97 (m, 2H), 3.64 (td, J = 12.8, 3.4 Hz, 2H), 2.09-1.86 (m, 4H), 1.49 (d, J = 6.4 Hz, 6H). |
| 173 | 1H NMR (400 MHz, Methanol-d4) δ 8.81 (d, J = 5.1 Hz, 1H), 8.80-8.77 (m, 1H), 8.71 (d, J = 2.1 Hz, 1H), 8.55 (s, 1H), 8.09 (d, J = 5.1 Hz, 1H), 7.90 (s, 1H), 7.25 (d, J = 5.1 Hz, 1H), 4.32 (p, J = 6.3 Hz, 1H), 4.06-3.89 (m, 4H), 3.78 (t, J = 5.0 Hz, 1H), 2.78-2.66 (m, 1H), 2.62 (d, J = 6.3 Hz, 2H), 2.05 (s, 3H), 1.69 (dd, J = 10.2, 5.7 Hz, 1H), 1.50 (d, J = 6.4 Hz, 6H). |
| 174 | 1H NMR (400 MHz, Methanol-d4) δ 8.80 (d, J = 2.2 Hz, 1H), 8.72 (d, J = 2.2 Hz, 1H), 8.69 (s, 1H), 8.14 (d, J = 5.1 Hz, 1H), 8.12 (s, 1H), 7.27 (d, J = 5.0 Hz, 1H), 5.26 (q, J = 6.8 Hz, 1H), 4.03-3.88 (m, 4H), 3.78 (d, J = 5.5 Hz, 1H), 2.72 (dd, J = 10.2, 6.2 Hz, 1H), 2.63 (d, J = 6.3 Hz, 2H), 2.05 (s, 3H), 1.93 (d, J = 7.0 Hz, 3H), 1.70 (dd, J = 10.2, 5.9 Hz, 1H). |
| 175 | 1H NMR (400 MHz, Methanol-d4) δ 8.79 (d, J = 2.2 Hz, 1H), 8.75 (d, J = 2.2 Hz, 1H), 8.59 (s, 1H), 7.96 (d, J = 5.1 Hz, 1H), 7.68 (s, 1H), 7.25 (d, J = 5.0 Hz, 1H), 5.03 (d, J = 6.6 Hz, 2H), 4.88 (d, J = 6.6 Hz, 2H), 4.03-3.90 (m, 4H), 3.78 (d, J = 5.5 Hz, 1H), 2.72 (dd, J = 10.6, 6.0 Hz, 1H), 2.62 (d, J = 6.3 Hz, 2H), 2.05 (s, 3H), 1.95 (s, 3H), 1.69 (dd, J = 10.2, 5.8 Hz, 1H). |
| 176 | 1H NMR (400 MHz, Methanol-d4) δ 8.79 (d, J = 2.1 Hz, 1H), 8.71 (d, J = 2.1 Hz, 1H), 8.53 (s, 1H), 8.12 (d, J = 5.1 Hz, 1H), 7.84 (s, 1H), 7.26 (d, J = 5.1 Hz, 1H), 4.02-3.90 (m, 4H), 3.77 (d, J = 5.6 Hz, 1H), 3.35 (s, 3H), 2.77-2.67 (m, 1H), 2.62 (d, J = 6.3 Hz, 2H), 2.05 (s, 3H), 1.69 (dd, J = 10.2, 5.8 Hz, 1H). |
| 177 | 1H NMR (400 MHz, Methanol-d4) δ 8.80 (d, J = 2.2 Hz, 1H), 8.71 (d, J = 2.2 Hz, 1H), 8.59 (s, 1H), 8.14 (d, J = 5.0 Hz, 1H), 7.95 (s, 1H), 7.26 (d, J = 5.1 Hz, 1H), 4.82 (d, J = 6.7 Hz, 2H), 4.33 (dq, J = 9.9, 5.4, 4.9 Hz, 1H), 4.06 (dt, J = 12.1, 4.0 Hz, 2H), 3.95 (d, J = 11.7 Hz, 2H), 3.85 (d, J = 11.7 Hz, 2H), 3.80-3.66 (m, 2H), 3.44-3.37 (m, 3H), 2.22 (d, J = 13.1 Hz, 2H), 2.10 (d, J = 9.4 Hz, 1H), 1.88-1.77 (m, 2H). |
| 178 | 1H NMR (400 MHz, Methanol-d4) δ 8.80 (d, J = 2.1 Hz, 1H), 8.72 (d, J = 2.1 Hz, 1H), 8.70 (s, 1H), 8.16-8.08 (m, 2H), 7.27 (d, J = 5.1 Hz, 1H), 5.25 (q, J = 6.9 Hz, 1H), 4.82 (d, J = 7.1 Hz, 2H), 3.99-3.78 (m, 4H), 2.10 (d, J = 9.5 Hz, 3H), 1.93 (d, J = 7.0 Hz, 6H), 1.83-1.74 (m, 1H), 1.44-1.35 (m, 1H). |
| 179 | 1H NMR (400 MHz, Methanol-d4) δ 8.79 (d, J = 2.1 Hz, 1H), 8.73 (d, J = 2.2 Hz, 1H), 8.61 (s, 1H), 8.08 (d, J = 5.1 Hz, 1H), 7.67 (s, 1H), 7.25 (d, J = 5.1 Hz, 1H), 5.33-5.15 (m, 3H), 4.85-4.76 (m, 3H), 3.98 (s, 4H), 3.79 (t, J = 5.1 Hz, 1H), 2.72 (dd, J = 10.4, 6.0 Hz, 1H), 2.63 (d, J = 6.3 Hz, 2H), 2.05 (s, 3H), 1.70 (dd, J = 10.3, 5.8 Hz, 1H). |
| 180 | 1H NMR (400 MHz, Methanol-d4) δ 8.78 (d, J = 2.2 Hz, 1H), 8.70 (d, J = 2.2 Hz, 1H), 8.62 (s, 1H), 8.14 (s, 1H), 8.11 (d, J = 5.0 Hz, 1H), 7.26 (d, J = 5.0 Hz, 1H), 5.22 (q, J = 7.1 Hz, 1H), 3.83 (d, J = 12.9 Hz, 2H), 3.79-3.64 (m, 2H), 1.91 (d, J = 7.0 Hz, 3H), 1.86-1.73 (m, 4H), 1.32 (s, 3H). |

TABLE 1-continued

| Compound | 1H-NMR |
|---|---|
| 181 | 1H NMR (400 MHz, Methanol-d4) δ 8.78 (d, J = 2.2 Hz, 1H), 8.74 (d, J = 2.2 Hz, 1H), 8.53 (s, 1H), 7.96 (d, J = 5.1 Hz, 1H), 7.66 (s, 1H), 7.25 (d, J = 5.1 Hz, 1H), 5.02 (d, J = 6.7 Hz, 2H), 4.87 (d, J = 6.7 Hz, 2H), 3.83 (dt, J = 12.9, 4.1 Hz, 2H), 3.74-3.64 (m, 2H), 1.94 (s, 3H), 1.86-1.72 (m, 4H), 1.32 (s, 3H). |
| 182 | 1H NMR (400 MHz, Methanol-d4) δ 8.78 (d, J = 2.1 Hz, 1H), 8.70 (d, J = 2.2 Hz, 1H), 8.50 (s, 1H), 8.09 (d, J = 5.0 Hz, 1H), 7.88 (s, 1H), 7.25 (d, J = 5.1 Hz, 1H), 4.38-4.21 (m, 2H), 4.19-4.07 (m, 2H), 4.01 (d, J = 13.3 Hz, 2H), 3.95-3.79 (m, 4H), 2.13 (s, 2H), 2.06 (s, 3H), 1.49 (d, J = 6.4 Hz, 6H). |
| 183 | 1H NMR (400 MHz, Methanol-d4) δ 8.80 (d, J = 2.2 Hz, 1H), 8.73 (d, J = 2.2 Hz, 1H), 8.59 (s, 1H), 8.51 (d, J = 9.0 Hz, 1H), 8.08 (d, J = 5.1 Hz, 1H), 7.67 (s, 1H), 7.25 (d, J = 5.0 Hz, 1H), 5.32-5.17 (m, 3H), 4.80 (t, J = 6.0 Hz, 2H), 4.68-4.50 (m, 1H), 4.46 (d, J = 10.6 Hz, 1H), 4.15 (d, J = 13.8 Hz, 1H), 3.81 (dd, J = 29.4, 14.0 Hz, 1H), 3.63 (t, J = 11.7 Hz, 1H), 2.17-1.92 (m, 5H). |
| 184 | 1H NMR (400 MHz, Methanol-d4) δ 8.79 (d, J = 2.2 Hz, 1H), 8.73 (d, J = 2.2 Hz, 1H), 8.57 (s, 1H), 8.08 (d, J = 5.1 Hz, 1H), 8.05 (d, J = 5.9 Hz, 1H), 7.65 (s, 1H), 7.25 (d, J = 5.1 Hz, 1H), 5.32-5.14 (m, 3H), 4.80 (t, J = 6.0 Hz, 2H), 4.01 (s, 1H), 3.84 (d, J = 11.8 Hz, 2H), 3.58 (d, J = 11.9 Hz, 2H), 2.46 (s, 2H), 2.11-1.95 (m, 5H), 1.70 (d, J = 8.5 Hz, 2H). |
| 185 | 1H NMR (400 MHz, Methanol-d4) δ 8.80-8.76 (m, 2H), 8.70 (d, J = 2.2 Hz, 1H), 8.10 (d, J = 5.1 Hz, 1H), 8.05-7.99 (m, 2H), 7.98 (s, 1H), 7.78 (d, J = 8.8 Hz, 2H), 7.26 (d, J = 5.0 Hz, 1H), 4.34 (hept, J = 6.4 Hz, 1H), 2.19 (s, 3H), 1.55 (d, J = 6.4 Hz, 6H). |
| 186 | 1H NMR (400 MHz, Methanol-d4) δ 8.78 (d, J = 2.1 Hz, 1H), 8.70 (d, J = 2.2 Hz, 1H), 8.50 (s, 1H), 8.08 (d, J = 5.1 Hz, 1H), 7.89 (s, 1H), 7.25 (d, J = 5.0 Hz, 1H), 4.53 (ddd, J = 47.1, 8.5, 4.2 Hz, 1H), 4.31 (p, J = 6.4 Hz, 1H), 4.03 (td, J = 13.0, 4.2 Hz, 1H), 3.90-3.64 (m, 3H), 2.05-1.90 (m, 1H), 1.82 (ddd, J = 14.1, 9.6, 4.7 Hz, 1H), 1.49 (d, J = 6.4 Hz, 6H), 1.40 (d, J = 1.0 Hz, 3H). |
| 187 | 1H NMR (400 MHz, Methanol-d4) δ 8.79 (d, J = 2.2 Hz, 1H), 8.72 (d, J = 2.2 Hz, 1H), 8.55 (s, 1H), 8.07 (d, J = 5.0 Hz, 1H), 7.65 (s, 1H), 7.25 (d, J = 5.1 Hz, 1H), 5.31-5.17 (m, 3H), 4.80 (dd, J = 6.6, 5.2 Hz, 2H), 3.88-3.79 (m, 2H), 3.77-3.63 (m, 2H), 1.86-1.71 (m, 4H), 1.33 (s, 3H). |
| 188 | 1H NMR (400 MHz, Methanol-d4) δ 8.79 (d, J = 2.1 Hz, 1H), 8.70 (d, J = 2.2 Hz, 1H), 8.52 (s, 1H), 8.12 (d, J = 5.1 Hz, 1H), 7.92 (s, 1H), 7.25 (d, J = 5.1 Hz, 1H), 4.31 (dt, J = 9.8, 5.4 Hz, 1H), 4.05 (dt, J = 11.9, 4.1 Hz, 2H), 3.89-3.64 (m, 6H), 2.20 (d, J = 13.1 Hz, 2H), 1.87-1.73 (m, 6H), 1.32 (s, 3H). |
| 189 | 1H NMR (400 MHz, Methanol-d4) δ 8.78 (d, J = 2.1 Hz, 1H), 8.70 (d, J = 2.1 Hz, 1H), 8.49 (s, 1H), 8.09 (d, J = 5.1 Hz, 1H), 7.89 (s, 1H), 7.25 (d, J = 5.0 Hz, 1H), 4.36-4.27 (m, 2H), 4.21 (s, 1H), 3.98-3.87 (m, 2H), 3.69 (td, J = 12.7, 3.4 Hz, 2H), 1.88 (td, J = 13.0, 12.6, 4.9 Hz, 2H), 1.81-1.71 (m, 2H), 1.49 (d, J = 6.4 Hz, 6H). |
| 190 | 1H NMR (400 MHz, Methanol-d4) δ 8.78 (d, J = 2.2 Hz, 1H), 8.70 (d, J = 2.1 Hz, 1H), 8.48 (s, 1H), 8.09 (d, J = 5.1 Hz, 1H), 7.88 (s, 1H), 7.25 (d, J = 5.1 Hz, 1H), 4.53-4.33 (m, 1H), 4.33-4.25 (m, 1H), 4.13 (t, J = 13.3 Hz, 1H), 3.99-3.81 (m, 2H), 3.68 (td, J = 12.8, 3.1 Hz, 1H), 2.04 (tt, J = 13.3, 4.3 Hz, 1H), 1.68 (d, J = 14.0 Hz, 1H), 1.49 (d, J = 6.4 Hz, 6H), 1.35 (s, 3H). |
| 191 | 1H NMR (400 MHz, Methanol-d4) δ 8.78 (d, J = 2.1 Hz, 1H), 8.70 (d, J = 2.2 Hz, 1H), 8.48 (s, 1H), 8.08 (d, J = 5.0 Hz, 1H), 7.88 (s, 1H), 7.25 (d, J = 5.0 Hz, 1H), 4.53-4.23 (m, 2H), 4.13 (t, J = 13.3 Hz, 1H), 4.03-3.83 (m, 2H), 3.68 (td, J = 12.8, 3.1 Hz, 1H), 2.13-1.92 (m, 1H), 1.68 (d, J = 14.1 Hz, 1H), 1.49 (d, J = 6.4 Hz, 6H), 1.35 (d, J = 2.2 Hz, 3H). |
| 192 | 1H NMR (400 MHz, Methanol-d4) δ 8.78 (d, J = 2.2 Hz, 1H), 8.70 (d, J = 2.2 Hz, 1H), 8.50 (s, 1H), 8.08 (d, J = 5.0 Hz, 1H), 7.89 (s, 1H), 7.25 (d, J = 5.1 Hz, 1H), 4.53 (ddd, J = 47.1, 8.5, 4.2 Hz, 1H), 4.38-4.25 (m, 1H), 4.03 (td, J = 13.0, 4.2 Hz, 1H), 3.89-3.60 (m, 3H), 2.05-1.90 (m, 1H), 1.88-1.76 (m, 1H), 1.49 (d, J = 6.4 Hz, 6H), 1.40 (s, 3H). |
| 193 | 1H NMR (400 MHz, Methanol-d4) δ 8.78 (d, J = 2.2 Hz, 1H), 8.70 (d, J = 2.2 Hz, 1H), 8.48 (s, 1H), 8.09 (d, J = 5.1 Hz, 1H), 7.88 (s, 1H), 7.25 (d, J = 5.0 Hz, 1H), 4.38-4.18 (m, 3H), 4.08 (d, J = 12.6 Hz, 2H), 3.95-3.80 (m, 5H), 2.08 (s, 3H), 2.05 (d, J = 7.4 Hz, 2H), 1.49 (d, J = 6.4 Hz, 6H). |
| 194 | ¹H NMR (400 MHz, Methanol-d₄) δ 8.84-8.77 (m, 2H), 8.72 (dd, J = 2.1, 1.2 Hz, 1H), 8.11 (dd, J =5.1, 1.5 Hz, 1H), 8.00 (d, 7 = 4.3 Hz, 1H), 7.26 (dd, J = 5.0, 1.1 Hz, 1H), 4.45-4.25 (m, 1H), 4.12-3.84 (m, 1H), 2.59-2.33 (m, 2H), 2.33-2.17 (m, 2H), 2.15-1.68 (m, 7H), 1.52 (dd, 7= 6.4, 2.4 Hz, 6H). |
| 194 Isomer 1 | 1H NMR (400 MHz, Methanol-d4) δ 8.83-8.75 (m, 2H), 8.72 (d, J = 2.1 Hz, 1H), 8.10 (d, J = 5.0 Hz, 1H), 8.01 (s, 1H), 7.26 (d, J = 5.0 Hz, 1H), 4.35 (hept, J = 6.3 Hz, 1H), 4.09-3.99 (m, 1H), 2.51 (dddd, J = 23.6, 13.7, 9.2, 4.3 Hz, 2H), 2.34-2.17 (m, 2H), 2.17-2.02 (m, 2H), 1.99 (s, 3H), 1.90 (dq, J = 13.7, 7.1 Hz, 2H), 1.52 (d, J = 6.4 Hz, 6H). |
| 194 Isomer 2 | 1H NMR (400 MHz, Methanol-d4) δ 8.85-8.77 (m, 2H), 8.71 (d, J = 2.2 Hz, 1H), 8.10 (d, J = 5.0 Hz, 1H), 8.00 (s, 1H), 7.26 (d, J = 5.1 Hz, 1H), 4.34 (hept, J = 6.4 Hz, 1H), 3.98-3.80 (m, 1H), 2.53-2.20 (m, 4H), 2.12-1.94 (m, 5H), 1.77 (qd, J = 12.5, 4.3 Hz, 2H), 1.51 (d, J = 6.4 Hz, 6H). |
| 195 | 1H NMR (400 MHz, Methanol-d4) δ 8.87 (s, 1H), 8.81 (d, J = 2.2 Hz, 1H), 8.75 (d, J = 2.2 Hz, 1H), 8.10 (d, J = 5.1 Hz, 1H), 7.75 (s, 1H), 7.27 (d, J = 5.1 Hz, 1H), 5.38-5.26 (m, 1H), 5.22 (q, J = 6.8, 6.1 Hz, 2H), 4.83 (dd, J = 6.9, 5.6 Hz, 2H), 3.98-3.85 (m, 1H), 2.50-2.22 (m, 2H), 2.04 (d, J = 14.2 Hz, 4H), 1.98 (s, 3H), 1.86-1.70 (m, 2H). |

TABLE 1-continued

| Compound | 1H-NMR |
|---|---|
| 196 | 1H NMR (400 MHz, Methanol-d4) δ 8.88 (s, 1H), 8.80 (d, J = 2.2 Hz, 1H), 8.75 (d, J = 2.1 Hz, 1H), 8.10 (d, J = 5.1 Hz, 1H), 7.77 (s, 1H), 7.26 (d, J = 5.1 Hz, 1H), 5.38-5.26 (m, 1H), 5.26-5.19 (m, 2H), 4.82 (dd, J = 6.9, 5.5 Hz, 2H), 4.09-3.99 (m, 1H), 2.53 (dddd, J = 23.8, 13.7, 9.2, 4.2 Hz, 2H), 2.35-2.19 (m, 2H), 2.09 (ddd, J = 14.3, 9.3, 4.6 Hz, 2H), 2.00 (s, 3H), 1.98-1.81 (m, 2H). |
| 197 | 1H NMR (400 MHz, Methanol-d4) δ 8.81-8.78 (m, 1H), 8.73 (s, 1H), 8.71 (d, J = 2.5 Hz, 1H), 8.12-8.08 (m, 1H), 7.98 (s, 1H), 7.25 (d, J = 5.0 Hz, 1H), 4.39-4.25 (m, 6H), 2.01 (s, 3H), 1.51 (d, J = 5.9 Hz, 6H). |
| 198 | 1H NMR (400 MHz, Methanol-d4) δ 8.82 (s, 1H), 8.79 (d, J = 2.1 Hz, 1H), 8.74 (d, J = 2.1 Hz, 1H), 8.09 (d, J = 5.1 Hz, 1H), 7.73 (s, 1H), 7.26 (d, J = 5.0 Hz, 1H), 5.37-5.14 (m, 3H), 4.81 (dd, J = 6.8, 5.5 Hz, 2H), 4.30 (s, 2H), 2.49 (t, J = 12.3 Hz, 2H), 2.42-2.26 (m, 4H), 2.12 (t, J = 11.8 Hz, 2H), 1.94 (s, 3H). |
| 199 | 1H NMR (400 MHz, Methanol-d4) δ 8.78 (d, J = 2.2 Hz, 1H), 8.75-8.68 (m, 2H), 8.09 (d, J = 5.1 Hz, 1H), 7.99 (s, 1H), 7.25 (d, J = 5.1 Hz, 1H), 4.38-4.25 (m, 1H), 3.80-3.63 (m, 1H), 2.69 (ddd, J = 9.4, 8.2, 2.6 Hz, 2H), 2.62-2.47 (m, 2H), 1.54-1.46 (m, 9H). |
| 200 | 1H NMR (400 MHz, Methanol-d4) δ 8.81-8.77 (m, 2H), 8.73 (d, J = 2.2 Hz, 1H), 8.08 (d, J = 5.1 Hz, 1H), 7.75 (s, 1H), 7.25 (d, J = 5.1 Hz, 1H), 5.32-5.15 (m, 3H), 4.82 (dd, J = 6.6, 5.1 Hz, 2H), 3.84-3.64 (m, 1H), 2.70 (ddd, J = 9.4, 8.2, 2.7 Hz, 2H), 2.61-2.50 (m, 2H), 1.52 (s, 3H). |
| 201 | 1H NMR (400 MHz, Methanol-d4) δ 8.80 (d, J = 2.2 Hz, 1H), 8.77 (s, 1H), 8.72 (d, J = 2.2 Hz, 1H), 8.14 (d, J = 5.1 Hz, 1H), 8.02 (s, 1H), 7.27 (d, J = 5.0 Hz, 1H), 4.67 (t, J = 7.8 Hz, 1H), 4.34 (dt, J = 9.9, 5.4 Hz, 1H), 4.14-4.00 (m, 3H), 3.80-3.69 (m, 2H), 2.87-2.76 (m, 2H), 2.74-2.60 (m, 2H), 2.22 (d, J = 13.1 Hz, 2H), 1.98 (s, 3H), 1.93-1.78 (m, 2H). |
| 202 | 1H NMR (400 MHz, Methanol-d4) δ 8.83-8.78 (m, 2H), 8.74 (d, J = 2.1 Hz, 1H), 8.10 (d, J = 5.1 Hz, 1H), 7.75 (s, 1H), 7.26 (d, J = 5.1 Hz, 1H), 5.33-5.17 (m, 3H), 4.84 (dd, J = 6.9, 5.6 Hz, 2H), 4.73-4.64 (m, 1H), 4.18-4.05 (m, 1H), 2.90-2.76 (m, 2H), 2.70 (ddd, J = 12.9, 9.8, 7.6 Hz, 2H), 1.99 (s, 3H). |
| 203 | 1H NMR (400 MHz, Methanol-d4) δ 8.85-8.77 (m, 2H), 8.74 (d, J = 2.2 Hz, 1H), 8.10 (d, J = 5.1 Hz, 1H), 7.74 (s, 1H), 7.26 (d, J = 5.1 Hz, 1H), 5.38-5.26 (m, 1H), 5.23 (t, J = 6.8 Hz, 2H), 4.83 (dd, J = 6.9, 5.5 Hz, 2H), 4.06-3.94 (m, 1H), 3.56-3.47 (m, 1H), 2.17 (ddd, J = 24.5, 13.9, 8.0 Hz, 4H), 1.91-1.78 (m, 4H), 1.66 (td, J = 8.0, 4.1 Hz, 1H), 0.86 (dt, J = 4.6, 3.1 Hz, 2H), 0.76 (dt, J = 8.1, 3.2 Hz, 2H). |
| 204 | 1H NMR (400 MHz, Methanol-d4) δ 8.78 (d, J = 2.1 Hz, 1H), 8.70 (d, J = 2.2 Hz, 1H), 8.51 (s, 1H), 8.12 (d, J = 5.1 Hz, 1H), 7.93 (s, 1H), 7.25 (d, J = 5.1 Hz, 1H), 4.56-4.24 (m, 2H), 4.21-4.00 (m, 3H), 4.00-3.80 (m, 2H), 3.80-3.61 (m, 3H), 2.20 (d, J = 13.1 Hz, 2H), 2.11-1.96 (m, 1H), 1.86-1.61 (m, 3H), 1.35 (d, J = 2.2 Hz, 3H). |
| 205 | 1H NMR (400 MHz, Methanol-d4) δ 8.84-8.78 (m, 2H), 8.74 (d, J = 2.2 Hz, 1H), 8.09 (d, J = 5.0 Hz, 1H), 7.74 (s, 1H), 7.26 (d, J = 5.1 Hz, 1H), 5.34-5.19 (m, 3H), 4.83 (dd, J = 6.8, 5.4 Hz, 2H), 3.77 (t, J = 5.1 Hz, 1H), 3.66 (s, 3H), 3.53-3.43 (m, 1H), 2.24-2.03 (m, 4H), 1.92-1.79 (m, 4H). |
| 206 | 1H NMR (400 MHz, Methanol-d4) δ 8.80-8.76 (m, 2H), 8.72 (d, J = 2.2 Hz, 1H), 8.07 (d, J = 5.0 Hz, 1H), 7.78 (s, 1H), 7.24 (d, J = 5.1 Hz, 1H), 5.30-5.19 (m, 3H), 4.86-4.78 (m, 2H), 3.45-3.36 (m, 1H), 2.35-2.20 (m, 2H), 1.99-1.78 (m, 4H), 1.78-1.64 (m, 2H), 1.31 (s, 3H). |
| 207 | 1H NMR (400 MHz, Methanol-d4) δ 8.79 (d, J = 2.2 Hz, 1H), 8.72 (d, J = 2.2 Hz, 1H), 8.55 (s, 1H). 8.07 (d, J = 5.0 Hz, 1H), 7.66 (s, 1H), 7.25 (d, J = 5.1 Hz, 1H), 5.31-5.16 (m, 3H), 4.80 (dd, J = 6.7, 5.3 Hz, 2H), 4.42 (d, J = 46.4 Hz, 1H), 4.16 (t, J = 13.1 Hz, 1H), 4.02-3.80 (m, 2H), 3.73-3.61 (m, 1H), 2.05 (t, J = 13.6 Hz, 1H), 1.69 (d, J = 14.0 Hz, 1H), 1.35 (s, 3H). |
| 208 | 1H NMR (400 MHz, Methanol-d4) δ 8.80-8.76 (m, 2H), 8.72 (d, J = 2.2 Hz, 1H), 8.07 (d, J = 5.0 Hz, 1H), 7.78 (s, 1H), 7.24 (d, J = 5.1 Hz, 1H), 5.30-5.19 (m, 3H), 4.86-4.78 (m, 2H), 3.45-3.36 (m, 1H), 2.35-2.20 (m, 2H), 1.99-1.78 (m, 4H), 1.78-1.64 (m, 2H), 1.31 (s, 3H). |
| 209 | 1H NMR (400 MHz, Methanol-d4) δ 8.79 (d, J = 2.2 Hz, 1H), 8.70 (d, J = 2.2 Hz, 1H), 8.51 (s, 1H), 8.09 (d, J = 5.1 Hz, 1H), 7.90 (s, 1H), 7.25 (d, J = 5.1 Hz, 1H), 5.25-5.10 (m, 1H), 4.40-4.24 (m, 1H), 4.16 (s, 2H), 4.14-4.04 (m, 2H), 4.03-3.87 (m, 3H), 2.25 (dd, J = 13.3, 5.7 Hz, 2H), 1.97-1.81 (m, 5H), 1.49 (d, J = 6.4 Hz, 6H). |
| 210 | 1H NMR (400 MHz, Methanol-d4) δ 8.76 (s, 1H), 8.73 (s, 1H), 8.54 (s, 1H), 7.94 (d, J = 5.0 Hz, 1H), 7.70 (s, 1H), 7.44 (d, J = 6.2 Hz, 1H), 7.24 (d, J = 5.0 Hz, 1H), 5.04-5.00 (m, 2H), 4.86 (d, J = 6.7 Hz, 2H), 4.00 (d, J = 6.4 Hz, 2H), 3.85 (d, J = 11.6 Hz, 2H), 3.58 (d, J = 12.2 Hz, 2H), 2.55-2.45 (m, 2H), 2.07-1.97 (m, 2H), 1.94 (s, 3H), 1.75 (d, J = 8.8 Hz, 2H), 1.40 (d, J = 6H). |
| 211 | 1H NMR (400 MHz, Methanol-d4) δ 9.62 (s, 1H), 8.83 (s, 1H), 8.78 (d, J = 2.2 Hz, 1H), 8.71 (d, J = 2.2 Hz, 1H), 8.10 (d, J = 5.0 Hz, 1H), 8.02 (s, 1H), 7.26 (d, J = 5.1 Hz, 1H), 4.35 (hept, J = 6.3 Hz, 1H), 1.53 (d, J = 6.4 Hz, 6H). |
| 212 | 1H NMR (400 MHz, Methanol-d4) δ 8.82-8.63 (m, 3H), 8.07 (d, J = 5.3 Hz, 2H), 7.24 (d, J = 5.0 Hz, 1H), 4.31 (p, J = 6.4 Hz, 1H), 3.66-3.55 (m, 4H), 1.50 (d, J = 6.4 Hz, 6H). |
| 213 | 1H NMR (400 MHz, Methanol-d4) δ 8.79 (s, 1H), 8.72 (d, J = 2.1 Hz, 1H), 8.66 (d, J = 2.2 Hz, 1H), 8.13 (s, 1H), 8.03 (d, J = 5.0 Hz, 1H), 7.21 (d, J = 5.0 Hz, 1H), 4.65 (dd, J = 9.8, 4.7 Hz, 1H), 4.55-4.47 (m, 1H), 4.26 (p, J = 6.4 Hz, 1H), 2.58-2.47 (m, 2H), 2.40 (ddd, J = 12.8, 8.3, 4.2 Hz, 2H), 1.50 (d, J = 6.4 Hz, 6H). |

TABLE 1-continued

| Compound | 1H-NMR |
|---|---|
| 214 | 1H NMR (400 MHz, Methanol-d4) δ 8.85 (d, J = 1.2 Hz, 1H), 8.79 (d, J = 2.1 Hz, 1H), 8.72 (d, J = 2.2 Hz, 1H), 8.11 (d, J = 5.1 Hz, 1H), 8.02 (s, 1H), 7.26 (d, J = 5.0 Hz, 1H), 4.36 (tdd, J = 14.5, 8.2, 4.5 Hz, 2H), 4.26 (dt, J = 11.9, 7.2 Hz, 1H), 4.17 (ddd, J = 12.3, 7.5, 5.3 Hz, 1H), 3.89-3.70 (m, 2H), 3.63 (dd, J = 11.1, 7.1 Hz, 0H), 2.31-1.90 (m, 4H), 1.53 (d, J = 6.4 Hz, 6H). |
| 215 | 1H NMR (400 MHz, Methanol-d4) δ 8.82 (s, 1H), 8.77 (d, J = 2.1 Hz, 1H), 8.69 (d, J = 2.2 Hz, 1H), 8.08 (d, J = 5.1 Hz, 1H), 8.01 (s, 1H), 7.24 (d, J = 5.0 Hz, 1H), 4.33 (p, J = 6.4 Hz, 1H), 4.14-4.01 (m, 2H), 2.77 (dtd, J = 9.7, 7.0, 3.1 Hz, 2H), 2.17-2.03 (m, 2H), 1.50 (d, J = 6.4 Hz, 6H). |
| 216 | 1H NMR (400 MHz, Methanol-d4) δ 8.86 (d, J = 0.9 Hz, 1H), 8.80 (d, J = 2.2 Hz, 1H), 8.73 (d, J = 2.2 Hz, 1H), 8.13 (d, J = 5.1 Hz, 1H), 8.01 (s, 1H), 7.27 (d, J = 5.1 Hz, 1H), 4.43-4.32 (m, 2H), 4.14 (dt, J = 12.0, 7.8 Hz, 1H), 4.00-3.83 (m, 2H), 3.75-3.58 (m, 3H), 3.52 (dd, J = 12.8, 7.2 Hz, 1H), 2.58 (dp, J = 33.2, 7.1 Hz, 1H), 2.32-2.10 (m, 1H), 1.89 (ddq, J = 44.3, 12.6, 8.2 Hz, 1H), 1.53 (d, J = 6.4 Hz, 6H). |
| 217 | 1H NMR (400 MHz, Methanol-d4) δ 8.86 (d, J = 1.6 Hz, 1H), 8.79 (d, J = 2.1 Hz, 1H), 8.73 (d, J = 2.1 Hz, 1H), 8.14 (d, J = 5.1 Hz, 1H), 8.01 (s, 1H), 7.27 (d, J = 5.0 Hz, 1H), 4.44-4.30 (m, 2H), 4.30-4.12 (m, 1H), 3.89-3.69 (m, 2H), 3.62 (dd, J = 11.1, 7.1 Hz, 0H), 2.26-1.98 (m, 4H), 1.53 (d, J = 6.3 Hz, 6H). |
| 218 | 1H NMR (400 MHz, Methanol-d4) δ 8.83 (s, 1H), 8.78 (d, J = 2.2 Hz, 1H), 8.71 (d, J = 2.2 Hz, 1H), 8.09 (d, J = 5.0 Hz, 1H), 8.04 (s, 1H), 7.25 (d, J = 5.1 Hz, 1H), 4.34 (hept, J = 6.3 Hz, 1H), 4.23-4.11 (m, 1H), 2.54 (ddd, J = 10.1, 7.6, 2.8 Hz, 2H), 2.29 (dd, J = 11.7, 8.7 Hz, 2H), 1.52 (d, J = 6.4 Hz, 6H), 1.42 (s, 3H). |
| 219 | 1H NMR (400 MHz, DMSO-d6) δ 9.60 (d, J = 7.7 Hz, 1H), 9.13 (s, 1H), 8.93 (d, J = 2.2 Hz, 1H), 8.87 (s, 1H), 8.81 (d, J = 2.2 Hz, 1H), 8.22 (s, 1H), 7.98 (d, J = 4.9 Hz, 1H), 7.19 (d, J = 4.9 Hz, 1H), 4.54 (p, J = 7.9 Hz, 1H), 4.08 (dt, J = 13.1, 6.5 Hz, 1H), 2.33-2.16 (m, 4H), 1.39 (d, J = 6.3 Hz, 6H), 1.29 (s, 3H). |
| 220 | 1H NMR (400 MHz, Methanol-d4) δ 8.80 (s, 1H), 8.74 (d, J = 2.2 Hz, 1H), 8.68 (d, J = 2.2 Hz, 1H), 8.09 (s, 1H), 8.06 (d, J = 5.0 Hz, 1H), 7.22 (d, J = 5.0 Hz, 1H), 2.05 (d, J = 11.7 Hz, 4H), 1.65-1.51 (m, 2H), 1.50 (d, J = 6.4 Hz, 6H), 1.48-1.36 (m, 2H). |
| 221 | 1H NMR (400 MHz, Methanol-d4) δ 8.86 (s, 1H), 8.79 (d, J = 2.1 Hz, 1H), 8.72 (d, J = 2.2 Hz, 1H), 8.13 (d, J = 5.0 Hz, 1H), 8.03 (s, 1H), 7.26 (d, J = 5.0 Hz, 1H), 4.38 (ddt, J = 19.3, 12.9, 6.9 Hz, 2H), 4.14 (dt, J = 12.2, 7.7 Hz, 1H), 4.01-3.80 (m, 2H), 3.76-3.58 (m, 3H), 3.55-3.48 (m, 1H), 2.68-2.48 (m, 1H), 2.26-2.10 (m, 1H), 2.00-1.78 (m, 1H), 1.53 (d, J = 6.4 Hz, 6H). |
| 222 | 1H NMR (400 MHz, Methanol-d4) δ 8.85 (d, J = 1.9 Hz, 1H), 8.79 (d, J = 2.1 Hz, 1H), 8.72 (d, J = 2.1 Hz, 1H), 8.11 (d, J = 5.1 Hz, 1H), 8.02 (d, J = 1.3 Hz, 1H), 7.26 (d, J = 5.0 Hz, 1H), 4.41-4.20 (m, 4H), 4.12-4.03 (m, 1H), 3.92 (dd, J = 13.0, 6.2 Hz, 1H), 3.87-3.73 (m, 1H), 3.63 (dd, J = 12.9, 4.5 Hz, 0H), 2.38-2.20 (m, 1H), 2.04 (ddq, J = 36.4, 13.0, 6.4 Hz, 1H), 1.53 (d, J = 6.4 Hz, 6H), 1.48 (d, J = 3.9 Hz, 9H). |
| 223 | 1H NMR (400 MHz, Methanol-d4) δ 8.85 (d, J = 1.8 Hz, 1H), 8.79 (d, J = 2.2 Hz, 1H), 8.72 (d, J = 2.1 Hz, 1H), 8.11 (d, J = 5.1 Hz, 1H), 8.02 (d, J = 1.2 Hz, 1H), 7.26 (d, J = 5.1 Hz, 1H), 4.43-4.20 (m, 4H), 4.08 (d, J = 12.1 Hz, 1H), 3.92 (dd, J = 12.9, 6.2 Hz, 0H), 3.81 (qt, J = 12.9, 7.1 Hz, 1H), 3.63 (dd, J = 13.0, 4.4 Hz, 0H), 2.28 (ddt, J = 33.8, 13.4, 6.6 Hz, 1H), 2.04 (ddq, J = 32.8, 13.3, 6.4 Hz, 1H), 1.53 (d, J = 6.4 Hz, 6H), 1.48 (d, J = 4.0 Hz, 10H). |
| 224 | 1H NMR (400 MHz, Methanol-d4) δ 8.80 (s, 1H), 8.72 (d, J = 2.1 Hz, 1H), 8.66 (d, J = 2.2 Hz, 1H), 8.15 (s, 1H), 8.04 (d, J = 5.0 Hz, 1H), 7.21 (d, J = 5.0 Hz, 1H), 4.32-4.19 (m, 1H), 3.98 (t, J = 3.9 Hz, 2H), 1.99-1.66 (m, 8H), 1.50 (d, J = 6.4 Hz, 6H). |
| 225 | 1H NMR (400 MHz, Methanol-d4) δ 8.85 (d, J = 1.8 Hz, 1H), 8.80 (d, J = 2.2 Hz, 1H), 8.72 (d, J = 2.2 Hz, 1H), 8.11 (d, J = 5.1 Hz, 1H), 8.02 (s, 1H), 7.26 (d, J = 5.1 Hz, 1H), 4.67 (d, J = 13.8 Hz, 1H), 4.37 (td, J = 12.9, 11.5, 5.0 Hz, 2H), 4.05 (s, 1H), 3.89 (s, 0H), 3.71-3.59 (m, 2H), 3.21-3.13 (m, 1H), 2.11-1.89 (m, 1H), 1.79-1.61 (m, 2H), 1.55-1.39 (m, 16H). |
| 226 | 1H NMR (400 MHz, Methanol-d4) δ 8.86 (d, J = 4.9 Hz, 1H), 8.79 (d, J = 2.2 Hz, 1H), 8.72 (d, J = 2.2 Hz, 1H), 8.11 (dd, J = 5.1, 1.4 Hz, 1H), 8.02 (d, J = 1.3 Hz, 1H), 7.26 (d, J = 5.1 Hz, 1H), 4.50-4.29 (m, 2H), 4.20 (q, J = 6.9 Hz, 1H), 3.78 (dq, J = 18.9, 9.6, 8.5 Hz, 1H), 3.56-3.36 (m, 1H), 3.21 (dd, J = 14.1, 5.4 Hz, 0H), 2.26-1.93 (m, 5H), 1.53 (dd, J = 6.4, 2.1 Hz, 6H), 1.42 (d, J = 15.1 Hz, 9H). |
| 227 | 1H NMR (400 MHz, Methanol-d4) δ 8.79 (d, J = 2.2 Hz, 1H), 8.75 (s, 1H), 8.73 (d, J = 2.1 Hz, 1H), 8.12 (d, J = 5.1 Hz, 1H), 8.09-7.99 (m, 1H), 7.95 (s, 1H), 7.72 (s, 1H), 7.44 (t, J = 59.9 Hz, 1H), 7.26 (d, J = 5.1 Hz, 1H), 4.10 (s, 1H), 3.78 (s, 1H), 2.77 (s, 1H), 2.43-2.26 (m, 4H), 2.23 (d, J = 10.5 Hz, 2H), 2.12 (d, J = 12.7 Hz, 2H), 1.97 (s, 3H), 1.88-1.59 (m, 6H), 1.50 (q, J = 12.3 Hz, 1H). |
| 228 | 1H NMR (400 MHz, Methanol-d4) δ 8.86 (d, J = 5.0 Hz, 1H), 8.79 (d, J = 2.2 Hz, 1H), 8.72 (d, J = 2.1 Hz, 1H), 8.12 (dd, J = 5.1, 1.4 Hz, 1H), 8.02 (s, 1H), 7.26 (d, J = 5.0 Hz, 1H), 4.47-4.31 (m, 2H), 4.20 (q, J = 7.1 Hz, 1H), 3.78 (dq, J = 17.8, 9.5, 8.5 Hz, 1H), 3.55-3.37 (m, 1H), 3.21 (dd, J = 14.1, 5.4 Hz, 0H), 2.31-1.90 (m, 5H), 1.53 (d, J = 6.4 Hz, 6H), 1.42 (d, J = 14.7 Hz, 9H). |
| 229 | 1H NMR (400 MHz, Methanol-d4) δ 8.84 (d, J = 5.6 Hz, 1H), 8.76 (d, J = 2.2 Hz, 1H), 8.69 (d, J = 2.2 Hz, 1H), 8.13 (s, 1H), 8.06 (d, J = 5.0 Hz, 1H), 7.24 (d, J = 5.0 Hz, 1H), 4.61 (dd, J = 8.4, 4.2 Hz, 1H), 4.42-4.18 (m, 3H), 3.29-3.20 |

TABLE 1-continued

| Compound | 1H-NMR |
|---|---|
| | (m, 1H), 2.35-2.08 (m, 4H), 1.94 (dq, J = 11.1, 5.2, 4.7 Hz, 1H), 1.52 (d, J = 6.4 Hz, 6H). |
| 230 | 1H NMR (400 MHz, Methanol-d4) δ 8.87 (s, 1H), 8.79 (d, J = 2.2 Hz, 1H), 8.72 (d, J = 2.2 Hz, 1H), 8.11 (d, J = 5.1 Hz, 1H), 8.06 (s, 1H), 7.26 (d, J = 5.0 Hz, 1H), 4.62 (ddd, J = 12.4, 8.1, 4.7 Hz, 1H), 4.42-4.30 (m, 2H), 4.29-4.18 (m, 1H), 3.31-3.17 (m, 2H), 2.20 (dddd, J = 43.9, 18.0, 12.4, 6.4 Hz, 3H), 1.95 (td, J = 11.3, 5.4 Hz, 1H), 1.53 (d, J = 6.4 Hz, 6H). |
| 231 | 1H NMR (400 MHz, Methanol-d4) δ 8.78 (d, J = 2.2 Hz, 1H), 8.70 (d, J = 2.2 Hz, 1H), 8.49 (s, 1H), 8.08 (d, J = 5.0 Hz, 1H), 7.89 (s, 1H), 7.25 (d, J = 5.1 Hz, 1H), 4.34 (s, 2H), 4.33-4.25 (m, 1H), 4.23 (s, 3H), 2.71 (ddd, J = 10.5, 7.7, 3.0 Hz, 2H), 2.39-2.23 (m, 2H), 1.94 (s, 3H), 1.48 (d, J = 6.4 Hz, 6H), 1.42-1.28 (m, 1H). |
| 232 | 1H NMR (400 MHz, Methanol-d4) δ 8.78 (d, J = 2.2 Hz, 1H), 8.69 (d, J = 2.2 Hz, 1H), 8.52 (s, 1H), 8.09 (d, J = 5.0 Hz, 1H), 7.90 (s, 1H), 7.25 (d, J = 5.0 Hz, 1H), 4.31 (p, J = 6.4 Hz, 1H), 3.83 (t, J = 5.4 Hz, 2H), 3.78 (s, 4H), 3.69 (dd, J = 6.6, 4.0 Hz, 2H), 2.20 (s, 3H), 1.49 (d, J = 6.4 Hz, 6H). |
| 233 | 1H NMR (400 MHz, Methanol-d4) δ 8.78 (d, J = 2.2 Hz, 1H), 8.70 (d, J = 2.1 Hz, 1H), 8.55 (s, 1H), 8.09 (d, J = 5.1 Hz, 1H), 7.91 (s, 1H), 7.25 (d, J = 5.1 Hz, 1H), 4.82 (d, J = 6.7 Hz, 2H), 4.32 (p, J = 6.4 Hz, 1H), 4.01-3.76 (m, 4H), 3.40 (dd, J = 16.4, 7.3 Hz, 1H), 2.10 (d, J = 9.4 Hz, 1H), 1.50 (d, J = 6.4 Hz, 6H). |
| 234 | 1H NMR (400 MHz, Methanol-d4) δ 8.78 (d, J = 2.2 Hz, 1H), 8.70 (d, J = 2.2 Hz, 1H), 8.53 (s, 1H), 8.09 (d, J = 5.0 Hz, 1H), 7.92 (s, 1H), 7.25 (d, J = 5.0 Hz, 1H), 4.48 (dd, J = 24.4, 8.7 Hz, 4H), 4.39-4.24 (m, 1H), 3.94 (d, J = 11.2 Hz, 2H), 3.05 (q, J = 7.0 Hz, 1H), 2.11 (d, J = 8.5 Hz, 1H), 2.06 (s, 2H), 1.50 (d, J = 6.4 Hz, 6H). |
| 235 | 1H NMR (400 MHz, Methanol-d4) δ 8.78 (d, J = 2.1 Hz, 1H), 8.70 (d, J = 2.2 Hz, 1H), 8.50 (s, 1H), 8.08 (d, J = 5.1 Hz, 1H), 7.89 (s, 1H), 7.25 (d, J = 5.0 Hz, 1H), 4.54 (s, 2H), 4.39-4.24 (m, 1H), 3.75-3.52 (m, 4H), 2.21-2.00 (m, 2H), 1.95 (d, J = 7.2 Hz, 2H), 1.49 (d, J = 6.4 Hz, 6H). |
| 236 | 1H NMR (400 MHz, Methanol-d4) δ 8.78 (d, J = 2.2 Hz, 1H), 8.70 (d, J = 2.2 Hz, 1H), 8.51 (s, 1H), 8.09 (d, J = 5.0 Hz, 1H), 7.91 (s, 1H), 7.25 (d, J = 5.1 Hz, 1H), 4.31 (d, J = 8.7 Hz, 3H), 3.94 (d, J = 11.3 Hz, 2H), 3.81-3.63 (m, 2H), 2.19 (dd, J = 13.6, 2.2 Hz, 5H), 1.49 (d, J = 6.4 Hz, 6H). |
| 237 | 1H NMR (400 MHz, Methanol-d4) δ 8.78 (d, J = 2.2 Hz, 1H), 8.70 (d, J = 2.2 Hz, 1H), 8.50 (s, 1H), 8.09 (d, J = 5.0 Hz, 1H), 7.90 (s, 1H), 7.25 (d, J = 5.1 Hz, 1H), 4.79 (d, J = 17.4 Hz, 2H), 4.31 (p, J = 6.4 Hz, 1H), 4.03-3.86 (m, 2H), 3.80-3.62 (m, 1H), 3.59-3.47 (m, 1H), 2.24-2.04 (m, 2H), 1.49 (d, J = 6.4 Hz, 6H), 1.42-1.27 (m, 2H). |
| 238 | 1H NMR (400 MHz, Methanol-d4) δ 8.78 (s, 1H), 8.70 (s, 1H), 8.51 (s, 1H), 8.09 (d, J = 5.1 Hz, 1H), 7.90 (s, 1H), 7.25 (d, J = 5.0 Hz, 1H), 4.83-4.67 (m, 2H), 4.41-4.24 (m, 1H), 4.08-3.88 (m, 2H), 3.74 (d, J = 1.5 Hz, 1H), 3.58-3.47 (m, 1H), 2.28-2.03 (m, 2H), 1.49 (d, J = 6.3 Hz, 6H), 1.31 (s, 1H). |
| 239 | 1H NMR (400 MHz, Methanol-d4) δ 8.78 (d, J = 2.2 Hz, 1H), 8.70 (d, J = 2.2 Hz, 1H), 8.51 (s, 1H), 8.39 (s, 0H), 8.08 (d, J = 5.1 Hz, 1H), 7.89 (s, 1H), 7.25 (d, J = 5.1 Hz, 1H), 4.37-4.24 (m, 1H), 3.91-3.75 (m, 4H), 2.53 (s, 1H), 2.01 (s, 2H), 1.96 (s, 3H), 1.48 (d, J = 6.4 Hz, 6H), 1.42 (dd, J = 23.4, 6.4 Hz, 1H). |
| 240 | 1H NMR (400 MHz, Methanol-d4) δ 8.78 (d, J = 2.2 Hz, 1H), 8.70 (d, J = 2.2 Hz, 1H), 8.50 (s, 1H), 8.38 (s, 0H), 8.08 (d, J = 5.1 Hz, 1H), 7.89 (s, 1H), 7.25 (d, J = 5.0 Hz, 1H), 4.36-4.23 (m, 1H), 3.94-3.74 (m, 4H), 2.53 (s, 1H), 2.01 (s, 2H), 1.96 (s, 3H), 1.48 (d, J = 6.3 Hz, 6H). |
| 241 | 1H NMR (400 MHz, Methanol-d4) δ 8.79 (d, J = 2.2 Hz, 1H), 8.74 (d, J = 2.1 Hz, 1H), 8.71 (s, 1H), 8.43 (s, 1H), 8.02 (d, J = 5.0 Hz, 1H), 7.26 (d, J = 5.1 Hz, 1H), 3.77 (tt, J = 11.6, 4.0 Hz, 1H), 3.27 (dt, J = 12.0, 3.6 Hz, 1H), 2.60-2.21 (m, 7H), 2.17-1.97 (m, 6H), 1.97 (s, 3H), 1.95-1.70 (m, 3H), 1.49 (qd, J = 12.9, 3.4 Hz, 2H). |
| 242 | 1H NMR (400 MHz, Methanol-d4) δ 8.82 (s, 1H), 8.75 (d, J = 2.2 Hz, 1H), 8.68 (d, J = 2.1 Hz, 1H), 8.07 (d, J = 5.0 Hz, 1H), 8.03 (s, 1H), 7.22 (d, J = 5.1 Hz, 1H), 5.13-4.98 (m, 1H), 4.75-4.59 (m, 1H), 4.55 (t, J = 9.7 Hz, 1H), 4.42-4.23 (m, 1H), 4.13 (dd, J = 10.9, 5.6 Hz, 1H), 2.00 (s, 3H), 1.49 (d, J = 6.4 Hz, 6H). |
| 243 | 1H NMR (400 MHz, Methanol-d4) δ 10.00 (s, 1H), 9.96 (s, 1H), 9.94 (s, 1H), 9.31 (d, J = 5.0 Hz, 1H), 9.05 (s, 1H), 8.47 (d, J = 5.0 Hz, 1H), 5.40 (d, J = 7.3 Hz, 1H), 4.99 (s, 1H), 4.09 (t, J = 9.4 Hz, 2H), 3.53 (q, J = 11.6, 10.2 Hz, 4H), 3.34 (d, J = 12.5 Hz, 2H), 3.19 (s, 3H), 3.12-2.92 (m, 2H), 2.74 (s, 4H), 2.70 (s, 1H). |
| 244 | 1H NMR (400 MHz, Methanol-d4) δ 10.00 (s, 1H), 9.96 (s, 1H), 9.94 (s, 1H), 9.31 (d, J = 5.0 Hz, 1H), 9.05 (s, 1H), 8.47 (d, J = 5.0 Hz, 1H), 5.49-5.31 (m, 1H), 4.99 (s, 1H), 4.09 (t, J = 9.4 Hz, 2H), 3.53 (q, J = 11.6, 10.2 Hz, 5H), 3.34 (d, J = 12.5 Hz, 2H), 3.19 (s, 3H), 3.14-2.95 (m, 2H), 2.74 (s, 4H). |
| 245 | 1H NMR (400 MHz, Methanol-d4) δ 8.76 (d, J = 2.1 Hz, 1H), 8.70 (s, 1H), 8.68 (d, J = 2.1 Hz, 1H), 8.07 (d, J = 5.0 Hz, 1H), 7.97 (s, 1H), 7.23 (d, J = 5.1 Hz, 1H), 4.10 (s, 0H), 3.84 (d, J = 10.2 Hz, 1H), 3.76 (d, J = 11.8 Hz, 1H), 3.47 (s, 0H), 2.41 (d, J = 12.4 Hz, 1H), 2.30 (d, J = 13.1 Hz, 2H), 2.09 (d, J = 13.8 Hz, 3H), 1.98 (s, 1H), 1.94 (s, 3H), 1.93 (s, 0H), 1.79 (q, J = 11.9 Hz, 2H), 1.61-1.36 (m, 4H). |

TABLE 1-continued

| Compound | 1H-NMR |
|---|---|
| 246 | 1H NMR (400 MHz, Methanol-d4) δ 8.79 (d, J = 2.1 Hz, 1H), 8.77-8.66 (m, 2H), 8.10 (d, J = 5.0 Hz, 1H), 7.98 (s, 1H), 7.26 (d, J = 5.1 Hz, 1H), 4.33 (hept, J = 6.4 Hz, 1H), 2.63 (s, 5H), 1.96 (s, 3H), 1.51 (d, J = 6.4 Hz, 6H). |
| 247 | 1H NMR (400 MHz, Methanol-d4) δ 9.39 (s, 0H), 8.80 (d, J = 2.1 Hz, 1H), 8.75-8.67 (m, 2H), 8.11 (dd, J = 5.1, 1.7 Hz, 1H), 7.97 (s, 1H), 7.26 (d, J = 5.1 Hz, 1H), 4.34 (p, J = 6.4 Hz, 1H), 3.93 (p, J = 8.1 Hz, 1H), 2.71 (dt, J = 12.5, 7.4 Hz, 0H), 2.43-2.27 (m, 1H), 2.27-2.13 (m, 1H), 2.13-2.01 (m, 1H), 1.97 (d, J = 3.8 Hz, 3H), 1.97-1.83 (m, 1H), 1.85-1.67 (m, 1H), 1.51 (d, J = 6.4 Hz, 6H). |
| 248 | 1H NMR (400 MHz, Methanol-d4) δ 8.80 (d, J = 2.2 Hz, 1H), 8.73 (s, 1H), 8.71 (d, J = 2.2 Hz, 1H), 8.11 (d, J = 5.1 Hz, 1H), 7.97 (s, 1H), 7.26 (d, J = 5.0 Hz, 1H), 4.45-4.26 (m, 2H), 3.96-3.73 (m, 1H), 2.71 (dt, J = 14.1, 7.4 Hz, 1H), 2.42-2.28 (m, 1H), 2.27-2.01 (m, 2H), 1.97 (d, J = 3.9 Hz, 3H), 1.96-1.86 (m, 1H), 1.85-1.71 (m, 0H), 1.54-1.40 (m, 6H). |
| 249 | 1H NMR (400 MHz, Methanol-d4) δ 8.78 (d, J = 2.2 Hz, 1H), 8.70 (d, J = 2.2 Hz, 1H), 8.49 (d, J = 0.8 Hz, 1H), 8.08 (d, J = 5.1 Hz, 1H), 7.89 (s, 1H), 7.25 (d, J = 5.1 Hz, 1H), 4.31 (p, J = 6.4 Hz, 1H), 4.05-3.90 (m, 1H), 3.92-3.73 (m, 1H), 3.65-3.53 (m, 1H), 2.03 (s, 3H), 1.98 (d, J = 10.8 Hz, 3H), 1.79 (td, J = 12.9, 12.5, 5.5 Hz, 1H), 1.60 (td, J = 12.8, 5.3 Hz, 1H), 1.49 (d, J = 6.2 Hz, 7H). |
| 250 | 1H NMR (400 MHz, Methanol-d4) δ 8.76 (d, J = 2.2 Hz, 1H), 8.68 (d, J = 2.1 Hz, 1H), 8.48 (s, 1H), 8.05 (d, J = 5.0 Hz, 1H), 7.94 (s, 1H), 7.23 (d, J = 5.0 Hz, 1H), 4.39-4.17 (m, 2H), 3.84-3.43 (m, 4H), 2.01 (s, 3H), 1.89 (d, J = 3.8 Hz, 1H), 1.60 (d, J = 26.1 Hz, 1H), 1.48 (d, J = 6.4 Hz, 6H). |
| 251 | $^1$H NMR (400 MHz, Methanol-d$_4$) δ 8.75 (d, J = 2.2 Hz, 1H), 8.67 (d, J = 2.2 Hz, 1H), 8.49 (s, 1H), 8.05 (d, J = 5.1 Hz, 1H), 7.91 (s, 1H), 7.22 (d, J =5.1 Hz, 1H), 4.32-4.23 (m, 1H), 3.85-3.51 (m, 3H), 2.02 (s, 3H), 1.47 (d, J = 6.4 Hz, 6H). |
| 252 | 1H NMR (400 MHz, Methanol-d4) δ 8.78 (d, J = 2.2 Hz, 1H), 8.70 (d, J = 2.1 Hz, 1H), 8.50 (s, 1H), 8.08 (d, J = 5.1 Hz, 1H), 7.89 (s, 1H), 7.25 (d, J = 5.0 Hz, 1H), 4.47 (s, 4H), 4.38-4.24 (m, 1H), 1.48 (d, J = 6.4 Hz, 6H). |
| 253 | 1H NMR (400 MHz, Methanol-d4) δ 8.78 (d, J = 2.2 Hz, 1H), 8.73 (d, J = 2.2 Hz, 1H), 8.69 (s, 1H), 8.45 (s, 1H), 8.00 (d, J = 5.0 Hz, 1H), 7.25 (d, J = 5.0 Hz, 1H), 3.65 (d, J = 6.7 Hz, 3H), 3.58-3.42 (m, 1H), 3.20-3.07 (m, 0H), 2.41-2.26 (m, 7H), 2.26-2.04 (m, 2H), 2.04-1.89 (m, 6H), 1.74 (dq, J = 43.0, 14.0, 13.2 Hz, 2H), 1.59-1.20 (m, 2H). |
| 254 | 1H NMR (400 MHz, Methanol-d4) δ 8.74 (s, 1H), 8.72 (s, 1H), 8.48 (s, 1H), 8.00 (d, J = 4.9 Hz, 1H), 7.88 (s, 1H), 7.20 (d, J = 5.2 Hz, 1H), 4.52 (s, 2H), 4.08 (s, 1H), 3.74 (d, J = 29.8 Hz, 1H), 3.69 (s, 3H), 3.53 (d, J = 41.9 Hz, 1H), 3.37 (d, J = 7.4 Hz, 2H), 3.13 (s, 1H), 2.51 (s, 3H), 2.30 (s, 2H), 2.02 (s, 3H), 1.98 (s, 1H), 1.29 (s, 1H). |
| 255 | 1H NMR (400 MHz, Methanol-d4) δ 8.80 (d, J = 2.2 Hz, 1H), 8.78 (s, 1H), 8.72 (d, J = 2.2 Hz, 1H), 8.14 (d, J = 5.0 Hz, 1H), 8.02 (s, 1H), 7.26 (d, J = 5.0 Hz, 1H), 4.33 (dt, J = 10.1, 5.3 Hz, 1H), 4.14-4.01 (m, 2H), 3.76 (q, J = 11.3, 10.3 Hz, 3H), 2.34 (d, J = 12.9 Hz, 2H), 2.28-2.18 (m, 2H), 2.12 (d, J = 12.8 Hz, 2H), 1.97 (s, 3H), 1.92-1.74 (m, 5H), 1.59-1.40 (m, 2H). |
| 256 | 1H NMR (400 MHz, Methanol-d4) δ 8.79 (d, J = 2.2 Hz, 1H), 8.70 (d, J = 2.2 Hz, 1H), 8.54 (s, 1H), 8.13 (d, J = 5.0 Hz, 1H), 7.93 (s, 1H), 7.25 (d, J = 5.1 Hz, 1H), 4.54 (s, 2H), 4.37-4.25 (m, 1H), 4.11-4.00 (m, 2H), 3.79-3.70 (m, 2H), 3.68 (d, J = 12.1 Hz, 2H), 3.60-3.55 (m, 2H), 2.20 (d, J = 13.1 Hz, 2H), 2.14-2.02 (m, 2H), 1.95 (d, J = 7.4 Hz, 2H), 1.88-1.71 (m, 2H). |
| 257 | 1H NMR (400 MHz, Methanol-d4) δ 8.79 (d, J = 2.2 Hz, 1H), 8.70 (d, J = 2.2 Hz, 1H), 8.53 (s, 1H), 8.09 (d, J = 5.0 Hz, 1H), 7.91 (s, 1H), 7.25 (d, J = 5.1 Hz, 1H), 4.36-4.28 (m, 1H), 4.24 (s, 4H), 3.37 (s, 4H), 1.49 (d, J = 6.4 Hz, 6H). |
| 258 | 1H NMR (400 MHz, Methanol-d4) δ 8.79 (d, J = 2.3 Hz, 1H), 8.70 (d, J = 2.1 Hz, 1H), 8.55 (s, 1H), 8.09 (d, J = 4.9 Hz, 1H), 7.91 (s, 1H), 7.25 (d, J = 5.1 Hz, 1H), 4.76 (s, 1H), 4.61 (s, 1H), 4.37-4.26 (m, 1H), 4.17-4.04 (m, 2H), 3.92 (d, J = 11.6 Hz, 1H), 3.80 (d, J = 10.6 Hz, 1H), 2.01 (s, 3H), 1.84 (d, J = 9.6 Hz, 1H), 1.50 (d, J = 6.4 Hz, 6H), 1.38 (d, J = 6.2 Hz, 1H). |
| 259 | 1H NMR (400 MHz, Methanol-d4) δ 8.78 (d, J = 2.2 Hz, 1H), 8.70 (d, J = 2.2 Hz, 1H), 8.52 (s, 1H). 8.08 (d, J = 5.1 Hz, 1H), 7.90 (s, 1H), 7.25 (d, J = 5.0 Hz, 1H), 4.82 (s, 1H), 4.55 (d, J = 6.7 Hz, 1H), 4.31 (p, J = 6.4 Hz, 1H), 3.92 (d, J = 12.4 Hz, 1H), 3.78 (d, J = 11.6 Hz, 1H), 3.57 (t, J = 12.2 Hz, 2H), 2.20 (s, 3H), 2.12-1.85 (m, 4H), 1.49 (d, J = 6.4 Hz, 6H) |
| 260 | 1H NMR (400 MHz, Methanol-d4) δ 8.78 (d, J = 2.2 Hz, 1H), 8.70 (d, J = 2.1 Hz, 1H), 8.52 (s, 1H), 8.08 (d, J = 5.1 Hz, 1H), 7.92 (s, 1H), 7.25 (d, J = 5.0 Hz, 1H), 4.48 (d, J = 28.2 Hz, 3H), 4.38 (d, J = 13.3 Hz, 2H), 4.35-4.26 (m, 1H), 3.83 (d, J = 12.7 Hz, 1H), 3.68 (d, J = 12.7 Hz, 1H), 2.21 (s, 2H), 2.16 (s, 3H), 2.00 (d, J = 8.4 Hz, 1H), 1.88 (d, J = 7.7 Hz, 1H), 1.49 (d, J = 6.4 Hz, 6H). |
| 261 | 1H NMR (400 MHz, Methanol-d4) δ 8.77 (d, J = 2.2 Hz, 1H), 8.69 (d, J = 2.2 Hz, 1H), 8.54 (s, 1H), 8.07 (d, J = 5.0 Hz, 1H), 7.93 (s, 1H), 7.24 (d, J = 5.1 Hz, 1H), 4.76 (s, 1H), 4.61 (s, 1H), 4.34-4.26 (m, 1H), 4.17-4.05 (m, 2H), 3.92 (d, J = 11.4 Hz, 1H), 3.80 (d, J = 11.0 Hz, 1H), 2.92 (d, J = 8.5 Hz, 1H), 2.01 (s, 3H), 1.84 (d, J = 9.3 Hz, 1H), 1.49 (d, J = 6.4 Hz, 6H), 1.43 (s, 2H). |
| 262 | 1H NMR (400 MHz, Methanol-d4) δ 8.78 (d, J = 2.2 Hz, 1H), 8.70 (d, J = 2.1 Hz, 1H), 8.54 (s, 1H), 8.09 (d, J = 5.1 Hz, 1H), 7.92 (s, 1H), 7.25 (d, J = 5.1 Hz, 1H), 4.28 (s, 2H), 4.14 (d, J = 6.6 Hz, 4H), 4.01 (dd, J = 8.4, 3.2 Hz, 2H), 3.96 (d, J = 3.5 Hz, 1H), 1.49 (d, J = 6.4 Hz, 6H). |

TABLE 1-continued

| Compound | 1H-NMR |
|---|---|
| 263 | ¹H NMR (400 MHz, Acetonitrile-d₃) δ 8.70-8.55 (m, 2H), 8.50 (s, 1H), 8.07 (d, J = 5.1 Hz, 1H), 7.73 (s, 1H), 7.20 (d, J = 5.1 Hz, 1H), 4.73 (s, 3H), 4.31-4.13 (m, 1H), 3.94-3.76 (m, 1H), 3.77-3.63 (m, 1H), 3.65-3.39 (m, 1H), 2.21-2.05 (m, 1H), 1.94-1.81 (m, 1H), 1.47 (s, 1H), 1.45 (d, 7 = 6.4 Hz, 6H), 0.97-0.73 (m, 6H). |
| 264 | ¹H NMR (400 MHz, Acetonitrile-d₃) δ 8.67 (s, 1H), 8.65 (d, J = 2.1 Hz, 1H), 8.59 (d, J = 2.2 Hz, 1H), 8.04 (d, J = 5.1 Hz, 1H), 7.51 (s, 1H), 7.19 (d, J = 5.1 Hz, 1H), 4.93 (d, J = 6.5 Hz, 2H), 4.78 (d, J = 6.7 Hz, 2H), 4.76-4.72 (m, 1H), 4.39 (d, J = 6.8 Hz, 1H), 3.75 (dd, J = 27.4, 12.0 Hz, 2H), 3.51 (dd, J = 18.3, 11.7 Hz, 2H), 2.69 (m, 4H), 2.10 (s, 3H), 1.89 (s, 3H). |
| 265 | ¹H NMR (400 MHz, Methanol-d₄) δ 8.73 (d, J = 2.2 Hz, 1H), 8.64 (d, J = 2.1 Hz, 1H), 7.96 (d, J = 5.1 Hz, 1H), 7.89 (s, 1H), 7.54 (s, 1H), 7.20 (d, J = 5.0 Hz, 1H), 4.37-4.23 (m, 2H), 4.23-4.13 (m, 2H), 4.15-4.03 (m, 3H), 3.93-3.85 (m, 1H), 3.84-3.75 (m, 2H), 3.76-3.65 (m, 1H), 2.23 (s, 3H), 1.38 (d, J = 6.4 Hz, 6H). |
| 266 | 1H NMR (400 MHz, Methanol-d4) δ 8.78 (d, J = 2.2 Hz, 1H), 8.70 (d, J = 2.2 Hz, 1H), 8.51 (d, J = 11.3 Hz, 1H), 8.09 (d, J = 5.0 Hz, 1H), 7.90 (d, J = 9.3 Hz, 1H), 7.25 (d, J = 5.0 Hz, 1H), 4.69 (s, 1H), 4.30 (dd, J = 13.9, 7.8 Hz, 2H), 4.22-4.02 (m, 5H), 3.93-3.66 (m, 4H), 2.21 (d, J = 14.4 Hz, 3H), 1.49 (d, J = 6.4 Hz, 6H). |
| 267 | 1H NMR (400 MHz, Methanol-d4) δ 8.78 (d, J = 2.1 Hz, 1H), 8.70 (d, J = 2.2 Hz, 1H), 8.57 (s, 1H), 8.09 (d, J = 5.1 Hz, 1H), 7.91 (s, 1H), 7.25 (d, J = 5.0 Hz, 1H), 4.39-4.26 (m, 2H), 3.75 (dt, J = 12.1, 4.1 Hz, 1H), 3.69-3.57 (m, 1H), 3.45 (td, J = 6.9, 4.6 Hz, 1H), 3.33-3.22 (m, 2H), 2.28 (s, 3H), 2.20 (s, 1H), 1.52-1.48 (m, 6H), 1.48-1.35 (m, 1H), 1.00-0.91 (m, 1H). |
| 268 | 1H NMR (400 MHz, Methanol-d4) δ 8.79 (d, J = 2.2 Hz, 1H), 8.77 (s, 1H), 8.75 (d, J = 2.2 Hz, 1H), 8.38 (s, 1H), 8.01 (d, J = 5.0 Hz, 1H), 7.26 (d, J = 5.1 Hz, 1H), 3.94-3.71 (m, 5H), 3.34-3.25 (m, 1H), 2.33 (d, J = 14.0 Hz, 4H), 2.17-2.01 (m, 4H), 1.97 (s, 3H), 1.84 (td, J = 12.7, 3.2 Hz, 2H), 1.78 (s, 3H), 1.50 (qd, J = 12.8, 3.4 Hz, 2H). |
| 269 | 1H NMR (400 MHz, Methanol-d4) δ 8.79 (d, J = 2.1 Hz, 1H), 8.70 (d, J = 2.1 Hz, 1H), 8.53 (s, 1H), 8.13 (d, J = 5.1 Hz, 1H), 7.93 (s, 1H), 7.25 (d, J = 5.0 Hz, 1H), 4.69 (s, 1H), 4.33-4.17 (m, 4H), 4.14-4.01 (m, 4H), 3.89 (d, J = 11.9 Hz, 1H), 3.82 (d, J = 10.0 Hz, 2H), 3.79-3.68 (m, 4H), 2.23 (s, 3H), 2.19 (s, 2H), 1.88-1.74 (m, 2H). |
| 270 | 1H NMR (400 MHz, Methanol-d4) δ 8.79 (d, J = 2.1 Hz, 1H), 8.77 (s, 1H), 8.71 (d, J = 2.2 Hz, 1H), 8.13 (d, J = 5.1 Hz, 1H), 8.03 (s, 1H), 7.26 (d, J = 5.1 Hz, 1H), 4.33 (tt, J = 9.4, 4.2 Hz, 1H), 4.06 (dt, J = 12.0, 4.0 Hz, 2H), 3.74 (ddd, J = 12.1, 10.3, 2.5 Hz, 2H), 2.64 (s, 6H), 2.21 (d, J = 12.9 Hz, 2H), 1.96 (s, 3H), 1.90-1.75 (m, 2H), 0.12 (s, 0H). |
| 271 | 1H NMR (400 MHz, Chloroform-d) δ 8.68 (d, J = 7.1 Hz, 1H), 8.53 (s, 1H), 8.34 (d, J = 2.3 Hz, 1H), 8.19 (d, J = 2.2 Hz, 1H), 8.15 (s, 1H), 7.91 (d, J = 4.8 Hz, 1H), 7.00 (d, J = 4.8 Hz, 1H), 4.32 (d, J = 6.2 Hz, 2H), 4.22 (s, 2H), 3.98 (h, J = 6.5 Hz, 1H), 3.66-3.56 (m, 2H), 2.76 (dt, J = 8.9, 6.5 Hz, 1H), 1.60 (d, J = 9.1 Hz, 1H), 1.42 (d, J = 4.8 Hz, 16H). |
| 272 | ¹H NMR (400 MHz, Methanol-d₄) δ 8.78 (d, J = 2.2 Hz, 1H), 8.73 (d, J = 2.2 Hz, 1H), 8.52 (s, 1H), 8.27 (s, 1H), 8.06-8.01 (m, 1H), 7.98 (d, J = 5.1 Hz, 1H), 7.25 (d, J = 5.1 Hz, 1H), 4.01 (d, 7 = 4.9 Hz, 1H), 3.92-3.74 (m, 6H), 3.57 (d, J = 11.8 Hz, 2H), 2.46 (s, 2H), 2.30 (d, J = 14.2 Hz, 2H), 2.05 (td, J = 9.5, 9.1, 4.4 Hz, 4H), 2.00 (s, 3H), 1.76 (s, 3H), 1.70 (d, J = 8.3 Hz, 2H). |
| 273 | 1H NMR (400 MHz, Methanol-d4) δ 8.78 (d, J = 2.2 Hz, 1H), 8.70 (d, J = 2.2 Hz, 1H), 8.55 (s, 1H), 8.09 (d, J = 5.0 Hz, 1H), 7.90 (s, 1H), 7.25 (d, J = 5.1 Hz, 1H), 5.13 (s, 1H), 4.61 (s, 1H), 4.37-4.19 (m, 2H), 4.19-4.09 (m, 1H), 3.95-3.86 (m, 1H), 3.87-3.78 (m, 1H), 2.99-2.85 (m, 1H), 1.82 (d, J = 9.3 Hz, 1H), 1.50 (d, J = 6.4 Hz, 6H), 1.46 (s, 3H), 1.31 (s, 3H). |
| 274 | 1H NMR (400 MHz, Methanol-d4) δ 8.73 (d, J = 6.9 Hz, 1H), 8.55 (d, J = 2.1 Hz, 1H), 8.50 (d, J = 2.1 Hz, 1H), 8.44 (s, 1H), 8.25 (s, 1H), 7.82 (d, J = 4.9 Hz, 1H), 7.09 (d, J = 5.0 Hz, 1H), 4.09-3.87 (m, 7H), 2.94 (s, 1H), 1.88 (d, J = 9.4 Hz, 1H), 1.43 (d, J = 6.3 Hz, 7H). |
| 275 | 1H NMR (400 MHz, Methanol-d4) δ 8.78 (d, J = 2.2 Hz, 1H), 8.70 (d, J = 2.1 Hz, 1H), 8.55 (s, 1H), 8.09 (d, J = 5.1 Hz, 1H), 7.90 (s, 1H), 7.25 (d, J = 5.0 Hz, 1H), 5.13 (s, 1H), 4.61 (s, 1H), 4.38-4.21 (m, 2H), 4.14 (d, J = 10.6 Hz, 1H), 3.90 (d, J = 11.0 Hz, 1H), 3.82 (d, J = 11.0 Hz, 1H), 3.02-2.83 (m, 1H), 1.82 (d, J = 9.2 Hz, 1H), 1.50 (d, J = 6.4 Hz, 6H), 1.46 (s, 3H), 1.31 (s, 3H). |
| 276 | 1H NMR (400 MHz, Methanol-d4) δ 8.79 (d, J = 2.1 Hz, 1H), 8.70 (d, J = 2.1 Hz, 1H), 8.56 (s, 1H), 8.09 (d, J = 5.1 Hz, 1H), 7.90 (s, 1H), 7.25 (d, J = 5.1 Hz, 1H), 4.93 (s, 1H), 4.67 (s, 1H), 4.40-4.30 (m, 1H), 4.30-4.09 (m, 2H), 4.04-3.73 (m, 4H), 3.35 (s, 6H), 3.06-2.91 (m, 1H), 1.87 (d, J = 9.3 Hz, 1H), 1.49 (d, J = 6.4 Hz, 6H). |
| 277 | 1H NMR (400 MHz, Methanol-d4) δ 8.78 (d, J = 2.2 Hz, 1H), 8.70 (d, J = 2.2 Hz, 1H), 8.56 (s, 1H), 8.09 (d, J = 5.1 Hz, 1H), 7.91 (s, 1H), 7.25 (d, J = 5.0 Hz, 1H), 4.51 (d, J = 6.4 Hz, 2H), 4.33 (q, J = 6.3 Hz, 1H), 4.26 (d, J = 11.2 Hz, 2H), 3.75 (d, J = 11.3 Hz, 2H), 2.96-2.95 (m, 6H), 2.94-2.86 (m, 1H), 1.77 (d, J = 9.3 Hz, 1H), 1.49 (d, J = 6.4 Hz, 6H). |
| 278 | 1H NMR (400 MHz, Methanol-d4) δ 8.81-8.55 (m, 3H), 8.10-7.93 (m, 2H), 7.20 (d, J = 5.0 Hz, 1H), 4.68-4.55 (m, 1H), 4.23 (q, J = 6.4 Hz, 1H), 4.02 (tt, J = 9.1, 4.6 Hz, 1H), 2.79 (ddd, J = 10.7, 9.2, 4.2 Hz, 2H), 2.66 (td, J = 12.4, 11.0, 8.1 Hz, 2H), 1.95 (s, 3H), 1.49 (d, J = 6.4 Hz, 6H). |

TABLE 1-continued

| Compound | 1H-NMR |
|---|---|
| 279 | 1H NMR (400 MHz, Methanol-d4) δ 8.76 (d, J = 2.1 Hz, 1H), 8.73-8.62 (m, 2H), 8.08 (d, J = 5.0 Hz, 1H), 7.95 (s, 1H), 7.23 (d, J = 5.1 Hz, 1H), 4.49-4.23 (m, 2H), 3.89-3.72 (m, 1H), 3.03-2.83 (m, 2H), 2.44 (qd, J = 9.4, 2.7 Hz, 2H), 1.94 (s, 3H), 1.49 (d, J = 6.4 Hz, 6H). |
| 280 | 1H NMR (400 MHz, Methanol-d4) δ 8.76 (d, J = 2.2 Hz, 1H), 8.74-8.58 (m, 2H), 8.07 (d, J = 5.0 Hz, 1H), 7.94 (s, 1H), 7.23 (d, J = 5.1 Hz, 1H), 4.30 (h, J = 6.5 Hz, 1H), 2.27-2.16 (m, 6H), 2.16-2.06 (m, 6H), 1.89 (s, 3H), 1.48 (d, J = 6.4 Hz, 6H). |
| 281 | 1H NMR (400 MHz, Methanol-d4) δ 8.68 (s, 1H), 8.57 (t, J = 1.9 Hz, 2H), 8.05-7.91 (m, 2H), 7.17 (d, J = 5.1 Hz, 1H), 4.64 (p, J = 8.0 Hz, 1H), 4.18 (p, J = 6.5 Hz, 1H), 4.02 (dt, J = 9.5, 4.8 Hz, 1H), 2.78 (ddd, J = 12.6, 7.6, 4.0 Hz, 2H), 2.67 (td, J = 12.8, 11.2, 8.3 Hz, 2H), 1.49 (d, J = 6.4 Hz, 7H), 0.87 (p, J = 4.2 Hz, 2H), 0.74 (dq, J = 7.4, 4.3, 3.9 Hz, 2H). |
| 282 | 1H NMR (400 MHz, Methanol-d4) δ 8.76 (d, J = 2.2 Hz, 1H), 8.73-8.62 (m, 2H), 8.09 (d, J = 5.1 Hz, 1H), 7.89 (s, 1H), 7.23 (d, J = 5.1 Hz, 1H), 4.62 (q, J = 7.3, 6.8 Hz, 1H), 4.18-3.95 (m, 1H), 3.34 (s, 3H), 2.87-2.74 (m, 2H), 2.73-2.59 (m, 2H), 1.96 (s, 3H). |
| 283 | 1H NMR (400 MHz, Methanol-d4) δ 8.76 (d, J = 2.2 Hz, 1H), 8.72 (s, 1H), 8.67 (d, J = 2.2 Hz, 1H), 8.07 (d, J = 5.1 Hz, 1H), 7.99 (s, 1H), 7.23 (d, J = 5.1 Hz, 1H), 4.93 (t, J = 7.5 Hz, 2H), 4.68 (dd, J = 8.0, 5.2 Hz, 2H), 4.44 (h, J = 6.1, 5.6 Hz, 1H), 4.31 (p, J = 6.6 Hz, 1H), 4.23 (q, J = 6.9 Hz, 1H), 4.20-4.09 (m, 1H), 2.89 (t, J = 7.5 Hz, 4H), 1.48 (d, J = 6.4 Hz, 6H). |
| 284 | 1H NMR (400 MHz, Methanol-d4) δ 8.76 (d, J = 2.2 Hz, 1H), 8.71 (s, 1H), 8.68 (d, J = 2.1 Hz, 1H), 8.07 (d, J = 5.1 Hz, 1H), 7.94 (s, 1H), 7.23 (d, J = 5.1 Hz, 1H), 4.31 (p, J = 6.3 Hz, 1H), 2.36-2.03 (m, 8H), 1.94 (s, 5H), 1.49 (d, J = 6.4 Hz, 6H). |
| 285 | 1H NMR (400 MHz, Methanol-d4) δ 8.76 (d, J = 2.2 Hz, 1H), 8.71 (d, J = 2.7 Hz, 1H), 8.68 (d, J = 2.1 Hz, 1H), 8.07 (d, J = 5.0 Hz, 1H), 7.95 (s, 1H), 7.23 (d, J = 5.0 Hz, 1H), 4.31 (p, J = 6.4 Hz, 1H), 3.85-3.66 (m, 2H), 2.74 (s, 1H), 2.54-2.33 (m, 1H), 2.34-1.99 (m, 1H), 1.92 (d, J = 8.9 Hz, 3H), 1.82- 1.56 (m, 3H), 1.49 (dd, J = 6.4, 3.7 Hz, 6H), 1.37-1.22 (m, 1H), 1.19 (s, 1H). |
| 286 | 1H NMR (400 MHz, Methanol-d4) δ 8.75 (d, J = 2.2 Hz, 1H), 8.67 (d, J = 2.1 Hz, 1H), 8.47 (s, 1H), 8.05 (d, J = 5.1 Hz, 1H), 7.87 (s, 1H), 7.22 (d, J = 5.0 Hz, 1H), 4.28 (p, J = 6.4 Hz, 1H), 4.21-4.06 (m, 4H), 1.59 (s, 3H), 1.46 (d, J = 6.4 Hz, 6H). |
| 287 | 1H NMR (400 MHz, Methanol-d4) δ 8.75 (d, J = 2.1 Hz, 1H), 8.67 (d, J = 2.1 Hz, 1H), 8.45 (s, 1H), 8.05 (d, J = 5.1 Hz, 1H), 7.86 (s, 1H), 7.22 (d, J = 5.0 Hz, 1H), 4.28 (p, J = 6.4 Hz, 1H), 3.79 (d, J = 13.1 Hz, 2H), 3.75-3.51 (m, 2H), 1.85-1.63 (m, 4H), 1.46 (d, J = 6.4 Hz, 6H), 1.30 (s, 3H). |
| 288 | 1H NMR (400 MHz, Methanol-d4) δ 8.73 (d, J = 2.2 Hz, 1H), 8.70 (s, 1H), 8.66 (d, J = 2.2 Hz, 1H), 8.05 (d, J = 5.1 Hz, 1H), 7.96 (s, 1H), 7.21 (d, J = 5.1 Hz, 1H), 4.27 (q, J = 6.4 Hz, 1H), 2.50 (d, J = 3.6 Hz, 2H), 2.21 (dd, J = 8.3, 4.3 Hz, 2H), 2.16-2.01 (m, 4H), 1.95 (s, 3H), 1.48 (d, J = 6.4 Hz, 6H). |
| 289 | 1H NMR (400 MHz, Methanol-d4) δ 7.21 (d, J = 5.0 Hz, 1H), 4.29 (p, J = 6.4 Hz, 1H), 4.07-3.87 (m, 1H), 3.27 (d, J = 5.9 Hz, 2H), 2.77-2.57 (m, 3H), 2.18 (td, J = 9.4, 8.9, 6.8 Hz, 2H), 1.96 (s, 3H), 1.48 (d, J = 6.4 Hz, 6H). |
| 290 | 1H NMR (400 MHz, Methanol-d4) δ 8.75 (s, 1H), 8.72 (d, J = 2.2 Hz, 1H), 8.66 (d, J = 2.2 Hz, 1H), 8.08 (d, J = 5.1 Hz, 1H), 7.96 (s, 1H), 7.20 (d, J = 5.0 Hz, 1H), 4.38-4.24 (m, 1H), 4.18-4.00 (m, 1H), 3.39 (d, J = 7.3 Hz, 2H), 2.71 (tt, J = 8.5, 4.1 Hz, 1H), 2.56 (ddd, J = 11.7, 8.7, 6.6 Hz, 2H), 2.42 (dtd, J = 12.7, 5.5, 2.1 Hz, 2H), 1.97 (s, 3H), 1.48 (d, J = 6.4 Hz, 6H). |
| 291 | 1H NMR (400 MHz, Methanol-d4) δ 8.75 (d, J = 2.2 Hz, 1H), 8.66 (d, J = 2.1 Hz, 1H), 8.46 (s, 1H), 8.05 (d, J = 5.0 Hz, 1H), 7.86 (s, 1H), 7.22 (d, J = 5.1 Hz, 1H), 4.27 (p, J = 6.4 Hz, 1H), 3.70 (d, J = 11.7 Hz, 2H), 3.41 (d, J = 11.7 Hz, 2H), 2.43 (s, 2H), 1.88-1.80 (m, 2H), 1.80-1.69 (m, 2H), 1.66 (d, J = 7.9 Hz, 2H), 1.46 (d, J = 6.4 Hz, 6H). |
| 292 | 1H NMR (400 MHz, Methanol-d4) δ 8.77 (d, J = 2.1 Hz, 1H), 8.69 (d, J = 2.1 Hz, 1H), 8.48 (s, 1H), 8.09 (d, J = 4.9 Hz, 1H), 7.85 (s, 1H), 7.24 (d, J = 5.0 Hz, 1H), 4.00 (s, 1H), 3.82 (d, J = 12.2 Hz, 1H), 3.55 (d, J = 12.0 Hz, 2H), 2.45 (s, 2H), 2.03 (d, J = 22.7 Hz, 11H). |
| 293 | 1H NMR (400 MHz, Methanol-d4) δ 8.74 (d, J = 2.2 Hz, 1H), 8.66 (d, J = 2.1 Hz, 1H), 8.46 (s, 1H), 8.04 (d, J = 5.0 Hz, 1H), 7.87 (s, 1H), 7.22 (d, J = 5.1 Hz, 1H), 4.58 (t, J = 7.5 Hz, 2H), 4.49 (d, J = 9.8 Hz, 2H), 4.40 (d, J = 10.3 Hz, 2H), 4.27 (p, J = 6.2 Hz, 1H), 2.99 (t, J = 7.5 Hz, 2H), 1.45 (d, J = 6.4 Hz, 6H). |
| 294 | 1H NMR (400 MHz, Methanol-d4) δ 8.75 (d, J = 2.2 Hz, 1H), 8.67 (d, J = 2.1 Hz, 1H), 8.48 (s, 1H), 8.06 (d, J = 5.1 Hz, 1H), 7.87 (s, 1H), 7.22 (d, J = 5.0 Hz, 1H), 4.28 (p, J = 6.4 Hz, 1H), 3.83 (t, J = 5.9 Hz, 4H), 2.20 (tt, J = 13.0, 5.9 Hz, 4H), 1.46 (d, J = 6.4 Hz, 6H). |
| 295 | 1H NMR (400 MHz, Methanol-d4) δ 8.78 (d, J = 2.2 Hz, 1H), 8.70 (d, J = 2.1 Hz, 1H), 8.51 (s, 1H), 8.09 (d, J = 5.0 Hz, 1H), 7.88 (s, 1H), 7.25 (d, J = 5.1 Hz, 1H), 4.31 (p, J = 6.4 Hz, 1H), 3.94 (d, J = 12.5 Hz, 2H), 3.63 (dd, J = 12.5, 3.8 Hz, 2H), 2.13 (s, 2H), 1.99-1.74 (m, 8H), 1.49 (d, J = 6.4 Hz, 6H). |
| 296 | 1H NMR (400 MHz, Methanol-d4) δ 8.78 (d, J = 2.1 Hz, 1H), 8.70 (d, J = 2.1 Hz, 1H), 8.49 (s, 1H), 8.08 (d, J = 5.0 Hz, 1H), 7.89 (s, 1H), 7.25 (d, J = 5.1 Hz, 1H), 4.35-4.24 (m, 1H), 3.96 (dd, J = 37.0, 12.3 Hz, 2H), 3.55-3.49 (m, 1H), 2.03 (s, 1H), 1.99 (s, 3H), 1.85 (d, J = 26.8 Hz, 1H), 1.67 (d, J = 10.8 Hz, 1H), 1.48 (d, J = 6.4 Hz, 6H). several aliphatic peaks obscured by solvent |

TABLE 1-continued

| Compound | 1H-NMR |
|---|---|
| 297 | 1H NMR (400 MHz, Methanol-d4) δ 8.75 (d, J = 2.2 Hz, 1H), 8.66 (d, J = 2.1 Hz, 1H), 8.50 (s, 1H), 8.05 (d, J = 5.0 Hz, 1H), 7.90 (s, 1H), 7.22 (d, J = 5.1 Hz, 1H), 4.52 (d, J = 9.8 Hz, 2H), 4.31-4.23 (m, 3H), 1.46 (d, J = 6.4 Hz, 6H). |
| 298 | 1H NMR (400 MHz, Methanol-d4) δ 8.78 (d, J = 2.2 Hz, 1H), 8.70 (d, J = 2.2 Hz, 1H), 8.50 (s, 1H), 8.09 (d, J = 5.1 Hz, 1H), 7.88 (s, 1H), 7.25 (d, J = 5.0 Hz, 1H), 4.31 (p, J = 6.3 Hz, 1H), 3.93-3.81 (m, 3H), 3.79-3.60 (m, 2H), 2.20 (d, J = 14.1 Hz, 1H), 2.06 (d, J = 7.0 Hz, 0H), 1.94 (s, 6H), 1.92-1.81 (m, 1H), 1.70-1.56 (m, 1H), 1.49 (d, J = 6.4 Hz, 6H). |
| 299 | 1H NMR (400 MHz, Methanol-d4) δ 8.78 (d, J = 2.1 Hz, 1H), 8.70 (d, J = 2.2 Hz, 1H), 8.49 (s, 1H), 8.21 (d, J = 6.8 Hz, 1H), 8.08 (d, J = 5.1 Hz, 1H), 7.89 (s, 1H), 7.25 (d, J = 5.1 Hz, 1H), 4.30 (p, J = 6.4 Hz, 1H), 3.95 (dd, J = 37.3, 12.2 Hz, 2H), 3.55-3.43 (m, 1H), 1.99 (s, 4H), 1.80 (dd, J = 13.7, 3.9 Hz, 1H), 1.67 (d, J = 10.9 Hz, 1H), 1.48 (d, J = 6.4 Hz, 6H). several aliphatic peaks obscured by solvent |
| 300 | 1H NMR (400 MHz, Methanol-d4) δ 8.78 (d, J = 2.2 Hz, 1H), 8.69 (d, J = 2.1 Hz, 1H), 8.50 (s, 1H), 8.08 (d, J = 5.1 Hz, 1H), 7.90 (s, 1H), 7.24 (d, J = 5.0 Hz, 1H), 4.29 (dd, J = 13.1, 6.7 Hz, 2H), 3.85 (d, J = 11.6 Hz, 2H), 3.63 (d, J = 11.6 Hz, 2H), 3.07 (s, 3H), 2.66 (s, 2H), 2.18 (s, 3H), 2.02 (s, 2H), 1.81 (s, 2H), 1.49 (d, J = 6.4 Hz, 6H). |
| 301 | 1H NMR (400 MHz, Methanol-d4) δ 8.78 (d, J = 2.2 Hz, 1H), 8.70 (d, J = 2.2 Hz, 1H), 8.50 (s, 1H), 8.09 (d, J = 5.0 Hz, 1H), 7.89 (s, 1H), 7.25 (d, J = 5.1 Hz, 1H), 4.42-4.34 (m, 2H), 4.34-4.26 (m, 1H), 3.91-3.82 (m, 3H), 3.74-3.68 (m, 2H), 3.58 (d, J = 12.1 Hz, 2H), 2.86 (s, 2H), 2.03 (d, J = 10.4 Hz, 2H), 1.77 (d, J = 8.2 Hz, 2H), 1.49 (d, J = 6.3 Hz, 6H). |
| 302 | 1H NMR (400 MHz, Methanol-d4) δ 8.79 (d, J = 2.1 Hz, 1H), 8.70 (d, J = 2.1 Hz, 1H), 8.51 (d, J = 2.7 Hz, 1H), 8.09 (d, J = 5.0 Hz, 1H), 7.89 (s, 1H), 7.25 (d, J = 5.0 Hz, 1H), 4.88 (s, 1H), 4.31 (p, J = 6.4 Hz, 1H), 3.84 (ddd, J = 24.2, 9.5, 2.0 Hz, 1H), 3.77 (d, J = 2.1 Hz, 1H), 3.69-3.51 (m, 2H), 2.32-2.09 (m, 4H), 2.02 (s, 2H), 1.49 (d, J = 6.4 Hz, 6H). |
| 303 | 1H NMR (400 MHz, Methanol-d4) δ 8.79 (d, J = 2.1 Hz, 1H), 8.70 (d, J = 2.2 Hz, 1H), 8.51 (d, J = 2.7 Hz, 1H), 8.09 (d, J = 5.1 Hz, 1H), 7.89 (s, 1H), 7.25 (d, J = 5.1 Hz, 1H), 4.88 (s, 1H), 4.31 (p, J = 6.4 Hz, 1H), 3.84 (ddd, J = 24.2, 9.5, 2.0 Hz, 1H), 3.77 (d, J = 2.1 Hz, 1H), 3.59 (ddd, J = 27.3, 17.4, 9.2 Hz, 2H), 2.33-2.08 (m, 4H), 2.02 (s, 2H), 1.49 (d, J = 6.4 Hz, 6H). |
| 304 | 1H NMR (400 MHz, Methanol-d4) δ 8.76 (d, J = 2.1 Hz, 1H), 8.67 (d, J = 2.1 Hz, 1H), 8.50 (s, 1H), 8.06 (d, J = 5.0 Hz, 1H), 7.87 (s, 1H), 7.22 (d, J = 5.1 Hz, 1H), 4.79 (t, J = 6.9 Hz, 2H), 4.70 (t, J = 6.3 Hz, 2H), 4.29 (p, J = 6.5 Hz, 1H), 3.86 (t, J = 6.2 Hz, 1H), 3.80 (t, J = 5.2 Hz, 4H), 2.82 (t, J = 5.2 Hz, 4H), 1.46 (d, J = 6.4 Hz, 6H). |
| 305 | 1H NMR (400 MHz, Methanol-d4) δ 8.74 (s, 1H), 8.66 (d, J = 2.1 Hz, 1H), 8.46 (s, 1H), 8.04 (d, J = 5.1 Hz, 1H), 7.88 (s, 1H), 7.21 (d, J = 4.9 Hz, 1H), 4.31-4.20 (m, 1H), 4.08 (d, J = 13.2 Hz, 2H), 3.37 (d, J = 14.7 Hz, 4H), 2.74 (d, J = 4.4 Hz, 3H), 1.89 (d, J = 13.8 Hz, 3H), 1.46 (d, J = 6.4 Hz, 6H). |
| 306 | 1H NMR (400 MHz, Methanol-d4) δ 8.76 (d, J = 2.2 Hz, 1H), 8.67 (d, J = 2.1 Hz, 1H), 8.48 (s, 1H), 8.08 (d, J = 5.1 Hz, 1H), 7.82 (s, 1H), 7.23 (d, J = 5.1 Hz, 1H), 4.55 (d, J = 22.7 Hz, 1H), 4.38 (d, J = 15.2 Hz, 1H), 4.09 (d, J = 14.0 Hz, 1H), 3.76 (dd, J = 29.3, 14.0 Hz, 1H), 3.58 (t, J = 12.5 Hz, 1H), 2.01 (s, 4H). Several peaks obscured by solvent |
| 307 | 1H NMR (400 MHz, Methanol-d4) δ 8.76 (d, J = 2.1 Hz, 1H), 8.67 (d, J = 2.2 Hz, 1H), 8.48 (s, 1H), 8.43 (d, J = 8.8 Hz, 1H), 8.08 (d, J = 5.0 Hz, 1H), 7.82 (s, 1H), 7.23 (d, J = 5.0 Hz, 1H), 4.39 (s, 1H), 4.10 (d, J = 13.3 Hz, 1H), 3.76 (dd, J = 29.2, 14.2 Hz, 1H), 3.58 (s, 1H), 2.01 (s, 3H). Several peaks obscured by solvent |
| 308 | 1H NMR (400 MHz, Methanol-d4) δ 8.75 (d, J = 2.2 Hz, 1H), 8.67 (d, J = 2.2 Hz, 1H), 8.48 (s, 1H), 8.34 (d, J = 4.9 Hz, 2H), 8.05 (d, J = 5.1 Hz, 1H), 7.86 (s, 1H), 7.22 (d, J = 5.1 Hz, 1H), 6.69 (t, J = 4.9 Hz, 1H), 4.28 (p, J = 6.3 Hz, 1H), 4.10 (s, 1H), 3.85 (dd, J = 12.3, 3.1 Hz, 2H), 3.61 (d, J = 12.0 Hz, 2H), 2.57 (s, 2H), 2.14-2.03 (m, 2H), 1.72 (t, J = 7.4 Hz, 2H), 1.47 (d, J = 6.4 Hz, 6H). |
| 309 | 1H NMR (400 MHz, Methanol-d4) δ 8.75 (d, J = 2.2 Hz, 1H), 8.67 (d, J = 2.2 Hz, 1H), 8.48 (s, 1H), 8.05 (d, J = 5.0 Hz, 1H), 7.86 (s, 1H), 7.84 (d, J = 5.3 Hz, 1H), 7.39-7.29 (m, 1H), 7.22 (d, J = 5.0 Hz, 1H), 6.69-6.60 (m, 1H), 4.29 (p, J = 6.2 Hz, 1H), 4.12 (s, 1H), 3.89-3.80 (m, 2H), 3.65 (d, J = 12.0 Hz, 2H), 2.62 (s, 2H), 2.10 (d, J = 10.0 Hz, 2H), 1.71 (d, J = 8.4 Hz, 2H), 1.47 (d, J = 6.4 Hz, 6H). |
| 310 | 1H NMR (400 MHz, Methanol-d4) δ 8.75 (d, J = 2.1 Hz, 1H), 8.67 (d, J = 2.1 Hz, 1H), 8.47 (s, 1H), 8.05 (d, J = 5.0 Hz, 1H), 7.86 (s, 1H), 7.22 (d, J = 5.0 Hz, 1H), 4.28 (p, J = 6.4 Hz, 1H), 3.92-3.84 (m, 2H), 3.69-3.56 (m, 2H), 2.13 (t, J = 10.0 Hz, 3H), 2.07-1.90 (m, 2H), 1.46 (d, J = 6.4 Hz, 6H). |
| 311 | 1H NMR (400 MHz, Methanol-d4) δ 8.81 (s, 1H), 8.80 (s, 1H), 8.74 (d, J = 2.1 Hz, 1H), 8.09 (d, J = 5.1 Hz, 1H), 7.75 (s, 1H), 7.60 (d, J = 7.7 Hz, 1H), 7.26 (d, J = 5.1 Hz, 1H), 5.32-5.25 (m, 1H), 5.22 (t, J = 6.7 Hz, 2H), 4.83 (dd, J = 6.9, 5.4 Hz, 2H), 3.97 (s, 1H), 3.54 (t, J = 6.0 Hz, 1H), 2.17 (d, J = 6.7 Hz, 5H), 1.88 (p, J = 6.0, 5.5 Hz, 4H), 1.38 (s, 6H). |
| 312 | 1H NMR (400 MHz, Methanol-d4) δ 8.80 (d, J = 2.1 Hz, 1H), 8.75 (s, 1H), 8.71 (d, J = 2.1 Hz, 1H), 8.11 (d, J = 5.1 Hz, 1H), 7.98 (s, 1H), 7.60 (d, J = 7.8 Hz, 1H), 7.26 (d, J = 5.0 Hz, 1H), 4.35 (p, J = 6.4 Hz, 1H), 3.97 (d, J = 5.8 Hz, 1H), 3.56-3.47 (m, 1H), 2.15 (d, J = 6.7 Hz, 4H), 1.87 (p, J = 6.3, 5.7 Hz, 4H), 1.52 (d, J = 6.4 Hz, 6H), 1.38 (s, 6H). |

TABLE 1-continued

| Compound | 1H-NMR |
|---|---|
| 313 | 1H NMR (400 MHz, Methanol-d4) δ 8.76 (d, J = 2.1 Hz, 1H), 8.71 (s, 1H), 8.68 (d, J = 2.2 Hz, 1H), 8.07 (d, J = 5.0 Hz, 1H), 7.95 (s, 1H), 7.23 (d, J = 5.1 Hz, 1H), 6.81 (s, 1H), 4.31 (p, J = 6.4 Hz, 1H), 4.05 (s, 1H), 2.90 (d, J = 18.0 Hz, 1H), 2.71 (t, J = 19.3 Hz, 2H), 2.33-2.18 (m, 1H), 2.08 (d, J = 12.8 Hz, 1H), 1.96 (s, 3H), 1.86-1.71 (m, 1H), 1.49 (d, J = 6.4 Hz, 6H). |
| 314 | 1H NMR (400 MHz, Methanol-d4) δ 8.79 (d, J = 2.2 Hz, 1H), 8.74 (s, 1H), 8.71 (d, J = 2.1 Hz, 1H), 8.10 (d, J = 5.1 Hz, 1H), 7.97 (s, 1H), 7.88 (d, J = 7.8 Hz, 1H), 7.26 (d, J = 5.1 Hz, 1H), 4.42 (d, J = 6.1 Hz, 2H), 4.34 (p, J = 6.4 Hz, 1H), 3.93-3.77 (m, 1H), 2.35 (d, J = 13.0 Hz, 2H), 2.12 (d, J = 12.6 Hz, 2H), 1.84 (qd, J = 13.1, 3.4 Hz, 3H), 1.62 (s, 3H), 1.51 (d, J = 6.4 Hz, 8H). Additional peak obscured by solvent. |
| 315 | 1H NMR (400 MHz, Methanol-d4) δ 8.79 (d, J = 2.1 Hz, 1H), 8.74 (s, 1H), 8.71 (d, J = 2.2 Hz, 1H), 8.10 (d, J = 5.0 Hz, 1H), 7.97 (s, 1H), 7.26 (d, J = 5.1 Hz, 1H), 4.34 (p, J = 6.4 Hz, 1H), 3.85-3.71 (m, 1H), 3.36 (q, J = 3.4 Hz, 0H), 2.34 (d, J = 13.0 Hz, 2H), 2.15-2.03 (m, 2H), 1.84 (qd, J = 12.9, 3.3 Hz, 2H), 1.59 (qd, J = 12.9, 3.7 Hz, 2H), 1.51 (d, J = 6.4 Hz, 6H), 1.39 (s, 6H). Peak obscured by solvent. |
| 316 | 1H NMR (400 MHz, Methanol-d4) δ 8.83 (s, 1H), 8.73 (d, J = 2.1 Hz, 1H), 8.67 (d, J = 2.1 Hz, 1H), 8.23 (s, 1H), 8.08 (d, J = 5.0 Hz, 1H), 7.22 (d, J = 5.1 Hz, 1H), 5.20 (q, J = 6.9 Hz, 1H), 3.75 (ddq, J = 12.1, 7.8, 4.2 Hz, 1H), 2.31 (d, J = 13.2 Hz, 1H), 2.09 (d, J = 12.3 Hz, 2H), 1.94 (s, 3H), 1.91 (d, J = 6.9 Hz, 3H), 1.80 (qd, J = 12.7, 2.4 Hz, 3H), 1.47 (qd, J = 12.9, 12.4, 2.9 Hz, 3H). |
| 317 | 1H NMR (400 MHz, Methanol-d4) δ 8.81-8.62 (m, 3H), 8.07 (d, J = 5.1 Hz, 1H), 7.95 (s, 1H), 7.23 (d, J = 5.1 Hz, 1H), 4.31 (hept, J = 6.3 Hz, 1H), 3.33 (d, J = 6.0 Hz, 2H), 2.12-1.97 (m, 2H), 1.49 (d, J = 6.4 Hz, 6H). |
| 318 | 1H NMR (400 MHz, Chloroform-d) δ 10.02 (d, J = 7.2 Hz, 1H), 9.24 (s, 1H), 8.50-8.35 (m, 3H), 8.32 (d, J = 2.2 Hz, 1H), 7.11 (d, J = 5.1 Hz, 1H), 4.30 (q, J = 7.1 Hz, 2H), 4.23 (s, 2H), 4.09 (h, J = 6.6 Hz, 1H), 1.51 (d, J = 6.4 Hz, 6H), 1.34 (t, J = 7.2 Hz, 3H). |
| 319 | 1H NMR (400 MHz, Methanol-d4) δ 9.58 (s, 1H), 8.87-8.74 (m, 2H), 8.68 (d, J = 2.1 Hz, 1H), 8.13-7.92 (m, 2H), 7.22 (d, J = 5.1 Hz, 1H), 4.42-4.25 (m, 1H), 2.99 (s, 1H), 2.86 (d, J = 0.8 Hz, 1H), 1.49 (dd, J = 6.4, 4.8 Hz, 6H). |
| 320 | 1H NMR (400 MHz, Methanol-d4) δ 8.82-8.74 (m, 2H), 8.68 (d, J = 2.2 Hz, 1H), 8.08 (d, J = 5.1 Hz, 1H), 7.95 (d, J = 1.9 Hz, 1H), 7.23 (d, J = 5.0 Hz, 1H), 4.38-4.25 (m, 1H), 3.34 (s, 2H), 1.73 (s, 1H), 1.49 (dd, J = 6.5, 2.4 Hz, 6H), 1.31 (s, 5H). |
| 321 | 1H NMR (400 MHz, Methanol-d4) δ 8.81-8.73 (m, 2H), 8.68 (d, J = 2.1 Hz, 1H), 8.07 (d, J = 5.0 Hz, 1H), 7.99 (s, 1H), 7.23 (d, J = 5.0 Hz, 1H), 4.63 (d, J = 5.7 Hz, 2H), 4.32 (h, J = 6.4 Hz, 1H), 1.49 (d, J = 6.4 Hz, 6H). |
| 322 | 1H NMR (400 MHz, Methanol-d4) δ 8.82-8.61 (m, 3H), 8.07 (d, J = 5.1 Hz, 1H), 7.95 (s, 1H), 7.23 (d, J = 5.1 Hz, 1H), 4.31 (hept, J = 6.4 Hz, 1H), 4.20-3.89 (m, 7H), 3.76-3.61 (m, 2H), 2.67-2.51 (m, 1H), 2.39-2.22 (m, 1H), 1.49 (d, J = 6.5 Hz, 6H). |
| 323 | 1H NMR (400 MHz, Methanol-d4) δ 8.76 (d, J = 2.2 Hz, 1H), 8.68 (d, J = 2.1 Hz, 1H), 8.50 (s, 1H), 8.07 (d, J = 5.1 Hz, 1H), 7.98 (s, 1H), 7.87 (s, 1H), 7.23 (d, J = 5.1 Hz, 1H), 4.29 (p, J = 6.4 Hz, 1H), 4.11 (dd, J = 5.6, 2.2 Hz, 1H), 4.05 (dd, J = 10.7, 5.6 Hz, 1H), 3.91 (d, J = 10.2 Hz, 1H), 3.68 (dd, J = 10.6, 2.2 Hz, 1H), 3.44 (d, J = 10.2 Hz, 1H), 3.00 (s, 1H), 2.86 (d, J = 0.7 Hz, 1H), 2.70 (s, 1H), 1.98 (s, 3H), 1.47 (d, J = 6.4 Hz, 6H), 1.00-0.93 (m, 1H), 0.89 (dd, J = 8.3, 5.0 Hz, 1H). |
| 324 | 1H NMR (400 MHz, Methanol-d4) δ 8.76 (d, J = 2.1 Hz, 1H), 8.68 (d, J = 2.1 Hz, 1H), 8.50 (s, 1H), 8.07 (d, J = 5.1 Hz, 1H), 7.87 (s, 1H), 7.23 (dd, J = 5.1, 1.6 Hz, 1H), 4.29 (p, J = 6.3 Hz, 1H), 4.11 (dd, J = 5.6, 2.2 Hz, 1H), 4.05 (dd, J = 10.6, 5.6 Hz, 1H), 3.91 (d, J = 10.2 Hz, 1H), 3.68 (dd, J = 10.7, 2.3 Hz, 1H), 3.44 (d, J = 10.2 Hz, 1H), 1.98 (s, 3H), 1.47 (d, J = 6.4 Hz, 6H), 1.00-0.84 (m, 2H). |
| 325 | 1H NMR (400 MHz, Acetonitrile-d3) δ 9.87 (s, 1H), 8.66 (d, J = 2.1 Hz, 1H), 8.62 (d, J = 2.1 Hz, 1H), 8.54 (d, J = 2.6 Hz, 1H), 8.51 (s, 1H), 8.05 (d, J = 5.1 Hz, 1H), 7.92 (d, J = 1.7 Hz, 1H), 7.53 (s, 1H), 7.20 (d, J = 5.1 Hz, 1H), 6.68 (dd, J = 2.8, 1.7 Hz, 1H), 4.29 (dq, J = 12.9, 6.4 Hz, 1H), 1.45 (d, J = 6.4 Hz, 6H). |
| 326 | 1H NMR (400 MHz, Acetonitrile-d3) δ 9.56 (s, 1H), 9.17 (d, J = 1.7 Hz, 1H), 9.14 (s, 2H), 8.66 (d, J = 2.2 Hz, 1H), 8.51 (s, 1H), 8.10-8.04 (m, 1H), 7.78 (s, 0H), 7.78 (s, 1H), 7.77 (t, J = 1.2 Hz, 1H), 7.55 (s, 1H), 7.25-7.19 (m, 1H), 5.35 (t, J = 4.8 Hz, 2H), 2.25 (t, J = 7.6 Hz, 4H), 1.44 (d, J = 6.4 Hz, 6H). |
| 327 | 1H NMR (400 MHz, Acetonitrile-d3) δ 9.94 (d, J = 7.7 Hz, 1H), 8.62-8.54 (m, 2H), 8.36 (s, 1H), 8.01 (d, J = 5.1 Hz, 1H), 7.56 (s, 1H), 7.16 (d, J = 5.0 Hz, 1H), 6.96 (d, J = 8.9 Hz, 1H), 5.03 (dt, J = 14.5, 8.4 Hz, 2H), 4.20 (dq, J = 13.1, 6.5 Hz, 1H), 3.57-3.49 (m, 1H), 1.98 (s, 3H), 1.42 (d, J = 6.4 Hz, 6H). |
| 328 | 1H NMR (400 MHz, Acetonitrile-d3) δ 9.86 (d, J = 7.8 Hz, 1H), 8.62-8.55 (m, 2H), 8.24 (s, 1H), 7.99 (d, J = 5.1 Hz, 1H), 7.43 (s, 1H), 7.17 (d, J = 5.1 Hz, 1H), 4.59-4.48 (m, 2H), 4.46-4.36 (m, 3H), 4.21 (dq, J = 7.8, 6.3 Hz, 1H), 3.85 (t, J = 11.7 Hz, 2H), 3.67 (t, J = 7.6 Hz, 2H), 2.66 (tt, J = 14.2, 7.6 Hz, 2H), 1.38 (d, J = 6.4 Hz, 6H). |
| 329 | 1H NMR (400 MHz, Acetonitrile-d3) δ 10.08 (d, J = 7.6 Hz, 1H), 8.66-8.60 (m, 2H), 8.37 (s, 1H), 8.05 (d, J = 5.1 Hz, 1H), 7.59 (s, 1H), 7.20 (dd, J = 5.1, |

TABLE 1-continued

| Compound | 1H-NMR |
|---|---|
| | 1.8 Hz, 1H), 4.24 (dq, J = 13.2, 6.6 Hz, 2H), 4.05 (d, J = 6.7 Hz, 2H), 3.81-3.75 (m, 1H), 3.73-3.67 (m, 2H), 3.58-3.49 (m, 2H), 1.80 (p, J = 2.5 Hz, 1H), 1.45 (d, J = 6.4 Hz, 6H). |
| 330 | 1H NMR (400 MHz, Acetonitrile-d3) δ 10.09 (d, J = 7.7 Hz, 1H), 8.67-8.61 (m, 2H), 8.30 (s, 1H), 8.02 (d, J = 5.1 Hz, 1H), 7.52 (s, 1H), 7.20 (d, J = 5.1 Hz, 1H), 6.99 (d, J = 6.9 Hz, 1H), 4.54 (q, J = 5.5 Hz, 1H), 4.32-4.18 (m, 1H), 3.83 (dd, J = 10.7, 6.1 Hz, 1H), 3.68 (dtt, J = 13.2, 5.0, 2.8 Hz, 1H), 3.46 (dd, J = 10.7, 4.1 Hz, 1H), 1.91 (s, 3H), 1.44 (d, J = 6.4 Hz, 6H). |
| 331 | 1H NMR (400 MHz, Acetonitrile-d3) δ 10.09 (d, J = 7.8 Hz, 1H), 8.64 (t, J = 1.6 Hz, 2H), 8.61-8.58 (m, 1H), 8.30 (s, 1H), 8.02 (d, J = 5.1 Hz, 1H), 7.52 (s, 1H), 4.54 (dt, J = 11.1, 5.4 Hz, 1H), 4.25 (dq, J = 13.1, 6.4 Hz, 1H), 3.83 (dd, J = 10.7, 6.1 Hz, 1H), 3.72-3.62 (m, 2H), 3.46 (dd, J = 10.8, 4.1 Hz, 1H), 1.91 (s, 3H), 1.44 (d, J = 6.4 Hz, 6H), 1.36 (d, J = 6.4 Hz, 2H). |
| 332 | 1H NMR (400 MHz, Acetonitrile-d3) δ 10.42 (s, 1H), 8.64 (d, J = 2.2 Hz, 1H), 8.59 (d, J = 2.1 Hz, 1H), 8.50 (s, 1H), 8.06-8.01 (m, 1H), 7.41 (s, 1H), 7.18 (d, J = 5.1 Hz, 1H), 5.16-5.07 (m, 3H), 4.72 (d, J = 2.3 Hz, 2H), 4.63 (dd, J = 8.8, 3.1 Hz, 1H), 3.77 (s, 2H), 3.75-3.67 (m, 2H), 3.67-3.55 (m, 2H), 2.55-2.43 (m, 1H), 2.23-2.15 (m, 2H), 2.11 (s, 3H). |
| 333 | 1H NMR (400 MHz, Acetonitrile-d3) δ 9.91 (s, 1H), 8.81 (s, 1H), 8.67-8.54 (m, 2H), 8.08 (d, J = 5.1 Hz, 1H), 8.04-7.84 (m, 1H), 7.18 (d, J = 5.0 Hz, 1H), 4.22 (dq, J = 13.1, 6.5 Hz, 1H), 3.36 (tt, J = 10.7, 3.7 Hz, 1H), 3.18-3.07 (m, 1H), 2.24 (dd, J = 13.7, 3.9 Hz, 2H), 2.17-2.04 (m, 2H), 1.88 (dt, J = 13.6, 3.9 Hz, 2H), 1.47 (d, J = 6.4 Hz, 6H). |
| 334 | 1H NMR (400 MHz, Acetonitrile-d3) δ 10.32 (s, 1H), 8.79 (s, 1H), 8.65 (d, J = 2.2 Hz, 1H), 8.60 (d, J = 2.2 Hz, 1H), 8.06 (d, J = 5.1 Hz, 1H), 7.62 (s, 1H), 7.19 (d, J = 5.0 Hz, 1H), 6.97 (s, 1H), 5.13 (dd, J = 4.0, 2.4 Hz, 3H), 4.75 (q, J = 3.8 Hz, 2H), 2.51 (s, 2H), 2.23-2.17 (m, 2H), 2.07 (d, J = 7.6 Hz, 1H), 2.05 (dd, J = 3.9, 1.8 Hz, 3H), 1.99 (s, 1H), 1.89 (s, 3H). |
| 335 | 1H NMR (400 MHz, Acetonitrile-d3) δ 10.22 (s, 1H), 8.72 (s, 1H), 8.62 (dd, J = 21.6, 2.2 Hz, 2H), 8.06 (d, J = 5.0 Hz, 1H), 7.63 (s, 1H), 7.49 (s, 1H), 7.18 (d, J = 5.0 Hz, 1H), 5.13 (d, J = 3.4 Hz, 3H), 4.77-4.71 (m, 2H), 2.48 (s, 2H), 2.26-2.20 (m, 2H), 2.12 (s, 2H), 1.36 (s, 6H). |
| 336 | 1H NMR (400 MHz, Acetonitrile-d3) δ 9.90 (s, 1H), 8.69 (d, J = 2.1 Hz, 1H), 8.65 (d, J = 2.1 Hz, 1H), 8.57 (d, J = 2.7 Hz, 1H), 8.54 (s, 1H), 8.07 (d, J = 5.1 Hz, 1H), 7.94 (d, J = 1.7 Hz, 1H), 7.55 (s, 1H), 7.23 (d, J = 5.1 Hz, 1H), 6.71 (dd, J = 2.8, 1.7 Hz, 1H), 5.48 (s, 2H), 5.38 (t, J = 4.9 Hz, 1H), 4.32 (dq, J = 13.1, 6.5 Hz, 1H), 2.30-2.25 (m, 1H), 2.23-2.16 (m, 1H), 2.11 (s, 1H), 2.05 (q, J = 6.7 Hz, 3H), 1.47 (d, J = 6.4 Hz, 7H). |
| 337 | 1H NMR (400 MHz, Acetonitrile-d3) δ 10.14 (d, J = 7.7 Hz, 1H), 8.69 (s, 1H), 8.65-8.60 (m, 2H), 8.11 (d, J = 5.1 Hz, 1H), 7.80 (s, 1H), 7.21 (d, J = 5.1 Hz, 1H), 6.71 (s, 1H), 4.24-4.14 (m, 1H), 4.01 (dt, J = 12.0, 3.8 Hz, 3H), 3.67 (ddd, J = 12.0, 10.6, 2.4 Hz, 3H), 2.19 (dd, J = 10.8, 4.4 Hz, 6H), 2.10 (dd, J = 10.6, 4.6 Hz, 6H), 1.32 (s, 6H). |
| 338 | 1H NMR (400 MHz, Acetonitrile-d3) δ 10.22 (d, J = 7.8 Hz, 1H), 8.74-8.61 (m, 2H), 8.60 (s, 1H), 8.11 (d, J = 5.1 Hz, 1H), 7.67 (s, 1H), 7.22 (d, J = 5.1 Hz, 1H), 6.88 (s, 1H), 4.01 (dt, J = 11.9, 3.8 Hz, 2H), 3.67 (td, J = 11.9, 11.4, 2.4 Hz, 2H), 3.60 (s, 2H), 3.23 (s, 6H), 2.24-2.07 (m, 15H), 1.87-1.69 (m, 2H). |
| 339 | 1H NMR (400 MHz, Acetonitrile-d3) δ 9.70 (s, 1H), 8.73 (s, 1H), 8.62-8.55 (m, 3H), 8.05 (d, J = 4.9 Hz, 2H), 7.99 (s, 1H), 7.17 (d, J = 5.1 Hz, 1H), 7.12 (d, J = 8.5 Hz, 1H), 4.18 (dt, J = 13.1, 6.5 Hz, 1H), 3.57 (d, J = 3.8 Hz, 2H), 3.31-3.20 (m, 1H), 3.05 (s, 8H), 1.80 (p, J = 2.4 Hz, 2H), 1.55-1.49 (m, 1H), 1.46 (d, J = 6.4 Hz, 6H). |
| 340 | 1H NMR (400 MHz, Acetonitrile-d3) δ 9.52 (s, 1H), 8.70 (s, 1H), 8.58-8.54 (m, 2H), 8.04-7.99 (m, 2H), 7.15 (d, J = 5.0 Hz, 1H), 6.49 (d, J = 7.8 Hz, 1H), 4.16 (q, J = 6.7 Hz, 1H), 3.76 (s, 1H), 3.50 (d, J = 12.3 Hz, 2H), 3.24 (dd, J = 14.2, 10.5 Hz, 2H), 2.86 (s, 2H), 2.76 (s, 4H), 2.06 (d, J = 9.2 Hz, 1H), 1.80 (p, J = 2.5 Hz, 2H), 1.45 (d, J = 6.4 Hz, 6H). *Some peaks are obscured by the water peak |
| 341 | 1H NMR (400 MHz, Acetonitrile-d3) δ 10.01 (d, J = 7.6 Hz, 1H), 8.69 (s, 1H), 8.67-8.57 (m, 2H), 8.09 (d, J = 5.1 Hz, 1H), 7.81 (s, 1H), 7.21 (d, J = 5.1 Hz, 1H), 6.64 (d, J = 8.1 Hz, 1H), 4.25 (dq, J = 13.3, 6.7 Hz, 1H), 3.84 (ddd, J = 11.7, 7.9, 3.8 Hz, 1H), 3.27 (tt, J = 12.0, 3.6 Hz, 1H), 2.15-2.12 (m, 1H), 1.86-1.73 (m, 3H), 1.56 (td, J = 12.6, 3.5 Hz, 2H), 1.47 (d, J = 6.4 Hz, 6H), 1.44 (s, 6H). |
| 342 | 1H NMR (400 MHz, Methanol-d4) δ 8.80 (d, J = 2.1 Hz, 1H), 8.78 (s, 1H), 8.73 (d, J = 2.1 Hz, 1H), 8.12 (d, J = 5.0 Hz, 1H), 8.01 (s, 1H), 7.26 (d, J = 5.1 Hz, 1H), 4.77 (ddt, J = 7.6, 5.3, 2.7 Hz, 1H), 4.16-4.07 (m, 2H), 3.99 (tt, J = 8.6, 4.0 Hz, 2H), 3.77 (tt, J = 11.7, 4.0 Hz, 1H), 2.62 (ddt, J = 13.2, 8.6, 7.1 Hz, 1H), 2.33 (d, J = 13.1 Hz, 2H), 2.23-2.07 (m, 4H), 1.97 (s, 3H), 1.82 (qd, J = 13.1, 3.4 Hz, 3H), 1.50 (qd, J = 12.9, 3.4 Hz, 2H). |
| 343 | 1H NMR (400 MHz, Acetonitrile-d3) δ 10.85 (d, J = 46.3 Hz, 1H), 10.03 (d, J = 7.5 Hz, 1H), 8.76 (s, 1H), 8.65-8.56 (m, 2H), 8.10 (dd, J = 5.1, 2.6 Hz, 1H), 7.93 (s, 1H), 7.19 (d, J = 5.1 Hz, 1H), 6.26 (s, 1H), 4.21-4.10 (m, 1H), 4.01 (dt, J = 12.0, 3.9 Hz, 2H), 3.66 (td, J = 11.9, 11.4, 2.3 Hz, 2H), 3.49 (d, J = 12.4 Hz, 2H), 3.28 (dd, J = 8.8, 5.8 Hz, 1H), 2.92 (s, 1H), 2.80 (s, 1H), 2.75 (d, J = 2.6 Hz, 3H), 2.20-2.13 (m, 8H), 2.10-2.03 (m, 5H), 1.84-1.71 (m, 3H). |

Compounds comprising the following components or combined with other components exemplified herein might be prepared according to the Examples and Procedures described herein using the appropriate starting materials and protecting group chemistry as needed.

R¹ and Het pairings to form the below components present in these compounds would be generated from intermediates I-2 and I-3. These would be paired with a thiadiazole-R² component.

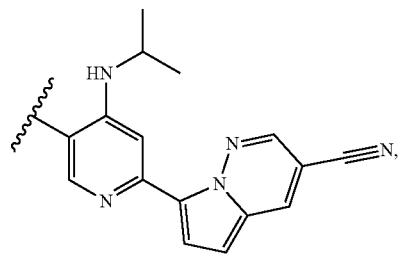

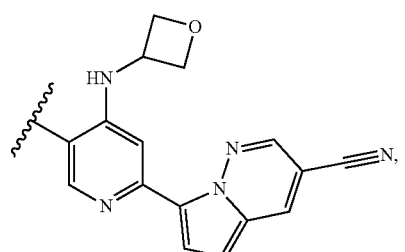

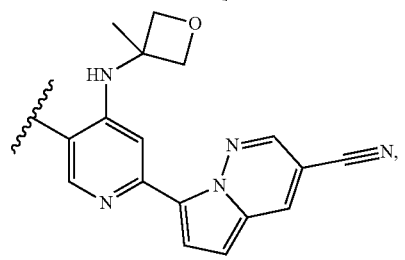

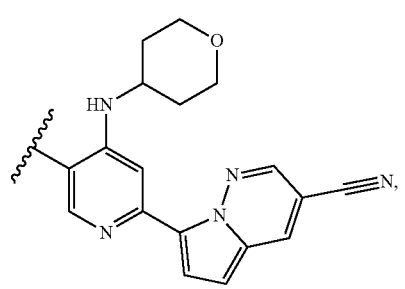

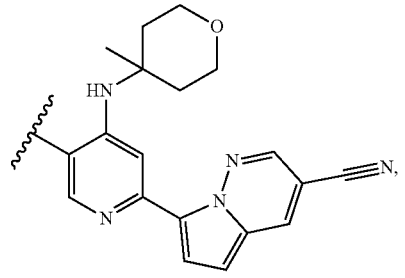

-continued

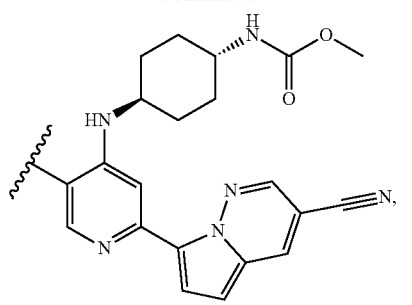

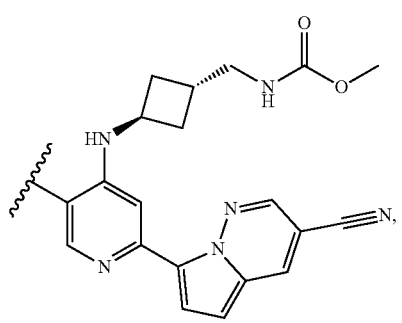

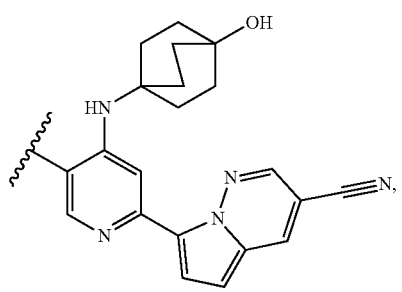

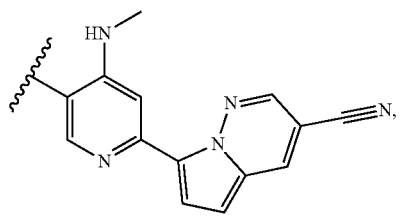

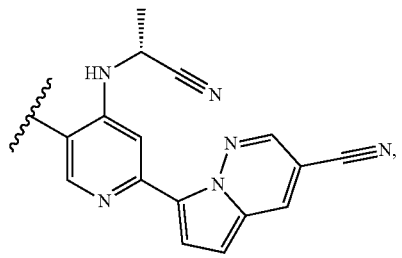

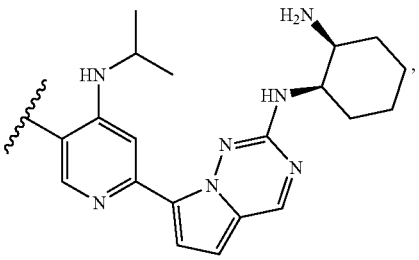

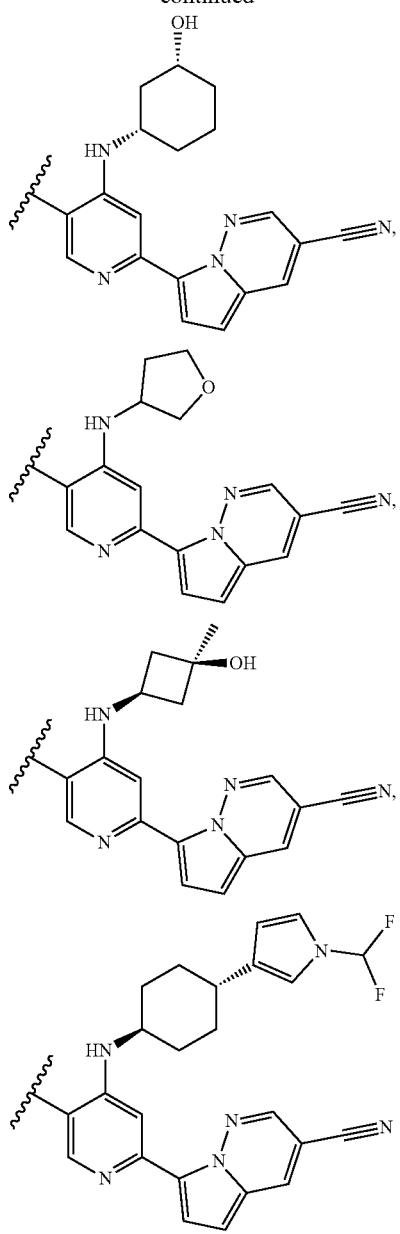
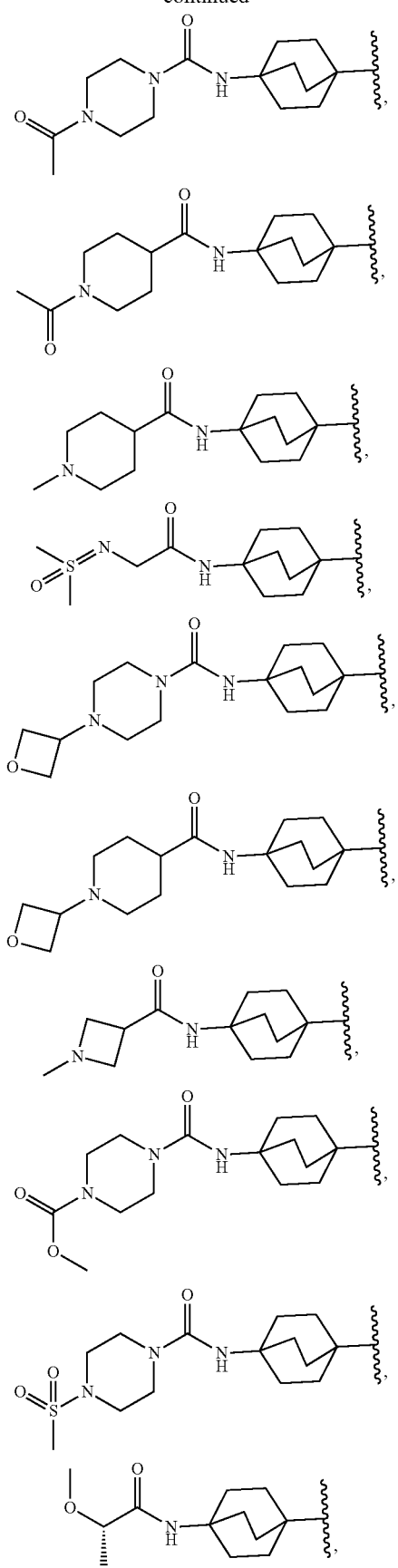
The above components would be combined with intermediates and components attached to the below $R^2$ groups and/or to exemplified $R^2$ groups by the methods described herein.

-continued
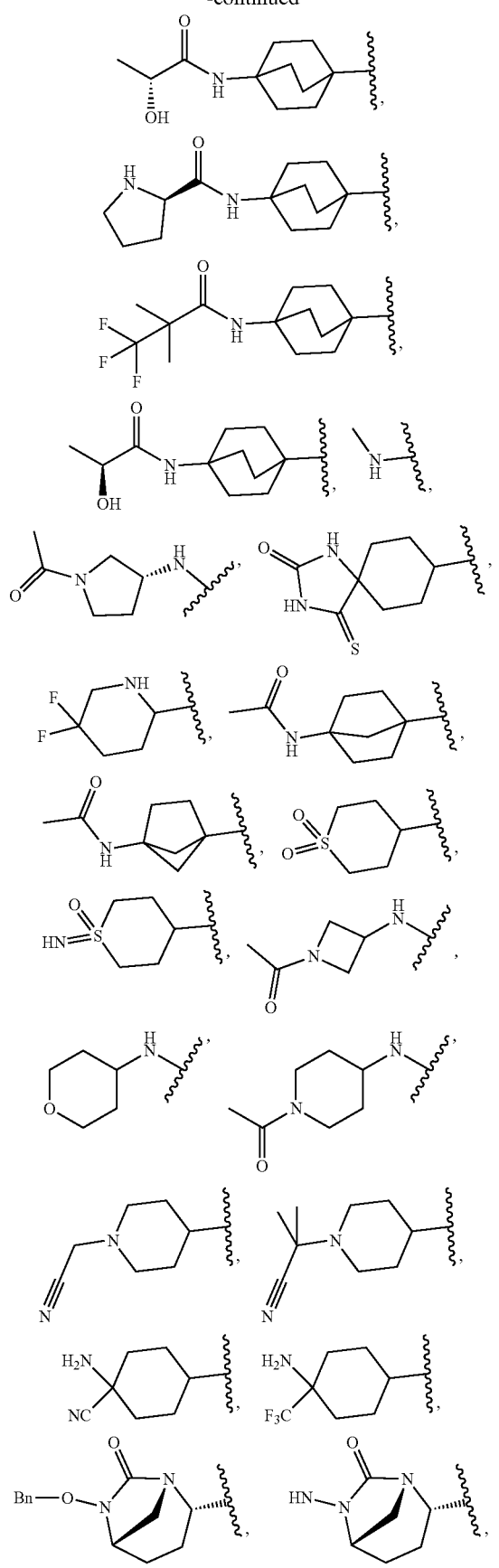
-continued
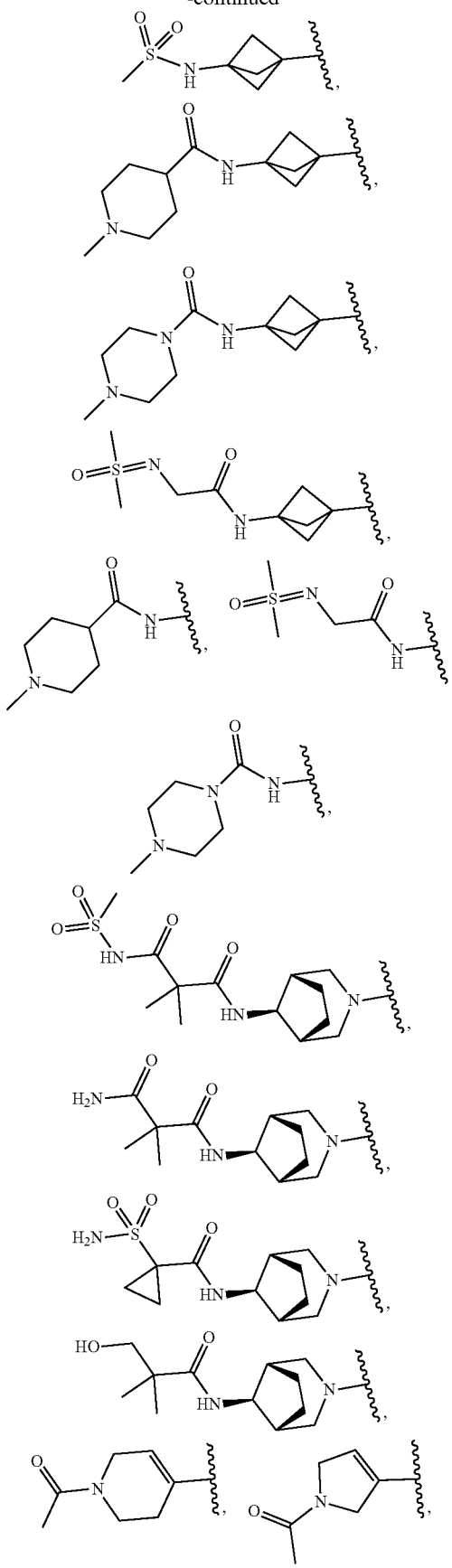

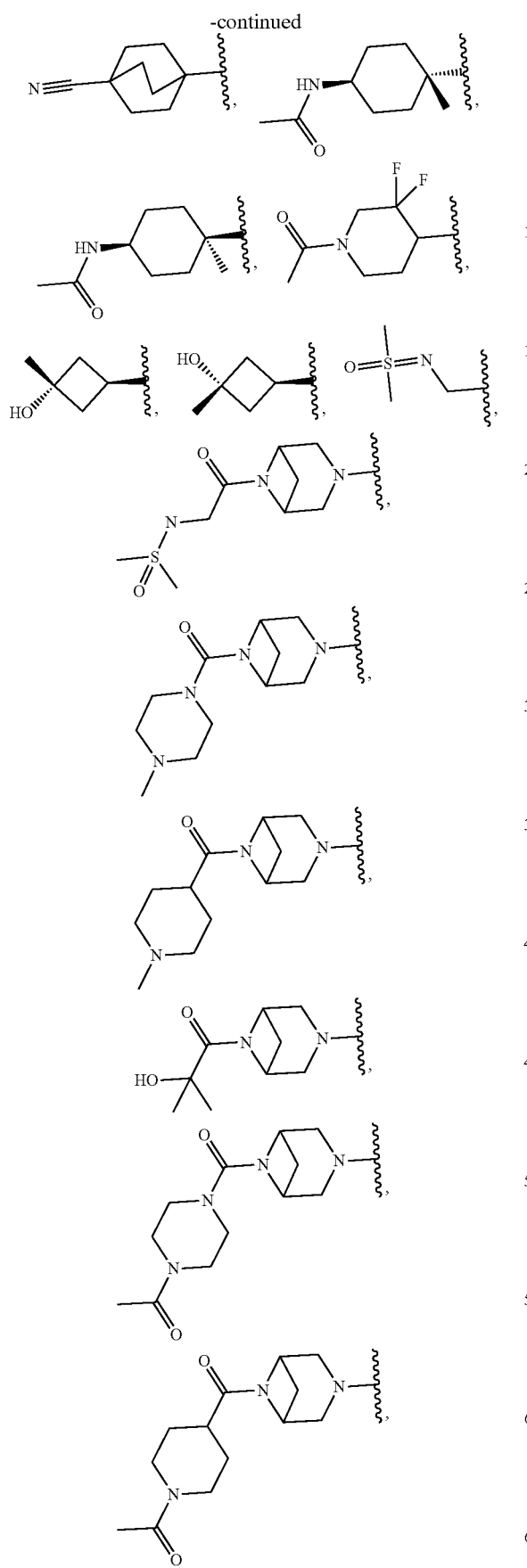
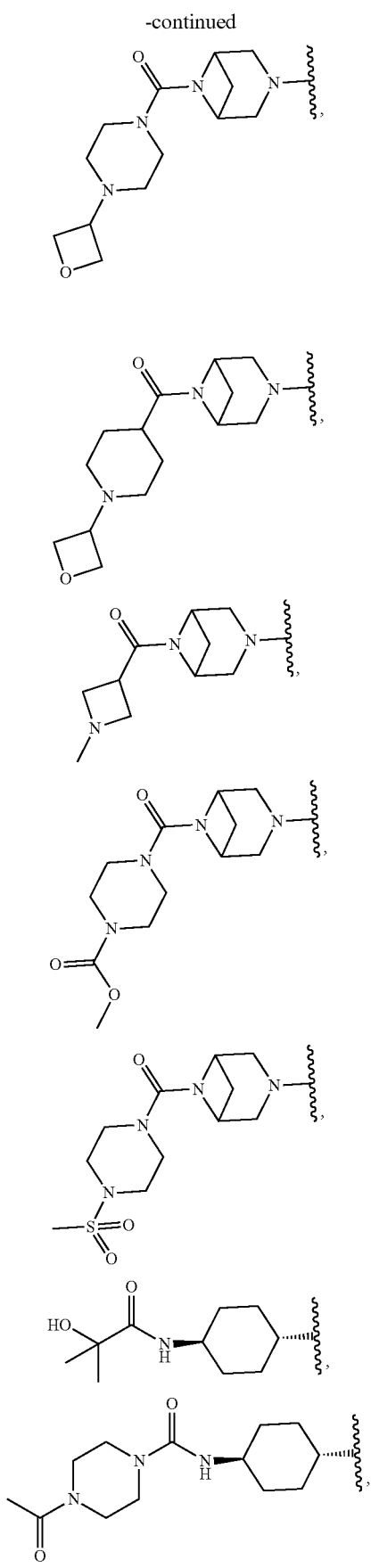

261
-continued
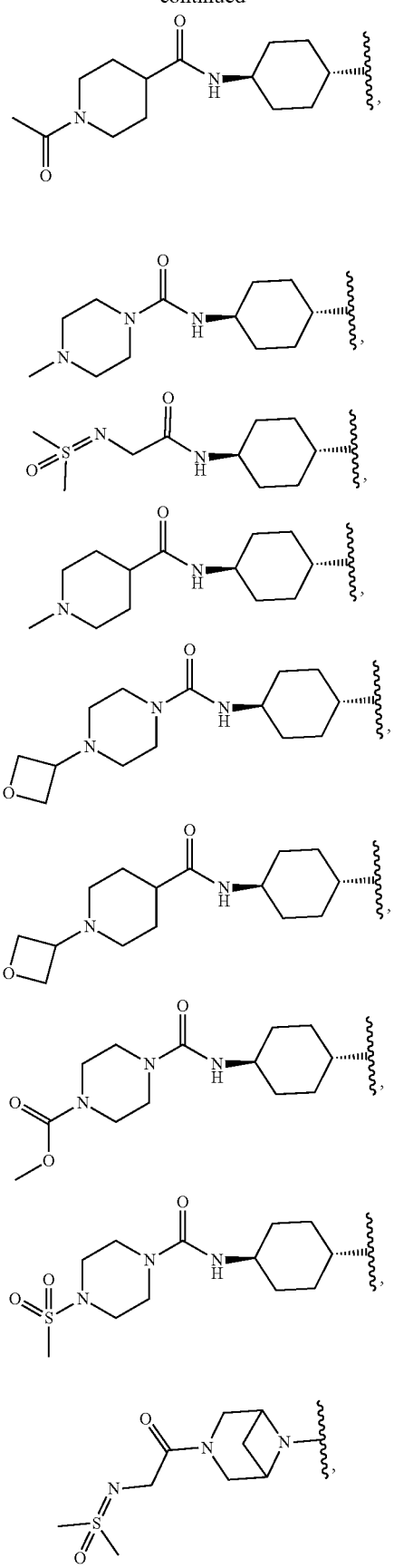
262
-continued
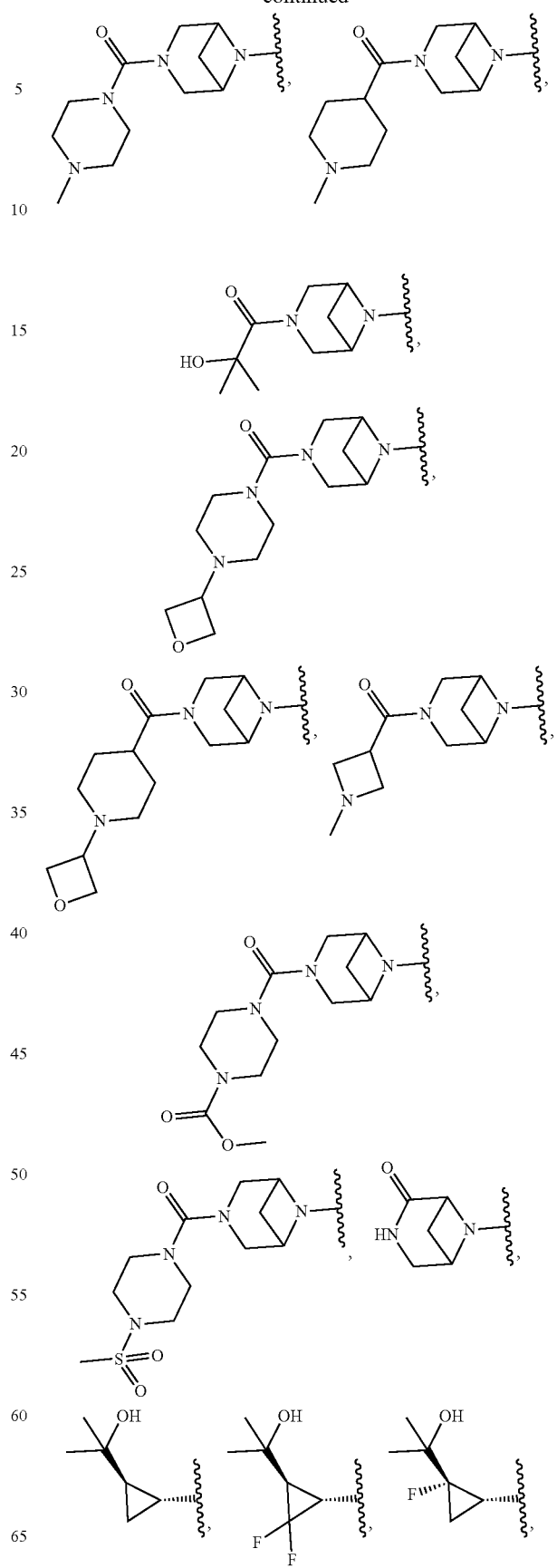

-continued

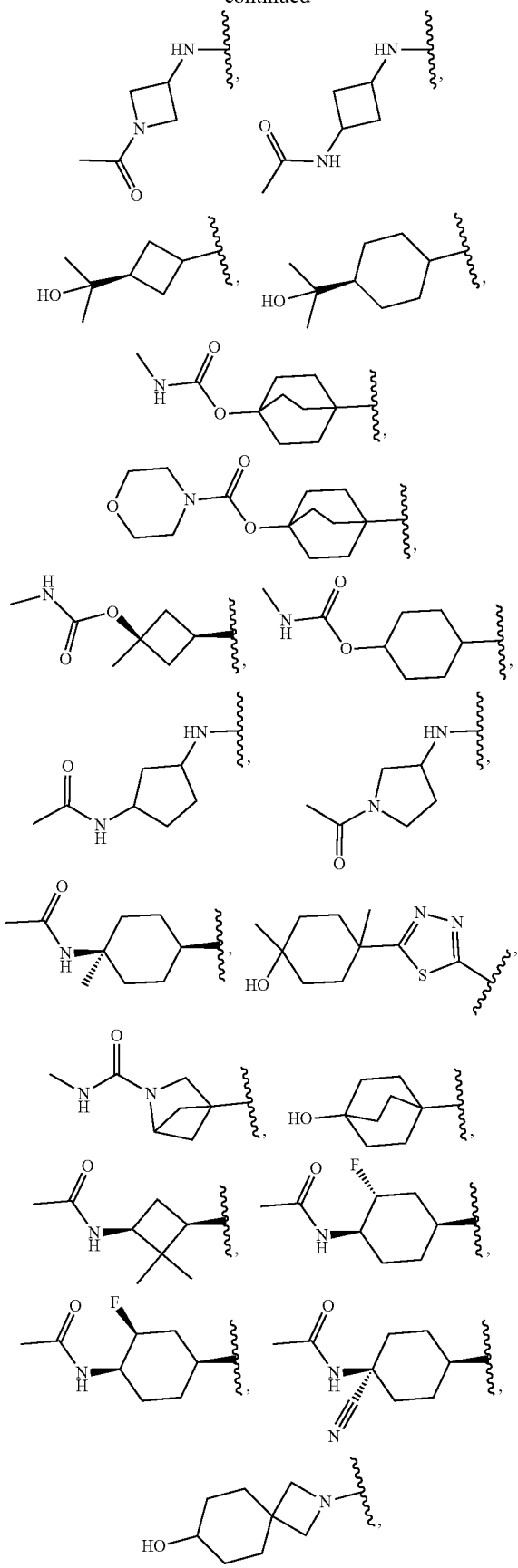

-continued

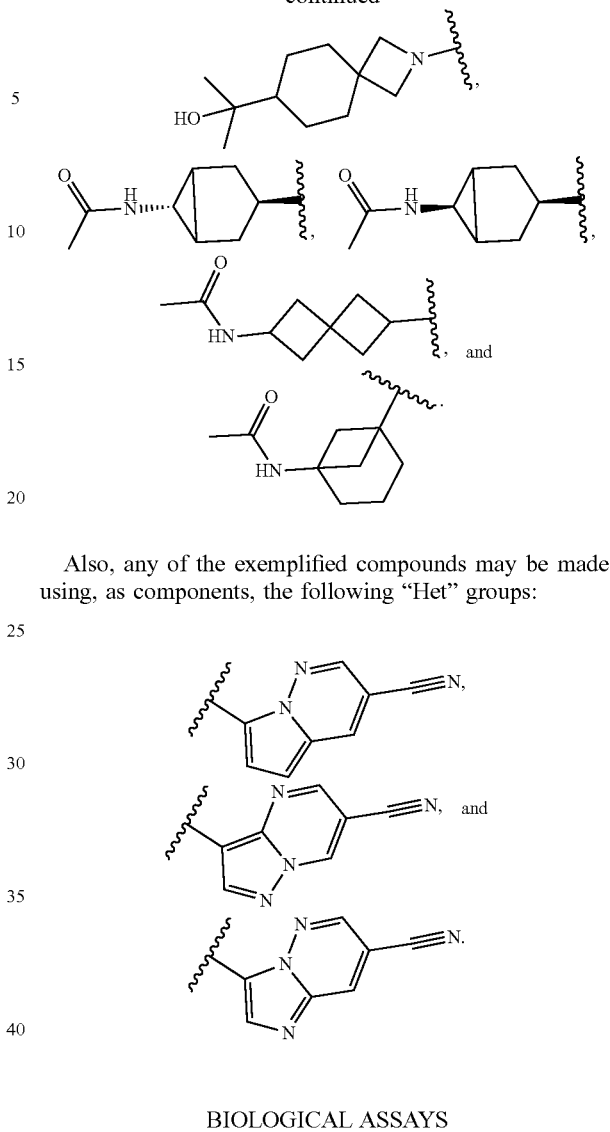

Also, any of the exemplified compounds may be made, using, as components, the following "Het" groups:

BIOLOGICAL ASSAYS

Biological assays were conducted to measure activity against TNFα and IRAK4. As summarized in Table 2, the test compounds are inhibitors of IRAK4.

IRAK4 Monocyte TNFα Cell Based Assay Procedure:

Cryopreserved human monocytes (Stem Cell Technologies) were thawed, diluted in RPMI with GlutaMAX™ (Gibco® 200 mM L-alanyl-L-glutamine) (10 mM HEPES, 1× Pen-Strep, 55 µM β-mercaptoethanol, 1 mM Sodium pyruvate) media containing 10% FBS to $0.125 \times 10^6$ cells/ml and recovered at 37° C. for 2 hours. The cell suspension was then plated at a density of 5,000 cells/well onto black 384 well Greiner clear bottom plates. Plates were pre-spotted with test compounds and serially diluted in DMSO where 40 nL/well were delivered using the Echo 550 acoustic liquid dispenser (Labcyte®) for a final DMSO concentration of 0.1%. Plated cells were treated with compound for 1 hour at 37° C. Cells were then stimulated with 50 pg/ml of LPS (Sigma) excluding outside columns of plate used for unstimulated cell control wells. Cells were incubated for an additional 4 hours at 37° C. Cells were then spun out of the media and 5µl of sample were taken and analyzed for total TNFα content using the TR-FRET Human TNFα detection system (CisBio). This system utilizes two labeled antibodies (cryptate and XL665) that bind to two different epitopes of the TNFα molecule and produce FRET signal proportional to the concentration of TNFα in the sample. Detection antibodies are mixed 50:50 and 5 μL were dispensed into each well. Plates were covered with clear seals and incubated at room temp overnight. The following morning plates were read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent of control was calculated as follows:

% Control=100×(Ratio$_{Sample}$−Ratio$_{0\% Stimulation}$)/(Ratio$_{100\% Stimulation}$−Ratio$_{0\% Stimulation}$)

where unstimulated cells (0% stimulation) were the negative control and stimulated cells (100% stimulation) were used as the positive control.

IRAK4 Biochemical Assay Procedure:

IRAK4 enzyme (Carna Biosciences, Chuo-ku, Kobe, Japan) activity was measured by detecting phosphorylated peptide substrate formation using an antibody against the phosphorylated peptide substrate. This is a time-resolved fluorescence resonance energy transfer (TR-FRET) immunoassay, based on the STK1 KinEASE Assay (Cisbio, Bedford, Mass.). The assay was designed as a simple two-step, endpoint assay (a 5 μl enzyme reaction followed by 5 μl stop and detect Solution) performed in ProxiPlate-384 Plus plates (Perkin Elmer, Waltham, Mass.). Staurosporine, a non-selective kinase inhibitor was used as a positive control. Compounds diluted in DMSO were spotted into 384 well plates using a Labcyte® Echo 550 Liquid Handling System prior to addition of IRAK4 enzyme and peptide substrate. Reaction solutions were delivered using a Multi-Flo (Bio-Tek Instruments). The enzyme and peptide solution was incubated with compound for 15 minutes at room temp before the reaction was initiated by the addition of ATP. The standard 5 μl reaction mixture contained 500 μM ATP, 2 μM peptide (STK1 Peptide), 0.75 nM of IRAK4 in reaction buffer (50 mM HEPES, pH 7.0, 0.02% NaN$_3$, 0.01% BSA, 0.1 mM Orthovanadate, 5 mM MgCl$_2$, 0.025% NP-40, 1 mM DTT). After 120 min of incubation at room temperature, 5 μl of Stop and Detect Solution (1:100 Cryptate labeled anti-phosphorylated peptide antibody solution and 125 nM Tracer in a 50 mM HEPES pH 7.0 detection buffer containing sufficient EDTA) was added. The plate was then further incubated for 60 minutes at room temperature and read on Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percentage of inhibition was calculated as below:

% Inhibition=100×(Ratio$_{Sample}$−Ratio$_{0\% Inhibition}$)/(Ratio$_{100\% Inhibition}$−Ratio$_{0\% Inhibition}$)

The 0% inhibition value comes from control wells lacking inhibitor. The 100% inhibition value comes from control wells containing a saturating amount of known inhibitor staurosporine.

TABLE 2

| Compound | EC50 TNF(nM) | IC50 HTRF (nM) |
|---|---|---|
| 1 | 309 | 1.5 |
| 2 | 8 | 1 |
| 3 | 15 | <1 |
| 4 | 23 | 1 |
| 5 | 76 | 1 |
| 6 | 19 | <1 |
| 7 | >10000 | 9 |
| 8 | 7544 | |
| 9 | 2128 | |
| 10 | 157 | <1 |
| 11 | 1171 | <1 |
| 12 | 9 | <1 |
| 13 | 23 | <1 |
| 14 | 79 | <1 |
| 15 | 3388 | <1 |
| 16 | 35 | <1 |
| 17 | 55 | 1 |
| 18 | >10000 | 1000 |
| 19 | 5873 | 1 |
| 20 | 6 | <1 |
| 21 | 10 | <1 |
| 22 | 25 | <1 |
| 23 | 6 | <1 |
| 24 | 14 | <1 |
| 25 | 1461 | <1 |
| 26 | 305 | 1 |
| 27 | 67 | 1 |
| 28 | 6340 | 1.7 |
| 29 | 4182 | 1.8 |
| 30 | 78 | 1 |
| 31 | 5 | <1 |
| 32 | 211 | <1 |

| Compound | IC$_{50}$ IRAK4-HTBS | EC$_{50}$MONO TNF HTRF |
|---|---|---|
| 33 | 0.49 | 3971.1 |
| 34 | 0.55 | 4.9 |
| 35 | 0.87 | 78.2 |
| 36 | 0.48 | 5.0 |
| 37 | 1000.00 | 10000.0 |
| 38 | 0.80 | 3.5 |
| 39 | 0.89 | 10.4 |
| 40 | 3.09 | 87.6 |
| 41 | 1.38 | 11.6 |
| 42 | 1.50 | 35.7 |
| 43 | 0.72 | 21.9 |
| 44 | 0.53 | 27.4 |
| 45 | 1.13 | 11.8 |
| 46 | 0.67 | 16.7 |
| 47 | 1.42 | 5675.0 |
| 48 | 1.91 | 37.5 |
| 49 | 1.75 | 34.3 |
| 50 | 0.92 | 3.6 |
| 51 | 1.73 | 4.7 |
| 52 | 0.82 | 4.1 |
| 53 | 0.35 | 0.6 |
| 54 | 0.73 | 2.4 |
| 55 | 0.54 | 115.4 |
| 56 | 0.49 | 8.3 |
| 57 | 1.16 | 6.8 |
| 58 | 1.88 | 9.3 |
| 59 | 1.97 | 14.7 |
| 60 | 0.97 | 8.5 |
| 61 | 1.01 | 5.3 |
| 62 | 0.38 | 12.5 |
| 63 | 0.29 | 13.8 |
| 64 | 0.28 | 6.9 |
| 65 | 0.30 | 10.6 |
| 66 | 0.42 | 13.6 |
| 67 | 0.59 | 10.4 |
| 68 | 0.45 | 37.9 |
| 69 | 1.16 | 11.8 |
| 70 | 0.58 | 8.8 |
| 71 | 0.58 | 3.2 |
| 72 | 0.54 | 2.8 |
| 73 | 0.61 | 64.1 |
| 74 | 0.54 | 11.0 |

TABLE 2-continued

| | | |
|---|---|---|
| 75 | 0.24 | 3.2 |
| 76 | 0.85 | 4.4 |
| 77 | 1.06 | 3.9 |
| 78 | 0.85 | 8.9 |
| 79 | 0.48 | 2.6 |
| 80 | 1.16 | 114.4 |
| 81 | 0.66 | 21.4 |
| 82 | 1.18 | 23.1 |
| 83 | 1.37 | 52.5 |
| 84 | 0.47 | 8.6 |
| 85 | 1.04 | 3.3 |
| 86 | 0.65 | 0.6 |
| 87 | 0.60 | 2.1 |
| 88 | 0.83 | 27.1 |
| 89 | 1.01 | 11.3 |
| 90 | 1.39 | 3.6 |
| 91 | 0.93 | 3.9 |
| 92 | 1.72 | 5.0 |
| 93 | 1.78 | 5.9 |
| 94 | 0.90 | 4.0 |
| 95 | 0.70 | 4.1 |
| 96 | 0.58 | 2.3 |
| 97 | 0.82 | 21.7 |
| 98 | 1.13 | 3.2 |
| 99 | 0.63 | 5.8 |
| 100 | 0.80 | 2.1 |
| 101 | 0.89 | 1.2 |
| 102 | 1.22 | 31.4 |
| 103 | 0.51 | 1.4 |
| 104 | 0.99 | 1.7 |
| 105 | 0.98 | 4.2 |
| 106 | 1.09 | 2.6 |
| 107 | | 18.4 |
| 108 | | 20.6 |
| 109 | | 4.1 |
| 110 | | 1.8 |
| 111 | | 8.8 |
| 112 | | 13.1 |
| 113 | | 47.4 |
| 114 | | 24.4 |
| 115 | | 3.5 |
| 116 | | 4.1 |
| 117 | | 11.1 |
| 118 | | 29.0 |
| 119 | | 1.2 |
| 120 | | |
| 121 | | |
| 122 | | |
| 123 | | |
| 124 | | |
| 125 | 0.25 | 5.4 |
| 126 | 0.89 | 26.2 |
| 127 | 0.64 | 9.9 |
| 128 | 0.59 | 18.8 |
| 129 | 0.59 | 21.7 |
| 130 | 0.64 | 18.7 |
| 131 | 0.53 | 14.3 |
| 132 | | |
| 132 Isomer 1 | 1.29 | 12.5 |
| 132 Isomer 2 | 1.30 | 15.2 |
| 133 | 1.47 | 531.3 |
| 134 | 0.94 | 6.9 |
| 135 | 0.52 | 10.5 |
| 136 | | |
| 136 Isomer 1 | 0.57 | 4.2 |
| 136 Isomer 2 | 0.53 | 4.0 |
| 136 Isomer 3 | 0.64 | 39.0 |
| 136 Isomer 4 | 0.74 | 30.5 |
| 137 | 0.85 | 6.5 |
| 138 | 0.61 | 15.0 |
| 139 | 0.65 | 5.9 |
| 140 | 0.84 | 6.4 |
| 141 | 0.50 | 18.6 |
| 142 | 0.38 | 9.2 |
| 143 | 0.34 | 3.1 |
| 144 | 0.63 | 2.3 |
| 145 | 0.33 | 5.6 |
| 146 | 0.48 | 5.2 |
| 147 | | |
| 147 Isomer 1 | 0.63 | 8.2 |
| 147 Isomer 2 | 0.62 | 24.2 |
| 148 | 0.31 | 1.4 |
| 149 | 0.31 | 4.9 |
| 150 | 0.46 | 5.2 |
| 151 | 1.03 | 5.0 |
| 152 | 0.58 | 10.7 |
| 153 | 0.91 | 7.2 |
| 154 | 1.57 | 13.3 |
| 155 | 1.52 | 7.4 |
| 156 | 1.42 | 10.9 |
| 157 | 1.03 | 1.8 |
| 158 | 1.15 | 19.8 |
| 159 | 6.38 | 25.7 |
| 160 | 0.52 | 2.8 |
| 161 | 1.48 | 34.7 |
| 162 | 2.29 | 26.5 |
| 163 | 0.54 | 15.0 |
| 164 | 0.55 | 17.5 |
| 165 | 1.15 | 39.1 |
| 166 | 0.66 | 2.3 |
| 167 | 1.81 | 1000.0 |
| 168 | 0.65 | 8.4 |
| 169 | 0.93 | 219.5 |
| 170 | 0.36 | 16.0 |
| 171 | 0.46 | 2.1 |
| 172 | 2.99 | 34.4 |
| 173 | 1.52 | 11.6 |
| 174 | 0.49 | 3.5 |
| 175 | 0.57 | 9.0 |
| 176 | 0.76 | 23.5 |
| 177 | 0.41 | 8.3 |
| 178 | 0.45 | 4.9 |
| 179 | 0.37 | 6.4 |
| 180 | 0.40 | 6.8 |
| 181 | 0.36 | 18.4 |
| 182 | 0.53 | 37.8 |
| 183 | 0.50 | 8.8 |
| 184 | 0.54 | 2.4 |
| 185 | | |
| 186 | 0.95 | 8.4 |
| 187 | 0.66 | 10.8 |
| 188 | 1.07 | 7.6 |
| 189 | 1.02 | 16.3 |
| 190 | 1.39 | 11.7 |
| 191 | 1.15 | 22.9 |
| 192 | 1.21 | 24.6 |
| 193 | 0.68 | 4.1 |
| 194 | 0.75 | 64.0 |
| 194 Isomer 1 | 0.61 | 50.8 |
| 194 Isomer 2 | 0.57 | 40.6 |
| 195 | 1.09 | 334.2 |
| 196 | 1.62 | 107.2 |
| 197 | 1.57 | 32.9 |
| 198 | 0.79 | 27.4 |
| 199 | 0.69 | 38.3 |
| 200 | 0.63 | 24.1 |
| 201 | 1.17 | 34.9 |
| 202 | 1.23 | 166.1 |
| 203 | 0.83 | 13.7 |
| 204 | 0.35 | 3.5 |
| 205 | 0.62 | 20.1 |
| 206 | 0.56 | 13.9 |
| 207 | 0.69 | 7.9 |
| 208 | 0.67 | 13.6 |
| 209 | 0.89 | 9.6 |
| 210 | 0.84 | 2.8 |
| 211 | 0.98 | 78.2 |
| 212 | 1.01 | 305.4 |
| 213 | 0.31 | 1830.0 |
| 214 | 0.46 | 33.2 |
| 215 | 0.70 | 3102.5 |
| 216 | 0.78 | 18.1 |
| 217 | 0.81 | 11.1 |
| 218 | 1.12 | 858.4 |
| 219 | 0.68 | 2073.2 |
| 220 | 1.39 | 131.2 |
| 221 | 0.92 | 2320.8 |
| 222 | 1.79 | 1780.9 |
| 223 | 1.43 | 1359.2 |
| 224 | 1.12 | 4767.2 |

TABLE 2-continued

| | | |
|---|---|---|
| 225 | | |
| 226 | | |
| 227 | | 14.4 |
| 228 | | |
| 229 | 0.64 | 16.5 |
| 230 | 0.74 | 29.9 |
| 231 | 1.17 | 22.2 |
| 232 | 0.62 | 7.4 |
| 233 | 0.35 | 6.4 |
| 234 | 1.28 | 178.3 |
| 235 | 0.48 | 4.4 |
| 236 | 0.83 | 25.8 |
| 237 | 0.14 | 8.4 |
| 238 | 0.46 | 12.6 |
| 239 | 0.11 | 4.9 |
| 240 | 0.15 | 8.9 |
| 241 | 1.39 | 4.8 |
| 242 | 2.76 | 752.4 |
| 243 | 0.55 | 6.4 |
| 244 | 0.93 | 9.1 |
| 245 | 0.55 | 3.2 |
| 246 | 1.37 | 43.3 |
| 247 | 0.80 | 25.1 |
| 248 | 0.93 | 16.3 |
| 249 | 0.91 | 8.9 |
| 250 | 1.17 | 8.3 |
| 251 | 0.48 | 4.4 |
| 252 | 0.29 | 7.0 |
| 253 | | |
| 254 | | |
| 255 | 0.63 | 5.1 |
| 256 | 0.68 | 4.6 |
| 257 | 0.95 | 10000.0 |
| 258 | 1.26 | 5.8 |
| 259 | 0.94 | 2.6 |
| 260 | 2.56 | 15.8 |
| 261 | 0.73 | 18.3 |
| 262 | 3.81 | 69.9 |
| 263 | 1.08 | 5.1 |
| 264 | 0.59 | 2.7 |
| 265 | 2.43 | 11.3 |
| 266 | 0.49 | 3.2 |
| 267 | 0.65 | 18.9 |
| 268 | 0.61 | 14.1 |
| 269 | 0.80 | 5.8 |
| 270 | 0.65 | 10.7 |
| 271 | 3.22 | 89.0 |
| 272 | 1.10 | 4.1 |
| 273 | 0.68 | 4.1 |
| 274 | 1.59 | 41.0 |
| 275 | 0.78 | 6.4 |
| 276 | 0.89 | 7.8 |
| 277 | 0.93 | 11.3 |
| 278 | 0.07 | 10000.0 |
| 279 | 0.40 | 15.9 |
| 280 | 1.03 | 7.4 |
| 281 | 0.40 | 8281.4 |
| 282 | 0.59 | 22.4 |
| 283 | 0.66 | 19.9 |
| 284 | 0.69 | 17.6 |
| 285 | 0.78 | 68.0 |
| 286 | 0.63 | 21.4 |
| 287 | 0.86 | 9.8 |
| 288 | 0.72 | 19.8 |
| 289 | 0.24 | 21.4 |
| 290 | 0.33 | 16.2 |
| 291 | 1.78 | 59.3 |
| 292 | 0.20 | 6.7 |
| 293 | 1.52 | 364.7 |
| 294 | | 1000.0 |
| 295 | 57.69 | 1000.0 |
| 296 | 1.02 | 1000.0 |
| 297 | 0.67 | 10.0 |
| 298 | 0.61 | 36.3 |
| 299 | 0.52 | 41.6 |
| 300 | 0.98 | 5.3 |
| 301 | 1.04 | 4.9 |
| 302 | 0.59 | 5.3 |
| 303 | 0.51 | 12.5 |
| 304 | 0.54 | 9.8 |
| 305 | 1.02 | 15.9 |
| 306 | 1.21 | 18.4 |
| 307 | 0.83 | 53.7 |
| 308 | 1.85 | 18.4 |
| 309 | 29.40 | 687.4 |
| 310 | 0.66 | 25.9 |
| 311 | 0.80 | 22.6 |
| 312 | 0.91 | 17.5 |
| 313 | 1.47 | 48.6 |
| 314 | 0.55 | 10.1 |
| 315 | 0.77 | 10.9 |
| 316 | 0.59 | 5.3 |
| 317 | 0.60 | 4.4 |
| 318 | 0.94 | 101.8 |
| 319 | 1.68 | 126.1 |
| 320 | 1.18 | 68.3 |
| 321 | 1.46 | 53.5 |
| 322 | 0.31 | 419.1 |
| 323 | 0.62 | 3.7 |
| 324 | 0.99 | 19.1 |
| 325 | 8.07 | 1000.0 |
| 326 | 6.01 | |
| 327 | 0.37 | 10.2 |
| 328 | 1.02 | 80.5 |
| 329 | 0.84 | 54.2 |
| 330 | 1.80 | 47.1 |
| 331 | 1.21 | 81.4 |
| 332 | 1.61 | 434.9 |
| 333 | 1.99 | 1000.0 |
| 334 | 2.41 | 98.9 |
| 335 | 0.64 | 48.9 |
| 336 | 0.70 | 11.0 |
| 337 | | 3.3 |
| 338 | | 2.7 |
| 339 | | 9.1 |
| 340 | | 9.1 |
| 341 | | 72.4 |
| 342 | | |
| 343 | | |

What is claimed is:

1. A compound, or a pharmaceutically acceptable salt thereof, selected from the group consisting of: methyl ((1R, 4r)-4-((5-(5-(((1r,4R)-4-acetamidocyclohexyl)-1,3,4-thiadiazol-2-yl)-2-(3-cyanopyrrolo[1,2-b]pyridazin-7-yl)pyridin-4-yl)amino)cyclohexyl)carbamate;
(S)-7-(5-(5-(hexahydropyrazino[2,1-c][1,4]oxazin-8 (1H)-yl)-1,3,4-thiadiazol-2-yl)-4-(isopropylamino) pyridin-2-yl)pyrrolo[1,2-b]pyridazine-3-carbonitrile;
(R)-7-(5-(5-(hexahydropyrazino[2,1-c][1,4]oxazin-8 (1H)-yl)-1,3,4-thiadiazol-2-yl)-4-(isopropylamino) pyridin-2-yl)pyrrolo[1,2-b]pyridazine-3-carbonitrile;
N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)acetamide;
N-((1R,5S,8r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)acetamide;
(S)-N-((1-(5-(6-(3-cyanopyrrolo[1,2-b]pyridazin-7-yl)-4-(isopropylamino)pyridin-3-yl)-1,3,4-thiadiazole-2-carbonyl)pyrrolidin-2-yl)methyl)acetamide;
(R)-N-((1-(5-(6-(3-cyanopyrrolo[1,2-b]pyridazin-7-yl)-4-(isopropylamino)pyridin-3-yl)-1,3,4-thiadiazole-2-carbonyl)pyrrolidin-2-yl)methyl)acetamide;
methyl (S)-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)carbamate;
methyl (R)-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)carbamate;

N-((1R,5S,6r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.1]heptan-6-yl)acetamide;
(S)-N-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)cyclopropanecarboxamide;
(S)-N-(1-(5-(6-(3-cyanopyrrolo[1,2-b]pyridazin-7-yl)-4-(isopropylamino)pyridin-3-yl)-1,3,4-thiadiazole-2-carbonyl)piperidin-3-yl)acetamide;
(R)-N-(1-(5-(6-(3-cyanopyrrolo[1,2-b]pyridazin-7-yl)-4-(isopropylamino)pyridin-3-yl)-1,3,4-thiadiazole-2-carbonyl)piperidin-3-yl)acetamide;
N-((1r,4r)-4-(5-(6-(2-(((1R,2S)-2-aminocyclohexyl)amino)pyrrolo[2,1-f][1,2,4]triazin-7-yl)-4-(isopropylamino)pyridin-3-yl)-1,3,4-thiadiazol-2-yl)cyclohexyl)acetamide;
methyl (((1R,3r)-3-((2-(3-cyanopyrrolo[1,2-b]pyridazin-7-yl)-5-(5-(5-((R)-hexahydropyrazino[2,1-c][1,4]oxazin-8(1H)-yl)-1,3,4-thiadiazol-2-yl)pyridin-4-yl)amino)cyclobutyl)methyl)carbamate;
methyl (((1R,3r)-3-((5-(5-((1R,5S,8S)-8-acetamido-3-azabicyclo[3.2.1]octan-3-yl)-1,3,4-thiadiazol-2-yl)-2-(3-cyanopyrrolo[1,2-b]pyridazin-7-yl)pyridin-4-yl)amino)cyclobutyl)methyl)carbamate;
N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)acetamide;
methyl ((1R,4r)-4-((5-(5-((1R,5S,8S)-8-acetamido-3-azabicyclo[3.2.1]octan-3-yl)-1,3,4-thiadiazol-2-yl)-2-(3-cyanopyrrolo[1,2-b]pyridazin-7-yl)pyridin-4-yl)amino)cyclohexyl)carbamate;
N-((1R,3r,5S)-8-(5-(6-(3-cyanopyrrolo[1,2-b]pyridazin-7-yl)-4-(isopropylamino)pyridin-3-yl)-1,3,4-thiadiazol-2-yl)-8-azabicyclo[3.2.1]octan-3 -yl)acetamide;
N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)morpholine-4-carboxamide;
N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)methanesulfonamide;
methyl ((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamate;
7-(5-(5-((1R,5S,8s)-8-amino-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;
N-((1R,5S,8S)-3-(5-(6-(2-(((1R,2S)-2-aminocyclohexyl)amino)pyrrolo[2,1-f][1,2,4]triazin-7-yl)-4-4(R)-1-cyanoethyl)amino)pyridin-3-yl)-1,3,4-thiadiazol-2-yl)-3-azabicyclo[3.2.1]octan-8-yl)acetamide;
N-((3R,4S)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;
N-((3S,4R)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;
N-((3S,4S)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;
N-((3R,4R)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;
N-(2-(5-(6-(3-cyanopyrrolo[1,2-b]pyridazin-7-yl)-4-(isopropylamino)pyridin-3-yl)-1,3,4-thiadiazol-2-yl)-2-azabicyclo[2.2.2]octan-4-yl)acetamide;
7-(5-(5-(7-acetyl-2,7-diazaspiro[3.5]nonan-2-yl)-1,3,4-thiadiazol-2-yl)-4-(isopropylamino)pyridin-2-yl)pyrrolo[1,2-b]pyridazine-3-carbonitrile;
7-(5-(5-(6-acetyl-2,6-diazaspiro[3.3]heptan-2-yl)-1,3,4-thiadiazol-2-yl)-4-(isopropylamino)pyridin-2-yl)pyrrolo[1,2-b]pyridazine-3-carbonitrile;
N-(2-(5-(6-(3-cyanopyrrolo[1,2-b]pyridazin-7-yl)-4-(isopropylamino)pyridin-3-yl)-1,3,4-thiadiazol-2-yl)-2-azaspiro[3.5]nonan-7-yl)acetamide;
N-(4-(5-(6-(3-cyanopyrrolo[1,2-b]pyridazin-7-yl)-4-(oxetan-3-ylamino)pyridin-3-yl)-1,3,4-thiadiazol-2-yl)bicyclo[2.2.2]octan-1-yl)acetamide;
N-(4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[2.2.2]octan-1-yl)acetamide;
(R)-N-(4-(5-(4-((1-cyanoethyl)amino)-6-(3-cyanopyrrolo[1,2-b]pyridazin-7-yl)pyridin-3-yl)-1,3,4-thiadiazol-2-yl)bicyclo[2.2.1]octan-1-yl)acetamide;
N-((1S,4S,5S)-2-(5-(6-(3-cyanopyrrolo[1,2-b]pyridazin-7-yl)-4-(isopropylamino)pyridin-3-yl)-1,3,4-thiadiazol-2-yl)-2-azabicyclo[2.2.1]heptan-5-yl)acetamide;
7-(5-(5-(7-acetyl-2,7-diazaspiro[3.5]nonan-2-yl)-1,3,4-thiadiazol-2-yl)-4-(oxetan-3-ylamino)pyridin-2-yl)pyrrolo[1,2-b]pyridazine-3-carbonitrile;
7-(5-(5-(7-acetyl-2,7-diazaspiro[3.5]nonan-2-yl)-1,3,4-thiadiazol-2-yl)-4-((tetrahydro-2H-pyran-4-yl)amino)pyridin-2-yl)pyrrolo[1,2-b]pyridazine-3-carbonitrile;
(R)-N-(2-(5-(4-((1-cyanoethyl)amino)-6-(3-cyanopyrrolo[1,2-b]pyridazin-7-yl)pyridin-3-yl)-1,3,4-thiadiazol-2-yl)-2-azaspiro[3.5]nonan-7-yl)acetamide;
N-(2-(5-(6-(3-cyanopyrrolo[1,2-b]pyridazin-7-yl)-4-(oxetan-3-ylamino)pyridin-3-yl)-1,3,4-thiadiazol-2-yl)-2-azaspiro[3.5]nonan-7-yl)acetamide;
N-(2-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-2-azaspiro[3.5]nonan-7-yl)acetamide;
N-((3R,6S)-6-(5-(6-(3-cyanopyrrolo[1,2-b]pyridazin-7-yl)-4-(isopropylamino)pyridin-3-yl)-1,3,4-thiadiazol-2-yl)tetrahydro-2H-pyran-3-yl)acetamide;
7-(5-(5 -(7-hydroxy-7-methyl-2-azaspiro[3.5]nonan-2-yl)-1,3,4-thiadiazol-2-yl)-4-(isopropylamino)pyridin-2-yl)pyrrolo[1,2-b]pyridazine-3-carbonitrile;
N-((3S,6S)-6-(5 -(6-(3-cyanopyrrolo[1,2-b]pyridazin-7-yl)-4-(isopropylamino)pyridin-3-yl)-1,3,4-thiadiazol-2-yl)tetrahydro-2H-pyran-3-yl)acetamid ;
N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-2-hydroxy-2-methylpropanamide;
N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)-2-hydroxy-2-methylpropanamide;
N-((1R,5S,8s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.2.1]octan-8-yl)-2-hydroxy-2-methylpropanamide;
7-(5-(5-((1R,2R)-2-(2-hydroxypropan-2-yl)cyclobutyl)-1,3,4-thiadiazol-2-yl)-4-(isopropylamino)pyridin-2-yl)pyrrolo[1,2-b]pyridazine-3-carbonitrile;
7-(5-(5-(4-hydroxybicyclo[2.2 2]octan-1-yl)-1,3,4-thiadiazol-2-yl)-4-(isopropylamino)pyridin-2-yl)pyrrolo[1,2-b]pyridazine-3-carbonitrile;

(R)-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-2-hydroxypropanamide;

(S)-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-2-hydroxypropanamide;

(1r,3R)-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-3-hydroxy-3-methylcyclobutane-1-carboxamide;

(1s,3S)-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-3-hydroxy-3-methylcyclobutane-1-carboxamide;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-3-methyloxetane-3-carboxamide;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-methyltetrahydro-2H-pyran-4-carboxamide;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-methylpiperazine-1-carboxamide;

3-(((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)amino)-2,2-dimethyl-3-oxopropanoic acid;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-2-((dimethyl(oxo)-l6-sulfanylidene)amino)acetamide;

N-(2-(5-(6-(3-cyanopyrrolo[1,2-b]pyridazin-7-yl)-4-((3-methyloxetan-3-yl)amino)pyridin-3-yl)-1,3,4-thiadiazol-2-yl)-2-azaspiro[3.5]nonan-7-yl)acetamide;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-1-methylpiperidine-4-carboxamide;

N-((1R,5S,8s)-3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-3-azabicyclo[3.2.1]octan-8-yl)-2-hydroxy-2-methylpropanamide;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-1-methylazetidine-3-carboxamide;

N1-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-N2-(dimethyl(oxo)-l6-sulfanylidene)oxalamide;

4-acetyl-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperazine-1-carboxamide;

methyl 4-(((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamoyl)piperazine-1-carboxylate;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-(methylsulfonyl)piperazine-1-carboxamide;

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)cyclopropanecarboxamide;

methyl ((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)carbamate;

N-((1s,4s)-4-(5-(6-(3-cyanopyrrolo[1,2-b]pyridazin-7-yl)-4-(isopropylamino)pyridin-3-yl)-1,3,4-thiadiazol-2-yl)cyclohexyl)acetamide;

7-(5-(5-(1-acetylpiperidin-4-yl)-1,3,4-thiadiazol-2-yl)-4-(isopropylamino)pyridin-2-yl)pyrrolo[1,2-b]pyridazine-3-carbonitrile;

7-(4-(isopropylamino)-5-(5-(piperidin-4-yl)-1,3,4-thiadiazol-2-yl)pyridin-2-yl)pyrrolo[1,2-b]pyridazine-3-carbonitrile;

7-(4-(isopropylamino)-5-(5-(piperazin-1-yl)-1,3,4-thiadiazol-2-yl)pyridin-2-yl)pyrrolo[1,2-b]pyridazine-3-carbonitrile;

7-(4-(isopropylamino)-5-(5-morpholino-1,3,4-thiadiazol-2-yl)pyridin-2-yl)pyrrolo[1,2-b]pyridazine-3-carbonitrile;

7-(5-(5-((1R,2R)-2-(2-hydroxypropan-2-yl)cyclopropyl)-1,3,4-thiadiazol-2-yl)-4-(isopropylamino)pyridin-2-yl)pyrrolo[1,2-b]pyridazine-3-carbonitrile;

7-(5-(5 -((1S,2S)-2-(2-hydroxypropan-2-yl)cyclopropyl)-1,3,4-thiadiazol-2-yl)-4-(isopropylamino)pyridin-2-yl)pyrrolo[1,2-b]pyridazine-3-carbonitrile;

7-(5-(5-(1-(2,2-difluoroethyl)piperidin-4-yl)-1,3,4-thiadiazol-2-yl)-4-(isopropylamino)pyridin-2-yl)pyrrolo[1,2-b]pyridazine-3-carbonitrile;

methyl (((1R,3r)-3-((2-(3-cyanopyrrolo[1,2-b]pyridazin-7-yl)-5-(5-((1r,4R)-4-(cyclopropanecarboxamido)cyclohexyl)-1,3,4-thiadiazol-2-yl)pyridin-4-yl)amino)cyclobutyl)methyl)carbamate;

N-((1r,4r)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)cyclopropanecarboxamide;

7-(5-(5-((1S,2S)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;

7-(5-(5-((1R,2R)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;

7-(5-(5-((1S,2R)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;

7-(5-(5-((1R,2S)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;

N-((1R,4R,7R)-2-(5-(6-(3-cyanopyrrolo[1,2-b]pyridazin-7-yl)-4-(isopropylamino)pyridin-3-yl)-1,3,4-thiadiazol-2-yl)-2-azabicyclo[2.2.1]heptan-7-yl)acetamide;

7-(4-(isopropylamino)-5-(5-(1-(oxetan-3-yl)piperidin-4-yl)-1,3,4-thiadiazol-2-yl)pyridin-2-yl)pyrrolo[1,2-b]pyridazine-3-carbonitrile;

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)morpholine-4-carboxamide;

1-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-methylurea;

N-((1R,2R,4S)-7-(5-(6-(3-cyanopyrrolo[1,2-b]pyridazin-7-yl)-4-(isopropylamino)pyridin-3-yl)-1,3,4-thiadiazol-2-yl)-7-azabicyclo[2.2.1]heptan-2-yl)acetamide;

N-((1r,4r)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)morpholine-4-carboxamide;

methyl (((1R,3r)-3-((2-(3-cyanopyrrolo[1,2-b]pyridazin-7-yl)-5-(5-((1r,4R)-4-(morpholine-4-carboxamido)cyclohexyl)-1,3,4-thiadiazol-2-yl)pyridin-4-yl)amino)cyclobutyl)methyl)carbamate;

N-((1R,5S,8s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.2.1]octan-8-yl)acetamide;

7-(5-(5-((1R,5S)-8-oxa-3-azabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile;

7-(5-(5 -((1R,5S,8r)-8-hydroxy-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

(R)-N-(1-(5-(6-(3-cyanopyrrolo[1,2-b]pyridazin-7-yl)-4-((3-methyloxetan-3-yl)amino)pyridin-3-yl)-1,3,4-thiadiazol-2-yl)-3,3-difluoropiperidin-4-yl)acetamide;

(S)-N-(1-(5-(6-(3-cyanopyrrolo[1,2-b]pyridazin-7-yl)-4-((3-methyloxetan-3-yl)amino)pyridin-3-yl)-1,3,4-thiadiazol-2-yl)-3,3-difluoropiperidin-4-yl)acetamide;

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)cyclopropanecarboxamide;

7-(5-(5-((1R,5S,8r)-8-hydroxy-3-azabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)cyclopropanecarboxamide;

N-((R)-1-(5-(4-(((R)-1-cyanoethyl)amino)-6-(3-cyanopyrrolo[1,2-b]pyridazin-7-yl)pyridin-3-yl)-1,3,4-thiadiazol-2-yl)-3,3 -difluoropiperidin-4-yl)acetamide;

N-((S)-1-(5-(4-(((R)-1-cyanoethyl)amino)-6-(3-cyanopyrrolo[1,2-b]pyridazin-7-yl)pyridin-3-yl)-1,3,4-thiadiazol-2-yl)-3,3-difluoropiperidin-4-yl)acetamide;

7-(5-(5-((1R,5S,8r)-8-hydroxy-8-methyl-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

7-(5-(5-((1R,5S,8s)-8-hydroxy-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-8-methyl-3-azabicyclo[3.2.1]octan-8-yl)acetamide;

N-((1r,4r)-4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)cyclohexyl)cyclopropanecarboxamide;

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-8-methyl-3-azabicyclo[3.2.1]octan-8-yl)acetamide;

N-((1r,4r)-4-(5-(6-(3-cyanopyrrolo[1,2-b]pyridazin-7-yl)-4-((3-methyloxetan-3-yl)amino)pyridin-3-yl)-1,3,4-thiadiazol-2-yl)cyclohexyl)cyclopropanecarboxamide;

7-(5-(5-(8-hydroxy-8-(trifluoromethyl)-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

N-((1R,4r)-4-(5-(4-(((R)-1-cyanoethyl)amino)-6-(3-cyanopyrrolo[1,2-b]pyridazin-7-yl)pyridin-3-yl)-1,3,4-thiadiazol-2-yl)cyclohexyl)cyclopropanecarboxamide;

(S)-7-(5-(5-(3,3-difluoro-4-hydroxypiperidin-1-yl)-1,3,4-thiadiazol-2-yl)-4-(isopropylamino)pyridin-2-yl)pyrrolo[1,2-b]pyridazine-3-carbonitrile;

(R)-7-(5-(5-(3,3-difluoro-4-hydroxypiperidin-1-yl)-1,3,4-thiadiazol-2-yl)-4-(isopropylamino)pyridin-2-yl)pyrrolo[1,2-b]pyridazine-3-carbonitrile;

7-(4-(isopropylamino)-5-(5-(7-oxo-2,6-diazaspiro[3.4]octan-2-yl)-1,3,4-thiadiazol-2-yl)pyridin-2-yl)pyrrolo[1,2-b]pyridazine-3-carbonitrile;

7-(4-(isopropylamino)-5-(5-(5-oxo-2,6-diazaspiro[3.4]octan-2-yl)-1,3,4-thiadiazol-2-yl)pyridin-2-yl)pyrrolo[1,2-b]pyridazine-3-carbonitrile;

N-((1R,5S,9r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.3.1]nonan-9-yl)acetamide;

N-((1R,5S,9s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.3 1]nonan-9-yl)acetamide;

7-(5-(5-(2,2-difluoromorpholino)-1,3,4-thiadiazol-2-yl)-4-(isopropylamino)pyridin-2-yl)pyrrolo[1,2-b]pyridazine-3-carbonitrile;

(R)-N-(1-(5-(6-(3-cyanopyrrolo[1,2-b]pyridazin-7-yl)-4-(isopropylamino)pyridin-3-yl)-1,3,4-thiadiazol-2-yl)-3,3-difluoropiperidin-4-yl)acetamide;

(S)-N-(1-(5-(6-(3-cyanopyrrolo[1,2-b]pyridazin-7-yl)-4-(isopropylamino)pyridin-3-yl)-1,3,4-thiadiazol-2-yl)-3,3-difluoropiperidin-4-yl)acetamide;

N-(2-(5-(6-(3-cyanopyrrolo[1,2-b]pyridazin-7-yl)-4-(isopropylamino)pyridin-3-yl)-1,3,4-thiadiazol-2-yl)-2-azaspiro[3.4]octan-6-yl)acetamide;

N-((1R,5S,8s)-3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-3-azabicyclo[3.2.1]octan-8-yl)acetamide;

7-(5-(5-(4-hydroxy-4-(trifluoromethyl)piperidin-1-yl)-1,3,4-thiadiazol-2-yl)-4-(isopropylamino)pyridin-2-yl)pyrrolo[1,2-b]pyridazine-3-carbonitrile;

N-((1R,5S,6s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.1]heptan-6-yl)acetamide;

N-((1R,5S,6S)-3-(5 -(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.1.1]heptan-6-yl)acetamide;

N-((1R,5S,6s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.1.1]heptan-6-yl)acetamide;

N-((1R,5S,6s)-3-(5-(6-(3-cyanopyrrolo[1,2-b]pyridazin-7-yl)-4-(methylamino)pyridin-3-yl)-1,3,4-thiadiazol-2-yl)-3-azabicyclo[3.1.1]heptan-6-yl)acetamide;

7-(5-(5-(6-oxa-3-azabicyclo[3.1.1]heptan-3-yl)-1,3,4-thiadiazol-2-yl)-4-((tetrahydro-2H-pyran-4-yl)amino)pyridin-2-yl)pyrrolo[1,2-b]pyridazine-3-carbonitrile;

7-(5-(5-(6-oxa-3-azabicyclo[3.1.1]heptan-3-yl)-1,3,4-thiadiazol-2-yl)-4-(((R)-1-cyanoethyl)amino)pyridin-2-yl)pyrrolo[1,2-b]pyridazine-3-carbonitrile;

N-((1R,5S,6s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.1.1]heptan-6-yl)acetamide;

(R)-7-(4-((1-cyanoethyl)amino)-5-(5-(4-hydroxy-4-methylpiperidin-1-yl)-1,3,4-thiadiazol-2-yl)pyridin-2-yl)pyrrolo[1,2-b]pyridazine-3-carbonitrile;

7-(5-(5-(4-hydroxy-4-methylpiperidin-1-yl)-1,3,4-thiadiazol-2-yl)-4-((3-methyloxetan-3-yl)amino)pyridin-2-yl)pyrrolo[1,2-b]pyridazine-3-carbonitrile;
N-((1R,5S,9r)-7-(5-(6-(3-cyanopyrrolo[1,2-b]pyridazin-7-yl)-4-(isopropylamino)pyridin-3-yl)-1,3,4-thiadiazol-2-yl)-3-oxa-7-azabicyclo[3.3.1]nonan-9-yl)acetamide;
(R)-N-(1-(5-(6-(3-cyanopyrrolo[1,2-b]pyridazin-7-yl)-4-(oxetan-3-ylamino)pyridin-3-yl)-1,3,4-thiadiazol-2-yl)-3,3-difluoropiperidin-4-yl)acetamide;
N-((1R,5S, 8s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.2.1]octan-8-yl)acetamide;
7-(5-(5-((3S,4R)-3-fluoro-4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile;
7-(5-(5-(4-hydroxy-4-methylpiperidin-1-yl)-1,3,4-thiadiazol-2-yl)-4-(oxetan-3-ylamino)pyridin-2-yl)pyrrolo[1,2-b]pyridazine-3-carbonitrile;
7-(5-(5-(4-hydroxy-4-methylpiperidin-1-yl)-1,3,4-thiadiazol-2-yl)-4-((tetrahydro-2H-pyran-4-yl)amino)pyridin-2-yl)pyrrolo[1,2-b]pyridazine-3-carbonitrile;
7-(5-(5-(4-(fluoromethyl)-4-hydroxypiperidin-1-yl)-1,3,4-thiadiazol-2-yl)-4-(isopropylamino)pyridin-2-yl)pyrrolo[1,2-b]pyridazine-3-carbonitrile;
7-(5-(5-((3S,4S)-3-fluoro-4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile;
7-(5-(5-((3R,4R)-3-fluoro-4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile;
7-(5-(5-((3R,4S)-3-fluoro-4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile;
N-((1R,5S)-7-(5-(6-(3-cyanopyrrolo[1,2-b]pyridazin-7-yl)-4-(isopropylamino)pyridin-3-yl)-1,3,4-thiadiazol-2-yl)-3-oxa-7-azabicyclo[3.3.1]nonan-9-yl)acetamide;
N-(4-(5-(6-(3-cyanopyrrolo[1,2-b]pyridazin-7-yl)-4-(isopropylamino)pyridin-3-yl)-1,3,4-thiadiazol-2-yl)-4-fluorocyclohexyl)acetamide;
N-((1r,4r)-4-(5-(6-(3-cyanopyrrolo[1,2-b]pyridazin-7-yl)-4-(isopropylamino)pyridin-3-yl)-1,3,4-thiadiazol-2-yl)-4-fluorocyclohexyl)acetamide;
N-((1s,4s)-4-(5-(6-(3-cyanopyrrolo[1,2-b]pyridazin-7-yl)-4-(isopropylamino)pyridin-3-yl)-1,3,4-thiadiazol-2-yl)-4-fluorocyclohexyl)acetamide;
N-((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)-4-fluorocyclohexyl)acetamide;
N-((1r,4r)-4-(5-(6-(3-cyanopyrrolo[1,2-b]pyridazin-7-yl)-4-(oxetan-3-ylamino)pyridin-3-yl)-1,3,4-thiadiazol-2-yl)-4-fluorocyclohexyl)acetamide;
N-(4-(5-(6-(3-cyanopyrrolo[1,2-b]pyridazin-7-yl)-4-(isopropylamino)pyridin-3-yl)-1,3,4-thiadiazol-2-yl)cuban-1-yl)acetamide;
N-(1-(5-(6-(3-cyanopyrrolo[1,2-b]pyridazin-7-yl)-4-(oxetan-3-ylamino)pyridin-3-yl)-1,3,4-thiadiazol-2-yl)-2-oxabicyclo[2.2.2]octan-4-yl)acetamide;
7-(5-(5-((1s,3s)-3-hydroxy-3-methylcyclobutyl)-1,3,4-thiadiazol-2-yl)-4-(isopropylamino)pyridin-2-yl)pyrrolo[1,2-b]pyridazine-3-carbonitrile;
7-(5-(5-((1s,3s)-3-hydroxy-3-methylcyclobutyl)-1,3,4-thiadiazol-2-yl)-4-(oxetan-3-ylamino)pyridin-2-yl)pyrrolo[1,2-b]pyridazine-3-carbonitrile;
N-((1r,3r)-3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)cyclobutyl)acetamide;
N-((1r,3r)-3-(5-(6-(3-cyanopyrrolo[1,2-b]pyridazin-7-yl)-4-(oxetan-3-ylamino)pyridin-3-yl)-1,3,4-thiadiazol-2-yl)cyclobutyl)acetamide;
N-((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)cyclopropanecarboxamide;
7-(5-(5-((3S,4S)-3-fluoro-4-hydroxy-4-methylpiperidin-1-yl)-1,3,4-thiadiazol-2-yl)-4-((tetrahydro-2H-pyran-4-yl)amino)pyridin-2-yl)pyrrolo[1,2-b]pyridazine-3-carbonitrile;
methyl ((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)carbamate;
7-(5-(5-((1r,4r)-4-hydroxy-4-methylcyclohexyl)-1,3,4-thiadiazol-2-yl)-4-(oxetan-3-ylamino)pyridin-2-yl)pyrrolo[1,2-b]pyridazine-3-carbonitrile;
7-(5-(5-((3S,4S)-3-fluoro-4-hydroxy-4-methylpiperidin-1-yl)-1,3,4-thiadiazol-2-yl)-4-(oxetan-3-ylamino)pyridin-2-yl)pyrrolo[1,2-b]pyridazine-3-carbonitrile;
7-(5-(5-((1s,4s)-4-hydroxy-4-methylcyclohexyl)-1,3,4-thiadiazol-2-yl)-4-(oxetan-3 -ylamino)pyridin-2-yl)pyrrolo[1,2-b]pyridazine-3-carbonitrile;
N-((1R,5S,7r)-9-(5-(6-(3-cyanopyrrolo[1,2-b]pyridazin-7-yl)-4-(isopropylamino)pyridin-3-yl)-1,3,4-thiadiazol-2-yl)-3-oxa-9-azabicyclo[3.3.1]nonan-7-yl)acetamide;
N-((1R,5S,8s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.2.1]octan-8-yl)-2-hydroxy-2-methylpropanamide;
7-(4-(isopropylamino)-5-(1,3,4-thiadiazol-2-yl)pyridin-2-yl)pyrrolo[1,2-b]pyridazine-3-carbonitrile;
7-(5-(5-(2-aminoethyl)-1,3,4-thiadiazol-2-yl)-4-(isopropylamino)pyridin-2-yl)pyrrolo[1,2-b]pyridazine-3-carbonitrile;
5-(6-(3-cyanopyrrolo[1,2-b]pyridazin-7-yl)-4-(isopropylamino)pyridin-3-yl)-N-((1r,3r)-3-hydroxycyclobutyl)-1,3,4-thiadiazole-2-carboxamide;
(R)-7-(5-(5-(2-(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile;
5-(6-(3-cyanopyrrolo[1,2-b]pyridazin-7-yl)-4-(isopropylamino)pyridin-3-yl)-N-((1s,3s)-3-hydroxycyclobutyl)-1,3,4-thiadiazole-2-carboxamide;
(R)-7-(5-(5-(3 -(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile;
(S)-7-(5-(5-(2-(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile;
5-(6-(3-cyanopyrrolo[1,2-b]pyridazin-7-yl)-4-(isopropylamino)pyridin-3-yl)-N-((1s,3s)-3-hydroxy-3-methylcyclobutyl)-1,3,4-thiadiazole-2-carboxamide;
5-(6-(3-cyanopyrrolo[1,2-b]pyridazin-7-yl)-4-(isopropylamino)pyridin-3-yl)-N-((1r,3r)-3-hydroxy-3-methylcyclobutyl)-1,3,4-thiadiazole-2-carboxamide;
5-(6-(3-cyanopyrrolo[1,2-b]pyridazin-7-yl)-4-(isopropylamino)pyridin-3-yl)-N-((1r,4r)-4-hydroxycyclohexyl)-1,3,4-thiadiazole-2-carboxamide;
(S)-7-(5-(5-(3-(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile;
tert-butyl (R)-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)carbamate;

tert-butyl (S)-(1-(5-(6-(3-cyanopyrrolo[1,2-b]pyridazin-7-yl)-4-(isopropylamino)pyridin-3-yl)-1,3,4-thiadiazole-2-carbonyl)pyrrolidin-3-yl)carbamate;

5-(6-(3-cyanopyrrolo[1,2-b]pyridazin-7-yl)-4-(isopropylamino)pyridin-3-yl)-N-((1s,4s)-4-hydroxycyclohexyl)-1,3,4-thiadiazole-2-carboxamide;

(S)-7-(5-(5-(2-(aminomethyl)pyrrolidine-1-carbonyl)-1,3,4-thiadiazol-2-yl)-4-(isopropylamino)pyridin-2-yl)pyrrolo[1,2-b]pyridazine-3-carbonitrile;

(R)-7-(5-(5-(2-(aminomethyl)pyrrolidine-1-carbonyl)-1,3,4-thiadiazol-2-yl)-4-(isopropylamino)pyridin-2-yl)pyrrolo[1,2-b]pyridazine-3-carbonitrile;

N-(2-(5-(6-(3-cyanopyrrolo[1,2-b]pyridazin-7-yl)-4-(isopropylamino)pyridin-3-yl)-1,3,4-thiadiazol-2-yl)-2-azaspiro[3.3]heptan-6-yl)acetamide;

7-(5-(5-(4-acetylpiperazin-1-yl)-1,3,4-thiadiazol-2-yl)-4-(isopropylamino)pyridin-2-yl)pyrrolo[1,2-b]pyridazine-3-carbonitrile;

7-(5-(5-(6-oxa-3-azabicyclo[3.1.1]heptan-3-yl)-1,3,4-thiadiazol-2-yl)-4-(isopropylamino)pyridin-2-yl)pyrrolo[1,2-b]pyridazine-3-carbonitrile;

7-(5-(5-(3-oxa-6-azabicyclo[3.1.1]heptan-6-yl)-1,3,4-thiadiazol-2-yl)-4-(isopropylamino)pyridin-2-yl)pyrrolo[1,2-b]pyridazine-3-carbonitrile;

7-(5-(5-(8-oxa-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

7-(5-(5-(3-oxa-8-azabicyclo[3.2.1]octan-8-yl)-1,3,4-thiadiazol-2-yl)-4-(isopropylamino)pyridin-2-yl)pyrrolo[1,2-b]pyridazine-3-carbonitrile;

7-(5-(5-(((1R,4R)-2-oxa-5-azabicyclo[2.2.1]heptan-5-yl)-1,3,4-thiadiazol-2-yl)-4-(isopropylamino)pyridin-2-yl)pyrrolo[1,2-b]pyridazine-3-carbonitrile;

7-(5-(5-(((1S,4S)-2-oxa-5-azabicyclo[2.2.1]heptan-5-yl)-1,3,4-thiadiazol-2-yl)-4-(isopropylamino)pyridin-2-yl)pyrrolo[1,2-b]pyridazine-3-carbonitrile;

N-((1R,5S,6r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.0]hexan-6-yl)acetamide;

N-((1R,5S,6s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.0]hexan-6-yl)acetamide;

N-((1r,4r)-4-(5-(6-(3-cyanopyrrolo[1,2-b]pyridazin-7-yl)-4-((4-hydroxybicyclo[2.2.2]octan-1-yl)amino)pyridin-3-yl)-1,3,4-thiadiazol-2-yl)cyclohexyl)acetamide;

(S)-7-(5-(5-(2-(aminomethyl)pyrrolidine-1-carbonyl)-1,3,4-thiadiazol-2-yl)-4-(isopropylamino)pyridin-2-yl)pyrrolo[1,2-b]pyridazine-3-carbonitrile;

N-((1R,4r)-4-(5-(6-(3-cyanopyrrolo[1,2-b]pyridazin-7-yl)-4-(((1s,3S)-3-hydroxy-3-methylcyclobutyl)amino)pyridin-3-yl)-1,3,4-thiadiazol-2-yl)cyclohexyl)acetamide;

N-((1R,4r)-4-(5-(6-(3-cyanopyrrolo[1,2-b]pyridazin-7-yl)-4-(((1s,4S)-4-hydroxycyclohexyl)amino)pyridin-3-yl)-1,3,4-thiadiazol-2-yl)cyclohexyl)acetamide;

N-((1S,4r)-4-(5-(6-(3-cyanopyrrolo[1,2-b]pyridazin-7-yl)-4-(((1S,3R)-3-hydroxycyclohexyl)amino)pyridin-3-yl)-1,3,4-thiadiazol-2-yl)cyclohexyl)acetamide;

N-(3-(5-(6-(3-cyanopyrrolo[1,2-b]pyridazin-7-yl)-4-(isopropylamino)pyridin-3-yl)-1,3,4-thiadiazol-2-yl)bicyclo[1.1.1]pentan-1-yl)acetamide;

N-((1S,3S)-3-(5-(6-(3-cyanopyrrolo[1,2-b]pyridazin-7-yl)-4-(isopropylamino)pyridin-3-yl)-1,3,4-thiadiazol-2-yl)cyclopentyl)acetamide;

N-((1R,3S)-3-(5-(6-(3-cyanopyrrolo[1,2-b]pyridazin-7-yl)-4-(isopropylamino)pyridin-3-yl)-1,3,4-thiadiazol-2-yl)cyclopentyl)acetamide;

N-((2S)-1-(5-(6-(3-cyanopyrrolo[1,2-b]pyridazin-7-yl)-4-(isopropylamino)pyridin-3-yl)-1,3,4-thiadiazol-2-yl)-2-methylpiperidin-4-yl)acetamide;

N-((3S,4R)-1-(5-(6-(3-cyanopyrrolo[1,2-b]pyridazin-7-yl)-4-(isopropylamino)pyridin-3-yl)-1,3,4-thiadiazol-2-yl)-3-fluoropiperidin-4-yl)acetamide;

N-(1-(5-(6-(3-cyanopyrrolo[1,2-b]pyridazin-7-yl)-4-(isopropylamino)pyridin-3-yl)-1,3,4-thiadiazol-2-yl)-3,3-difluoropiperidin-4-yl)acetamide;

7-(5-(5-(2-oxa-6-azaspiro[3.3]heptan-6-yl)-1,3,4-thiadiazol-2-yl)-4-(isopropylamino)pyridin-2-yl)pyrrolo[1,2-b]pyridazine-3-carbonitrile;

N-((1r,4r)-4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)cyclohexyl)acetamide;

7-(5-(5-(8-oxa-3-azabicyclo[3.2.1]octan-3-yl)-1,3,4-thiadiazol-2-yl)-4-((tetrahydro-2H-pyran-4-yl)amino)pyridin-2-yl)pyrrolo[1,2-b]pyridazine-3-carbonitrile;

7-(5-(5-(1,1-dioxidothiomorpholino)-1,3,4-thiadiazol-2-yl)-4-(isopropylamino)pyridin-2-yl)pyrrolo[1,2-b]pyridazine-3-carbonitrile;

7-(5-(5-(6-acetyl-3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile;

7-(5-(5-(8-acetyl-3,8-diazabicyclo[3.2.1]octan-3-yl)-1,3,4-thiadiazol-2-yl)-4-(isopropylamino)pyridin-2-yl)pyrrolo[1,2-b]pyridazine-3-carbonitrile;

7-(5-(5-(3-acetyl-3,8-diazabicyclo[3.2.1]octan-8-yl)-1,3,4-thiadiazol-2-yl)-4-(isopropylamino)pyridin-2-yl)pyrrolo[1,2-b]pyridazine-3-carbonitrile;

7-(5-(5-(3-acetyl-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile;

7-(5-(5-(1-imino-1-oxido-1l6-thiomorpholino)-1,3,4-thiadiazol-2-yl)-4-(isopropylamino)pyridin-2-yl)pyrrolo[1,2-b]pyridazine-3-carbonitrile;

7-(5-(5-(8-(cyclopropanecarbonyl)-3,8-diazabicyclo[3.2.1]octan-3-yl)-1,3,4-thiadiazol-2-yl)-4-(isopropylamino)pyridin-2-yl)pyrrolo[1,2-b]pyridazine-3-carbonitrile;

7-(5-(5-(8-acetyl-3,8-diazabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile;

7-(5-(5-((1R,5S)-9-acetyl-3-oxa-7,9-diazabicyclo[3.3.1]nonan-7-yl)-1,3,4-thiadiazol-2-yl)-4-(isopropylamino)pyridin-2-yl)pyrrolo[1,2-b]pyridazine-3-carbonitrile;

7-(5-(5-((1R,5S)-7-acetyl-3-oxa-7,9-diazabicyclo[3.3.1]nonan-9-yl)-1,3,4-thiadiazol-2-yl)-4-(isopropylamino)pyridin-2-yl)pyrrolo[1,2-b]pyridazine-3-carbonitrile;

7-(5-(5-(5-acetyl-2,5-diazabicyclo[4.1.0]heptan-2-yl)-1,3,4-thiadiazol-2-yl)-4-(isopropylamino)pyridin-2-yl)pyrrolo[1,2-b]pyridazine-3-carbonitrile;

N-((1r,4r)-4-(5-(6-(3-cyanopyrrolo[1,2-b]pyridazin-7-yl)-4-((4-methyltetrahydro-2H-pyran-4-yl)amino)pyridin-3-yl)-1,3,4-thiadiazol-2-yl)cyclohexyl)acetamide;

7-(5-(5-((1R,5S)-9-acetyl-3-oxa-7,9-diazabicyclo[3.3.1]nonan-7-yl)-1,3,4-thiadiazol-2-yl)-4-((tetrahydro-2H-pyran-4-yl)amino)pyridin-2-yl)pyrrolo[1,2-b]pyridazine-3-carbonitrile;

N-(3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[1.1.1]pentan-1-yl)acetamide;

tert-butyl 3-(5-(6-(3-cyanopyrrolo[1,2-b]pyridazin-7-yl)-4-(isopropylamino)pyridin-3-yl)-1,3,4-thiadiazol-2-yl)-3,6-diazabicyclo[3.1.1]heptane-6-carboxylate;

N-((1R,5S,8s)-3-(5-(6-(3-cyanopyrrolo[1,2-b]pyridazin-7-yl)-4-((4-methyltetrahydro-2H-pyran-4-yl)amino)

pyridin-3-yl)-1,3,4-thiadiazol-2-yl)-3-azabicyclo[3.2.1]octan-8-yl)acetamide;

7-(5-(5-(6-(2-hydroxy-2-methylpropanoyl)-3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile;

7-(5-(5-(3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile;

7-(5-(5-(3-(2-hydroxy-2-methylpropanoyl)-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile;

7-(5-(5-(3-(2-((dimethyl(oxo)-16-sulfanylidene)amino)acetyl)-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile;

7-(4-(isopropylamino)-5-(5-(3-(4-methylpiperazine-1-carbonyl)-3,6-diazabicyclo[3.1.1]heptan-6-yl)-1,3,4-thiadiazol-2-yl)pyridin-2-yl)pyrrolo[1,2-b]pyridazine-3-carbonitrile;

N-((1r,3r)-3-(5-(6-(3-cyanopyrrolo[1,2-b]pyridazin-7-yl)-4-(isopropylamino)pyridin-3-yl)-1,3,4-thiadiazol-2-yl)cyclobutyl)acetamide;

N-((1s,3s)-3-(5-(6-(3-cyanopyrrolo[1,2-b]pyridazin-7-yl)-4-(isopropylamino)pyridin-3-yl)-1,3,4-thiadiazol-2-yl)cyclobutyl)acetamide;

N-(4-(5-(6-(3-cyanopyrrolo[1,2-b]pyridazin-7-yl)-4-(isopropylamino)pyridin-3-yl)-1,3,4-thiadiazol-2-yl)bicyclo[2.2.2]octan-1-yl)acetamide;

N-((1r,3r)-3-(5-(6-(3-cyanopyrrolo[1,2-b]pyridazin-7-yl)-4-(isopropylamino)pyridin-3-yl)-1,3,4-thiadiazol-2-yl)cyclobutyl)cyclopropanecarboxamide;

N-((1r,3r)-3-(5-(6-(3-cyanopyrrolo[1,2-b]pyridazin-7-yl)-4-(methylamino)pyridin-3-yl)-1,3,4-thiadiazol-2-yl)cyclobutyl)acetamide;

7-(4-(isopropylamino)-5-(5-((1r,3r)-3-(oxetan-3-ylamino)cyclobutyl)-1,3,4-thiadiazol-2-yl)pyridin-2-yl)pyrrolo[1,2-b]pyridazine-3-carbonitrile;

N-(4-(5-(6-(3-cyanopyrrolo[1,2-b]pyridazin-7-yl)-4-(isopropylamino)pyridin-3-yl)-1,3,4-thiadiazol-2-yl)bicyclo[2.2.1]heptan-1-yl)acetamide;

N-(5-(5-(6-(3-cyanopyrrolo[1,2-b]pyridazin-7-yl)-4-(isopropylamino)pyridin-3-yl)-1,3,4-thiadiazol-2-yl)bicyclo[2.2.1]heptan-2-yl)acetamide;

7-(5-(5-(3-hydroxy-3-methylazetidin-1-yl)-1,3,4-thiadiazol-2-yl)-4-(isopropylamino)pyridin-2-yl)pyrrolo[1,2-b]pyridazine-3-carbonitrile;

7-(5-(5-(4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile;

N-(4-(5-(6-(3-cyanopyrrolo[1,2-b]pyridazin-7-yl)-4-(isopropylamino)pyridin-3-yl)- 1,3,4-thiadiazol-2-yl)bicyclo[2.1.1]hexan-1-yl)acetamide;

N-(((1s,3s)-3-(5-(6-(3-cyanopyrrolo[1,2-b]pyridazin-7-yl)-4-(isopropylamino)pyridin-3-yl)-1,3,4-thiadiazol-2-yl)cyclobutyl)methyl)acetamide;

N-(((1r,3r)-3-(5-(6-(3-cyanopyrrolo[1,2-b]pyridazin-7-yl)-4-(isopropylamino)pyridin-3-yl)-1,3,4-thiadiazol-2-yl)cyclobutyl)methyl)acetamide;

7-(5-(5-(3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

N-((1R,5S,8s)-3-(5-(6-(3-cyanopyrrolo[1,2-b]pyridazin-7-yl)-4-(methylamino)pyridin-3-yl)-1,3,4-thiadiazol-2-yl)-3-azabicyclo[3.2.1]octan-8-yl)acetamide;

7-(5-(5-(1-oxa-6-azaspiro[3.3]heptan-6-yl)-1,3,4-thiadiazol-2-yl)-4-(isopropylamino)pyridin-2-yl)pyrrolo[1,2-b]pyridazine-3-carbonitrile;

7-(5-(5-(3-azabicyclo[3.3.1]nonan-3-yl)-1,3,4-thiadiazol-2-yl)-4-(isopropylamino)pyridin-2-yl)pyrrolo[1,2-b]pyridazine-3-carbonitrile;

(R)-N-(1-(5-(6-(3-cyanopyrrolo[1,2-b]pyridazin-7-yl)-4-(isopropylamino)pyridin-3-yl)-1,3,4-thiadiazol-2-yl)piperidin-3-yl)acetamide;

7-(5-(5-(3-hydroxy-3-(trifluoromethyl)azetidin-1-yl)-1,3,4-thiadiazol-2-yl)-4-(isopropylamino)pyridin-2-yl)pyrrolo[1,2-b]pyridazine-3-carbonitrile;

N-(1-(5-(6-(3-cyanopyrrolo[1,2-b]pyridazin-7-yl)-4-(isopropylamino)pyridin-3-yl)-1,3,4-thiadiazol-2-yl)azepan-4-yl)acetamide;

(S)-N-(1-(5-(6-(3-cyanopyrrolo[1,2-b]pyridazin-7-yl)-4-(isopropylamino)pyridin-3-yl)-1,3,4-thiadiazol-2-yl)piperidin-3-yl)acetamide;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-N-methylacetamide;

7-(4-(isopropylamino)-5-(5-((1R,5S,8s)-8-(2-oxooxazolidin-3-yl)-3-azabicyclo[3.2.1]octan-3-yl)-1,3,4-thiadiazol-2-yl)pyridin-2-yl)pyrrolo[1,2-b]pyridazine 3-carbonitrile;

7-(5-(5-((1S,4S)-5-acetyl-2,5-diazabicyclo[2.2.1]heptan-2-yl)-1,3,4-thiadiazol-2-yl)-4-(isopropylamino)pyridin-2-yl)pyrrolo[1,2-b]pyridazine-3-carbonitrile;

7-(5-(5-((1R,4R)-5-acetyl-2,5-diazabicyclo[2.2.1]heptan-2-yl)-1,3,4-thiadiazol-2-yl)-4-(isopropylamino)pyridin-2-yl)pyrrolo[1,2-b]pyridazine-3-carbonitrile;

7-(4-(isopropylamino)-5-(5-(4-(oxetan-3-yl)piperazin-1-yl)-1,3,4-thiadiazol-2-yl)pyridin-2-yl)pyrrolo[1,2-b]pyridazine-3-carbonitrile;

1-(5-(6-(3-cyanopyrrolo[1,2-b]pyridazin-7-yl)-4-(isopropylamino)pyridin-3-yl)-1,3,4-thiadiazol-2-yl)-N-methylpiperidine-4-carboxamide;

(R)-N-(1-(5-(6-(3-cyanopyrrolo[1,2-b]pyridazin-7-yl)-4-(methylamino)pyridin-3-yl)-1,3,4-thiadiazol-2-yl)-3,3-difluoropiperidin-4-yl)acetamide;

(S)-N-(1-(5-(6-(3-cyanopyrrolo[1,2-b]pyridazin-7-yl)-4-(methylamino)pyridin-3-yl)-1,3,4-thiadiazol-2-yl)-3,3-difluoropiperidin-4-yl)acetamide;

7-(4-(isopropylamino)-5-(5-((1R,5 S,8s)-8-(pyrimidin-2-ylamino)--azabicyclo[3.2.1]octan-3-yl)-1,3,4-thiadiazol-2-yl)pyridin-2-yl)pyrrolo[1,2-b]pyridazine-3-carbonitrile;

7-(5-(5-((1R,5S,8s)-8-((3-fluoropyridin-2-yl)amino)-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

7-(5-(5-(4-cyanopiperidin-1-yl)-1,3,4-thiadiazol-2-yl)-4-(isopropylamino)pyridin-2-yl)pyrrolo[1,2-b]pyridazine-3-carbonitrile;

N-((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)-2-hydroxy-2-methylpropanamide;

N-((1s,4s)-4-(5-(6-(3-cyanopyrrolo[1,2-b]pyridazin-7-yl)-4-(isopropylamino)pyridin-3-yl)-1,3,4-thiadiazol-2-yl)cyclohexyl)-2-hydroxy-2-methylpropanamide;

N-(4-(5-(6-(3-cyanopyrrolo[1,2-b]pyridazin-7-yl)-4-(isopropylamino)pyridin-3-yl)-1,3,4-thiadiazol-2-yl)cyclohex-3-en-1-yl)acetamide;

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-methyloxetane-3-carboxamide;

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-2-hydroxy-2-methylpropanamide;

N-((1R,4r)-4-(5-(4-(((R)-1-cyanoethyl)amino)-6-(3-cyanopyrrolo[1,2-b]pyridazin-7-yl)pyridin-3-yl)-1,3,4-thiadiazol-2-yl)cyclohexyl)acetamide;

7-(5-(5-(3-hydroxy-3-(methyl-d3)butyl-4,4,4-d3)-1,3,4-thiadiazol-2-yl)-4-(isopropylamino)pyridin-2-yl)pyrrolo[1,2-b]pyridazine-3-carbonitrile;

ethyl 2-(5-(6-(3-cyanopyrrolo[1,2-b]pyridazin-7-yl)-4-(isopropylamino)pyridin-3-yl)-1,3,4-thiadiazol-2-yl)acetate;

2-(5-(6-(3-cyanopyrrolo[1,2-b]pyridazin-7-yl)-4-(isopropylamino)pyridin-3-yl)-1,3,4-thiadiazol-2-yl)acetic acid;

7-(5-(5-(2-hydroxy-2-methylpropyl)-1,3,4-thiadiazol-2-yl)-4-(isopropylamino)pyridin-2-yl)pyrrolo[1,2-b]pyridazine-3-carbonitrile;

7-(5-(5-(cyanomethyl)-1,3,4-thiadiazol-2-yl)-4-(isopropylamino)pyridin-2-yl)pyrrolo[1,2-b]pyridazine-3-carbonitrile;

7-(4-(isopropylamino)-5-(5-(tetrahydrofuran-3-yl)-1,3,4-thiadiazol-2-yl)pyridin-2-yl)pyrrolo[1,2-b]pyridazine-3-carbonitrile;

(R)-N-(5-(5-(6-(3-cyanopyrrolo[1,2-b]pyridazin-7-yl)-4-(isopropylamino)pyridin-3-yl)-1,3,4-thiadiazol-2-yl)-5-azaspiro[2.4]heptan-7-yl)acetamide;

(S)-N-(5-(5-(6-(3-cyanopyrrolo[1,2-b]pyridazin-7-yl)-4-(isopropylamino)pyridin-3-yl)-1,3,4-thiadiazol-2-yl)-5-azaspiro[2.4]heptan-7-yl)acetamide;

7-(5-(5-(1H-pyrazol-1-yl)-1,3,4-thiadiazol-2-yl)-4-(isopropylamino)pyridin-2-yl)pyrrolo[1,2-b]pyridazine-3-carbonitrile;

N-(1-(5-(6-(3-cyanopyrrolo[1,2-b]pyridazin-7-yl)-4-(isopropylamino)pyridin-3-yl)-1,3,4-thiadiazol-2-yl)-4,4-difluoropyrrolidin-3-yl)acetamide;

7-(5-(5-(3-(3,3-difluoropyrrolidin-1-yl)azetidin-1-yl)-1,3,4-thiadiazol-2-yl)-4-(isopropylamino)pyridin-2-yl)pyrrolo[1,2-b]pyridazine-3-carbonitrile;

(S)-7-(5-(5-(2-(hydroxymethyl)pyrrolidin-1-yl)-1,3,4-thiadiazol-2-yl)-4-(isopropylamino)pyridin-2-yl)pyrrolo[1,2-b]pyridazine-3-carbonitrile;

(R)-N-(1-(5-(6-(3-cyanopyrrolo[1,2-b]pyridazin-7-yl)-4-(isopropylamino)pyridin-3-yl)-1,3,4-thiadiazol-2-yl)pyrrolidin-3-yl)acetamide;

(S)-N-(1-(5-(6-(3-cyanopyrrolo[1,2-b]pyridazin-7-yl)-4-(isopropylamino)pyridin-3-yl)-1,3,4-thiadiazol-2-yl)pyrrolidin-3-yl)acetamide;

(S)-1-(5-(6-(3-cyanopyrrolo[1,2-b]pyridazin-7-yl)-4-(oxetan-3-ylamino)pyridin-3-yl)-1,3,4-thiadiazol-2-yl)-N-methylpyrrolidine-2-carboxamide;

7-(5-(5-(4-cyanocyclohexyl)-1,3,4-thiadiazol-2-yl)-4-(isopropylamino)pyridin-2-yl)pyrrolo[1,2-b]pyridazine-3-carbonitrile;

N-(4-(5-(6-(3-cyanopyrrolo[1,2-b]pyridazin-7-yl)-4-(oxetan-3-ylamino)pyridin-3-yl)-1,3,4-thiadiazol-2-yl)bicyclo[2.1.1]hexan-1-yl)acetamide;

N-(4-(5-(6-(3-cyanopyrrolo[1,2-b]pyridazin-7-yl)-4-(oxetan-3-ylamino)pyridin-3-yl)-1,3,4-thiadiazol-2-yl)bicyclo[2.1.1]hexan-1-yl)-2-hydroxy-2-methylpropanamide; and 7-(5-(5-(4-aminobicyclo[2.2.2]octan-1-yl)-1,3,4-thiadiazol-2-yl)-4-((tetrahydro-2H-pyran-4-yl)amino)pyridin-2-yl)pyrrolo[1,2-b]pyridazine-3-carbonitrile.

2. The compound of claim 1, or a pharmaceutically acceptable salt thereof, selected from the group consisting of: methyl ((1R,4r)-4-((5-(5-((1r,4R)-4-acetamidocyclohexyl)-1,3,4-thiadiazol-2-yl)-2-(3-cyanopyrrolo[1,2-b]pyridazin-7-yl)pyridin-4-yl)amino)cyclohexyl)carbamate;

(S)-7-(5-(5-(hexahydropyrazino[2,1-c][1,4]oxazin-8(1H)-yl)-1,3,4-thiadiazol-2-yl)-4-(isopropylamino)pyridin-2-yl)pyrrolo[1,2-b]pyridazine-3-carbonitrile;

(R)-7-(5-(5-(hexahydropyrazino[2,1-c][1,4]oxazin-8(1H)-yl)-1,3,4-thiadiazol-2-yl)-4-(isopropylamino)pyridin-2-yl)pyrrolo[1,2-b]pyridazine-3-carbonitrile;

N-((1R,5S,8r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)acetamide;

N-((1r,4r)-4-(5-(6-(2-(((1R,2S)-2-aminocyclohexyl)amino)pyrrolo[2,1-f][1,2,4]triazin-7-yl)-4-(isopropylamino)pyridin-3-yl)-1,3,4-thiadiazol-2-yl)cyclohexyl)acetamide;

methyl (((1R,3r)-3-((5-(5-((1R,5S,8S)-8-acetamido-3-azabicyclo[3.2.1]octan-3-yl)-1,3,4-thiadiazol-2-yl)-2-(3-cyanopyrrolo[1,2-b]pyridazin-7-yl)pyridin-4-yl)amino)cyclobutyl)methyl)carbamate;

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)acetamide;

methyl ((1R,4r)-4-((5-(5-((1R,5S,8S)-8-acetamido-3-azabicyclo[3.2.1]octan-3-yl)-1,3,4-thiadiazol-2-yl)-2-(3-cyanopyrrolo[1,2-b]pyridazin-7-yl)pyridin-4-yl)amino)cyclohexyl)carbamate;

N-((1R,3r,5S)-8-(5-(6-(3-cyanopyrrolo[1,2-b]pyridazin-7-yl)-4-(isopropylamino)pyridin-3-yl)-1,3,4-thiadiazol-2-yl)-8-azabicyclo[3.2.1]octan-3-yl)acetamide;

7-(5-(5-((1R,5S,8s)-8-amino-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

N-((3R,4S)-1-(5 -(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

N-((3S,4R)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

N-((3S,4S)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

N-((3R,4R)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

N-(2-(5-(6-(3-cyanopyrrolo[1,2-b]pyridazin-7-yl)-4-(isopropylamino)pyridin-3-yl)-1,3,4-thiadiazol-2-yl)-2-azabicyclo[2.2.2]octan-4-yl)acetamide;

7-(5-(5-(7-acetyl-2,7-diazaspiro[3.5]nonan-2-yl)-1,3,4-thiadiazol-2-yl)-4-(isopropylamino)pyridin-2-yl)pyrrolo[1,2-b]pyridazine-3-carbonitrile;

7-(5-(5-(6-acetyl-2,6-diazaspiro[3.3]heptan-2-yl)-1,3,4-thiadiazol-2-yl)-4-(isopropylamino)pyridin-2-yl)pyrrolo[1,2-b]pyridazine-3-carbonitrile;

7-(5-(5-(7-acetyl-2,7-diazaspiro[3.5]nonan-2-yl)-1,3,4-thiadiazol-2-yl)-4-(oxetan-3-ylamino)pyridin-2-yl)pyrrolo[1,2-b]pyridazine-3-carbonitrile;

7-(5-(5-(7-acetyl-2,7-diazaspiro[3.5]nonan-2-yl)-1,3,4-thiadiazol-2-yl)-4-((tetrahydro-2H-pyran-4-yl)amino)pyridin-2-yl)pyrrolo[1,2-b]pyridazine-3-carbonitrile;

N-(2-(5-(6-(3-cyanopyrrolo[1,2-b]pyridazin-7-yl)-4-(oxetan-3-ylamino)pyridin-3-yl)-1,3,4-thiadiazol-2-yl)-2-azaspiro[3.5]nonan-7-yl)acetamide;

N-(2-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-2-azaspiro[3.5]nonan-7-yl)acetamide;
N-((3S,6S)-6-(5-(6-(3-cyanopyrrolo[1,2-b]pyridazin-7-yl)-4-(isopropylamino)pyridin-3-yl)-1,3,4-thiadiazol-2-yl)tetrahydro-2H-pyran-3-yl)acetamide;
N-((1R,5S,8S)-3-(5-(4-(((R)-1-cyanoethy)pamino)-6-(3-cyanopyrrolo[1,2-b]pyridazin-7-yl)pyridin-3-yl)-1,3,4-thiadiazol-2-yl)-3-azabicyclo[3.2.1]octan-8-yl)-2-hydroxy-2-methylpropanamide;
7-(5-(5-(((1R,2R)-2-(2-hydroxypropan-2-yl)cyclobutyl)-1,3,4-thiadiazol-2-yl)-4-(isopropylamino)pyridin-2-yl)pyrrolo[1,2-b]pyridazine-3-carbonitrile;
(S)-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-2-hydroxypropanamide;
N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-3-methyloxetane-3-carboxamide;
N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-methyltetrahydro-2H-pyran-4-carboxamide;
N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-methylpiperazine-1-carboxamide;
3-(((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)amino)-2,2-dimethyl-3-oxopropanoic acid;
N-(2-(5-(6-(3-cyanopyrrolo[1,2-b]pyridazin-7-yl)-4-((3-methyloxetan-3-yl)amino)pyridin-3-yl)-1,3,4-thiadiazol-2-yl)-2-azaspiro[3.5]nonan-7-yl)acetamide;
N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-1-methylpiperidine-4-carboxamide;
N-((1R,5S,8s)-3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-3-azabicyclo[3.2.1]octan-8-yl)-2-hydroxy-2-methylpropanamide;
N1-((1R,5S,8s)-3-(5 -(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-N2-(dimethyl(oxo)-16-sulfanylidene)oxalamide;
4-acetyl-N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)piperazine-1-carboxamide;
methyl 4-(((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)carbamoyl)piperazine-1-carboxylate;
N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)cyclopropanecarboxamide;
methyl ((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)carbamate;
N-((1s,4s)-4-(5-(6-(3-cyanopyrrolo[1,2-b]pyridazin-7-yl)-4-(isopropylamino)pyridin-3-yl)-1,3,4-thiadiazol-2-yl)cyclohexyl)acetamide;
7-(5-(5-(1-acetylpiperidin-4-yl)-1,3,4-thiadiazol-2-yl)-4-(isopropylamino)pyridin-2-yl)pyrrolo[1,2-b]pyridazine-3-carbonitrile;
7-(4-(isopropylamino)-5-(5-(piperidin-4-yl)-1,3,4-thiadiazol-2-yl)pyridin-2-yl)pyrrolo[1,2-b]pyridazine-3-carbonitrile;
7-(4-(isopropylamino)-5-(5-(piperazin-1-yl)-1,3,4-thiadiazol-2-yl)pyridin-2-yl)pyrrolo[1,2-b]pyridazine-3-carbonitrile;
7-(4-(isopropylamino)-5-(5-morpholino-1,3,4-thiadiazol-2-yl)pyridin-2-yl)pyrrolo[1,2-b]pyridazine-3-carbonitrile;
methyl (((1R,3r)-3-((2-(3-cyanopyrrolo[1,2-b]pyridazin-7-yl)-5-(5-((1r,4R)-4-(cyclopropanecarboxamido)cyclohexyl)-1,3,4-thiadiazol-2-yl)pyridin-4-yl)amino)cyclobutyl)methyl)carbamate;
N-((1r,4r)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)cyclopropanecarboxamide;
7-(5-(5-((1S,2S)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;
7-(5-(5-((1R,2R)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;
7-(5-(5-((1S,2R)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;
7-(5-(5-((1R,2S)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;
N-((1R,4R,7R)-2-(5-(6-(3-cyanopyrrolo[1,2-b]pyridazin-7-yl)-4-(isopropylamino)pyridin-3-yl)-1,3,4-thiadiazol-2-yl)-2-azabicyclo[2.2.1]heptan-7-yl)acetamide;
7-(4-(isopropylamino)-5-(5-(1-(oxetan-3-yl)piperidin-4-yl)-1,3,4-thiadiazol-2-yl)pyridin-2-yl)pyrrolo[1,2-b]pyridazine-3-carbonitrile;
N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)morpholine-4-carboxamide;
1-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3 -methylurea;
N-((1R,2R,4S)-7-(5-(6-(3-cyanopyrrolo[1,2-b]pyridazin-7-yl)-4-(isopropylamino)pyridin-3-yl)-1,3,4-thiadiazol-2-yl)-7-azabicyclo[2.2.1]heptan-2-yl)acetamide;
N-((1r,4r)-4-(5-(6-(3-cyanopyrrolo[1,2-b]pyridazin-7-yl)-4-(oxetan-3 -ylamino)pyridin-3-yl)-1,3,4-thiadiazol-2-yl)cyclohexyl)morpholine-4-carboxamide;
methyl (((1R,3r)-3-((2-(3-cyanopyrrolo[1,2-b]pyridazin-7-yl)-5-(5-((1r,4R)-4-(morpholine-4-carboxamido)cyclohexyl)-1,3,4-thiadiazol-2-yl)pyridin-4-yl)amino)cyclobutypmethyl)carbamate;
N-((1R,5S,8s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.2.1]octan-8-yl)acetamide;
7-(5-(5-((1R,5S)-8-oxa-3-azabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile;
7-(5-(5-((1R,5S,8r)-8-hydroxy-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;
(R)-N-(1-(5-(6-(3-cyanopyrrolo[1,2-b]pyridazin-7-yl)-4-((3-methyloxetan-3-yl)amino)pyridin-3-yl)-1,3,4-thiadiazol-2-yl)-3,3 -difluoropiperidin-4-yl)acetamide;

(S)-N-(1-(5-(6-(3-cyanopyrrolo[1,2-b]pyridazin-7-yl)-4-((3-methyloxetan-3-yl)amino)pyridin-3-yl)-1,3,4-thiadiazol-2-yl)-3,3-difluoropiperidin-4-yl)acetamide;

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)cyclopropanecarboxamide;

7-(5-(5-((1R,5S,8r)-8-hydroxy-3-azabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)cyclopropanecarboxamide;

N-((S)-1-(5-(4-(((R)-1-cyanoethyl)amino)-6-(3-cyanopyrrolo[1,2-b]pyridazin-7-yl)pyridin-3-yl)-1,3,4-thiadiazol-2-yl)-3,3-difluoropiperidin-4-yl)acetamide;

7-(5-(5-((1R,5S,8r)-8-hydroxy-8-methyl-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

N-((1R,4r)-4-(5-(4-(((R)-1-cyanoethyl)amino)-6-(3-cyanopyrrolo[1,2-b]pyridazin-7-yl)pyridin-3-yl)-1,3,4-thiadiazol-2-yl)cyclohexyl)cyclopropanecarboxamide;

7-(4-(isopropylamino)-5-(5-(7-oxo-2,6-diazaspiro[3.4]octan-2-yl)-1,3,4-thiadiazol-2-yl)pyridin-2-yl)pyrrolo[1,2-b]pyridazine-3-carbonitrile;

7-(4-(isopropylamino)-5-(5-(5-oxo-2,6-diazaspiro[3.4]octan-2-yl)-1,3,4-thiadiazol-2-yl)pyridin-2-yl)pyrrolo[1,2-b]pyridazine-3-carbonitrile;

N-((1R,5S,9s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.3.1]nonan-9-yl)acetamide;

(R)-N-(1-(5-(6-(3-cyanopyrrolo[1,2-b]pyridazin-7-yl)-4-(isopropylamino)pyridin-3-yl)-1,3,4-thiadiazol-2-yl)-3,3-difluoropiperidin-4-yl)acetamide;

(S)-N-(1-(5-(6-(3-cyanopyrrolo[1,2-b]pyridazin-7-yl)-4-(isopropylamino)pyridin-3-yl)-1,3,4-thiadiazol-2-yl)-3,3-difluoropiperidin-4-yl)acetamide;

N-(2-(5-(6-(3-cyanopyrrolo[1,2-b]pyridazin-7-yl)-4-(isopropylamino)pyridin-3-yl)-1,3,4-thiadiazol-2-yl)-2-azaspiro[3.4]octan-6-yl)acetamide;

N-((1R,5S,8s)-3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-3-azabicyclo[3.2.1]octan-8-yl)acetamide;

N-((1R,5S,6S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.1.1]heptan-6-yl)acetamide;

N-((1R,5S,6s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.1.1]heptan-6-yl)acetamide;

N-((1R,5S,6s)-3-(5-(6-(3-cyanopyrrolo[1,2-b]pyridazin-7-yl)-4-(methylamino)pyridin-3-yl)-1,3,4-thiadiazol-2-yl)-3-azabicyclo[3.1.1]heptan-6-yl)acetamide;

7-(5-(5-(6-oxa-3-azabicyclo[3.1.1]heptan-3-yl)-1,3,4-thiadiazol-2-yl)-4-((tetrahydro-2H-pyran-4-yl)amino)pyridin-2-yl)pyrrolo[1,2-b]pyridazine-3-carbonitrile;

7-(5-(5-(6-oxa-3-azabicyclo[3.1.1]heptan-3-yl)-1,3,4-thiadiazol-2-yl)-4-(((R)-1-cyanoethyl)amino)pyridin-2-yl)pyrrolo[1,2-b]pyridazine-3-carbonitrile;

N-((1R,5S,6s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.1.1]heptan-6-yl)acetamide;

(R)-7-(4-((1-cyanoethyl)amino)-5-(5-(4-hydroxy-4-methylpiperidin-1-yl)-1,3,4-thiadiazol-2-yl)pyridin-2-yl)pyrrolo[1,2-b]pyridazine-3-carbonitrile;

7-(5-(5-(4-hydroxy-4-methylpiperidin-1-yl)-1,3,4-thiadiazol-2-yl)-4-((3-methyloxetan-3-yl)amino)pyridin-2-yl)pyrrolo[1,2-b]pyridazine-3-carbonitrile;

N-((1R,5S,9r)-7-(5-(6-(3-cyanopyrrolo[1,2-b]pyridazin-7-yl)-4-(isopropylamino)pyridin-3-yl)-1,3,4-thiadiazol-2-yl)-3-oxa-7-azabicyclo[3.3.1]nonan-9-yl)acetamide;

(R)-N-(1-(5-(6-(3-cyanopyrrolo[1,2-b]pyridazin-7-yl)-4-(oxetan-3-ylamino)pyridin-3-yl)-1,3,4-thiadiazol-2-yl)-3,3-difluoropiperidin-4-yl)acetamide;

N-((1R,5S,8s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.2.1]octan-8-yl)acetamide;

7-(5-(5-((3S,4R)-3-fluoro-4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile;

7-(5-(5-(4-hydroxy-4-methylpiperidin-1-yl)-1,3,4-thiadiazol-2-yl)-4-(oxetan-3-ylamino)pyridin-2-yl)pyrrolo[1,2-b]pyridazine-3-carbonitrile;

N-((1R,5S)-7-(5-(6-(3-cyanopyrrolo[1,2-b]pyridazin-7-yl)-4-(isopropylamino)pyridin-3-yl)-1,3,4-thiadiazol-2-yl)-3-oxa-7-azabicyclo[3.3.1]nonan-9-yl)acetamide;

N-(4-(5-(6-(3-cyanopyrrolo[1,2-b]pyridazin-7-yl)-4-(isopropylamino)pyridin-3-yl)-1,3,4-thiadiazol-2-yl)-4-fluorocyclohexyl)acetamide;

N-((1r,4r)-4-(5-(6-(3-cyanopyrrolo[1,2-b]pyridazin-7-yl)-4-(isopropylamino)pyridin-3-yl)-1,3,4-thiadiazol-2-yl)-4-fluorocyclohexyl)acetamide;

N-((1s,4s)-4-(5-(6-(3-cyanopyrrolo[1,2-b]pyridazin-7-yl)-4-(isopropylamino)pyridin-3-yl)-1,3,4-thiadiazol-2-yl)-4-fluorocyclohexyl)acetamide;

N-(1-(5-(6-(3-cyanopyrrolo[1,2-b]pyridazin-7-yl)-4-(oxetan-3-ylamino)pyridin-3-yl)-1,3,4-thiadiazol-2-yl)-2-oxabicyclo[2.2.2]octan-4-yl)acetamide;

7-(5-(5-((1s,3s)-3-hydroxy-3-methylcyclobutyl)-1,3,4-thiadiazol-2-yl)-4-(isopropylamino)pyridin-2-yl)pyrrolo[1,2-b]pyridazine-3-carbonitrile;

7-(5-(5-((1s,3s)-3-hydroxy-3-methylcyclobutyl)-1,3,4-thiadiazol-2-yl)-4-(oxetan-3-ylamino)pyridin-2-yl)pyrrolo[1,2-b]pyridazine-3-carbonitrile;

N-((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)cyclopropanecarboxamide;

7-(5-(5-((3S,4S)-3-fluoro-4-hydroxy-4-methylpiperidin-1-yl)-1,3,4-thiadiazol-2-yl)-4-((tetrahydro-2H-pyran-4-yl)amino)pyridin-2-yl)pyrrolo[1,2-b]pyridazine-3-carbonitrile;

methyl ((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)carbamate;

7-(5-(5-((1r,4r)-4-hydroxy-4-methylcyclohexyl)-1,3,4-thiadiazol-2-yl)-4-(oxetan-3-ylamino)pyridin-2-yl)pyrrolo[1,2-b]pyridazine-3-carbonitrile;

7-(5-(5-((3S,4S)-3-fluoro-4-hydroxy-4-methylpiperidin-1-yl)-1,3,4-thiadiazol-2-yl)-4-(oxetan-3-ylamino)pyridin-2-yl)pyrrolo[1,2-b]pyridazine-3-carbonitrile;

7-(5-(5-((1s,4s)-4-hydroxy-4-methylcyclohexyl)-1,3,4-thiadiazol-2-yl)-4-(oxetan-3-ylamino)pyridin-2-yl)pyrrolo[1,2-b]pyridazine-3-carbonitrile;

N-((1R,5S,7r)-9-(5-(6-(3-cyanopyrrolo[1,2-b]pyridazin-7-yl)-4-(isopropylamino)pyridin-3-yl)-1,3,4-thiadiazol-2-yl)-3-oxa-9-azabicyclo[3.3.1]nonan-7-yl)acetamide;

N-((1R,5S,8s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.2.1]octan-8-yl)-2-hydroxy-2-methylpropanamide;

7-(4-(isopropylamino)-5-(1,3,4-thiadiazol-2-yl)pyridin-2-yl)pyrrolo[1,2-b]pyridazine-3-carbonitrile;

(R)-7-(5-(5-(2-(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile;

(R)-7-(5-(5-(3-(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile;

(S)-7-(5-(5-(2-(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile;

(S)-7-(5-(5-(2-(aminomethyl)pyrrolidine-1-carbonyl)-1,3,4-thiadiazol-2-yl)-4-(isopropylamino)pyridin-2-yl)pyrrolo[1,2-b]pyridazine-3-carbonitrile;

(R)-7-(5-(5-(2-(aminomethyl)pyrrolidine-1-carbonyl)-1,3,4-thiadiazol-2-yl)-4-(isopropylamino)pyridin-2-yl)pyrrolo[1,2-b]pyridazine-3-carbonitrile;

7-(5-(5-(4-acetylpiperazin-1-yl)-1,3,4-thiadiazol-2-yl)-4-(isopropylamino)pyridin-2-yl)pyrrolo[1,2-b]pyridazine-3-carbonitrile;

7-(5-(5-(6-oxa-3-azabicyclo[3.1.1]heptan-3-yl)-1,3,4-thiadiazol-2-yl)-4-(isopropylamino)pyridin-2-yl)pyrrolo[1,2-b]pyridazine-3-carbonitrile;

7-(5-(5-(8-oxa-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

7-(5-(5-(3-oxa-8-azabicyclo[3.2.1]octan-8-yl)-1,3,4-thiadiazol-2-yl)-4-(isopropylamino)pyridin-2-yl)pyrrolo[1,2-b]pyridazine-3-carbonitrile;

7-(5-(5-((1R,4R)-2-oxa-5-azabicyclo[2.2.1]heptan-5-yl)-1,3,4-thiadiazol-2-yl)-4-(isopropylamino)pyridin-2-yl)pyrrolo[1,2-b]pyridazine-3-carbonitrile;

7-(5-(5-((1S,4S)-2-oxa-5-azabicyclo[2.2.1]heptan-5-yl)-1,3,4-thiadiazol-2-yl)-4-(isopropylamino)pyridin-2-yl)pyrrolo[1,2-b]pyridazine-3-carbonitrile;

N-((1R,5S,6r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.0]hexan-6-yl)acetamide;

N-((1R,5S,6s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.0]hexan-6-yl)acetamide;

N-((1R,4r)-4-(5-(6-(3-cyanopyrrolo[1,2-b]pyridazin-7-yl)-4-(((1s,3S)-3-hydroxy-3-methylcyclobutyl)amino)pyridin-3-yl)-1,3,4-thiadiazol-2-yl)cyclohexyl)acetamide;

N-((1R,4r)-4-(5-(6-(3-cyanopyrrolo[1,2-b]pyridazin-7-yl)-4-(((1s,4S)-4-hydroxycyclohexyl)amino)pyridin-3-yl)-1,3,4-thiadiazol-2-yl)cyclohexyl)acetamide;

N-((1S,4r)-4-(5-(6-(3-cyanopyrrolo[1,2-b]pyridazin-7-yl)-4-(((1S,3R)-3-hydroxycyclohexyl)amino)pyridin-3-yl)-1,3,4-thiadiazol-2-yl)cyclohexyl)acetamide;

N-((1S,3S)-3-(5-(6-(3-cyanopyrrolo[1,2-b]pyridazin-7-yl)-4-(isopropylamino)pyridin-3-yl)-1,3,4-thiadiazol-2-yl)cyclopentyl)acetamide;

N-((1R,3S)-3-(5-(6-(3-cyanopyrrolo[1,2-b]pyridazin-7-yl)-4-(isopropylamino)pyridin-3-yl)-1,3,4-thiadiazol-2-yl)cyclopentyl)acetamide;

N-((2S)-1-(5-(6-(3-cyanopyrrolo[1,2-b]pyridazin-7-yl)-4-(isopropylamino)pyridin-3-yl)-1,3,4-thiadiazol-2-yl)-2-methylpiperidin-4-yl)acetamide;

N-(1-(5-(6-(3-cyanopyrrolo[1,2-b]pyridazin-7-yl)-4-(isopropylamino)pyridin-3-yl)-1,3,4-thiadiazol-2-yl)-3,3-difluoropiperidin-4-yl)acetamide;

7-(5-(5-(2-oxa-6-azaspiro[3.3]heptan-6-yl)-1,3,4-thiadiazol-2-yl)-4-(isopropylamino)pyridin-2-yl)pyrrolo[1,2-b]pyridazine-3-carbonitrile;

N-((1r,4r)-4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)cyclohexyl)acetamide;

7-(5-(5-(8-oxa-3-azabicyclo[3.2.1]octan-3-yl)-1,3,4-thiadiazol-2-yl)-4-((tetrahydro-2H-pyran-4-yl)amino)pyridin-2-yl)pyrrolo[1,2-b]pyridazine-3-carbonitrile;

7-(5-(5-(8-acetyl-3,8-diazabicyclo[3.2.1]octan-3-yl)-1,3,4-thiadiazol-2-yl)-4-(isopropylamino)pyridin-2-yl)pyrrolo[1,2-b]pyridazine-3-carbonitrile;

7-(5-(5-(3-acetyl-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile;

7-(5-(5-(8-acetyl-3,8-diazabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile;

7-(5-(5-((1R,5S)-7-acetyl-3-oxa-7,9-diazabicyclo[3.3.1]nonan-9-yl)-1,3,4-thiadiazol-2-yl)-4-(isopropylamino)pyridin-2-yl)pyrrolo[1,2-b]pyridazine-3-carbonitrile;

7-(5-(5-(5-acetyl-2,5-diazabicyclo[4.1.0]heptan-2-yl)-1,3,4-thiadiazol-2-yl)-4-(isopropylamino)pyridin-2-yl)pyrrolo[1,2-b]pyridazine-3-carbonitrile;

N-((1r,4r)-4-(5-(6-(3-cyanopyrrolo[1,2-b]pyridazin-7-yl)-4-((4-methyltetrahydro-2H-pyran-4-yl)amino)pyridin-3-yl)-1,3,4-thiadiazol-2-yl)cyclohexyl)acetamide;

7-(5-(5-((1R,5S)-9-acetyl-3-oxa-7,9-diazabicyclo[3.3.1]nonan-7-yl)-1,3,4-thiadiazol-2-yl)-4-((tetrahydro-2H-pyran-4-yl)amino)pyridin-2-yl)pyrrolo[1,2-b]pyridazine-3-carbonitrile;

N-(3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[1.1.1]pentan-1-yl)acetamide;

7-(5-(5-(6-(2-hydroxy-2-methylpropanoyl)-3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile;

7-(5-(5-(3-(2-hydroxy-2-methylpropanoyl)-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile;

7-(5-(5-(3-(2-((dimethyl(oxo)-16-sulfanylidene)amino)acetyl)-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile;

7-(4-(isopropylamino)-5-(5-(3-(4-methylpiperazine-1-carbonyl)-3,6-diazabicyclo[3.1.1]heptan-6-yl)-1,3,4-thiadiazol-2-yl)pyridin-2-yl)pyrrolo[1,2-b]pyridazine-3-carbonitrile;

N-((1s,3s)-3-(5-(6-(3-cyanopyrrolo[1,2-b]pyridazin-7-yl)-4-(isopropylamino)pyridin-3-yl)-1,3,4-thiadiazol-2-yl)cyclobutyl)acetamide;

N-((1r,3r)-3-(5-(6-(3-cyanopyrrolo[1,2-b]pyridazin-7-yl)-4-(methylamino)pyridin-3-yl)-1,3,4-thiadiazol-2-yl)cyclobutyl)acetamide;

7-(4-(isopropylamino)-5-(5-((1r,3r)-3-(oxetan-3-ylamino)cyclobutyl)-1,3,4-thiadiazol-2-yl)pyridin-2-yl)pyrrolo[1,2-b]pyridazine-3-carbonitrile;

N-(4-(5-(6-(3-cyanopyrrolo[1,2-b]pyridazin-7-yl)-4-(isopropylamino)pyridin-3-yl)-1,3,4-thiadiazol-2-yl)bicyclo[2.2.1]heptan-1-yl)acetamide;

N-(5-(5-(6-(3-cyanopyrrolo[1,2-b]pyridazin-7-yl)-4-(isopropylamino)pyridin-3-yl)-1,3,4-thiadiazol-2-yl)bicyclo[2.2.1]heptan-2-yl)acetamide;

7-(5-(5-(3-hydroxy-3-methylazetidin-1-yl)-1,3,4-thiadiazol-2-yl)-4-(isopropylamino)pyridin-2-yl)pyrrolo[1,2-b]pyridazine-3-carbonitrile;

7-(5-(5-(4-hydroxy-4-methylpiperidin-1-yl)-1,3,4-thiadiazol-2-yl)-4-(isopropylamino)pyridin-2-yl)pyrrolo[1,2-b]pyridazine-3-carbonitrile;

N-(4-(5-(6-(3-cyanopyrrolo[1,2-b]pyridazin-7-yl)-4-(isopropylamino)pyridin-3-yl)-1,3,4-thiadiazol-2-yl)bicyclo[2.1.1]hexan-1-yl)acetamide;

N-(((1s,3s)-3-(5-(6-(3-cyanopyrrolo[1,2-b]pyridazin-7-yl)-4-(isopropylamino)pyridin-3-yl)-1,3,4-thiadiazol-2-yl)cyclobutyl)methyl)acetamide;

N-(((1r,3r)-3-(5-(6-(3-cyanopyrrolo[1,2-b]pyridazin-7-yl)-4-(isopropylamino)pyridin-3-yl)-1,3,4-thiadiazol-2-yl)cyclobutyl)methyl)acetamide;

N-((1R,5S,8s)-3-(5-(6-(3-cyanopyrrolo[1,2-b]pyridazin-7-yl)-4-(methylamino)pyridin-3-yl)-1,3,4-thiadiazol-2-yl)-3-azabicyclo[3.2.1]octan-8-yl)acetamide;

7-(5-(5-(3-hydroxy-3-(trifluoromethyl)azetidin-1-yl)-1,3,4-thiadiazol-2-yl)-4-(isopropylamino)pyridin-2-yl)pyrrolo[1,2-b]pyridazine-3-carbonitrile;

N-(1-(5-(6-(3-cyanopyrrolo[1,2-b]pyridazin-7-yl)-4-(isopropylamino)pyridin-3-yl)-1,3,4-thiadiazol-2-yl)azepan-4-yl)acetamide;

(S)-N-(1-(5-(6-(3-cyanopyrrolo[1,2-b]pyridazin-7-yl)-4-(isopropylamino)pyridin-3-yl)-1,3,4-thiadiazol-2-yl)piperidin-3-yl)acetamide;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-N-methylacetamide;

7-(5-(5-(((1S,4S)-5-acetyl-2,5-diazabicyclo[2.2.1]heptan-2-yl)-1,3,4-thiadiazol-2-yl)-4-(isopropylamino)pyridin-2-yl)pyrrolo[1,2-b]pyridazine-3-carbonitrile;

7-(5-(5-(((1R,4R)-5-acetyl-2,5-diazabicyclo[2.2.1]heptan-2-yl)-1,3,4-thiadiazol-2-yl)-4-(isopropylamino)pyridin-2-yl)pyrrolo[1,2-b]pyridazine-3-carbonitrile;

7-(4-(isopropylamino)-5-(5-(4-(oxetan-3-yl)piperazin-1-yl)-1,3,4-thiadiazol-2-yl)pyridin-2-yl)pyrrolo[1,2-b]pyridazine-3-carbonitrile;

(S)-N-(1-(5-(6-(3-cyanopyrrolo[1,2-b]pyridazin-7-yl)-4-(methylamino)pyridin-3-yl)-1,3,4-thiadiazol-2-yl)-3,3-difluoropiperidin-4-yl)acetamide;

7(5-(5-(4-cyanopiperidin-1-yl)-1,3,4-thiadiazol-2-yl)-4-(isopropylamino)pyridin-2-yl)pyrrolo[1,2-b]pyridazine-3-carbonitrile;

N-((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)-2-hydroxy-2-methylpropanamide;

N-((1s,4s)-4-(5-(6-(3-cyanopyrrolo[1,2-b]pyridazin-7-yl)-4-(isopropylamino)pyridin-3-yl)-1,3,4-thiadiazol-2-yl)cyclohexyl)-2-hydroxy-2-methylpropanamide;

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-methyloxetane-3-carboxamide;

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-2-hydroxy-2-methylpropanamide;

N-((1R,4r)-4-(5-(4-(((R)-1-cyanoethyl)amino)-6-(3-cyanopyrrolo[1,2-b]pyridazin-7-yl)pyridin-3-yl)-1,3,4-thiadiazol-2-yl)cyclohexyl)acetamide;

7-(5-(5-(3-hydroxy-3-(methyl-d3)butyl-4,4,4-d3)-1,3,4-thiadiazol-2-yl)-4-(isopropylamino)pyridin-2-yl)pyrrolo[1,2-b]pyridazine-3-carbonitrile;

7-(5-(5-(2-hydroxy-2-methylpropyl)-1,3,4-thiadiazol-2-yl)-4-(isopropylamino)pyridin-2-yl)pyrrolo[1,2-b]pyridazine-3-carbonitrile;

(R)-N-(5-(5-(6-(3-cyanopyrrolo[1,2-b]pyridazin-7-yl)-4-(isopropylamino)pyridin-3-yl)-1,3,4-thiadiazol-2-yl)-5-azaspiro[2.4]heptan-7-yl)acetamide;

(S)-N-(5-(5-(6-(3-cyanopyrrolo[1,2-b]pyridazin-7-yl)-4-(isopropylamino)pyridin-3-yl)-1,3,4-thiadiazol-2-yl)-5-azaspiro[2.4]heptan-7-yl)acetamide;

N-(1-(5-(6-(3-cyanopyrrolo[1,2-b]pyridazin-7-yl)-4-(isopropylamino)pyridin-3-yl)-1,3,4-thiadiazol-2-yl)-4,4-difluoropyrrolidin-3-yl)acetamide;

(S)-7-(5 -(5-(2-(hydroxymethyl)pyrrolidin-1-yl)-1,3,4-thiadiazol-2-yl)-4-(isopropylamino)pyridin-2-yl)pyrrolo[1,2-b]pyridazine-3-carbonitrile; and N-(4-(5-(6-(3-cyanopyrrolo[1,2-b]pyridazin-7-yl)-4-(oxetan-3-ylamino)pyridin-3-yl)-1,3,4-thiadiazol-2-yl)bicyclo[2.1.1]hexan-1-yl)-2-hydroxy-2-methylpropanamide.

3. The compound of claim 2, or a pharmaceutically acceptable salt thereof, selected from the group consisting of:

(R)-7-(5-(5-(hexahydropyrazino[2,1-c][1,4]oxazin-8(1H)-yl)-1,3,4-thiadiazol-2-yl)-4-(isopropylamino)pyridin-2-yl)pyrrolo[1,2-b]pyridazine-3-carbonitrile;

N-((1R,5S,8r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)acetamide;

N-((1r,4r)-4-(5-(6-(2-(((1R,2S)-2-aminocyclohexyl)amino)pyrrolo[2,1-f][1,2,4]triazin-7-yl)-4-(isopropylamino)pyridin-3-yl)-1,3,4-thiadiazol-2-yl)cyclohexyl)acetamide;

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)acetamide;

methyl ((1R,4r)-4-((5-(5-((1R,5S,8S)-8-acetamido-3-azabicyclo[3.2.1]octan-3-yl)-1,3,4-thiadiazol-2-yl)-2-(3-cyanopyrrolo[1,2-b]pyridazin-7-yl)pyridin-4-yl)amino)cyclohexyl)carbamate;

N-((1R,3r,5S)-8-(5-(6-(3-cyanopyrrolo[1,2-b]pyridazin-7-yl)-4-(isopropylamino)pyridin-3-yl)-1,3,4-thiadiazol-2-yl)-8-azabicyclo[3.2.1]octan-3-yl)acetamide;

N-((3R,4S)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

N-((3S,4R)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

N-((3S,4S)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

N-((3R,4R)-1-(5-(6-(3-cyanopyrrolo[1,2-b]pyridazin-7-yl)-4-(isopropylamino)pyridin-3 -yl)-1,3,4-thiadiazol-2-yl)-3-hydroxypiperidin-4-yl)acetamide;

N-(2-(5-(6-(3-cyanopyrrolo[1,2-b]pyridazin-7-yl)-4-(isopropylamino)pyridin-3-yl)-1,3,4-thiadiazol-2-yl)-2-azabicyclo[2.2.2]octan-4-yl)acetamide;

7-(5-(5-(7-acetyl-2,7-diazaspiro[3.5]nonan-2-yl)-1,3,4-thiadiazol-2-yl)-4-(isopropylamino)pyridin-2-yl)pyrrolo[1,2-b]pyridazine-3-carbonitrile;

7-(5-(5-(6-acetyl-2,6-diazaspiro[3.3]heptan-2-yl)-1,3,4-thiadiazol-2-yl)-4-(isopropylamino)pyridin-2-yl)pyrrolo[1,2-b]pyridazine-3-carbonitrile;

7-(5-(5-(7-acetyl-2,7-diazaspiro[3.5]nonan-2-yl)-1,3,4-thiadiazol-2-yl)-4-(oxetan-3-ylamino)pyridin-2-yl)pyrrolo[1,2-b]pyridazine-3-carbonitrile;

N-(2-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-2-azaspiro[3.5]nonan-7-yl)acetamide;

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)-2-hydroxy-2-methylpropanamide;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-4-methylpiperazine-1-carboxamide;

N-(2-(5-(6-(3-cyanopyrrolo[1,2-b]pyridazin-7-yl)-4-((3-methyloxetan-3-yl)amino)pyridin-3-yl)-1,3,4-thiadiazol-2-yl)-2-azaspiro[3.5]nonan-7-yl)acetamide;

N1-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)-N2-(dimethyl(oxo)-16-sulfanylidene)oxalamide;

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)cyclopropanecarboxamide;

N-((1s,4s)-4-(5-(6-(3-cyanopyrrolo[1,2-b]pyridazin-7-yl)-4-(isopropylamino)pyridin-3-yl)-1,3,4-thiadiazol-2-yl)cyclohexyl)acetamide;

7-(5-(5-(1-acetylpiperidin-4-yl)-1,3,4-thiadiazol-2-yl)-4-(isopropylamino)pyridin-2-yl)pyrrolo[1,2-b]pyridazine-3-carbonitrile;

7-(4-(isopropylamino)-5-(5-(piperidin-4-yl)-1,3,4-thiadiazol-2-yl)pyridin-2-yl)pyrrolo[1,2-b]pyridazine-3-carbonitrile;

7-(4-(isopropylamino)-5-(5-(piperazin-1-yl)-1,3,4-thiadiazol-2-yl)pyridin-2-yl)pyrrolo[1,2-b]pyridazine-3-carbonitrile;

7-(4-(isopropylamino)-5-(5-morpholino-1,3,4-thiadiazol-2-yl)pyridin-2-yl)pyrrolo[1,2-b]pyridazine-3-carbonitrile;

N-((1r,4r)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)cyclopropanecarboxamide;

7-(5-(5-((1S,2S)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;

7-(5-(5-((1R,2R)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;

7-(5-(5-((1S,2R)-2-(2-hydroxypropan-2-yl)cyclopropyl)-1,3,4-thiadiazol-2-yl)-4-(oxetan-3-ylamino)pyridin-2-yl)pyrrolo[1,2-b]pyridazine-3-carbonitrile;

7-(4-(isopropylamino)-5-(5-(1-(oxetan-3-yl)piperidin-4-yl)-1,3,4-thiadiazol-2-yl)pyridin-2-yl)pyrrolo[1,2-b]pyridazine-3-carbonitrile;

N-((1R,2R,4S)-7-(5-(6-(3-cyanopyrrolo[1,2-b]pyridazin-7-yl)-4-(isopropylamino)pyridin-3-yl)-1,3,4-thiadiazol-2-yl)-7-azabicyclo[2.2.1]heptan-2-yl)acetamide;

N-((1r,4r)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)morpholine-4-carboxamide;

N-((1R,5S,8s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.2.1]octan-8-yl)acetamide;

7-(5-(5-((1R,5S,8r)-8-hydroxy-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

(R)-N-(1-(5-(6-(3-cyanopyrrolo[1,2-b]pyridazin-7-yl)-4-((3-methyloxetan-3-yl)amino)pyridin-3-yl)-1,3,4-thiadiazol-2-yl)-3,3-difluoropiperidin-4-yl)acetamide;

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)cyclopropanecarboxamide;

7-(5-(5-((1R,5S,8r)-8-hydroxy-3-azabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile;

N-((1R,5S,8s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.2.1]octan-8-yl)cyclopropanecarboxamide;

N-((S)-1-(5-(4-(((R)-1-cyanoethyl)amino)-6-(3-cyanopyrrolo[1,2-b]pyridazin-7-yl)pyridin-3-yl)-1,3,4-thiadiazol-2-yl)-3,3-difluoropiperidin-4-yl)acetamide;

N-((1R,4r)-4-(5-(4-(((R)-1-cyanoethyl)amino)-6-(3-cyanopyrrolo[1,2-b]pyridazin-7-yl)pyridin-3-yl)-1,3,4-thiadiazol-2-yl)cyclohexyl)cyclopropanecarboxamide;

7-(4-(isopropylamino)-5-(5-(7-oxo-2,6-diazaspiro[3.4]octan-2-yl)-1,3,4-thiadiazol-2-yl)pyridin-2-yl)pyrrolo[1,2-b]pyridazine-3-carbonitrile;

7-(4-(isopropylamino)-5-(5-(5-oxo-2,6-diazaspiro[3.4]octan-2-yl)-1,3,4-thiadiazol-2-yl)pyridin-2-yl)pyrrolo[1,2-b]pyridazine-3-carbonitrile;

N-(2-(5-(6-(3-cyanopyrrolo[1,2-b]pyridazin-7-yl)-4-(isopropylamino)pyridin-3-yl)-1,3,4-thiadiazol-2-yl)-2-azaspiro[3.4]octan-6-yl)acetamide;

N-((1R,5S,8s)-3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)-3-azabicyclo[3.2.1]octan-8-yl)acetamide;

N-((1R,5S,6S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.1.1]heptan-6-yl)acetamide;

N-((1R,5S,6s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.1.1]heptan-6-yl)acetamide;

7-(5-(5-(6-oxa-3-azabicyclo[3.1.1]heptan-3-yl)-1,3,4-thiadiazol-2-yl)-4-((tetrahydro-2H-pyran-4-yl)amino)pyridin-2-yl)pyrrolo[1,2-b]pyridazine-3-carbonitrile;

7-(5-(5-(6-oxa-3-azabicyclo[3.1.1]heptan-3-yl)-1,3,4-thiadiazol-2-yl)-4-(((R)-1-cyanoethyl)amino)pyridin-2-yl)pyrrolo[1,2-b]pyridazine-3-carbonitrile;

N-((1R,5S,6s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.1.1]heptan-6-yl)acetamide;

(R)-7-(4-((1-cyanoethyl)amino)-5-(5-(4-hydroxy-4-methylpiperidin-1-yl)-1,3,4-thiadiazol-2-yl)pyridin-2-yl)pyrrolo[1,2-b]pyridazine-3-carbonitrile;

7-(5-(5-(4-hydroxy-4-methylpiperidin-1-yl)-1,3,4-thiadiazol-2-yl)-4-((3-methyloxetan-3-yl)amino)pyridin-2-yl)pyrrolo[1,2-b]pyridazine-3-carbonitrile;

N-((1R,5S,9r)-7-(5-(6-(3-cyanopyrrolo[1,2-b]pyridazin-7-yl)-4-(isopropylamino)pyridin-3-yl)-1,3,4-thiadiazol-2-yl)-3-oxa-7-azabicyclo[3.3.1]nonan-9-yl)acetamide;

(R)-N-(1-(5-(6-(3-cyanopyrrolo[1,2-b]pyridazin-7-yl)-4-(oxetan-3-ylamino)pyridin-3-yl)-1,3,4-thiadiazol-2-yl)-3,3-difluoropiperidin-4-yl)acetamide;

N-((1R,5S,8s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.2.1]octan-8-yl)acetamide;

7-(5-(5-(4-hydroxy-4-methylpiperidin-1-yl)-1,3,4-thiadiazol-2-yl)-4-(oxetan-3-ylamino)pyridin-2-yl)pyrrolo[1,2-b]pyridazine-3-carbonitrile;

N-((1R,5S)-7-(5-(6-(3-cyanopyrrolo[1,2-b]pyridazin-7-yl)-4-(isopropylamino)pyridin-3-yl)-1,3,4-thiadiazol-2-yl)-3-oxa-7-azabicyclo[3.3.1]nonan-9-yl)acetamide;

7-(5-(5-((1s,3s)-3-hydroxy-3-methylcyclobutyl)-1,3,4-thiadiazol-2-yl)-4-(isopropylamino)pyridin-2-yl)pyrrolo[1,2-b]pyridazine-3-carbonitrile;

7-(5-(5-((1s,3s)-3-hydroxy-3-methylcyclobutyl)-1,3,4-thiadiazol-2-yl)-4-(oxetan-3-ylamino)pyridin-2-yl)pyrrolo[1,2-b]pyridazine-3-carbonitrile;

7-(5-(5-((3S,4S)-3-fluoro-4-hydroxy-4-methylpiperidin-1-yl)-1,3,4-thiadiazol-2-yl)-4-((tetrahydro-2H-pyran-4-yl)amino)pyridin-2-yl)pyrrolo[1,2-b]pyridazine-3-carbonitrile;

methyl ((1s,4s)-4-(5-(6-(3-cyanopyrrolo[1,2-b]pyridazin-7-yl)-4-(oxetan-3-ylamino)pyridin-3-yl)-1,3,4-thiadiazol-2-yl)cyclohexyl)carbamate;

7-(5-(5-((1r,4r)-4-hydroxy-4-methylcyclohexyl)-1,3,4-thiadiazol-2-yl)-4-(oxetan-3-ylamino)pyridin-2-yl)pyrrolo[1,2-b]pyridazine-3-carbonitrile;

7-(5-(5-((3S,4S)-3-fluoro-4-hydroxy-4-methylpiperidin-1-yl)-1,3,4-thiadiazol-2-yl)-4-(oxetan-3-ylamino)pyridin-2-yl)pyrrolo[1,2-b]pyridazine-3-carbonitrile;

7-(5-(5-((1s,4s)-4-hydroxy-4-methylcyclohexyl)-1,3,4-thiadiazol-2-yl)-4-(oxetan-3-ylamino)pyridin-2-yl)pyrrolo[1,2-b]pyridazine-3-carbonitrile;

N-((1R,5S,7r)-9-(5-(6-(3-cyanopyrrolo[1,2-b]pyridazin-7-yl)-4-(isopropylamino)pyridin-3-yl)-1,3,4-thiadiazol-2-yl)-3-oxa-9-azabicyclo[3.3.1]nonan-7-yl)acetamide;

N-((1R,5S,8s)-3-(5-(6-(3-cyanopyrrolo[1,2-b]pyridazin-7-yl)-4-((3-methyloxetan-3-yl)amino)pyridin-3-yl)-1,3,4-thiadiazol-2-yl)-3-azabicyclo[3.2.1]octan-8-yl)-2-hydroxy-2-methylpropanamide;

(R)-7-(5-(5-(2-(hydroxymethyl)pyrrolidine-1-carbonyl)-1,3,4-thiadiazol-2-yl)-4-(isopropylamino)pyridin-2-yl)pyrrolo[1,2-b]pyridazine-3-carbonitrile;

(S)-7-(5-(5-(2-(aminomethyl)pyrrolidine-1-carbonyl)-1,3,4-thiadiazol-2-yl)-4-(isopropylamino)pyridin-2-yl)pyrrolo[1,2-b]pyridazine-3-carbonitrile;

7-(5-(5-(6-oxa-3-azabicyclo[3.1.1]heptan-3-yl)-1,3,4-thiadiazol-2-yl)-4-(isopropylamino)pyridin-2-yl)pyrrolo[1,2-b]pyridazine-3-carbonitrile;

7-(5-(5-(8-oxa-3-azabicyclo[3.2.1]octan-3-yl)-1,3,4-thiadiazol-2-yl)-4-(isopropylamino)pyridin-2-yl)pyrrolo[1,2-b]pyridazine-3-carbonitrile;

7-(5-(5-((1R,4R)-2-oxa-5-azabicyclo[2.2.1]heptan-5-yl)-1,3,4-thiadiazol-2-yl)-4-(isopropylamino)pyridin-2-yl)pyrrolo[1,2-b]pyridazine-3-carbonitrile;

7-(5-(5-((1S,4S)-2-oxa-5-azabicyclo[2.2.1]heptan-5-yl)-1,3,4-thiadiazol-2-yl)-4-(isopropylamino)pyridin-2-yl)pyrrolo[1,2-b]pyridazine-3-carbonitrile;

N-((1R,5S,6r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.0]hexan-6-yl)acetamide;

N-((1R,5S,6s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.0]hexan-6-yl)acetamide;

N-((1R,4r)-4-(5-(6-(3-cyanopyrrolo[1,2-b]pyridazin-7-yl)-4-(((1s,3S)-3-hydroxy-3-methylcyclobutyl)amino)pyridin-3-yl)-1,3,4-thiadiazol-2-yl)cyclohexyl)acetamide;

N-((1S,4r)-4-(5-(6-(3-cyanopyrrolo[1,2-b]pyridazin-7-yl)-4-(((1S,3R)-3-hydroxycyclohexyl)amino)pyridin-3-yl)-1,3,4-thiadiazol-2-yl)cyclohexyl)acetamide;

N-((1S,3S)-3-(5-(6-(3-cyanopyrrolo[1,2-b]pyridazin-7-yl)-4-(isopropylamino)pyridin-3-yl)-1,3,4-thiadiazol-2-yl)cyclopentyl)acetamide;

N-((2S)-1-(5-(6-(3-cyanopyrrolo[1,2-b]pyridazin-7-yl)-4-(isopropylamino)pyridin-3-yl)-1,3,4-thiadiazol-2-yl)-2-methylpiperidin-4-yl)acetamide;

7-(5-(5-(2-oxa-6-azaspiro[3.3]heptan-6-yl)-1,3,4-thiadiazol-2-yl)-4-(isopropylamino)pyridin-2-yl)pyrrolo[1,2-b]pyridazine-3-carbonitrile;

N-((1r,4r)-4-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)cyclohexyl)acetamide;

7-(5-(5-(8-oxa-3-azabicyclo[3.2.1]octan-3-yl)-1,3,4-thiadiazol-2-yl)-4-((tetrahydro-2H-pyran-4-yl)amino)pyridin-2-yl)pyrrolo[1,2-b]pyridazine-3-carbonitrile;

7-(5-(5-(8-acetyl-3,8-diazabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile;

7-(5-(5-((1R,5S)-7-acetyl-3-oxa-7,9-diazabicyclo[3.3.1]nonan-9-yl)-1,3,4-thiadiazol-2-yl)-4-(isopropylamino)pyridin-2-yl)pyrrolo[1,2-b]pyridazine-3-carbonitrile;

7-(5-(5-(5-acetyl-2,5-diazabicyclo[4.1.0]heptan-2-yl)-1,3,4-thiadiazol-2-yl)-4-(isopropylamino)pyridin-2-yl)pyrrolo[1,2-b]pyridazine-3-carbonitrile;

N-((1r,4r)-4-(5-(6-(3-cyanopyrrolo[1,2-b]pyridazin-7-yl)-4-((4-methyltetrahydro-2H-pyran-4-yl)amino)pyridin-3-yl)-1,3,4-thiadiazol-2-yl)cyclohexyl)acetamide;

7-(5-(5-((1R,5S)-9-acetyl-3-oxa-7,9-diazabicyclo[3.3.1]nonan-7-yl)-1,3,4-thiadiazol-2-yl)-4-((tetrahydro-2H-pyran-4-yl)amino)pyridin-2-yl)pyrrolo[1,2-b]pyridazine-3-carbonitrile;

N-(3-(5-(6-(3-cyanopyrrolo[1,2-b]pyridazin-7-yl)-4-((tetrahydro-2H-pyran-4-yl)amino)pyridin-3-yl)-1,3,4-thiadiazol-2-yl)bicyclo[1.1.1]pentan-1-yl)acetamide;

7-(5-(5-(6-(2-hydroxy-2-methylpropanoyl)-3,6-diazabicyclo[3.1.1]heptan-3-yl)-1,3,4-thiadiazol-2-yl)-4-(isopropylamino)pyridin-2-yl)pyrrolo[1,2-b]pyridazine-3-carbonitrile;

7-(5-(5-(3-(2-hydroxy-2-methylpropanoyl)-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile;

7-(5-(5-(3-(2-((dimethyl(oxo)-16-sulfanylidene)amino)acetyl)-3,6-diazabicyclo[3.1.1]heptan-6-yl)-1,3,4-thiadiazol-2-yl)-4-(isopropylamino)pyridin-2-yl)pyrrolo[1,2-b]pyridazine-3-carbonitrile;

N-((1s,3s)-3-(5-(6-(3-cyanopyrrolo[1,2-b]pyridazin-7-yl)-4-(isopropylamino)pyridin-3-yl)-1,3,4-thiadiazol-2-yl)cyclobutyl)acetamide;

N-((1r,3r)-3-(5-(6-(3-cyanopyrrolo[1,2-b]pyridazin-7-yl)-4-(methylamino)pyridin-3-yl)-1,3,4-thiadiazol-2-yl)cyclobutyl)acetamide;

7-(4-(isopropylamino)-5-(5-((1r,3r)-3-(oxetan-3-ylamino)cyclobutyl)-1,3,4-thiadiazol-2-yl)pyridin-2-yl)pyrrolo[1,2-b]pyridazine-3-carbonitrile;

N-(((1s,3s)-3-(5-(6-(3-cyanopyrrolo[1,2-b]pyridazin-7-yl)-4-(isopropylamino)pyridin-3-yl)-1,3,4-thiadiazol-2-yl)cyclobutyl)methyl)acetamide;

N-(((1r,3r)-3-(5-(6-(3-cyanopyrrolo[1,2-b]pyridazin-7-yl)-4-(isopropylamino)pyridin-3-yl)-1,3,4-thiadiazol-2-yl)cyclobutyl)methyl)acetamide;

N-((1R,5S,8s)-3-(5-(6-(3-cyanopyrrolo[1,2-b]pyridazin-7-yl)-4-(methylamino)pyridin-3-yl)-1,3,4-thiadiazol-2-yl)-3-azabicyclo[3.2.1]octan-8-yl)acetamide;

7-(5-(5-(3-hydroxy-3-(trifluoromethyl)azetidin-1-yl)-1,3,4-thiadiazol-2-yl)-4-(isopropylamino)pyridin-2-yl)pyrrolo[1,2-b]pyridazine-3-carbonitrile;

(S)-N-(1-(5-(6-(3-cyanopyrrolo[1,2-b]pyridazin-7-yl)-4-(isopropylamino)pyridin-3-yl)-1,3,4-thiadiazol-2-yl)piperidin-3-yl)acetamide;

7-(5-(5-(((1S,4S)-5-acetyl-2,5-diazabicyclo[2.2.1]heptan-2-yl)-1,3,4-thiadiazol-2-yl)-4-(isopropylamino)pyridin-2-yl)pyrrolo[1,2-b]pyridazine-3-carbonitrile;

7-(5-(5-(((1R,4R)-5-acetyl-2,5-diazabicyclo[2.2.1]heptan-2-yl)-1,3,4-thiadiazol-2-yl)-4-(isopropylamino)pyridin-2-yl)pyrrolo[1,2-b]pyridazine-3-carbonitrile;

7-(4-(isopropylamino)-5-(5-(4-(oxetan-3-yl)piperazin-1-yl)-1,3,4-thiadiazol-2-yl)pyridin-2-yl)pyrrolo[1,2-b]pyridazine-3-carbonitrile;

7-(5-(5-(4-cyanopiperidin-1-yl)-1,3,4-thiadiazol-2-yl)-4-(isopropylamino)pyridin-2-yl)pyrrolo[1,2-b]pyridazine-3-carbonitrile;

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-3-methyloxetane-3-carboxamide;

N-((1r,4r)-4-(5-(6-(3-cyanopyrrolo[1,2-b]pyridazin-7-yl)-4-(isopropylamino)pyridin-3-yl)-1,3,4-thiadiazol-2-yl)cyclohexyl)-2-hydroxy-2-methylpropanamide;

N-((1R,4r)-4-(5-(4-(((R)-1-cyanoethyl)amino)-6-(3-cyanopyrrolo[1,2-b]pyridazin-7-yl)pyridin-3-yl)-1,3,4-thiadiazol-2-yl)cyclohexyl)acetamide;

7-(5-(5-(3-hydroxy-3-(methyl-d3)butyl-4,4,4-d3)-1,3,4-thiadiazol-2-yl)-4-(isopropylamino)pyridin-2-yl)pyrrolo[1,2-b]pyridazine-3-carbonitrile;

(R)-N-(5-(5-(6-(3-cyanopyrrolo[1,2-b]pyridazin-7-yl)-4-(isopropylamino)pyridin-3-yl)-1,3,4-thiadiazol-2-yl)-5-azaspiro[2.4]heptan-7-yl)acetamide; and N-(1-(5-(6-(3-cyanopyrrolo[1,2-b]pyridazin-7-yl)-4-(isopropylamino)pyridin-3-yl)-1,3,4-thiadiazol-2-yl)-4,4-difluoropyrrolidin-3-yl)acetamide.

4. The compound of claim 3, or a pharmaceutically acceptable salt thereof, selected from the group consisting of:

(R)-7-(5-(5-(hexahydropyrazino[2,1-c][1,4]oxazin-8(1H)-yl)-1,3,4-thiadiazol-2-yl)-4-(isopropylamino)pyridin-2-yl)pyrrolo[1,2-b]pyridazine-3-carbonitrile;

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)acetamide;

N-((3R,4S)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

N-((3S,4R)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

N-((3S,4S)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

N-((3R,4R)-1-(5-(6-(3-cyanopyrrolo[1,2-b]pyridazin-7-yl)-4-(isopropylamino)pyridin-3-yl)-1,3,4-thiadiazol-2-yl)-3-hydroxypiperidin-4-yl)acetamide;

7-(5-(5-(7-acetyl-2,7-diazaspiro[3.5]nonan-2-yl)-1,3,4-thiadiazol-2-yl)-4-(oxetan-3-ylamino)pyridin-2-yl)pyrrolo[1,2-b]pyridazine-3-carbonitrile;

N-((1R,5S,8S)-3-(5-(4-(((R)-1-cyanoethyl)amino)-6-(3-cyanopyrrolo[1,2-b]pyridazin-7-yl)pyridin-3-yl)-1,3,4-thiadiazol-2-yl)-3-azabicyclo[3.2.1]octan-8-yl)cyclopropanecarboxamide;

7-(5-(5-((1R,5S,8r)-8-hydroxy-3-azabicyclo[3.2.1]octan-3-yl)-1,3,4-thiadiazol-2-yl)-4-((3-methyloxetan-3-yl)amino)pyridin-2-yl)pyrrolo[1,2-b]pyridazine-3-carbonitrile;

N-((1R,5S,6s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.1.1]heptan-6-yl)acetamide;

N-((1R,5S,8s)-3-(5-(6-(3-cyanopyrrolo[1,2-b]pyridazin-7-yl)-4-(oxetan-3-ylamino)pyridin-3-yl)-1,3,4-thiadiazol-2-yl)-3-azabicyclo[3.2.1]octan-8-yl)acetamide;

7-(5-(5-((3S,4S)-3-fluoro-4-hydroxy-4-methylpiperidin-1-yl)-1,3,4-thiadiazol-2-yl)-4-((tetrahydro-2H-pyran-4-yl)amino)pyridin-2-yl)pyrrolo[1,2-b]pyridazine-3-carbonitrile;

7-(5-(5-(6-oxa-3-azabicyclo[3.1.1]heptan-3-yl)-1,3,4-thiadiazol-2-yl)-4-(isopropylamino)pyridin-2-yl)pyrrolo[1,2-b]pyridazine-3-carbonitrile;

7-(5-(5-((1R,4R)-2-oxa-5-azabicyclo[2.2.1]heptan-5-yl)-1,3,4-thiadiazol-2-yl)-4-(isopropylamino)pyridin-2-yl)pyrrolo[1,2-b]pyridazine-3-carbonitrile;

N-((1R,5S,6r)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.0]hexan-6-yl)acetamide;

N-((1R,5S,6s)-3-(5-(6-(3-cyanopyrrolo[1,2-b]pyridazin-7-yl)-4-(isopropylamino)pyridin-3-yl)-1,3,4-thiadiazol-2-yl)-3-azabicyclo[3.1.0]hexan-6-yl)acetamide; and 7-(5-(5-(2-oxa-6-azaspiro[3.3]heptan-6-yl)-1,3,4-thiadiazol-2-yl)-4-(isopropylamino)pyridin-2-yl)pyrrolo[1,2-b]pyridazine-3-carbonitrile.

* * * * *